(12) United States Patent
Chang et al.

(10) Patent No.: US 12,084,712 B2
(45) Date of Patent: Sep. 10, 2024

(54) SAMPLE INDEXING FOR SINGLE CELLS

(71) Applicant: BECTON, DICKINSON AND COMPANY, Franklin Lakes, NJ (US)

(72) Inventors: Christina Chang, San Jose, CA (US); Christina Fan, San Jose, CA (US); Eleen Shum, San Jose, CA (US); Jody Martin, San Jose, CA (US); Nidhanjali Bansal, San Jose, CA (US); James Ghadiali, San Jose, CA (US); Katherine Lazaruk, San Jose, CA (US); Gretchen Yinbon Lam, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1179 days.

(21) Appl. No.: 16/848,241

(22) Filed: Apr. 14, 2020

(65) Prior Publication Data

US 2020/0385780 A1 Dec. 10, 2020

Related U.S. Application Data

(63) Continuation of application No. 15/937,713, filed on Mar. 27, 2018, now Pat. No. 10,676,779.
(Continued)

(51) Int. Cl.
*C12Q 1/6804* (2018.01)
*C12Q 1/6806* (2018.01)
(Continued)

(52) U.S. Cl.
CPC ......... *C12Q 1/6804* (2013.01); *C12Q 1/6806* (2013.01); *C12Q 1/6809* (2013.01);
(Continued)

(58) Field of Classification Search
CPC .. C12Q 1/6804; C12Q 1/6806; C12Q 1/6809; C12Q 1/6816; C12Q 1/6837;
(Continued)

(56) References Cited

U.S. PATENT DOCUMENTS

| 4,510,244 A | 4/1985 | Parks et al. |
| 4,725,536 A | 2/1988 | Fritsch et al. |

(Continued)

FOREIGN PATENT DOCUMENTS

| CA | 2474509 | 2/2003 |
| CA | 2961210 A1 | 3/2016 |

(Continued)

OTHER PUBLICATIONS (Data Processing technical note from 2012) (Year: 2012).*
(Continued)

*Primary Examiner* — Jeremy C Flinders
(74) *Attorney, Agent, or Firm* — Sheppard, Mullin, Richter & Hampton LLP

(57) ABSTRACT

Disclosed herein include systems, methods, compositions, and kits for sample identification. A sample indexing composition can comprise, for example, a protein binding reagent associated with a sample indexing oligonucleotide. Different sample indexing compositions can include sample indexing oligonucleotides with different sequences. Sample origin of cells can be identified based on the sequences of the sample indexing oligonucleotides. Sample indexing oligonucleotides can be barcoded using barcoded and lengthened using daisy-chaining primers.

26 Claims, 112 Drawing Sheets
Specification includes a Sequence Listing.

Related U.S. Application Data

(60) Provisional application No. 62/645,703, filed on Mar. 20, 2018, provisional application No. 62/578,957, filed on Oct. 30, 2017, provisional application No. 62/554,425, filed on Sep. 5, 2017, provisional application No. 62/532,949, filed on Jul. 14, 2017, provisional application No. 62/532,905, filed on Jul. 14, 2017, provisional application No. 62/532,971, filed on Jul. 14, 2017, provisional application No. 62/515,285, filed on Jun. 5, 2017.

(51) Int. Cl.

| | |
|---|---|
| *C12Q 1/6809* | (2018.01) |
| *C12Q 1/6811* | (2018.01) |
| *C12Q 1/6816* | (2018.01) |
| *C12Q 1/6855* | (2018.01) |
| *C12Q 1/6865* | (2018.01) |
| *C12Q 1/6869* | (2018.01) |
| *C12Q 1/6876* | (2018.01) |
| *G01N 33/532* | (2006.01) |
| *B82Y 5/00* | (2011.01) |
| *C12Q 1/6834* | (2018.01) |
| *C12Q 1/6837* | (2018.01) |

(52) U.S. Cl.
CPC .......... *C12Q 1/6811* (2013.01); *C12Q 1/6816* (2013.01); *C12Q 1/6855* (2013.01); *C12Q 1/6865* (2013.01); *C12Q 1/6869* (2013.01); *C12Q 1/6876* (2013.01); *G01N 33/532* (2013.01); *B82Y 5/00* (2013.01); *C12Q 1/6834* (2013.01); *C12Q 1/6837* (2013.01); *C12Q 2563/149* (2013.01); *C12Q 2563/179* (2013.01); *C12Q 2563/185* (2013.01); *C12Q 2600/16* (2013.01); *G01N 2458/10* (2013.01)

(58) Field of Classification Search
CPC .. C12Q 1/6855; C12Q 1/6869; C12Q 1/6876; C12Q 2600/16; C12Q 2563/131; C12Q 2563/179; C12Q 2525/179
See application file for complete search history.

(56) References Cited

U.S. PATENT DOCUMENTS

| | | |
|---|---|---|
| 5,124,246 A | 6/1992 | Urdea et al. |
| 5,137,809 A | 8/1992 | Loken et al. |
| 5,149,625 A | 9/1992 | Church et al. |
| 5,200,314 A | 4/1993 | Urdea |
| 5,308,990 A | 5/1994 | Takahashi et al. |
| 5,424,186 A | 6/1995 | Fodor et al. |
| 5,424,413 A | 6/1995 | Hogan et al. |
| 5,445,934 A | 8/1995 | Fodor et al. |
| 5,470,570 A | 11/1995 | Taylor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,830,712 A | 11/1998 | Rampersad et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,962,271 A | 10/1999 | Chenchik et al. |
| 5,962,272 A | 10/1999 | Chenchik et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,064,755 A | 5/2000 | Some |
| 6,114,149 A | 9/2000 | Fry et al. |
| 6,117,631 A | 9/2000 | Nilsen |
| 6,124,092 A | 9/2000 | O'Neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,197,554 B1 | 3/2001 | Lin et al. |
| 6,214,558 B1 | 4/2001 | Shuber et al. |
| 6,235,475 B1 | 5/2001 | Brenner et al. |
| 6,235,483 B1 | 5/2001 | Wolber et al. |
| 6,265,163 B1 | 7/2001 | Albrecht et al. |
| 6,268,152 B1 | 7/2001 | Fodor et al. |
| 6,284,460 B1 | 9/2001 | Fodor et al. |
| 6,284,485 B1 | 9/2001 | Boyle et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Willis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |

(56) References Cited

U.S. PATENT DOCUMENTS

| | | |
|---|---|---|
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet et al. |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,841,071 B2 | 9/2014 | Link |
| 8,856,410 B2 | 10/2014 | Park |
| 8,865,470 B2 | 10/2014 | Yan et al. |
| 9,150,852 B2 | 10/2015 | Samuels et al. |
| 9,181,582 B2 | 11/2015 | Kurn |
| 9,188,586 B2 | 11/2015 | Fan et al. |
| 9,228,229 B2 | 1/2016 | Olson et al. |
| 9,262,376 B2 | 2/2016 | Tsuto |
| 9,297,047 B2 | 3/2016 | Furchak et al. |
| 9,371,598 B2 | 6/2016 | Chee |
| 9,582,877 B2 | 2/2017 | Fu et al. |
| 9,593,365 B2 | 3/2017 | Frisen et al. |
| 9,644,204 B2 | 5/2017 | Hindson et al. |
| 9,677,131 B2 | 6/2017 | Fredriksson et al. |
| 9,689,024 B2 | 6/2017 | Hindson et al. |
| 9,695,468 B2 | 7/2017 | Hindson et al. |
| 9,787,810 B1 | 10/2017 | Chiang |
| 9,850,515 B2 | 12/2017 | McCoy et al. |
| 9,856,530 B2 | 1/2018 | Hindson et al. |
| 9,868,979 B2 | 1/2018 | Chee et al. |
| 9,879,313 B2 | 1/2018 | Chee et al. |
| 9,905,005 B2 | 2/2018 | Fu et al. |
| 9,938,523 B2 | 4/2018 | LaBaer |
| 9,951,386 B2 | 4/2018 | Hindson et al. |
| 9,988,660 B2 | 6/2018 | Rashtchian et al. |
| 10,002,316 B2 | 6/2018 | Fodor et al. |
| 10,011,872 B1 | 7/2018 | Belgrader et al. |
| 10,017,761 B2 | 7/2018 | Weissman et al. |
| 10,023,910 B2 | 7/2018 | Drmanac et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,138,518 B2 | 11/2018 | Chun |
| 10,151,003 B2 | 12/2018 | Fan et al. |
| 10,208,343 B2 | 2/2019 | Hindson et al. |
| 10,227,648 B2 | 3/2019 | Hindson et al. |
| 10,246,703 B2 | 4/2019 | Church et al. |
| 10,253,364 B2 | 4/2019 | Hindson et al. |
| 10,266,874 B2 | 4/2019 | Weissleder et al. |
| 10,273,541 B2 | 4/2019 | Hindson et al. |
| 10,288,608 B2 | 5/2019 | Kozlov et al. |
| 10,294,511 B2 | 5/2019 | Sanches-Kuiper et al. |
| 10,308,982 B2 | 6/2019 | Chee |
| 10,323,278 B2 | 6/2019 | Belgrader et al. |
| 10,337,061 B2 | 7/2019 | Hindson et al. |
| 10,344,329 B2 | 7/2019 | Hindson et al. |
| 10,450,607 B2 | 10/2019 | Hindson et al. |
| 10,550,429 B2 | 2/2020 | Harada et al. |
| RE47,983 E | 5/2020 | Gao et al. |
| 11,092,607 B2 | 8/2021 | Gaublomme et al. |
| 11,460,468 B2 | 10/2022 | Fan et al. |
| 11,467,157 B2 | 10/2022 | Fan et al. |
| 11,535,882 B2 | 12/2022 | Fu et al. |
| 2001/0024784 A1 | 9/2001 | Wagner |
| 2001/0036632 A1 | 11/2001 | Yu et al. |
| 2002/0019005 A1 | 2/2002 | Kamb |
| 2002/0051986 A1 | 5/2002 | Baez et al. |
| 2002/0065609 A1 | 5/2002 | Ashby |
| 2002/0072058 A1 | 6/2002 | Voelker et al. |
| 2002/0094116 A1 | 7/2002 | Forst et al. |
| 2002/0106666 A1 | 8/2002 | Hayashizaki |
| 2002/0132241 A1 | 9/2002 | Fan et al. |
| 2002/0168665 A1 | 11/2002 | Okawa |
| 2002/0172953 A1 | 11/2002 | Mirkin et al. |
| 2002/0187480 A1 | 12/2002 | Brandon |
| 2002/0192687 A1 | 12/2002 | Mirkin et al. |
| 2003/0003490 A1 | 1/2003 | Fan et al. |
| 2003/0013091 A1 | 1/2003 | Dimitrov |
| 2003/0032049 A1 | 2/2003 | Wagner |
| 2003/0049616 A1 | 3/2003 | Brenner et al. |
| 2003/0077611 A1 | 4/2003 | Slepnev |
| 2003/0082818 A1 | 5/2003 | Bahnson et al. |
| 2003/0087242 A1 | 5/2003 | Mirkin et al. |
| 2003/0104436 A1 | 6/2003 | Morris et al. |
| 2003/0165935 A1 | 9/2003 | Vann et al. |
| 2003/0175908 A1 | 9/2003 | Linnarsson |
| 2003/0186251 A1 | 10/2003 | Dunn et al. |
| 2003/0207296 A1 | 11/2003 | Park et al. |
| 2003/0207300 A1 | 11/2003 | Matray et al. |
| 2004/0047769 A1 | 3/2004 | Tanaami |
| 2004/0091864 A1 | 5/2004 | French et al. |
| 2004/0096368 A1 | 5/2004 | Davis et al. |
| 2004/0096892 A1 | 5/2004 | Wang et al. |
| 2004/0121342 A1 | 6/2004 | McKeown |
| 2004/0146901 A1 | 7/2004 | Morris et al. |
| 2004/0147435 A1 | 7/2004 | Hawiger et al. |
| 2004/0157243 A1 | 8/2004 | Huang et al. |
| 2004/0209298 A1 | 10/2004 | Kamberov et al. |
| 2004/0224325 A1 | 11/2004 | Knapp et al. |
| 2004/0259118 A1 | 12/2004 | Macevicz |
| 2005/0019776 A1 | 1/2005 | Callow et al. |
| 2005/0032110 A1 | 2/2005 | Shen et al. |
| 2005/0048500 A1 | 3/2005 | Lawton |
| 2005/0053952 A1 | 3/2005 | Hong et al. |
| 2005/0105077 A1 | 5/2005 | Padmanabhan et al. |
| 2005/0170373 A1 | 8/2005 | Monforte |
| 2005/0175993 A1 | 8/2005 | Wei |
| 2005/0196760 A1 | 9/2005 | Pemov et al. |
| 2005/0214825 A1 | 9/2005 | Stuelpnagel |
| 2005/0250146 A1 | 11/2005 | McMillan |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0057634 A1 | 3/2006 | Rye |
| 2006/0073506 A1 | 4/2006 | Christians et al. |
| 2006/0211030 A1 | 9/2006 | Brenner |
| 2006/0257902 A1 | 11/2006 | Mendoza et al. |
| 2006/0263709 A1 | 11/2006 | Matsumura et al. |
| 2006/0263789 A1 | 11/2006 | Kincaid |
| 2006/0280352 A1 | 12/2006 | Muschler et al. |
| 2006/0281092 A1 | 12/2006 | Wille et al. |
| 2006/0286570 A1 | 12/2006 | Rowlen et al. |
| 2007/0020640 A1 | 1/2007 | Mccloskey et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0065823 A1 | 3/2007 | Dressman et al. |
| 2007/0065844 A1 | 3/2007 | Golub et al. |
| 2007/0105090 A1 | 5/2007 | Cassidy et al. |
| 2007/0117121 A1 | 5/2007 | Hutchison et al. |
| 2007/0117134 A1 | 5/2007 | Kou |

(56) References Cited

U.S. PATENT DOCUMENTS

| | | |
|---|---|---|
| 2007/0117177 A1 | 5/2007 | Luo et al. |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker et al. |
| 2007/0281317 A1 | 12/2007 | Becker et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0268508 A1 | 10/2008 | Sowlay |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053669 A1 | 2/2009 | Liu et al. |
| 2009/0061513 A1 | 3/2009 | Andersson Svahn et al. |
| 2009/0105959 A1 | 4/2009 | Braverman et al. |
| 2009/0131269 A1 | 5/2009 | Martin et al. |
| 2009/0137407 A1 | 5/2009 | Church et al. |
| 2009/0208936 A1 | 8/2009 | Tan et al. |
| 2009/0220385 A1 | 9/2009 | Brown et al. |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal et al. |
| 2009/0298709 A1 | 12/2009 | Ma |
| 2009/0311694 A1 | 12/2009 | Gallagher et al. |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |
| 2010/0255471 A1 | 10/2010 | Clarke |
| 2010/0267028 A1 | 10/2010 | Pasche |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2012/0004132 A1 | 1/2012 | Zhang et al. |
| 2012/0010091 A1 | 1/2012 | Linnarson |
| 2012/0014977 A1 | 1/2012 | Furihata et al. |
| 2012/0034607 A1 | 2/2012 | Rothberg et al. |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney et al. |
| 2012/0156675 A1 | 6/2012 | Lueerssen et al. |
| 2012/0163681 A1 | 6/2012 | Lohse |
| 2012/0165219 A1 | 6/2012 | Van Der Zaag et al. |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1 | 8/2013 | Buxbaum et al. |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0004569 A1 | 1/2014 | Lambowitz et al. |
| 2014/0057799 A1 | 2/2014 | Johnson et al. |
| 2014/0066318 A1 | 3/2014 | Frisen et al. |
| 2014/0147860 A1 | 5/2014 | Kaduchak et al. |
| 2014/0155274 A1 | 6/2014 | Xie et al. |
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski et al. |
| 2014/0206547 A1 | 7/2014 | Wang |
| 2014/0216128 A1 | 8/2014 | Trotter et al. |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0322716 A1 | 10/2014 | Robins |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005199 A1 | 1/2015 | Hindson et al. |
| 2015/0005200 A1 | 1/2015 | Hindson et al. |
| 2015/0011396 A1 | 1/2015 | Schroeder et al. |
| 2015/0017654 A1 | 1/2015 | Gorfinkel et al. |
| 2015/0066385 A1 | 3/2015 | Schnall-Levin et al. |
| 2015/0072867 A1 | 3/2015 | Soldatov et al. |
| 2015/0072873 A1 | 3/2015 | Heinz et al. |
| 2015/0080266 A1* | 3/2015 | Volkmuth ............ G16B 20/00 702/19 |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0152409 A1 | 6/2015 | Seitz et al. |
| 2015/0203897 A1 | 7/2015 | Robons et al. |
| 2015/0211050 A1 | 7/2015 | Iafrate et al. |
| 2015/0218620 A1 | 8/2015 | Behlke et al. |

(56) References Cited

U.S. PATENT DOCUMENTS

| | | |
|---|---|---|
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0253237 A1 | 9/2015 | Castellarnau et al. |
| 2015/0259734 A1 | 9/2015 | Asbury et al. |
| 2015/0275295 A1 | 10/2015 | Wang et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060621 A1 | 3/2016 | Agresti et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen et al. |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0153973 A1 | 6/2016 | Smith |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0265027 A1 | 9/2016 | Sanches-Kuiper et al. |
| 2016/0265069 A1 | 9/2016 | Fan et al. |
| 2016/0266094 A1 | 9/2016 | Ankrum et al. |
| 2016/0289669 A1 | 10/2016 | Fan et al. |
| 2016/0289670 A1 | 10/2016 | Samuels et al. |
| 2016/0298180 A1 | 10/2016 | Chee |
| 2016/0312276 A1 | 10/2016 | Fu et al. |
| 2016/0320720 A1 | 11/2016 | Murata et al. |
| 2016/0355879 A1 | 12/2016 | Kamberov et al. |
| 2016/0362730 A1 | 12/2016 | Alexander et al. |
| 2017/0044525 A1 | 2/2017 | Kaper et al. |
| 2017/0136458 A1 | 5/2017 | Dunne et al. |
| 2017/0154421 A1 | 6/2017 | Fu et al. |
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0016634 A1 | 1/2018 | Hindson et al. |
| 2018/0024139 A1 | 1/2018 | Peikon et al. |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0088112 A1 | 3/2018 | Fan et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Larson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0216174 A1 | 8/2018 | Shum et al. |
| 2018/0230527 A1 | 8/2018 | Fang et al. |
| 2018/0251825 A1 | 9/2018 | Stoeckius et al. |
| 2018/0258482 A1 | 9/2018 | Hindson et al. |
| 2018/0276332 A1 | 9/2018 | Fan et al. |
| 2018/0282803 A1 | 10/2018 | Belgrader et al. |
| 2018/0002738 A1 | 11/2018 | Wang et al. |
| 2018/0320241 A1 | 11/2018 | Nolan et al. |
| 2018/0340170 A1 | 11/2018 | Belhocine et al. |
| 2018/0346969 A1 | 12/2018 | Chang et al. |
| 2018/0346970 A1 | 12/2018 | Chang et al. |
| 2018/0371536 A1 | 12/2018 | Fu et al. |
| 2019/0010552 A1 | 1/2019 | Xu et al. |
| 2019/0025304 A1 | 1/2019 | Vigneault et al. |
| 2019/0032129 A1 | 1/2019 | Hindson et al. |
| 2019/0095578 A1 | 3/2019 | Shum et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0161743 A1 | 5/2019 | Church et al. |
| 2019/0177788 A1 | 6/2019 | Hindson et al. |
| 2019/0177800 A1 | 6/2019 | Boutet et al. |
| 2019/0203270 A1 | 7/2019 | Amit et al. |
| 2019/0203291 A1 | 7/2019 | Hindson et al. |
| 2019/0211395 A1 | 7/2019 | Tsao et al. |
| 2019/0218276 A1 | 7/2019 | Regev et al. |
| 2019/0218607 A1 | 7/2019 | Love et al. |
| 2019/0221287 A1 | 7/2019 | Tsujimoto |
| 2019/0221292 A1 | 7/2019 | Tsujimoto |
| 2019/0256888 A1 | 8/2019 | Weissleder et al. |
| 2019/0256907 A1 | 8/2019 | Ryan et al. |
| 2019/0292592 A1 | 9/2019 | Shum et al. |
| 2019/0338353 A1 | 11/2019 | Belgrader et al. |
| 2019/0338357 A1 | 11/2019 | Fan et al. |
| 2019/0390253 A1 | 12/2019 | Kennedy et al. |
| 2020/0102598 A1 | 4/2020 | Xie et al. |
| 2020/0109437 A1 | 4/2020 | Chang et al. |
| 2020/0115753 A1 | 4/2020 | Shalek et al. |
| 2020/0149037 A1 | 5/2020 | Shum |
| 2021/0039582 A1 | 2/2021 | Patton et al. |
| 2021/0123044 A1 | 4/2021 | Zhang et al. |
| 2021/0132078 A1 | 5/2021 | Peikon et al. |
| 2021/0198754 A1 | 7/2021 | Fan et al. |
| 2021/0213413 A1 | 7/2021 | Saligrama et al. |
| 2021/0214770 A1 | 7/2021 | Prosen et al. |
| 2021/0214784 A1 | 7/2021 | Prosen et al. |
| 2021/0222163 A1 | 7/2021 | Wu et al. |
| 2021/0222244 A1 | 7/2021 | Martin et al. |
| 2021/0230582 A1 | 7/2021 | Fu et al. |
| 2021/0230583 A1 | 7/2021 | Lam et al. |
| 2021/0230666 A1 | 7/2021 | Wu et al. |
| 2021/0246492 A1 | 8/2021 | Song et al. |
| 2021/0263019 A1 | 8/2021 | Martin et al. |
| 2021/0355484 A1 | 11/2021 | Jensen et al. |
| 2021/0371909 A1 | 12/2021 | Lazaruk |
| 2021/0371914 A1 | 12/2021 | Stoeckius et al. |
| 2022/0010361 A1 | 1/2022 | Song et al. |
| 2022/0010362 A1 | 1/2022 | Campbell |
| 2022/0033810 A1 | 2/2022 | Song et al. |
| 2022/0154288 A1 | 5/2022 | Mortimer |
| 2022/0162695 A1 | 5/2022 | Sakofsky et al. |
| 2022/0162773 A1 | 5/2022 | Sakofsky et al. |
| 2022/0178909 A1 | 6/2022 | Huang et al. |
| 2022/0214356 A1 | 7/2022 | Henikoff et al. |
| 2022/0219170 A1 | 7/2022 | Khurana et al. |
| 2022/0220549 A1 | 7/2022 | Shum et al. |
| 2022/0267759 A1 | 8/2022 | Sanjana et al. |
| 2022/0333185 A1 | 10/2022 | Fu et al. |
| 2022/0348904 A1 | 11/2022 | Shum et al. |
| 2023/0083422 A1 | 3/2023 | Fu et al. |
| 2023/0109336 A1 | 4/2023 | Shum et al. |
| 2023/0125113 A1 | 4/2023 | Fan et al. |
| 2023/0193372 A1 | 6/2023 | Shum et al. |

FOREIGN PATENT DOCUMENTS

| | | |
|---|---|---|
| CN | 106460033 A | 2/2017 |
| CN | 107208158 A | 9/2017 |
| DE | 102008025656 | 12/2009 |
| EP | 1473080 | 11/2004 |
| EP | 1647600 | 4/2006 |

(56) References Cited

FOREIGN PATENT DOCUMENTS

| | | |
|---|---|---|
| EP | 1845160 | 10/2007 |
| EP | 2036989 | 3/2009 |
| EP | 1379693 | 5/2009 |
| EP | 2204456 | 7/2010 |
| EP | 2431465 | 3/2012 |
| EP | 2203749 | 8/2012 |
| EP | 2511708 | 10/2012 |
| EP | 2538220 | 12/2012 |
| EP | 2623613 | 8/2013 |
| EP | 1745155 | 10/2014 |
| EP | 2805769 | 11/2014 |
| EP | 2556171 | 9/2015 |
| EP | 2970958 | 12/2017 |
| EP | 3263715 | 1/2018 |
| EP | 2670863 B1 | 6/2018 |
| EP | 3136103 | 8/2018 |
| EP | 2954102 | 12/2018 |
| EP | 3428290 | 1/2019 |
| EP | 2970957 | 4/2019 |
| EP | 3058092 | 5/2019 |
| EP | 3256606 | 5/2019 |
| EP | 3327123 | 8/2019 |
| GB | 2293238 A | 3/1996 |
| JP | H04108385 | 4/1992 |
| JP | 2001078768 A | 3/2001 |
| JP | 2002253237 | 9/2002 |
| JP | 2005233974 | 9/2005 |
| JP | 2007504831 | 3/2007 |
| JP | 2008256428 | 10/2008 |
| JP | 2013039275 | 2/2013 |
| JP | 2018509896 A | 4/2018 |
| WO | WO1989001050 | 2/1989 |
| WO | WO1996024061 | 8/1996 |
| WO | WO1997010365 | 3/1997 |
| WO | WO1999015702 | 4/1999 |
| WO | WO1999028505 | 6/1999 |
| WO | WO2000058516 | 10/2000 |
| WO | WO2001020035 | 3/2001 |
| WO | WO2001048242 | 7/2001 |
| WO | WO2001053539 | 7/2001 |
| WO | WO2002018643 | 3/2002 |
| WO | WO2002046472 | 6/2002 |
| WO | WO2002056014 | 7/2002 |
| WO | WO2002059355 | 8/2002 |
| WO | WO2002070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003031591 | 4/2003 |
| WO | WO2003035829 | 5/2003 |
| WO | WO2004017374 | 2/2004 |
| WO | WO2004021986 | 3/2004 |
| WO | WO2004033669 | 4/2004 |
| WO | WO2004066185 | 8/2004 |
| WO | WO2004081225 | 9/2004 |
| WO | WO2005017206 | 2/2005 |
| WO | WO2005021731 | 3/2005 |
| WO | WO2005042759 | 5/2005 |
| WO | WO2005071110 | 8/2005 |
| WO | WO2005080604 | 9/2005 |
| WO | WO2005111242 | 11/2005 |
| WO | WO2005111243 | 11/2005 |
| WO | WO2006026828 | 3/2006 |
| WO | WO2006071776 | 7/2006 |
| WO | WO2006102264 | 9/2006 |
| WO | WO2006137932 | 12/2006 |
| WO | WO2007087310 | 8/2007 |
| WO | WO2007087312 | 8/2007 |
| WO | WO2007147079 | 12/2007 |
| WO | WO2008047428 | 4/2008 |
| WO | WO2008051928 | 5/2008 |
| WO | WO2008057163 | 5/2008 |
| WO | WO2008096318 | 8/2008 |
| WO | WO2008104380 | 9/2008 |
| WO | WO2008147428 | 12/2008 |
| WO | WO2008150432 | 12/2008 |
| WO | WO2009048530 | 4/2009 |
| WO | WO2009148560 | 12/2009 |
| WO | WO2009152928 | 12/2009 |
| WO | WO2010048605 | 4/2010 |
| WO | WO2010059820 | 5/2010 |
| WO | WO2010117620 | 10/2010 |
| WO | WO2010131645 | 11/2010 |
| WO | WO2011091393 | 7/2011 |
| WO | WO2011106738 | 9/2011 |
| WO | WO2011123246 | 10/2011 |
| WO | WO2011127099 | 10/2011 |
| WO | WO2011143659 | 11/2011 |
| WO | WO2011155833 | 12/2011 |
| WO | WO2012038839 | 3/2012 |
| WO | WO2012041802 | 4/2012 |
| WO | WO2012042374 | 4/2012 |
| WO | WO2012047297 | 4/2012 |
| WO | WO2012048341 | 4/2012 |
| WO | WO2012083225 | 6/2012 |
| WO | WO2012099896 | 7/2012 |
| WO | WO2012103154 | 8/2012 |
| WO | WO2012106385 | 8/2012 |
| WO | WO2012106546 | 8/2012 |
| WO | WO2012108864 | 8/2012 |
| WO | WO2012112804 | 8/2012 |
| WO | WO2012129363 | 9/2012 |
| WO | WO2012140224 | 10/2012 |
| WO | WO2012142213 | 10/2012 |
| WO | WO2012148477 | 11/2012 |
| WO | WO2012148497 | 11/2012 |
| WO | WO2012149042 | 11/2012 |
| WO | WO2012156744 | 11/2012 |
| WO | WO2012162267 | 11/2012 |
| WO | WO2012177639 | 12/2012 |
| WO | WO2013019075 | 2/2013 |
| WO | WO2013070990 | 5/2013 |
| WO | WO2013096802 | 6/2013 |
| WO | WO2013117595 | 8/2013 |
| WO | WO2013130674 | 9/2013 |
| WO | WO2013137737 | 9/2013 |
| WO | WO2013148525 | 10/2013 |
| WO | WO2013173394 | 11/2013 |
| WO | WO2013176767 | 11/2013 |
| WO | WO2013177206 | 11/2013 |
| WO | WO2013188831 | 12/2013 |
| WO | WO2013188872 | 12/2013 |
| WO | WO2013191775 | 12/2013 |
| WO | WO2014015084 | 1/2014 |
| WO | WO2014015098 | 1/2014 |
| WO | WO2014018093 | 1/2014 |
| WO | WO2014018460 | 1/2014 |
| WO | WO2014028537 | 2/2014 |
| WO | WO2014031997 | 2/2014 |
| WO | WO2014065756 | 5/2014 |
| WO | WO2014093676 | 6/2014 |
| WO | WO2014108850 | 7/2014 |
| WO | WO2014124046 | 8/2014 |
| WO | WO2014124336 | 8/2014 |
| WO | WO2014124338 | 8/2014 |
| WO | WO2014126937 | 8/2014 |
| WO | WO2014144495 | 9/2014 |
| WO | WO2014145458 | 9/2014 |
| WO | WO2014176575 | 10/2014 |
| WO | WO2014200767 | 12/2014 |
| WO | WO2014201273 | 12/2014 |
| WO | WO2014204939 | 12/2014 |
| WO | WO2014210223 | 12/2014 |
| WO | WO2014210225 | 12/2014 |
| WO | WO2014210353 | 12/2014 |
| WO | WO2015002908 | 1/2015 |
| WO | WO2018015365 | 1/2015 |
| WO | WO2015017586 | 2/2015 |
| WO | WO2015031691 | 3/2015 |
| WO | WO2015035087 | 3/2015 |
| WO | WO2015044428 | 4/2015 |
| WO | WO2015047186 | 4/2015 |
| WO | WO2015057985 | 4/2015 |

(56) References Cited

FOREIGN PATENT DOCUMENTS

| | | |
|---|---|---|
| WO | WO2014071361 | 5/2015 |
| WO | WO2015061844 | 5/2015 |
| WO | WO2015103339 | 7/2015 |
| WO | WO2015117163 | 8/2015 |
| WO | WO2015134787 | 9/2015 |
| WO | WO2015160439 | 10/2015 |
| WO | WO2015168161 | 11/2015 |
| WO | WO2015179339 | 11/2015 |
| WO | WO2015200869 | 12/2015 |
| WO | WO2015200893 | 12/2015 |
| WO | WO2016044227 | 3/2016 |
| WO | WO2016049418 | 3/2016 |
| WO | WO2016061517 | 4/2016 |
| WO | WO2016100976 | 6/2016 |
| WO | WO2016118915 | 7/2016 |
| WO | WO2016126871 | 8/2016 |
| WO | WO2016130578 | 8/2016 |
| WO | WO2016160965 | 8/2016 |
| WO | WO2016138496 | 9/2016 |
| WO | WO2016138500 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016172373 | 10/2016 |
| WO | WO2016176091 | 11/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017087873 | 5/2017 |
| WO | WO2017096239 | 6/2017 |
| WO | WO2017097939 | 6/2017 |
| WO | WO2017117358 | 7/2017 |
| WO | WO2017125508 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018017949 | 1/2018 |
| WO | WO2018018008 | 1/2018 |
| WO | WO2018020489 | 2/2018 |
| WO | WO2018031631 | 2/2018 |
| WO | WO2018058073 | 3/2018 |
| WO | WO2018064640 | 4/2018 |
| WO | WO2018075693 | 4/2018 |
| WO | WO2018111872 | 6/2018 |
| WO | WO2018115852 | 6/2018 |
| WO | WO2018119447 | 6/2018 |
| WO | WO2018132635 | 7/2018 |
| WO | WO2018140966 | 8/2018 |
| WO | WO2018144240 | 8/2018 |
| WO | WO2018144813 | 8/2018 |
| WO | WO2018174827 | 9/2018 |
| WO | WO2018217862 | 11/2018 |
| WO | WO2018218222 | 11/2018 |
| WO | WO2018222548 | 12/2018 |
| WO | WO2018226293 | 12/2018 |
| WO | WO2019055852 | 3/2019 |
| WO | WO2019076768 | 4/2019 |
| WO | WO2019084046 | 5/2019 |
| WO | WO2019099906 | 5/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |
| WO | WO2019178164 | 9/2019 |
| WO | WO2019213237 | 11/2019 |
| WO | WO2019213294 | 11/2019 |
| WO | WO2019218101 | 11/2019 |
| WO | WO2020028266 | 2/2020 |
| WO | WO2020033164 | 2/2020 |
| WO | WO2020037065 | 2/2020 |
| WO | WO2020046833 | 3/2020 |
| WO | WO2020072380 | 4/2020 |
| WO | WO2020097315 | 5/2020 |
| WO | WO2020123384 | 6/2020 |
| WO | WO2020131699 | 6/2020 |
| WO | WO2020154247 | 7/2020 |
| WO | WO2020159757 | 8/2020 |
| WO | WO2020167920 | 8/2020 |
| WO | WO2020214642 | 10/2020 |
| WO | WO2020219721 | 10/2020 |
| WO | WO2020242377 | 12/2020 |
| WO | WO2021092386 | 5/2021 |
| WO | WO2021142233 | 7/2021 |
| WO | WO2021146207 | 7/2021 |
| WO | WO2021146219 | 7/2021 |
| WO | WO2021146636 | 7/2021 |
| WO | WO2021155057 | 8/2021 |
| WO | WO2021155284 | 8/2021 |
| WO | WO2021163374 | 8/2021 |
| WO | WO2021168015 | 8/2021 |
| WO | WO2021168261 | 8/2021 |
| WO | WO2021178199 | 9/2021 |
| WO | WO2021247593 | 12/2021 |
| WO | WO2022015667 | 1/2022 |
| WO | WO2022026909 | 2/2022 |
| WO | WO2022040453 | 2/2022 |
| WO | WO2022143221 | 7/2022 |
| WO | WO2022256324 | 12/2022 |
| WO | WO2023034739 | 3/2023 |
| WO | WO2023034789 | 3/2023 |
| WO | WO2023034790 | 3/2023 |
| WO | WO2023034794 | 3/2023 |
| WO | WO2023034872 | 3/2023 |
| WO | WO2023039433 | 3/2023 |

OTHER PUBLICATIONS

Examination Report dated Sep. 21, 2020 in European Patent Application No. 18703156.2.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
International Search Report and Written Opinion dated May 18, 2020 in PCT Application No. PCT/US2020/014339.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Notice of Allowance dated Sep. 23, 2020 in Korean Patent Application No. 10-2016-7008144.
Notice of Allowance dated Oct. 29, 2020 in U.S. Appl. No. 15/987,851.
Office Action dated Oct. 29, 2020 in Chinese Patent Application No. 2018800377201.
Search Report and Written Opinion dated Aug. 26, 2020 in Singapore Patent Application No. 10201806890V.
10X Genomics, Inc., 2019, User Guide: Visium Spatial Gene Expression Reagent Kits, www.10xGenomics.com, 76 pp.
2018 Top 10 Innovations, The Scientist Magazine® (2018). Available at: https://www.thescientist.com/features/2018-top-10-innovations-65140, 16 pp.
Achim et al., "High-throughput spatial mapping of single-cell RNA-seq data to tissue of origin," Nature Biotechnology 2015, 33(5), 503-511.
Advisory Action dated Nov. 29, 2019 in U.S. Appl. No. 15/084,307.
Advisory Action dated Dec. 2, 2019 in U.S. Appl. No. 15/055,407.
Advisory Action dated Aug. 25, 2020 in U.S. Appl. No. 15/084,307.
Agasti et al., "Photocleavable DNA barcode-antibody conjugates allow sensitive and multiplexed protein analysis in single cell," J Am Chem Soc. 2012, 134(45), 18499-18502.

(56) References Cited

OTHER PUBLICATIONS

Alexandra M. Ewing of Richards, Layton and Finger, P.A., Entry of Appearance dated Jan. 18, 2019 in the USDC District of Delaware, C.A. No. 18-1800-RGA, 1 pp.
Alkan et al., "Personalized copy number and segmental duplication maps using next-generation sequencing," Nat Genet. 2009, 41(10):1061-1067.
Anderson, "Study Describes RNA Sequencing Applications for Molecular Indexing Methods," GenomeWeb 2014, 5 pp.
Ansorge, "Next-generation DNA sequencing techniques," New Biotechnology 2009, 25(4), 195-203.
Applied Biosystems, Apr. 2008, SOLiD™ System Barcoding, Application Note, 4 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Atanur et al., "The genome sequence of the spontaneously hypertensive rat: Analysis and functional significance." Genome Res. 2010, 20(6), 791-803.
Audic et al., "The Significance of Digital Gene Expression Profiles," Genome Res. 1997, 7, 986-995.
Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Bendall et al., "Single-Cell Mass Cytometry of Differential Immune and Drug Responses Across a Human Hematopoietic Continuum," Science 2011, 332(6030), 687-696.
Bionumbers, "Useful fundamental numbers in molecular biology," http://bionumbers.hms.harvard.edu/KeyNumbers/aspx, 1-4.
Biosciences Product Catalogue, Dynal® Catalog 1999, Oslo, Norway, 49-51.
Bioscribe "Massively parallel sequencing technology for single-cell gene expression published" (press release), PhysOrg 2015, 1-2.
Blainey, "The future is now: single-cell genomics of bacteria and archaea," FEMS Microbiol Rev. 2013, 37(3), 407-427.
Bogdanova et al., "Normalization of full-length enriched cDNA," Molecular Biosystems 2008, 4(3), 205-212.
Bonaldo et al., "Normalization and Subtraction: Two Approaches to facilitate Gene Discovery," Genome Res. 1996, 6, 791-806.
Bontoux et al., "Integrating whole transcriptome assays on a lab-on-a-chip for single cell gene profiling", Lab on a Chip 2008, 8(3), 443-450.
Bose et al., "Scalable microfluidics for single-cell RNA printing and sequencing," Genome Biology 2015, 16(120), 1-16.
Brady et al., "Construction of cDNA libraries form single cells", Methods in Enzymology 1993, (225), 611-623.
Braha et al., "Simultaneous stochastic sensing of divalent metal ions," Nature Biotechnology 2000, 18, 1005-1007.
Bratke et al., "Differential expression of human granzymes A, B, and K in natural killer cells and during CD8+ T cell differentiation in peripheral blood," Eur J Immunol. 2005, 35, 2608-2616.
Brenner et al., "Gene expression analysis by massively parallel signature sequencing (MPSS) on microbead arrays," Nature Biotechnology 2000, 18, 630-634.
Brenner et al., "In vitro cloning of complex mixtures of DNA on microbeads: Physical separation of differentially expressed cDNAs," PNAS 2000, 97(4), 1665-1670.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Brisco et al., "Quantification of RNA integrity and its use for measurement of transcript number," Nucleic Acids Research 2012, 40(18), e144, 1-9.
Brodin et al., "Challenges with Using Primer IDs to Improve Accuracy of Next Generation Sequencing," PLoS One 2015, 19(3), 1-12.
Buggenum et al., "A covalent and cleavable antibody DNA conjugation strategy for sensitive protein detection via immunoPCR," Scientific Reports 2016, 6(22675), 1-12.
Buschmann et al., Enhancing the detection of barcoded reads in high throughput DNA sequencing DNA by controlling the false discovery rate, BMC Bioinformatics, 15(1), 264, 1-16.
Bustin, "Absolute quantification of mRNA using real-time reverse transcription polymerase chain reaction assays," Journal of Molecular Endocrinology 2000, 25, 169-193.
Butkus, "Cellular research set to launch first gene expression platform using 'molecular indexing' technology," GenomeWeb 2014, 1-5.
Cai, "Turning single cells in microarrays by super-resolution barcoding," Briefings in Functional Genomics 2012, 12(2), 75-80.
Cao et al., "Comprehensive single-cell transcriptional profiling of a multicellular organism," Science 2017, 357, 661-667.
Carr et al., "Inferring relative proportions of DNA variants from sequencing electropherograms," Bioinformatics 2009, 25(24), 3244-3250.
Caruccio et al., "Nextera (TM) Technology for NGS DNA Library Preparation: Simultaneous Fragmentation and Tagging by in Vitro Transposition," EpiBio 2009, 16(3), 4-6.
Casbon et al., "A method for counting PCR template molecules with application to next-generation sequencing," Nucleic Acids Res. 2011, 39(12), e81, 1-8.
Castellarnau et al., "Stochastic particle barcoding for single-cell tracking and multiparametric analysis," Small 2015, 11(4), 489-498.
Castle et al., "DNA copy number, including telomeres and mitochondria, assayed using next-generation sequencing," BMC Genomics 2010, 11(244), 1-11.
Chamberlain et al., "Deletion screening of the Duchenne muscular dystrophy locus via multiplex DNA amplification," Nucleic Acids Res. 1988, 16(23), 11141-11156.
Chang et al., "Detection of Allelic Imbalance in Ascitic Supernatant by Digital Single Nucleotide Polymorphism Analysis," Clinical Cancer Research, 8, 2580-2585.
Chapin et al., "Rapid microRNA Profiling on Encoded Gel Microparticles," Angew Chem Int Ed Engl. 2011, 50(10), 2289-2293.
Chee et al., "Accessing genetic information with high-density DNA arrays," Science 1996, 274, 610-614.
Chee, "Enzymatic multiplex DNA sequencing," Nucleic Acids Research 1991, 19(12), 3301-3305.
Chen et al., "Spatially resolved, highly multiplexed RNA profiling in single cells," Science Express 2015, 348(6233), aaa6090, 1-36.
Church et al., "Multiplex DNA sequencing," Science 1988, 240(4849), 185-188.
Civil Cover Sheet filed Nov. 15, 2018 in the USDC for the District of Delaware, C.A. 18-1800-RGA, 1 pp.
Clontech Laboratories, Inc., "SMART™ PCR cDNA Synthesis Kit User Manual," Clontech 2007, 1-39.
Cloonan et al., "Stem cell transcriptome profiling via massive-scale mRNA sequencing", Nature Methods 2008, 5(7), 613-619.
Combined Search and Examination Report dated Aug. 6, 2014 in UK Patent Application No. 1408829.8.
Combined Search and Examination Report dated Feb. 21, 2017 in UK Patent Application No. 1609740.4.
Communication of a Notice of Opposition dated Jul. 21, 2016 in European Patent Application No. EP 10762102.1.
Complaint filed in *Becton, Dickinson and Company and Cellular Research Inc. v. 10X Genomics, Inc.* dated Nov. 15, 2018 in the USDC for the District of Delaware, C.A. 18-1800-RGA, 141 pp.
Costa et al., "Single-Tube Nested Real-Time PCR as a New Highly Sensitive Approach to Trace Hazelnut," Journal of Agricultural and Food Chemistry 2012, 60, 8103-8110.

(56) References Cited

OTHER PUBLICATIONS

Costello et al., "Discovery and characterization of artefactual mutations in deep coverage targeted capture sequencing data due to oxidative DNA damage during sample preparation," Nucleic Acids Res 2013, 41(6), e67, 1-12.
Cotten et al., "Selection of proteins with desired properties from natural proteome libraries using mRNA display," Nature Protocols 2011, 6, 1163-1182.
Cox, "Bar coding objects with DNA," Analyst 2001, 126, 545-547.
Craig et al., "Identification of genetic variants using bar-coded multiplexed sequencing," Nat Methods 2008, 5(10), 887-893.
Cusanovich et al., "Multiplex single-cell profiling of chromatin accessibility by combinatorial cellular indexing," Science 2015, 348(6237), 910-914.
Custom Antibody Services, Precision Antibody, accessed Apr. 16, 2014, 2 pp.
Daines et al., "High-throughput multiplex sequencing to discover copy number variants in *Drosophila*," Genetics 2009, 182(4), 182, 935-941.
Dalerba et al., "Single-cell dissection of transcriptional heterogeneity in human colon tumors," Nat Biotechnol. 2011, 29(12), 1120-1127.
D'Antoni et al., "Rapid quantitative analysis using a single molecule counting approach," Anal Biochem. 2006, 352, 97-109.
Daser et al., "Interrogation of genomes by molecular copy-number counting (MCC)," Nature Methods 2006, 3(6), 447-453.
Day et al., "Immobilization of polynucleotides on magnetic particles," Biochem. J. 1991, 278, 735-740.
Decision of Refusal dated Aug. 21, 2017 in Japanese Patent Application No. 2014-558975.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomic's Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Defendant 10X Genomic's Notice of Service for Initial Disclosures served to Opposing Counsel, dated Jun. 7, 2019 in the USDC for the District of Delaware, C.A. 18-1800-RGA, 2 pp.
Defendant 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomic's Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant 10X Genomic's Request for Oral Argument Under D. Del. LR 7.1.4, dated Apr. 18, 2019 in the USDC for the District of Delaware, C.A. 18-1800-RGA 2 pp.
Defendant 10X Genomic's Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.
Delley et al., "Combined aptamer and transcriptome sequencing of single cells," bioRxiv 2017, 1-10.
De Saizieu et al., "Bacterial transcript imaging by hybridization of total RNA to oligonucleotide arrays," Nature Biotechnology 1988, 16, 45-48.
Di Carlo et al., "Dynamic single-cell analysis for quantitative biology," Analytical Chemistry 2006, 78(23), 7918-7925.
Dirks et al., Triggered amplification by hybridization chain reaction., Proc Natl Acad Sci 2014, 101(43), 15275-15278.
Dube et al., "Mathematical Analysis of Copy Number Variation in a DNA Sample Using Digital PCR on a Nanofluidic Device," PLoS One 2008, 3(8) e2876.
Eberwine et al., "Analysis of gene expression in single live neurons," Proc. Natl. Acad. Sci. 1992, 89, 3010-3014.
Evanko et al., "Hybridization chain reaction," Nature Methods 2004, 1(3), 186-187.
Examination Report dated Oct. 24, 2017 in Australian Patent Application No. 2013226081.
Examination Report dated Jul. 20, 2018 in Australian Patent Application No. 2014312208.
Examination Report dated May 12, 2020 in Australian Patent Application No. 2018220004.
Examination Report dated Jul. 12, 2016 in European Patent Application No. 13755319.4.
Examination Report dated Apr. 10, 2017 in European Patent Application No. 14761937.3.
Examination Report dated Oct. 10, 2017 in European Patent Application No. 14761937.3.
Examination Report dated Mar. 16, 2018 in European Patent Application No. 13754428.4.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.

(56) References Cited

OTHER PUBLICATIONS

Examination Report dated Jul. 6, 2020 in European Patent Application No. 17781265.8.
Examination Report dated Mar. 18, 2019 in Singapore Patent Application No. 11201405274W.
Examination Report dated Jan. 27, 2016 in United Kingdom Patent Application No. 1408829.8.
Examination Report dated Feb. 19, 2016 in United Kingdom Patent Application No. GB1511591.8.
Examination Report dated Jun. 8, 2016 in United Kingdom Patent Application No. 1408829.8.
Examination Report dated Jun. 15, 2016 in United Kingdom Patent Application No. GB1511591.8.
Examination Report dated Jan. 3, 2018 in United Kingdom Patent Application No. 1609740.4.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Jul. 17, 2015 in European Patent Application No. 13755319.4.
Extended European Search Report dated Dec. 14, 2015 in European Patent Application No. 13754428.4.
Extended European Search Report dated Feb. 8, 2018 in European Patent Application No. 17202409.3.
Extended European Search Report dated Jun. 11, 2018 in European Patent Application No. 16740872.3.
Extended European Search Report dated Mar. 22, 2019 in European Patent Application No. 18195513.9.
Fan et al., "Parallel Genotyping of Human SNPs Using Generic High-density Oligonucleotide Tag Arrays," Genome Research 2000, 10, 853-860.
Fan et al., "Microfluidic digital PCR enables rapid prenatal diagnosis of fetal aneuploidy," Am Obstet Gynecol. 2009, 200, 543e1-543e7.
Fan, "Molecular counting: from noninvasive prenatal diagnostics to whole-genome haplotyping," Doctoral Dissertation, Stanford University 2010, 1-185.
Fan et al., "Non-invasive Prenatal Measurement of the Fetal Genome," Nature 2012, 487(7407), 320-324.
Fan et al., "Combinatorial labeling of single cells for gene expression cytometry," Science 2015, 347(6222), 1258366-1258369.
Feldhaus et al., "Oligonucleotide-conjugated beads for transdominant genetic experiments," Nucleic Acids Res. 2000, 28(2), 534-543.
Final Office Action dated Sep. 1, 2015 for U.S. Appl. No. 14/540,029.
Final Office Action dated Sep. 24, 2015 for U.S. Appl. No. 14/540,007.
Final Office Action dated Oct. 6, 2015 in U.S. Appl. No. 14/540,018.
Final Office Action dated Apr. 11, 2016 for U.S. Appl. No. 14/800,526.
Final Office Action dated Jul. 20, 2016 for U.S. Appl. No. 14/281,706.
Final Office Action dated Aug. 12, 2016 in U.S. Appl. No. 14/381,488.
Final Office Action dated Feb. 13, 2017 in U.S. Appl. No. 14/381,488.
Final Office Action dated May 8, 2017 in U.S. Appl. No. 15/224,460.
Final Office Action dated Oct. 16, 2017 in U.S. Appl. No. 15/409,355.
Final Office Action dated Nov. 16, 2017 in U.S. Appl. No. 14/381,488.
Final Office Action dated Jan. 25, 2018 in U.S. Appl. No. 14/381,526.
Final Office Action dated May 3, 2018 in U.S. Appl. No. 15/046,225.
Final Office Action dated May 10, 2018 in U.S. Appl. No. 14/381,488.
Final Office Action dated Jul. 5, 2018 in U.S. Appl. No. 15/004,618.
Final Office Action dated Jul. 20, 2018 in U.S. Appl. No. 15/217,886.
Final Office Action dated Nov. 16, 2018 in U.S. Appl. No. 15/134,967.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.
Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Apr. 28, 2020 in U.S. Appl. No. 15/134,967.
Final Office Action dated Jun. 5, 2020 in U.S. Appl. No. 15/084,307.
Final Office Action dated Aug. 19, 2020 in U.S. Appl. No. 15/875,816.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.
Fox-Walsh et al., "A multiplex RNA-seq strategy to profile poly(A+) RNA: application to analysis of transcription response and 3' end formation," Genomics 2011, 98, 266-721.
Fu et al., "Counting individual DNA molecules by the stochastic attachment of diverse labels," Proc Natl Acad Sci 2011, 108(22), 9026-9031.
Fu et al., Digital Encoding of Cellular mRNAs Enabling Precise and Absolute Gene Expression Measurement by Single-Molecule Counting. Anal Chem. 2014, 86, 2867-2870.
Fu et al., "Molecular indexing enables quantitative targeted RNA sequencing and reveals poor efficiencies in standard library preparation," PNAS 2014, 111(5), 1891-1896.
Gerry et al., "Universal DNA Microarray Method for Multiplex Detection of Low Abundance Point Mutations," Journal of Molecular Biology 1999, 292, 251-262.
Gillespie, "Exact Stochastic Simulation of Coupled Chemical Reactions," Journal of Physical Chemistry 1977, 81(25), 2340-2361.
Gong et al., "Massively parallel detection of gene expression in single cells using subnanolitre wells," Lab Chip 2010, 10, 2334-2337.
Gong et al., "Simple Method Prepare Oligonucleotide-Conjugated Antibodies and Its Application in Multiplex Protein Detection in Single Cells," Bioconjugate Chem. 2016, 27, 217-225.
Grant et al., "SNP genotyping on a genome-wide amplified DOP-PCR template," Nucleic Acids Res 2002, 30(22), e25, 1-6.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications," Genome Biology 2016, 17(41) 1-13.
Gunderson et al., "Decoding Randomly Ordered DNA Arrays," Genome Research 2004, 14, 870-877.
Gundry et al., "Direct, genome-wide assessment of DNA mutations in single cells," Nucleic Acids Research 2011, 40(5), 2032-2040.
Gundry et al., "Direct mutation analysis by high-throughput sequencing: from germline to low-abundant, somatic variants," Mutat Res. 2012, 729(1-2), 1-15.
Hacia et al., "Determination of ancestral alleles for human single-nucleotide polymorphisms using high-density oligonucleotide arrays," Nature Genetics 1999, 22, 164-167.
Haff, "Improved Quantitative PCR Using Nested Primers," PCR Methods and Applications 1994, 3, 332-337.
Hamady et al., "Error-correcting barcoded primers for pyrosequencing hundreds of samples in multiplex," Nat Methods 2008, 5(3), 235-237.
Han et al., "An approach to multiplexing an immunosorbent assay with antibody-oligonucleotide conjugates," Bioconjug Chem. 2010, 21(12), 2190-2196.
Harbers, "The current status of cDNA cloning," Genomics 2008, 91, 232-242.

(56) References Cited

OTHER PUBLICATIONS

Harrington et al., Cross-sectional characterization of HIV-1 env compartmentalization in cerebrospinal fluid over the full disease course, AIDS 2009, 23(8), 907-915.
Hartmann, "Gene expression profiling of single cells on large-scale oligonucleotide arrays", Nucleic Acids Research, (Oct. 2006) vol. 34, No. 21, p. e143, 1-12.
Hashimshony et al., "CEL-Seq: Single-Cell RNA-Seq by Multiplexed Linear Amplification," Cell Rep. 2012, 2(3), 666-673.
Hensel et al., "Simultaneous identification of bacterial virulence genes by negative selection," Science 1995, 269(5222), 400-403.
Hiatt et al., "Parallel, tag-directed assembly of locally derived short sequence reads," Nat Methods 2010, 7(2), 119-122.
Hiatt et al., "Single molecule molecular inversion probes for targeted, high-accuracy detection of low-frequency variation," Genome Res. 2013, 23(5), 843-854.
Holcomb et al., "Abstract 1853: Single-cell multiplexed profiling of protein-level changes induced by EGFR inhibitor gefitinib," Cancer Res 2016, 76(14 Suppl), Abstract 1853.
Hollas et al., "A stochastic approach to count RNA molecules using DNA sequencing methods," Algorithms in Bioinformatics. WABI 2003, Lecture Notes in Computer Science, 2812, 55-62.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
Hug et al., Measure of the Number of Molecular of a Single mRNA Species in a Complex mRNA Preparation, Journal of Theoretical Biology 2003, 221, 615-624.
Ingolia et al., Genome-Wide Analysis in Vivo of Translation with Nucleotide Resolution Using Ribosome Profiling, Science 2009, 324(5924), 218-223.
International Preliminary Report on Patentability dated Mar. 26, 2019 in PCT Application No. PCT/US2017/053331.
International Preliminary Report on Patentability dated Aug. 15, 2019 in PCT Application No. PCT/US2018/014385.
International Search Report and Written Opinion dated May 7, 2012 for PCT Application No. PCT/IB2011/003160.
International Search Report and Written Opinion dated Jun. 6, 2012 in PCT Application No. PCT/US2011/065291.
International Search Report and Written Opinion dated Jun. 14, 2013 in PCT Application No. PCT/US2013/028103.
International Search Report and Written Opinion dated Aug. 16, 2013 for PCT Application No. PCT/US2013/027891.
International Search Report and Written Opinion dated Dec. 19, 2014 in PCT Application No. PCT/US2014/059542.
International Search Report and Written Opinion dated Feb. 3, 2015 in PCT Application No. PCT/US2014/053301.
International Search Report and Written Opinion dated May 3, 2016 in PCT Application No. PCT/US2016/018354.
International Search Report and Written Opinion dated Jun. 9, 2016 in PCT Application No. PCT/US2016/022712.
International Search Report and Written Opinion dated Jun. 17, 2016 in PCT Application No. PCT/US2016/019962.
International Search Report and Written Opinion dated Jun. 20, 2016 in PCT Application No. PCT/US2016/014612.
International Search Report and Written Opinion dated Aug. 9, 2016 in PCT Application No. PCT/US2016/019971.
International Search Report and Written Opinion dated Sep. 27, 2016 in PCT Application No. PCT/US2016/034473.
International Search Report and Written Opinion dated Sep. 28, 2016 in PCT Application No. PCT/US2016/028694.
International Search Report and Written Opinion dated Dec. 5, 2016 in PCT Application No. PCT/US2016/024783.
International Search Report and Written Opinion dated Jan. 31, 2017 in PCT Application No. PCT/US2016/050694.
International Search Report and Written Opinion dated Aug. 7, 2017 in PCT Application No. PCT/US2017/034576.
International Search Report and Written Opinion dated Sep. 8, 2017 in PCT Application No. PCT/US2017/030097.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.
International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
International Search Report and Written Opinion dated Jun. 30, 2020 in PCT Application No. PCT/US2020/017890.
Invitation to Pay Fees dated Mar. 16, 2016 in PCT Application No. PCT/US2016/019971.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Additional Search Fees dated May 7, 2020 in PCT Application No. PCT/US2020/017890.
Invitation to Respond to Written Opinion dated May 26, 2017 in Singapore Patent Application No. 11201405274W.
Islam et al., "Characterization of the single-cell transcriptional landscape by highly multiplex RNA-seq," Genome Research 2011, 21, 1160-1167.
Islam et al., "Highly multiplexed and strand specific single-cell RNA 5' end sequencing," Nature Protocols 2012, 7(5), 813-828.
Islam et al., "Quantitative single-cell RNA-seq with unique molecular identifiers," Nature Methods 2014, 11(2), 163-168.
Jabara, "Capturing the cloud: High throughput sequencing of multiple individual genomes from a retroviral population," Biology Lunch Bunch Series, Training Initiatives in Biomedical & Biological Sciences of the University of North Carolina at Chapel Hill 2010.
Jabara et al., "Accurate sampling and deep sequencing of the HIV-1 protease gene using a Primer ID," PNAS 2011, 108(50), 20166-20171.
Jason J. Rawnsley of Richards, Layton and Finger, P.A., Entry of Appearance dated Jan. 18, 2019 in the USDC District of Delaware, C.A. No. 18-1800-RGA, 1 pp.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Extended Time to Submit Agreed Document Production Protocol, filed Jun. 28, 2019 in the USDC for the District of Delaware, C.A. 18-1800 (RGA), 1 pp.

(56) References Cited

OTHER PUBLICATIONS

Joint Stipulation and Order to Request Extended Time to Submit Agreed Document Production Protocol, dated Jul. 11, 2019 in the USDC for the District of Delaware, C.A. 18-1800 (RGA), 1 pp.
Junker et al., "Single-Cell Transcriptomics Enters the Age of Mass Production," Molecular Cell 2015, 58, 563-564.
Kanagawa, "Bias and artifacts in multi-template polymerase chain reactions (PCR)," Journal of Bioscience and Bioengineering 2003, 96(4), 317-323.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells," Ann Biotechnol. 2018, 2(1007), 1-8.
Karrer et al., "In situ isolation of mRNA from individual plant cells: creation of cell-specific cDNA libraries," Proc. Natl. Acad. Sci. USA 1995, 92, 3814-3818.
Kausch et al., "Organelle Isolation by Magnetic Immunoabsorption," BioTechniques 1999, 26(2), 336-343.
Kebschull et al., "Sources of PCR-induced distortions in high-throughput sequencing data sets," Nucleic Acids Research 2015, 1-15.
Keys et al., Primer ID Informs Next-Generation Sequencing Platforms and Reveals Preexisting Drug Resistance Mutations in the HIV-1 Reverse Transcriptase Coding Domain, AIDS Research and Human Retroviruses 2015, 31(6), 658-668.
Kim et al., Polony Multiplex Analysis of Gene Expression (PMAGE) in Mouse Hypertrophic Cardiomyopathy, Science 2007, 316(5830), 1481-1484.
Kinde et al., "Detection and quantification of rare mutations with massively parallel sequencing," Proc. Natl Acad Sci 2011, 108(23), 9530-0535.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kivioja et al., "Counting absolute numbers of molecules using unique molecular identifiers," Nature Proceedings 2011, 1-18.
Klein et al., Droplet Barcoding for Single-Cell Transcriptomics Applied to Embryonic Stem Cells, Cell 2015, 161, 1187-1201.
Ko et al., "RNA-conjugated template-switching RT-PCR method for generating an *Escherichia coli* cDNA library for small RNAs," Journal of Microbiological Methods 2006, 64, 297-304.
Koboldt et al., 'VarScan: variant detection in massively parallel sequencing of individual and pooled samples, Bioinformatics 2009, 25(17), 2283-2285.
Kolodziejczyk et al., 'The Technology and Biology of Single-Cell RNA Sequencing, Molecular Cell 2015, 58, 610-620.
Konig et al., "iCLIP reveals the function of hnRNAP particles in splicing at individual nucleotide resolution," Nature Structural & Molecular Biology 2010, 17(7), 909-916.
Kooiker & Xue, "cDNA Library Preparation," Cereal Genomics 2013, 1099, 29-40.
Kotake et al., "A simple nested RT-PCR method for quantitation of the relative amounts of multiple cytokine mRNAs in small tissue samples," Journal of Immunological Methods 1996, 199, 193-203.
Kozlov et al., "A high-complexity, multiplexed solution-phase assay for profiling protease activity on microarrays," Comb Chem High Throughput Screen 2008, 11(1), 24-35.
Kurimoto et al., "An improved single-cell cDNA amplification method for efficient high-density oligonucleotide microarray analysis," Nucleic Acids Res. 2006, 34(5), e42, 1-17.
Kurimoto et al., "Global single-cell cDNA amplification to provide a template for representative high-density oligonucleotide microarray analysis," Nature Protocols 2007, 2(3), 739-752.
Lamble et al., "Improved workflows for high throughput library preparation using the transposome-based nextera system," BMC Biotechnology 2013, 13, 104, 1-10.
Larson et al., "A single molecule view of gene expression," Trends Cell Biol. 2009, 19(11), 630-637.

Lass-Napiorkowska et al., "Detection methodology based on target molecule-induced sequence-specific binding to a single-stranded oligonucleotide," Anal Chem. 2012, 84(7), 3382-3389.
Leamon et al., A massively parallel PicoTiterPlate based platform for discrete picoliter-scale polymerase chain reactions, Electrophoresis 2003, 24, 3769-3777.
Lee et al., "Large-scale arrays of picolitre chambers for single-cell analysis of large cell populations," Lab Chip 2010, 10, 2952-2958.
Lee et al., "Highly Multiplexed Subcellular RNA Sequencing in Situ," Science 2014, 343,1360-1363.
Lee et al., "Universal process-inert encoding architecture for polymer microparticles," Nature Materials 2014, 13(5), 524-529.
Letter regarding the opposition procedure dated Jul. 22, 2015 for European Patent Application No. 11810645.9.
Letter to Judge Richard G. Andrews Requesting a Rule 16 Conference, dated Apr. 15, 2019 in the USDC for the District of Delaware, C.A. 18-1800 (RGA), 1 pp.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.
Lin et al., "Self-Assembled Combinatorial Encoding Nanoarrays for Multiplexed Biosensin," Nano Lett. 2007, 7 (2), 507-512.
Liu et al., "Single-cell transcriptome sequencing: recent advances and remaining challenges," F1000Research 2016, 5(F1000 Faculty Rev)(182), 1-9.
Lizardi et al., "Mutation detection and single-molecule counting using isothermal rolling-circle amplification," Nat Genet. 1998, 19, 225-232.
Lockhart et al., "Expression monitoring by hybridization to high-density oligonucleotide arrays," Nature Biotechnology 1996, 14, 1675-1680.
Lovatt et al., "Transcriptome in vivo analysis (TIVA) of spatially defined single cells in live tissue," Nat Methods 2014, 11(2), 190-196.
Loy et al., "A rapid library preparation method with custom assay designs for detection of variants at 0.1% allelic frequency in liquid biopsy samples," Oct. 2, 2018, 1 p.
Lucito et al., "Representational Oligonucleotide Microarray Analysis: A High-Resolution Method to Detect Genome Copy Number Variation," Genome Research 2003, 13, 2291-2305.
Lundberg et al., "Practical innovations for high-throughput amplicon sequencing," Nature Methods 2013, 10(10), 999-1007.
Lundberg et al., "Supplementary Information for: Practical innovations for high-throughput amplicon sequencing," Nature Methods 2013, 1-24.
Maamar et al., "Noise in Gene Expression Determines Cell Fate in Bacillus subtilis," Science 2007, 317, 526-529.
Macaulay et al., "Single Cell Genomics: Advances and Future Perspectives," PLoS Genetics 2014, 10(1), 1-9.
Macaulay et al., "G&T-seq: parallel sequencing of single-cell genomes and transcriptomes," Nature Methods 2015, 1-7.
Macosko et al., "Highly parallel genome-wide expression profiling of individual cells using nanoliter droplets," Cell 2015, 161, 1202-1214.
Maeda et al., "Development of a DNA barcode tagging method for monitoring dynamic changes in gene expression by using an ultra high-throughput sequencer," BioTechniques 2008, 45(1), 95-97.
Makrigiorgos et al., "A PCR-Based amplification method retaining quantities difference between two complex genomes," Nature Biotech 2002, 20(9), 936-939.
Marcus et al., "Microfluidic single-cell mRNA isolation and analysis," Anal Chem. 2006, 78, 3084-3089.
Mardis, "Next-generation DNA sequencing methods", Annu. Rev. Genomics Hum. Genet. 2008, 9, 387-402.
Marguerat et al., "Next-generation sequencing: applications beyond genomes," Biochem. Soc. Trans. 2008, 36(5), 1091-1096.
Marguiles et al., Genome sequencing in microfabricated high-density picolitre reactors, Nature 2005, 437, 376-380.

(56) References Cited

OTHER PUBLICATIONS

Martinez et al., "A microfluidic approach to encapsulate living cells in uniform alginate hydrogel microparticles," Macromol. Biosci 2012, 12, 946-951.
Massachusetts General Hospital, Overview of Illumina Chemistry, http://nextgen.mgh.harvard.edu/IlluminaChemistry.html, downloaded Jan. 28, 2020, 2 pp.
McCloskey et al., "Encoding PCR products with batch-stamps and barcodes," Biochem Genet. 2007, 45(11-12), 761-767.
Medvedev et al., "Detecting copy number variation with mated short reads," Genome Res. 2010, 20, 1613-1622.
Mei et al., "Identification of recurrent regions of Copy-Number Variants across multiple individuals," BMC Bioinformatics 2010, 11, 147, 1-14.
Merriam-Webster, definition of associate: http://www.merriam-webster.com/dictionary/associate, accessed Apr. 5, 2016.
Meyer et al., "Parallel tagged sequencing on the 454 platform," Nature Protocols 2008, 3(2), 267-278.
Miller et al., Directed evolution by in vitro compartmentalization, Nature Methods 2006, 3(7), 561-570.
Miner et al., "Molecular barcodes detect redundancy and contamination in hairpin-bisulfite PCR," Nucleic Acids Research 2004, 32(17), e135, 1-4.
Mortazavi et al., "Mapping and quantifying mammalian transcriptomes by RNA-Seq," Nat. Methods 2008, 5(7), 621-628.
Motion and Order for Admission Pro Hac Vice Pursuant to Local Rule 83.5, dated Jan. 24, 2019 in the USDC District of Delaware, C.A. No. 18-1800-RGA, 7 pp.
Nadai et al., Protocol for nearly full-length sequencing of HIV-1 RNA from plasma, PLoS One 2008, 3(1), e1420, 1-6.
Nagai et al., "Development of a microchamber array for picoleter PCR," Anal. Chem. 2001, 73, 1043-1047.
Navin et al., "The first five years of single-cell cancer genomics and beyond," Genome Research 2015, 25, 1499-1507.
Newell et al., Cytometry by time-of-flight shows combinatorial cytokine expression and virus-specific cell niches within a continuum of CD8+ T cell phenotypes. Immunity 2012, 36(1), 142-152.
Non-Final Office Action dated Oct. 3, 2013 in U.S. Appl. No. 12/969,581.
Non-Final Office Action dated Feb. 18, 2015 for U.S. Appl. No. 14/540,007.
Non-Final Office Action dated Feb. 26, 2015 for U.S. Appl. No. 14/540,029.
Non-Final Office Action dated Mar. 19, 2015 in U.S. Appl. No. 14/540,018.
Non-Final Office Action dated May 7, 2015 for U.S. Appl. No. 13/327,526.
Non-Final Office Action dated Dec. 3, 2015 for U.S. Appl. No. 14/281,706.
Non-Final Office Action dated Dec. 31, 2015 for U.S. Appl. No. 14/800,526.
Non-Final Office Action dated Apr. 11, 2016 in U.S. Appl. No. 14/472,363.
Non-Final Office Action dated May 10, 2016 in U.S. Appl. No. 14/381,488.
Non-Final Office Action dated May 13, 2016 in U.S. Appl. No. 14/508,911.
Non-Final Office Action dated Aug. 17, 2016 for U.S. Appl. No. 14/800,526.
Non-Final Office Action dated Sep. 26, 2016 in U.S. Appl. No. 15/167,807.
Non-Final Office Action dated Oct. 11, 2016 in U.S. Appl. No. 15/224,460.
Non-Final Office Action dated Jan. 19, 2017 in U.S. Appl. No. 15/055,445.
Non-Final Office Action dated Mar. 24, 2017 in U.S. Appl. No. 15/409,355.
Non-Final Office Action dated Jun. 2, 2017 in U.S. Appl. No. 14/381,526.
Non-Final Office Action dated Jun. 7, 2017 in U.S. Appl. No. 14/381,488.
Non-Final Office Action dated Jul. 28, 2017 in U.S. Appl. No. 14/975,441.
Non-Final Office Action dated Sep. 8, 2017 in U.S. Appl. No. 15/046,225.
Non-Final Office Action dated Sep. 8, 2017 in U.S. Appl. No. 15/134,967.
Non-Final Office Action dated Nov. 1, 2017 in U.S. Appl. No. 15/667,125.
Non-Final Office Action dated Nov. 9, 2017 in U.S. Appl. No. 15/004,618.
Non-Final Office Action dated Jan. 9, 2018 in U.S. Appl. No. 15/217,896.
Non-Final Office Action dated Jan. 12, 2018 in U.S. Appl. No. 15/217,886.
Non-Final Office Action dated Mar. 8, 2018 in U.S. Appl. No. 15/608,780.
Non-Final Office Action dated Apr. 6, 2018 in U.S. Appl. No. 15/603,239.
Non-Final Office Action dated Jul. 25, 2018 in U.S. Appl. No. 15/108,268.
Non-Final Office Action dated Oct. 4, 2018 in U.S. Appl. No. 15/260,106.
Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.
Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.
Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Notice of Allowability dated Jun. 19, 2014 for U.S. Appl. No. 12/969,581.

(56) References Cited

OTHER PUBLICATIONS

Notice of Allowance dated Mar. 21, 2014 for U.S. Appl. No. 12/969,581.
Notice of Allowance dated Aug. 22, 2014 for U.S. Appl. No. 12/969,581.
Notice of Allowance dated Dec. 15, 2015 for U.S. Appl. No. 14/540,007.
Notice of Allowance dated Dec. 21, 2015 in U.S. Appl. No. 14/540,018.
Notice of Allowance dated Jan. 21, 2016 for U.S. Appl. No. 13/327,526.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Apr. 15, 2020 in U.S. Appl. No. 16/012,635.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 9, 2015 for European Patent Application No. 11810645.9.
Notice of Opposition dated Jul. 27, 2016 for European Patent Application No. 10762102.1.
Notice of Reasons for Rejection dated Dec. 28, 2016 in Japanese Patent Application No. 2014-558975.
Notice of Reasons for Rejection dated Apr. 2, 2018 in Japanese Patent Application No. 2014-558975.
Notice of Reasons for Rejection dated Jul. 30, 2018 in Japanese Patent Application No. 2016-537867.
Notice of Reasons for Rejection dated Aug. 31, 2018 in Japanese Patent Application No. 2016-520632.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notification Prior to Examination dated Nov. 27, 2019 in Israeli Patent Application No. 265478.
Novak et al., "Single-Cell Multiplex Gene Detection and Sequencing with Microfluidically Generated Agarose Emulsions," Angew. Chem. Int. Ed. 2011, 50, 390-395.
Office Action dated Jun. 6, 2016 in Chinese Patent Application No. 201380022187.9.
Office Action dated Dec. 27, 2016 in Chinese Patent Application No. 201380022187.9.
Office Action dated Feb. 17, 2017 in Canadian Patent Application No. 2,865,575.
Office Action dated Jul. 14, 2017 in Chinese Patent Application No. 201380022187.9.
Office Action dated Dec. 19, 2017 in Chinese Patent Application No. 201480061859.1.
Office Action dated Feb. 15, 2018 in Canadian Patent Application No. 2,865,575.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Ogino et al., "Quantification of PCR bias caused by a single nucleotide polymorphism in SMN gene dosage analysis," J Mol Diagn. 2002, 4(4), 185-190.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Order Scheduling ADR Mediation Teleconference, filed May 13, 2019 in the USDC for the District of Delaware, C.A. 18-1800-RGA, 4pp.
Ozkumur et al., "Inertial Focusing for Tumor Antigen-Dependent and -Independent Sorting of Rare Circulating Tumor Cells," Science Translational Medicine 2013, 5(179), 1-20.
Parameswaran et al., "A pyrosequencing-tailored nucleotide barcode design unveils opportunities for large-scale sample multiplexing," Nucleic Acids Res. 2007, 35(19), e130, 1-9.
Park et al., "Discovery of common Asian copy number variants using integrated high-resolution array CGH and massively parallel DNA sequencing," Nat Genet. 2010, 42(5), 400-405.
Patanjali et al., "Construction of a uniform-abundance (normalized) CNDA library," Proceedings of the National Academy of Sciences 1991, 88(5), 1943-1947.
Peng et al., "Reducing amplification artifacts in high multiplex amplicon sequencing by using molecular barcodes," BMC Genomics 2015, 16(589), 1-12.
Pérez-Rentero et al., "Synthesis of Oligonucleotides Carrying Thiol Groups Using a Simple Reagent Derived from Threoninol," Molecules 2012, 17, 10026-10045.
Peterson et al., "Multiplexed quantification of proteins and transcripts in single cells," Nature Biotechnology 2017, 35, 936-939.
Pfaffl et al., "Determination of stable housekeeping genes, differentially regulated target genes and sample integrity: BestKeeper—Excel-based tool using pair-wise correlations," Biotechnology Letters, 26(6), 505-515.
Picelli et al., "Tn5 transposase and tagmentation procedures for massively scaled sequencing projects," Genome Research 2014, 24(12), 2033-2040.
Picelli et al., "Single-cell RNA-sequencing: The future of genome biology is now," RNA Biology 2017, 14(5), 637-650.
Pihlak et al., "Rapid genome sequencing with short universal tiling probes," Nature Biotechnology 2008, 26, 1-9.
Pinkel et al., "Comparative Genomic Hybridization," Annual Review of Genomics and Human Genetics 2005, 6, 331-354.

(56) References Cited

OTHER PUBLICATIONS

Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Pleasance et al., "A small-cell lung cancer genome with complex signatures of tobacco exposure," Nature 2010, 463(7278), 184-190.
Plessy et al., "Population transcriptomics with single-cell resolution: a new field made possible by microfluidics: a technology for high throughput transcript counting and data-driven definition of cell types," Bioessays 2012, 35, 131-140.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) of the Federal Rules of Civil Procedure, filed Jun. 20, 2019 In the USDC for the District of Delaware, C.A. 18-1800 (RGA), 26 pp.
Qiu et al., "DNA Sequence-Based "Bar Codes" for Tracking the Origins of Expressed Sequence Tags from a Maize cDNA Library Constructed Using Multiple mRNA Sources," Plant Physiol. 2003, 133, 475-481.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Rajeevan et al., "Global amplification of sense RNA: a novel method to replicate and archive mRNA for gene expression analysis," Genomics 2003, 82, 491-497.
Report on the Filing or Determination of an Action Regarding a Patent or Trademark filed Nov. 15, 2018 in the USDC for the District of Delaware, C.A. 18-1800-RGA, 2 pp.
Restriction Requirement dated Mar. 15, 2016 in U.S. Appl. No. 14/381,488.
Restriction Requirement dated Mar. 17, 2016 in U.S. Appl. No. 14/472,363.
Restriction Requirement dated Mar. 29, 2019 in U.S. Appl. No. 15/715,028.
Restriction Requirement dated Jun. 19, 2019 in U.S. Appl. No. 15/596,364.
Restriction Requirement dated Sep. 20, 2019 in U.S. Appl. No. 15/875,816.
Rhee et al., "Simultaneous detection of mRNA and protein stem cell markers in live cells," BMC Biotechnology 2009, 9(30), 1-10.
Roche Diagnostics GmbH, "Genome Sequencer 20 System: First to the Finish," 2006, 1-40.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-COV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody-DNA Conjugates," Science 1992, 258, 120-122.
Sasagawa et al., "Quartz-Seq: a highly reproducible and sensitive single-cell RNA sequencing method, reveals non-genetic gene-expression heterogeneity," Genome Biology 2013, 14, R31.
Sasuga et al., Single-cell chemical lysis method for analyses of intracellular molecules using an array of picoliter-scale microwells, Anal Chem 2008, 80(23), 9141-9149.
Satija et al., Spatial reconstruction of single-cell gene expression data, Nature Biotechnology 2015, 33(5), 495-508.
Scheduling Order pursuant to Local Rule 16.1(b), filed May 7, 2019 in the USDC for the District of Delaware, C.A. 18-1800-RGA, 10 pp.

Scheduling Order Signed by Judge Andrews, dated May 8, 2019 in the USDC for the District of Delaware, C.A. 18-1800-RGA, 10 pp.
Schmitt et al., "Detection of ultra-rare mutations by next-generation sequencing," Proc Natl Acad Sci 2012, 109(36), 1-6.
Search and Examination Report dated Aug. 26, 2015 in United Kingdom Patent Application No. 1511591.8.
Search Report and Written Opinion dated Jan. 26, 2016 in Singapore Patent Application No. 1120140527W.
Sebat et al., "Large-Scale Copy Number Polymorphism in the Human Genome," Science 2004, 305, 525-528.
Shahi et al., "Abseq: ultrahigh-throughput single cell protein profiling with droplet microfluidic barcoding," Scientific Reports 2017, 7(44447), 1-10.
Shalek et al., "Single-cell transcriptomics reveals bimodality in expression and splicing in immune cells," Nature 2013, 498(7453), 236-240.
Shendure et al., "Next-generation DNA sequencing," Nature Biotechnology 2008, 26(10), 1135-1145.
Shiroguchi et al., "Digital RNA sequencing minimizes sequence-dependent bias and amplification noise with optimized single-molecule barcodes," Proc Natl Acad Sci 2012, 109(4):1347-1352.
S.H.Ko, "An 'equalized cDNA library' by the reassociation of short double-stranded cDNAs," Nucleic Acids Res. 1990, 18(19), 5705-5711.
Shoemaker et al., "Quantitative phenotypic analysis of yeast deletion mutants using a highly parallel molecular bar-coding strategy," Nature Genetics 1996, 14, 450-456.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019, 1129, 63-79.
Simpson et al., "Copy number variant detection in inbred strains from short read sequence data," Bioinformatics 2010, 26(4), 565-567.
Smith et al., "Highly-multiplexed barcode sequencing: an efficient method for parallel analysis of pooled samples," Nucleic Acids Research 2010, 38(13), e142, 1-7.
Soares et al., "Construction and characterization of a normalized cDNA library," Proc. Natl., Acad. Sci. 1994, 91, 9228-9232.
Sogin et al., "Microbial diversity in the deep sea and the underexplored "rare biosphere"," PNAS 2008, 103(32), 12115-12120.
Sommer et al., "Minimal homology requirements for PCR primers," Nucleic Acids Research 1989, 17(16), 6749.
Song et al., "Design rules for size-based cell sorting and sheathless cell focusing by hydrophoresis," Journal of Chromatography A 2013, 1302, 191-196.
Soumillon et al., "Characterization of directed differentiation by high-throughput single-cell RNA-Seq," bioRxiv 2014, 1-13.
Speicher et al., "The new cytogenetics: blurring the boundaries with molecular biology," Nature Reviews Genetics 2005, 6(10), 782-792.
Statement of Opposition of Strawman Limited filed against European Patent No. EP2414548B1 on Jul. 19, 2016.
Statement of Opposition dated Jul. 21, 2016 filed against European Patent No. EP2414548B1.
Statement of Opposition filed against European Patent No. EP2414548B1 on Jul. 26, 2016.
Statement regarding Third-Party Submission filed on Jun. 6, 2018 for U.S. Appl. No. 15/847,752.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Stratagene 1988 Catalog, Gene Characterization Kits, 39.
Subkhankulova et al., "Comparative evaluation of linear and exponential amplification techniques for expression profiling at the single cell level," Genome Biology 2006, 7(3), 1-16.

(56) References Cited

OTHER PUBLICATIONS

Submission dated Jan. 15, 2018 in preparation for upcoming oral proceedings in opposition against European Patent No. EP2414548B1.
Summons in a Civil Action to Defendant 10X Genomics, Inc. filed Nov. 16, 2018 in the USDC for the District of Delaware, Civil Action No. 18-1800, 2 pp.
Sun et al., "Ultra-deep profiling of alternatively spliced *Drosophila* Dscam isoforms by circularization-assisted multi-segment sequencing," EMBO J. 2013, 32(14), 2029-2038.
Takahashi et al., "Novel technique of quantitative nested real-time PCR assay for mycobacterium tuberculosis DNA," Journal of Clinical Microbiology 2006, 44, 1029-1039.
Tan et al., "Genome-wide comparison of DNA hydroxymethylation in mouse embryonic stem cells and neural progenitor cells by a new comparative hMeDIP-seq method," Nucleic Acids Res. 2013, 41(7), e84, 1-12.
Tang et al., "RNA-Seq analysis to capture the transcriptome landscape of a single cell," Nature Protocols 2010, 5(3), 516-535.
Taudien et al., "Haplotyping and copy number estimation of the highly polymorphic human beta-defensin locus on 8p23 by 454 amplicon sequencing," BMC Genomics 2010, 11, 252, 1-14.
The Tibbs Times, UNC bioscience newsletter, Apr. 2010, 1-17.
Third-Party Submission filed on May 21, 2018 for U.S. Appl. No. 15/847,752.
Tomaz et al., "Differential methylation as a cause of allele dropout at the imprinted GNAS locus," Genet Test Mol Biomarkers 2010, 14(4), 455-460.
Treutlein et al., Reconstructing lineage hierarchies of the distal lung epithelium using single-cell RNA-seq, Nature 2014, 509, 371-375.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vandesompele et al., "Accurate normalization of real-time quantitative RT-PCR data by geometric averaging of multiple internal control genes," Genome Biology 2002, 3(7), 1-12.
Velculescu et al., "Serial Analysis of Gene Expression," Science 1995, 270(5235), 484-487.
Velculescu et al., "Characterization of the Yeast Transcriptome," Cell 1997, 88, 243-251.
Vogelstein et al., "Digital PCR," Proc. Natl. Acad. Sci. 1999, 96, 9236-9241.
Vollbrecht et al., "Validation and comparison of two NGS assays for the detection of EGFR T790M resistance mutation in liquid biopsies of NSCLC patients," Oncotarget 2018, 9(26), 18529-18539.
Walker et al., "Isothermal in vitro amplification of DNA by a restriction enzyme/DNA polymerase system," Proc Natl Acad Sci 1992, 89, 392-396.
Walsh et al., "Detection of inherited mutations for breast and ovarian cancer using genomic capture and massively parallel sequencing," Proc Natl Acad Sci 2010, 107(28), 12629-12633.
Wang et al., "Combining Gold Nanoparticles with Real-Time Immuno-PCR for Analysis of HIV p24 Antigens," Proceedings of ICBBE 2007, 1198-1201.
Wang et al., "RNA-Seq: a revolutionary tool for transcriptomics," Nature Reviews Genetics 2009, 10(1), 57-63.
Wang et al., "iCLIP predicts the dual splicing effects of TIA-RNA interactions," PLoS Biol 2010, 8(10), e1000530, 1-16.
Wang et al., "Advances and applications of single-cell sequencing technologies," Molecular Cell 2015, 58, 598-609.
Warren et al., "Transcription factor profiling in individual hematopoietic progenitors by digital RT-PCR," PNAS 2006, 103(47), 17807-17812.
Weber et al., "A real-time polymerase chain reaction assay for quantification of allele ratios and correction of amplification bias," Anal Biochem. 2003, 320, 252-258.
Weibrecht et al., "Proximity ligation assays: a recent addition to the proteomics toolbox," Expert Rev. Proteomics 2010, 7(3), 401-409.
Weiner et al., "Kits and their unique role in molecular biology: a brief retrospective," BioTechniques 2008, 44(5), 701-704.
White et al., "High-throughput microfluidic single-cell RT-qPCR," PNAS 2011, 108(34), 13999-14004.
Wittes et al., "Searching for Evidence of Altered Gene Expression: a Comment on Statistical Analysis of Microarray Data," Journal of the National Cancer Institute 1999, 91(5), 400-401.
Wodicka et al., "Genome-wide expression monitoring in *Saccharomyces cerevisiae*," Nature Biotechnology 1997, 15, 1359-1367.
Wojdacz et al., "Primer design versus PCR bias in methylation independent PCR amplifications," Epigenetics 2009, 4(4), 231-234.
Wood et al., "Using next-generation sequencing for high resolution multiplex analysis of copy number variation from nanogram quantities of DNA from formalin-fixed paraffin-embedded specimens," Nucleic Acids Res. 2010, 38(14), 1-14.
Written Submission of Publications dated Jun. 14, 2018 in Japanese Patent Application No. 2016-537867.
Wu et al., "Quantitative assessment of single-cell RNA-sequencing methods," Nat Methods 2014, 11(1), 41-46.
Yandell et al., "A probabilistic disease-gene finder for personal genomes," Genome Res. 2011, 21(9), 1529-1542.
Ye et al., "Fluorescent microsphere-based readout technology for multiplexed human single nucleotide polymorphism analysis and bacterial identification, Human Mutation 2001, 17(4), 305-316.
Yoon et al., Sensitive and accurate detection of copy number variants using read depth of coverage, Genome Res. 2009, 19, 1586-1592.
Zagordi et al., "Error correction of next-generation sequencing data and reliable estimation of HIV quasispecies," Nucleic Acids Research 2010, 38(21), 7400-7409.
Zhang et al., "The impact of next-generation sequencing on genomics," J Genet Genomics 2011, 38(3), 95-109.
Zhang et al., "DNA-based hybridization chain reaction for amplified bioelectronic signal and ultrasensitive detection of proteins," Anal Chem. 2012, 84, 5392-5399.
Zhao et al., "Homozygous Deletions and Chromosome Amplifications in Human Lung Carcinomas Revealed by Single Nucleotide Polymorphism Array Analysis," Cancer Research 2005, 65(13), 5561-5570.
Zheng et al., "Haplotyping germline and cancer genomes with high-throughput linked-read sequencing," Nature Biotechnology 2016, 34(3), 303-311.
Zhou et al., "Counting alleles reveals a connection between chromosome 18q loss and vascular invasion," Nature Biotechnology 2001, 19, 78-81.
Zhou et al., "Photocleavable Peptide-Oligonucleotide Conjugates for Protein Kinase Assays by MALDI-TOF MS," Mol. BioSyst. 2012, 8, 2395-2404.
Zhu et al., "Reverse Transcriptase Template Switching: A SMART Approach for Full-Length cDNA Library Construction," BioTechniques 2001, 30(4), 892-897.
10X Genomics, Inc., 2022, "Chromium Fixed RNA Profiling Reagent Kits," 10xGenomics.com, User Guide, in 95 pages.
10x_LIT099_Product-Sheet_Chromium-Single-Cell-Multiome-ATAC-Gene-Expression_Letter_digital.
Adey et al., "Rapid, low-input, low-bias construction of shotgun fragment libraries by high-density in vitro transposition," Genome Biology 2010, 11(R19), in 17 pages.
Advisory Action dated May 31, 2023 in U.S. Appl. No. 16/789,311.
Ahern, "Biochemical, Reagent Kits Offer Scientists Good Return on Investment," The Scientist 1995, 9(15), in 5 pages.
Arguel et al., "A cost effective 5' selective single cell transcriptome profiling approach with improved UMI design," Nucleic Acids Research 2017, 45(7), e48, in 11 pages.
Armbrecht, et al. "Single-cell protein profiling in microchambers with barcoded beads", Microsystems & Nanoengineering, 2019, 5:55.
Bolivar et al., "Targeted next-generation sequencing of endometrial cancer and matched circulating tumor DNA: identification of plasma-based, tumor-associated mutations in early stage patients," Modern Pathology 2019, 32(3), 405-414.

(56) References Cited

OTHER PUBLICATIONS

Brouilette et al., "A Simple and Novel Method for RNA-seq Library Preparation of Single Cell cDNA Analysis by Hyperactive Tn5 Transposase," Developmental Dynamics 2012, 241, 1584-1590.
Buenrostro et al., "Transposition of native chromatin for multimodal regulatory analysis and personal epigenomics," Nat Methods 2013, 10(12), 1213-1218.
Buenrostro et al., "ATAC-seq: A Method for Assaying Chromatin Accessibility Genome-Wide," Curr Protoc Mol Biol 2016, 109, 1-21.
CG000209_Chromium_NextGEM_SingleCell_ATAC_ReagentKits_v1.1_UserGuide_RevG.
CG000496_Chromium_NextGEM_SingleCell_ATAC_ReagentKits_v2_UserGuide_RevB.
CG000505_Chromium_Nuclei_Isolation_Kit_UG_RevA.
Chang et al., "Single-cell protein and gene expression profiling of stem memory T cells by BD Ab-seq," Annual Joint Meeting of the American Society for Cell Biology and the European Molecular Biology Organization 2017, 28(26), p. 1896.
Chen et al., "High-throughput sequencing of the transcriptome and chromatin accessibility in the same cell," Nature Biotechnology 2019, 37, 1452-1457.
De Simone et al., "Single Cell T Cell Receptor Sequencing: Techniques and Future Challenges," Frontiers in Immunology 2018, 9(1638), 1-7.
Decision of Grant dated Aug. 21, 2023 in Japanese Patent Application 2020-561800.
Delebecque et al. "Designing and using RNA scaffolds to assemble proteins in vivo". Nature protocols, 2012, 7(10), 1797-1807.
Dengl et al., "Engineered hapten-binding antibody derivatives for modulation of pharmacokinetic properties of small molecules and targeted payload delivery," Immunol Rev. 2016, 270, 165-177.
Dickey and Giangrande. "Oligonucleotide Aptamers: A Next-Generation Technology for the Capture and Detection of Circulating Tumor Cells." Methods, 2016 97:94-103.
Dovgan et al., "Antibody-Oligonucleotide Conjugates as Therapeutic, Imaging, and Detection Agents," Bioconjugate Chem. 2019, 30, 2483-2501.
Dua, et al. "Patents on SELEX and therapeutic aptamers. Recent patents on DNA & gene sequences," 2008, 2( 3), 172-186.
Erickson et al., "AbSeq Protocol Using the Nano-Well Cartridge-Based Rhapsody Platform to Generate Protein and Transcript Expression Data on the Single-Cell Level," STAR Protocols 2020, in 31 pages.
Eulberg, et al. "Development of an automated in vitro selection protocol to obtain RNA-based aptamers: identification of a biostable substance P antagonist," Nucleic acids research, 2005, 33(4), e45. https://doi.org/ 10.1093/nar/gni044.
Examination Report dated Nov. 12, 2020 in European Patent Application No. 18716877.8.
Examination Report dated Dec. 3, 2020 in European Patent Application No. 16719706.0.
Examination Report dated Mar. 25, 2021 in European Patent Application No. 17781265.8.
Examination Report dated Oct. 8, 2021 in European Patent Application No. 18716877.8.
Examination Report dated Nov. 18, 2021 in European Patent Application No. 19724003.9.
Examination Report dated Nov. 24, 2021 in European Patent Application No. 19762517.1.
Examination Report dated Dec. 6, 2021 in European Patent Application No. 18703156.2.
Examination Report dated Dec. 9, 2021 in European Patent Application No. 19723988.2.
Examination Report dated Apr. 7, 2022 in Singapore Patent Application No. 10201806890V.
Examination Report dated Apr. 8, 2022 in Australian Patent Application No. 2018281745.
Examination Report dated Oct. 31, 2023 in European Patent Application 20753616.0.
Examination Report dated Nov. 9, 2023 in European Patent Application 20711394.5.
Extended European Search Report dated May 6, 2021 in European Patent Application No. 20207621.2.
Extended European Search Report dated May 28, 2021 in European Patent Application No. 20209777.0.
Extended European Search Report Dated Oct. 4, 2023 in European Patent Application No. 23166582.9.
Fathi,, P. Design and Characterization of SSDNA Aptamer Candidates to Bind Bacteroides Fragilis Toxin Subtypes BFT-1 and BFT-2 (Doctoral dissertation, Johns Hopkins University).2017.
Final Office Action dated Dec. 7, 2020 in U.S. Appl. No. 16/012,584.
Final Office Action dated Feb. 11, 2021 in U.S. Appl. No. 15/134,967.
Final Office Action dated Mar. 16, 2021 in U.S. Appl. No. 15/715,028.
Final Office Action dated Mar. 25, 2021 in U.S. Appl. No. 16/374,626.
Final Office Action dated Jun. 15, 2021 in U.S. Appl. No. 15/084,307.
Final Office Action dated Jul. 15, 2021 in U.S. Appl. No. 16/836,750.
Final Office Action dated Aug. 10, 2021 in U.S. Appl. No. 16/012,584.
Final Office Action dated Aug. 27, 2021 in U.S. Appl. No. 15/055,407.
Final Office Action dated Sep. 24, 2021 in U.S. Appl. No. 16/788,743.
Final Office Action dated Oct. 1, 2021 in U.S. Appl. No. 16/677,012.
Final Office Action dated Nov. 2, 2021 in U.S. Appl. No. 16/789,311.
Final Office Action dated Jan. 18, 2022 in U.S. Appl. No. 16/588,405.
Final Office Action dated Feb. 23, 2022 in U.S. Appl. No. 16/707,780.
Final Office Action dated Mar. 15, 2022 in U.S. Appl. No. 16/374,626.
Final Office Action dated Mar. 25, 2022 in U.S. Appl. No. 16/551,620.
Final Office Action dated Apr. 12, 2022 in U.S. Appl. No. 15/084,307.
Final Office Action dated May 26, 2022 in U.S. Appl. No. 16/747,737.
Final Office Action dated Jun. 14, 2022 in U.S. Appl. No. 15/055,407.
Final Office Action dated Aug. 23, 2022 in U.S. Appl. No. 16/012,584.
Final Office Action dated Nov. 15, 2022 in U.S. Appl. No. 16/525,054.
Final Office Action dated Nov. 16, 2022 in U.S. Appl. No. 16/588,405.
Final Office Action dated Jan. 25, 2023 in U.S. Appl. No. 16/789,311.
Final Office Action dated Jan. 26, 2023 in U.S. Appl. No. 16/459,444.
Final Office Action dated Feb. 21, 2023 in U.S. Appl. No. 16/551,620.
Final Office Action dated Apr. 25, 2023 in U.S. Appl. No. 16/525,054.
Final Office Action dated May 15, 2023 in U.S. Appl. No. 16/551,638.
Final Office Action dated May 19, 2023 in U.S. Appl. No. 17/163,177.
Final Office Action dated May 31, 2023 in U.S. Appl. No. 16/934,530.
Final Office Action dated Jun. 8, 2023 in U.S. Appl. No. 17/147,283.
Final Office Action dated Oct. 5, 2023 in U.S. Appl. No. 17/151,050.
Final Office Action dated Oct. 13, 2023 in U.S. Appl. No. 15/055,407.
Final Office Action dated Oct. 23, 2023 in U.S. Appl. No. 16/540,971.
Fitzgerald and Grivel, "A Universal Nanoparticle Cell Secretion Capture Assay," Cytometry Part A 2012, 83A(2), 205-211.
Gertz et al., "Transposase mediated construction of RNA-seq libraries," Genome Research 2012, 22, 134-141.
Goodridge et al., "Synthesis of Albumin and Malic Enzyme in Wheat-Germ Lysates and *Xenopus laevis* Oocytes Programmed with Chicken-Liver Messenger RNA," Eur. J. Biochem. 1979, 96, 1-8.
Gratton et al., "Cell-permeable peptides improve cellular uptake and therapeutic gene delivery of replication-deficient viruses in cells and in vivo," Nature Medicine 2003, 9(3), 357-362.
Hoinka and Przytycka. "AptaPLEX—A Dedicated, Multithreaded Demultiplexer for HT-SE LEX Data." Methods, 2016, 106:82-85.
Illumina, "Data Processing of Nextera Mate Pair Reads on Illumina Sequencing Platforms", Data Processing Technical Note from 2012.
International Search Report and Written Opinion dated Nov. 12, 2020 in PCT Application No. PCT/US2020/042880.
International Search Report and Written Opinion dated Jan. 19, 2021 in PCT Application No. PCT/US2020/059419.
International Search Report and Written Opinion dated Apr. 9, 2021 in PCT Application No. PCT/US2021/013137.
International Search Report and Written Opinion dated Apr. 21, 2021 in PCT Application No. PCT/US2021/015571.
International Search Report and Written Opinion dated May 4, 2021 in PCT Application No. PCT/US2021/013109.
International Search Report and Written Opinion dated May 11, 2021 in PCT Application No. PCT/US2021/013748.
International Search Report and Written Opinion dated Jul. 15, 2021 in PCT Application No. PCT/US2021/019475.

(56) References Cited

OTHER PUBLICATIONS

International Search Report and Written Opinion dated Jul. 20, 2021 in PCT Application No. PCT/US2021/015898.
International Search Report and Written Opinion dated Aug. 31, 2021 in PCT Application No. PCT/US2021/035270.
International Search Report and Written Opinion dated Sep. 22, 2021, in PCT Application No. PCT/US2021/013747.
International Search Report and Written Opinion dated Sep. 27, 2021, in PCT Application No. PCT/US2021/017719.
International Search Report and Written Opinion dated Oct. 12, 2021, in PCT Application No. PCT/US2021/041327.
International Search Report and Written Opinion dated Oct. 29, 2021, in PCT Application No. PCT/US2021/032319.
International Search Report and Written Opinion dated Dec. 6, 2021, in PCT Application No. PCT/US2021/046750.
International Search Report and Written Opinion dated Nov. 12, 2021, in PCT Application No. PCT/US2021/044036.
International Search Report and Written Opinion dated Mar. 10, 2022, in PCT Application No. PCT/US2021/060206.
International Search Report and Written Opinion dated Apr. 12, 2022, in PCT Application No. PCT/US2021/059573.
International Search Report and Written Opinion dated Mar. 11, 2022, in PCT Application No. PCT/US2021/060197.
International Search Report and Written Opinion dated Apr. 5, 2022, in PCT Application No. PCT/US2021/062473.
International Search Report and Written Opinion dated Jun. 8, 2022, in PCT Application No. PCT/US2022/021015.
International Search Report and Written Opinion dated Jul. 29, 2022, in PCT Application No. PCT/US2022/029023.
International Search Report and Written Opinion dated Jul. 29, 2022, in PCT Application No. PCT/US2022/029057.
International Search Report and Written Opinion dated Dec. 5, 2022, in PCT Application No. PCT/US2022/075774.
International Search Report and Written Opinion dated Dec. 15, 2022, in PCT Application No. PCT/US2022/075655.
International Search Report and Written Opinion dated Dec. 20, 2022, in PCT Application No. PCT/US2022/075661.
International Search Report and Written Opinion dated Dec. 22, 2022, in PCT Application No. PCT/US2022/075577.
International Search Report and Written Opinion dated Jan. 9, 2023, in PCT Application No. PCT/US2022/076366.
International Search Report and Written Opinion dated Jan. 17, 2023, in PCT Application No. PCT/US2022/076056.
International Search Report and Written Opinion dated Feb. 13, 2023, in PCT Application No. PCT/US2022/075656.
International Search Report and Written Opinion dated Jun. 5, 2023, in PCT Application No. PCT/US2023/061980.
International Search Report and Written Opinion dated Jun. 23, 2023 in PCT Application No. PCT/US2023/062070.
Invitation to Pay Fees dated May 25, 2021 in PCT Application No. PCT/US2021/01598.
Invitation to Pay Additional Search Fees dated Sep. 8, 2021 in PCT Application No. PCT/US2021/032319.
Invitation to Provide Informal Clarification dated Jun. 9, 2021 in PCT Application No. PCT/US2021/019475.
Invitrogen, "The attraction is simply magnetisk, Dynabeads® Streptavidin products and applications" Invitrogen, 2010, 1-8.
Jacobsen et al., "33rd Annual Meeting & Pre-Conference Programs of the Society for Immunotherapy of Cancer," Journal for Immunotherapy of Cancer 2018, 6(S1), 7-11.
Janeway et al., "Structural variation in immunoglobulin constant regions," Immunology: The Immune System in Health and Disease 1999, 101-103.
Ku, et al. "Nucleic Acid Aptamers: An Emerging Tool for Biotechnology and Biomedical Sensing." Sensors, 2015, 15, 16281-16313.
Lake et al., "Integrative single-cell analysis of transcriptional and epigenetic states in the human adult brain," Nature Biotechnology 2018, 36(1), 70-80.
Lan et al., "Droplet barcoding for massively parallel single-molecule deep sequencing," Nature Communications 2016, 7(11784), in 10 pages.
Ko, "An 'equalized cDNA library' by the reassociation of short double-stranded cDNAs," Nucleic Acids Res. 1990, 18(19), 5705-5711.
Livingstone, "rRNA depletion, poly(A) enrichment, or exonuclease treatment?" Tebu-Bio Blog 2015,. 5 pgs.
Lutz et al., "Isolation and analysis of high quality nuclear DNA with reduced organellar DNA for plant genome sequencing and resequencing," BMC Biotechnology 2011, 11(54), in 9 pages.
Mair et al., "A Targeted Multi-omic Analysis Approach Measures Protein Expression and Low-Abundance Transcripts on the Single-Cell Level", Cell Reports 2020, 31(1), 107499, in 20 pages.
Mairal et al. "Aptamers: Molecular Tools for Analytical Applications." Analytical and bioanalytical chemistry 2008,390: 989-1007.
Mayer et al., "Obtaining deeper insights into microbiome diversity using a simple method to block host and nontargets in amplicon sequencing," Molecular Ecology Resources 2021, 21(6), 1952-1965.
Minnoye et al., "Chromatin accessibility profiling methods," Nature Reviews Method Primers 2021, 1-24.
Monneron, "One-step Isolation and Characterization of Nuclear Membranes, 1974 Electron Microscopy and Composition of Biological Membranes and Envelops," The Royal Publishing Society 1974, 268, 101-108.
Non-Final Office Action dated Dec. 4, 2020 in U.S. Appl. No. 16/677,012.
Non-Final Office Action dated Dec. 9, 2020 in U.S. Appl. No. 16/788,743.
Non-Final Office Action dated Jan. 19, 2021 in U.S. Appl. No. 16/836,750.
Non-Final Office Action dated Feb. 2, 2021 in U.S. Appl. No. 16/535,080.
Non-Final Office Action dated Feb. 25, 2021 in U.S. Appl. No. 15/055,407.
Non-Final Office Action dated Feb. 25, 2021 in U.S. Appl. No. 15/084,307.
Non-Final Office Action dated Mar. 29, 2021 in U.S. Appl. No. 16/789,358.
Non-Final Office Action dated Apr. 14, 2021 in U.S. Appl. No. 16/789,311.
Non-Final Office Action dated Apr. 20, 2021 in U.S. Appl. No. 15/875,816.
Non-Final Office Action dated May 18, 2021 in U.S. Appl. No. 16/535,080.
Non-Final Office Action dated Jun. 9, 2021 in U.S. Appl. No. 16/588,405.
Non-Final Office Action dated Aug. 17, 2021 in U.S. Appl. No. 16/551,620.
Non-Final Office Action dated Aug. 19, 2021 in U.S. Appl. No. 16/781,814.
Non-Final Office Action dated Aug. 31, 2021 in U.S. Appl. No. 15/715,028.
Non-Final Office Action dated Sep. 1, 2021 in U.S. Appl. No. 16/789,358.
Non-Final Office Action dated Sep. 14, 2021 in U.S. Appl. No. 16/707,780.
Non-Final Office Action dated Sep. 28, 2021 in U.S. Appl. No. 16/400,885.
Non-Final Office Action dated Sep. 30, 2021 in U.S. Appl. No. 16/374,626.
Non-Final Office Action dated Oct. 1, 2021 in U.S. Appl. No. 16/677,012.
Non-Final Office Action dated Oct. 8, 2021 in U.S. Appl. No. 16/400,866.
Non-Final Office Action dated Dec. 15, 2021 in U.S. Appl. No. 15/875,816.
Non-Final Office Action dated Dec. 21, 2021 in U.S. Appl. No. 15/055,407.
Non-Final Office Action dated Jan. 6, 2022 in U.S. Appl. No. 15/084,307.

(56) References Cited

OTHER PUBLICATIONS

Non-Final Office Action dated Feb. 3, 2022 in U.S. Appl. No. 16/747,737.
Non-Final Office Action dated Feb. 9, 2022 in U.S. Appl. No. 16/525,054.
Non-Final Office Action dated Apr. 5, 2022 in U.S. Appl. No. 16/400,885.
Non-Final Office Action dated Apr. 8, 2022 in U.S. Appl. No. 16/232,287.
Non-Final Office Action dated May 3, 2022 in U.S. Appl. No. 16/012,584.
Non-Final Office Action dated May 11, 2022 in U.S. Appl. No. 16/588,405.
Non-Final Office Action dated May 19, 2022 in U.S. Appl. No. 16/459,444.
Non-Final Office Action dated Jul. 7, 2022 in U.S. Appl. No. 16/788,743.
Non-Final Office Action dated Jul. 7, 2022 in U.S. Appl. No. 16/677,012.
Non-Final Office Action dated Jul. 18, 2022 in U.S. Appl. No. 16/551,620.
Non-Final Office Action dated Jul. 27, 2022 in U.S. Appl. No. 16/747,737.
Non-Final Office Action dated Oct. 13, 2022 in U.S. Appl. No. 17/147,272.
Non-Final Office Action dated Nov. 17, 2022 in U.S. Appl. No. 16/551,638.
Non-Final Office Action dated Dec. 8, 2022 in U.S. Appl. No. 16/934,530.
Non-Final Office Action dated Dec. 21, 2022 in U.S. Appl. No. 15/055,407.
Non-Final Office Action dated Jan. 10, 2023 in U.S. Appl. No. 17/163,177.
Non-Final Office Action dated Jan. 19, 2023 in U.S. Appl. No. 17/091,639.
Non-Final Office Action dated Jan. 23, 2023 in U.S. Appl. No. 17/183,840.
Non-Final Office Action dated Jan. 24, 2023 in U.S. Appl. No. 17/157,872.
Non-Final Office Action dated Feb. 10, 2023 in U.S. Appl. No. 17/390,640.
Non-Final Office Action dated Feb. 23, 2023 in U.S. Appl. No. 17/408,374.
Non-Final Office Action dated Mar. 13, 2023 in U.S. Appl. No. 17/151,050.
Non-Final Office Action dated Apr. 26, 2023 in U.S. Appl. No. 16/540,971.
Non-Final Office Action dated Apr. 26, 2023 in U.S. Appl. No. 16/374,626.
Non-Final Office Action dated Jun. 14, 2023 In U.S. Appl. No. 17/174,249.
Non-Final Office Action dated Jun. 30, 2023 In U.S. Appl. No. 17/684,289.
Non-Final Office Action dated Jul. 27, 2023 in U.S. Appl. No. 17/373,519.
Non-Final Office Action dated Sep. 21, 2023 in Canadian Patent Application No. 3,034,924.
Non-Final Office Action dated Sep. 28, 2023 in U.S. Appl. No. 16/789,311.
Non-Final Office Action Dated Sep. 28, 2023 in U.S. Appl. No. 17/184,405.
Non-Final Office Action Dated Oct. 5, 2023 in U.S. Appl. No. 16/848,241.
Non-Final Office Action Dated Nov. 7, 2023 in U.S. Appl. No. 17/528,104.
Notice of Allowance dated Jan. 13, 2021 in U.S. Appl. No. 14/381,488.
Notice of Allowance dated Jan. 13, 2021 in U.S. Appl. No. 15/459,977.
Notice of Allowance dated Apr. 26, 2021 in Japanese Patent Application No. 2019-014564.
Notice of Allowance dated Aug. 16, 2021 in Japanese Patent Application No. 2018-512152.
Notice of Allowance dated Nov. 16, 2021 in U.S. Appl. No. 16/836,750.
Notice of Allowance dated Jan. 24, 2022 in Korean Patent Application No. 16/836,750.
Notice of Allowance dated Feb. 9, 2022 in U.S. Appl. No. 16/781,814.
Notice of Allowance dated Feb. 11, 2022 in Chinese Patent Application No. 201680007351.2.
Notice of Allowance dated Feb. 16, 2022 in U.S. Appl. No. 15/875,816.
Notice of Allowance dated Feb. 21, 2022 in Korean Patent Application No. 10-2020-7033213.
Notice of Allowance dated Apr. 11, 2022 in U.S. Appl. No. 15/134,967.
Notice of Allowance dated Apr. 25, 2022 in Korean Patent Application No. 10-2018-7008560.
Notice of Allowance dated Apr. 26, 2022 in Chinese Patent Application No. 201780058799.1.
Notice of Allowance dated Apr. 27, 2022 in U.S. Appl. No. 16/400,886.
Notice of Allowance dated May 9, 2022 in Australian Patent Application No. 2018281745.
Notice of Allowance dated May 15, 2022 in Japanese Patent Application No. 2019-540515.
Notice of Allowance dated May 23, 2022 in U.S. Appl. No. 15/715,028.
Notice of Allowance dated May 26, 2022 in Korean Patent Application No. 10-2019-7038794.
Notice of Allowance dated Jun. 6, 2022 in U.S. Appl. No. 16/789,358.
Notice of Allowance dated Jul. 20, 2022 in U.S. Appl. No. 16/707,780.
Notice of Allowance dated Aug. 9, 2022 in U.S. Appl. No. 16/232,287.
Notice of Allowance dated Sep. 26, 2022, 2022 in U.S. Appl. No. 16/232,287.
Notice of Allowance dated Oct. 17, 2022, 2022 in U.S. Appl. No. 16/400,885.
Notice of Allowance dated Oct. 20, 2022 in Australian Patent Application No. 2019204928.
Notice of Allowance dated Oct. 21, 2022 in European Patent Application No. 19762517.1.
Notice of Allowance dated Oct. 24, 2022 in European Patent Application No. 20708266.0.
Notice of Allowance dated Oct. 25, 2022 in European Patent Application No. 19724003.9.
Notice of Allowance dated Nov. 7, 2022 in U.S. Appl. No. 16/012,584.
Notice of Allowance dated Jan. 10, 2023 in U.S. Appl. No. 16/588,405.
Notice of Allowance dated Jan. 19, 2023 in Korean Patent Application No. 10-2022-7004715.
Notice of Allowance dated Jan. 31, 2023 in U.S. Appl. No. 16/747,737.
Notice of Allowance dated Feb. 1, 2023 in U.S. Appl. No. 17/147,272.
Notice of Allowance dated Feb. 21, 2023 in Korean Patent Application No. 10-2022-7017261.
Notice of Allowance dated Mar. 1, 2023 in U.S. Appl. No. 17/192,814.
Notice of Allowance dated Mar. 10, 2023 in European Patent Application No. 19762517.1.
Notice of Allowance dated Mar. 10, 2023 in European Patent Application No. 20708266.0.
Notice of Allowance dated Mar. 10, 2023 in European Patent Application No. 19724003.9.
Notice of Allowance dated Mar. 13, 2023 in European Patent Application No. 17781265.8.
Notice of Allowance dated Apr. 4, 2023 in Australian Patent Application No. 2017331459.
Notice of Allowance dated Jun. 8, 2023 in U.S. Appl. No. 16/459,444.
Notice of Allowance dated Aug. 23, 2023 in Canadian Patent Application No. 2,865,575.
Notice of Allowance dated Aug. 25, 2023 in European Patent Application No. 22 200 785.8.
Notice of Allowance dated Aug. 28, 2023 in U.S. Appl. No. 16/374,626.
Notice of Allowance dated Sep. 14, 2023 in Canada Application No. 2982467.

(56) References Cited

OTHER PUBLICATIONS

Notice of Allowance dated Sep. 29, 2023 in European Application No. 22165594.7.
Notice of Allowance dated Oct. 2, 2023 in European Application 21735067.8.
Notice of Allowance dated Oct. 25, 2023 in European Application 20816802.1.
Novus Biologicals, "Fixation and Permeability in ICC IF," Novus Biologicals 2021, 1-3.
Nowak et al., "Does the KIR2DS5 gene protect from some human diseases?," PLoS One 2010, 5(8), in 6 pages.
Office Action dated Jan. 4, 2021 in Japanese Patent Application No. 2017-549390.
Office Action dated Jan. 6, 2021 in Chinese Patent Application No. 201680052330.2.
Office Action dated Jan. 14, 2021 in Japanese Patent Application No. 2019-014564.
Office Action dated Jan. 15, 2021 in Korean Patent Application No. 10-2020-7033213.
Office Action dated Jan. 26, 2021 in Chinese Patent Application No. 201680007351.2.
Office Action dated Feb. 4, 2021 in Canadian Patent Application No. 2,865,575.
Office Action dated Feb. 20, 2021 in Chinese Patent Application No. 201680022865.5.
Office Action dated Mar. 1, 2021 in Chinese Patent Application No. 201680007652.5.
Office Action dated Mar. 2, 2021 in Chinese Patent Application No. 2016800157452.
Office Action dated Mar. 8, 2021 in Japanese Patent Application No. 2018-512152.
Office Action dated Mar. 16, 2021 in Chinese Patent Application No. 2018800377201.
Office Action dated May 10, 2021 in Japanese Patent Application No. 2019-566787.
Office Action dated May 21, 2021 in Chinese Patent Application No. 201680007351.2.
Office Action dated Jul. 26, 2021 in Korean Patent Application No. 10-2019-7011635.
Office Action dated Jul. 28, 2021 in Korean Patent Application No. 10-2020-7033213.
Office Action dated Aug. 13, 2021 in Chinese Patent Application No. 2017800587991.
Office Action dated Aug. 27, 2021 in Chinese Patent Application No. 2016800076525.
Office Action dated Aug. 30, 2021 in Japanese Patent Application No. 2019-540515.
Office Action dated Aug. 31, 2021 in Chinese Patent Application No. 2016800157452.
Office Action dated Aug. 31, 2021, in Korean Patent Application No. 10-2019-7038794.
Office Action dated Sep. 14, 2021, in Chinese Patent Application No. 2016800523302.
Office Action dated Oct. 21, 2021, in Chinese Patent Application No. 2016800073512.
Office Action dated Nov. 2, 2021, in Japanese Patent Application No. 2017-549390.
Office Action dated Dec. 23, 2021, in Japanese Patent Application No. 2019-566787.
Office Action dated Dec. 17, 2021 in Korean Patent Application No. 10-2018-7008560.
Office Action dated Jan. 13, 2022 in Chinese Patent Application 2017800587991.
Office Action dated Feb. 9, 2022 in Japanese Patent Application No. 2019-540515.
Office Action dated Feb. 23, 2022 in Chinese Patent Application No. 2016800523302.
Office Action dated Mar. 7, 2022 in Korean Patent Application No. 10-2022-7004715.
Office Action dated May 2, 2022 in European Patent Application No. 19787547.9.
Office Action dated May 17, 2022 in Australian Patent Application No. 2019204928.
Office Action dated May 24, 2022 in European Patent Application No. 20708266.0.
Office Action dated Jun. 28, 2022 in European Patent Application No. 16719706.0.
Office Action dated Aug. 2, 2022 in European Patent Application No. 19765601.0.
Office Action dated Aug. 1, 2022 in Korean Patent Application No. 10-2022-7017261.
Office Action dated Sep. 21, 2022 in Israel Patent Application No. 265478.
Office Action dated Jan. 30, 2023 in European Patent Application No. 19752792.2.
Office Action dated Feb. 8, 2023 in Australian Patent Application No. 2017331459.
Office Action dated Feb. 20, 2023 in European Patent Application No. 19723988.2.
Office Action dated Feb. 23, 2023 in European Patent Application No. 20816802.1.
Office Action dated Feb. 28, 2023 in Chinese Patent Application No. 2019111653930.
Office Action dated Nov. 24, 2022 in Chinese Patent Application No. 2018800147939.
Office Action dated Mar. 15, 2023 in European Patent Application No. 19787547.9.
Office Action dated Mar. 27, 2023 in European Patent Application No. 19836036.4.
Office Action dated Mar. 29, 2023 in Chinese Patent Application No. 2020800144092.
Office Action dated Apr. 10, 2023 in Japanese Patent Application No. 2022-030956.
Office Action dated Apr. 14, 2023 in Chinese Patent Application No. 201980082680.7.
Office Action dated Apr. 24, 2023 in Japanese Patent Application No. 2020-561800.
Office Action dated Apr. 24, 2023 in European Patent Application No. 21714995.4.
Office Action dated Apr. 26, 2023 in European Patent Application No. 18703156.2.
Office Action dated May 16, 2023 in European Patent Application No. 21707112.5.
Office Action dated May 26, 2023 in Chinese Patent Application No. 2019800373421.
Office Action dated May 27, 2023 in Chinese Patent Application No. 2019800656859.
Office Action dated May 30, 2023 in Chinese Patent Application No. 2019800653102.
Office Action dated Jun. 1, 2023 in Japanese Patent Application No. 2020-561807.
Office Action dated Jun. 16, 2023 in Chinese Patent Application No. 2019800708938.
Office Action dated Jun. 22, 2023 in Japanese Patent Application No. 2022-071002.
Office Action dated Jun. 28, 2023 in European Patent Application 19836239.4.
Office Action dated Jul. 12, 2023 in Chinese Patent Application No. 2020800212600.
Office Action dated Jul. 12, 2023 in Canadian Patent Application No. 3,059,559.
Office Action Dated Jul. 13, 2023 in Chinese Patent Application No. 202080077712.7.
Office Action dated Jul. 28, 2023 in Chinese Patent Application No. 201880014793.9.
Office Action dated Jul. 29, 2023 in Chinese Patent Application No. 201980073850.5.
Office Action dated Jul. 31, 2023 in Chinese Patent Application No. 201980068704.3.
Office Action dated Jul. 31, 2023 in Chinese Patent Application No. 201980037175.0.

(56) References Cited

OTHER PUBLICATIONS

Office Action dated Aug. 11, 2023 in European Patent Application 19752792.2.
Office Action dated Aug. 21, 2023 in Japanese Patent Application No. 2021-507836.
Office Action dated Aug. 30, 2023 in Chinese Patent Application 2019111653930.
Office Action dated Aug. 31, 2023 in Chinese Patent Application 2020800483617.
Office Action dated Sep. 21, 2023 in Japanese Patent Application 2022-030956.
Office Action dated Sep. 21, 2023 in Israel Patent Application 265478.
Office Action dated Oct. 10, 2023 in European Patent Application 16719706.0.
Office Action dated Oct. 13, 2023 in Chinese Patent Application 202080014409.2.
Office Action dated Oct. 19, 2023 in Japanese Patent Application 2019-566787.
Office Action dated Oct. 23, 2023 in Japanese Patent Application 2021-517856.
Office Action dated Oct. 26, 2023 In Japanese Patent Application 2022-525692.
Office Action Dated Oct. 30, 2023 in Japanese Patent Application 2021-523956.
Office Action Dated Nov. 9, 2023 in Japanese Patent Application 2017-549390.
Ogawa, T. et al., "The Efficacy and further functional advantages of random-base molecular barcodes for absolute and digital quantification of nucleic acid molecules", Sci Rep 7, 2017 12576.
O'Shea et al., "Analysis of T Cell Receptor Beta Chain CDR3 Size Using RNA Extracted from Formalin Fixed Paraffin Wax Embedded Tissue," Journal of Clinical Pathology 1997, 50(10), 811-814.
Prevette et al., "Polycation-Induced Cell Membrane Permeability Does Not Enhance Cellular Uptake or Expression Efficiency of Delivered DNA," Molecular Pharmaceutics 2010, 7(3), 870-883.
Pringle et al., "In Situ Hybridization Demonstration of Poly-Adenylated RNA Sequences in Formalin-Fixed Parafin Sections Using a Biotinylated Oligonucleotide Poly d(T) Probe," Journal of Pathology 1989, 158, 279-286.
Quail et al., "SASI-Seq: sample assurance Spike-Ins, and highly differentiating 384 barcoding for Illumina sequencing," BMC Genomics 2014, 15(110), in 13 pages.
Restriction Requirement dated Jun. 4, 2021 in U.S. Appl. No. 16/551,620.
Restriction Requirement dated Aug. 8, 2022 in U.S. Appl. No. 17/163,177.
Restriction Requirement dated Aug. 11, 2022 in U.S. Appl. No. 17/091,639.
Restriction Requirement dated Aug. 19, 2022 in U.S. Appl. No. 17/147,283.
Restriction Requirement dated Sep. 16, 2022 in U.S. Appl. No. 17/151,050.
Restriction Requirement dated Sep. 19, 2022 in U.S. Appl. No. 16/934,530.
Restriction Requirement dated Oct. 21, 2022 in U.S. Appl. No. 17/320,052.
Restriction Requirement dated Nov. 8, 2022 in U.S. Appl. No. 17/157,872.
Restriction Requirement dated Dec. 23, 2022 in U.S. Appl. No. 17/531,618.
Restriction Requirement dated Jan. 20, 2023 in U.S. Appl. No. 17/373,519.
Restriction Requirement dated Feb. 27, 2023 in U.S. Appl. No. 17/151,058.
Restriction Requirement dated Apr. 3, 2023 in U.S. Appl. No. 17/161,558.
Restriction Requirement dated Jun. 28, 2023 in U.S. Appl. No. 17/336,055.
Restriction Requirement dated Oct. 5, 2023 in U.S. Appl. No. 17/373,653.
Restriction Requirement dated Oct. 11, 2023 in U.S. Appl. No. 17/531,555.
Schouten et al., "Relative quantification of 40 nucleic acid sequences by multiplex ligation-dependent probe amplification," Nucleic Acids Research 2002, 30(12), e57.
Shapiro et al., "Single-cell sequencing-based technologies will revolutionize whole-organism science," Nature Reviews Genetics 2013, 14, 618-629.
Song et al., DNase-seq: a high-resolution technique for mapping active gene regulatory elements across the genome from mammalian cells, Cold Spring Harb Protoc 2010, 2, in 13 pages.
Sos et al., "Characterization of chromatin accessibility with a transposome hypersensitive sites sequencing (THS-seq) assay," Genome Biology 2016, 17(20), in 15 pages.
Spanova et al., "Magnetic hydrophilic methacrylate-based polymer microspheres designed for polymerase chain reaction applications", Journal of Chromatography vol. 800, 2004, 27-32.
Stoeckius et al., "Cell Hashing with barcoded antibodies enables multiplexing and doublet detection for single cell genomics," Genome Biology 2018, 19(224), 1-12.
Summons to Attend Oral Proceedings dated Nov. 16, 2020 in European Patent Application No. 17202409.3.
Summons to Attend Oral Proceedings Dated Aug. 8, 2023 in European Patent Application No. 14749671.5.
Takara Bio, "SMARTer Human BCR IgG IgM H/K/L Profiling Kit User Manual," Takara Bio USA Inc. 2019, 1-22.
TotalSeq™-A0251 anti-human Hashtag 1 Antibody, BioLegend®, Jul. 2018, 1-10.
Trzupek et al., "Discovery of CD8O and CD86 as recent activation markers on regulatory T cells by protein-RNA single-cell analysis", Genome Medicine 2020, 12(1), in 22 pages.
Uellendahl-Werth et al., "A benchmark of hemoglobin blocking during library preparation for mRNA Sequencing of human blood samples," Scientific Reports 2020, 10(1), 5630.
Vestheim et al., "Application of Blocking Oligonucleotides to Improve Signal-to-Noise Ratio in a PCR," Methods in Molecular Biology 2011, 687, 265-274.
Wang et al., "Development of Multicolor Flow Cytometry Calibration Standards: Assignment of Equivalent Reference Fluorophores (ERF) Unit" J. Res. Natl. Inst. Stand. Technol. 2011 116, 671-683.
Wang et al., "Tagmentation-based whole-genome bisulfite sequencing," Nature Protocols 2013, 8(10), 2022-2032.
Wangsanuwat et al., "Efficient and cost-effective bacterial mRNA sequencing from low input samples through ribosomal RNA depletion," BMC Genomics 2020, 21(1), 1-12.
Wu & Lambowitz, "Facile single-stranded DNA sequencing of human plasma DNA via thermostable group II intron reverse transcriptase template switching," Scientific Reports 2017, 7(8421), 1-14.
Yang & Zhao, "Quantitative Analysis of Nonoxynol-9 in Blood," Contraception 1991, 43(2), 161-166.
Zeberg et al., "The major genetic risk factor for severe COVID-19 is inherited from Neanderthals," Nature 2020, 587(7835), 1-13.
Zhang et al., "Immunoaffinity Purification of Plasma Membrane with Secondary Antibody Superparamagnetic Beads," Journal of Proteome 2006, 6, 34-43.
Zheng, et al. "Aptamer-Functionalized Barcode Particles for the Capture and Detection of Multiple Types of Circulating Tumor Cells." Advanced materials (Weinheim), 2014, 26, 7333-7338.
Zhou and Rossi. "Aptamers as Targeted Therapeutics: Current Potential and Challenges." Nature reviews. Drug discovery, 2017, 16:181-202.
Zhulidov et al., "Simple cDNA normalization using kamchatka crab duplex-specific nuclease," Nucleic Acids Research. 2004, 32(3)e37.

* cited by examiner

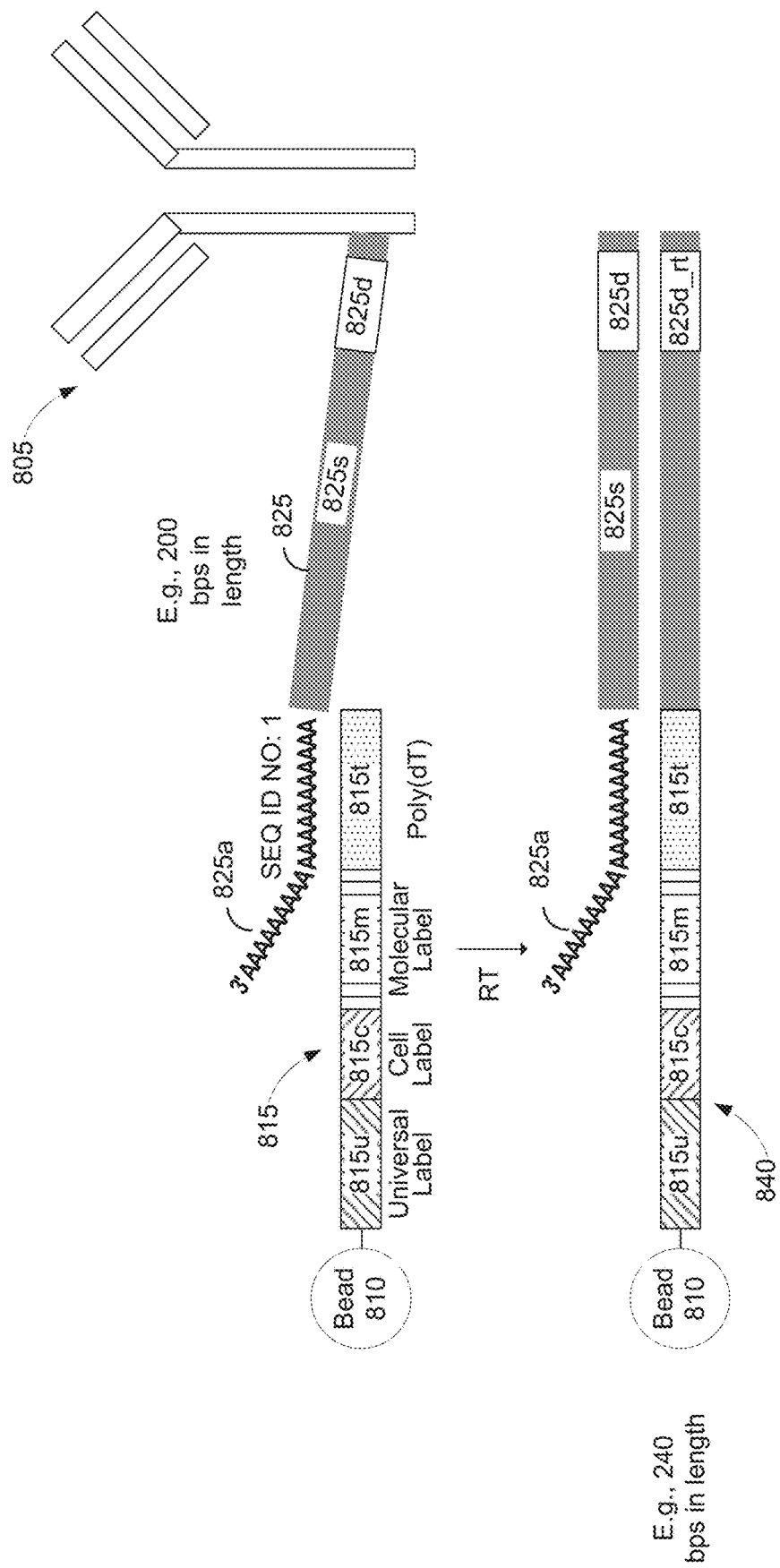
FIG. 8A1

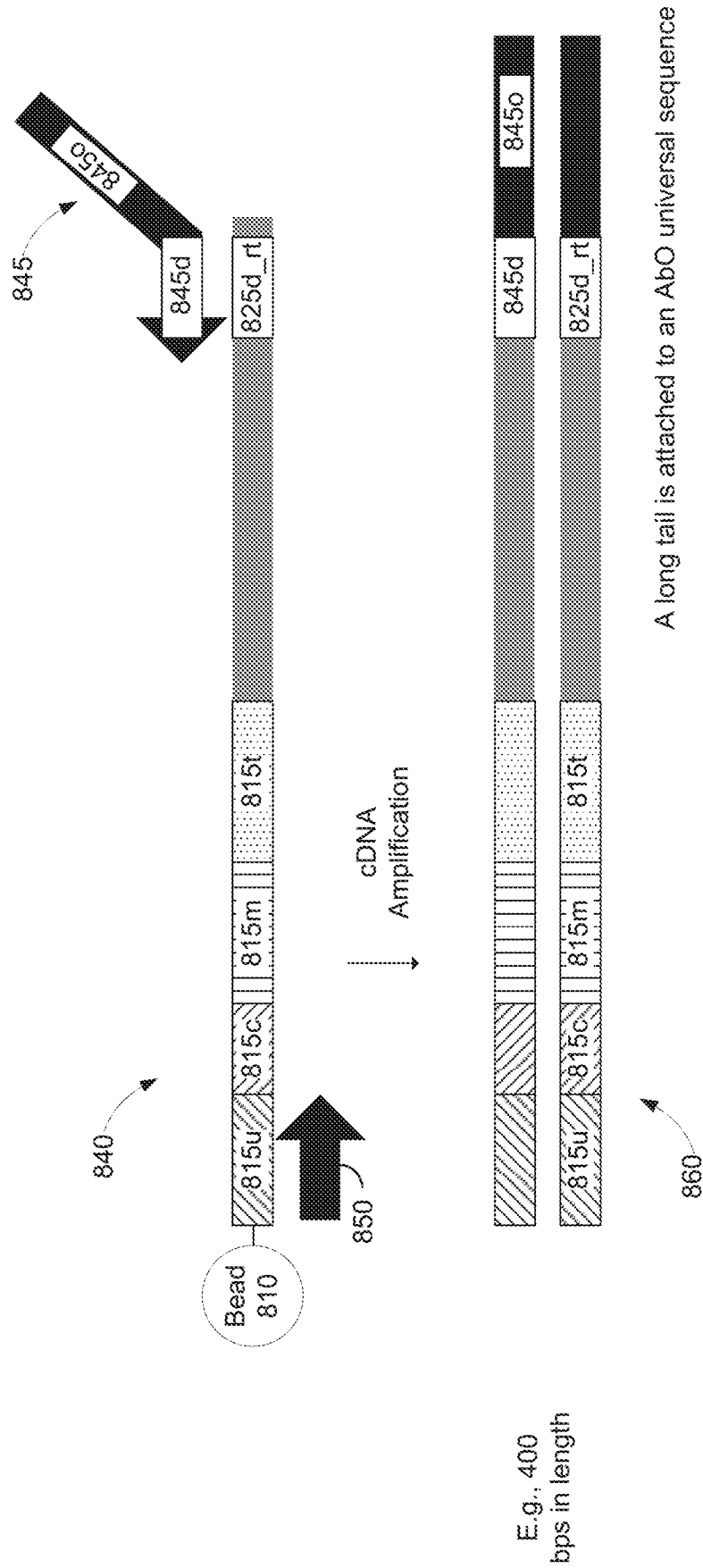
FIG. 8A2

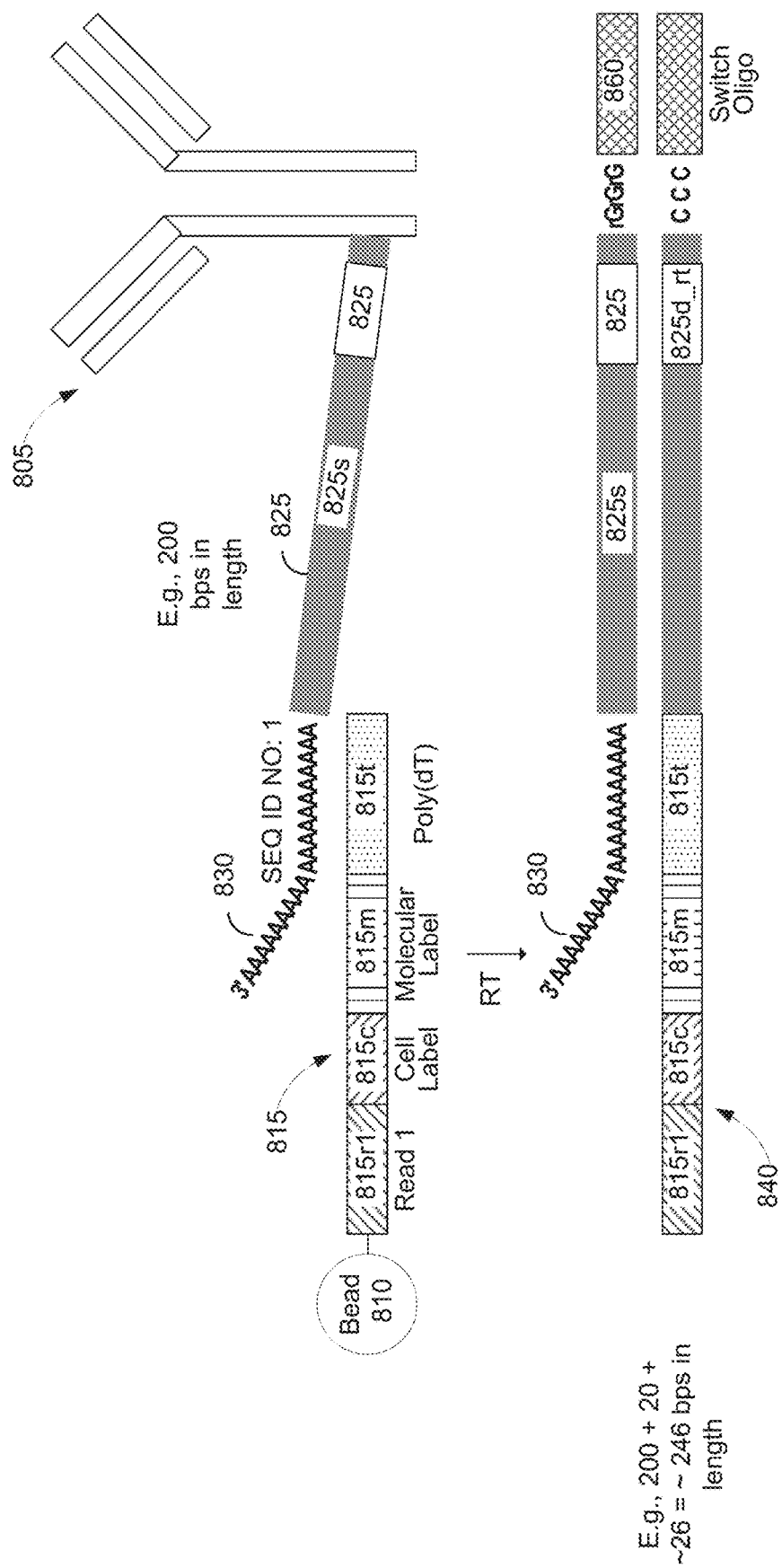
FIG. 8B1

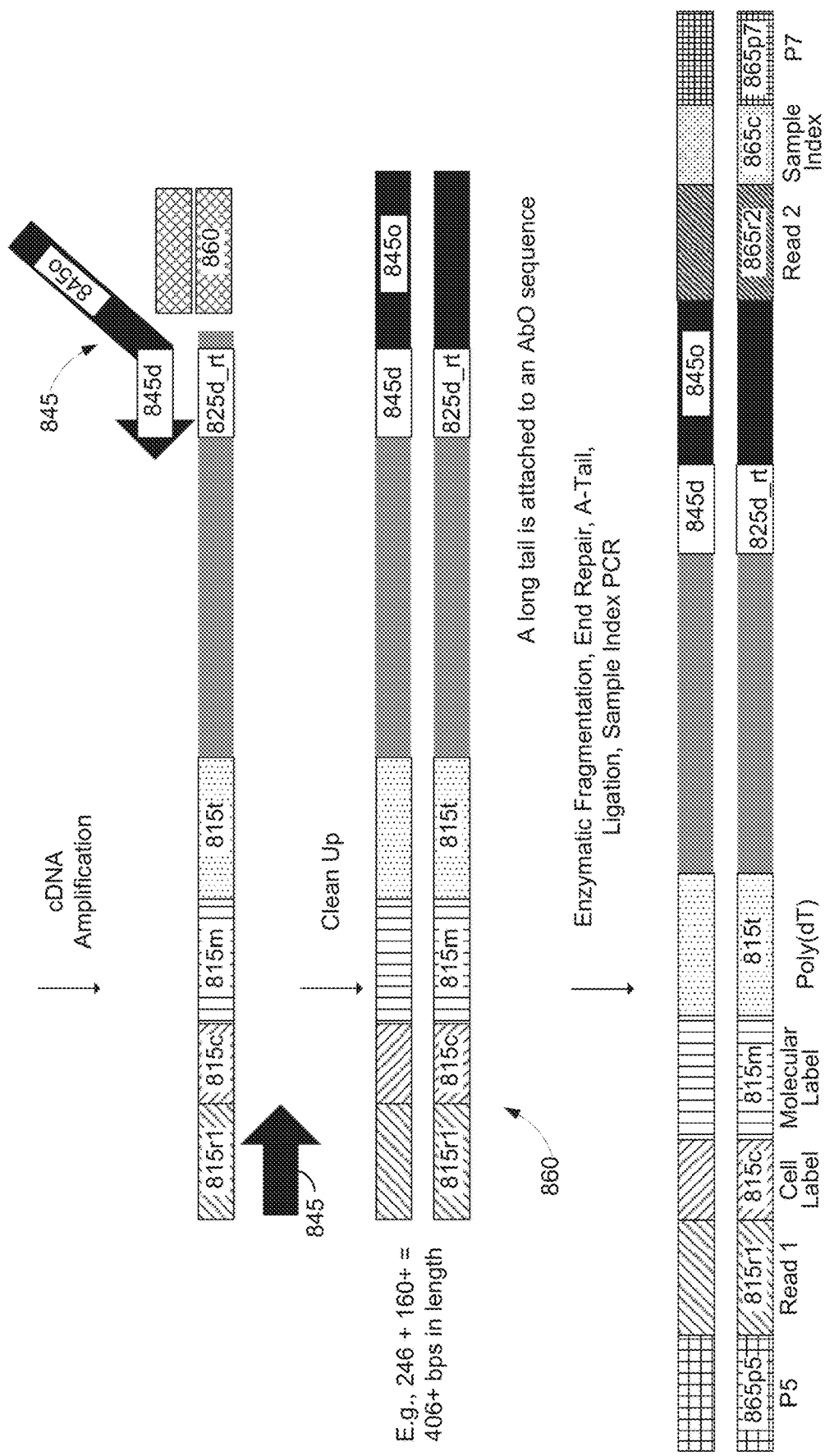
FIG. 8B2

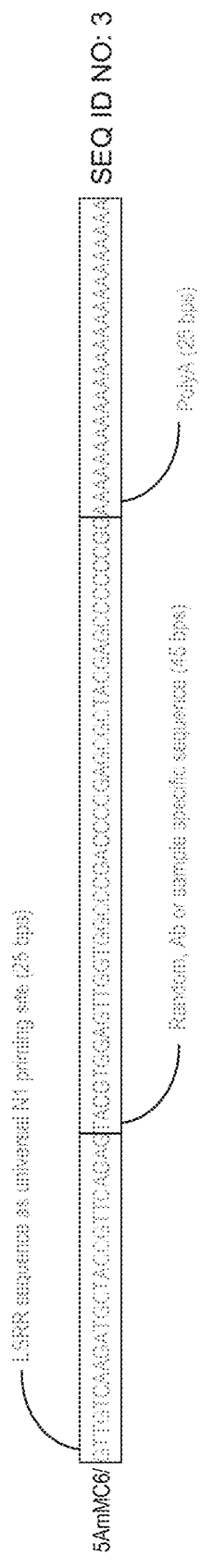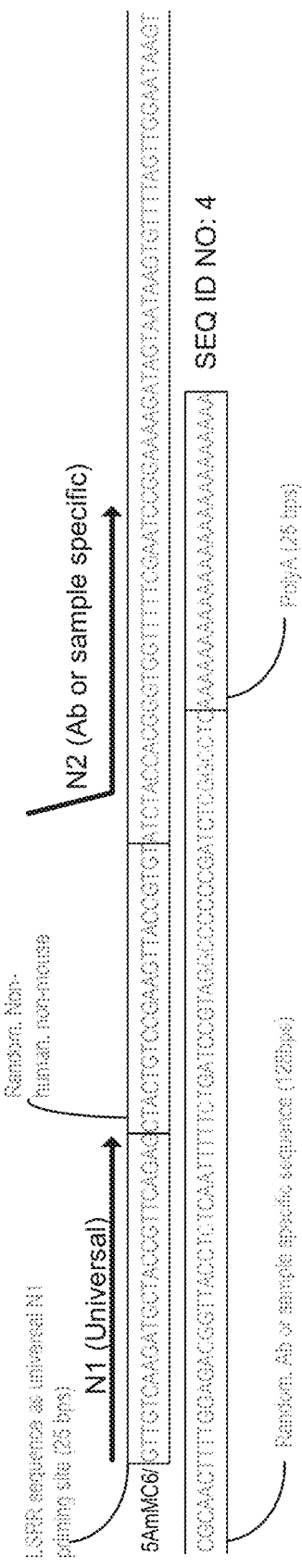

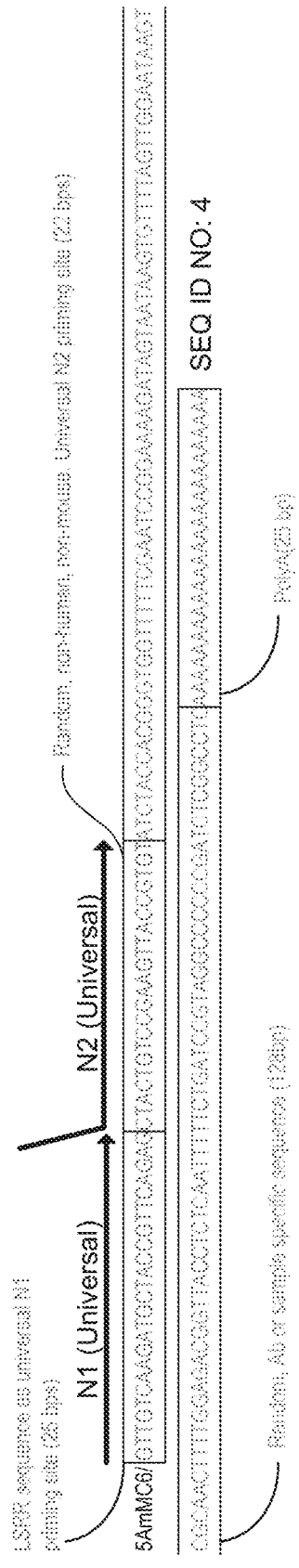
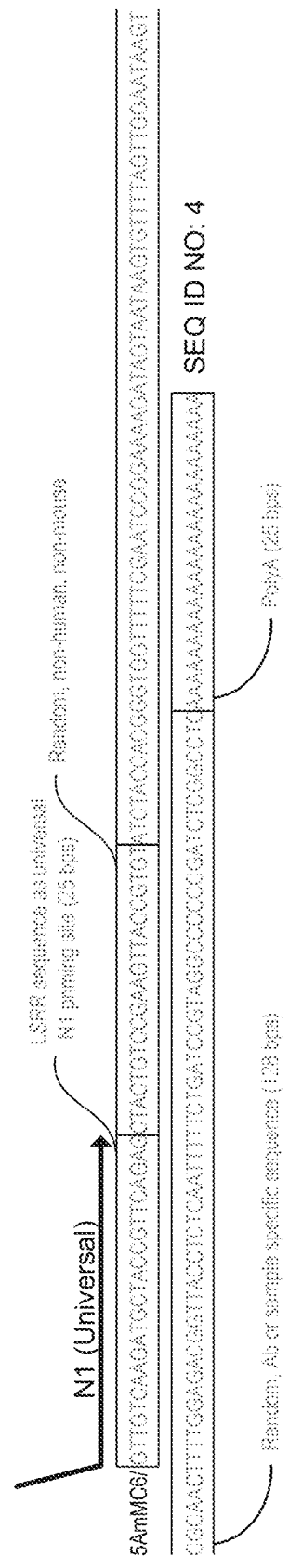

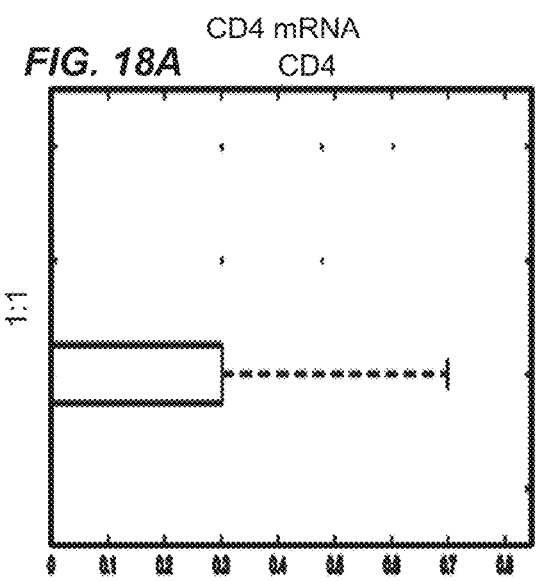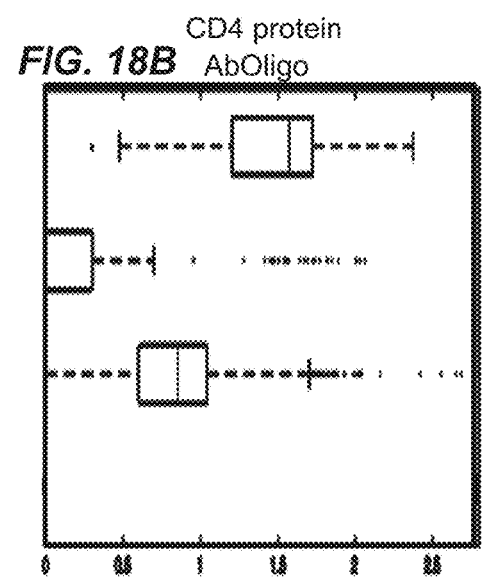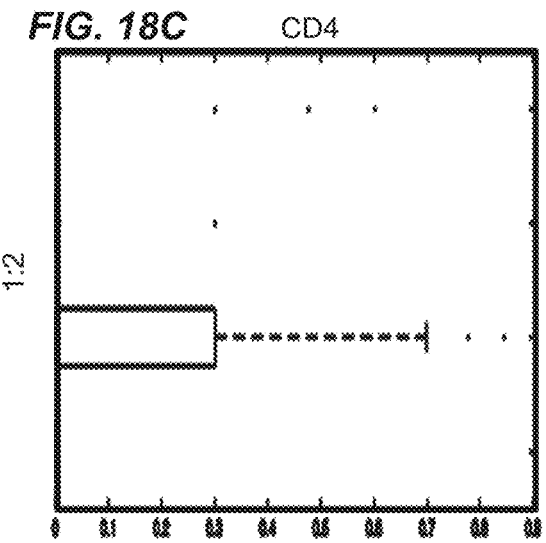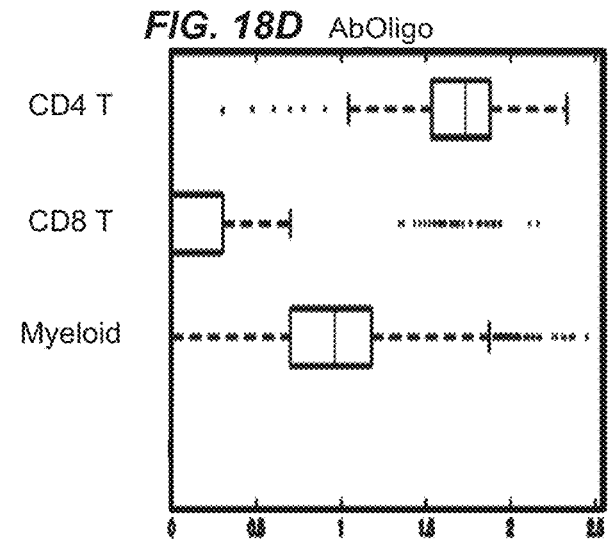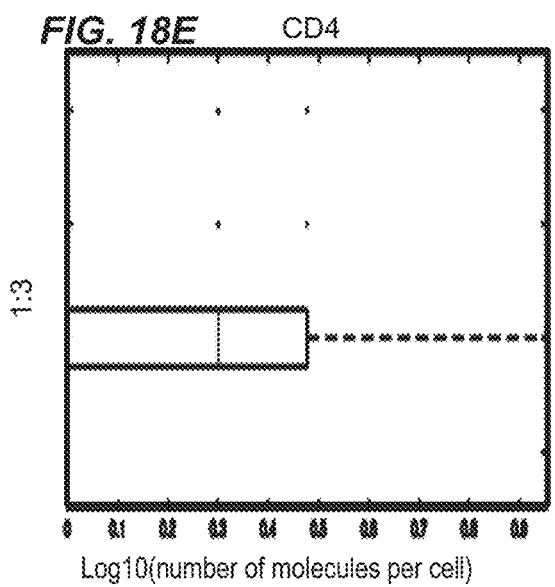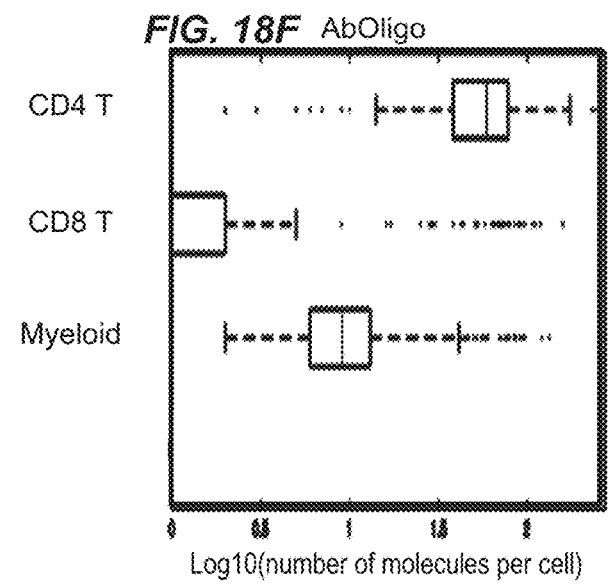
Log10(number of molecules per cell)      Log10(number of molecules per cell)

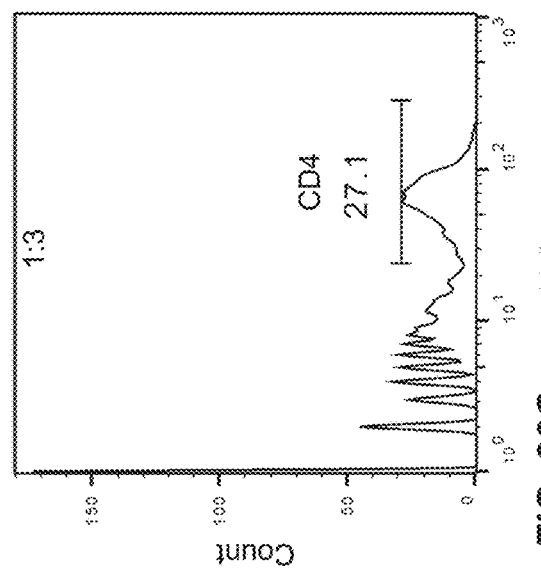
FIG. 20A  FIG. 20B  FIG. 20C
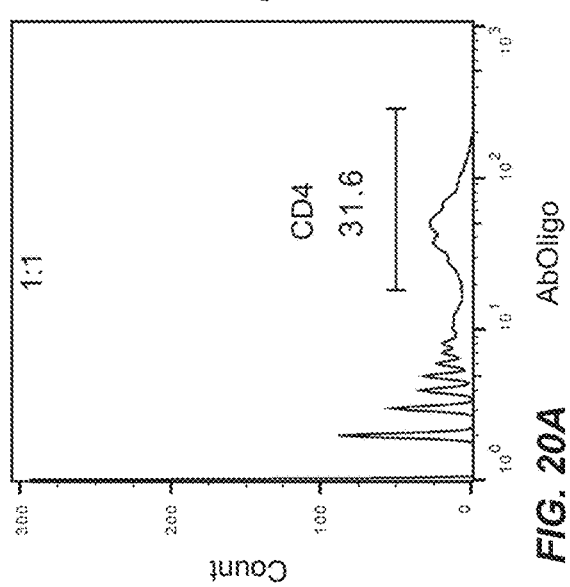
FIG. 20D
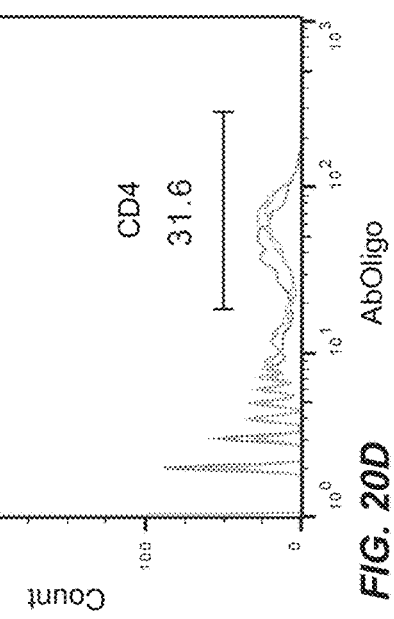

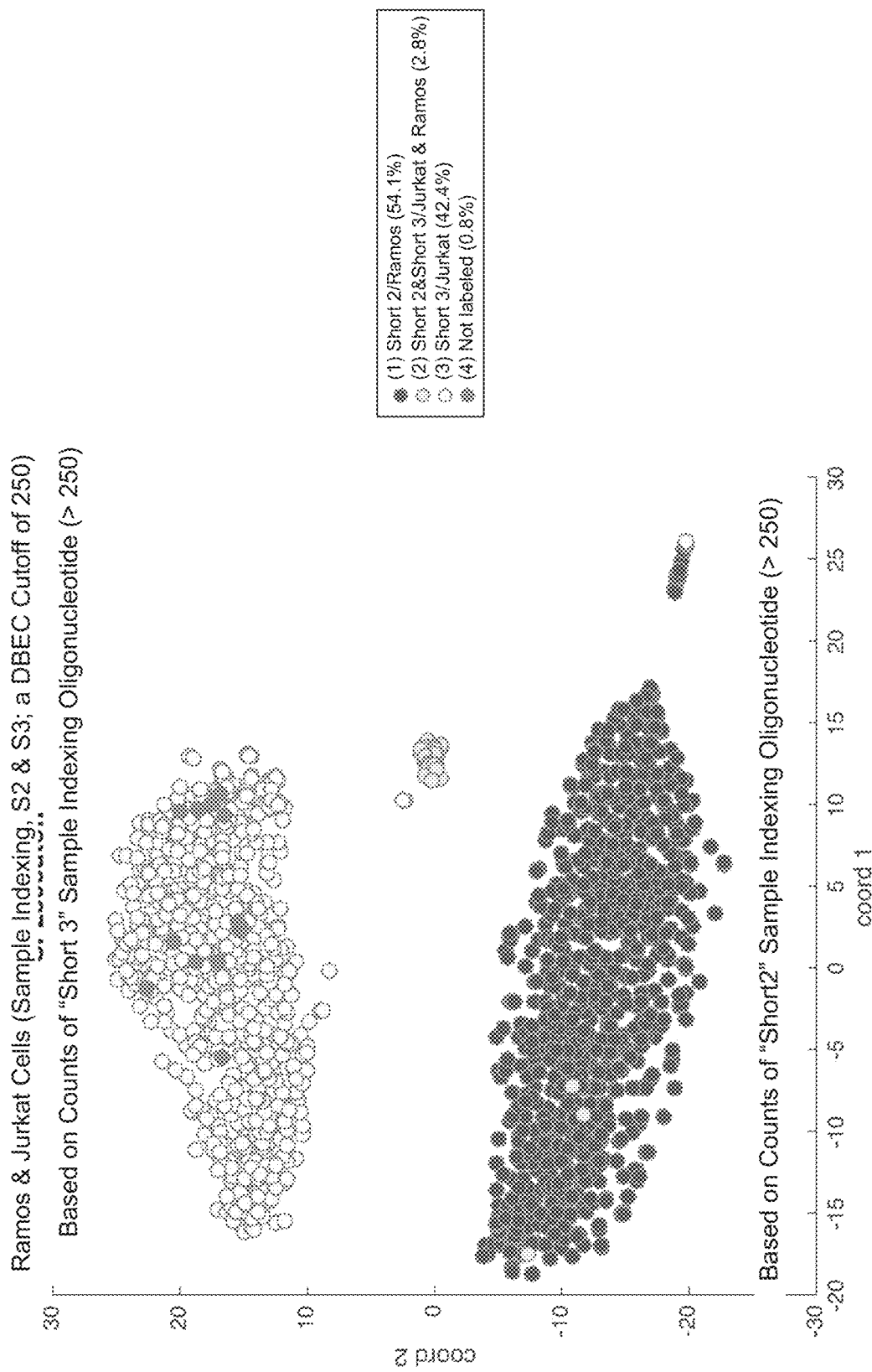

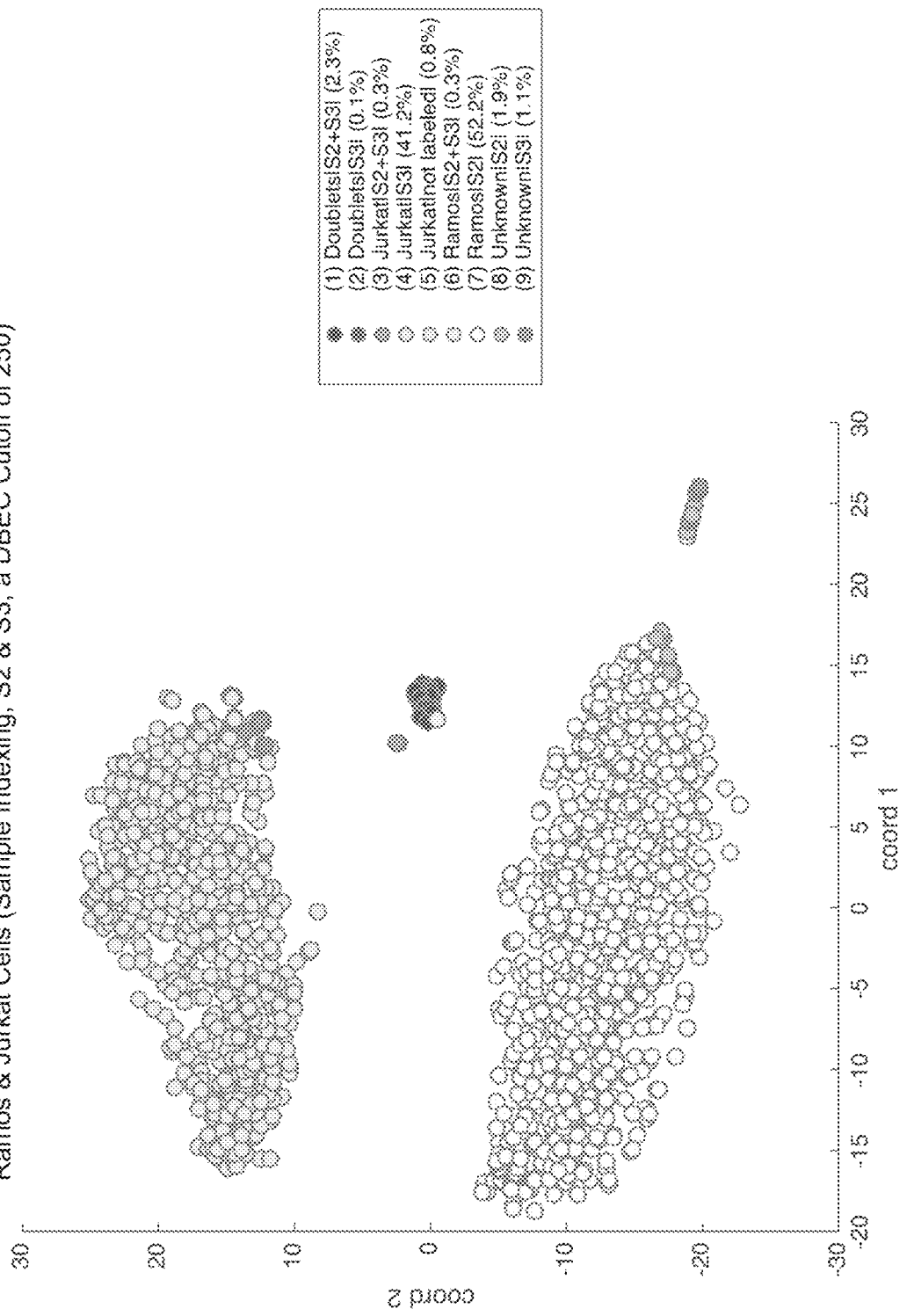

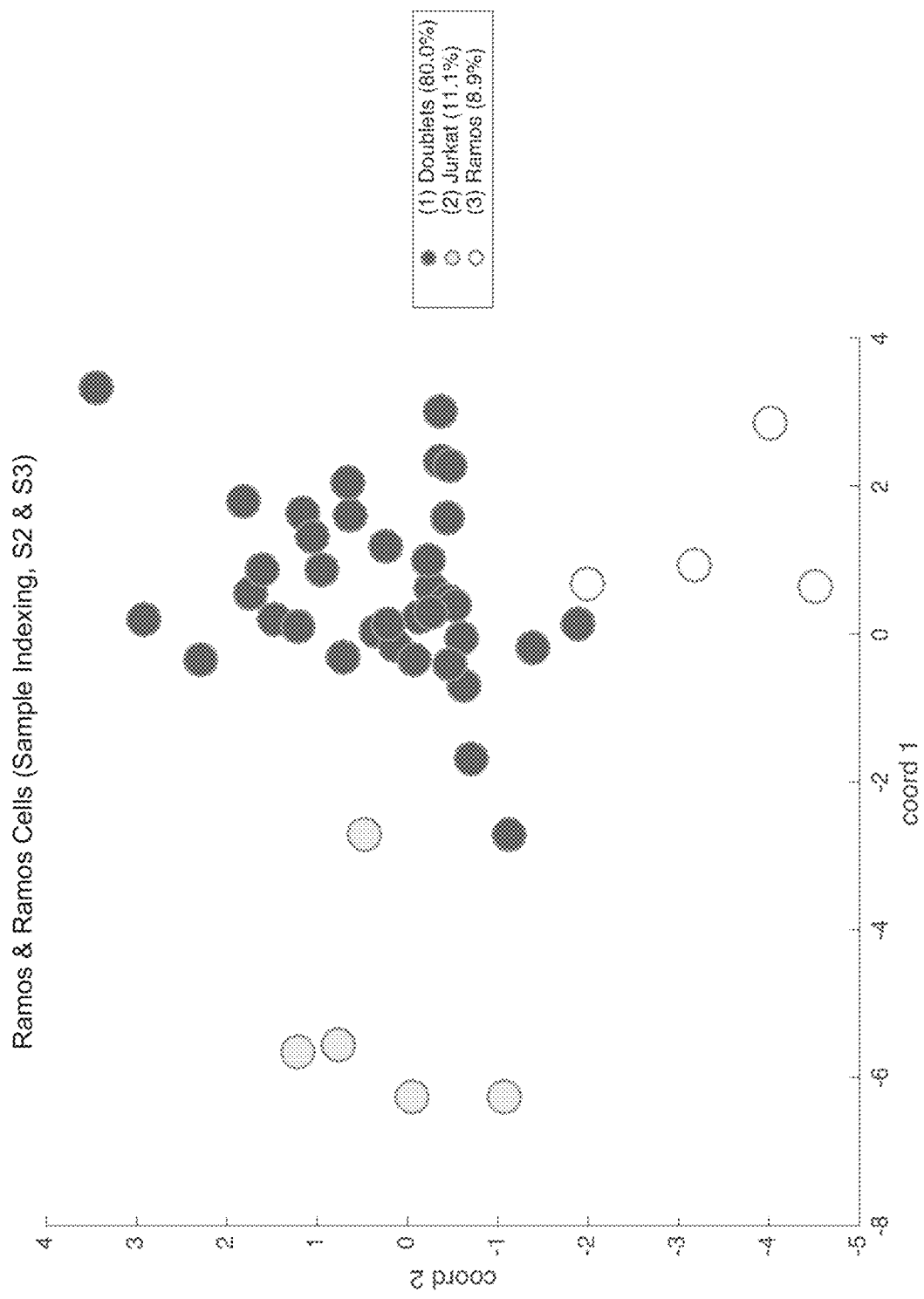

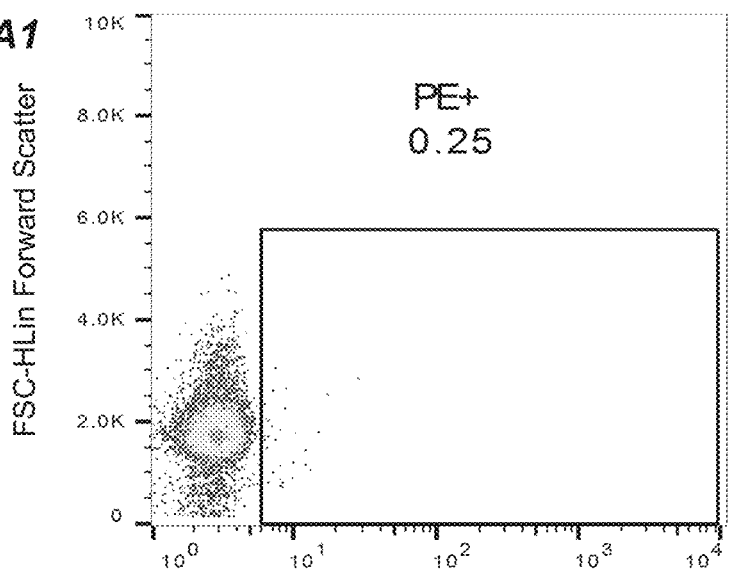
FIG. 36A1
No stain control
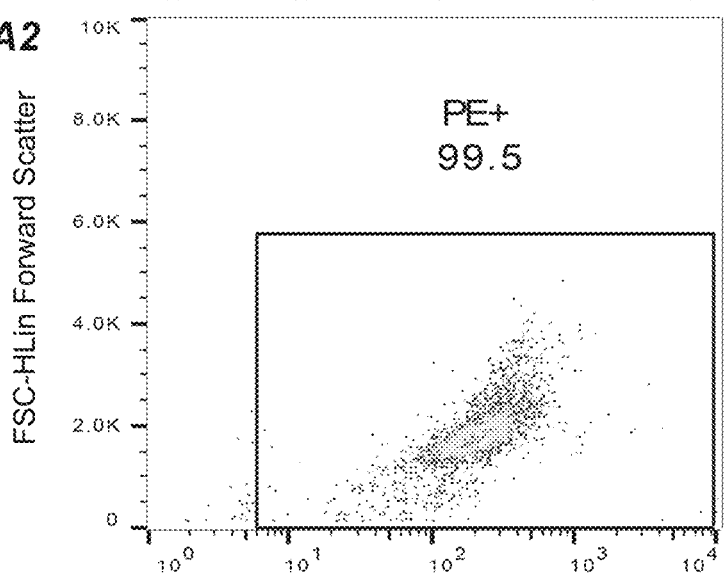
FIG. 36A2
(b) 1:50
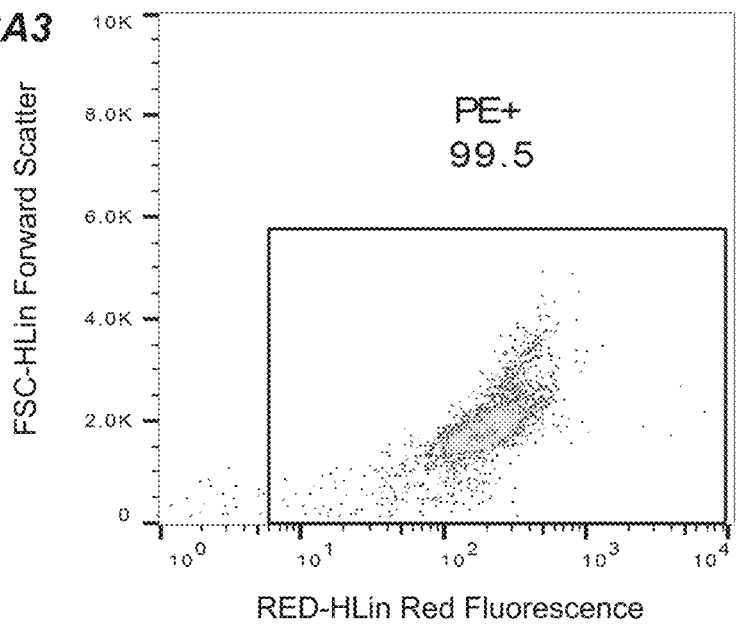
FIG. 36A3
1:100

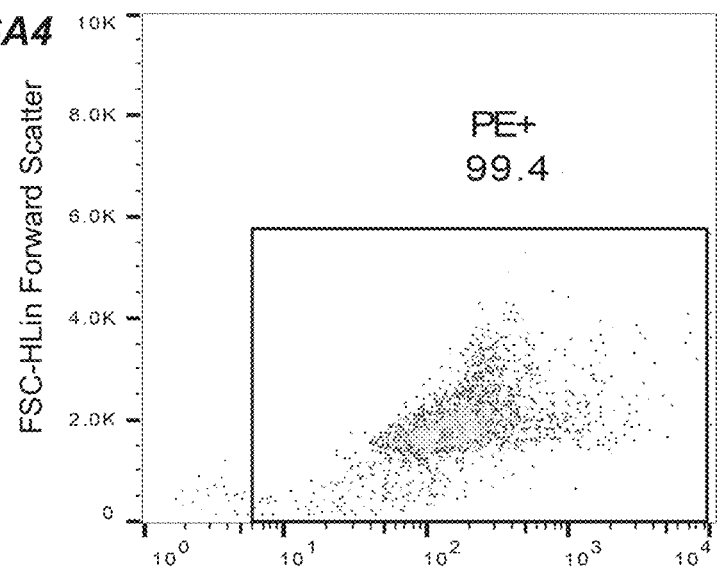
FIG. 36A4
1:200
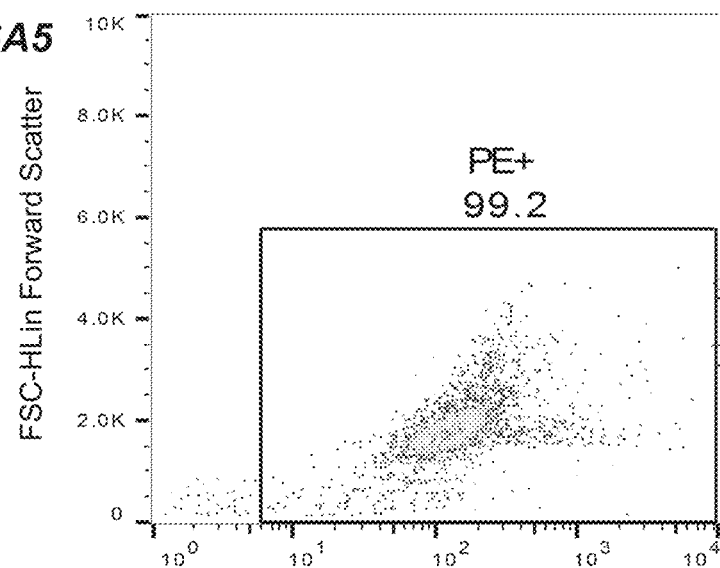
FIG. 36A5
1:300
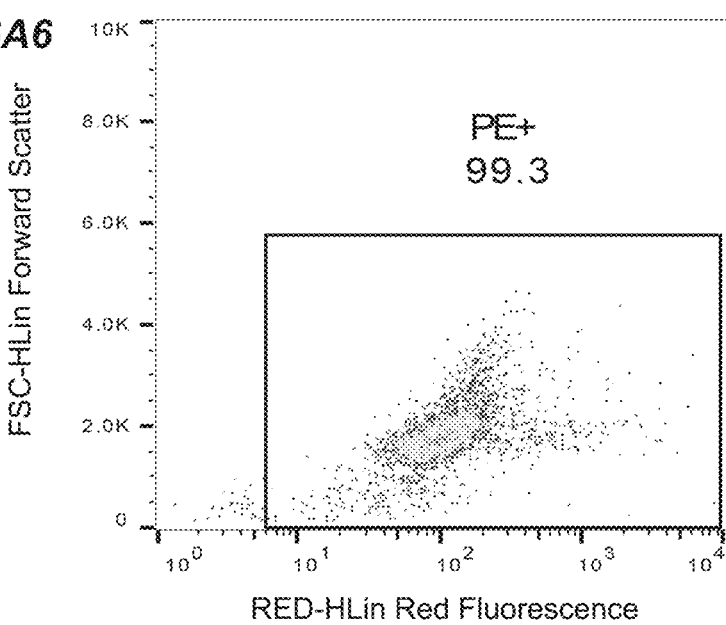
FIG. 36A6
1:400

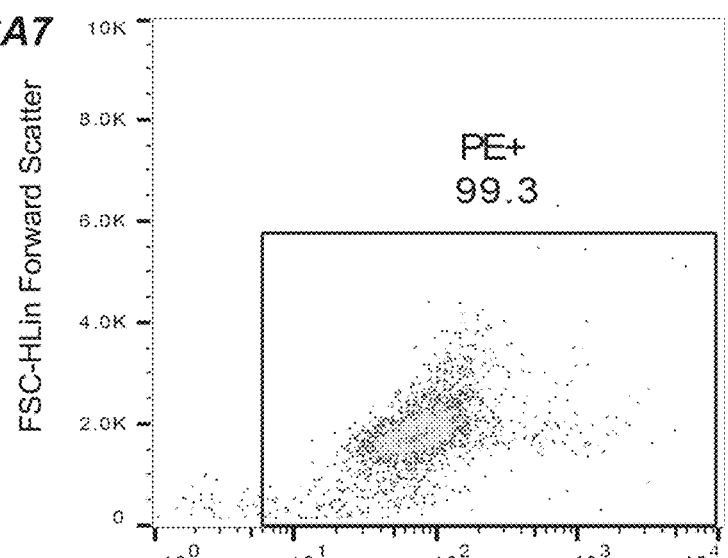
FIG. 36A7
1:600
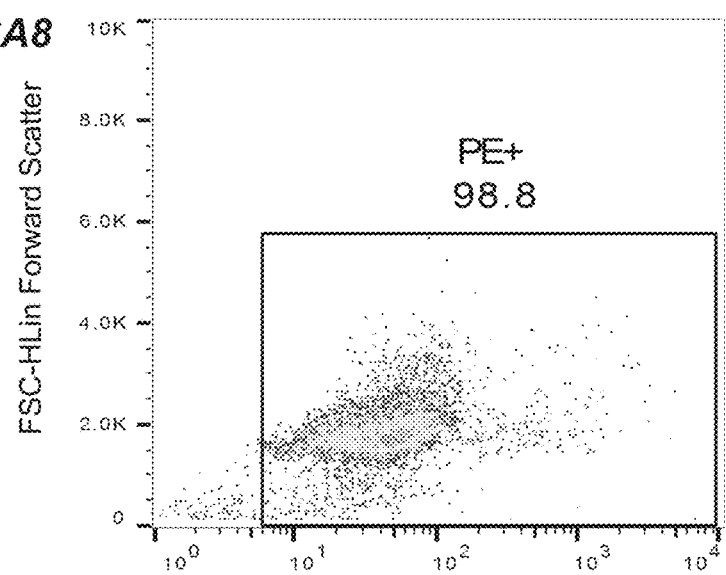
FIG. 36A8
1:800
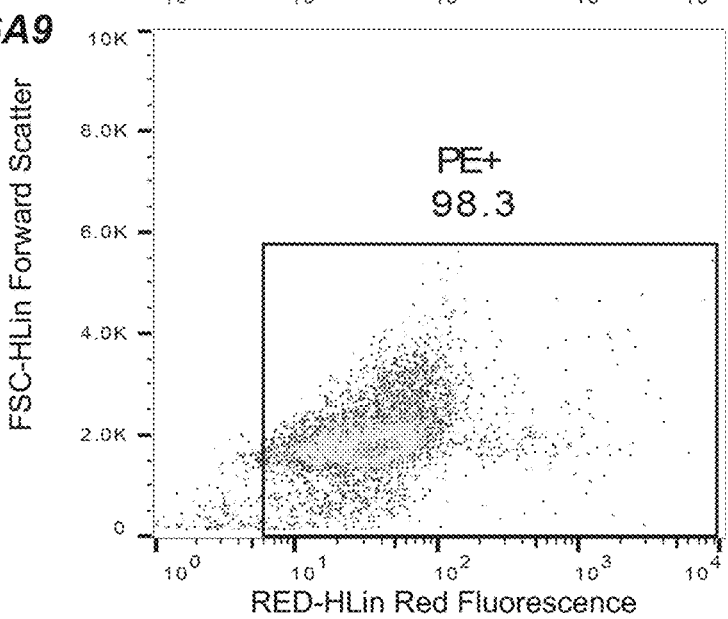
FIG. 36A9
1:1000

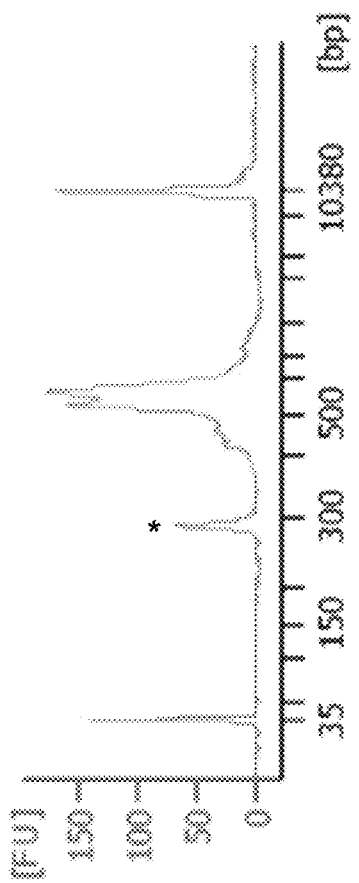
FIG. 38A FC1 - 1:100 Dilution, 100% Hot
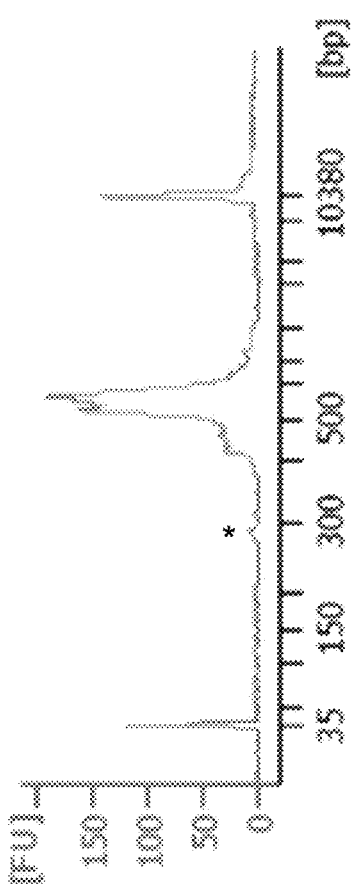
FIG. 38B FC1 - 1:800 Dilution, 100% Hot
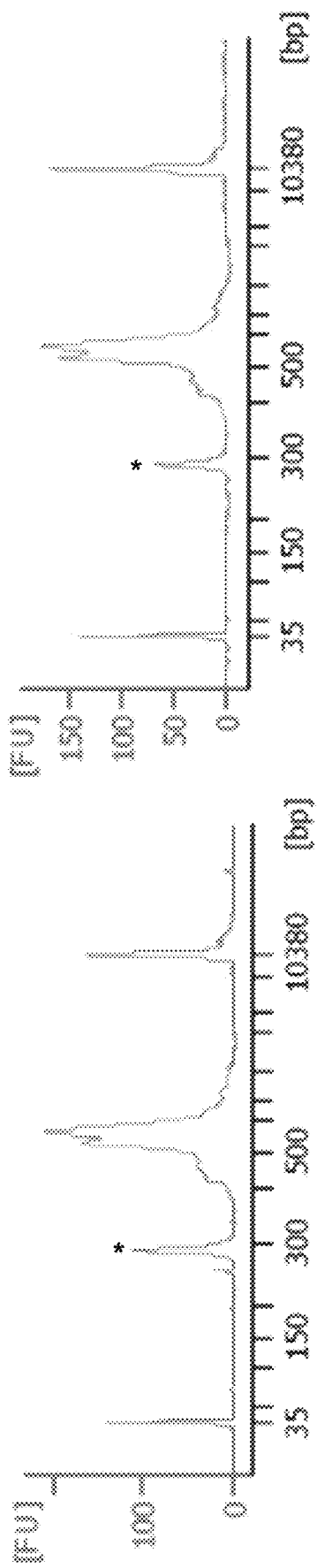
FIG. 38C FC1 - 1:100 Dilution, 10% Hot
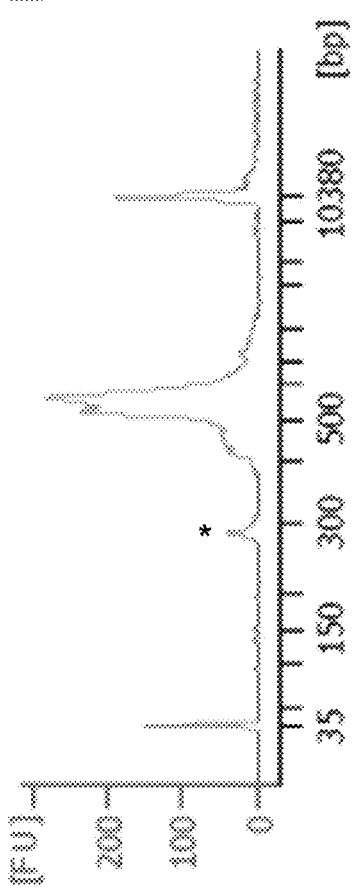
FIG. 38D FC1 - 1:100 Dilution, 1% Hot

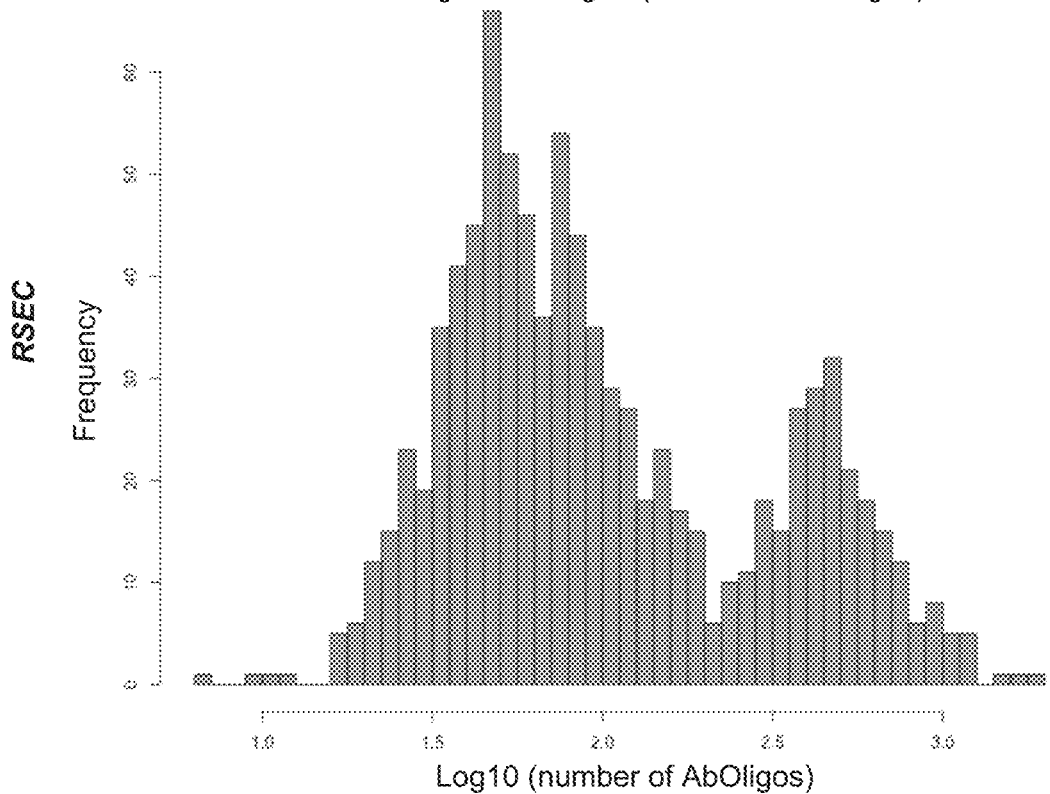
FIG. 39A1 — FC2 (1:100 10% hot Ab) Histogram of Log10 (number of AbOligos)
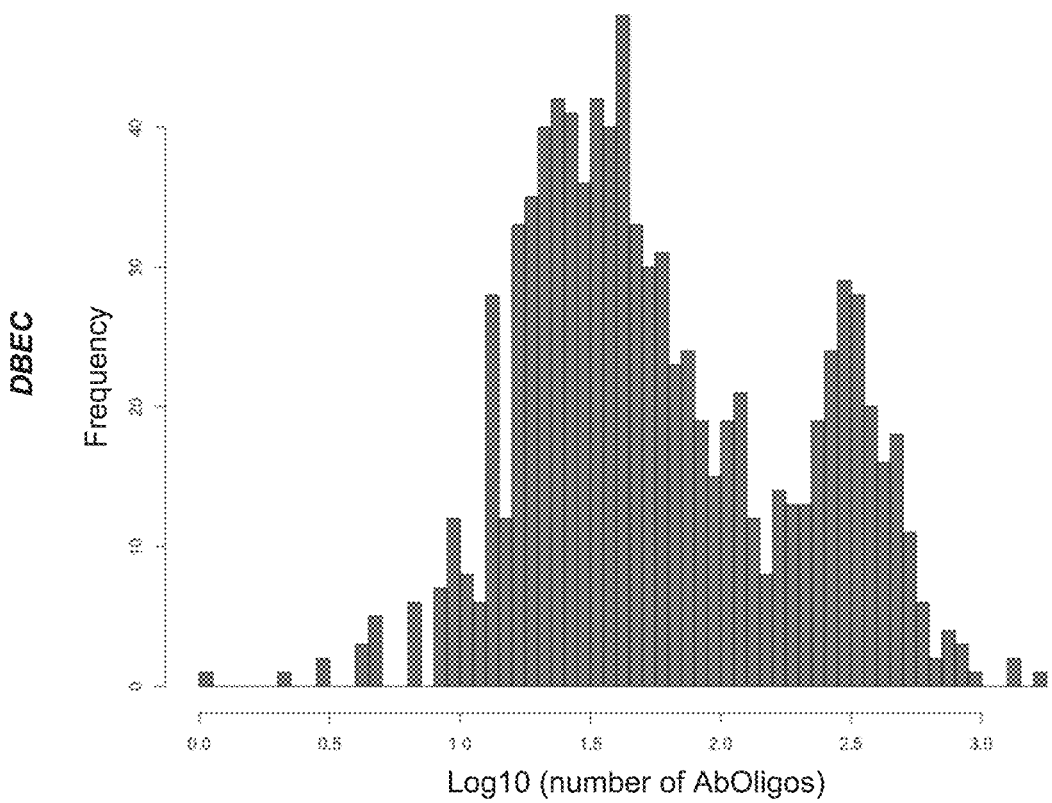
FIG. 39B1 — Histogram of Log10 (number of AbOligos)

FIG. 39A2
FC3 (1:100 1% hot Ab)
Histogram of Log10 (number of AbOligos)
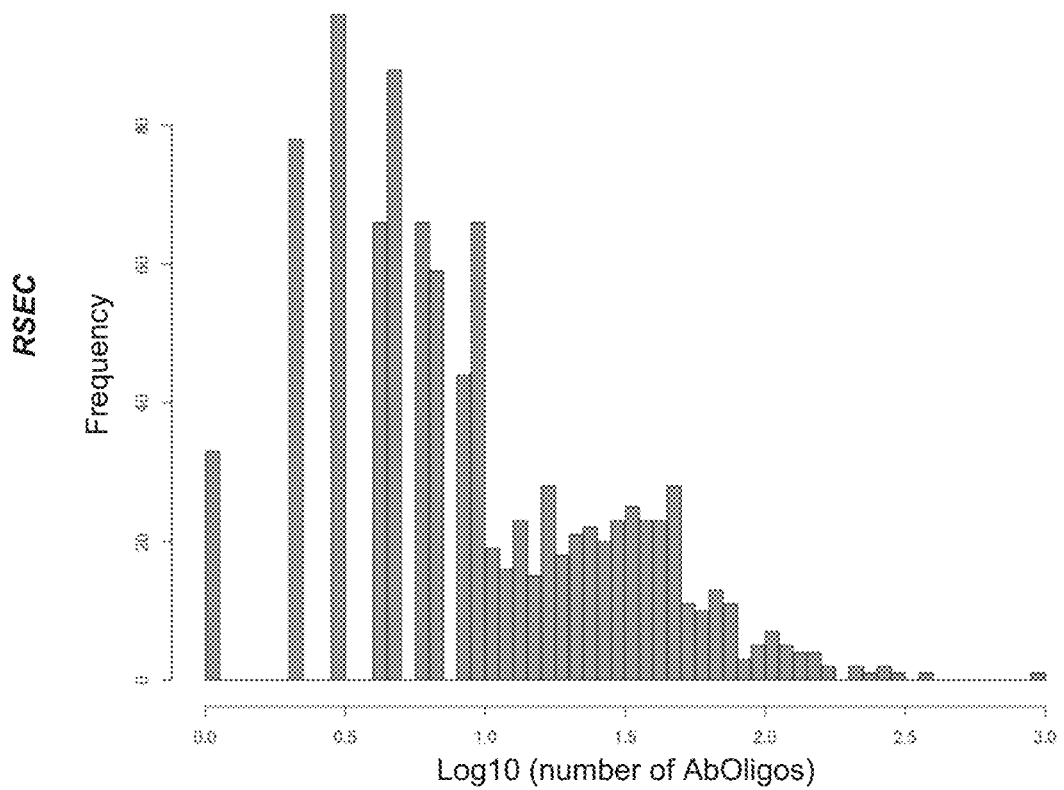
Log10 (number of AbOligos)
FIG. 39B2  Histogram of Log10 (number of AbOligos)
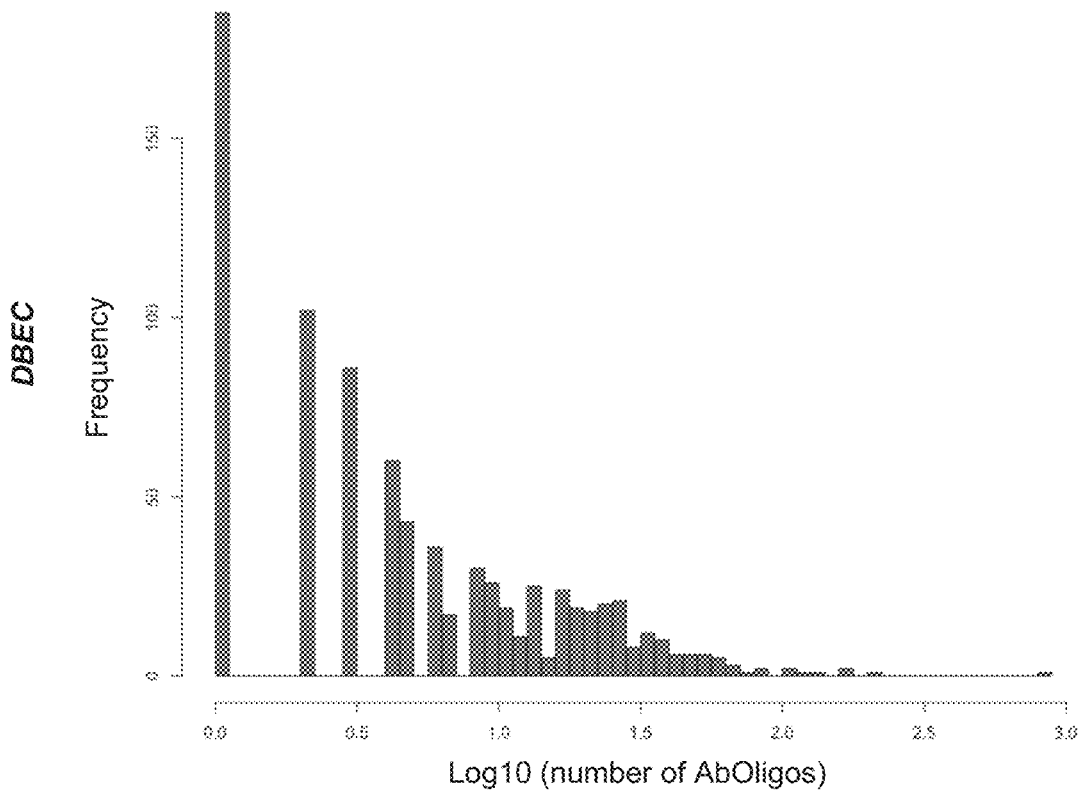
Log10 (number of AbOligos)

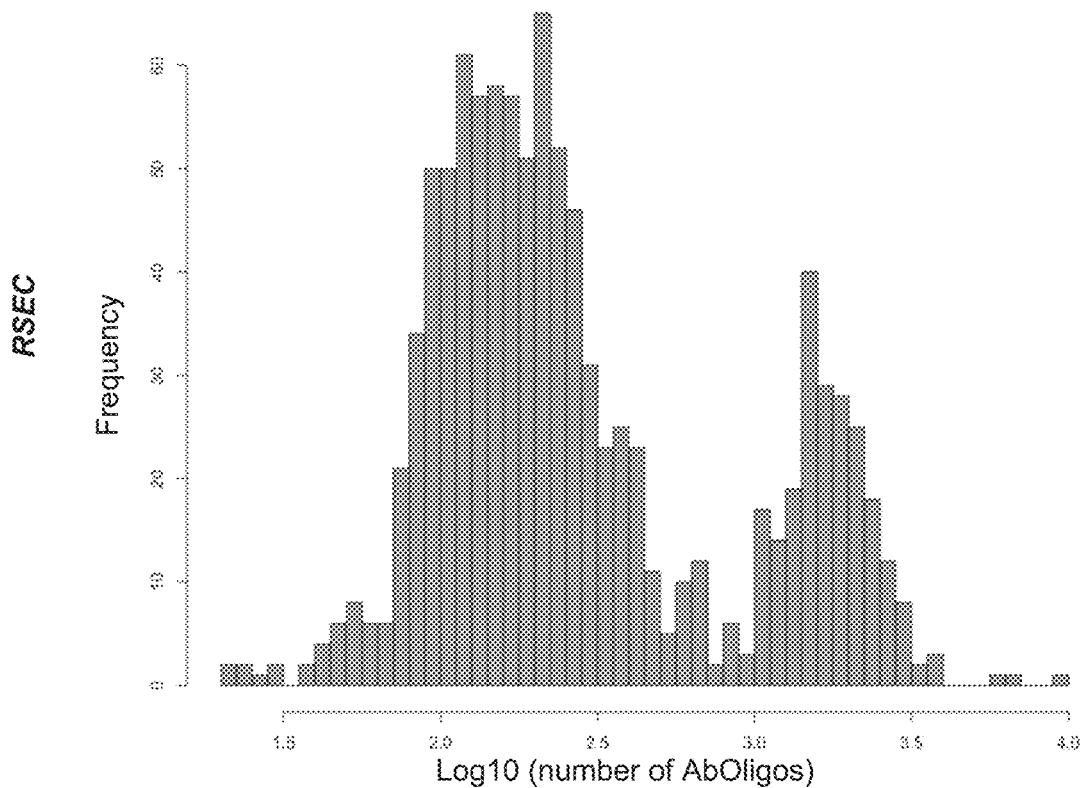
FIG. 39A3 FC4 (1:800 100% hot Ab)
Histogram of Log10 (number of AbOligos)
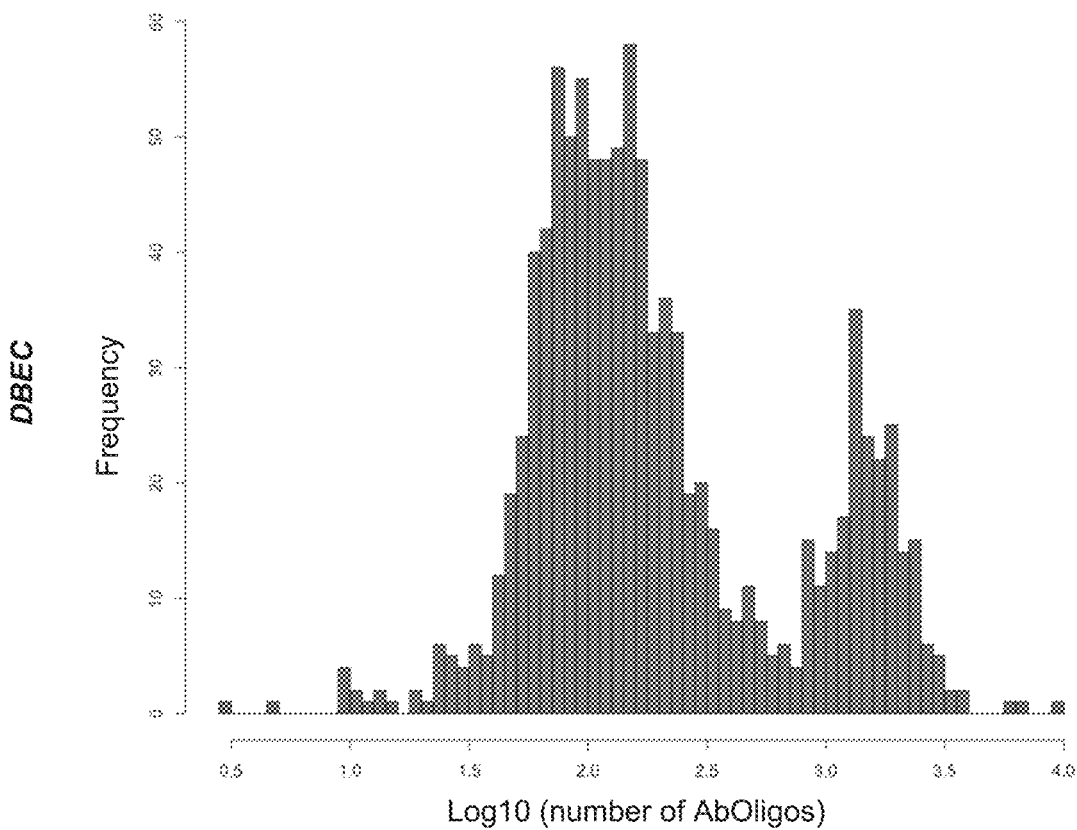
FIG. 39B3 Histogram of Log10 (number of AbOligos)

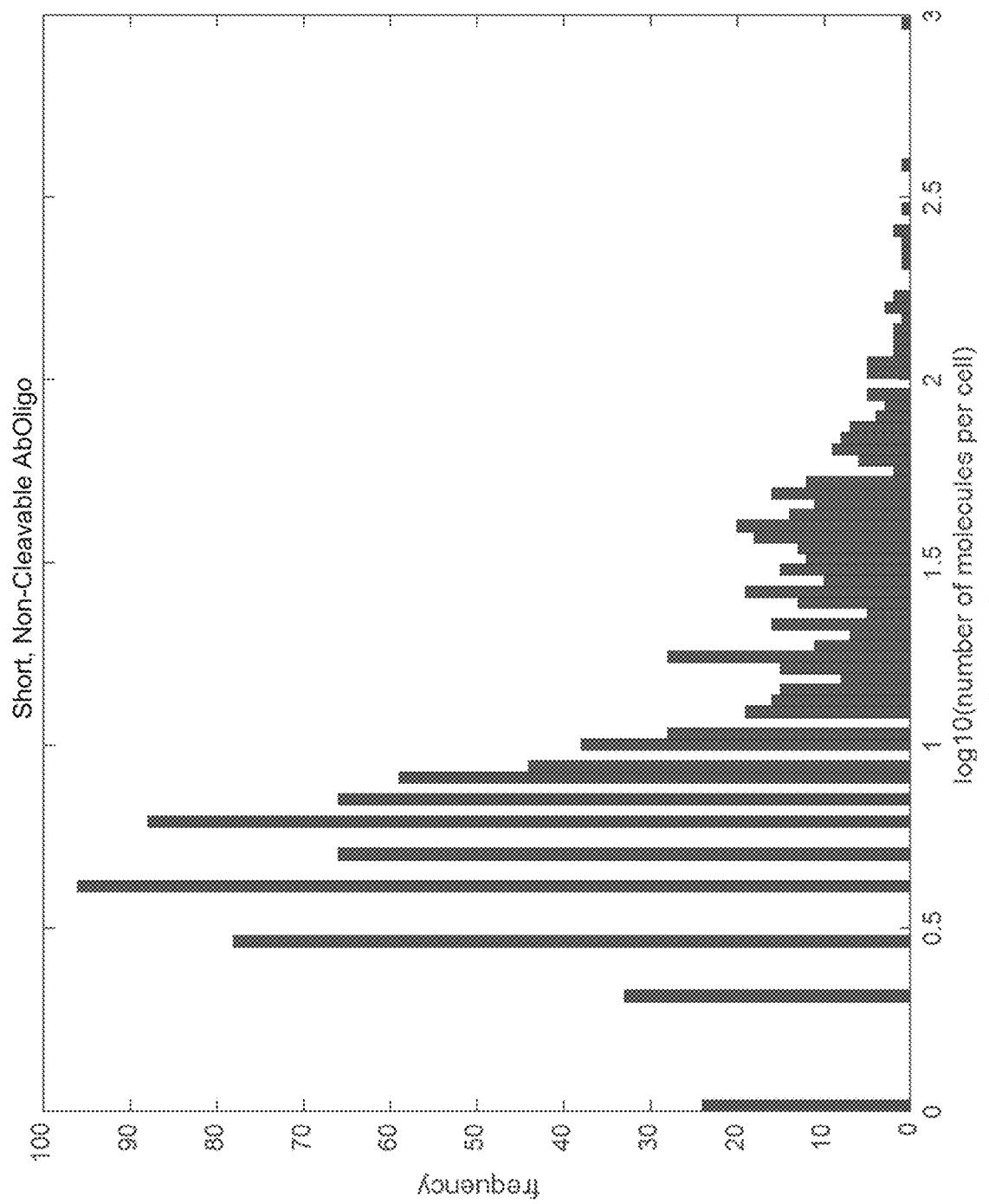

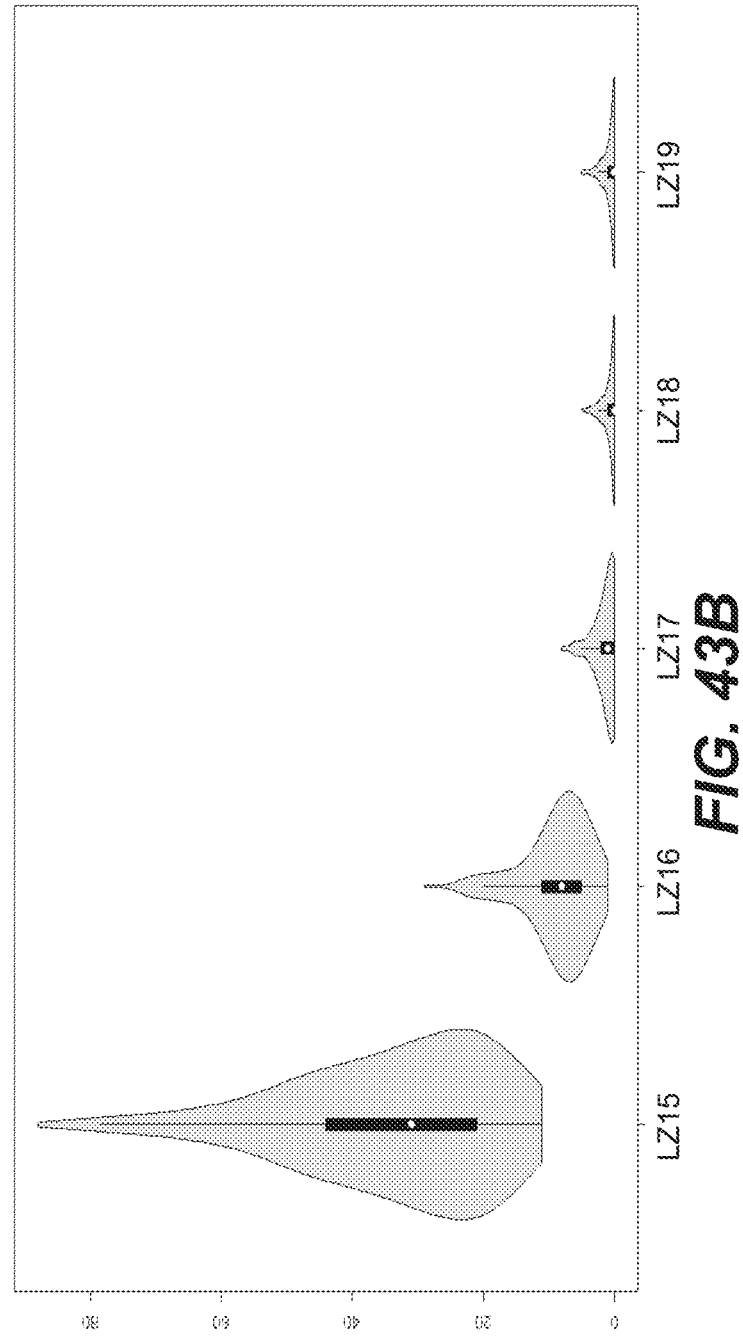
FIG. 43A
FIG. 43B

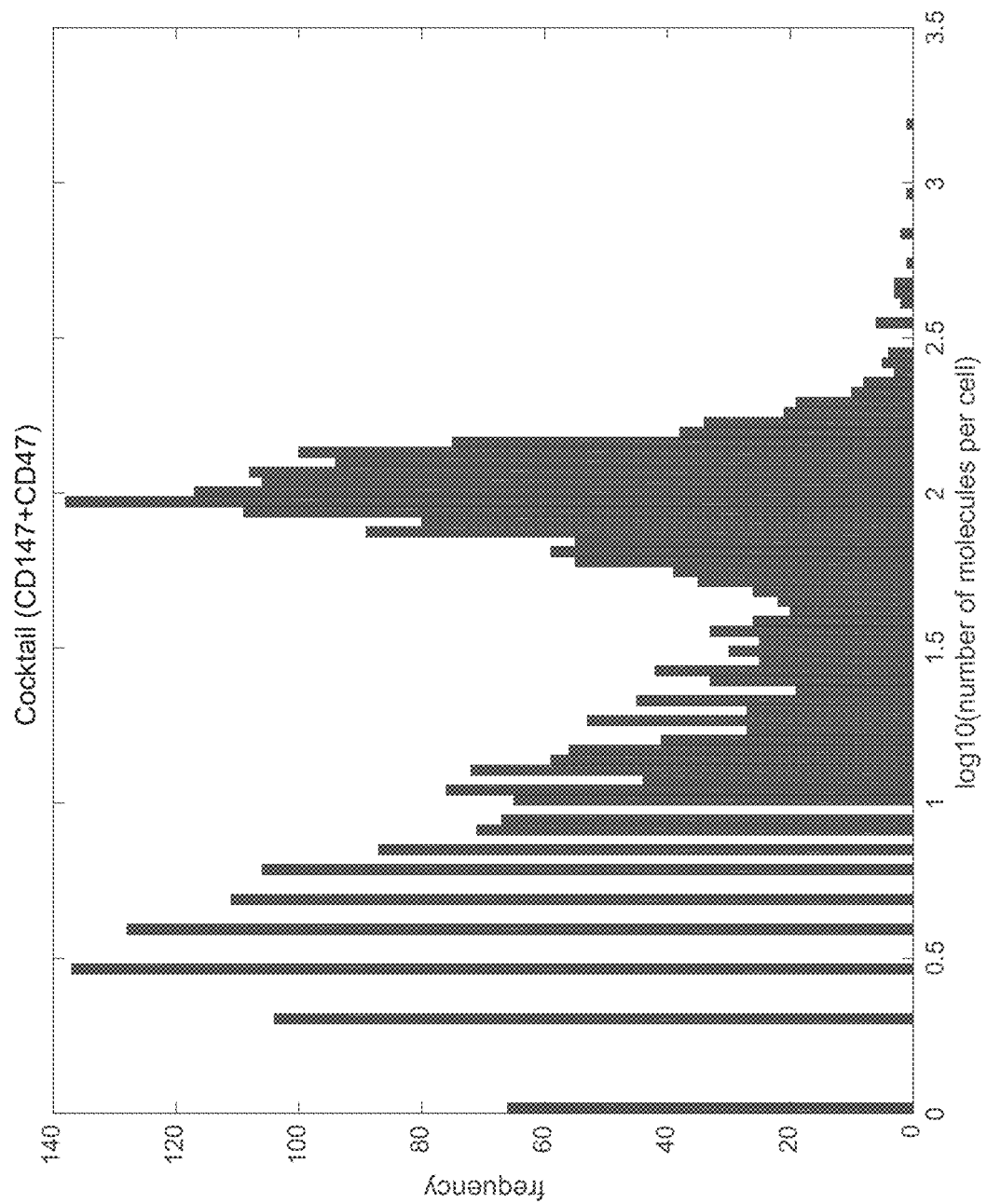

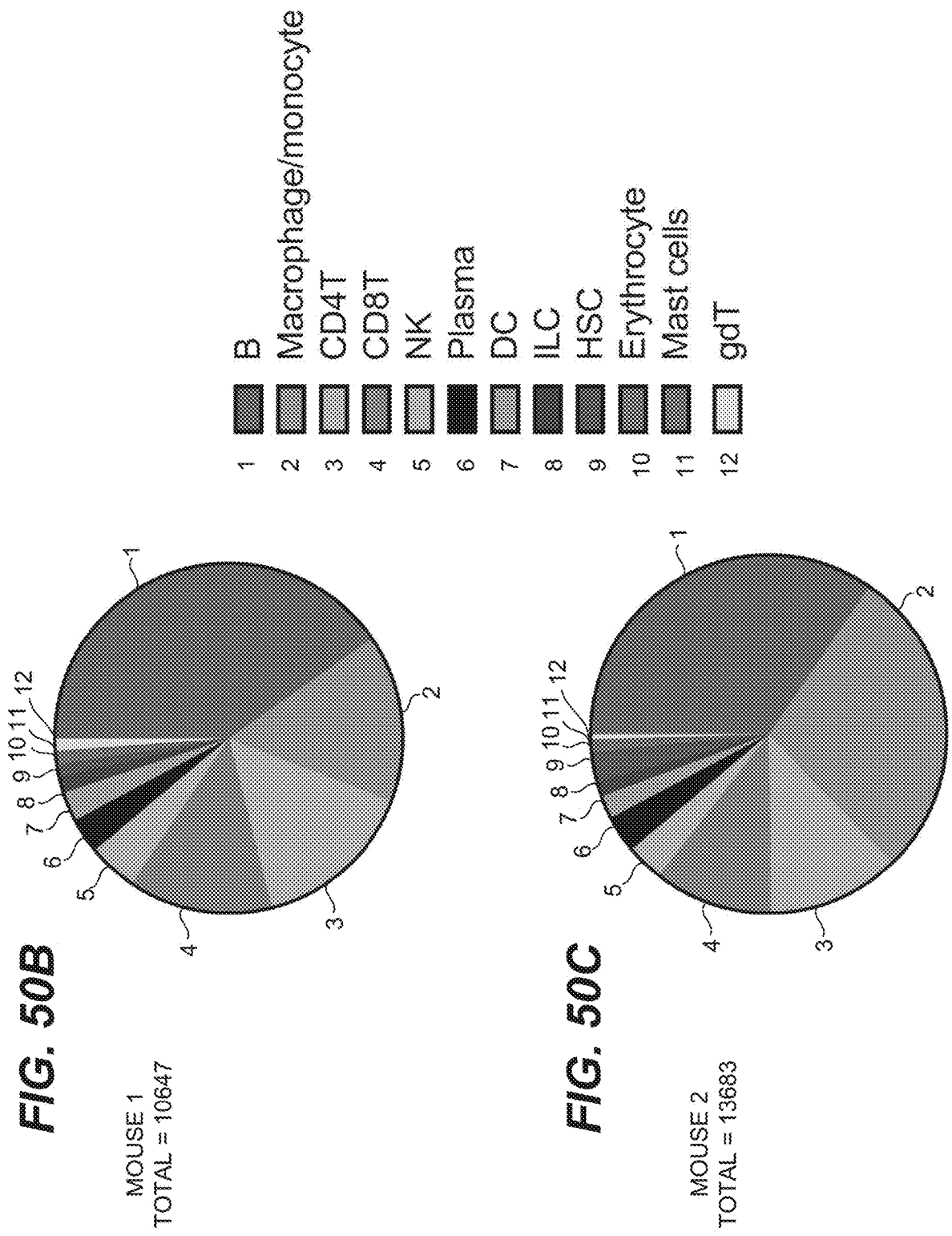

SAMPLE INDEXING FOR SINGLE CELLS

RELATED APPLICATIONS

The present application is a continuation of U.S. patent application Ser. No. 15/937,713, filed on Mar. 27, 2018, which claims priority under 35 U.S.C. § 119(e) to U.S. Provisional Application No. 62/645,703, filed on Mar. 20, 2018; U.S. Provisional Application No. 62/578,957, filed on Oct. 30, 2017; U.S. Provisional Application No. 62/554,425, filed on Sep. 5, 2017; U.S. Provisional Application No. 62/532,971, filed on Jul. 14, 2017; U.S. Provisional Application No. 62/532,949, filed on Jul. 14, 2017; U.S. Provisional Application No. 62/532,905, filed on Jul. 14, 2017; and U.S. Provisional Application No. 62/515,285, filed on Jun. 5, 2017. The content of each of these related applications is incorporated herein by reference in its entirety.

REFERENCE TO SEQUENCE LISTING

The present application is being filed along with a Sequence Listing in electronic format. The Sequence Listing is provided as a file entitled Sequence Listing 68EB-298707-US4, created Apr. 13, 2020, which is 4 kilobytes in size. The information in the electronic format of the Sequence Listing is incorporated herein by reference in its entirety.

BACKGROUND

Field

The present disclosure relates generally to the field of molecular biology, for example identifying cells of different samples and detecting interactions between cellular components using molecular barcoding.

Description of the Related Art

Current technology allows measurement of gene expression of single cells in a massively parallel manner (e.g., >10000 cells) by attaching cell specific oligonucleotide barcodes to poly(A) mRNA molecules from individual cells as each of the cells is co-localized with a barcoded reagent bead in a compartment. Gene expression may affect protein expression. Protein-protein interaction may affect gene expression and protein expression. There is a need for systems and methods that can quantitatively analyze protein expression, simultaneously measure protein expression and gene expression in cells, and determining protein-protein interactions in cells.

SUMMARY

Disclosed herein include methods for sample identification. In some embodiments, the method comprises: contacting one or more cells from each of a plurality of samples with a sample indexing composition of a plurality of sample indexing compositions, wherein the of the one or more cells comprises one or more antigen targets, wherein at least one sample indexing composition of the plurality of sample indexing compositions comprises two or more antigen binding reagents (e.g., protein binding reagents and antibodies), wherein each of the two or more antigen binding reagents is associated with a sample indexing oligonucleotide, wherein at least one of the two or more antigen binding reagents is capable of specifically binding to at least one of the one or more antigen targets, wherein the sample indexing oligonucleotide comprises a sample indexing sequence, and wherein sample indexing sequences of at least two sample indexing compositions of the plurality of sample indexing compositions comprise different sequences; barcoding the sample indexing oligonucleotides using a plurality of barcodes to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides (e.g., identifying sample origin of the plurality of barcoded targets based on the sample indexing sequence of the at least one barcoded sample indexing oligonucleotide). The method can, for example, comprise removing unbound sample indexing compositions of the plurality of sample indexing compositions.

In some embodiments, the sample indexing sequence is 25-60 nucleotides in length (e.g., 45 nucleotides in length), about 128 nucleotides in length, or at least 128 nucleotides in length. Sample indexing sequences of at least 10 sample indexing compositions of the plurality of sample indexing compositions can comprise different sequences. Sample indexing sequences of at least 100 or 1000 sample indexing compositions of the plurality of sample indexing compositions can comprise different sequences.

In some embodiments, the antigen binding reagent comprises an antibody, a tetramer, an aptamer, a protein scaffold, or a combination thereof. The sample indexing oligonucleotide can be conjugated to the antigen binding reagent through a linker. The oligonucleotide can comprise the linker. The linker can comprise a chemical group. The chemical group can be reversibly or irreversibly attached to the antigen binding reagent. The chemical group can be selected from the group consisting of a UV photocleavable group, a disulfide bond, a streptavidin, a biotin, an amine, and any combination thereof.

In some embodiments, at least one sample of the plurality of samples comprises a single cell. The at least one of the one or more antigen targets can be on a cell surface or inside of a cell. A sample of the plurality of samples can comprise a plurality of cells, a tissue, a tumor sample, or any combination thereof. The plurality of samples can comprise a mammalian sample, a bacterial sample, a viral sample, a yeast sample, a fungal sample, or any combination thereof.

In some embodiments, removing the unbound sample indexing compositions comprises washing the one or more cells from each of the plurality of samples with a washing buffer. The method can comprise lysing the one or more cells from each of the plurality of samples. The sample indexing oligonucleotide can be configured to be detachable or non-detachable from the antigen binding reagent. The method can comprise detaching the sample indexing oligonucleotide from the antigen binding reagent. Detaching the sample indexing oligonucleotide can comprise detaching the sample indexing oligonucleotide from the antigen binding reagent by UV photocleaving, chemical treatment (e.g., using a reducing reagent, such as dithiothreitol), heating, enzyme treatment, or any combination thereof.

In some embodiments, the sample indexing oligonucleotide is not homologous to genomic sequences of the cells of the plurality of samples. The sample indexing oligonucleotide can comprise a molecular label sequence, a poly(A) region, or a combination thereof. The sample indexing oligonucleotide can comprise a sequence complementary to a capture sequence of at least one barcode of the plurality of barcodes. A target binding region of the barcode can comprise the capture sequence. The target binding region can comprise a poly(dT) region. The sequence of the sample indexing oligonucleotide complementary to the capture sequence of the barcode can comprise a poly(A) tail. The sample indexing oligonucleotide can comprise a molecular label.

In some embodiments, the antigen target is, or comprises, an extracellular protein, an intracellular protein, or any combination thereof. The antigen target can be, or comprise, a cell-surface protein, a cell marker, a B-cell receptor, a T-cell receptor, a major histocompatibility complex, a tumor antigen, a receptor, an integrin, or any combination thereof. The antigen target can be, or comprise, a lipid, a carbohydrate, or any combination thereof. The antigen target can be selected from a group comprising 10-100 different antigen targets. The antigen binding reagent can be associated with two or more sample indexing oligonucleotides with an identical sequence. The antigen binding reagent can be associated with two or more sample indexing oligonucleotides with different sample indexing sequences. The sample indexing composition of the plurality of sample indexing compositions can comprise a second antigen binding reagent not conjugated with the sample indexing oligonucleotide. The antigen binding reagent and the second antigen binding reagent can be identical.

In some embodiments, a barcode of the plurality of barcodes comprises a target binding region and a molecular label sequence. Molecular label sequences of at least two barcodes of the plurality of barcodes comprise different molecule label sequences. The barcode can comprise a cell label, a binding site for a universal primer, or any combination thereof. The target binding region can comprise a poly(dT) region.

In some embodiments, the plurality of barcodes is associated with a particle. At least one barcode of the plurality of barcodes can be immobilized on the particle, partially immobilized on the particle, enclosed in the particle, partially enclosed in the particle, or any combination thereof. The particle can be degradable. The particle can be a bead. The bead can be selected from the group consisting of streptavidin beads, agarose beads, magnetic beads, conjugated beads, protein A conjugated beads, protein G conjugated beads, protein A/G conjugated beads, protein L conjugated beads, oligo(dT) conjugated beads, silica beads, silica-like beads, anti-biotin microbead, anti-fluorochrome microbead, and any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise at least 10000 barcodes. In some embodiments, the barcodes of the particle can comprise molecular label sequences selected from at least 1000 or 10000 different molecular label sequences. The molecular label sequences of the barcodes can comprise random sequences.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises amplifying the plurality of barcoded sample indexing oligonucleotides to produce a plurality of amplicons. Amplifying the plurality of barcoded sample indexing oligonucleotides can comprise amplifying, using polymerase chain reaction (PCR) at least a portion of the molecular label sequence and at least a portion of the sample indexing oligonucleotide. Obtaining the sequencing data of the plurality of barcoded sample indexing oligonucleotides can comprise obtaining sequencing data of the plurality of amplicons. Obtaining the sequencing data can comprise sequencing at least a portion of the molecular label sequence and at least a portion of the sample indexing oligonucleotide.

In some embodiments, identifying the sample origin of the at least one cell can comprise identifying sample origin of the plurality of barcoded targets based on the sample indexing sequence of the at least one barcoded sample indexing oligonucleotide. Barcoding the sample indexing oligonucleotides using the plurality of barcodes to create the plurality of barcoded sample indexing oligonucleotides can comprise stochastically barcoding the sample indexing oligonucleotides using a plurality of stochastic barcodes to create a plurality of stochastically barcoded sample indexing oligonucleotides.

In some embodiments, the method comprises: barcoding a plurality of targets of the cell using the plurality of barcodes to create a plurality of barcoded targets, wherein each of the plurality of barcodes comprises a cell label, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target binding regions of the barcodes; and reverse transcribing the plurality targets using the plurality of barcodes to create a plurality of reverse transcribed targets. Prior to obtaining the sequencing data of the plurality of barcoded targets, the method can comprise amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, each of the plurality of sample indexing compositions comprises the antigen binding reagent. The sample indexing sequences of the sample indexing oligonucleotides associated with the two or more antigen binding reagents can be identical. The sample indexing sequences of the sample indexing oligonucleotides associated with the two or more antigen binding reagents can comprise different sequences. Each of the plurality of sample indexing compositions can comprise the two or more antigen binding reagents.

Disclosed herein include methods for sample identification. In some embodiments, the method comprise: contacting one or more cells from each of a plurality of samples with a sample indexing composition of a plurality of sample indexing compositions, wherein each of the one or more cells comprises one or more cellular component targets, wherein at least one sample indexing composition of the plurality of sample indexing compositions comprises two or more cellular component binding reagents (e.g., antigen binding reagents or antibodies), wherein each of the two or more cellular component binding reagents is associated with a sample indexing oligonucleotide, wherein at least one of the two or more cellular component binding reagents is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; barcoding the sample indexing oligonucleotides using a plurality of barcodes to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides. The method can comprise removing unbound sample indexing compositions of the plurality of sample indexing compositions.

In some embodiments, the sample indexing sequence is 25-60 nucleotides in length (e.g., 45 nucleotides in length), about 128 nucleotides in length, or at least 128 nucleotides in length. Sample indexing sequences of at least 10 sample indexing compositions of the plurality of sample indexing compositions can comprise different sequences. Sample indexing sequences of at least 10 sample indexing compositions of the plurality of sample indexing compositions can comprise different sequences. Sample indexing sequences of at least 10 sample indexing compositions of the plurality of sample indexing compositions comprise different sequences.

In some embodiments, the cellular component binding reagent comprises a cell surface binding reagent, an antibody, a tetramer, an aptamer, a protein scaffold, an integrin, or a combination thereof. The sample indexing oligonucleotide can be conjugated to the cellular component binding reagent through a linker. The oligonucleotide can comprise the linker. The linker can comprise a chemical group. The chemical group can be reversibly or irreversibly attached to the cellular component binding reagent. The chemical group can be selected from the group consisting of a UV photocleavable group, a disulfide bond, a streptavidin, a biotin, an amine, and any combination thereof.

In some embodiments, at least one sample of the plurality of samples comprises a single cell. The at least one of the one or more cellular component targets can be expressed on a cell surface. A sample of the plurality of samples can comprise a plurality of cells, a tissue, a tumor sample, or any combination thereof. The plurality of samples can comprise a mammalian sample, a bacterial sample, a viral sample, a yeast sample, a fungal sample, or any combination thereof.

In some embodiments, removing the unbound sample indexing compositions comprises washing the one or more cells from each of the plurality of samples with a washing buffer. The method can comprise lysing the one or more cells from each of the plurality of samples. The sample indexing oligonucleotide can be configured to be detachable or non-detachable from the cellular component binding reagent. The method can comprise detaching the sample indexing oligonucleotide from the cellular component binding reagent. Detaching the sample indexing oligonucleotide can comprise detaching the sample indexing oligonucleotide from the cellular component binding reagent by UV photocleaving, chemical treatment (e.g., using a reducing reagent, such as dithiothreitol), heating, enzyme treatment, or any combination thereof.

In some embodiments, the sample indexing oligonucleotide is not homologous to genomic sequences of the cells of the plurality of samples. The sample indexing oligonucleotide can comprise a molecular label sequence, a poly(A) region, or a combination thereof. The sample indexing oligonucleotide can comprise a sequence complementary to a capture sequence of at least one barcode of the plurality of barcodes. A target binding region of the barcode can comprise the capture sequence. The target binding region can comprise a poly(dT) region. The sequence of the sample indexing oligonucleotide complementary to the capture sequence of the barcode can comprise a poly(A) tail. The sample indexing oligonucleotide can comprise a molecular label.

In some embodiments, the cellular component target is, or comprises, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. The cellular component target can be selected from a group comprising 10-100 different cellular component targets. The cellular component binding reagent can be associated with two or more sample indexing oligonucleotides with an identical sequence. The cellular component binding reagent can be associated with two or more sample indexing oligonucleotides with different sample indexing sequences. The sample indexing composition of the plurality of sample indexing compositions can comprise a second cellular component binding reagent not conjugated with the sample indexing oligonucleotide. The cellular component binding reagent and the second cell binding reagent can be identical.

In some embodiments, a barcode of the plurality of barcodes comprises a target binding region and a molecular label sequence. Molecular label sequences of at least two barcodes of the plurality of barcodes can comprise different molecule label sequences. The barcode can comprise a cell label, a binding site for a universal primer, or any combination thereof. The target binding region can comprise a poly(dT) region.

In some embodiments, the plurality of barcodes is enclosed in a particle. The particle can be a bead. At least one barcode of the plurality of barcodes can be immobilized on the particle, partially immobilized on the particle, enclosed in the particle, partially enclosed in the particle, or any combination thereof. The particle can be degradable. The bead can be selected from the group consisting of streptavidin beads, agarose beads, magnetic beads, conjugated beads, protein A conjugated beads, protein G conjugated beads, protein A/G conjugated beads, protein L conjugated beads, oligo(dT) conjugated beads, silica beads, silica-like beads, anti-biotin microbead, anti-fluorochrome microbead, and any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise at least 10000 barcodes. In some embodiments, the barcodes of the particle can comprise molecular label sequences selected from at least 1000 or 10000 different molecular label sequences. The molecular label sequences of the barcodes can comprise random sequences.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises amplifying the plurality of barcoded sample indexing oligonucleotides to produce a plurality of amplicons. Amplifying the plurality of barcoded sample indexing oligonucleotides can comprise amplifying, using polymerase chain reaction (PCR) at least a portion of the molecular label sequence and at least a portion of the sample indexing oligonucleotide. Obtaining the sequencing data of the plurality of barcoded sample indexing oligonucleotides can comprise obtaining sequencing data of the plurality of amplicons. Obtaining the sequencing data can comprise sequencing at least a portion of the molecular label sequence and at least a portion of the sample indexing oligonucleotide.

In some embodiments, identifying the sample origin of the at least one cell can comprise identifying sample origin of the plurality of barcoded targets based on the sample indexing sequence of the at least one barcoded sample indexing oligonucleotide. Barcoding the sample indexing oligonucleotides using the plurality of barcodes to create the plurality of barcoded sample indexing oligonucleotides can comprise stochastically barcoding the sample indexing oligonucleotides using a plurality of stochastic barcodes to create a plurality of stochastically barcoded sample indexing oligonucleotides.

In some embodiments, the method comprises: barcoding a plurality of targets of the cell using the plurality of barcodes to create a plurality of barcoded targets, wherein each of the plurality of barcodes comprises a cell label, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target binding regions of the barcodes; and reverse transcribing the plurality targets using the plurality of barcodes to create a plurality of reverse transcribed targets. The method can comprise: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, each of the plurality of sample indexing compositions comprises the cellular component binding reagent. The sample indexing sequences of the sample indexing oligonucleotides associated with the two or more cellular component binding reagents can be identical. The sample indexing sequences of the sample indexing oligonucleotides associated with the two or more cellular component binding reagents can comprise different sequences. Each of the plurality of sample indexing compositions can comprise the two or more cellular component binding reagents.

Disclosed herein include methods for sample identification. In some embodiments, the method comprises: contacting one or more cells from each of a plurality of samples with a sample indexing composition of a plurality of sample indexing compositions, wherein each of the one or more cells comprises one or more cellular component targets, wherein at least one sample indexing composition of the plurality of sample indexing compositions comprises two or more cellular component binding reagents, wherein each of the two or more cellular component binding reagents is associated with a sample indexing oligonucleotide, wherein at least one of the two or more cellular component binding reagents is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; and identifying sample origin of at least one cell of the one or more cells based on the sample indexing sequence of at least one sample indexing oligonucleotide of the plurality of sample indexing compositions. The method can, for example, include removing unbound sample indexing compositions of the plurality of sample indexing compositions.

In some embodiments, the sample indexing sequence is 25-60 nucleotides in length (e.g., 45 nucleotides in length), about 128 nucleotides in length, or at least 128 nucleotides in length. Sample indexing sequences of at least 10 sample indexing compositions of the plurality of sample indexing compositions can comprise different sequences. Sample indexing sequences of at least 100 or 1000 sample indexing compositions of the plurality of sample indexing compositions can comprise different sequences.

In some embodiments, the antigen binding reagent comprises an antibody, a tetramer, an aptamer, a protein scaffold, or a combination thereof. The sample indexing oligonucleotide can be conjugated to the antigen binding reagent through a linker. The oligonucleotide can comprise the linker. The linker can comprise a chemical group. The chemical group can be reversibly or irreversibly attached to the antigen binding reagent. The chemical group can be selected from the group consisting of a UV photocleavable group, a disulfide bond, a streptavidin, a biotin, an amine, and any combination thereof.

In some embodiments, at least one sample of the plurality of samples comprises a single cell. The at least one of the one or more antigen targets can be expressed on a cell surface. A sample of the plurality of samples can comprise a plurality of cells, a tissue, a tumor sample, or any combination thereof. The plurality of samples can comprise a mammalian sample, a bacterial sample, a viral sample, a yeast sample, a fungal sample, or any combination thereof.

In some embodiments, removing the unbound sample indexing compositions comprises washing the one or more cells from each of the plurality of samples with a washing buffer. The method can comprise lysing the one or more cells from each of the plurality of samples. The sample indexing oligonucleotide can be configured to be detachable or non-detachable from the antigen binding reagent. The method can comprise detaching the sample indexing oligonucleotide from the antigen binding reagent. Detaching the sample indexing oligonucleotide can comprise detaching the sample indexing oligonucleotide from the antigen binding reagent by UV photocleaving, chemical treatment (e.g., using a reducing reagent, such as dithiothreitol), heating, enzyme treatment, or any combination thereof.

In some embodiments, the sample indexing oligonucleotide is not homologous to genomic sequences of the cells of the plurality of samples. The sample indexing oligonucleotide can comprise a molecular label sequence, a poly(A) region, or a combination thereof. The sample indexing oligonucleotide can comprise a sequence complementary to a capture sequence of at least one barcode of the plurality of barcodes. A target binding region of the barcode can comprise the capture sequence. The target binding region can comprise a poly(dT) region. The sequence of the sample indexing oligonucleotide complementary to the capture sequence of the barcode can comprise a poly(A) tail. The sample indexing oligonucleotide can comprise a molecular label.

In some embodiments, the antigen target is, or comprises, a carbohydrate, a lipid, a protein, an extracellular protein, a cell-surface protein, a cell marker, a B-cell receptor, a T-cell receptor, a major histocompatibility complex, a tumor antigen, a receptor, an intracellular protein, or any combination thereof. The antigen target can be selected from a group comprising 10-100 different antigen targets. The antigen binding reagent can be associated with two or more sample indexing oligonucleotides with an identical sequence. The antigen binding reagent can associated with two or more sample indexing oligonucleotides with different sample indexing sequences. The sample indexing composition of the plurality of sample indexing compositions can comprise a second antigen binding reagent not conjugated with the sample indexing oligonucleotide. The antigen binding reagent and the second antigen binding reagent can be identical.

In some embodiments, identifying the sample origin of the at least one cell comprises: barcoding sample indexing oligonucleotides of the plurality of sample indexing compositions using a plurality of barcodes to create a plurality of barcoded sample indexing oligonucleotides; obtaining sequencing data of the plurality of barcoded sample indexing oligonucleotides; and identifying the sample origin of the cell based on the sample indexing sequence of at least one barcoded sample indexing oligonucleotide of the plurality of barcoded sample indexing oligonucleotides.

In some embodiments, a barcode of the plurality of barcodes comprises a target binding region and a molecular label sequence. Molecular label sequences of at least two barcodes of the plurality of barcodes can comprise different molecule label sequences. The barcode can comprise a cell label, a binding site for a universal primer, or any combination thereof. The target binding region can comprise a poly(dT) region.

In some embodiments, the plurality of barcodes is immobilized on a particle. At least one barcode of the plurality of barcodes can be immobilized on the particle, partially immobilized on the particle, enclosed in the particle, partially enclosed in the particle, or any combination thereof. The particle can be degradable. The particle can be a bead. The bead can be selected from the group consisting of streptavidin beads, agarose beads, magnetic beads, conjugated beads, protein A conjugated beads, protein G conjugated beads, protein A/G conjugated beads, protein L conjugated beads, oligo(dT) conjugated beads, silica beads, silica-like beads, anti-biotin microbead, anti-fluorochrome microbead, and any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise at least 10000 barcodes. In some embodiments, the barcodes of the particle can comprise molecular label sequences selected from at least 1000 or 10000 different molecular label sequences. The molecular label sequences of the barcodes can comprise random sequences.

In some embodiments, barcoding the sample indexing oligonucleotides using the plurality of barcodes can comprise: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises amplifying the plurality of barcoded sample indexing oligonucleotides to produce a plurality of amplicons. Amplifying the plurality of barcoded sample indexing oligonucleotides can comprise amplifying, using polymerase chain reaction (PCR) at least a portion of the molecular label sequence and at least a portion of the sample indexing oligonucleotide. Obtaining the sequencing data of the plurality of barcoded sample indexing oligonucleotides can comprise obtaining sequencing data of the plurality of amplicons. Obtaining the sequencing data can comprise sequencing at least a portion of the molecular label sequence and at least a portion of the sample indexing oligonucleotide.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides. Identifying the sample origin of the at least one cell can comprise identifying the presence or absence of the sample indexing sequence of at least one sample indexing oligonucleotide of the plurality of sample indexing compositions. Identifying the presence or absence of the sample indexing sequence can comprise: replicating the at least one sample indexing oligonucleotide to generate a plurality of replicated sample indexing oligonucleotides; obtaining sequencing data of the plurality of replicated sample indexing oligonucleotides; and identifying the sample origin of the cell based on the sample indexing sequence of a replicated sample indexing oligonucleotide of the plurality of sample indexing oligonucleotides that correspond to the least one barcoded sample indexing oligonucleotide in the sequencing data.

In some embodiments, replicating the at least one sample indexing oligonucleotide to generate the plurality of replicated sample indexing oligonucleotides comprises: prior to replicating the at least one barcoded sample indexing oligonucleotide, ligating a replicating adaptor to the at least one barcoded sample indexing oligonucleotide. Replicating the at least one barcoded sample indexing oligonucleotide can comprise replicating the at least one barcoded sample indexing oligonucleotide using the replicating adaptor ligated to the at least one barcoded sample indexing oligonucleotide to generate the plurality of replicated sample indexing oligonucleotides.

In some embodiments, replicating the at least one sample indexing oligonucleotide to generate the plurality of replicated sample indexing oligonucleotides comprises: prior to replicating the at least one barcoded sample indexing oligonucleotide, contacting a capture probe with the at least one sample indexing oligonucleotide to generate a capture probe hybridized to the sample indexing oligonucleotide; and extending the capture probe hybridized to the sample indexing oligonucleotide to generate a sample indexing oligonucleotide associated with the capture probe. Replicating the at least one sample indexing oligonucleotide can comprise replicating the sample indexing oligonucleotide associated with the capture probe to generate the plurality of replicated sample indexing oligonucleotides.

In some embodiments, the method comprises: barcoding a plurality of targets of the cell using the plurality of barcodes to create a plurality of barcoded targets, wherein each of the plurality of barcodes comprises a cell label, and wherein at least two barcodes of the plurality of barcodes comprise an identical cell label sequence; and obtaining sequencing data of the barcoded targets. Identifying the sample origin of the at least one barcoded sample indexing oligonucleotide can comprise identifying the sample origin of the plurality of barcoded targets based on the sample indexing sequence of the at least one barcoded sample indexing oligonucleotide. Barcoding the plurality of targets using the plurality of barcodes to create the plurality of barcoded targets can comprise: contacting copies of the targets with target binding regions of the barcodes; and reverse transcribing the plurality targets using the plurality of barcodes to create a plurality of reverse transcribed targets. The method can comprise: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, each of the plurality of sample indexing compositions comprises the antigen binding reagent. The sample indexing sequences of the sample indexing oligonucleotides associated with the two or more antigen binding reagents can be identical. The sample indexing sequences of the sample indexing oligonucleotides associated with the two or more antigen binding reagents can comprise different sequences. Each of the plurality of sample indexing compositions can comprise the two or more antigen binding reagents.

Disclosed herein includes a plurality of sample indexing compositions. Each of the plurality of sample indexing compositions can comprise two or more antigen binding reagents. Each of the two or more antigen binding reagents can be associated with a sample indexing oligonucleotide. At least one of the two or more antigen binding reagents can be capable of specifically binding to at least one antigen target. The sample indexing oligonucleotide can comprise a sample indexing sequence for identifying sample origin of one or more cells of a sample. Sample indexing sequences of at least two sample indexing compositions of the plurality of sample indexing compositions can comprise different sequences.

In some embodiments, the sample indexing sequence comprises a nucleotide sequence of 25-60 nucleotides in length (e.g., 45 nucleotides in length), about 128 nucleotides in length, or at least 128 nucleotides in length. Sample indexing sequences of at least 10, 100, or 1000 sample indexing compositions of the plurality of sample indexing compositions comprise different sequences.

In some embodiments, the antigen binding reagent comprises an antibody, a tetramer, an aptamers, a protein scaffold, or a combination thereof. The sample indexing oligonucleotide can be conjugated to the antigen binding reagent through a linker. The at least one sample indexing oligonucleotide can comprise the linker. The linker can comprise a chemical group. The chemical group can be reversibly or irreversibly attached to the molecule of the antigen binding reagent. The chemical group can be selected from the group consisting of a UV photocleavable group, a disulfide bond, a streptavidin, a biotin, an amine, and any combination thereof.

In some embodiments, the sample indexing oligonucleotide is not homologous to genomic sequences of a species. The sample indexing oligonucleotide can comprise a molecular label sequence, a poly(A) region, or a combination thereof. In some embodiments, at least one sample of the plurality of samples can comprise a single cell, a plurality of cells, a tissue, a tumor sample, or any combination thereof. The sample can comprise a mammalian sample, a bacterial sample, a viral sample, a yeast sample, a fungal sample, or any combination thereof.

In some embodiments, the antigen target is, or comprises, a cell-surface protein, a cell marker, a B-cell receptor, a T-cell receptor, a major histocompatibility complex, a tumor antigen, a receptor, or any combination thereof. The antigen target can be selected from a group comprising 10-100 different antigen targets. The antigen binding reagent can be associated with two or more sample indexing oligonucleotides with an identical sequence. The antigen binding reagent can be associated with two or more sample indexing oligonucleotides with different sample indexing sequences. The sample indexing composition of the plurality of sample indexing compositions can comprise a second antigen binding reagent not conjugated with the sample indexing oligonucleotide. The antigen binding reagent and the second antigen binding reagent can be identical.

Disclosed herein include control particle compositions. In some embodiments, the control particle composition comprises a plurality of control particle oligonucleotides associated with a control particle, wherein each of the plurality of control particle oligonucleotides comprises a control barcode sequence and a poly(dA) region. At least two of the plurality of control particle oligonucleotides can comprise different control barcode sequences. The control particle oligonucleotide can comprise a molecular label sequence. The control particle oligonucleotide can comprise a binding site for a universal primer.

In some embodiments, the control barcode sequence is at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. The control barcode sequences of at least 5, 10, 100, 1000, or more of the plurality of control particle oligonucleotides can be identical. The control barcode sequences of about 10, 100, 1000, or more of the plurality of control particle oligonucleotides can be identical. At least 3, 5, 10, 100, or more of the plurality of control particle oligonucleotides can comprise different control barcode sequences.

In some embodiments, the plurality of control particle oligonucleotides comprises a plurality of first control particle oligonucleotides each comprising a first control barcode sequence, and a plurality of second control particle oligonucleotides each comprising a second control barcode sequence, and wherein the first control barcode sequence and the second control barcode sequence have different sequences. The number of the plurality of first control particle oligonucleotides and the number of the plurality of second control particle oligonucleotides can be about the same. The number of the plurality of first control particle oligonucleotides and the number of the plurality of second control particle oligonucleotides can be different. The number of the plurality of first control particle oligonucleotides can be at least 2 times, 10 times, 100 times, or more greater than the number of the plurality of second control particle oligonucleotides.

In some embodiments, the control barcode sequence is not homologous to genomic sequences of a species. The control barcode sequence can be homologous to genomic sequences of a species. The species can be a non-mammalian species. The non-mammalian species can be a phage species. The phage species can be T7 phage, a PhiX phage, or a combination thereof.

In some embodiments, at least one of the plurality of control particle oligonucleotides is associated with the control particle through a linker. The at least one of the plurality of control particle oligonucleotides can comprise the linker. The linker can comprise a chemical group. The chemical group can be reversibly attached to the at least one of the plurality of control particle oligonucleotides. The chemical group can comprise a UV photocleavable group, a streptavidin, a biotin, an amine, a disulfide linkage, or any combination thereof.

In some embodiments, the diameter of the control particle is about 1-1000 micrometers, about 10-100 micrometers, 7.5 micrometer, or a combination thereof.

In some embodiments, the plurality of control particle oligonucleotides is immobilized on the control particle. The plurality of control particle oligonucleotides can be partially immobilized on the control particle. The plurality of control particle oligonucleotides can be enclosed in the control particle. The plurality of control particle oligonucleotides can be partially enclosed in the control particle. The control particle can be disruptable. The control particle can be a bead. The bead can be, or comprise, a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The control particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or any combination thereof. The control particle can comprise a disruptable hydrogel particle.

In some embodiments, the control particle is associated with a detectable moiety. The control particle oligonucleotide can be associated with a detectable moiety.

In some embodiments, the control particle is associated with a plurality of first protein binding reagents, and at least one of the plurality of first protein binding reagents is associated with one of the plurality of control particle oligonucleotides. The first protein binding reagent can comprise a first antibody. The control particle oligonucleotide can be conjugated to the first protein binding reagent through a linker. The first control particle oligonucleotide can comprise the linker. The linker can comprise a chemical group. The chemical group can be reversibly attached to the first protein binding reagent. The chemical group can comprise a UV photocleavable group, a streptavidin, a biotin, an amine, a disulfide linkage, or any combination thereof.

In some embodiments, the first protein binding reagent is associated with two or more of the plurality of control particle oligonucleotides with an identical control barcode sequence. The first protein binding reagent can be associated with two or more of the plurality of control particle oligonucleotides with different control barcode sequences. In some embodiments, at least one of the plurality of first protein binding reagents is not associated with any of the plurality of control particle oligonucleotides. The first protein binding reagent associated with the control particle oligonucleotide and the first protein binding reagent not associated with any control particle oligonucleotide can be identical protein binding reagents.

In some embodiments, the control particle is associated with a plurality of second protein binding reagents. At least one of the plurality of second protein binding reagents can be associated with one of the plurality of control particle oligonucleotides. The control particle oligonucleotide associated with the first protein binding reagent and the control particle oligonucleotide associated with the second protein binding reagent can comprise different control barcode sequences. The first protein binding reagent and the second protein binding reagent can be identical protein binding reagents.

In some embodiments, the first protein binding reagent can be associated with a partner binding reagent, and wherein the first protein binding reagent is associated with the control particle using the partner binding reagent. The partner binding reagent can comprise a partner antibody. The partner antibody can comprise an anti-cat antibody, an anti-chicken antibody, an anti-cow antibody, an anti-dog antibody, an anti-donkey antibody, an anti-goat antibody, an anti-guinea pig antibody, an anti-hamster antibody, an anti-horse antibody, an anti-human antibody, an anti-llama antibody, an anti-monkey antibody, an anti-mouse antibody, an anti-pig antibody, an anti-rabbit antibody, an anti-rat antibody, an anti-sheep antibody, or a combination thereof. The partner antibody can comprise an immunoglobulin G (IgG), a F(ab') fragment, a F(ab')2 fragment, a combination thereof, or a fragment thereof.

In some embodiments, the first protein binding reagent can be associated with a detectable moiety. The second protein binding reagent can be associated with a detectable moiety.

Disclosed herein include methods for determining the numbers of targets. In some embodiments, the method comprises: stochastically barcoding a plurality of targets of a cell of a plurality of cells and a plurality of control particle oligonucleotides using a plurality of stochastic barcodes to create a plurality of stochastically barcoded targets and a plurality of stochastically barcoded control particle oligonucleotides, wherein each of the plurality of stochastic barcodes comprises a cell label sequence, a molecular label sequence, and a target-binding region, wherein the molecular label sequences of at least two stochastic barcodes of the plurality of stochastic barcodes comprise different sequences, and wherein at least two stochastic barcodes of the plurality of stochastic barcodes comprise an identical cell label sequence, wherein a control particle composition comprises a control particle associated with the plurality of control particle oligonucleotides, wherein each of the plurality of control particle oligonucleotides comprises a control barcode sequence and a pseudo-target region comprising a sequence substantially complementary to the target-binding region of at least one of the plurality of stochastic barcodes. The method can comprise: obtaining sequencing data of the plurality of stochastically barcoded targets and the plurality of stochastically barcoded control particle oligonucleotides; counting the number of molecular label sequences with distinct sequences associated with the plurality of control particle oligonucleotides with the control barcode sequence in the sequencing data. The method can comprise: for at least one target of the plurality of targets: counting the number of molecular label sequences with distinct sequences associated with the target in the sequencing data; and estimating the number of the target, wherein the number of the target estimated correlates with the number of molecular label sequences with distinct sequences associated with the target counted and the number of molecular label sequences with distinct sequences associated with the control barcode sequence.

In some embodiments, the pseudo-target region comprises a poly(dA) region. The pseudo-target region can comprise a subsequence of the target. In some embodiments, the control barcode sequence can be at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or any combination thereof. The control barcode sequences of at least 5, 10, 100, 1000, or more of the plurality of control particle oligonucleotides can be identical. At least 3, 5, 10, 100, or more of the plurality of control particle oligonucleotides can comprise different control barcode sequences.

In some embodiments, the plurality of control particle oligonucleotides comprises a plurality of first control particle oligonucleotides each comprising a first control barcode sequence, and a plurality of second control particle oligonucleotides each comprising a second control barcode sequence. The first control barcode sequence and the second control barcode sequence can have different sequences. The number of the plurality of first control particle oligonucleotides and the number of the plurality of second control particle oligonucleotides can be about the same. The number of the plurality of first control particle oligonucleotides and the number of the plurality of second control particle oligonucleotides can be different. The number of the plurality of first control particle oligonucleotides can be at least 2 times, 10 times, 100 times, or more greater than the number of the plurality of second control particle oligonucleotides.

In some embodiments, counting the number of molecular label sequences with distinct sequences associated with the plurality of control particle oligonucleotides with the control barcode sequence in the sequencing data comprises: counting the number of molecular label sequences with distinct sequences associated with the first control barcode sequence in the sequencing data; and counting the number of molecular label sequences with distinct sequences associated with the second control barcode sequence in the sequencing data. The number of the target estimated can correlate with the number of molecular label sequences with distinct sequences associated with the target counted, the number of molecular label sequences with distinct sequences associated with the first control barcode sequence, and the number of molecular label sequences with distinct sequences associated with the second control barcode sequence. The number of the target estimated can correlate with the number of molecular label sequences with distinct sequences associated with the target counted, the number of molecular label sequences with distinct sequences associated with the control barcode sequence, and the number of the plurality of control particle oligonucleotides comprising the control barcode sequence. The number of the target estimated can correlate with the number of molecular label sequences with distinct sequences associated with the target counted, and a ratio of the number of the plurality of control particle oligonucleotides comprising the control barcode sequence and the number of molecular label sequences with distinct sequences associated with the control barcode sequence.

In some embodiments, the control particle oligonucleotide is not homologous to genomic sequences of the cell. The control particle oligonucleotide can be not homologous to genomic sequences of the species. The control particle oligonucleotide can be homologous to genomic sequences of a species. The species can be a non-mammalian species. The non-mammalian species can be a phage species. The phage species can be T7 phage, a PhiX phage, or a combination thereof.

In some embodiments, the control particle oligonucleotide can be conjugated to the control particle through a linker. At least one of the plurality of control particle oligonucleotides can be associated with the control particle through a linker. The at least one of the plurality of control particle oligonucleotides can comprise the linker. The chemical group can be reversibly attached to the at least one of the plurality of control particle oligonucleotides. The chemical group can comprise a UV photocleavable group, a streptavidin, a biotin, an amine, a disulfide linkage, or any combination thereof.

In some embodiments, the diameter of the control particle is about 1-1000 micrometers, about 10-100 micrometers, about 7.5 micrometer, or a combination thereof. The plurality of control particle oligonucleotides is immobilized on the control particle. The plurality of control particle oligonucleotides can be partially immobilized on the control particle. The plurality of control particle oligonucleotides can be enclosed in the control particle. The plurality of control particle oligonucleotides can be partially enclosed in the control particle.

In some embodiments, the method comprises releasing the at least one of the plurality of control particle oligonucleotides from the control particle prior to stochastically barcoding the plurality of targets and the control particle and the plurality of control particle oligonucleotides.

In some embodiments, the control particle is disruptable. The control particle can be a control particle bead. The control particle bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The control particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or any combination thereof. The control particle can comprise a disruptable hydrogel particle.

In some embodiments, the control particle is associated with a detectable moiety. The control particle oligonucleotide can be associated with a detectable moiety.

In some embodiments, the control particle can be associated with a plurality of first protein binding reagents, and at least one of the plurality of first protein binding reagents can be associated with one of the plurality of control particle oligonucleotides. The first protein binding reagent can comprise a first antibody. The control particle oligonucleotide can be conjugated to the first protein binding reagent through a linker. The first control particle oligonucleotide can comprise the linker. The linker can comprise a chemical group. The chemical group can be reversibly attached to the first protein binding reagent. The chemical group can comprise a UV photocleavable group, a streptavidin, a biotin, an amine, a disulfide linkage, or any combination thereof.

In some embodiments, the first protein binding reagent can be associated with two or more of the plurality of control particle oligonucleotides with an identical control barcode sequence. The first protein binding reagent can be associated with two or more of the plurality of control particle oligonucleotides with different control barcode sequences. At least one of the plurality of first protein binding reagents can be not associated with any of the plurality of control particle oligonucleotides. The first protein binding reagent associated with the control particle oligonucleotide and the first protein binding reagent not associated with any control particle oligonucleotide can be identical protein binding reagents. The control particle can associated with a plurality of second protein binding reagents At least one of the plurality of second protein binding reagents can be associated with one of the plurality of control particle oligonucleotides. The control particle oligonucleotide associated with the first protein binding reagent and the control particle oligonucleotide associated with the second protein binding reagent can comprise different control barcode sequences. The first protein binding reagent and the second protein binding reagent can be identical protein binding reagents.

In some embodiments, the first protein binding reagent is associated with a partner binding reagent, and wherein the first protein binding reagent is associated with the control particle using the partner binding reagent. The partner binding reagent can comprise a partner antibody. The partner antibody can comprise an anti-cat antibody, an anti-chicken antibody, an anti-cow antibody, an anti-dog antibody, an anti-donkey antibody, an anti-goat antibody, an anti-guinea pig antibody, an anti-hamster antibody, an anti-horse antibody, an anti-human antibody, an anti-llama antibody, an anti-monkey antibody, an anti-mouse antibody, an anti-pig antibody, an anti-rabbit antibody, an anti-rat antibody, an anti-sheep antibody, or a combination thereof. The partner antibody can comprise an immunoglobulin G (IgG), a F(ab') fragment, a F(ab')2 fragment, a combination thereof, or a fragment thereof.

In some embodiments, the first protein binding reagent can be associated with a detectable moiety. The second protein binding reagent can be associated with a detectable moiety.

In some embodiments, the stochastic barcode comprises a binding site for a universal primer. The target-binding region can comprise a poly(dT) region.

In some embodiments, the plurality of stochastic barcodes is associated with a barcoding particle. At least one stochastic barcode of the plurality of stochastic barcodes can be immobilized on the barcoding particle. At least one stochastic barcode of the plurality of stochastic barcodes can be partially immobilized on the barcoding particle. At least one stochastic barcode of the plurality of stochastic barcodes can be enclosed in the barcoding particle. At least one stochastic barcode of the plurality of stochastic barcodes can be partially enclosed in the barcoding particle.

In some embodiments, the barcoding particle is disruptable. The barcoding particle can be a barcoding bead. The barcoding bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or any combination thereof. The barcoding particle can comprise a disruptable hydrogel particle.

In some embodiments, the stochastic barcodes of the barcoding particle comprise molecular label sequences selected from at least 1000, 10000, or more different molecular label sequences. In some embodiments, the molecular label sequences of the stochastic barcodes comprise random sequences. In some embodiments, The barcoding particle comprises at least 10000 stochastic barcodes.

In some embodiments, stochastically barcoding the plurality of targets and the plurality of control particle oligonucleotides using the plurality of stochastic barcodes comprises: contacting the plurality of stochastic barcodes with targets of the plurality of targets and control particle oligonucleotides of the plurality of control particle oligonucleotides to generate stochastic barcodes hybridized to the targets and the control particle oligonucleotides; and extending the stochastic barcodes hybridized to the targets and the control particle oligonucleotides to generate the plurality of stochastically barcoded targets and the plurality of stochastically barcoded control particle oligonucleotides. Extending the stochastic barcodes can comprise extending the stochastic barcodes using a DNA polymerase, a reverse transcriptase, or a combination thereof.

In some embodiments, the method comprises amplifying the plurality of stochastically barcoded targets and the plurality of stochastically barcoded control particle oligonucleotides to produce a plurality of amplicons. Amplifying the plurality of stochastically barcoded targets and the plurality of stochastically barcoded control particle oligonucleotides can comprise amplifying, using polymerase chain reaction (PCR), at least a portion of the molecular label sequence and at least a portion of the control particle oligonucleotide or at least a portion of the molecular label sequence and at least a portion of the control particle oligonucleotide. Obtaining the sequencing data can comprise obtaining sequencing data of the plurality of amplicons. Obtaining the sequencing data can comprise sequencing the at least a portion of the molecular label sequence and the at least a portion of the control particle oligonucleotide, or the at least a portion of the molecular label sequence and the at least a portion of the control particle oligonucleotide.

Disclosed herein also include kits for sequencing control. In some embodiments, the kit comprises: a control particle composition comprising a plurality of control particle oligonucleotides associated with a control particle, wherein each of the plurality of control particle oligonucleotides comprises a control barcode sequence and a poly(dA) region.

In some embodiments, at least two of the plurality of control particle oligonucleotides comprise different control barcode sequences. In some embodiments, the control barcode sequence can be at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or any combination thereof. The control barcode sequences of at least 5, 10, 100, 1000, or more of the plurality of control particle oligonucleotides can be identical. At least 3, 5, 10, 100, or more of the plurality of control particle oligonucleotides can comprise different control barcode sequences.

In some embodiments, the plurality of control particle oligonucleotides comprises a plurality of first control particle oligonucleotides each comprising a first control barcode sequence, and a plurality of second control particle oligonucleotides each comprising a second control barcode sequence. The first control barcode sequence and the second control barcode sequence can have different sequences. The number of the plurality of first control particle oligonucleotides and the number of the plurality of second control particle oligonucleotides can be about the same. The number of the plurality of first control particle oligonucleotides and the number of the plurality of second control particle oligonucleotides can be different. The number of the plurality of first control particle oligonucleotides can be at least 2 times, 10 times, 100 times, or more greater than the number of the plurality of second control particle oligonucleotides.

In some embodiments, the control particle oligonucleotide is not homologous to genomic sequences of the cell. The control particle oligonucleotide can be not homologous to genomic sequences of the species. The control particle oligonucleotide can be homologous to genomic sequences of a species. The species can be a non-mammalian species. The non-mammalian species can be a phage species. The phage species can be T7 phage, a PhiX phage, or a combination thereof.

In some embodiments, the control particle oligonucleotide can be conjugated to the control particle through a linker. At least one of the plurality of control particle oligonucleotides can be associated with the control particle through a linker. The at least one of the plurality of control particle oligonucleotides can comprise the linker. The chemical group can be reversibly attached to the at least one of the plurality of control particle oligonucleotides. The chemical group can comprise a UV photocleavable group, a streptavidin, a biotin, an amine, a disulfide linkage, or any combination thereof.

In some embodiments, the diameter of the control particle is about 1-1000 micrometers, about 10-100 micrometers, about 7.5 micrometer, or a combination thereof. The plurality of control particle oligonucleotides is immobilized on the control particle. The plurality of control particle oligonucleotides can be partially immobilized on the control particle.

The plurality of control particle oligonucleotides can be enclosed in the control particle. The plurality of control particle oligonucleotides can be partially enclosed in the control particle.

In some embodiments, the kit comprises a plurality of barcodes. A barcode of the plurality of barcodes can comprise a target-binding region and a molecular label sequence, and molecular label sequences of at least two barcodes of the plurality of barcodes can comprise different molecule label sequences. The barcode can comprise a cell label sequence, a binding site for a universal primer, or any combination thereof. The target-binding region comprises a poly(dT) region.

In some embodiments, the plurality of barcodes can be associated with a barcoding particle. At least one barcode of the plurality of barcodes can be immobilized on the barcoding particle. At least one barcode of the plurality of barcodes is partially immobilized on the barcoding particle. At least one barcode of the plurality of barcodes can be enclosed in the barcoding particle. At least one barcode of the plurality of barcodes can be partially enclosed in the barcoding particle. The barcoding particle can be disruptable. The barcoding particle can be a second bead. The bead can be, or comprise, a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. The barcoding particle can comprise a disruptable hydrogel particle.

In some embodiments, the barcodes of the barcoding particle comprise molecular label sequences selected from at least 1000, 10000, or more different molecular label sequences. The molecular label sequences of the barcodes can comprise random sequences. The barcoding particle can comprise at least 10000 barcodes. The kit can comprise a DNA polymerase. The kit can comprise reagents for polymerase chain reaction (PCR).

Methods disclosed herein for cell identification can comprise: contacting a first plurality of cells and a second plurality of cells with two sample indexing compositions respectively, wherein each of the first plurality of cells and each of the second plurality of cells comprises one or more protein targets, wherein each of the two sample indexing compositions comprises a protein binding reagent associated with a sample indexing oligonucleotide, wherein the protein binding reagent is capable of specifically binding to at least one of the one or more protein targets, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a molecular label sequence, and a target-binding region, wherein the molecular label sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying a cell label sequence associated with two or more sample indexing sequences in the sequencing data obtained; and removing sequencing data associated with the cell label sequence from the sequencing data obtained. In some embodiments, the sample indexing oligonucleotide comprises a molecular label sequence, a binding site for a universal primer, or a combination thereof. As described herein, the first plurality of cells can be obtained or derived from a different tissue or organ than the second plurality of cells, and the first plurality of cells and the second plurality of cells can be from the same or different subjects (e.g., a mammal). For example, the first plurality of cells can be obtained or derived from a different human subject than the second plurality of cells. In some embodiments, the first plurality of cells and the second plurality of cells are obtained or derived from different tissues of the same human subject.

In some embodiments, contacting the first plurality of cells and the second plurality of cells with the two sample indexing compositions respectively comprises: contacting the first plurality of cells with a first sample indexing compositions of the two sample indexing compositions; and contacting the first plurality of cells with a second sample indexing compositions of the two sample indexing compositions.

As described herein, the sample indexing sequence can be, for example, at least 6 nucleotides in length, 25-45 nucleotides in length, about 128 nucleotides in length, at least 128 nucleotides in length, about 200-500 nucleotides in length, or a combination thereof. The sample indexing oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. In some embodiments, sample indexing sequences of at least 10, 100, 1000, or more sample indexing compositions of the plurality of sample indexing compositions comprise different sequences.

In some embodiments, the protein binding reagent comprises an antibody, a tetramer, an aptamers, a protein scaffold, or a combination thereof. The sample indexing oligonucleotide can be conjugated to the protein binding reagent through a linker. The oligonucleotide can comprise the linker. The linker can comprise a chemical group. The chemical group can be reversibly attached to the protein binding reagent. The chemical group can comprise a UV photocleavable group, a streptavidin, a biotin, an amine, a disulfide linkage or any combination thereof.

In some embodiments, at least one sample of the plurality of samples comprises a single cell. The at least one of the one or more protein targets can be on a cell surface.

In some embodiments, the method comprises: removing unbound sample indexing compositions of the two sample indexing compositions. Removing the unbound sample indexing compositions can comprise washing cells of the first plurality of cells and the second plurality of cells with a washing buffer. Removing the unbound sample indexing compositions can comprise selecting cells bound to at least one protein binding reagent of the two sample indexing compositions using flow cytometry. In some embodiments, the method comprises: lysing the one or more cells from each of the plurality of samples.

In some embodiments, the sample indexing oligonucleotide is configured to be detachable or non-detachable from the protein binding reagent. The method can comprise detaching the sample indexing oligonucleotide from the protein binding reagent. Detaching the sample indexing oligonucleotide can comprise detaching the sample indexing oligonucleotide from the protein binding reagent by UV photocleaving, chemical treatment, heating, enzyme treatment, or any combination thereof.

In some embodiments, the sample indexing oligonucleotide is not homologous to genomic sequences of any of the one or more cells. The control barcode sequence may be not homologous to genomic sequences of a species. The species can be a non-mammalian species. The non-mammalian species can be a phage species. The phage species is T7 phage, a PhiX phage, or a combination thereof.

In some embodiments, a sample of the plurality of samples comprises a plurality of cells, a tissue, a tumor sample, or any combination thereof. The plurality of sample can comprise a mammalian cell, a bacterial cell, a viral cell, a yeast cell, a fungal cell, or any combination thereof. The sample indexing oligonucleotide can comprise a sequence complementary to a capture sequence of at least one barcode of the plurality of barcodes. The barcode can comprise a target-binding region which comprises the capture sequence. The target-binding region can comprise a poly(dT) region. The sequence of the sample indexing oligonucleotide complementary to the capture sequence of the barcode can comprise a poly(dA) region.

In some embodiments, the protein target is, or comprises, an extracellular protein, an intracellular protein, or any combination thereof. The protein target can be, or comprise, a cell-surface protein, a cell marker, a B-cell receptor, a T-cell receptor, a major histocompatibility complex, a tumor antigen, a receptor, an integrin, or any combination thereof. The protein target can be, or comprise, a lipid, a carbohydrate, or any combination thereof. The protein target can be selected from a group comprising 10-100 different protein targets.

In some embodiments, the protein binding reagent is associated with two or more sample indexing oligonucleotides with an identical sequence. The protein binding reagent can be associated with two or more sample indexing oligonucleotides with different sample indexing sequences. The sample indexing composition of the plurality of sample indexing compositions can comprise a second protein binding reagent not conjugated with the sample indexing oligonucleotide. The protein binding reagent and the second protein binding reagent can be identical.

In some embodiments, a barcode of the plurality of barcodes comprises a target-binding region and a molecular label sequence, and molecular label sequences of at least two barcodes of the plurality of barcodes comprise different molecule label sequences. The barcode can comprise a cell label sequence, a binding site for a universal primer, or any combination thereof. The target-binding region can comprise a poly(dT) region.

In some embodiments, the plurality of barcodes can be associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can be a bead. The bead can be, or comprise, a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. The particle can comprise a disruptable hydrogel particle.

In some embodiments, the protein binding reagent is associated with a detectable moiety. In some embodiments, the particle is associated with a detectable moiety. The sample indexing oligonucleotide is associated with an optical moiety.

In some embodiments, the barcodes of the particle can comprise molecular label sequences selected from at least 1000, 10000, or more different molecular label sequences. The molecular label sequences of the barcodes can comprise random sequences. The particle can comprise at least 10000 barcodes.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises: amplifying the plurality of barcoded sample indexing oligonucleotides to produce a plurality of amplicons. Amplifying the plurality of barcoded sample indexing oligonucleotides can comprise amplifying, using polymerase chain reaction (PCR), at least a portion of the molecular label sequence and at least a portion of the sample indexing oligonucleotide. In some embodiments, obtaining the sequencing data of the plurality of barcoded sample indexing oligonucleotides can comprise obtaining sequencing data of the plurality of amplicons. Obtaining the sequencing data comprises sequencing at least a portion of the molecular label sequence and at least a portion of the sample indexing oligonucleotide. In some embodiments, identifying the sample origin of the at least one cell comprises identifying sample origin of the plurality of barcoded targets based on the sample indexing sequence of the at least one barcoded sample indexing oligonucleotide.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, the method comprises: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create a plurality of barcoded targets can comprise: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

Also disclosed herein include methods and compositions that can be used for sequencing control. In some embodiments, the method for sequencing control comprises: contacting one or more cells of a plurality of cells with a control composition of a plurality of control compositions, wherein a cell of the plurality of cells comprises a plurality of targets and a plurality of protein targets, wherein each of the plurality of control compositions comprises a protein binding reagent associated with a control oligonucleotide, wherein the protein binding reagent is capable of specifically binding to at least one of the plurality of protein targets, and wherein the control oligonucleotide comprises a control barcode sequence and a pseudo-target region comprising a sequence substantially complementary to the target-binding region of at least one of the plurality of barcodes; barcoding the control oligonucleotides using a plurality of barcodes to create a plurality of barcoded control oligonucleotides, wherein each of the plurality of barcodes comprises a cell label sequence, a molecular label sequence, and a target-binding region, wherein the molecular label sequences of at least two barcodes of the plurality of barcodes comprise different sequences, and wherein at least two barcodes of the plurality of barcodes comprise an identical cell label sequence; obtaining sequencing data of the plurality of barcoded control oligonucleotides; determining at least one characteristic of the one or more cells using at least one characteristic of the plurality of barcoded control oligonucleotides in the sequencing data. In some embodiments, the pseudo-target region comprises a poly(dA) region.

In some embodiments, the control barcode sequence is at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. The control barcode sequences of at least 2, 10, 100, 1000, or more of the plurality of control particle oligonucleotides can be identical. At least 2, 10, 100, 1000, or more of the plurality of control particle oligonucleotides can comprise different control barcode sequences.

In some embodiments, determining the at least one characteristic of the one or more cells comprises: determining the number of cell label sequences with distinct sequences associated with the plurality of barcoded control oligonucleotides in the sequencing data; and determining the number of the one or more cells using the number of cell label sequences with distinct sequences associated with the plurality of barcoded control oligonucleotides. The method can comprise: determining single cell capture efficiency based the number of the one or more cells determined. The method can comprise: comprising determining single cell capture efficiency based on the ratio of the number of the one or more cells determined and the number of the plurality of cells.

In some embodiments, determining the at least one characteristic of the one or more cells using the characteristics of the plurality of barcoded control oligonucleotides in the sequencing data comprises: for each cell label in the sequencing data, determining the number of molecular label sequences with distinct sequences associated with the cell label and the control barcode sequence; and determining the number of the one or more cells using the number of molecular label sequences with distinct sequences associated with the cell label and the control barcode sequence. Determining the number of molecular label sequences with distinct sequences associated with the cell label and the control barcode sequence can comprise: for each cell label in the sequencing data, determining the number of molecular label sequences with the highest number of distinct sequences associated with the cell label and the control barcode sequence. Determining the number of the one or more cells using the number of molecular label sequences with distinct sequences associated with the cell label and the control barcode sequence can comprise: generating a plot of the number of molecular label sequences with the highest number of distinct sequences with the number of cell labels in the sequencing data associated with the number of molecular label sequences with the highest number of distinct sequences; and determining a cutoff in the plot as the number of the one or more cells.

In some embodiments, the control oligonucleotide is not homologous to genomic sequences of any of the plurality of cells. The control oligonucleotide can be homologous to genomic sequences of a species. The species can be a non-mammalian species. The non-mammalian species can be a phage species. The phage species can be T7 phage, a PhiX phage, or a combination thereof.

In some embodiments, the method comprises releasing the control oligonucleotide from the protein binding reagent prior to barcoding the control oligonucleotides. In some embodiments, the method comprises removing unbound control compositions of the plurality of control compositions. Removing the unbound control compositions can comprise washing the one or more cells of the plurality of cells with a washing buffer. Removing the unbound sample indexing compositions can comprise selecting cells bound to at least one protein binding reagent of the control composition using flow cytometry.

In some embodiments, at least one of the plurality of protein targets is on a cell surface. At least one of the plurality of protein targets can comprise a cell-surface protein, a cell marker, a B-cell receptor, a T-cell receptor, a major histocompatibility complex, a tumor antigen, a receptor, an integrin, or any combination thereof. The protein binding reagent can comprise an antibody. The control oligonucleotide can be conjugated to the protein binding reagent through a linker. The control oligonucleotide can comprise the linker. The linker can comprise a chemical group. The chemical group can be reversibly attached to the first protein binding reagent. The chemical group can comprise a UV photocleavable group, a streptavidin, a biotin, an amine, a disulfide linkage, or any combination thereof.

In some embodiments, the protein binding reagent is associated with two or more control oligonucleotides with an identical control barcode sequence. The protein binding reagent can be associated with two or more control oligonucleotides with different identical control barcode sequences. In some embodiments, a second protein binding reagent of the plurality of control compositions is not associated with the control oligonucleotide. The protein binding reagent and the second protein binding reagent can be identical.

In some embodiments, the barcode comprises a binding site for a universal primer. The target-binding region can comprise a poly(dT) region. In some embodiments, the plurality of barcodes is associated with a barcoding particle. At least one barcode of the plurality of barcodes can be immobilized on the barcoding particle. At least one barcode of the plurality of barcodes can be partially immobilized on the barcoding particle. At least one barcode of the plurality of barcodes is enclosed in the barcoding particle. At least one barcode of the plurality of barcodes is partially enclosed in the barcoding particle. The barcoding particle can be disruptable. The barcoding particle can be a barcoding bead. The barcoding bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or any combination thereof. The barcoding particle can comprise a disruptable hydrogel particle.

In some embodiments, the barcoding particle is associated with an optical moiety. The control oligonucleotide can be associated with an optical moiety.

In some embodiments, the barcodes of the barcoding particle comprise molecular label sequences selected from at least 1000, 10000, or more different molecular label sequences. In some embodiments, the molecular label sequences of the barcodes comprise random sequences. In some embodiments, the barcoding particle comprises at least 10000 barcodes.

In some embodiments, barcoding the control oligonucleotides comprises: barcoding the control oligonucleotides using a plurality of stochastic barcodes to create a plurality of stochastically barcoded control oligonucleotides. In some embodiments, barcoding the plurality of control oligonucleotides using the plurality of barcodes comprises: contacting the plurality of barcodes with control oligonucleotides of the plurality of control compositions to generate barcodes hybridized to the control oligonucleotides; and extending the stochastic barcodes hybridized to the control oligonucleotides to generate the plurality of barcoded control oligonucleotides. Extending the barcodes can comprise extending the barcodes using a DNA polymerase, a reverse transcriptase, or a combination thereof. In some embodiments, the method comprises amplifying the plurality of barcoded control oligonucleotides to produce a plurality of amplicons. Amplifying the plurality of barcoded control oligonucleotides can comprise amplifying, using polymerase chain reaction (PCR), at least a portion of the molecular label sequence and at least a portion of the control oligonucleotide. In some embodiments, obtaining the sequencing data comprises obtaining sequencing data of the plurality of amplicons. Obtaining the sequencing data can comprise sequencing the at least a portion of the molecular label sequence and the at least a portion of the control oligonucleotide.

Disclosed herein include methods for sequencing control. In some embodiments, the method comprises: contacting one or more cells of a plurality of cells with a control composition of a plurality of control compositions, wherein a cell of the plurality of cells comprises a plurality of targets and a plurality of binding targets, wherein each of the plurality of control compositions comprises a cellular component binding reagent associated with a control oligonucleotide, wherein the cellular component binding reagent is capable of specifically binding to at least one of the plurality of binding targets, and wherein the control oligonucleotide comprises a control barcode sequence and a pseudo-target region comprising a sequence substantially complementary to the target-binding region of at least one of the plurality of barcodes; barcoding the control oligonucleotides using a plurality of barcodes to create a plurality of barcoded control oligonucleotides, wherein each of the plurality of barcodes comprises a cell label sequence, a molecular label sequence, and a target-binding region, wherein the molecular label sequences of at least two barcodes of the plurality of barcodes comprise different sequences, and wherein at least two barcodes of the plurality of barcodes comprise an identical cell label sequence; obtaining sequencing data of the plurality of barcoded control oligonucleotides; determining at least one characteristic of the one or more cells using at least one characteristic of the plurality of barcoded control oligonucleotides in the sequencing data. In some embodiments, the pseudo-target region comprises a poly(dA) region.

In some embodiments, the control barcode sequence is at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. The control barcode sequences of at least 2, 10, 100, 1000, or more of the plurality of control particle oligonucleotides can be identical. At least 2, 10, 100, 1000, or more of the plurality of control particle oligonucleotides can comprise different control barcode sequences.

In some embodiments, determining the at least one characteristic of the one or more cells comprises: determining the number of cell label sequences with distinct sequences associated with the plurality of barcoded control oligonucleotides in the sequencing data; and determining the number of the one or more cells using the number of cell label sequences with distinct sequences associated with the plurality of barcoded control oligonucleotides. In some embodiments, the method comprises: determining single cell capture efficiency based the number of the one or more cells determined. In some embodiments, the method comprises: determining single cell capture efficiency based on the ratio of the number of the one or more cells determined and the number of the plurality of cells.

In some embodiments, determining the at least one characteristic of the one or more cells can comprise: for each cell label in the sequencing data, determining the number of molecular label sequences with distinct sequences associated with the cell label and the control barcode sequence; and determining the number of the one or more cells using the number of molecular label sequences with distinct sequences associated with the cell label and the control barcode sequence. Determining the number of molecular label sequences with distinct sequences associated with the cell label and the control barcode sequence comprises: for each cell label in the sequencing data, determining the number of molecular label sequences with the highest number of distinct sequences associated with the cell label and the control barcode sequence. Determining the number of the one or more cells using the number of molecular label sequences with distinct sequences associated with the cell label and the control barcode sequence can comprise: generating a plot of the number of molecular label sequences with the highest number of distinct sequences with the number of cell labels in the sequencing data associated with the number of molecular label sequences with the highest number of distinct sequences; and determining a cutoff in the plot as the number of the one or more cells.

In some embodiments, the control oligonucleotide is not homologous to genomic sequences of any of the plurality of cells. The control oligonucleotide can be homologous to genomic sequences of a species. The species can be a non-mammalian species. The non-mammalian species can be a phage species. The phage species can be T7 phage, a PhiX phage, or a combination thereof.

In some embodiments, the method comprises: releasing the control oligonucleotide from the cellular component binding reagent prior to barcoding the control oligonucleotides. At least one of the plurality of binding targets can be expressed on a cell surface. At least one of the plurality of binding targets can comprise a cell-surface protein, a cell marker, a B-cell receptor, a T-cell receptor, a major histocompatibility complex, a tumor antigen, a receptor, an integrin, or any combination thereof. The cellular component binding reagent can comprise a cell surface binding reagent, an antibody, a tetramer, an aptamers, a protein scaffold, an invasion, or a combination thereof.

In some embodiments, binding target of the cellular component binding reagent is selected from a group comprising 10-100 different binding targets. Aa binding target of the cellular component binding reagent can comprise a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. The control oligonucleotide can be conjugated to the cellular component binding reagent through a linker. The control oligonucleotide can comprise the linker. The linker can comprise a chemical group. The chemical group can be reversibly attached to the first cellular component binding reagent. The chemical group can comprise a UV photocleavable group, a streptavidin, a biotin, an amine, a disulfide linkage, or any combination thereof.

In some embodiments, the cellular component binding reagent can be associated with two or more control oligonucleotides with an identical control barcode sequence. The cellular component binding reagent can be associated with two or more control oligonucleotides with different identical control barcode sequences. In some embodiments, a second cellular component binding reagent of the plurality of control compositions is not associated with the control oligonucleotide. The cellular component binding reagent and the second cellular component binding reagent can be identical.

In some embodiments, the barcode comprises a binding site for a universal primer. In some embodiments, the target-binding region comprises a poly(dT) region.

In some embodiments, the plurality of barcodes is associated with a barcoding particle. At least one barcode of the plurality of barcodes can be immobilized on the barcoding particle. At least one barcode of the plurality of barcodes can be partially immobilized on the barcoding particle. At least one barcode of the plurality of barcodes can be enclosed in the barcoding particle. At least one barcode of the plurality of barcodes can be partially enclosed in the barcoding particle. The barcoding particle can be disruptable. The barcoding particle can be a barcoding bead. In some embodiments, the barcoding bead comprises a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and a combination thereof. The barcoding particle can comprise a disruptable hydrogel particle. The barcoding particle can be associated with an optical moiety.

In some embodiments, the control oligonucleotide can be associated with an optical moiety. In some embodiments, the barcodes of the barcoding particle comprise molecular label sequences selected from at least 1000, 10000, or more different molecular label sequences. In some embodiments, the molecular label sequences of the barcodes comprise random sequences. The barcoding particle can comprise at least 10000 barcodes.

In some embodiments, barcoding the control oligonucleotides comprises: barcoding the control oligonucleotides using a plurality of stochastic barcodes to create a plurality of stochastically barcoded control oligonucleotides Barcoding the plurality of control oligonucleotides using the plurality of barcodes can comprise: contacting the plurality of barcodes with control oligonucleotides of the plurality of control compositions to generate barcodes hybridized to the control oligonucleotides; and extending the stochastic barcodes hybridized to the control oligonucleotides to generate the plurality of barcoded control oligonucleotides. Extending the barcodes can comprise extending the barcodes using a DNA polymerase, a reverse transcriptase, or a combination thereof. In some embodiment, the method comprises amplifying the plurality of barcoded control oligonucleotides to produce a plurality of amplicons. Amplifying the plurality of barcoded control oligonucleotides can comprise amplifying, using polymerase chain reaction (PCR), at least a portion of the molecular label sequence and at least a portion of the control oligonucleotide. Obtaining the sequencing data can comprise obtaining sequencing data of the plurality of amplicons. Obtaining the sequencing data can comprise sequencing the at least a portion of the molecular label sequence and the at least a portion of the control oligonucleotide.

The methods for sequencing control can, in some embodiments, comprise: contacting one or more cells of a plurality of cells with a control composition of a plurality of control compositions, wherein a cell of the plurality of cells comprises a plurality of targets and a plurality of protein targets, wherein each of the plurality of control compositions comprises a protein binding reagent associated with a control oligonucleotide, wherein the protein binding reagent is capable of specifically binding to at least one of the plurality of protein targets, and wherein the control oligonucleotide comprises a control barcode sequence and a pseudo-target region comprising a sequence substantially complementary to the target-binding region of at least one of the plurality of barcodes; and determining at least one characteristic of the one or more cells using at least one characteristic of the plurality of control oligonucleotides. The pseudo-target region can comprise a poly(dA) region.

In some embodiments, the control barcode sequence is at least 6 nucleotides in length, 25-45 nucleotides in length, about 128 nucleotides in length, at least 128 nucleotides in length, about 200-500 nucleotides in length, or a combination thereof. The control particle oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. The control barcode sequences of at least 2, 10, 100, 1000, or more of the plurality of control particle oligonucleotides can be identical. At least 2, 10, 100, 1000, or more of the plurality of control particle oligonucleotides can comprise different control barcode sequences.

In some embodiments, determining the at least one characteristic of the one or more cells comprises: determining the number of cell label sequences with distinct sequences associated with the plurality of barcoded control oligonucleotides in the sequencing data; and determining the number of the one or more cells using the number of cell label sequences with distinct sequences associated with the plurality of barcoded control oligonucleotides. The method can comprise: determining single cell capture efficiency based the number of the one or more cells determined. The method can comprise: comprising determining single cell capture efficiency based on the ratio of the number of the one or more cells determined and the number of the plurality of cells.

In some embodiments, determining the at least one characteristic of the one or more cells using the characteristics of the plurality of barcoded control oligonucleotides in the sequencing data comprises: for each cell label in the sequencing data, determining the number of molecular label sequences with distinct sequences associated with the cell label and the control barcode sequence; and determining the number of the one or more cells using the number of molecular label sequences with distinct sequences associated with the cell label and the control barcode sequence. Determining the number of molecular label sequences with distinct sequences associated with the cell label and the control barcode sequence can comprise: for each cell label in the sequencing data, determining the number of molecular label sequences with the highest number of distinct sequences associated with the cell label and the control barcode sequence. Determining the number of the one or more cells using the number of molecular label sequences with distinct sequences associated with the cell label and the control barcode sequence can comprise: generating a plot of the number of molecular label sequences with the highest number of distinct sequences with the number of cell labels in the sequencing data associated with the number of molecular label sequences with the highest number of distinct sequences; and determining a cutoff in the plot as the number of the one or more cells.

In some embodiments, the control oligonucleotide is not homologous to genomic sequences of any of the plurality of cells. The control oligonucleotide can be homologous to genomic sequences of a species. The species can be a non-mammalian species. The non-mammalian species can be a phage species. The phage species can be T7 phage, a PhiX phage, or a combination thereof.

In some embodiments, the method comprises releasing the control oligonucleotide from the protein binding reagent prior to barcoding the control oligonucleotides. In some embodiments, the method comprises removing unbound control compositions of the plurality of control compositions. Removing the unbound control compositions can comprise washing the one or more cells of the plurality of cells with a washing buffer. Removing the unbound sample indexing compositions can comprise selecting cells bound to at least one protein binding reagent of the control composition using flow cytometry.

In some embodiments, at least one of the plurality of protein targets is on a cell surface. At least one of the plurality of protein targets can comprise a cell-surface protein, a B-cell receptor, a T-cell receptor, a major histocompatibility complex, a tumor antigen, a receptor, an integrin, or any combination thereof. The protein binding reagent can comprise an antibody. The control oligonucleotide can be conjugated to the protein binding reagent through a linker. The control oligonucleotide can comprise the linker. The linker can comprise a chemical group. The chemical group can be reversibly attached to the first protein binding reagent. The chemical group can comprise a UV photocleavable group, a streptavidin, a biotin, an amine, a disulfide linkage, or any combination thereof.

In some embodiments, the protein binding reagent is associated with two or more control oligonucleotides with an identical control barcode sequence. The protein binding reagent can be associated with two or more control oligonucleotides with different identical control barcode sequences. In some embodiments, a second protein binding reagent of the plurality of control compositions is not associated with the control oligonucleotide. The protein binding reagent and the second protein binding reagent can be identical.

In some embodiments, the barcode comprises a binding site for a universal primer. The target-binding region can comprise a poly(dT) region. In some embodiments, the plurality of barcodes is associated with a barcoding particle. At least one barcode of the plurality of barcodes can be immobilized on the barcoding particle. At least one barcode of the plurality of barcodes can be partially immobilized on the barcoding particle. At least one barcode of the plurality of barcodes is enclosed in the barcoding particle. At least one barcode of the plurality of barcodes is partially enclosed in the barcoding particle. The barcoding particle can be disruptable. The barcoding particle can be a barcoding bead. The barcoding bead can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The barcoding particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, or any combination thereof. The barcoding particle can comprise a disruptable hydrogel particle.

In some embodiments, the barcoding particle is associated with an optical moiety. The control oligonucleotide can be associated with an optical moiety.

In some embodiments, the method comprises: barcoding the control oligonucleotides using a plurality of barcodes to create a plurality of barcoded control oligonucleotides, wherein each of the plurality of barcodes comprises a cell label sequence, a molecular label sequence, and a target-binding region, wherein the molecular label sequences of at least two barcodes of the plurality of barcodes comprise different sequences, and wherein at least two barcodes of the plurality of barcodes comprise an identical cell label sequence; and obtaining sequencing data of the plurality of barcoded control oligonucleotides;

In some embodiments, the barcodes of the barcoding particle comprise molecular label sequences selected from at least 1000, 10000, or more different molecular label sequences. In some embodiments, the molecular label sequences of the barcodes comprise random sequences. In some embodiments, the barcoding particle comprises at least 10000 barcodes.

In some embodiments, barcoding the control oligonucleotides comprises: barcoding the control oligonucleotides using a plurality of stochastic barcodes to create a plurality of stochastically barcoded control oligonucleotides. In some embodiments, barcoding the plurality of control oligonucleotides using the plurality of barcodes comprises: contacting the plurality of barcodes with control oligonucleotides of the plurality of control compositions to generate barcodes hybridized to the control oligonucleotides; and extending the stochastic barcodes hybridized to the control oligonucleotides to generate the plurality of barcoded control oligonucleotides. Extending the barcodes can comprise extending the barcodes using a DNA polymerase, a reverse transcriptase, or a combination thereof. In some embodiments, the method comprises amplifying the plurality of barcoded control oligonucleotides to produce a plurality of amplicons. Amplifying the plurality of barcoded control oligonucleotides can comprise amplifying, using polymerase chain reaction (PCR), at least a portion of the molecular label sequence and at least a portion of the control oligonucleotide. In some embodiments, obtaining the sequencing data comprises obtaining sequencing data of the plurality of amplicons. Obtaining the sequencing data can comprise sequencing the at least a portion of the molecular label sequence and the at least a portion of the control oligonucleotide.

Methods for cell identification can, in some embodiments, comprise: contacting a first plurality of cells and a second plurality of cells with two sample indexing compositions respectively, wherein each of the first plurality of cells and each of the second plurality of cells comprise one or more antigen targets, wherein each of the two sample indexing compositions comprises an antigen binding reagent associated with a sample indexing oligonucleotide, wherein the antigen binding reagent is capable of specifically binding to at least one of the one or more antigen targets, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a molecular label sequence, and a target-binding region, wherein the molecular label sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying a cell label sequence associated with two or more sample indexing sequences in the sequencing data obtained; and removing sequencing data associated with the cell label sequence from the sequencing data obtained and/or excluding the sequencing data associated with the cell label sequence from subsequent analysis. In some embodiments, the sample indexing oligonucleotide comprises a molecular label sequence, a binding site for a universal primer, or a combination thereof.

Disclosed herein also includes methods for multiplet identification. A multiplet expression profile, or a multiplet, can be an expression profile comprising expression profiles of multiplet cells. When determining expression profiles of single cells, n cells may be identified as one cell and the expression profiles of the n cells may be identified as the expression profile for one cell (referred to as a multiplet or n-plet expression profile). For example, when determining expression profiles of two cells using barcoding (e.g., stochastic barcoding), the mRNA molecules of the two cells may be associated with barcodes having the same cell label. As another example, two cells may be associated with one particle (e.g., a bead). The particle can include barcodes with the same cell label. After lysing the cells, the mRNA molecules in the two cells can be associated with the barcodes of the particle, thus the same cell label. Doublet expression profiles can skew the interpretation of the expression profiles. Multiplets can be different in different implementations. In some embodiments, the plurality of multiplets can include a doublet, a triplet, a quartet, a quintet, a sextet, a septet, an octet, a nonet, or any combination thereof.

A multiplet can be any n-plet. In some embodiments, n is, or is about, 2, 3, 4, 5, 6, 7, 8, 9, 10, 11, 12, 13, 14, 15, 16, 17, 18, 19, 20, or a range between any two of these values. In some embodiments, n is at least, or is at most, 2, 3, 4, 5, 6, 7, 8, 9, 10, 11, 12, 13, 14, 15, 16, 17, 18, 19, or 20. A singlet can be an expression profile that is not a multiplet expression profile.

The performance of using sample indexing oligonucleotides to index samples and identify multiplets can be comparable to the performance of using synthetic multiplet expression profiles to identify multiplets (described in U.S. application Ser. No. 15/926,977, filed on Mar. 20, 2018, entitled "SYNTHETIC MULTIPLETS FOR MULTIPLETS DETERMINATION," the content of which is incorporated herein in its entirety). In some embodiments, mutliplets can be identified using both sample indexing oligonucleotides and synthetic multiplet expression profiles.

In some embodiments, the methods of multiplet identification disclosed herein comprise: contacting a first plurality of cells and a second plurality of cells with two sample indexing compositions respectively, wherein each of the first plurality of cells and each of the second plurality of cells comprise one or more antigen targets, wherein each of the two sample indexing compositions comprises an antigen binding reagent associated with a sample indexing oligonucleotide, wherein the antigen binding reagent is capable of specifically binding to at least one of the one or more antigen targets, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a molecular label sequence, and a target-binding region, wherein the molecular label sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying one or more multiplet cell label sequences that is each associated with two or more sample indexing sequences in the sequencing data obtained. In some embodiments, the method comprises: removing the sequencing data associated with the one or more multiplet cell label sequences from the sequencing data obtained and/or excluding the sequencing data associated with the one or more multiplet cell label sequences from subsequent analysis. In some embodiments, the sample indexing oligonucleotide comprises a molecular label sequence, a binding site for a universal primer, or a combination thereof.

In some embodiments, contacting the first plurality of cells and the second plurality of cells with the two sample indexing compositions respectively comprises: contacting the first plurality of cells with a first sample indexing compositions of the two sample indexing compositions; and contacting the first plurality of cells with a second sample indexing compositions of the two sample indexing compositions.

In some embodiments, the sample indexing sequence is at least 6 nucleotides in length, 25-60 nucleotides in length (e.g., 45 nucleotides in length), about 128 nucleotides in length, at least 128 nucleotides in length, about 200-500 nucleotides in length, or a combination thereof. The sample indexing oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. In some embodiments, sample indexing sequences of at least 10, 100, 1000, or more sample indexing compositions of the plurality of sample indexing compositions comprise different sequences.

In some embodiments, the antigen binding reagent comprises an antibody, a tetramer, an aptamers, a protein scaffold, or a combination thereof. The sample indexing oligonucleotide can be conjugated to the antigen binding reagent through a linker. The oligonucleotide can comprise the linker. The linker can comprise a chemical group. The chemical group can be reversibly or irreversibly attached to the antigen binding reagent. The chemical group can comprise a UV photocleavable group, a disulfide bond, a streptavidin, a biotin, an amine, a disulfide linkage or any combination thereof.

In some embodiments, at least one of the first plurality of cells and the second plurality of cells comprises single cells. The at least one of the one or more antigen targets can be on a cell surface.

In some embodiments, the method comprises: removing unbound sample indexing compositions of the two sample indexing compositions. Removing the unbound sample indexing compositions can comprise washing cells of the first plurality of cells and the second plurality of cells with a washing buffer. Removing the unbound sample indexing compositions can comprise selecting cells bound to at least one antigen binding reagent of the two sample indexing compositions using flow cytometry. In some embodiments, the method comprises: lysing one or more cells of the first plurality of cells and the second plurality of cells.

In some embodiments, the sample indexing oligonucleotide is configured to be detachable or non-detachable from the antigen binding reagent. The method can comprise detaching the sample indexing oligonucleotide from the antigen binding reagent. Detaching the sample indexing oligonucleotide can comprise detaching the sample indexing oligonucleotide from the antigen binding reagent by UV photocleaving, chemical treatment (e.g., using reducing reagent, such as dithiothreitol), heating, enzyme treatment, or any combination thereof.

In some embodiments, the sample indexing oligonucleotide is not homologous to genomic sequences of any of the one or more cells. The control barcode sequence may be not homologous to genomic sequences of a species. The species can be a non-mammalian species. The non-mammalian species can be a phage species. The phage species is T7 phage, a PhiX phage, or a combination thereof.

In some embodiments, the first plurality of cells and the second plurality of cells comprise a tumor cells, a mammalian cell, a bacterial cell, a viral cell, a yeast cell, a fungal cell, or any combination thereof. The sample indexing oligonucleotide can comprise a sequence complementary to a capture sequence of at least one barcode of the plurality of barcodes. The barcode can comprise a target-binding region which comprises the capture sequence. The target-binding region can comprise a poly(dT) region. The sequence of the sample indexing oligonucleotide complementary to the capture sequence of the barcode can comprise a poly(dA) region.

In some embodiments, the antigen target is, or comprises, an extracellular protein, an intracellular protein, or any combination thereof. The antigen target can be, or comprise, a cell-surface protein, a cell marker, a B-cell receptor, a T-cell receptor, a major histocompatibility complex, a tumor antigen, a receptor, an integrin, or any combination thereof. The antigen target can be, or comprise, a lipid, a carbohydrate, or any combination thereof. The antigen target can be selected from a group comprising 10-100 different antigen targets.

In some embodiments, the antigen binding reagent is associated with two or more sample indexing oligonucleotides with an identical sequence. The antigen binding reagent can be associated with two or more sample indexing oligonucleotides with different sample indexing sequences. The sample indexing composition of the plurality of sample indexing compositions can comprise a second antigen binding reagent not conjugated with the sample indexing oligonucleotide. The antigen binding reagent and the second antigen binding reagent can be identical.

In some embodiments, a barcode of the plurality of barcodes comprises a target-binding region and a molecular label sequence, and molecular label sequences of at least two barcodes of the plurality of barcodes comprise different molecule label sequences. The barcode can comprise a cell label sequence, a binding site for a universal primer, or any combination thereof. The target-binding region can comprise a poly(dT) region.

In some embodiments, the plurality of barcodes can be associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can be a bead. The bead can be, or comprise, a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane/(PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. The particle can comprise a disruptable hydrogel particle.

In some embodiments, the antigen binding reagent is associated with a detectable moiety. In some embodiments, the particle is associated with a detectable moiety. The sample indexing oligonucleotide is associated with an optical moiety. In some embodiments, the barcodes of the particle can comprise molecular label sequences selected from at least 1000, 10000, or more different molecular label sequences. The molecular label sequences of the barcodes can comprise random sequences. The particle can comprise at least 10000 barcodes.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises: amplifying the plurality of barcoded sample indexing oligonucleotides to produce a plurality of amplicons. Amplifying the plurality of barcoded sample indexing oligonucleotides can comprise amplifying, using polymerase chain reaction (PCR), at least a portion of the molecular label sequence and at least a portion of the sample indexing oligonucleotide. In some embodiments, obtaining the sequencing data of the plurality of barcoded sample indexing oligonucleotides can comprise obtaining sequencing data of the plurality of amplicons. Obtaining the sequencing data comprises sequencing at least a portion of the molecular label sequence and at least a portion of the sample indexing oligonucleotide. In some embodiments, identifying the sample origin of the at least one cell comprises identifying sample origin of the plurality of barcoded targets based on the sample indexing sequence of the at least one barcoded sample indexing oligonucleotide.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, the method comprises: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

Methods for cell identification can, in some embodiments, comprise: contacting a first plurality of cells and a second plurality of cells with two sample indexing compositions respectively, wherein each of the first plurality of cells and each of the second plurality of cells comprise one or more cellular component targets, wherein each of the two sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of the two sample indexing compositions of the plurality of sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a molecular label sequence, and a target-binding region, wherein the molecular label sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; identifying one or more cell label sequences that is each associated with two or more sample indexing sequences in the sequencing data obtained; and removing the sequencing data associated with the one or more cell label sequences that is each associated with two or more sample indexing sequences from the sequencing data obtained and/or excluding the sequencing data associated with the one or more cell label sequences that is each associated with two or more sample indexing sequences from subsequent analysis. In some embodiments, the sample indexing oligonucleotide comprises a molecular label sequence, a binding site for a universal primer, or a combination thereof.

Disclosed herein includes methods for multiplet identification. In some embodiments, the method comprises: contacting a first plurality of cells and a second plurality of cells with two sample indexing compositions respectively, wherein each of the first plurality of cells and each of the second plurality of cells comprise one or more cellular component targets, wherein each of the two sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of the two sample indexing compositions of the plurality of sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a molecular label sequence, and a target-binding region, wherein the molecular label sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; identifying one or more multiplet cell label sequences that is each associated with two or more sample indexing sequences in the sequencing data obtained. In some embodiments, the method comprises: removing the sequencing data associated with the one or more multiplet cell label sequences from the sequencing data obtained and/or excluding the sequencing data associated with the one or more multiplet cell label sequences from subsequent analysis. In some embodiments, the sample indexing oligonucleotide comprises a molecular label sequence, a binding site for a universal primer, or a combination thereof.

In some embodiments, contacting the first plurality of cells and the second plurality of cells with the two sample indexing compositions respectively comprises: contacting the first plurality of cells with a first sample indexing compositions of the two sample indexing compositions; and contacting the first plurality of cells with a second sample indexing compositions of the two sample indexing compositions.

In some embodiments, the sample indexing sequence is at least 6 nucleotides in length, 25-60 nucleotides in length (e.g., 45 nucleotides in length), about 128 nucleotides in length, at least 128 nucleotides in length, about 200-500 nucleotides in length, or a combination thereof. The sample indexing oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. In some embodiments, sample indexing sequences of at least 10, 100, 1000, or more sample indexing compositions of the plurality of sample indexing compositions comprise different sequences.

In some embodiments, the cellular component binding reagent comprises an antibody, a tetramer, an aptamer, a protein scaffold, or a combination thereof. The sample indexing oligonucleotide can be conjugated to the cellular component binding reagent through a linker. The oligonucleotide can comprise the linker. The linker can comprise a chemical group. The chemical group can be reversibly or irreversibly attached to the cellular component binding reagent. The chemical group can comprise a UV photocleavable group, a disulfide bond, a streptavidin, a biotin, an amine, a disulfide linkage or any combination thereof.

In some embodiments, at least one of the first plurality of cells and the second plurality of cells comprises a single cell. The at least one of the one or more cellular component targets can be on a cell surface.

In some embodiments, the method comprises: removing unbound sample indexing compositions of the two sample indexing compositions. Removing the unbound sample indexing compositions can comprise washing cells of the first plurality of cells and the second plurality of cells with a washing buffer. Removing the unbound sample indexing compositions can comprise selecting cells bound to at least one cellular component binding reagent of the two sample indexing compositions using flow cytometry. In some embodiments, the method comprises: lysing one or more cells of the first plurality of cells and the second plurality of cells.

In some embodiments, the sample indexing oligonucleotide is configured to be detachable or non-detachable from the cellular component binding reagent. The method can comprise detaching the sample indexing oligonucleotide from the cellular component binding reagent. Detaching the sample indexing oligonucleotide can comprise detaching the sample indexing oligonucleotide from the cellular component binding reagent by UV photocleaving, chemical treatment (e.g., using reducing reagent, such as dithiothreitol), heating, enzyme treatment, or any combination thereof.

In some embodiments, the sample indexing oligonucleotide is not homologous to genomic sequences of any of the one or more cells. The control barcode sequence may be not homologous to genomic sequences of a species. The species can be a non-mammalian species. The non-mammalian species can be a phage species. The phage species is T7 phage, a PhiX phage, or a combination thereof.

In some embodiments, the first plurality of cells and the second plurality of cells comprise a tumor cell, a mammalian cell, a bacterial cell, a viral cell, a yeast cell, a fungal cell, or any combination thereof. The sample indexing oligonucleotide can comprise a sequence complementary to a capture sequence of at least one barcode of the plurality of barcodes. The barcode can comprise a target-binding region which comprises the capture sequence. The target-binding region can comprise a poly(dT) region. The sequence of the sample indexing oligonucleotide complementary to the capture sequence of the barcode can comprise a poly(dA) region.

In some embodiments, the antigen target is, or comprises, an extracellular protein, an intracellular protein, or any combination thereof. The antigen target can be, or comprise, a cell-surface protein, a cell marker, a B-cell receptor, a T-cell receptor, a major histocompatibility complex, a tumor antigen, a receptor, an integrin, or any combination thereof. The antigen target can be, or comprise, a lipid, a carbohydrate, or any combination thereof. The antigen target can be selected from a group comprising 10-100 different antigen targets.

In some embodiments, the cellular component binding reagent is associated with two or more sample indexing oligonucleotides with an identical sequence. The cellular component binding reagent can be associated with two or more sample indexing oligonucleotides with different sample indexing sequences. The sample indexing composition of the plurality of sample indexing compositions can comprise a second cellular component binding reagent not conjugated with the sample indexing oligonucleotide. The cellular component binding reagent and the second cellular component binding reagent can be identical.

In some embodiments, a barcode of the plurality of barcodes comprises a target-binding region and a molecular label sequence, and molecular label sequences of at least two barcodes of the plurality of barcodes comprise different molecule label sequences. The barcode can comprise a cell label sequence, a binding site for a universal primer, or any combination thereof. The target-binding region can comprise a poly(dT) region.

In some embodiments, the plurality of barcodes can be associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can be a bead. The bead can be, or comprise, a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. The particle can comprise a disruptable hydrogel particle.

In some embodiments, the cellular component binding reagent is associated with a detectable moiety. In some embodiments, the particle is associated with a detectable moiety. The sample indexing oligonucleotide is associated with an optical moiety.

In some embodiments, the barcodes of the particle can comprise molecular label sequences selected from at least 1000, 10000, or more different molecular label sequences. The molecular label sequences of the barcodes can comprise random sequences. The particle can comprise at least 10000 barcodes.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises: amplifying the plurality of barcoded sample indexing oligonucleotides to produce a plurality of amplicons. Amplifying the plurality of barcoded sample indexing oligonucleotides can comprise amplifying, using polymerase chain reaction (PCR), at least a portion of the molecular label sequence and at least a portion of the sample indexing oligonucleotide. In some embodiments, obtaining the sequencing data of the plurality of barcoded sample indexing oligonucleotides can comprise obtaining sequencing data of the plurality of amplicons. Obtaining the sequencing data comprises sequencing at least a portion of the molecular label sequence and at least a portion of the sample indexing oligonucleotide. In some embodiments, identifying the sample origin of the at least one cell comprises identifying sample origin of the plurality of barcoded targets based on the sample indexing sequence of the at least one barcoded sample indexing oligonucleotide.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, the method comprises: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

Disclosed herein includes methods for cell identification. In some embodiments, the method comprises: contacting one or more cells from each of a first plurality of cells and a second plurality of cells with a sample indexing composition of a plurality of two sample indexing compositions respectively, wherein each of the first plurality of cells and each of the second plurality of cells comprises one or more antigen targets, wherein each of the two sample indexing compositions comprises an antigen binding reagent associated with a sample indexing oligonucleotide, wherein the antigen binding reagent is capable of specifically binding to at least one of the one or more antigen targets, wherein the sample indexing oligonucleotide comprises a sample indexing sequence, and wherein sample indexing sequences of the two sample indexing compositions comprise different sequences; and identifying one or more cells that is each associated with two or more sample indexing sequences. In some embodiments, the sample indexing oligonucleotide comprises a molecular label sequence, a binding site for a universal primer, or a combination thereof.

Disclosed herein include methods for multiplet identification. In some embodiments, the method comprises: contacting one or more cells from each of a first plurality of cells and a second plurality of cells with a sample indexing composition of a plurality of two sample indexing compositions respectively, wherein each of the first plurality of cells and each of the second plurality of cells comprises one or more antigen targets, wherein each of the two sample indexing compositions comprises an antigen binding reagent associated with a sample indexing oligonucleotide, wherein the antigen binding reagent is capable of specifically binding to at least one of the one or more antigen targets, wherein the sample indexing oligonucleotide comprises a sample indexing sequence, and wherein sample indexing sequences of the two sample indexing compositions comprise different sequences; and identifying one or more cells that is each associated with two or more sample indexing sequences as multiplet cells.

In some embodiments, identifying the cells that is each associated with two or more sample indexing sequences comprises: barcoding the sample indexing oligonucleotides using a plurality of barcodes to create a plurality of barcoded sample indexing oligonucleotides, wherein each of the plurality of barcodes comprises a cell label sequence, a molecular label sequence, and a target-binding region, wherein the molecular label sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying one or more cell label sequences that is each associated with two or more sample indexing sequences in the sequencing data obtained. The method can comprise removing the sequencing data associated with the one or more cell label sequences that is each associated with two or more sample indexing sequences from the sequencing data obtained and/or excluding the sequencing data associated with the one or more cell label sequences that is each associated with the two or more sample indexing sequences from subsequent analysis.

In some embodiments, contacting the first plurality of cells and the second plurality of cells with the two sample indexing compositions respectively comprises: contacting the first plurality of cells with a first sample indexing compositions of the two sample indexing compositions; and contacting the first plurality of cells with a second sample indexing compositions of the two sample indexing compositions.

In some embodiments, the sample indexing sequence is at least 6 nucleotides in length, 25-60 nucleotides in length (e.g., 45 nucleotides in length), about 128 nucleotides in length, at least 128 nucleotides in length, about 200-500 nucleotides in length, or a combination thereof. The sample indexing oligonucleotide can be about 50 nucleotides in length, about 100 nucleotides in length, about 200 nucleotides in length, at least 200 nucleotides in length, less than about 200-300 nucleotides in length, about 500 nucleotides in length, or a combination thereof. In some embodiments, sample indexing sequences of at least 10, 100, 1000, or more sample indexing compositions of the plurality of sample indexing compositions comprise different sequences.

In some embodiments, the antigen binding reagent comprises an antibody, a tetramer, an aptamer, a protein scaffold, or a combination thereof. The sample indexing oligonucleotide can be conjugated to the antigen binding reagent through a linker. The oligonucleotide can comprise the linker. The linker can comprise a chemical group. The chemical group can be reversibly or irreversibly attached to the antigen binding reagent. The chemical group can comprise a UV photocleavable group, a disulfide bond, a streptavidin, a biotin, an amine, a disulfide linkage or any combination thereof.

In some embodiments, at least one of the first plurality of cells and the second plurality of cells comprises single cells. The at least one of the one or more antigen targets can be on a cell surface. In some embodiments, the method comprises: removing unbound sample indexing compositions of the two sample indexing compositions. Removing the unbound sample indexing compositions can comprise washing cells of the first plurality of cells and the second plurality of cells with a washing buffer. Removing the unbound sample indexing compositions can comprise selecting cells bound to at least one antigen binding reagent of the two sample indexing compositions using flow cytometry. In some embodiments, the method comprises: lysing one or more cells of the first plurality of cells and the second plurality of cells.

In some embodiments, the sample indexing oligonucleotide is configured to be detachable or non-detachable from the antigen binding reagent. The method can comprise detaching the sample indexing oligonucleotide from the antigen binding reagent. Detaching the sample indexing oligonucleotide can comprise detaching the sample indexing oligonucleotide from the antigen binding reagent by UV photocleaving, chemical treatment (e.g., using reducing reagent, such as dithiothreitol), heating, enzyme treatment, or any combination thereof.

In some embodiments, the sample indexing oligonucleotide is not homologous to genomic sequences of any of the one or more cells. The control barcode sequence may be not homologous to genomic sequences of a species. The species can be a non-mammalian species. The non-mammalian species can be a phage species. The phage species is T7 phage, a PhiX phage, or a combination thereof.

In some embodiments, the first plurality of cells and the second plurality of cells comprise a tumor cells, a mammalian cell, a bacterial cell, a viral cell, a yeast cell, a fungal cell, or any combination thereof. The sample indexing oligonucleotide can comprise a sequence complementary to a capture sequence of at least one barcode of the plurality of barcodes. The barcode can comprise a target-binding region which comprises the capture sequence. The target-binding region can comprise a poly(dT) region. The sequence of the sample indexing oligonucleotide complementary to the capture sequence of the barcode can comprise a poly(dA) region.

In some embodiments, the antigen target is, or comprises, an extracellular protein, an intracellular protein, or any combination thereof. The antigen target can be, or comprise, a cell-surface protein, a cell marker, a B-cell receptor, a T-cell receptor, a major histocompatibility complex, a tumor antigen, a receptor, an integrin, or any combination thereof. The antigen target can be, or comprise, a lipid, a carbohydrate, or any combination thereof. The antigen target can be selected from a group comprising 10-100 different antigen targets.

In some embodiments, the antigen binding reagent is associated with two or more sample indexing oligonucleotides with an identical sequence. The antigen binding reagent can be associated with two or more sample indexing oligonucleotides with different sample indexing sequences. The sample indexing composition of the plurality of sample indexing compositions can comprise a second antigen binding reagent not conjugated with the sample indexing oligonucleotide. The antigen binding reagent and the second antigen binding reagent can be identical.

In some embodiments, a barcode of the plurality of barcodes comprises a target-binding region and a molecular label sequence, and molecular label sequences of at least two barcodes of the plurality of barcodes comprise different molecule label sequences. The barcode can comprise a cell label sequence, a binding site for a universal primer, or any combination thereof. The target-binding region can comprise a poly(dT) region.

In some embodiments, the plurality of barcodes can be associated with a particle. At least one barcode of the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can be a bead. The bead can be, or comprise, a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, sepharose, cellulose, nylon, silicone, and any combination thereof. The particle can comprise a disruptable hydrogel particle.

In some embodiments, the antigen binding reagent is associated with a detectable moiety. In some embodiments, the particle is associated with a detectable moiety. The sample indexing oligonucleotide is associated with an optical moiety.

In some embodiments, the barcodes of the particle can comprise molecular label sequences selected from at least 1000, 10000, or more different molecular label sequences. The molecular label sequences of the barcodes can comprise random sequences. The particle can comprise at least 10000 barcodes.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises: amplifying the plurality of barcoded sample indexing oligonucleotides to produce a plurality of amplicons. Amplifying the plurality of barcoded sample indexing oligonucleotides can comprise amplifying, using polymerase chain reaction (PCR), at least a portion of the molecular label sequence and at least a portion of the sample indexing oligonucleotide. In some embodiments, obtaining the sequencing data of the plurality of barcoded sample indexing oligonucleotides can comprise obtaining sequencing data of the plurality of amplicons. Obtaining the sequencing data comprises sequencing at least a portion of the molecular label sequence and at least a portion of the sample indexing oligonucleotide. In some embodiments, identifying the sample origin of the at least one cell comprises identifying sample origin of the plurality of barcoded targets based on the sample indexing sequence of the at least one barcoded sample indexing oligonucleotide.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, the method comprises: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

Disclosed herein include systems, methods, and kits for determining interactions between cellular component targets, for example interactions between proteins. In some embodiments, the method comprises: contacting a cell with a first pair of interaction determination compositions, wherein the cell comprises a first protein target and a second protein target, wherein each of the first pair of interaction determination compositions comprises a protein binding reagent associated with an interaction determination oligonucleotide, wherein the protein binding reagent of one of the first pair of interaction determination compositions is capable of specifically binding to the first protein target and the protein binding reagent of the other of the first pair of interaction determination compositions is capable of specifically binding to the second protein target, and wherein the interaction determination oligonucleotide comprises an interaction determination sequence and a bridge oligonucleotide hybridization region, and wherein the interaction determination sequences of the first pair of interaction determination compositions comprise different sequences; ligating the interaction determination oligonucleotides of the first pair of interaction determination compositions using a bridge oligonucleotide to generate a ligated interaction determination oligonucleotide, wherein the bridge oligonucleotide comprises two hybridization regions capable of specifically binding to the bridge oligonucleotide hybridization regions of the first pair of interaction determination compositions; barcoding the ligated interaction determination oligonucleotide using a plurality of barcodes to create a plurality of barcoded interaction determination oligonucleotides, wherein each of the plurality of barcodes comprises a barcode sequence and a capture sequence; obtaining sequencing data of the plurality of barcoded interaction determination oligonucleotides; and determining an interaction between the first and second protein targets based on the association of the interaction determination sequences of the first pair of interaction determination compositions in the obtained sequencing data.

Disclosed herein include systems, methods, and kits for determining interactions between cellular component targets. In some embodiments, the method comprises: contacting a cell with a first pair of interaction determination compositions, wherein the cell comprises a first cellular component target and a second cellular component target, wherein each of the first pair of interaction determination compositions comprises a cellular component binding reagent associated with an interaction determination oligonucleotide, wherein the cellular component binding reagent of one of the first pair of interaction determination compositions is capable of specifically binding to the first cellular component target and the cellular component binding reagent of the other of the first pair of interaction determination compositions is capable of specifically binding to the second cellular component target, and wherein the interaction determination oligonucleotide comprises an interaction determination sequence and a bridge oligonucleotide hybridization region, and wherein the interaction determination sequences of the first pair of interaction determination compositions comprise different sequences; ligating the interaction determination oligonucleotides of the first pair of interaction determination compositions using a bridge oligonucleotide to generate a ligated interaction determination oligonucleotide, wherein the bridge oligonucleotide comprises two hybridization regions capable of specifically binding to the bridge oligonucleotide hybridization regions of the first pair of interaction determination compositions; barcoding the ligated interaction determination oligonucleotide using a plurality of barcodes to create a plurality of barcoded interaction determination oligonucleotides, wherein each of the plurality of barcodes comprises a barcode sequence and a capture sequence; obtaining sequencing data of the plurality of barcoded interaction determination oligonucleotides; and determining an interaction between the first and second cellular component targets based on the association of the interaction determination sequences of the first pair of interaction determination compositions in the obtained sequencing data. At least one of the two cellular component binding reagent can comprise a protein binding reagent. The protein binding reagent can be associated with one of the two interaction determination oligonucleotides. The one or more cellular component targets can comprise at least one protein target.

In some embodiments, contacting the cell with the first pair of interaction determination compositions comprises: contacting the cell with each of the first pair of interaction determination compositions sequentially or simultaneously. The first protein target can be the same as the second protein target, or the first protein target can be different from the second protein target.

The length of the interaction determination sequence can vary. For example, the interaction determination sequence can be 2 nucleotides to about 1000 nucleotides in length. In some embodiments, the interaction determination sequence can be at least 6 nucleotides in length, 25-60 nucleotides in length, about 45 nucleotides in length, about 50 nucleotides in length, about 100 nucleotides in length, about 128 nucleotides in length, at least 128 nucleotides in length, about 200 nucleotides in length, at least 200 nucleotides in length, about 200-300 nucleotides in length, about 200-500 nucleotides in length, about 500 nucleotides in length, or any combination thereof.

In some embodiments, the method comprises: contacting the cell with a second pair of interaction determination compositions, wherein the cell comprises a third protein target and a fourth protein target, wherein each of the second pair of interaction determination compositions comprises a protein binding reagent associated with an interaction determination oligonucleotide, wherein the protein binding reagent of one of the second pair of interaction determination compositions is capable of specifically binding to the third protein target and the protein binding reagent of the other of the second pair of interaction determination compositions is capable of specifically binding to the fourth protein target. At least one of the third and fourth protein targets can be different from one of the first and second protein targets. In some embodiments, at least one of the third and fourth protein targets and at least one of the first and second protein targets can be identical.

In some embodiments, the method comprises: contacting the cell with three or more pairs of interaction determination compositions. The interaction determination sequences of at least 10 interaction determination compositions of the plurality of pairs of interaction determination compositions can comprise different sequences. The interaction determination sequences of at least 100 interaction determination compositions of the plurality of pairs of interaction determination compositions can comprise different sequences. The interaction determination sequences of at least 1000 interaction determination compositions of the plurality of pairs of interaction determination compositions can comprise different sequences.

In some embodiments, the bridge oligonucleotide hybridization regions of the first pair of interaction determination compositions comprise different sequences. At least one of the bridge oligonucleotide hybridization regions can be complementary to at least one of the two hybridization regions of the bridge oligonucleotide.

In some embodiments, ligating the interaction determination oligonucleotides of the first pair of interaction determination compositions using the bridge oligonucleotide comprises: hybridizing a first hybridization regions of the bridge oligonucleotide with a first bridge oligonucleotide hybridization region of the bridge oligonucleotide hybridization regions of the interaction determination oligonucleotides; hybridizing a second hybridization region of the bridge oligonucleotide with a second bridge oligonucleotide hybridization region of the bridge oligonucleotide hybridization regions of the interaction determination oligonucleotides; and ligating the interaction determination oligonucleotides hybridized to the bridge oligonucleotide to generate a ligated interaction determination oligonucleotide.

In some embodiments, the protein binding reagent comprises an antibody, a tetramer, an aptamer, a protein scaffold, an integrin, or a combination thereof. The interaction determination oligonucleotide can be conjugated to the protein binding reagent through a linker. The oligonucleotide can comprise the linker. The linker can comprise a chemical group. The chemical group can be reversibly or irreversibly attached to the protein binding reagent. The chemical group can comprise a UV photocleavable group, a disulfide bond, a streptavidin, a biotin, an amine, a disulfide linkage or any combination thereof.

The location of the protein targets in the cell can vary, for example, on the cell surface or inside the cell. In some embodiments, the at least one of the one or more protein targets is on a cell surface. In some embodiments, the at least one of the one or more protein targets is an intracellular protein. In some embodiments, the at least one of the one or more protein targets is a transmembrane protein. In some embodiments, the at least one of the one or more protein targets is an extracellular protein. In some embodiments, the method can comprise: fixating the cell prior to contacting the cell with the first pair of interaction determination compositions. In some embodiments, the method can comprise: removing unbound interaction determination compositions of the first pair of interaction determination compositions. Removing the unbound interaction determination compositions can comprise washing the cell with a washing buffer. Removing the unbound interaction determination compositions can comprise selecting the cell using flow cytometry. In some embodiments, the method can comprise: lysing the cell.

In some embodiments, the interaction determination oligonucleotide is configured to be detachable or non-detachable from the protein binding reagent. The method can comprise: detaching the interaction determination oligonucleotide from the protein binding reagent. Detaching the interaction determination oligonucleotide can comprise detaching the interaction determination oligonucleotide from the protein binding reagent by UV photocleaving, chemical treatment, heating, enzyme treatment, or any combination thereof. The interaction determination oligonucleotide can be not homologous to genomic sequences of the cell. The interaction determination oligonucleotide can be homologous to genomic sequences of a species. The species can be a non-mammalian species. The non-mammalian species can be a phage species. The phage species can be T7 phage, a PhiX phage, or a combination thereof. In some embodiments, the interaction determination oligonucleotide of the one of the first pair of interaction determination compositions comprises a sequence complementary to the capture sequence. The capture sequence can comprise a poly(dT) region. The sequence of the interaction determination oligonucleotide complementary to the capture sequence can comprise a poly(dA) region. In some embodiments, the interaction determination oligonucleotide comprises a second barcode sequence. The interaction determination oligonucleotide of the other of the first pair of interaction identification compositions can comprise a binding site for a universal primer. The interaction determination oligonucleotide can be associated with a detectable moiety.

In some embodiments, the protein binding reagent can be associated with two or more interaction determination oligonucleotides with different interaction determination sequences. In some embodiments, the one of the plurality of interaction determination compositions comprises a second protein binding reagent not associated with the interaction determination oligonucleotide. The protein binding reagent and the second protein binding reagent can be identical. The protein binding reagent can be associated with a detectable moiety.

In some embodiments, the cell is a tumor cell or non-tumor cell. For example, the cell can be a mammalian cell, a bacterial cell, a viral cell, a yeast cell, a fungal cell, or any combination thereof. In some embodiments, the method comprises: contacting two or more cells with the first pair of interaction determination compositions, and wherein each of the two or more cells comprises the first and the second protein targets. At least one of the two or more cells can comprise a single cell.

In some embodiments, the protein target is, or comprises, an extracellular protein, an intracellular protein, or any combination thereof. The protein target can be, or comprise, a cell-surface protein, a cell marker, a B-cell receptor, a T-cell receptor, a major histocompatibility complex, a tumor antigen, a receptor, an integrin, or any combination thereof. The protein target can be, or comprise, a lipid, a carbohydrate, or any combination thereof. The protein target can be selected from a group comprising 10-100 different protein targets. The protein binding reagent can be associated with two or more interaction determination oligonucleotides with an identical sequence.

In some embodiments, the barcode comprises a cell label sequence, a binding site for a universal primer, or any combination thereof. At least two barcodes of the plurality of barcodes can comprise an identical cell label sequence. In some embodiments, the plurality of barcodes is associated with a particle. At least one barcode the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can comprise a bead. The particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise a disruptable hydrogel particle. The particle can be associated with a detectable moiety.

In some embodiments, the barcodes of the particle comprise barcode sequences selected from at least 1000 different barcode sequences. The barcodes of the particle can comprise barcode sequences selected from least 10000 different barcode sequences. The barcodes sequences of the barcodes can comprise random sequences. The particle can comprise at least 10000 barcodes.

In some embodiments, barcoding the interaction determination oligonucleotides using the plurality of barcodes comprises: contacting the plurality of barcodes with the interaction determination oligonucleotides to generate barcodes hybridized to the interaction determination oligonucleotides; and extending the barcodes hybridized to the interaction determination oligonucleotides to generate the plurality of barcoded interaction determination oligonucleotides. Extending the barcodes can comprise extending the barcodes using a DNA polymerase to generate the plurality of barcoded interaction determination oligonucleotides. Extending the barcodes can comprise extending the barcodes using a reverse transcriptase to generate the plurality of barcoded interaction determination oligonucleotides. Extending the barcodes can comprise extending the barcodes using a Moloney Murine Leukemia Virus (M-MLV) reverse transcriptase or a Taq DNA polymerase to generate the plurality of barcoded interaction determination oligonucleotides. Extending the barcodes can comprise displacing the bridge oligonucleotide from the ligated interaction determination oligonucleotide.

In some embodiments, the method comprises: amplifying the plurality of barcoded interaction determination oligonucleotides to produce a plurality of amplicons. Amplifying the plurality of barcoded interaction determination oligonucleotides can comprise amplifying, using polymerase chain reaction (PCR), at least a portion of the barcode sequence and at least a portion of the interaction determination oligonucleotide. Obtaining the sequencing data of the plurality of barcoded interaction determination oligonucleotides can comprise obtaining sequencing data of the plurality of amplicons. Obtaining the sequencing data can comprise sequencing at least a portion of the barcode sequence and at least a portion of the interaction determination oligonucleotide.

In some embodiments, obtaining sequencing data of the plurality of barcoded interaction determination oligonucleotides comprises obtaining partial and/or complete sequences of the plurality of barcoded interaction determination oligonucleotides.

In some embodiments, the plurality of barcodes comprises a plurality of stochastic barcodes. The barcode sequence of each of the plurality of stochastic barcodes can comprise a molecular label sequence. The molecular label sequences of at least two stochastic barcodes of the plurality of stochastic barcodes can comprise different sequences. Barcoding the interaction determination oligonucleotides using the plurality of barcodes to create the plurality of barcoded interaction determination oligonucleotides can comprise stochastically barcoding the interaction determination oligonucleotides using the plurality of stochastic barcodes to create a plurality of stochastically barcoded interaction determination oligonucleotides.

In some embodiments, the method comprises: barcoding a plurality of targets of the cell using the plurality of barcodes to create a plurality of barcoded targets; and obtaining sequencing data of the barcoded targets. Barcoding the plurality of targets using the plurality of barcodes to create the plurality of barcoded targets can comprise: contacting copies of the targets with target-binding regions of the barcodes; and reverse transcribing the plurality targets using the plurality of barcodes to create a plurality of reverse transcribed targets. The method can comprise: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using the plurality of stochastic barcodes to create a plurality of stochastically barcoded targets.

Disclosed herein include kits for identifying interactions between cellular components, for example protein-protein interactions. In some embodiments, the kit comprises: a first pair of interaction determination compositions, wherein each of the first pair of interaction determination compositions comprises a protein binding reagent associated with an interaction determination oligonucleotide, wherein the protein binding reagent of one of the first pair of interaction determination compositions is capable of specifically binding to a first protein target and a protein binding reagent of the other of the first pair of interaction determination compositions is capable of specifically binding to the second protein target, wherein the interaction determination oligonucleotide comprises an interaction determination sequence and a bridge oligonucleotide hybridization region, and wherein the interaction determination sequences of the first pair of interaction determination compositions comprise different sequences; and a plurality of bridge oligonucleotides each comprising two hybridization regions capable of specifically binding to the bridge oligonucleotide hybridization regions of the first pair of interaction determination compositions.

The length of the interaction determination sequence can vary. In some embodiments, the interaction determination sequence is at least 6 nucleotides in length, 25-60 nucleotides in length, about 45 nucleotides in length, about 50 nucleotides in length, about 100 nucleotides in length, about 128 nucleotides in length, at least 128 nucleotides in length, about 200-500 nucleotides in length, about 200 nucleotides in length, at least 200 nucleotides in length, less than about 200-300 nucleotides in length, about 500 nucleotides in length, or any combination thereof.

In some embodiments, the kit further comprises: a second pair of interaction determination compositions, wherein each of the second pair of interaction determination compositions comprises a protein binding reagent associated with an interaction determination oligonucleotide, wherein the protein binding reagent of one of the second pair of interaction determination compositions is capable of specifically binding to a third protein target and the protein binding reagent of the other of the second pair of interaction determination compositions is capable of specifically binding to a fourth protein target. At least one of the third and fourth protein targets can be different from one of the first and second protein targets. At least one of the third and fourth protein targets and at least one of the first and second protein targets can be identical.

In some embodiments, the kit can comprise three or more pairs of interaction determination compositions. The interaction determination sequences of at least 10 interaction determination compositions of the three or more pairs of interaction determination compositions can comprise different sequences. The interaction determination sequences of at least 100 interaction determination compositions of the three or more pairs of interaction determination compositions can comprise different sequences. The interaction determination sequences of at least 1000 interaction determination compositions of the three or more pairs of interaction determination compositions can comprise different sequences.

In some embodiments, the bridge oligonucleotide hybridization regions of two interaction determination compositions of the plurality of interaction determination compositions comprise different sequences. At least one of the bridge oligonucleotide hybridization regions can be complementary to at least one of the two hybridization regions of the bridge oligonucleotide.

In some embodiments, the protein binding reagent comprises an antibody, a tetramer, an aptamers, a protein scaffold, or a combination thereof. The interaction determination oligonucleotide can be conjugated to the protein binding reagent through a linker. The at least one interaction determination oligonucleotide can comprise the linker. The linker can comprise a chemical group. The chemical group can be reversibly or irreversibly attached to the protein binding reagent. The chemical group can comprise a UV photocleavable group, a disulfide bond, a streptavidin, a biotin, an amine, a disulfide linkage, or any combination thereof. The interaction determination oligonucleotide can be not homologous to genomic sequences of any cell of interest. The cell of interest can be a tumor cell or non-tumor cell. The cell of interest can be a single cell, a mammalian cell, a bacterial cell, a viral cell, a yeast cell, a fungal cell, or any combination thereof.

In some embodiments, the kit further comprises: a plurality of barcodes, wherein each of the plurality of barcodes comprises a barcode sequence and a capture sequence. The interaction determination oligonucleotide of the one of the first pair of interaction determination compositions can comprise a sequence complementary to the capture sequence of at least one barcode of a plurality of barcodes. The capture sequence can comprise a poly(dT) region. The sequence of the interaction determination oligonucleotide complementary to the capture sequence of the barcode can comprise a poly(dA) region. The interaction determination oligonucleotide of the other of the first pair of interaction identification compositions can comprise a cell label sequence, a binding site for a universal primer, or any combination thereof. The plurality of barcodes can comprise a plurality of stochastic barcodes, wherein the barcode sequence of each of the plurality of stochastic barcodes comprises a molecular label sequence, wherein the molecular label sequences of at least two stochastic barcodes of the plurality of stochastic barcodes comprise different sequences.

In some embodiments, the protein target is, or comprises, an extracellular protein, an intracellular protein, or any combination thereof. The protein target can be, or comprise, a cell-surface protein, a cell marker, a B-cell receptor, a T-cell receptor, a major histocompatibility complex, a tumor antigen, a receptor, or any combination thereof. The protein target can be selected from a group comprising 10-100 different protein targets. The protein binding reagent can be associated with two or more interaction determination oligonucleotides with an identical sequence. The protein binding reagent can be associated with two or more interaction determination oligonucleotides with different interaction determination sequences. In some embodiments, the protein binding reagent can be associated with a detectable moiety.

In some embodiments, the one of the first pair of interaction determination compositions comprises a second protein binding reagent not associated with the interaction determination oligonucleotide. The first protein binding reagent and the second protein binding reagent can be identical. The interaction determination oligonucleotide can be associated with a detectable moiety.

In some embodiments, the plurality of barcodes is associated with a particle. At least one barcode the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. The particle can comprise a bead. The particle can comprise a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise a disruptable hydrogel particle. The particle can be associated with a detectable moiety.

In some embodiments, the barcodes of the particle comprise barcode sequences selected from at least 1000 different barcode sequences. The barcodes of the particle can comprise barcode sequences selected from least 10000 different barcode sequences. The barcodes sequences of the barcodes can comprise random sequences. The particle can comprise at least 10000 barcodes.

In some embodiments, the kit comprises: a DNA polymerase, a reverse transcriptase, a Moloney Murine Leukemia Virus (M-MLV) reverse transcriptase, a Taq DNA polymerase, or any combination thereof. The kit can comprise a fixation agent.

Disclosed herein include methods for sample identification. In some embodiments, the method comprises: contacting one or more cells from each of a plurality of samples with a sample indexing composition of a plurality of sample indexing compositions, wherein the one or more cells comprises one or more cellular component targets, wherein each of the plurality of sample indexing compositions comprises a cellular component binding reagent (e.g., an antibody) associated with a sample indexing oligonucleotide, wherein the cellular component binding reagent is capable of specifically binding to at least one of the one or more cellular component targets (e.g., proteins), wherein the sample indexing oligonucleotide comprises a sample indexing sequence, and wherein sample indexing sequences of at least two sample indexing compositions of the plurality of sample indexing compositions comprise different sequences; barcoding the sample indexing oligonucleotides using a plurality of barcodes to create a plurality of barcoded sample indexing oligonucleotides; amplifying the plurality of barcoded sample indexing oligonucleotides using a plurality of daisy-chaining amplification primers to create a plurality of daisy-chaining elongated amplicons; obtaining sequencing data of the plurality of daisy-chaining elongated amplicons comprising sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides. The method can comprise removing unbound sample indexing compositions of the plurality of sample indexing compositions.

In some embodiments, the sample indexing sequence is at least 6 nucleotides in length, 25-45 nucleotides in length, about 128 nucleotides in length, or at least 128 nucleotides in length, or a combination thereof. The sample indexing oligonucleotide can be about 50 nucleotides in length, about 100 nucleotides in length, about 200 nucleotides in length, at least 200 nucleotides in length, less than about 200-300 nucleotides in length, about 200-500 nucleotides in length, about 500 nucleotides in length, or a combination thereof. Sample indexing sequences of at least 10 sample indexing compositions of the plurality of sample indexing compositions can comprise different sequences. Sample indexing sequences of at least 100 or 1000 sample indexing compositions of the plurality of sample indexing compositions can comprise different sequences.

In some embodiments, the cellular component binding reagent comprises an antibody, a tetramer, an aptamers, a protein scaffold, or a combination thereof. The sample indexing oligonucleotide can be conjugated to the cellular component binding reagent through a linker. The oligonucleotide can comprise the linker. The linker can comprise a chemical group. The chemical group can be reversibly or irreversibly attached to the cellular component binding reagent. The chemical group can be selected from the group consisting of a UV photocleavable group, a disulfide bond, a streptavidin, a biotin, an amine, and any combination thereof.

In some embodiments, at least one sample of the plurality of samples comprises a single cell. The at least one of the one or more cellular component targets can be on a cell surface. A sample of the plurality of samples can comprise a plurality of cells, a tissue, a tumor sample, or any combination thereof. The plurality of samples can comprise a mammalian sample, a bacterial sample, a viral sample, a yeast sample, a fungal sample, or any combination thereof.

In some embodiments, removing the unbound sample indexing compositions comprises washing the one or more cells from each of the plurality of samples with a washing buffer. The method can comprise lysing the one or more cells from each of the plurality of samples. The sample indexing oligonucleotide can be configured to be detachable or non-detachable from the cellular component binding reagent. The method can comprise detaching the sample indexing oligonucleotide from the cellular component binding reagent. Detaching the sample indexing oligonucleotide can comprise detaching the sample indexing oligonucleotide from the cellular component binding reagent by UV photocleaving, chemical treatment (e.g., using a reducing reagent, such as dithiothreitol), heating, enzyme treatment, or any combination thereof.

In some embodiments, the sample indexing oligonucleotide is not homologous to genomic sequences of the cells of the plurality of samples. The sample indexing oligonucleotide can comprise a molecular label sequence, a poly(A) region, or a combination thereof. The sample indexing oligonucleotide can comprise a sequence complementary to a capture sequence of at least one barcode of the plurality of barcodes. A target binding region of the barcode can comprise the capture sequence. The target binding region can comprise a poly(dT) region. The sequence of the sample indexing oligonucleotide complementary to the capture sequence of the barcode can comprise a poly(A) tail. The sample indexing oligonucleotide can comprise a molecular label.

In some embodiments, the cellular component target is, or comprises, an extracellular protein, an intracellular protein, or any combination thereof. The cellular component target can be, or comprise, a cell-surface protein, a cell marker, a B-cell receptor, a T-cell receptor, a major histocompatibility complex, a tumor antigen, a receptor, an integrin, or any combination thereof. The cellular component target can be, or comprise, a lipid, a carbohydrate, or any combination thereof. The cellular component target can be selected from a group comprising 10-100 different cellular component targets. The cellular component binding reagent can be associated with two or more sample indexing oligonucleotides with an identical sequence. The cellular component binding reagent can be associated with two or more sample indexing oligonucleotides with different sample indexing sequences. The sample indexing composition of the plurality of sample indexing compositions can comprise a second cellular component binding reagent not conjugated with the sample indexing oligonucleotide. The cellular component binding reagent and the second cellular component binding reagent can be identical.

In some embodiments, a barcode of the plurality of barcodes comprises a target binding region and a molecular label sequence. Molecular label sequences of at least two barcodes of the plurality of barcodes comprise different molecule label sequences. The barcode can comprise a cell label, a binding site for a universal primer, or any combination thereof. The target binding region can comprise a poly(dT) region.

In some embodiments, the plurality of barcodes is associated with a particle. At least one barcode of the plurality of barcodes can be immobilized on the particle, partially immobilized on the particle, enclosed in the particle, partially enclosed in the particle, or any combination thereof. The particle can be degradable. The particle can be a bead. The bead can be selected from the group consisting of streptavidin beads, agarose beads, magnetic beads, conjugated beads, protein A conjugated beads, protein G conjugated beads, protein A/G conjugated beads, protein L conjugated beads, oligo(dT) conjugated beads, silica beads, silica-like beads, anti-biotin microbead, anti-fluorochrome microbead, and any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise at least 10000 barcodes. In some embodiments, the barcodes of the particle can comprise molecular label sequences selected from at least 1000 or 10000 different molecular label sequences. The molecular label sequences of the barcodes can comprise random sequences.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, amplifying the plurality of barcoded sample indexing oligonucleotides comprises amplifying the plurality of barcoded sample indexing oligonucleotides using polymerase chain reaction (PCR). Amplifying the plurality of barcoded sample indexing oligonucleotides can comprise amplifying at least a portion of the molecular label sequence and at least a portion of the sample indexing oligonucleotide. Obtaining the sequencing data of the plurality of barcoded sample indexing oligonucleotides can comprise obtaining sequencing data of the plurality of daisy-chaining elongated amplicons. Obtaining the sequencing data can comprise sequencing at least a portion of the molecular label sequence and at least a portion of the sample indexing oligonucleotide.

In some embodiments, each daisy-chaining amplification primer of the plurality of daisy-chaining amplification primers comprises a barcoded sample indexing oligonucleotide-binding region and an overhang region, wherein the barcoded sample indexing oligonucleotide-binding region is capable of binding to a daisy-chaining sample indexing region of the sample indexing oligonucleotide. The barcoded sample indexing oligonucleotide-binding region can be at least 20 nucleotides in length, at least 30 nucleotides in length, about 40 nucleotides in length, at least 40 nucleotides in length, about 50 nucleotides in length, or a combination thereof. Two daisy-chaining amplification primers of the plurality of daisy-chaining amplification primers can comprise barcoded sample indexing oligonucleotide-binding regions with an identical sequence. The plurality of daisy-chaining amplification primers can comprise barcoded sample indexing oligonucleotide-binding regions with an identical sequence. The overhang region can be at least 50 nucleotides in length, at least 100 nucleotides in length, at least 150 nucleotides in length, about 150 nucleotides in length, at least 200 nucleotides in length, or a combination thereof. The overhang region can comprise a daisy-chaining amplification primer barcode sequence. Two daisy-chaining amplification primers of the plurality of daisy-chaining amplification primers can comprise overhang regions with an identical daisy-chaining amplification primer barcode sequence. Two daisy-chaining amplification primers of the plurality of daisy-chaining amplification primers can comprise overhang regions with two daisy-chaining amplification primer barcode sequences. Overhang regions of the plurality of daisy-chaining amplification primers can comprise different daisy-chaining amplification primer barcode sequences. A daisy-chaining elongated amplicon of the plurality of daisy-chaining elongated amplicons can be at least 250 nucleotides in length, at least 300 nucleotides in length, at least 350 nucleotides in length, at least 400 nucleotides in length, about 400 nucleotides in length, at least 450 nucleotides in length, at least 500 nucleotides in length, or a combination thereof.

In some embodiments, identifying the sample origin of the at least one cell can comprise identifying sample origin of the plurality of barcoded targets based on the sample indexing sequence of the at least one barcoded sample indexing oligonucleotide. Barcoding the sample indexing oligonucleotides using the plurality of barcodes to create the plurality of barcoded sample indexing oligonucleotides can comprise stochastically barcoding the sample indexing oligonucleotides using a plurality of stochastic barcodes to create a plurality of stochastically barcoded sample indexing oligonucleotides.

In some embodiments, the method comprises: barcoding a plurality of targets of the cell using the plurality of barcodes to create a plurality of barcoded targets, wherein each of the plurality of barcodes comprises a cell label, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target binding regions of the barcodes; and reverse transcribing the plurality targets using the plurality of barcodes to create a plurality of reverse transcribed targets. Prior to obtaining the sequencing data of the plurality of barcoded targets, the method can comprise amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, each of the plurality of sample indexing compositions comprises the cellular component binding reagent. The sample indexing sequences of the sample indexing oligonucleotides associated with two or more cellular component binding reagents can be identical. The sample indexing sequences of the sample indexing oligonucleotides associated with two or more cellular component binding reagents can comprise different sequences. Each of the plurality of sample indexing compositions can comprise two or more cellular component binding reagents. In some embodiments, the cellular component is an antigen. The cellular component binding reagent can be an antibody.

Disclosed herein include methods for sample identification. In some embodiments, the method comprise: contacting one or more cells from each of a plurality of samples with a sample indexing composition of a plurality of sample indexing compositions, wherein each of the one or more cells comprises one or more binding targets, wherein each of the plurality of sample indexing compositions comprises a cellular component binding reagent associated with a sample indexing oligonucleotide, wherein the cellular component binding reagent is capable of specifically binding to at least one of the one or more binding targets, wherein the sample indexing oligonucleotide comprises a sample indexing sequence, and wherein sample indexing sequences of at least two sample indexing compositions of the plurality of sample indexing compositions comprise different sequences; barcoding the sample indexing oligonucleotides using a plurality of barcodes to create a plurality of barcoded sample indexing oligonucleotides; obtaining sequencing data of the plurality of barcoded sample indexing oligonucleotides using a plurality of daisy-chaining amplification primers;

and identifying sample origin of at least one cell of the one or more cells based on the sample indexing sequence of at least one barcoded sample indexing oligonucleotide of the plurality of barcoded sample indexing oligonucleotides. The method can comprise removing unbound sample indexing compositions of the plurality of sample indexing compositions.

In some embodiments, the sample indexing sequence is at least 6 nucleotides in length, 25-45 nucleotides in length, about 128 nucleotides in length, or at least 128 nucleotides in length, or a combination thereof. The sample indexing oligonucleotide can be about 50 nucleotides in length, about 100 nucleotides in length, about 200 nucleotides in length, at least 200 nucleotides in length, less than about 200-300 nucleotides in length, about 200-500 nucleotides in length, about 500 nucleotides in length, or a combination thereof. Sample indexing sequences of at least 10 sample indexing compositions of the plurality of sample indexing compositions can comprise different sequences. Sample indexing sequences of at least 10 sample indexing compositions of the plurality of sample indexing compositions can comprise different sequences. Sample indexing sequences of at least 10 sample indexing compositions of the plurality of sample indexing compositions comprise different sequences.

In some embodiments, the cellular component binding reagent comprises a cell surface binding reagent, an antibody, a tetramer, an aptamer, a protein scaffold, an integrin, or a combination thereof. The sample indexing oligonucleotide can be conjugated to the cellular component binding reagent through a linker. The oligonucleotide can comprise the linker. The linker can comprise a chemical group. The chemical group can be reversibly or irreversibly attached to the cellular component binding reagent. The chemical group can be selected from the group consisting of a UV photo-cleavable group, a disulfide bond, a streptavidin, a biotin, an amine, and any combination thereof.

In some embodiments, at least one sample of the plurality of samples comprises a single cell. The at least one of the one or more cellular component targets can be expressed on a cell surface. A sample of the plurality of samples can comprise a plurality of cells, a tissue, a tumor sample, or any combination thereof. The plurality of samples can comprise a mammalian sample, a bacterial sample, a viral sample, a yeast sample, a fungal sample, or any combination thereof.

In some embodiments, removing the unbound sample indexing compositions comprises washing the one or more cells from each of the plurality of samples with a washing buffer. The method can comprise lysing the one or more cells from each of the plurality of samples. The sample indexing oligonucleotide can be configured to be detachable or non-detachable from the cellular component binding reagent. The method can comprise detaching the sample indexing oligonucleotide from the cellular component binding reagent. Detaching the sample indexing oligonucleotide can comprise detaching the sample indexing oligonucleotide from the cellular component binding reagent by UV photo-cleaving, chemical treatment (e.g., using a reducing reagent, such as dithiothreitol), heating, enzyme treatment, or any combination thereof.

In some embodiments, the sample indexing oligonucleotide is not homologous to genomic sequences of the cells of the plurality of samples. The sample indexing oligonucleotide can comprise a molecular label sequence, a poly(A) region, or a combination thereof. The sample indexing oligonucleotide can comprise a sequence complementary to a capture sequence of at least one barcode of the plurality of barcodes. A target binding region of the barcode can comprise the capture sequence. The target binding region can comprise a poly(dT) region. The sequence of the sample indexing oligonucleotide complementary to the capture sequence of the barcode can comprise a poly(A) tail. The sample indexing oligonucleotide can comprise a molecular label.

In some embodiments, the cellular component target is, or comprises, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. The cellular component target can be selected from a group comprising 10-100 different cellular component targets. The cellular component binding reagent can be associated with two or more sample indexing oligonucleotides with an identical sequence. The cellular component binding reagent can be associated with two or more sample indexing oligonucleotides with different sample indexing sequences. The sample indexing composition of the plurality of sample indexing compositions can comprise a second cellular component binding reagent not conjugated with the sample indexing oligonucleotide. The cellular component binding reagent and the second cell binding reagent can be identical.

In some embodiments, a barcode of the plurality of barcodes comprises a target binding region and a molecular label sequence. Molecular label sequences of at least two barcodes of the plurality of barcodes can comprise different molecule label sequences. The barcode can comprise a cell label, a binding site for a universal primer, or any combination thereof. The target binding region can comprise a poly(dT) region.

In some embodiments, the plurality of barcodes is enclosed in a particle. The particle can be a bead. At least one barcode of the plurality of barcodes can be immobilized on the particle, partially immobilized on the particle, enclosed in the particle, partially enclosed in the particle, or any combination thereof. The particle can be degradable. The bead can be selected from the group consisting of streptavidin beads, agarose beads, magnetic beads, conjugated beads, protein A conjugated beads, protein G conjugated beads, protein A/G conjugated beads, protein L conjugated beads, oligo(dT) conjugated beads, silica beads, silica-like beads, anti-biotin microbead, anti-fluorochrome microbead, and any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise at least 10000 barcodes. In some embodiments, the barcodes of the particle can comprise molecular label sequences selected from at least 1000 or 10000 different molecular label sequences. The molecular label sequences of the barcodes can comprise random sequences.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises amplifying the plurality of barcoded sample indexing oligonucleotides to produce a plurality of amplicons. Amplifying the plurality of barcoded sample indexing oligonucleotides can comprise amplifying, using polymerase chain reaction (PCR) at least a portion of the molecular label sequence and at least a portion of the sample indexing oligonucleotide. Amplifying the plurality of barcoded sample indexing oligonucleotides can comprise amplifying the plurality of barcoded sample indexing oligonucleotides using the plurality of daisy-chaining amplification primers to produce the plurality of daisy-chaining elongated amplicons. Obtaining the sequencing data of the plurality of barcoded sample indexing oligonucleotides can comprise obtaining sequencing data of the plurality of daisy-chaining elongated amplicons. Obtaining the sequencing data can comprise sequencing at least a portion of the molecular label sequence and at least a portion of the sample indexing oligonucleotide.

In some embodiments, a daisy-chaining amplification primer of the plurality of daisy-chaining amplification primers comprises a barcoded sample indexing oligonucleotide-binding region and an overhang region, wherein the barcoded sample indexing oligonucleotide-binding region is capable of binding to a daisy-chaining sample indexing region of the sample indexing oligonucleotide. The barcoded sample indexing oligonucleotide-binding region can be at least 20 nucleotides in length, at least 30 nucleotides in length, about 40 nucleotides in length, at least 40 nucleotides in length, about 50 nucleotides in length, or a combination thereof. Two daisy-chaining amplification primers of the plurality of daisy-chaining amplification primers can comprise barcoded sample indexing oligonucleotide-binding regions with an identical sequence. The plurality of daisy-chaining amplification primers can comprise barcoded sample indexing oligonucleotide-binding regions with an identical sequence. The overhang region can be at least 50 nucleotides in length, at least 100 nucleotides in length, at least 150 nucleotides in length, about 150 nucleotides in length, at least 200 nucleotides in length, or a combination thereof. The overhang region can comprise a daisy-chaining amplification primer barcode sequence. Two daisy-chaining amplification primers of the plurality of daisy-chaining amplification primers can comprise overhang regions with an identical daisy-chaining amplification primer barcode sequence. Two daisy-chaining amplification primers of the plurality of daisy-chaining amplification primers can comprise overhang regions with two daisy-chaining amplification primer barcode sequences. Overhang regions of the plurality of daisy-chaining amplification primers can comprise different daisy-chaining amplification primer barcode sequences. A daisy-chaining elongated amplicon of the plurality of daisy-chaining elongated amplicons can be at least 250 nucleotides in length, at least 300 nucleotides in length, at least 350 nucleotides in length, at least 400 nucleotides in length, about 400 nucleotides in length, at least 450 nucleotides in length, at least 500 nucleotides in length, or a combination thereof.

In some embodiments, identifying the sample origin of the at least one cell can comprise identifying sample origin of the plurality of barcoded targets based on the sample indexing sequence of the at least one barcoded sample indexing oligonucleotide. Barcoding the sample indexing oligonucleotides using the plurality of barcodes to create the plurality of barcoded sample indexing oligonucleotides can comprise stochastically barcoding the sample indexing oligonucleotides using a plurality of stochastic barcodes to create a plurality of stochastically barcoded sample indexing oligonucleotides.

In some embodiments, the method comprises: barcoding a plurality of targets of the cell using the plurality of barcodes to create a plurality of barcoded targets, wherein each of the plurality of barcodes comprises a cell label, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can comprise: contacting copies of the targets with target binding regions of the barcodes; and reverse transcribing the plurality targets using the plurality of barcodes to create a plurality of reverse transcribed targets. The method can comprise: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, each of the plurality of sample indexing compositions comprises the cellular component binding reagent. The sample indexing sequences of the sample indexing oligonucleotides associated with two or more cellular component binding reagents can be identical. The sample indexing sequences of the sample indexing oligonucleotides associated with two or more cellular component binding reagents can comprise different sequences. Each of the plurality of sample indexing compositions can comprise two or more cellular component binding reagents.

Disclosed herein include methods for sample identification. In some embodiments, the method comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; and identifying sample origin of at least one cell of the one or more cells based on the sample indexing sequence of at least one sample indexing oligonucleotide of the plurality of sample indexing compositions and a plurality of daisy-chaining amplification primers. Identifying the sample origin of the at least one cell can comprise: barcoding sample indexing oligonucleotides of the plurality of sample indexing compositions using a plurality of barcodes to create a plurality of barcoded sample indexing oligonucleotides; obtaining sequencing data of the plurality of barcoded sample indexing oligonucleotides; and identifying the sample origin of the cell based on the sample indexing sequence of at least one barcoded sample indexing oligonucleotide of the plurality of barcoded sample indexing oligonucleotides in the sequencing data. The method can, for example, include removing unbound sample indexing compositions of the plurality of sample indexing compositions.

In some embodiments, the sample indexing sequence is at least 6 nucleotides in length, 25-45 nucleotides in length, about 128 nucleotides in length, or at least 128 nucleotides in length, or a combination thereof. The sample indexing oligonucleotide can be about 50 nucleotides in length, about 100 nucleotides in length, about 200 nucleotides in length, at least 200 nucleotides in length, less than about 200-300 nucleotides in length, about 200-500 nucleotides in length, about 500 nucleotides in length, or a combination thereof. Sample indexing sequences of at least 10 sample indexing compositions of the plurality of sample indexing compositions can comprise different sequences. Sample indexing sequences of at least 100 or 1000 sample indexing compositions of the plurality of sample indexing compositions can comprise different sequences.

In some embodiments, the cellular component binding reagent comprises an antibody, a tetramer, an aptamer, a protein scaffold, or a combination thereof. The sample indexing oligonucleotide can be conjugated to the cellular component binding reagent through a linker. The oligonucleotide can comprise the linker. The linker can comprise a chemical group. The chemical group can be reversibly or irreversibly attached to the cellular component binding reagent. The chemical group can be selected from the group consisting of a UV photocleavable group, a disulfide bond, a streptavidin, a biotin, an amine, and any combination thereof.

In some embodiments, at least one sample of the plurality of samples comprises a single cell. The at least one of the one or more cellular component targets can be expressed on a cell surface. A sample of the plurality of samples can comprise a plurality of cells, a tissue, a tumor sample, or any combination thereof. The plurality of samples can comprise a mammalian sample, a bacterial sample, a viral sample, a yeast sample, a fungal sample, or any combination thereof.

In some embodiments, removing the unbound sample indexing compositions comprises washing the one or more cells from each of the plurality of samples with a washing buffer. The method can comprise lysing the one or more cells from each of the plurality of samples. The sample indexing oligonucleotide can be configured to be detachable or non-detachable from the cellular component binding reagent. The method can comprise detaching the sample indexing oligonucleotide from the cellular component binding reagent. Detaching the sample indexing oligonucleotide can comprise detaching the sample indexing oligonucleotide from the cellular component binding reagent by UV photocleaving, chemical treatment (e.g., using a reducing reagent, such as dithiothreitol), heating, enzyme treatment, or any combination thereof.

In some embodiments, the sample indexing oligonucleotide is not homologous to genomic sequences of the cells of the plurality of samples. The sample indexing oligonucleotide can comprise a molecular label sequence, a poly(A) region, or a combination thereof. The sample indexing oligonucleotide can comprise a sequence complementary to a capture sequence of at least one barcode of the plurality of barcodes. A target binding region of the barcode can comprise the capture sequence. The target binding region can comprise a poly(dT) region. The sequence of the sample indexing oligonucleotide complementary to the capture sequence of the barcode can comprise a poly(A) tail. The sample indexing oligonucleotide can comprise a molecular label.

In some embodiments, the cellular component target is, or comprises, a carbohydrate, a lipid, a protein, an extracellular protein, a cell-surface protein, a cell marker, a B-cell receptor, a T-cell receptor, a major histocompatibility complex, a tumor antigen, a receptor, an intracellular protein, or any combination thereof. The cellular component target can be selected from a group comprising 10-100 different cellular component targets. The cellular component binding reagent can be associated with two or more sample indexing oligonucleotides with an identical sequence. The cellular component binding reagent can be associated with two or more sample indexing oligonucleotides with different sample indexing sequences. The sample indexing composition of the plurality of sample indexing compositions can comprise a second cellular component binding reagent not conjugated with the sample indexing oligonucleotide. The cellular component binding reagent and the second cellular component binding reagent can be identical.

In some embodiments, identifying the sample origin of the at least one cell comprises: barcoding sample indexing oligonucleotides of the plurality of sample indexing compositions using a plurality of barcodes to create a plurality of barcoded sample indexing oligonucleotides; obtaining sequencing data of the plurality of barcoded sample indexing oligonucleotides; and identifying the sample origin of the cell based on the sample indexing sequence of at least one barcoded sample indexing oligonucleotide of the plurality of barcoded sample indexing oligonucleotides.

In some embodiments, a barcode of the plurality of barcodes comprises a target binding region and a molecular label sequence. Molecular label sequences of at least two barcodes of the plurality of barcodes can comprise different molecule label sequences. The barcode can comprise a cell label, a binding site for a universal primer, or any combination thereof. The target binding region can comprise a poly(dT) region.

In some embodiments, the plurality of barcodes is immobilized on a particle. At least one barcode of the plurality of barcodes can be immobilized on the particle, partially immobilized on the particle, enclosed in the particle, partially enclosed in the particle, or any combination thereof. The particle can be degradable. The particle can be a bead. The bead can be selected from the group consisting of streptavidin beads, agarose beads, magnetic beads, conjugated beads, protein A conjugated beads, protein G conjugated beads, protein A/G conjugated beads, protein L conjugated beads, oligo(dT) conjugated beads, silica beads, silica-like beads, anti-biotin microbead, anti-fluorochrome microbead, and any combination thereof. The particle can comprise a material selected from the group consisting of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, and any combination thereof. The particle can comprise at least 10000 barcodes. In some embodiments, the barcodes of the particle can comprise molecular label sequences selected from at least 1000 or 10000 different molecular label sequences. The molecular label sequences of the barcodes can comprise random sequences.

In some embodiments, barcoding the sample indexing oligonucleotides using the plurality of barcodes can comprise: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, amplifying the plurality of barcoded sample indexing oligonucleotides comprises amplifying the plurality of barcoded sample indexing oligonucleotides using polymerase chain reaction (PCR). Amplifying the plurality of barcoded sample indexing oligonucleotides can comprise amplifying at least a portion of the molecular label sequence and at least a portion of the sample indexing oligonucleotide. Amplifying the plurality of barcoded sample indexing oligonucleotides can comprise amplifying the plurality of barcoded sample indexing oligonucleotides using the plurality of daisy-chaining amplification primers to produce a plurality of daisy-chaining elongated amplicons. Obtaining the sequencing data of the plurality of barcoded sample indexing oligonucleotides can comprise obtaining sequencing data of the plurality of daisy-chaining elongated amplicons. Obtaining the sequencing data can comprise sequencing at least a portion of the molecular label sequence and at least a portion of the sample indexing oligonucleotide.

In some embodiments, a daisy-chaining amplification primer of the plurality of daisy-chaining amplification primers comprises a barcoded sample indexing oligonucleotide-binding region and an overhang region, wherein the barcoded sample indexing oligonucleotide-binding region is capable of binding to a daisy-chaining sample indexing region of the sample indexing oligonucleotide. The barcoded sample indexing oligonucleotide-binding region can be at least 20 nucleotides in length, at least 30 nucleotides in length, about 40 nucleotides in length, at least 40 nucleotides in length, about 50 nucleotides in length, or a combination thereof. Two daisy-chaining amplification primers of the plurality of daisy-chaining amplification primers can comprise barcoded sample indexing oligonucleotide-binding regions with an identical sequence. The plurality of daisy-chaining amplification primers can comprise barcoded sample indexing oligonucleotide-binding regions with an identical sequence. The overhang region can be at least 50 nucleotides in length, at least 100 nucleotides in length, at least 150 nucleotides in length, about 150 nucleotides in length, at least 200 nucleotides in length, or a combination thereof. The overhang region can comprise a daisy-chaining amplification primer barcode sequence. Two daisy-chaining amplification primers of the plurality of daisy-chaining amplification primers can comprise overhang regions with an identical daisy-chaining amplification primer barcode sequence. Two daisy-chaining amplification primers of the plurality of daisy-chaining amplification primers can comprise overhang regions with two daisy-chaining amplification primer barcode sequences. Overhang regions of the plurality of daisy-chaining amplification primers can comprise different daisy-chaining amplification primer barcode sequences. A daisy-chaining elongated amplicon of the plurality of daisy-chaining elongated amplicons can be at least 250 nucleotides in length, at least 300 nucleotides in length, at least 350 nucleotides in length, at least 400 nucleotides in length, at least 450 nucleotides in length, at least 500 nucleotides in length, or a combination thereof. A daisy-chaining elongated amplicon of the plurality of daisy-chaining elongated amplicons can be about 200 nucleotides in length, about 250 nucleotides in length, about 300 nucleotides in length, about 350 nucleotides in length, about 400 nucleotides in length, about 450 nucleotides in length, about 500 nucleotides in length, about 600 nucleotides in length, or a range between any two of these values.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides. Identifying the sample origin of the at least one cell can comprise identifying the presence or absence of the sample indexing sequence of at least one sample indexing oligonucleotide of the plurality of sample indexing compositions. Identifying the presence or absence of the sample indexing sequence can comprise: replicating the at least one sample indexing oligonucleotide to generate a plurality of replicated sample indexing oligonucleotides; obtaining sequencing data of the plurality of replicated sample indexing oligonucleotides; and identifying the sample origin of the cell based on the sample indexing sequence of a replicated sample indexing oligonucleotide of the plurality of sample indexing oligonucleotides that correspond to the least one barcoded sample indexing oligonucleotide in the sequencing data.

In some embodiments, replicating the at least one sample indexing oligonucleotide to generate the plurality of replicated sample indexing oligonucleotides comprises: prior to replicating the at least one barcoded sample indexing oligonucleotide, ligating a replicating adaptor to the at least one barcoded sample indexing oligonucleotide. Replicating the at least one barcoded sample indexing oligonucleotide can comprise replicating the at least one barcoded sample indexing oligonucleotide using the replicating adaptor ligated to the at least one barcoded sample indexing oligonucleotide to generate the plurality of replicated sample indexing oligonucleotides.

In some embodiments, replicating the at least one sample indexing oligonucleotide to generate the plurality of replicated sample indexing oligonucleotides comprises: prior to replicating the at least one barcoded sample indexing oligonucleotide, contacting a capture probe with the at least one sample indexing oligonucleotide to generate a capture probe hybridized to the sample indexing oligonucleotide; and extending the capture probe hybridized to the sample indexing oligonucleotide to generate a sample indexing oligonucleotide associated with the capture probe. Replicating the at least one sample indexing oligonucleotide can comprise replicating the sample indexing oligonucleotide associated with the capture probe to generate the plurality of replicated sample indexing oligonucleotides.

In some embodiments, the method comprises: barcoding a plurality of targets of the cell using the plurality of barcodes to create a plurality of barcoded targets, wherein each of the plurality of barcodes comprises a cell label, and wherein at least two barcodes of the plurality of barcodes comprise an identical cell label sequence; and obtaining sequencing data of the barcoded targets. Identifying the sample origin of the at least one barcoded sample indexing oligonucleotide can comprise identifying the sample origin of the plurality of barcoded targets based on the sample indexing sequence of the at least one barcoded sample indexing oligonucleotide. Barcoding the plurality of targets using the plurality of barcodes to create the plurality of barcoded targets can comprise: contacting copies of the targets with target binding regions of the barcodes; and reverse transcribing the plurality targets using the plurality of barcodes to create a plurality of reverse transcribed targets. The method can comprise: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, each of the plurality of sample indexing compositions comprises the cellular component binding reagent. The sample indexing sequences of the sample indexing oligonucleotides associated with the two or more cellular component binding reagents can be identical. The sample indexing sequences of the sample indexing oligonucleotides associated with the two or more cellular component binding reagents can comprise different sequences. Each of the plurality of sample indexing compositions can comprise the two or more cellular component binding reagents.

Disclosed herein includes a kit comprising: a plurality of sample indexing compositions; and a plurality of daisy-chaining amplification primers. Each of the plurality of sample indexing compositions can comprise two or more cellular component binding reagents. Each of the two or more cellular component binding reagents can be associated with a sample indexing oligonucleotide. At least one of the two or more cellular component binding reagents can be capable of specifically binding to at least one cellular component target. The sample indexing oligonucleotide can comprise a sample indexing sequence for identifying sample origin of one or more cells of a sample. The sample indexing oligonucleotide can comprise a daisy-chaining amplification primer binding sequence. Sample indexing sequences of at least two sample indexing compositions of the plurality of sample indexing compositions can comprise different sequences.

A daisy-chaining amplification primer of the plurality of daisy-chaining amplification primers can comprise a barcoded sample indexing oligonucleotide-binding region and an overhang region, wherein the barcoded sample indexing oligonucleotide-binding region is capable of binding to a daisy-chaining sample indexing region of the sample indexing oligonucleotide. The barcoded sample indexing oligonucleotide-binding region can be at least 20 nucleotides in length, at least 30 nucleotides in length, about 40 nucleotides in length, at least 40 nucleotides in length, about 50 nucleotides in length, or a combination thereof. Two daisy-chaining amplification primers of the plurality of daisy-chaining amplification primers can comprise barcoded sample indexing oligonucleotide-binding regions with an identical sequence. Two daisy-chaining amplification primers of the plurality of daisy-chaining amplification primers can comprise barcoded sample indexing oligonucleotide-binding regions with different sequences. The barcoded sample indexing oligonucleotide-binding regions can comprise the daisy-chaining amplification primer binding sequence, a complement thereof, a reverse complement thereof, or a combination thereof. Daisy-chaining amplification primer binding sequences of at least two sample indexing compositions of the plurality of sample indexing compositions can comprise an identical sequence. Daisy-chaining amplification primer binding sequences of at least two sample indexing compositions of the plurality of sample indexing compositions comprise different sequences. The overhang region can be at least 50 nucleotides in length, at least 100 nucleotides in length, at least 150 nucleotides in length, about 150 nucleotides in length, or a combination thereof. The overhang region can be at least 200 nucleotides in length. The overhang region can comprise a daisy-chaining amplification primer barcode sequence. Two daisy-chaining amplification primers of the plurality of daisy-chaining amplification primers can comprise overhang regions with an identical daisy-chaining amplification primer barcode sequence. Two daisy-chaining amplification primers of the plurality of daisy-chaining amplification primers can comprise overhang regions with two daisy-chaining amplification primer barcode sequences. Overhang regions of the plurality of daisy-chaining amplification primers can comprise different daisy-chaining amplification primer barcode sequences.

In some embodiments, the sample indexing sequence is at least 6 nucleotides in length, 25-45 nucleotides in length, about 128 nucleotides in length, or at least 128 nucleotides in length, or a combination thereof. The sample indexing oligonucleotide can be about 50 nucleotides in length, about 100 nucleotides in length, about 200 nucleotides in length, at least 200 nucleotides in length, less than about 200-300 nucleotides in length, about 200-500 nucleotides in length, about 500 nucleotides in length, or a combination thereof. Sample indexing sequences of at least 10, 100, or 1000 sample indexing compositions of the plurality of sample indexing compositions comprise different sequences.

In some embodiments, the cellular component binding reagent comprises an antibody, a tetramer, an aptamers, a protein scaffold, or a combination thereof. The sample indexing oligonucleotide can be conjugated to the cellular component binding reagent through a linker. The at least one sample indexing oligonucleotide can comprise the linker. The linker can comprise a chemical group. The chemical group can be reversibly or irreversibly attached to the molecule of the cellular component binding reagent. The chemical group can be selected from the group consisting of a UV photocleavable group, a disulfide bond, a streptavidin, a biotin, an amine, and any combination thereof.

In some embodiments, the sample indexing oligonucleotide is not homologous to genomic sequences of a species. The sample indexing oligonucleotide can comprise a molecular label sequence, a poly(A) region, or a combination thereof. In some embodiments, at least one sample of the plurality of samples can comprise a single cell, a plurality of cells, a tissue, a tumor sample, or any combination thereof. The sample can comprise a mammalian sample, a bacterial sample, a viral sample, a yeast sample, a fungal sample, or any combination thereof.

In some embodiments, the cellular component target is, or comprises, a cell-surface protein, a cell marker, a B-cell receptor, a T-cell receptor, a major histocompatibility complex, a tumor antigen, a receptor, or any combination thereof. The cellular component target can be selected from a group comprising 10-100 different cellular component targets. The cellular component binding reagent can be associated with two or more sample indexing oligonucleotides with an identical sequence. The cellular component binding reagent can be associated with two or more sample indexing oligonucleotides with different sample indexing sequences. The sample indexing composition of the plurality of sample indexing compositions can comprise a second cellular component binding reagent not conjugated with the sample indexing oligonucleotide. The cellular component binding reagent and the second cellular component binding reagent can be identical.

BRIEF DESCRIPTION OF THE DRAWINGS

FIGS. 8A1 and 8A2 show a schematic illustration of an exemplary workflow of daisy-chaining a barcoded oligonucleotide. FIGS. 8B1 and 8B2 show a schematic illustration of another exemplary workflow of daisy-chaining a barcoded oligonucleotide.

FIGS. 15A-15D show non-limiting exemplary designs of oligonucleotides for determining protein expression and gene expression simultaneously and for sample indexing.

FIGS. 18A-18F are non-limiting exemplary bar charts showing the expressions of CD4 mRNA and protein in CD4 T cells, CD8 T cells, and Myeloid cells.

FIGS. 20A-20D are plots showing the CD4 protein expression on cell surface of cells sorted using flow cytometry.

FIGS. 30A-30D are non-limiting exemplary plots comparing annotations of cell types determined based on mRNA expression of CD3D (for Jurkat cells) and JCHAIN (for Ramos cells) and sample indexing of Jurkat and Ramos cells.

FIG. 32 is a non-limiting exemplary tSNE projection plot of expression profiles of Jurkat and Ramos cells with an overlay of the cell types determined using sample indexing with a DBEC cutoff of 250.

FIGS. 34A-34C are non-limiting exemplary plots showing that less than 1% of single cells were labeled with both the "Short 2" and "Short 3" sample indexing oligonucleotides.

FIGS. 36A1-36A9, 36B and 36C are non-limiting exemplary plots showing determination of an optimal dilution of an antibody stock using dilution titration.

FIGS. 38A-38D are non-limiting exemplary bioanalyzer traces showing peaks (indicated by asterisks) consistent with the expected size of the antibody oligonucleotide.

FIGS. 39A1-39A3 and 39B1-39B3 are non-limiting exemplary histograms showing the numbers of molecules of antibody oligonucleotides detected for samples stained with different antibody dilutions and different percentage of the antibody molecules conjugated with the antibody oligonucleotides ("hot antibody").

FIGS. 41A-41C are non-limiting exemplary plots showing that oligonucleotide-conjugated anti-CD147 antibodies can be used to label various cell types. The cell types were determined using the expression profiles of 488 genes in a blood panel (FIG. 41A). The cells were stained with a mixture of 1% hot antibody:99% cold antibody prepared using a 1:100 diluted stock, resulting in no clear signal in a histogram showing the numbers of molecules of antibody oligonucleotides detected (FIG. 41B). The labeling of the various cell types by the antibody oligonucleotide is shown in FIG. 41C.

FIGS. 43A-43B are plots showing the composition of control particle oligonucleotides in a staining buffer and control particle oligonucleotides associated with control particles detected using the workflow illustrated in FIG. 10.

FIGS. 47A-47C are plots showing using an antibody cocktail for sample indexing can increase labeling sensitivity.

FIGS. 50B and 50C are non-limiting exemplary pie charts showing that after multiplet expression profiles were removed, the two mice, which were biological replicates, exhibited similar expression profiles.

DETAILED DESCRIPTION

Figure 1:
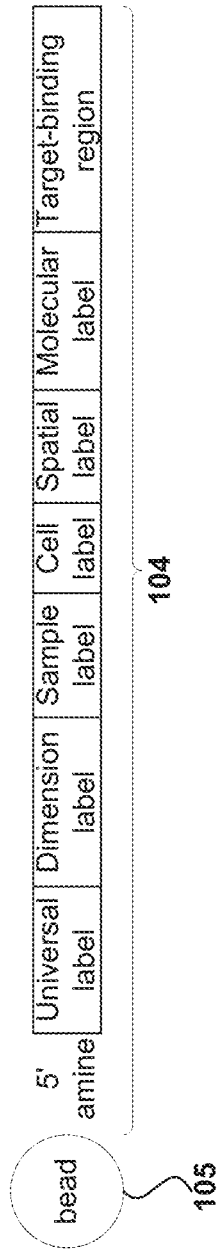
FIG. 1 illustrates a non-limiting exemplary stochastic barcode.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Quantifying small numbers of nucleic acids, for example messenger ribonucleotide acid (mRNA) molecules, is clinically important for determining, for example, the genes that are expressed in a cell at different stages of development or under different environmental conditions. However, it can also be very challenging to determine the absolute number of nucleic acid molecules (e.g., mRNA molecules), especially when the number of molecules is very small. One method to determine the absolute number of molecules in a sample is digital polymerase chain reaction (PCR). Ideally, PCR produces an identical copy of a molecule at each cycle. However, PCR can have disadvantages such that each molecule replicates with a stochastic probability, and this probability varies by PCR cycle and gene sequence, resulting in amplification bias and inaccurate gene expression measurements. Stochastic barcodes with unique molecular labels (also referred to as molecular indexes (MIs)) can be used to count the number of molecules and correct for amplification bias. Stochastic barcoding such as the Precise™ assay (Cellular Research, Inc. (Palo Alto, CA)) can correct for bias induced by PCR and library preparation steps by using molecular labels (MLs) to label mRNAs during reverse transcription (RT).

The Precise™ assay can utilize a non-depleting pool of stochastic barcodes with large number, for example 6561 to 65536, unique molecular labels on poly(T) oligonucleotides to hybridize to all poly(A)-mRNAs in a sample during the RT step. A stochastic barcode can comprise a universal PCR priming site. During RT, target gene molecules react randomly with stochastic barcodes. Each target molecule can hybridize to a stochastic barcode resulting to generate stochastically barcoded complementary ribonucleotide acid (cDNA) molecules). After labeling, stochastically barcoded cDNA molecules from microwells of a microwell plate can be pooled into a single tube for PCR amplification and sequencing. Raw sequencing data can be analyzed to produce the number of reads, the number of stochastic barcodes with unique molecular labels, and the numbers of mRNA molecules.

Methods for determining mRNA expression profiles of single cells can be performed in a massively parallel manner. For example, the Precise™ assay can be used to determine the mRNA expression profiles of more than 10000 cells simultaneously. The number of single cells (e.g., 100s or 1000s of singles) for analysis per sample can be lower than the capacity of the current single cell technology. Pooling of cells from different samples enables improved utilization of the capacity of the current single technology, thus lowering reagents wasted and the cost of single cell analysis. The disclosure provides methods of sample indexing for distinguishing cells of different samples for cDNA library preparation for cell analysis, such as single cell analysis. Pooling of cells from different samples can minimize the variations in cDNA library preparation of cells of different samples, thus enabling more accurate comparisons of different samples.

Disclosed herein include methods for sample identification. In some embodiments, the method comprises: contacting one or more cells from each of a plurality of samples with a sample indexing composition of a plurality of sample indexing compositions, wherein each of the one or more cells comprises one or more antigen targets, wherein each of the plurality of sample indexing compositions comprises a protein binding reagent associated with a sample indexing oligonucleotide, wherein the protein binding reagent is capable of specifically binding to at least one of the one or more antigen targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; barcoding (e.g., stochastically barcoding) the sample indexing oligonucleotides using a plurality of barcodes (e.g., stochastic barcodes) to create a plurality of barcoded sample indexing oligonucleotides (e.g., stochastically barcoded sample indexing oligonucleotides); obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, the method for sample identification disclosed herein comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; barcoding (e.g., stochastically barcoding) the sample indexing oligonucleotides using a plurality of barcodes (e.g., stochastic barcodes) to create a plurality of barcoded sample indexing oligonucleotides (e.g., stochastically barcoded sample indexing oligonucleotides); obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

Disclosed herein include methods for sample identification. In some embodiments, the method comprises: contacting one or more cells from each of a plurality of samples with a sample indexing composition of a plurality of sample indexing compositions, wherein each of the one or more cells comprises one or more antigen targets, wherein each of the plurality of sample indexing compositions comprises a protein binding reagent associated with a sample indexing oligonucleotide, wherein the protein binding reagent is capable of specifically binding to at least one of the one or more antigen targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; and identifying sample origin of at least one cell of the one or more cells based on the sample indexing sequence of at least one sample indexing oligonucleotide of the plurality of sample indexing compositions.

Disclosed herein is a plurality of sample indexing compositions. Each of the plurality of sample indexing compositions can comprise a protein binding reagent associated with a sample indexing oligonucleotide. The protein binding reagent can be capable of specifically binding to at least one antigen target. The sample indexing oligonucleotide can comprise a sample indexing sequence for identifying sample origin of one or more cells of a sample. Sample indexing sequences of at least two sample indexing compositions of the plurality of sample indexing compositions can comprise different sequences.

Disclosed herein include methods for sample identification. In some embodiments, the method comprises: contacting one or more cells from each of a plurality of samples with a sample indexing composition of a plurality of sample indexing compositions, wherein the one or more cells comprises one or more cellular component targets, wherein each of the plurality of sample indexing compositions comprises a cellular component binding reagent (e.g., an antibody) associated with a sample indexing oligonucleotide, wherein the cellular component binding reagent is capable of specifically binding to at least one of the one or more cellular component targets (e.g., proteins), wherein the sample indexing oligonucleotide comprises a sample indexing sequence, and wherein sample indexing sequences of at least two sample indexing compositions of the plurality of sample indexing compositions comprise different sequences; barcoding the sample indexing oligonucleotides using a plurality of barcodes to create a plurality of barcoded sample indexing oligonucleotides; amplifying the plurality of barcoded sample indexing oligonucleotides using a plurality of daisy-chaining amplification primers to create a plurality of daisy-chaining elongated amplicons; obtaining sequencing data of the plurality of daisy-chaining elongated amplicons comprising sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides. The method can comprise removing unbound sample indexing compositions of the plurality of sample indexing compositions.

In some embodiments, the sample indexing methods, kits, and compositions disclosed herein can increase sample throughput (e.g., for rare samples of low cell number, hard to isolate cells, and heterogeneous cells), lower reagent costs, reduce technical errors and batch effects by performing library preparation in a single tube reaction, and/or identify inter-sample multiplet cells during data analysis. In some embodiments, cells of tissues from different lymphoid organs and non-lymphoid organs can be tagged using different sample indexing compositions to, for example, increase sample throughput and reduce, or minimize, batch effects. In some embodiments, immune defense and tissue homeostasis and functions can be investigated using the methods, kits, and compositions of the disclosure.

Definitions

Unless defined otherwise, technical and scientific terms used herein have the same meaning as commonly understood by one of ordinary skill in the art to which the present disclosure belongs. See, e.g., Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the term "adaptor" can mean a sequence to facilitate amplification or sequencing of associated nucleic acids. The associated nucleic acids can comprise target nucleic acids. The associated nucleic acids can comprise one or more of spatial labels, target labels, sample labels, indexing label, or barcode sequences (e.g., molecular labels). The adaptors can be linear. The adaptors can be pre-adenylated adapters. The adaptors can be double- or single-stranded. One or more adaptor can be located on the 5' or 3' end of a nucleic acid. When the adaptors comprise known sequences on the 5' and 3' ends, the known sequences can be the same or different sequences. An adaptor located on the 5' and/or 3' ends of a polynucleotide can be capable of hybridizing to one or more oligonucleotides immobilized on a surface. An adapter can, in some embodiments, comprise a universal sequence. A universal sequence can be a region of nucleotide sequence that is common to two or more nucleic acid molecules. The two or more nucleic acid molecules can also have regions of different sequence. Thus, for example, the 5' adapters can comprise identical and/or universal nucleic acid sequences and the 3' adapters can comprise identical and/or universal sequences. A universal sequence that may be present in different members of a plurality of nucleic acid molecules can allow the replication or amplification of multiple different sequences using a single universal primer that is complementary to the universal sequence. Similarly, at least one, two (e.g., a pair) or more universal sequences that may be present in different members of a collection of nucleic acid molecules can allow the replication or amplification of multiple different sequences using at least one, two (e.g., a pair) or more single universal primers that are complementary to the universal sequences. Thus, a universal primer includes a sequence that can hybridize to such a universal sequence. The target nucleic acid sequence-bearing molecules may be modified to attach universal adapters (e.g., non-target nucleic acid sequences) to one or both ends of the different target nucleic acid sequences. The one or more universal primers attached to the target nucleic acid can provide sites for hybridization of universal primers. The one or more universal primers attached to the target nucleic acid can be the same or different from each other.

As used herein, an antibody can be a full-length (e.g., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

In some embodiments, an antibody is a functional antibody fragment. For example, an antibody fragment can be a portion of an antibody such as F(ab')2, Fab', Fab, Fv, sFv and the like. An antibody fragment can bind with the same antigen that is recognized by the full-length antibody. An antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (for example, CD8, CD34, and CD45), and therapeutic antibodies.

As used herein the term "associated" or "associated with" can mean that two or more species are identifiable as being co-located at a point in time. An association can mean that two or more species are or were within a similar container. An association can be an informatics association. For example, digital information regarding two or more species can be stored and can be used to determine that one or more of the species were co-located at a point in time. An association can also be a physical association. In some embodiments, two or more associated species are "tethered", "attached", or "immobilized" to one another or to a common solid or semisolid surface. An association may refer to covalent or non-covalent means for attaching labels to solid or semi-solid supports such as beads. An association may be a covalent bond between a target and a label. An association can comprise hybridization between two molecules (such as a target molecule and a label).

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This methodology, which can be stochastic in nature, transforms the problem of counting molecules from one of locating and identifying identical molecules to a series of yes/no digital questions regarding detection of a set of predefined labels.

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of barcodes (e.g., stochastic barcodes) made up of many different labels. A non-depleting reservoir can comprise large numbers of different barcodes such that when the non-depleting reservoir is associated with a pool of targets each target is likely to be associated with a unique barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of barcodes detected then allows calculation of the number of target molecules present in the original collection or sample. When the ratio of the number of copies of a target molecule present to the number of unique barcodes is low, the labeled target molecules are highly unique (i.e., there is a very low probability that more than one target molecule will have been labeled with a given label).

As used herein, the term "nucleic acid" refers to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g., altered backbone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within nucleic acids, the phosphate groups can commonly be referred to as forming the internucleoside backbone of the nucleic acid. The linkage or backbone can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkyl phosphotriesters, methyl and other alkyl phosphonate such as 3'-alkylene phosphonates, 5'-alkylene phosphonates, chiral phosphonates, phosphinates, phosphoramidates including 3'-amino phosphoramidate and amino alkyl phosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (e.g., morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C, 4'-C-oxymethylene linkage thereby forming a bicyclic sugar moiety. The linkage can be a methylene ($—CH_2$), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid may also include nucleobase (often referred to simply as "base") modifications or substitutions. As used herein, "unmodified" or "natural" nucleobases can include the purine bases, (e.g., adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5, 4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g., 9-(2-aminoethoxy)-H-pyrimido(5,4-(b) (1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2': 4,5)pyrrolo[2,3-d]pyrimidin-2-one).

As used herein, the term "sample" can refer to a composition comprising targets. Suitable samples for analysis by the disclosed methods, devices, and systems include cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "solid support" can refer to discrete solid or semi-solid surfaces to which a plurality of barcodes (e.g., stochastic barcodes) may be attached. A solid support may encompass any type of solid, porous, or hollow sphere, ball, bearing, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A plurality of solid supports spaced in an array may not comprise a substrate. A solid support may be used interchangeably with the term "bead."

As used herein, the term "stochastic barcode" can refer to a polynucleotide sequence comprising labels of the present disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "gene-specific stochastic barcode" can refer to a polynucleotide sequence comprising labels and a target-binding region that is gene-specific. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a barcode (e.g., a stochastic barcode). Exemplary suitable targets for analysis by the disclosed methods, devices, and systems include oligonucleotides, DNA, RNA, mRNA, microRNA, tRNA, and the like. Targets can be single or double stranded. In some embodiments, targets can be proteins, peptides, or polypeptides. In some embodiments, targets are lipids. As used herein, "target" can be used interchangeably with "species."

As used herein, the term "reverse transcriptases" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants or derivatives thereof. Non-retroviral reverse transcriptases include non-LTR retrotransposon reverse transcriptases, retroplasmid reverse transcriptases, retron reverse transcriptases, and group II intron reverse transcriptases. Examples of group II intron reverse transcriptases include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptases can include many classes of non-retroviral reverse transcriptases (i.e., retrons, group II introns, and diversity-generating retroelements among others).

The terms "universal adaptor primer," "universal primer adaptor" or "universal adaptor sequence" are used interchangeably to refer to a nucleotide sequence that can be used to hybridize to barcodes (e.g., stochastic barcodes) to generate gene-specific barcodes. A universal adaptor sequence can, for example, be a known sequence that is universal across all barcodes used in methods of the disclosure. For example, when multiple targets are being labeled using the methods disclosed herein, each of the target-specific sequences may be linked to the same universal adaptor sequence. In some embodiments, more than one universal adaptor sequences may be used in the methods disclosed herein. For example, when multiple targets are being labeled using the methods disclosed herein, at least two of the target-specific sequences are linked to different universal adaptor sequences. A universal adaptor primer and its complement may be included in two oligonucleotides, one of which comprises a target-specific sequence and the other comprises a barcode. For example, a universal adaptor sequence may be part of an oligonucleotide comprising a target-specific sequence to generate a nucleotide sequence that is complementary to a target nucleic acid. A second oligonucleotide comprising a barcode and a complementary sequence of the universal adaptor sequence may hybridize with the nucleotide sequence and generate a target-specific barcode (e.g., a target-specific stochastic barcode). In some embodiments, a universal adaptor primer has a sequence that is different from a universal PCR primer used in the methods of this disclosure.

Barcodes

Barcoding, such as stochastic barcoding, has been described in, for example, US20150299784, WO2015031691, and Fu et al, Proc Natl Acad Sci U.S.A. 2011 May 31; 108(22):9026-31, the content of these publications is incorporated hereby in its entirety. In some embodiments, the barcode disclosed herein can be a stochastic barcode which can be a polynucleotide sequence that may be used to stochastically label (e.g., barcode, tag) a target. Barcodes can be referred to stochastic barcodes if the ratio of the number of different barcode sequences of the stochastic barcodes and the number of occurrence of any of the targets to be labeled can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. Barcodes can be referred to as stochastic barcodes if the ratio of the number of different barcode sequences of the stochastic barcodes and the number of occurrence of any of the targets to be labeled is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1. Barcode sequences of stochastic barcodes can be referred to as molecular labels.

A barcode, for example a stochastic barcode, can comprise one or more labels. Exemplary labels can include a universal label, a cell label, a barcode sequence (e.g., a molecular label), a sample label, a plate label, a spatial label, and/or a pre-spatial label. FIG. 1 illustrates an exemplary barcode 104 with a spatial label. The barcode 104 can comprise a 5'amine that may link the barcode to a solid support 105. The barcode can comprise a universal label, a dimension label, a spatial label, a cell label, and/or a molecular label. The order of different labels (including but not limited to the universal label, the dimension label, the spatial label, the cell label, and the molecule label) in the barcode can vary. For example, as shown in FIG. 1, the universal label may be the 5'-most label, and the molecular label may be the 3'-most label. The spatial label, dimension label, and the cell label may be in any order. In some embodiments, the universal label, the spatial label, the dimension label, the cell label, and the molecular label are in any order. The barcode can comprise a target-binding region. The target-binding region can interact with a target (e.g., target nucleic acid, RNA, mRNA, DNA) in a sample. For example, a target-binding region can comprise an oligo (dT) sequence which can interact with poly(A) tails of mRNAs. In some instances, the labels of the barcode (e.g., universal label, dimension label, spatial label, cell label, and barcode sequence) may be separated by 1, 2, 3, 4, 5, 6, 7, 8, 9, 10, 11, 12, 13, 14, 15, 16, 17, 18, 19, or 20 or more nucleotides.

A label, for example the cell label, can comprise a unique set of nucleic acid sub-sequences of defined length, e.g., seven nucleotides each (equivalent to the number of bits used in some Hamming error correction codes), which can be designed to provide error correction capability. The set of error correction sub-sequences comprise seven nucleotide sequences can be designed such that any pairwise combination of sequences in the set exhibits a defined "genetic distance" (or number of mismatched bases), for example, a set of error correction sub-sequences can be designed to exhibit a genetic distance of three nucleotides. In this case, a review of the error correction sequences in the set of sequence data for labeled target nucleic acid molecules (described more fully below) can allow one to detect or correct amplification or sequencing errors. In some embodiments, the length of the nucleic acid sub-sequences used for creating error correction codes can vary, for example, they can be, or be about 1, 2, 3, 4, 5, 6, 7, 8, 9, 10, 15, 20, 30, 31, 40, 50, or a number or a range between any two of these values, nucleotides in length. In some embodiments, nucleic acid sub-sequences of other lengths can be used for creating error correction codes.

The barcode can comprise a target-binding region. The target-binding region can interact with a target in a sample. The target can be, or comprise, ribonucleic acids (RNAs), messenger RNAs (mRNAs), microRNAs, small interfering RNAs (siRNAs), RNA degradation products, RNAs each comprising a poly(A) tail, or any combination thereof. In some embodiments, the plurality of targets can include deoxyribonucleic acids (DNAs).

In some embodiments, a target-binding region can comprise an oligo(dT) sequence which can interact with poly(A) tails of mRNAs. One or more of the labels of the barcode (e.g., the universal label, the dimension label, the spatial label, the cell label, and the barcode sequences (e.g., molecular label)) can be separated by a spacer from another one or two of the remaining labels of the barcode. The spacer can be, for example, 1, 2, 3, 4, 5, 6, 7, 8, 9, 10, 11, 12, 13, 14, 15, 16, 17, 18, 19, or 20, or more nucleotides. In some embodiments, none of the labels of the barcode is separated by spacer.

Universal Labels

A barcode can comprise one or more universal labels. In some embodiments, the one or more universal labels can be the same for all barcodes in the set of barcodes attached to a given solid support. In some embodiments, the one or more universal labels can be the same for all barcodes attached to a plurality of beads. In some embodiments, a universal label can comprise a nucleic acid sequence that is capable of hybridizing to a sequencing primer. Sequencing primers can be used for sequencing barcodes comprising a universal label. Sequencing primers (e.g., universal sequencing primers) can comprise sequencing primers associated with high-throughput sequencing platforms. In some embodiments, a universal label can comprise a nucleic acid sequence that is capable of hybridizing to a PCR primer. In some embodiments, the universal label can comprise a nucleic acid sequence that is capable of hybridizing to a sequencing primer and a PCR primer. The nucleic acid sequence of the universal label that is capable of hybridizing to a sequencing or PCR primer can be referred to as a primer binding site. A universal label can comprise a sequence that can be used to initiate transcription of the barcode. A universal label can comprise a sequence that can be used for extension of the barcode or a region within the barcode. A universal label can be, or be about, 1, 2, 3, 4, 5, 10, 15, 20, 25, 30, 35, 40, 45, 50, or a number or a range between any two of these values, nucleotides in length. For example, a universal label can comprise at least about 10 nucleotides. A universal label can be at least, or be at most, 1, 2, 3, 4, 5, 10, 15, 20, 25, 30, 35, 40, 45, 50, 100, 200, or 300 nucleotides in length. In some embodiments, a cleavable linker or modified nucleotide can be part of the universal label sequence to enable the barcode to be cleaved off from the support.

Dimension Labels

A barcode can comprise one or more dimension labels. In some embodiments, a dimension label can comprise a nucleic acid sequence that provides information about a dimension in which the labeling (e.g., stochastic labeling) occurred. For example, a dimension label can provide information about the time at which a target was barcoded. A dimension label can be associated with a time of barcoding (e.g., stochastic barcoding) in a sample. A dimension label can be activated at the time of labeling. Different dimension labels can be activated at different times. The dimension label provides information about the order in which targets, groups of targets, and/or samples were barcoded. For example, a population of cells can be barcoded at the G0 phase of the cell cycle. The cells can be pulsed again with barcodes (e.g., stochastic barcodes) at the G1 phase of the cell cycle. The cells can be pulsed again with barcodes at the S phase of the cell cycle, and so on. Barcodes at each pulse (e.g., each phase of the cell cycle), can comprise different dimension labels. In this way, the dimension label provides information about which targets were labelled at which phase of the cell cycle. Dimension labels can interrogate many different biological times. Exemplary biological times can include, but are not limited to, the cell cycle, transcription (e.g., transcription initiation), and transcript degradation. In another example, a sample (e.g., a cell, a population of cells) can be labeled before and/or after treatment with a drug and/or therapy. The changes in the number of copies of distinct targets can be indicative of the sample's response to the drug and/or therapy.

A dimension label can be activatable. An activatable dimension label can be activated at a specific time point. The activatable label can be, for example, constitutively activated (e.g., not turned off). The activatable dimension label can be, for example, reversibly activated (e.g., the activatable dimension label can be turned on and turned off). The dimension label can be, for example, reversibly activatable at least 1, 2, 3, 4, 5, 6, 7, 8, 9, 10, or more times. The dimension label can be reversibly activatable, for example, at least 1, 2, 3, 4, 5, 6, 7, 8, 9, 10 or more times. In some embodiments, the dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can, in some embodiments, be identical for all barcodes (e.g., stochastic barcodes) attached to a given solid support (e.g., a bead), but different for different solid supports (e.g., beads). In some embodiments, at least 60%, 70%, 80%, 85%, 90%, 95%, 97%, 99% or 100%, of barcodes on the same solid support can comprise the same dimension label. In some embodiments, at least 60% of barcodes on the same solid support can comprise the same dimension label. In some embodiments, at least 95% of barcodes on the same solid support can comprise the same dimension label.

There can be as many as $10^6$ or more unique dimension label sequences represented in a plurality of solid supports (e.g., beads). A dimension label can be, or be about 1, 2, 3, 4, 5, 10, 15, 20, 25, 30, 35, 40, 45, 50, or a number or a range between any two of these values, nucleotides in length. A dimension label can be at least, or be at most, 1, 2, 3, 4, 5, 10, 15, 20, 25, 30, 35, 40, 45, 50, 100, 200, or 300, nucleotides in length. A dimension label can comprise between about 5 to about 200 nucleotides. A dimension label can comprise between about 10 to about 150 nucleotides. A dimension label can comprise between about 20 to about 125 nucleotides in length.

Spatial Labels

A barcode can comprise one or more spatial labels. In some embodiments, a spatial label can comprise a nucleic acid sequence that provides information about the spatial orientation of a target molecule which is associated with the barcode. A spatial label can be associated with a coordinate in a sample. The coordinate can be a fixed coordinate. For example, a coordinate can be fixed in reference to a substrate. A spatial label can be in reference to a two or three-dimensional grid. A coordinate can be fixed in reference to a landmark. The landmark can be identifiable in space. A landmark can be a structure which can be imaged. A landmark can be a biological structure, for example an anatomical landmark. A landmark can be a cellular landmark, for instance an organelle. A landmark can be a non-natural landmark such as a structure with an identifiable identifier such as a color code, bar code, magnetic property, fluorescents, radioactivity, or a unique size or shape. A spatial label can be associated with a physical partition (e.g., a well, a container, or a droplet). In some embodiments, multiple spatial labels are used together to encode one or more positions in space.

The spatial label can be identical for all barcodes attached to a given solid support (e.g., a bead), but different for different solid supports (e.g., beads). In some embodiments, the percentage of barcodes on the same solid support comprising the same spatial label can be, or be about, 60%, 70%, 80%, 85%, 90%, 95%, 97%, 99%, 100%, or a number or a range between any two of these values. In some embodiments, the percentage of barcodes on the same solid support comprising the same spatial label can be at least, or be at most, 60%, 70%, 80%, 85%, 90%, 95%, 97%, 99%, or 100%. In some embodiments, at least 60% of barcodes on the same solid support can comprise the same spatial label. In some embodiments, at least 95% of barcodes on the same solid support can comprise the same spatial label.

There can be as many as $10^6$ or more unique spatial label sequences represented in a plurality of solid supports (e.g., beads). A spatial label can be, or be about, 1, 2, 3, 4, 5, 10, 15, 20, 25, 30, 35, 40, 45, 50, or a number or a range between any two of these values, nucleotides in length. A spatial label can be at least or at most 1, 2, 3, 4, 5, 10, 15, 20, 25, 30, 35, 40, 45, 50, 100, 200, or 300 nucleotides in length. A spatial label can comprise between about 5 to about 200 nucleotides. A spatial label can comprise between about 10 to about 150 nucleotides. A spatial label can comprise between about 20 to about 125 nucleotides in length.

Cell Labels

A barcode (e.g., a stochastic barcode) can comprise one or more cell labels. In some embodiments, a cell label can comprise a nucleic acid sequence that provides information for determining which target nucleic acid originated from which cell. In some embodiments, the cell label is identical for all barcodes attached to a given solid support (e.g., a bead), but different for different solid supports (e.g., beads). In some embodiments, the percentage of barcodes on the same solid support comprising the same cell label can be, or be about 60%, 70%, 80%, 85%, 90%, 95%, 97%, 99%, 100%, or a number or a range between any two of these values. In some embodiments, the percentage of barcodes on the same solid support comprising the same cell label can be, or be about 60%, 70%, 80%, 85%, 90%, 95%, 97%, 99%, or 100%. For example, at least 60% of barcodes on the same solid support can comprise the same cell label. As another example, at least 95% of barcodes on the same solid support can comprise the same cell label.

There can be as many as $10^6$ or more unique cell label sequences represented in a plurality of solid supports (e.g., beads). A cell label can be, or be about, 1, 2, 3, 4, 5, 10, 15, 20, 25, 30, 35, 40, 45, 50, or a number or a range between any two of these values, nucleotides in length. A cell label can be at least, or be at most, 1, 2, 3, 4, 5, 10, 15, 20, 25, 30, 35, 40, 45, 50, 100, 200, or 300 nucleotides in length. For example, a cell label can comprise between about 5 to about 200 nucleotides. As another example, a cell label can comprise between about 10 to about 150 nucleotides. As yet another example, a cell label can comprise between about 20 to about 125 nucleotides in length.

Barcode Sequences

A barcode can comprise one or more barcode sequences. In some embodiments, a barcode sequence can comprise a nucleic acid sequence that provides identifying information for the specific type of target nucleic acid species hybridized to the barcode. A barcode sequence can comprise a nucleic acid sequence that provides a counter (e.g., that provides a rough approximation) for the specific occurrence of the target nucleic acid species hybridized to the barcode (e.g., target-binding region).

In some embodiments, a diverse set of barcode sequences are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, unique molecular label sequences. For example, a plurality of barcodes can comprise about 6561 barcodes sequences with distinct sequences. As another example, a plurality of barcodes can comprise about 65536 barcode sequences with distinct sequences. In some embodiments, there can be at least, or be at most, $10^2$, $10^3$, $10^4$, $10^5$, $10^6$, $10^7$, $10^8$, or $10^9$, unique barcode sequences. The unique molecular label sequences can be attached to a given solid support (e.g., a bead).

The length of a barcode can be different in different implementations. For example, a barcode can be, or be about, 1, 2, 3, 4, 5, 10, 15, 20, 25, 30, 35, 40, 45, 50, or a number or a range between any two of these values, nucleotides in length. As another example, a barcode can be at least, or be at most, 1, 2, 3, 4, 5, 10, 15, 20, 25, 30, 35, 40, 45, 50, 100, 200, or 300 nucleotides in length.

Molecular Labels

A barcode (e.g., a stochastic barcode) can comprise one or more molecular labels. Molecular labels can include barcode sequences. In some embodiments, a molecular label can comprise a nucleic acid sequence that provides identifying information for the specific type of target nucleic acid species hybridized to the barcode. A molecular label can comprise a nucleic acid sequence that provides a counter for the specific occurrence of the target nucleic acid species hybridized to the barcode (e.g., target-binding region).

In some embodiments, a diverse set of molecular labels are attached to a given solid support (e.g., a bead). In some embodiments, there can be, or be about, $10^2$, $10^3$, $10^4$, $10^5$, $10^6$, $10^7$, $10^8$, $10^9$, or a number or a range between any two of these values, of unique molecular label sequences. For example, a plurality of barcodes can comprise about 6561 molecular labels with distinct sequences. As another example, a plurality of barcodes can comprise about 65536 molecular labels with distinct sequences. In some embodiments, there can be at least, or be at most, $10^2$, $10^3$, $10^4$, $10^5$, $10^6$, $10^7$, $10^8$, or $10^9$, unique molecular label sequences. Barcodes with unique molecular label sequences can be attached to a given solid support (e.g., a bead).

For stochastic barcoding using a plurality of stochastic barcodes, the ratio of the number of different molecular label sequences and the number of occurrence of any of the targets can be, or be about, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, 100:1, or a number or a range between any two of these values. A target can be an mRNA species comprising mRNA molecules with identical or nearly identical sequences. In some embodiments, the ratio of the number of different molecular label sequences and the number of occurrence of any of the targets is at least, or is at most, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1, 80:1, 90:1, or 100:1.

A molecular label can be, or be about, 1, 2, 3, 4, 5, 10, 15, 20, 25, 30, 35, 40, 45, 50, or a number or a range between any two of these values, nucleotides in length. A molecular label can be at least, or be at most, 1, 2, 3, 4, 5, 10, 15, 20, 25, 30, 35, 40, 45, 50, 100, 200, or 300 nucleotides in length.

Target-Binding Region

A barcode can comprise one or more target binding regions, such as capture probes. In some embodiments, a target-binding region can hybridize with a target of interest. In some embodiments, the target binding regions can comprise a nucleic acid sequence that hybridizes specifically to a target (e.g., target nucleic acid, target molecule, e.g., a cellular nucleic acid to be analyzed), for example to a specific gene sequence. In some embodiments, a target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction enzyme site overhang (e.g., an EcoRI sticky-end overhang). The barcode can then ligate to any nucleic acid molecule comprising a sequence complementary to the restriction site overhang.

In some embodiments, a target binding region can comprise a non-specific target nucleic acid sequence. A non-specific target nucleic acid sequence can refer to a sequence that can bind to multiple target nucleic acids, independent of the specific sequence of the target nucleic acid. For example, target binding region can comprise a random multimer sequence, or an oligo(dT) sequence that hybridizes to the poly(A) tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all barcodes attached to a given bead. In some embodiments, the target binding regions for the plurality of barcodes attached to a given bead can comprise two or more different target binding sequences. A target binding region can be, or be about, 5, 10, 15, 20, 25, 30, 35, 40, 45, 50, or a number or a range between any two of these values, nucleotides in length. A target binding region can be at most about 5, 10, 15, 20, 25, 30, 35, 40, 45, 50 or more nucleotides in length.

In some embodiments, a target-binding region can comprise an oligo(dT) which can hybridize with mRNAs comprising polyadenylated ends. A target-binding region can be gene-specific. For example, a target-binding region can be configured to hybridize to a specific region of a target. A target-binding region can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these values, nucleotides in length. A target-binding region can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30, nucleotides in length. A target-binding region can be about 5-30 nucleotides in length. When a barcode comprises a gene-specific target-binding region, the barcode can be referred to herein as a gene-specific barcode.

Orientation Property

A stochastic barcode (e.g., a stochastic barcode) can comprise one or more orientation properties which can be used to orient (e.g., align) the barcodes. A barcode can comprise a moiety for isoelectric focusing. Different barcodes can comprise different isoelectric focusing points. When these barcodes are introduced to a sample, the sample can undergo isoelectric focusing in order to orient the barcodes into a known way. In this way, the orientation property can be used to develop a known map of barcodes in a sample. Exemplary orientation properties can include, electrophoretic mobility (e.g., based on size of the barcode), isoelectric point, spin, conductivity, and/or self-assembly. For example, barcodes with an orientation property of self-assembly, can self-assemble into a specific orientation (e.g., nucleic acid nanostructure) upon activation.

Affinity Property

A barcode (e.g., a stochastic barcode) can comprise one or more affinity properties. For example, a spatial label can comprise an affinity property. An affinity property can include a chemical and/or biological moiety that can facilitate binding of the barcode to another entity (e.g., cell receptor). For example, an affinity property can comprise an antibody, for example, an antibody specific for a specific moiety (e.g., receptor) on a sample. In some embodiments, the antibody can guide the barcode to a specific cell type or molecule. Targets at and/or near the specific cell type or molecule can be labeled (e.g., stochastically labeled). The affinity property can, in some embodiments, provide spatial information in addition to the nucleotide sequence of the spatial label because the antibody can guide the barcode to a specific location. The antibody can be a therapeutic antibody, for example a monoclonal antibody or a polyclonal antibody. The antibody can be humanized or chimeric. The antibody can be a naked antibody or a fusion antibody.

The antibody can be a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody fragment can be, for example, a portion of an antibody such as F(ab')2, Fab', Fab, Fv, sFv and the like. In some embodiments, the antibody fragment can bind with the same antigen that is recognized by the full-length antibody. The antibody fragment can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for cancer cells, antibodies for viruses, antibodies that bind to cell surface receptors (CD8, CD34, CD45), and therapeutic antibodies.

Universal Adaptor Primer

A barcode can comprise one or more universal adaptor primers. For example, a gene-specific barcode, such as a gene-specific stochastic barcode, can comprise a universal adaptor primer. A universal adaptor primer can refer to a nucleotide sequence that is universal across all barcodes. A universal adaptor primer can be used for building gene-specific barcodes. A universal adaptor primer can be, or be about, 1, 2, 3, 4, 5, 6, 7, 8, 9, 10, 11, 12, 13, 14, 15, 16, 17, 18, 19, 20, 21, 22, 23, 24, 25, 26 27, 28, 29, 30, or a number or a range between any two of these nucleotides in length. A universal adaptor primer can be at least, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 nucleotides in length. A universal adaptor primer can be from 5-30 nucleotides in length.

Linker

When a barcode comprises more than one of a type of label (e.g., more than one cell label or more than one barcode sequence, such as one molecular label), the labels may be interspersed with a linker label sequence. A linker label sequence can be at least about 5, 10, 15, 20, 25, 30, 35, 40, 45, 50 or more nucleotides in length. A linker label sequence can be at most about 5, 10, 15, 20, 25, 30, 35, 40, 45, 50 or more nucleotides in length. In some instances, a linker label sequence is 12 nucleotides in length. A linker label sequence can be used to facilitate the synthesis of the barcode. The linker label can comprise an error-correcting (e.g., Hamming) code.

Solid Supports

Barcodes, such as stochastic barcodes, disclosed herein can, in some embodiments, be associated with a solid support. The solid support can be, for example, a synthetic particle. In some embodiments, some or all of the barcode sequences, such as molecular labels for stochastic barcodes (e.g., the first barcode sequences) of a plurality of barcodes (e.g., the first plurality of barcodes) on a solid support differ by at least one nucleotide. The cell labels of the barcodes on the same solid support can be the same. The cell labels of the barcodes on different solid supports can differ by at least one nucleotide. For example, first cell labels of a first plurality of barcodes on a first solid support can have the same sequence, and second cell labels of a second plurality of barcodes on a second solid support can have the same sequence. The first cell labels of the first plurality of barcodes on the first solid support and the second cell labels of the second plurality of barcodes on the second solid support can differ by at least one nucleotide. A cell label can be, for example, about 5-20 nucleotides long. A barcode sequence can be, for example, about 5-20 nucleotides long. The synthetic particle can be, for example, a bead.

The bead can be, for example, a silica gel bead, a controlled pore glass bead, a magnetic bead, a Dynabead, a Sephadex/Sepharose bead, a cellulose bead, a polystyrene bead, or any combination thereof. The bead can comprise a material such as polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof.

In some embodiments, the bead can be a polymeric bead, for example a deformable bead or a gel bead, functionalized with barcodes or stochastic barcodes (such as gel beads from 10× Genomics (San Francisco, CA). In some implementation, a gel bead can comprise a polymer based gels. Gel beads can be generated, for example, by encapsulating one or more polymeric precursors into droplets. Upon exposure of the polymeric precursors to an accelerator (e.g., tetramethylethylenediamine (TEMED)), a gel bead may be generated.

In some embodiments, the particle can be degradable. For example, the polymeric bead can dissolve, melt, or degrade, for example, under a desired condition. The desired condition can include an environmental condition. The desired condition may result in the polymeric bead dissolving, melting, or degrading in a controlled manner. A gel bead may dissolve, melt, or degrade due to a chemical stimulus, a physical stimulus, a biological stimulus, a thermal stimulus, a magnetic stimulus, an electric stimulus, a light stimulus, or any combination thereof.

Analytes and/or reagents, such as oligonucleotide barcodes, for example, may be coupled/immobilized to the interior surface of a gel bead (e.g., the interior accessible via diffusion of an oligonucleotide barcode and/or materials used to generate an oligonucleotide barcode) and/or the outer surface of a gel bead or any other microcapsule described herein. Coupling/immobilization may be via any form of chemical bonding (e.g., covalent bond, ionic bond) or physical phenomena (e.g., Van der Waals forces, dipole-dipole interactions, etc.). In some embodiments, coupling/immobilization of a reagent to a gel bead or any other microcapsule described herein may be reversible, such as, for example, via a labile moiety (e.g., via a chemical cross-linker, including chemical cross-linkers described herein). Upon application of a stimulus, the labile moiety may be cleaved and the immobilized reagent set free. In some embodiments, the labile moiety is a disulfide bond. For example, in the case where an oligonucleotide barcode is immobilized to a gel bead via a disulfide bond, exposure of the disulfide bond to a reducing agent can cleave the disulfide bond and free the oligonucleotide barcode from the bead. The labile moiety may be included as part of a gel bead or microcapsule, as part of a chemical linker that links a reagent or analyte to a gel bead or microcapsule, and/or as part of a reagent or analyte. In some embodiments, at least one barcode of the plurality of barcodes can be immobilized on the particle, partially immobilized on the particle, enclosed in the particle, partially enclosed in the particle, or any combination thereof.

In some embodiments, a gel bead can comprise a wide range of different polymers including but not limited to: polymers, heat sensitive polymers, photosensitive polymers, magnetic polymers, pH sensitive polymers, salt-sensitive polymers, chemically sensitive polymers, polyelectrolytes, polysaccharides, peptides, proteins, and/or plastics. Polymers may include but are not limited to materials such as poly(N-isopropylacrylamide) (PNIPAAm), poly(styrene sulfonate) (PSS), poly(allyl amine) (Pam), poly(acrylic acid) (PAA), poly(ethylene imine) (PEI), poly(diallyldimethylammonium chloride) (PDADMAC), poly(pyrolle) (PPy), poly(vinylpyrrolidone) (PVPON), poly(vinyl pyridine) (PVP), poly(methacrylic acid) (PMAA), poly(methyl methacrylate) (PMMA), polystyrene (PS), poly(tetrahydrofuran) (PTHF), poly(phthaladehyde) (PTHF), poly(hexyl viologen) (PHV), poly(L-lysine) (PLL), poly(L-arginine) (PARG), poly(lactic-co-glycolic acid) (PLGA).

Numerous chemical stimuli can be used to trigger the disruption, dissolution, or degradation of the beads. Examples of these chemical changes may include, but are not limited to pH-mediated changes to the bead wall, disintegration of the bead wall via chemical cleavage of cross-link bonds, triggered depolymerization of the bead wall, and bead wall switching reactions. Bulk changes may also be used to trigger disruption of the beads.

Bulk or physical changes to the microcapsule through various stimuli also offer many advantages in designing capsules to release reagents. Bulk or physical changes occur on a macroscopic scale, in which bead rupture is the result of mechano-physical forces induced by a stimulus. These processes may include, but are not limited to pressure induced rupture, bead wall melting, or changes in the porosity of the bead wall.

Biological stimuli may also be used to trigger disruption, dissolution, or degradation of beads. Generally, biological triggers resemble chemical triggers, but many examples use biomolecules, or molecules commonly found in living systems such as enzymes, peptides, saccharides, fatty acids, nucleic acids and the like. For example, beads may comprise polymers with peptide cross-links that are sensitive to cleavage by specific proteases. More specifically, one example may comprise a microcapsule comprising GFLGK peptide cross links. Upon addition of a biological trigger such as the protease Cathepsin B, the peptide cross links of the shell well are cleaved and the contents of the beads are released. In other cases, the proteases may be heat-activated. In another example, beads comprise a shell wall comprising cellulose. Addition of the hydrolytic enzyme chitosan serves as biologic trigger for cleavage of cellulosic bonds, depolymerization of the shell wall, and release of its inner contents.

The beads may also be induced to release their contents upon the application of a thermal stimulus. A change in temperature can cause a variety changes to the beads. A change in heat may cause melting of a bead such that the bead wall disintegrates. In other cases, the heat may increase the internal pressure of the inner components of the bead such that the bead ruptures or explodes. In still other cases, the heat may transform the bead into a shrunken dehydrated state. The heat may also act upon heat-sensitive polymers within the wall of a bead to cause disruption of the bead.

Inclusion of magnetic nanoparticles to the bead wall of microcapsules may allow triggered rupture of the beads as well as guide the beads in an array. A device of this disclosure may comprise magnetic beads for either purpose. In one example, incorporation of $Fe_3O_4$ nanoparticles into polyelectrolyte containing beads triggers rupture in the presence of an oscillating magnetic field stimulus.

A bead may also be disrupted, dissolved, or degraded as the result of electrical stimulation. Similar to magnetic particles described in the previous section, electrically sensitive beads can allow for both triggered rupture of the beads as well as other functions such as alignment in an electric field, electrical conductivity or redox reactions. In one example, beads containing electrically sensitive material are aligned in an electric field such that release of inner reagents can be controlled. In other examples, electrical fields may induce redox reactions within the bead wall itself that may increase porosity.

A light stimulus may also be used to disrupt the beads. Numerous light triggers are possible and may include systems that use various molecules such as nanoparticles and chromophores capable of absorbing photons of specific ranges of wavelengths. For example, metal oxide coatings can be used as capsule triggers. UV irradiation of polyelectrolyte capsules coated with $SiO_2$ may result in disintegration of the bead wall. In yet another example, photo switchable materials such as azobenzene groups may be incorporated in the bead wall. Upon the application of UV or visible light, chemicals such as these undergo a reversible cis-to-trans isomerization upon absorption of photons. In this aspect, incorporation of photon switches result in a bead wall that may disintegrate or become more porous upon the application of a light trigger.

Figure 2:
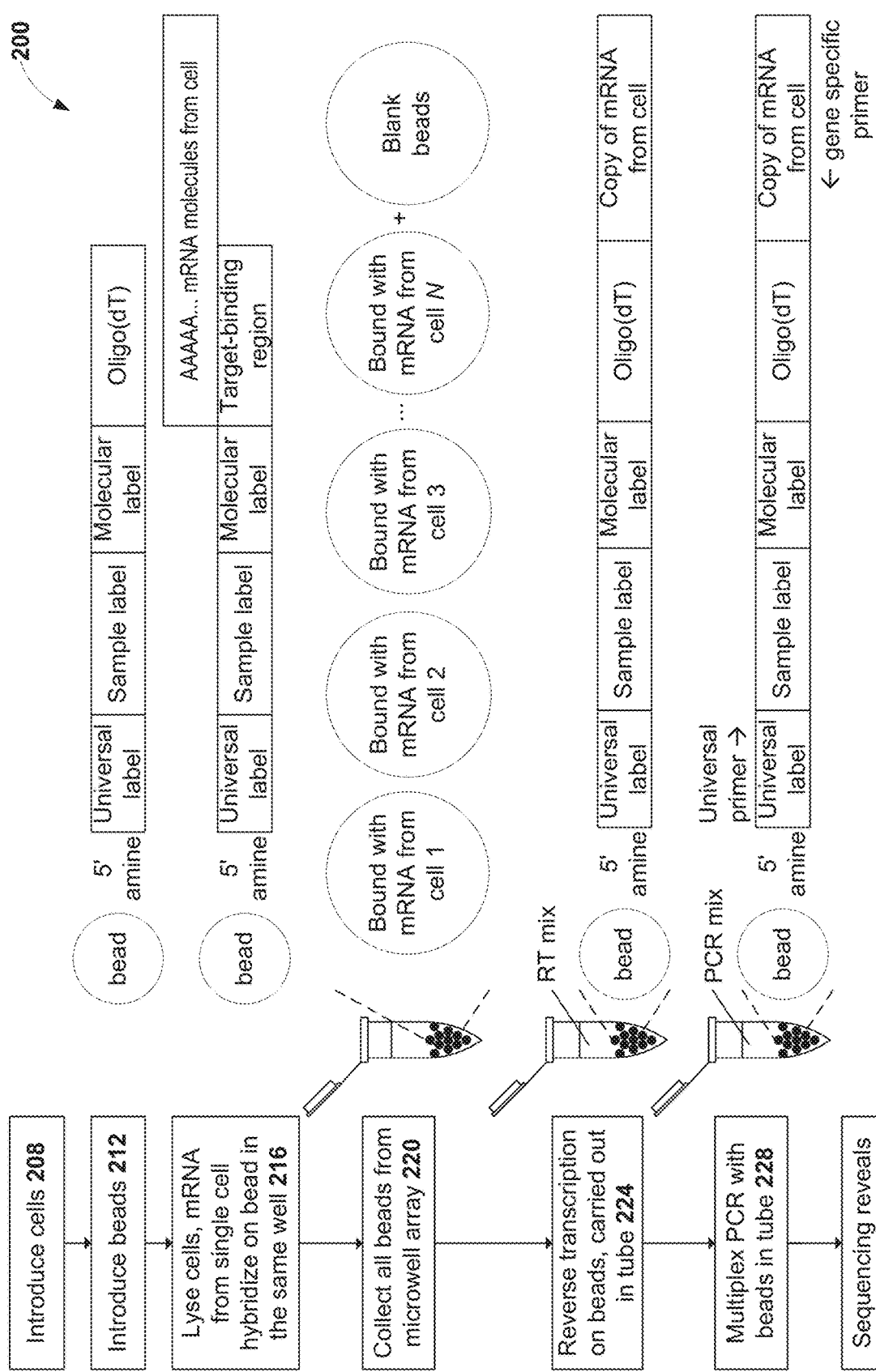
FIG. 2 shows a non-limiting exemplary workflow of stochastic barcoding and digital counting.

For example, in a non-limiting example of barcoding (e.g., stochastic barcoding) illustrated in FIG. 2, after introducing cells such as single cells onto a plurality of microwells of a microwell array at block 208, beads can be introduced onto the plurality of microwells of the microwell array at block 212. Each microwell can comprise one bead. The beads can comprise a plurality of barcodes. A barcode can comprise a 5' amine region attached to a bead. The barcode can comprise a universal label, a barcode sequence (e.g., a molecular label), a target-binding region, or any combination thereof.

The barcodes disclosed herein can be associated with (e.g., attached to) a solid support (e.g., a bead). The barcodes associated with a solid support can each comprise a barcode sequence selected from a group comprising at least 100 or 1000 barcode sequences with unique sequences. In some embodiments, different barcodes associated with a solid support can comprise barcode with different sequences. In some embodiments, a percentage of barcodes associated with a solid support comprises the same cell label. For example, the percentage can be, or be about 60%, 70%, 80%, 85%, 90%, 95%, 97%, 99%, 100%, or a number or a range between any two of these values. As another example, the percentage can be at least, or be at most 60%, 70%, 80%, 85%, 90%, 95%, 97%, 99%, or 100%. In some embodiments, barcodes associated with a solid support can have the same cell label. The barcodes associated with different solid supports can have different cell labels selected from a group comprising at least 100 or 1000 cell labels with unique sequences.

The barcodes disclosed herein can be associated to (e.g., attached to) a solid support (e.g., a bead). In some embodiments, barcoding the plurality of targets in the sample can be performed with a solid support including a plurality of synthetic particles associated with the plurality of barcodes. In some embodiments, the solid support can include a plurality of synthetic particles associated with the plurality of barcodes. The spatial labels of the plurality of barcodes on different solid supports can differ by at least one nucleotide. The solid support can, for example, include the plurality of barcodes in two dimensions or three dimensions. The synthetic particles can be beads. The beads can be silica gel beads, controlled pore glass beads, magnetic beads, Dynabeads, Sephadex/Sepharose beads, cellulose beads, polystyrene beads, or any combination thereof. The solid support can include a polymer, a matrix, a hydrogel, a needle array device, an antibody, or any combination thereof. In some embodiments, the solid supports can be free floating. In some embodiments, the solid supports can be embedded in a semi-solid or solid array. The barcodes may not be associated with solid supports. The barcodes can be individual nucleotides. The barcodes can be associated with a substrate.

As used herein, the terms "tethered," "attached," and "immobilized," are used interchangeably, and can refer to covalent or non-covalent means for attaching barcodes to a solid support. Any of a variety of different solid supports can be used as solid supports for attaching pre-synthesized barcodes or for in situ solid-phase synthesis of barcode.

In some embodiments, the solid support is a bead. The bead can comprise one or more types of solid, porous, or hollow sphere, ball, bearing, cylinder, or other similar configuration which a nucleic acid can be immobilized (e.g., covalently or non-covalently). The bead can be, for example, composed of plastic, ceramic, metal, polymeric material, or any combination thereof. A bead can be, or comprise, a discrete particle that is spherical (e.g., microspheres) or have a non-spherical or irregular shape, such as cubic, cuboid, pyramidal, cylindrical, conical, oblong, or disc-shaped, and the like. In some embodiments, a bead can be non-spherical in shape.

Beads can comprise a variety of materials including, but not limited to, paramagnetic materials (e.g., magnesium, molybdenum, lithium, and tantalum), superparamagnetic materials (e.g., ferrite ($Fe_3O_4$; magnetite) nanoparticles), ferromagnetic materials (e.g., iron, nickel, cobalt, some alloys thereof, and some rare earth metal compounds), ceramic, plastic, glass, polystyrene, silica, methylstyrene, acrylic polymers, titanium, latex, Sepharose, agarose, hydrogel, polymer, cellulose, nylon, or any combination thereof.

In some embodiments, the bead (e.g., the bead to which the labels are attached) is a hydrogel bead. In some embodiments, the bead comprises hydrogel.

Some embodiments disclosed herein include one or more particles (for example, beads). Each of the particles can comprise a plurality of oligonucleotides (e.g., barcodes). Each of the plurality of oligonucleotides can comprise a barcode sequence (e.g., a molecular label sequence), a cell label, and a target-binding region (e.g., an oligo(dT) sequence, a gene-specific sequence, a random multimer, or a combination thereof). The cell label sequence of each of the plurality of oligonucleotides can be the same. The cell label sequences of oligonucleotides on different particles can be different such that the oligonucleotides on different particles can be identified. The number of different cell label sequences can be different in different implementations. In some embodiments, the number of cell label sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, a number or a range between any two of these values, or more. In some embodiments, the number of cell label sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. In some embodiments, no more than 1, 2, 3, 4, 5, 6, 7, 8, 9, 10, 20, 30, 40, 50, 60, 70, 80, 90, 100, 200, 300, 400, 500, 600, 700, 800, 900, 1000, or more of the plurality of the particles include oligonucleotides with the same cell sequence. In some embodiment, the plurality of particles that include oligonucleotides with the same cell sequence can be at most 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, or more. In some embodiments, none of the plurality of the particles has the same cell label sequence.

The plurality of oligonucleotides on each particle can comprise different barcode sequences (e.g., molecular labels). In some embodiments, the number of barcode sequences can be, or be about 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, $10^9$, or a number or a range between any two of these values. In some embodiments, the number of barcode sequences can be at least, or be at most 10, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, $10^6$, $10^7$, $10^8$, or $10^9$. For example, at least 100 of the plurality of oligonucleotides comprise different barcode sequences. As another example, in a single particle, at least 100, 500, 1000, 5000, 10000, 15000, 20000, 50000, a number or a range between any two of these values, or more of the plurality of oligonucleotides comprise different barcode sequences. Some embodiments provide a plurality of the particles comprising barcodes. In some embodiments, the ratio of an occurrence (or a copy or a number) of a target to be labeled and the different barcode sequences can be at least 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, or more. In some embodiments, each of the plurality of oligonucleotides further comprises a sample label, a universal label, or both. The particle can be, for example, a nanoparticle or microparticle.

The size of the beads can vary. For example, the diameter of the bead can range from 0.1 micrometer to 50 micrometer. In some embodiments, the diameter of the bead can be, or be about, 0.1, 0.5, 1, 2, 3, 4, 5, 6, 7, 8, 9, 10, 20, 30, 40, 50 micrometer, or a number or a range between any two of these values.

The diameter of the bead can be related to the diameter of the wells of the substrate. In some embodiments, the diameter of the bead can be, or be about, 10%, 20%, 30%, 40%, 50%, 60%, 70%, 80%, 90%, 100%, or a number or a range between any two of these values, longer or shorter than the diameter of the well. The diameter of the beads can be related to the diameter of a cell (e.g., a single cell entrapped by a well of the substrate). In some embodiments, the diameter of the bead can be at least, or be at most, 10%, 20%, 30%, 40%, 50%, 60%, 70%, 80%, 90%, or 100% longer or shorter than the diameter of the well. The diameter of the beads can be related to the diameter of a cell (e.g., a single cell entrapped by a well of the substrate). In some embodiments, the diameter of the bead can be, or be about, 10%, 20%, 30%, 40%, 50%, 60%, 70%, 80%, 90%, 100%, 150%, 200%, 250%, 300%, or a number or a range between any two of these values, longer or shorter than the diameter of the cell. In some embodiments, the diameter of the beads can be at least, or be at most, 10%, 20%, 30%, 40%, 50%, 60%, 70%, 80%, 90%, 100%, 150%, 200%, 250%, or 300% longer or shorter than the diameter of the cell.

A bead can be attached to and/or embedded in a substrate. A bead can be attached to and/or embedded in a gel, hydrogel, polymer and/or matrix. The spatial position of a bead within a substrate (e.g., gel, matrix, scaffold, or polymer) can be identified using the spatial label present on the barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbeads), protein A conjugated beads, protein G conjugated beads, protein A/G conjugated beads, protein L conjugated beads, oligo(dT) conjugated beads, silica beads, silica-like beads, anti-biotin microbeads, anti-fluorochrome microbeads, and BcMag™ Carboxyl-Terminated Magnetic Beads.

A bead can be associated with (e.g., impregnated with) quantum dots or fluorescent dyes to make it fluorescent in one fluorescence optical channel or multiple optical channels. A bead can be associated with iron oxide or chromium oxide to make it paramagnetic or ferromagnetic. Beads can be identifiable. For example, a bead can be imaged using a camera. A bead can have a detectable code associated with the bead. For example, a bead can comprise a barcode. A bead can change size, for example, due to swelling in an organic or inorganic solution. A bead can be hydrophobic. A bead can be hydrophilic. A bead can be biocompatible.

A solid support (e.g., a bead) can be visualized. The solid support can comprise a visualizing tag (e.g., fluorescent dye). A solid support (e.g., a bead) can be etched with an identifier (e.g., a number). The identifier can be visualized through imaging the beads.

A solid support can comprise an insoluble, semi-soluble, or insoluble material. A solid support can be referred to as "functionalized" when it includes a linker, a scaffold, a building block, or other reactive moiety attached thereto, whereas a solid support may be "nonfunctionalized" when it lacks such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. A solid support can take the form of resins, gels, microspheres, or other geometric configurations. A solid support can comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can comprise a polymer matrix (e.g., gel, hydrogel). The polymer matrix may be able to permeate intracellular space (e.g., around organelles). The polymer matrix may able to be pumped throughout the circulatory system.

Substrates and Microwell Array

As used herein, a substrate can refer to a type of solid support. A substrate can refer to a solid support that can comprise barcodes or stochastic barcodes of the disclosure. A substrate can, for example, comprise a plurality of microwells. For example, a substrate can be a well array comprising two or more microwells. In some embodiments, a microwell can comprise a small reaction chamber of defined volume. In some embodiments, a microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., a bead). A microwell can comprise barcode reagents of the disclosure.

Methods of Barcoding

The disclosure provides for methods for estimating the number of distinct targets at distinct locations in a physical sample (e.g., tissue, organ, tumor, cell). The methods can comprise placing barcodes (e.g., stochastic barcodes) in close proximity with the sample, lysing the sample, associating distinct targets with the barcodes, amplifying the targets and/or digitally counting the targets. The method can further comprise analyzing and/or visualizing the information obtained from the spatial labels on the barcodes. In some embodiments, a method comprises visualizing the plurality of targets in the sample. Mapping the plurality of targets onto the map of the sample can include generating a two dimensional map or a three dimensional map of the sample. The two dimensional map and the three dimensional map can be generated prior to or after barcoding (e.g., stochastically barcoding) the plurality of targets in the sample. Visualizing the plurality of targets in the sample can include mapping the plurality of targets onto a map of the sample. Mapping the plurality of targets onto the map of the sample can include generating a two dimensional map or a three dimensional map of the sample. The two dimensional map and the three dimensional map can be generated prior to or after barcoding the plurality of targets in the sample. in some embodiments, the two dimensional map and the three dimensional map can be generated before or after lysing the sample. Lysing the sample before or after generating the two dimensional map or the three dimensional map can include heating the sample, contacting the sample with a detergent, changing the pH of the sample, or any combination thereof.

In some embodiments, barcoding the plurality of targets comprises hybridizing a plurality of barcodes with a plurality of targets to create barcoded targets (e.g., stochastically barcoded targets). Barcoding the plurality of targets can comprise generating an indexed library of the barcoded targets. Generating an indexed library of the barcoded targets can be performed with a solid support comprising the plurality of barcodes (e.g., stochastic barcodes).

Contacting a Sample and a Barcode

The disclosure provides for methods for contacting a sample (e.g., cells) to a substrate of the disclosure. A sample comprising, for example, a cell, organ, or tissue thin section, can be contacted to barcodes (e.g., stochastic barcodes). The cells can be contacted, for example, by gravity flow wherein the cells can settle and create a monolayer. The sample can be a tissue thin section. The thin section can be placed on the substrate. The sample can be one-dimensional (e.g., forms a planar surface). The sample (e.g., cells) can be spread across the substrate, for example, by growing/culturing the cells on the substrate.

When barcodes are in close proximity to targets, the targets can hybridize to the barcode. The barcodes can be contacted at a non-depletable ratio such that each distinct target can associate with a distinct barcode of the disclosure. To ensure efficient association between the target and the barcode, the targets can be cross-linked to barcode.

Cell Lysis

Following the distribution of cells and barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof. To increase the association of a target and a barcode, the rate of the diffusion of the target molecules can be altered by for example, reducing the temperature and/or increasing the viscosity of the lysate.

In some embodiments, the sample can be lysed using a filter paper. The filter paper can be soaked with a lysis buffer on top of the filter paper. The filter paper can be applied to the sample with pressure which can facilitate lysis of the sample and hybridization of the targets of the sample to the substrate.

In some embodiments, lysis can be performed by mechanical lysis, heat lysis, optical lysis, and/or chemical lysis. Chemical lysis can include the use of digestive enzymes such as proteinase K, pepsin, and trypsin. Lysis can be performed by the addition of a lysis buffer to the substrate. A lysis buffer can comprise Tris HCl. A lysis buffer can comprise at least about 0.01, 0.05, 0.1, 0.5, or 1 M or more Tris HCl. A lysis buffer can comprise at most about 0.01, 0.05, 0.1, 0.5, or 1 M or more Tris HCL. A lysis buffer can comprise about 0.1 M Tris HCl. The pH of the lysis buffer can be at least about 1, 2, 3, 4, 5, 6, 7, 8, 9, 10, or more. The pH of the lysis buffer can be at most about 1, 2, 3, 4, 5, 6, 7, 8, 9, 10, or more. In some embodiments, the pH of the lysis buffer is about 7.5. The lysis buffer can comprise a salt (e.g., LiCl). The concentration of salt in the lysis buffer can be at least about 0.1, 0.5, or 1 M or more. The concentration of salt in the lysis buffer can be at most about 0.1, 0.5, or 1 M or more. In some embodiments, the concentration of salt in the lysis buffer is about 0.5M. The lysis buffer can comprise a detergent (e.g., SDS, Li dodecyl sulfate, triton X, tween, NP-40). The concentration of the detergent in the lysis buffer can be at least about 0.0001%, 0.0005%, 0.001%, 0.005%, 0.01%, 0.05%, 0.1%, 0.5%, 1%, 2%, 3%, 4%, 5%, 6%, or 7%, or more. The concentration of the detergent in the lysis buffer can be at most about 0.0001%, 0.0005%, 0.001%, 0.005%, 0.01%, 0.05%, 0.1%, 0.5%, 1%, 2%, 3%, 4%, 5%, 6%, or 7%, or more. In some embodiments, the concentration of the detergent in the lysis buffer is about 1% Li dodecyl sulfate. The time used in the method for lysis can be dependent on the amount of detergent used. In some embodiments, the more detergent used, the less time needed for lysis. The lysis buffer can comprise a chelating agent (e.g., EDTA, EGTA). The concentration of a chelating agent in the lysis buffer can be at least about 1, 5, 10, 15, 20, 25, or 30 mM or more. The concentration of a chelating agent in the lysis buffer can be at most about 1, 5, 10, 15, 20, 25, or 30 mM or more. In some embodiments, the concentration of chelating agent in the lysis buffer is about 10 mM. The lysis buffer can comprise a reducing reagent (e.g., beta-mercaptoethanol, DTT). The concentration of the reducing reagent in the lysis buffer can be at least about 1, 5, 10, 15, or 20 mM or more. The concentration of the reducing reagent in the lysis buffer can be at most about 1, 5, 10, 15, or 20 mM or more. In some embodiments, the concentration of reducing reagent in the lysis buffer is about 5 mM. In some embodiments, a lysis buffer can comprise about 0.1M TrisHCl, about pH 7.5, about 0.5M LiCl, about 1% lithium dodecyl sulfate, about 10 mM EDTA, and about 5 mM DTT.

Lysis can be performed at a temperature of about 4, 10, 15, 20, 25, or 30° C. Lysis can be performed for about 1, 5, 10, 15, or 20 or more minutes. A lysed cell can comprise at least about 100000, 200000, 300000, 400000, 500000, 600000, or 700000 or more target nucleic acid molecules. A lysed cell can comprise at most about 100000, 200000, 300000, 400000, 500000, 600000, or 700000 or more target nucleic acid molecules.

Attachment of Barcodes to Target Nucleic Acid Molecules

Following lysis of the cells and release of nucleic acid molecules therefrom, the nucleic acid molecules can randomly associate with the barcodes of the co-localized solid support. Association can comprise hybridization of a barcode's target recognition region to a complementary portion of the target nucleic acid molecule (e.g., oligo(dT) of the barcode can interact with a poly(A) tail of a target). The assay conditions used for hybridization (e.g., buffer pH, ionic strength, temperature, etc.) can be chosen to promote formation of specific, stable hybrids. In some embodiments, the nucleic acid molecules released from the lysed cells can associate with the plurality of probes on the substrate (e.g., hybridize with the probes on the substrate). When the probes comprise oligo(dT), mRNA molecules can hybridize to the probes and be reverse transcribed. The oligo(dT) portion of the oligonucleotide can act as a primer for first strand synthesis of the cDNA molecule. For example, in a non-limiting example of barcoding illustrated in FIG. 2, at block 216, mRNA molecules can hybridize to barcodes on beads. For example, single-stranded nucleotide fragments can hybridize to the target-binding regions of barcodes.

Attachment can further comprise ligation of a barcode's target recognition region and a portion of the target nucleic acid molecule. For example, the target binding region can comprise a nucleic acid sequence that can be capable of specific hybridization to a restriction site overhang (e.g., an EcoRI sticky-end overhang). The assay procedure can further comprise treating the target nucleic acids with a restriction enzyme (e.g., EcoRI) to create a restriction site overhang. The barcode can then be ligated to any nucleic acid molecule comprising a sequence complementary to the restriction site overhang. A ligase (e.g., T4 DNA ligase) can be used to join the two fragments.

For example, in a non-limiting example of barcoding illustrated in FIG. 2, at block 220, the labeled targets from a plurality of cells (or a plurality of samples) (e.g., target-barcode molecules) can be subsequently pooled, for example, into a tube. The labeled targets can be pooled by, for example, retrieving the barcodes and/or the beads to which the target-barcode molecules are attached.

The retrieval of solid support-based collections of attached target-barcode molecules can be implemented by use of magnetic beads and an externally-applied magnetic field. Once the target-barcode molecules have been pooled, all further processing can proceed in a single reaction vessel. Further processing can include, for example, reverse transcription reactions, amplification reactions, cleavage reactions, dissociation reactions, and/or nucleic acid extension reactions. Further processing reactions can be performed within the microwells, that is, without first pooling the labeled target nucleic acid molecules from a plurality of cells.

Reverse Transcription

The disclosure provides for a method to create a target-barcode conjugate using reverse transcription (e.g., at block 224 of FIG. 2). The target-barcode conjugate can comprise the barcode and a complementary sequence of all or a portion of the target nucleic acid (i.e., a barcoded cDNA molecule, such as a stochastically barcoded cDNA molecule). Reverse transcription of the associated RNA molecule can occur by the addition of a reverse transcription primer along with the reverse transcriptase. The reverse transcription primer can be an oligo(dT) primer, a random hexanucleotide primer, or a target-specific oligonucleotide primer. Oligo(dT) primers can be, or can be about, 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

In some embodiments, reverse transcription of the labeled-RNA molecule can occur by the addition of a reverse transcription primer. In some embodiments, the reverse transcription primer is an oligo(dT) primer, random hexanucleotide primer, or a target-specific oligonucleotide primer. Generally, oligo(dT) primers are 12-18 nucleotides in length and bind to the endogenous poly(A) tail at the 3' end of mammalian mRNA. Random hexanucleotide primers can bind to mRNA at a variety of complementary sites. Target-specific oligonucleotide primers typically selectively prime the mRNA of interest.

Reverse transcription can occur repeatedly to produce multiple labeled-cDNA molecules. The methods disclosed herein can comprise conducting at least about 1, 2, 3, 4, 5, 6, 7, 8, 9, 10, 11, 12, 13, 14, 15, 16, 17, 18, 19, or 20 reverse transcription reactions. The method can comprise conducting at least about 25, 30, 35, 40, 45, 50, 55, 60, 65, 70, 75, 80, 85, 90, 95, or 100 reverse transcription reactions.

Amplification

One or more nucleic acid amplification reactions (e.g., at block 228 of FIG. 2) can be performed to create multiple copies of the labeled target nucleic acid molecules. Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular label and/or barcode sequence (e.g., a molecular label). The amplification reactions can comprise amplifying at least a portion of a sample tag, a cell label, a spatial label, a barcode sequence (e.g., a molecular label), a target nucleic acid, or a combination thereof. The amplification reactions can comprise amplifying 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, 100%, or a range or a number between any two of these values, of the plurality of nucleic acids. The method can further comprise conducting one or more cDNA synthesis reactions to produce one or more cDNA copies of target-barcode molecules comprising a sample label, a cell label, a spatial label, and/or a barcode sequence (e.g., a molecular label).

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a Qβ replicase (Qβ) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification does not produce circularized transcripts.

In some embodiments, the methods disclosed herein further comprise conducting a polymerase chain reaction on the labeled nucleic acid (e.g., labeled-RNA, labeled-DNA, labeled-cDNA) to produce a labeled amplicon (e.g., a stochastically labeled amplicon). The labeled amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cell label, and/or a barcode sequence (e.g., a molecular label). The labeled amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholine and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise, for example, 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of labeled targets (e.g., stochastically labeled targets). The one or more primers can anneal to the 3' end or 5' end of the plurality of labeled targets. The one or more primers can anneal to an internal region of the plurality of labeled targets. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise a universal primer. The universal primer can anneal to a universal primer binding site. The one or more custom primers can anneal to a first sample label, a second sample label, a spatial label, a cell label, a barcode sequence (e.g., a molecular label), a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total labeled targets in one or more samples.

The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules attached to the bead using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and barcode sequence (e.g., molecular label) on read 1, the gene on read 2, and the sample index on index 1 read.

In some embodiments, nucleic acids can be removed from the substrate using chemical cleavage. For example, a chemical group or a modified base present in a nucleic acid can be used to facilitate its removal from a solid support. For example, an enzyme can be used to remove a nucleic acid from a substrate. For example, a nucleic acid can be removed from a substrate through a restriction endonuclease digestion. For example, treatment of a nucleic acid containing a dUTP or ddUTP with uracil-d-glycosylase (UDG) can be used to remove a nucleic acid from a substrate. For example, a nucleic acid can be removed from a substrate using an enzyme that performs nucleotide excision, such as a base excision repair enzyme, such as an apurinic/apyrimidinic (AP) endonuclease. In some embodiments, a nucleic acid can be removed from a substrate using a photocleavable group and light. In some embodiments, a cleavable linker can be used to remove a nucleic acid from the substrate. For example, the cleavable linker can comprise at least one of biotin/avidin, biotin/streptavidin, biotin/neutravidin, Ig-protein A, a photo-labile linker, acid or base labile linker group, or an aptamer.

When the probes are gene-specific, the molecules can hybridize to the probes and be reverse transcribed and/or amplified. In some embodiments, after the nucleic acid has been synthesized (e.g., reverse transcribed), it can be amplified. Amplification can be performed in a multiplex manner, wherein multiple target nucleic acid sequences are amplified simultaneously. Amplification can add sequencing adaptors to the nucleic acid.

In some embodiments, amplification can be performed on the substrate, for example, with bridge amplification. cDNAs can be homopolymer tailed in order to generate a compatible end for bridge amplification using oligo(dT) probes on the substrate. In bridge amplification, the primer that is complementary to the 3' end of the template nucleic acid can be the first primer of each pair that is covalently attached to the solid particle. When a sample containing the template nucleic acid is contacted with the particle and a single thermal cycle is performed, the template molecule can be annealed to the first primer and the first primer is elongated in the forward direction by addition of nucleotides to form a duplex molecule consisting of the template molecule and a newly formed DNA strand that is complementary to the template. In the heating step of the next cycle, the duplex molecule can be denatured, releasing the template molecule from the particle and leaving the complementary DNA strand attached to the particle through the first primer. In the annealing stage of the annealing and elongation step that follows, the complementary strand can hybridize to the second primer, which is complementary to a segment of the complementary strand at a location removed from the first primer. This hybridization can cause the complementary strand to form a bridge between the first and second primers secured to the first primer by a covalent bond and to the second primer by hybridization. In the elongation stage, the second primer can be elongated in the reverse direction by the addition of nucleotides in the same reaction mixture, thereby converting the bridge to a double-stranded bridge. The next cycle then begins, and the double-stranded bridge can be denatured to yield two single-stranded nucleic acid molecules, each having one end attached to the particle surface via the first and second primers, respectively, with the other end of each unattached. In the annealing and elongation step of this second cycle, each strand can hybridize to a further complementary primer, previously unused, on the same particle, to form new single-strand bridges. The two previously unused primers that are now hybridized elongate to convert the two new bridges to double-strand bridges.

The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids.

Amplification of the labeled nucleic acids can comprise PCR-based methods or non-PCR based methods. Amplification of the labeled nucleic acids can comprise exponential amplification of the labeled nucleic acids. Amplification of the labeled nucleic acids can comprise linear amplification of the labeled nucleic acids. Amplification can be performed by polymerase chain reaction (PCR). PCR can refer to a reaction for the in vitro amplification of specific DNA sequences by the simultaneous primer extension of complementary strands of DNA. PCR can encompass derivative forms of the reaction, including but not limited to, RT-PCR, real-time PCR, nested PCR, quantitative PCR, multiplexed PCR, digital PCR, suppression PCR, semi-suppressive PCR and assembly PCR.

In some embodiments, amplification of the labeled nucleic acids comprises non-PCR based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), a Qβ replicase (Qβ), use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and/or ramification extension amplification (RAM).

In some embodiments, the methods disclosed herein further comprise conducting a nested polymerase chain reaction on the amplified amplicon (e.g., target). The amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample tag or molecular identifier label. Alternatively, the amplicon can be a single-stranded molecule. The single-stranded molecule can comprise DNA, RNA, or a combination thereof. The nucleic acids of the present invention can comprise synthetic or altered nucleic acids.

In some embodiments, the method comprises repeatedly amplifying the labeled nucleic acid to produce multiple amplicons. The methods disclosed herein can comprise conducting at least about 1, 2, 3, 4, 5, 6, 7, 8, 9, 10, 11, 12, 13, 14, 15, 16, 17, 18, 19, or 20 amplification reactions. Alternatively, the method comprises conducting at least about 25, 30, 35, 40, 45, 50, 55, 60, 65, 70, 75, 80, 85, 90, 95, or 100 amplification reactions.

Amplification can further comprise adding one or more control nucleic acids to one or more samples comprising a plurality of nucleic acids. Amplification can further comprise adding one or more control nucleic acids to a plurality of nucleic acids. The control nucleic acids can comprise a control label.

Amplification can comprise use of one or more non-natural nucleotides. Non-natural nucleotides can comprise photolabile and/or triggerable nucleotides. Examples of non-natural nucleotides include, but are not limited to, peptide nucleic acid (PNA), morpholine and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise one or more oligonucleotides. The one or more oligonucleotides can comprise at least about 7-9 nucleotides. The one or more oligonucleotides can comprise less than 12-15 nucleotides. The one or more primers can anneal to at least a portion of the plurality of labeled nucleic acids. The one or more primers can anneal to the 3' end and/or 5' end of the plurality of labeled nucleic acids. The one or more primers can anneal to an internal region of the plurality of labeled nucleic acids. The internal region can be at least about 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of labeled nucleic acids. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. The one or more custom primers can anneal to the first sample tag, the second sample tag, the molecular identifier label, the nucleic acid or a product thereof. The one or more primers can comprise a universal primer and a custom primer. The custom primer can be designed to amplify one or more target nucleic acids. The target nucleic acids can comprise a subset of the total nucleic acids in one or more samples. In some embodiments, the primers are the probes attached to the array of the disclosure.

In some embodiments, barcoding (e.g., stochastically barcoding) the plurality of targets in the sample further comprises generating an indexed library of the barcoded targets (e.g., stochastically barcoded targets) or barcoded fragments of the targets. The barcode sequences of different barcodes (e.g., the molecular labels of different stochastic barcodes) can be different from one another. Generating an indexed library of the barcoded targets includes generating a plurality of indexed polynucleotides from the plurality of targets in the sample. For example, for an indexed library of the barcoded targets comprising a first indexed target and a second indexed target, the label region of the first indexed polynucleotide can differ from the label region of the second indexed polynucleotide by, by about, by at least, or by at most, 1, 2, 3, 4, 5, 6, 7, 8, 9, 10, 20, 30, 40, 50, or a number or a range between any two of these values, nucleotides. In some embodiments, generating an indexed library of the barcoded targets includes contacting a plurality of targets, for example mRNA molecules, with a plurality of oligonucleotides including a poly(T) region and a label region; and conducting a first strand synthesis using a reverse transcriptase to produce single-strand labeled cDNA molecules each comprising a cDNA region and a label region, wherein the plurality of targets includes at least two mRNA molecules of different sequences and the plurality of oligonucleotides includes at least two oligonucleotides of different sequences. Generating an indexed library of the barcoded targets can further comprise amplifying the single-strand labeled cDNA molecules to produce double-strand labeled cDNA molecules; and conducting nested PCR on the double-strand labeled cDNA molecules to produce labeled amplicons. In some embodiments, the method can include generating an adaptor-labeled amplicon.

Barcoding (e.g., stochastic barcoding) can include using nucleic acid barcodes or tags to label individual nucleic acid (e.g., DNA or RNA) molecules. In some embodiments, it involves adding DNA barcodes or tags to cDNA molecules as they are generated from mRNA. Nested PCR can be performed to minimize PCR amplification bias. Adaptors can be added for sequencing using, for example, next generation sequencing (NGS). The sequencing results can be used to determine cell labels, molecular labels, and sequences of nucleotide fragments of the one or more copies of the targets, for example at block 232 of FIG. 2.

Figure 3:
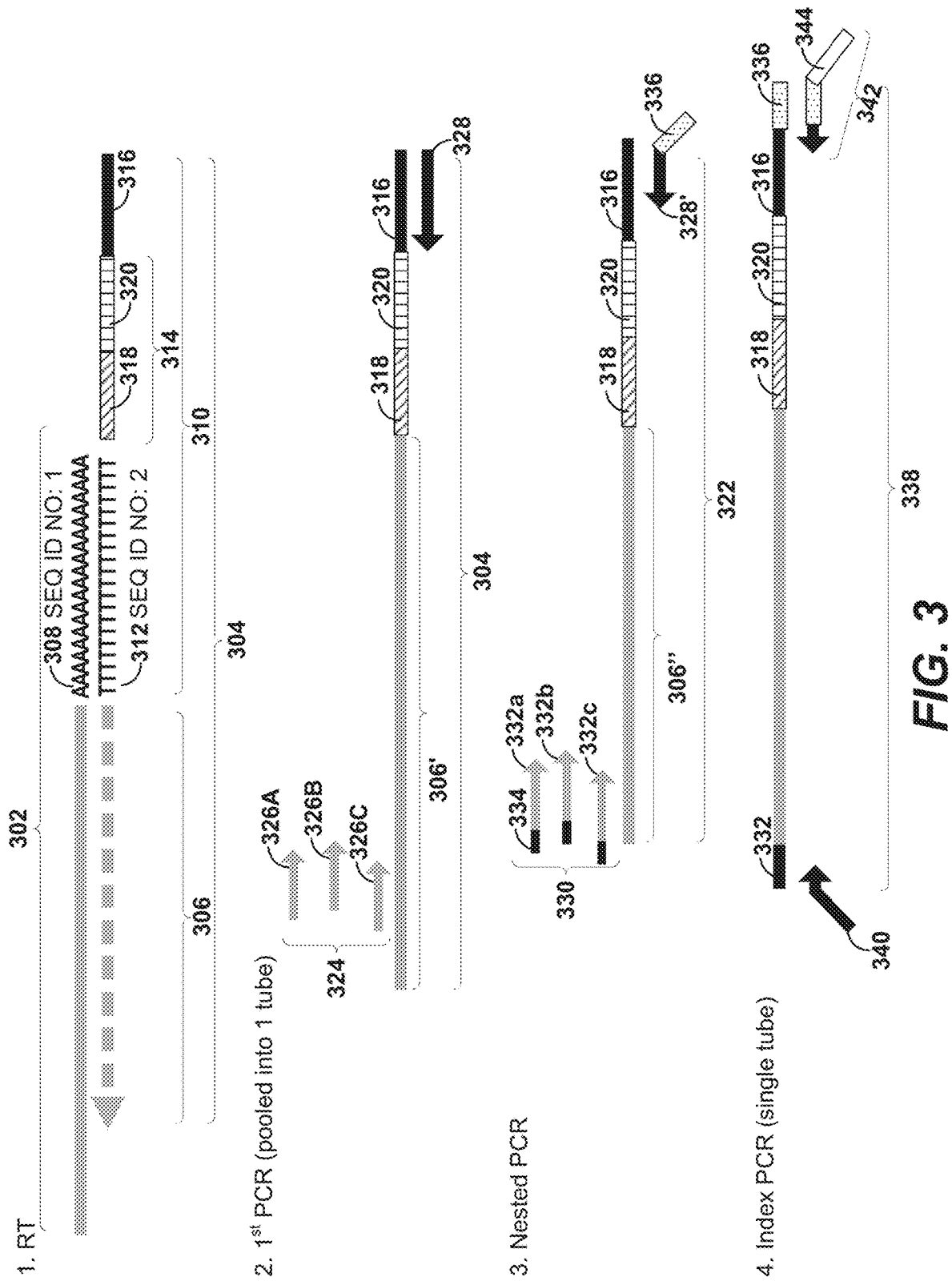
FIG. 3 is a schematic illustration showing a non-limiting exemplary process for generating an indexed library of the stochastically barcoded targets from a plurality of targets.

FIG. 3 is a schematic illustration showing a non-limiting exemplary process of generating an indexed library of the barcoded targets (e.g., stochastically barcoded targets), such as barcoded mRNAs or fragments thereof. As shown in step 1, the reverse transcription process can encode each mRNA molecule with a unique molecular label, a cell label, and a universal PCR site. In particular, RNA molecules 302 can be reverse transcribed to produce labeled cDNA molecules 304, including a cDNA region 306, by hybridization (e.g., stochastic hybridization) of a set of barcodes (e.g., stochastic barcodes) 310 to the poly(A) tail region 308 of the RNA molecules 302. Each of the barcodes 310 can comprise a target-binding region, for example a poly(dT) region 312, a label region 314 (e.g., a barcode sequence or a molecule), and a universal PCR region 316.

In some embodiments, the cell label can include 3 to 20 nucleotides. In some embodiments, the molecular label can include 3 to 20 nucleotides. In some embodiments, each of the plurality of stochastic barcodes further comprises one or more of a universal label and a cell label, wherein universal labels are the same for the plurality of stochastic barcodes on the solid support and cell labels are the same for the plurality of stochastic barcodes on the solid support. In some embodiments, the universal label can include 3 to 20 nucleotides. In some embodiments, the cell label comprises 3 to 20 nucleotides.

In some embodiments, the label region 314 can include a barcode sequence or a molecular label 318 and a cell label 320. In some embodiments, the label region 314 can include one or more of a universal label, a dimension label, and a cell label. The barcode sequence or molecular label 318 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The cell label 320 can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. The universal label can be, can be about, can be at least, or can be at most, 1, 2, 3, 4, 5, 6, 7, 8, 9, 10, 20, 30, 40, 50, 60, 70, 80, 90, 100, or a number or a range between any of these values, of nucleotides in length. Universal labels can be the same for the plurality of stochastic barcodes on the solid support and cell labels are the same for the plurality of stochastic barcodes on the solid support. The dimension label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length.

In some embodiments, the label region 314 can comprise, comprise about, comprise at least, or comprise at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different labels, such as a barcode sequence or a molecular label 318 and a cell label 320. Each label can be, can be about, can be at least, or can be at most 1, 2, 3, 4, 5, 6, 7, 8, 9, 10, 20, 30, 40, 50, 60, 70, 80, 90, 100, or a number or a range between any of these values, of nucleotides in length. A set of barcodes or stochastic barcodes 310 can contain, contain about, contain at least, or can be at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, barcodes or stochastic barcodes 310. And the set of barcodes or stochastic barcodes 310 can, for example, each contain a unique label region 314. The labeled cDNA molecules 304 can be purified to remove excess barcodes or stochastic barcodes 310. Purification can comprise Ampure bead purification.

As shown in step 2, products from the reverse transcription process in step 1 can be pooled into 1 tube and PCR amplified with a $1^{st}$ PCR primer pool and a $1^{st}$ universal PCR primer. Pooling is possible because of the unique label region 314. In particular, the labeled cDNA molecules 304 can be amplified to produce nested PCR labeled amplicons 322. Amplification can comprise multiplex PCR amplification. Amplification can comprise a multiplex PCR amplification with 96 multiplex primers in a single reaction volume. In some embodiments, multiplex PCR amplification can utilize, utilize about, utilize at least, or utilize at most, 10, 20, 40, 50, 70, 80, 90, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{20}$, or a number or a range between any of these values, multiplex primers in a single reaction volume. Amplification can comprise using a $1^{st}$ PCR primer pool 324 comprising custom primers 326A-C targeting specific genes and a universal primer 328. The custom primers 326 can hybridize to a region within the cDNA portion 306' of the labeled cDNA molecule 304. The universal primer 328 can hybridize to the universal PCR region 316 of the labeled cDNA molecule 304.

As shown in step 3 of FIG. 3, products from PCR amplification in step 2 can be amplified with a nested PCR primers pool and a $2^{nd}$ universal PCR primer. Nested PCR can minimize PCR amplification bias. In particular, the nested PCR labeled amplicons 322 can be further amplified by nested PCR. The nested PCR can comprise multiplex PCR with nested PCR primers pool 330 of nested PCR primers 332a-c and a $2^{nd}$ universal PCR primer 328' in a single reaction volume. The nested PCR primer pool 328 can contain, contain about, contain at least, or contain at most, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any of these values, different nested PCR primers 330. The nested PCR primers 332 can contain an adaptor 334 and hybridize to a region within the cDNA portion 306" of the labeled amplicon 322. The universal primer 328' can contain an adaptor 336 and hybridize to the universal PCR region 316 of the labeled amplicon 322. Thus, step 3 produces adaptor-labeled amplicon 338. In some embodiments, nested PCR primers 332 and the $2^{nd}$ universal PCR primer 328' may not contain the adaptors 334 and 336. The adaptors 334 and 336 can instead be ligated to the products of nested PCR to produce adaptor-labeled amplicon 338.

As shown in step 4, PCR products from step 3 can be PCR amplified for sequencing using library amplification primers. In particular, the adaptors 334 and 336 can be used to conduct one or more additional assays on the adaptor-labeled amplicon 338. The adaptors 334 and 336 can be hybridized to primers 340 and 342. The one or more primers 340 and 342 can be PCR amplification primers. The one or more primers 340 and 342 can be sequencing primers. The one or more adaptors 334 and 336 can be used for further amplification of the adaptor-labeled amplicons 338. The one or more adaptors 334 and 336 can be used for sequencing the adaptor-labeled amplicon 338. The primer 342 can contain a plate index 344 so that amplicons generated using the same set of barcodes or stochastic barcodes 310 can be sequenced in one sequencing reaction using next generation sequencing (NGS).

Compositions Comprising Cellular Component Binding Reagents Associated with Oligonucleotides Some embodiments disclosed herein provide a plurality of compositions each comprising a cellular component binding reagent (such as a protein binding reagent) that is conjugated with an oligonucleotide, wherein the oligonucleotide comprises a unique identifier for the cellular component binding reagent that it is conjugated with. In some embodiments, the cellular component binding reagent is capable of specifically binding to a cellular component target. For example, a binding target of the cellular component binding reagent can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component binding reagent (e.g., a protein binding reagent) is capable of specifically binding to an antigen target or a protein target. In some embodiments, each of the oligonucleotides can comprise a barcode, such as a stochastic barcode. A barcode can comprise a barcode sequence (e.g., a molecular label), a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., unanchored to a solid support or anchored to a solid support. The poly(A) tail can be from about 10 to 50 nucleotides in length. In some embodiments, the poly(A) tail can be 18 nucleotides in length. The oligonucleotides can comprise deoxyribonucleotides, ribonucleotides, or both.

The unique identifiers can be, for example, a nucleotide sequence having any suitable length, for example, from about 4 nucleotides to about 200 nucleotides. In some embodiments, the unique identifier is a nucleotide sequence of 25 nucleotides to about 45 nucleotides in length. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise, or comprise about, 20, 30, 40, 50, 60, 70, 80, 90, 100, 200, 300, 400, 500, 600, 700, 800, 900, 1000, 2000, 5000, or a number or a range between any two of these values, different unique identifiers. The diverse set of unique identifiers can comprise at least, or comprise at most, 20, 30, 40, 50, 60, 70, 80, 90, 100, 200, 300, 400, 500, 600, 700, 800, 900, 1000, 2000, or 5000, different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by, or by about, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a number or a range between any two of these values. In some embodiments, the sequences of the set of unique identifiers are different from each other, or the complement thereof, by at least, or by at most, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides. In some embodiments, the sequences of the set of unique identifiers are different from each other, or the complement thereof, by at least 3%, at least 5%, at least 8%, at least 10%, at least 15%, at least 20%, or more.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable cellular component binding reagents are contemplated in this disclosure, such as protein binding reagents, antibodies or fragments thereof, aptamers, small molecules, ligands, peptides, oligonucleotides, etc., or any combination thereof. In some embodiments, the cellular component binding reagents can be polyclonal antibodies, monoclonal antibodies, recombinant antibodies, single chain antibody (sc-Ab), or fragments thereof, such as Fab, Fv, etc. In some embodiments, the plurality of cellular component binding reagents can comprise, or comprise about, 20, 30, 40, 50, 60, 70, 80, 90, 100, 200, 300, 400, 500, 600, 700, 800, 900, 1000, 2000, 5000, or a number or a range between any two of these values, different cellular component reagents. In some embodiments, the plurality of cellular component binding reagents can comprise at least, or comprise at most, 20, 30, 40, 50, 60, 70, 80, 90, 100, 200, 300, 400, 500, 600, 700, 800, 900, 1000, 2000, or 5000, different cellular component reagents.

The oligonucleotide can be conjugated with the cellular component binding reagent through various mechanism. In some embodiments, the oligonucleotide can be conjugated with the cellular component binding reagent covalently. In some embodiment, the oligonucleotide can be conjugated with the cellular component binding reagent non-covalently. In some embodiments, the oligonucleotide is conjugated with the cellular component binding reagent through a linker. The linker can be, for example, cleavable or detachable from the cellular component binding reagent and/or the oligonucleotide. In some embodiments, the linker can comprise a chemical group that reversibly attaches the oligonucleotide to the cellular component binding reagents. The chemical group can be conjugated to the linker, for example, through an amine group. In some embodiments, the linker can comprise a chemical group that forms a stable bond with another chemical group conjugated to the cellular component binding reagent. For example, the chemical group can be a UV photocleavable group, a disulfide bond, a streptavidin, a biotin, an amine, etc. In some embodiments, the chemical group can be conjugated to the cellular component binding reagent through a primary amine on an amino acid, such as lysine, or the N-terminus. Commercially available conjugation kits, such as the Protein-Oligo Conjugation Kit (Solulink, Inc., San Diego, California), the Thunder-Link® oligo conjugation system (Innova Biosciences, Cambridge, United Kingdom), etc., can be used to conjugate the oligonucleotide to the cellular component binding reagent.

The oligonucleotide can be conjugated to any suitable site of the cellular component binding reagent (e.g., a protein binding reagent), as long as it does not interfere with the specific binding between the cellular component binding reagent and its cellular component target. In some embodiments, the cellular component binding reagent is a protein, such as an antibody. In some embodiments, the cellular component binding reagent is not an antibody. In some embodiments, the oligonucleotide can be conjugated to the antibody anywhere other than the antigen-binding site, for example, the Fc region, the $C_H1$ domain, the $C_H2$ domain, the $C_H3$ domain, the $C_L$ domain, etc. Methods of conjugating oligonucleotides to cellular component binding reagents (e.g., antibodies) have been previously disclosed, for example, in U.S. Pat. No. 6,531,283, the content of which is hereby expressly incorporated by reference in its entirety. Stoichiometry of oligonucleotide to cellular component binding reagent can be varied. To increase the sensitivity of detecting the cellular component binding reagent specific oligonucleotide in sequencing, it may be advantageous to increase the ratio of oligonucleotide to cellular component binding reagent during conjugation. In some embodiments, each cellular component binding reagent can be conjugated with a single oligonucleotide molecule. In some embodiments, each cellular component binding reagent can be conjugated with more than one oligonucleotide molecule, for example, at least, or at most, 2, 3, 4, 5, 10, 20, 30, 40, 50, 100, 1000, or a number or a range between any two of these values, oligonucleotide molecules wherein each of the oligonucleotide molecule comprises the same, or different, unique identifiers. In some embodiments, each cellular component binding reagent can be conjugated with more than one oligonucleotide molecule, for example, at least, or at most, 2, 3, 4, 5, 10, 20, 30, 40, 50, 100, 1000, oligonucleotide molecules, wherein each of the oligonucleotide molecule comprises the same, or different, unique identifiers.

In some embodiments, the plurality of cellular component binding reagents are capable of specifically binding to a plurality of cellular component targets in a sample, such as a single cell, a plurality of cells, a tissue sample, a tumor sample, a blood sample, or the like. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components (e.g., proteins) in a cell or an organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components (e.g., proteins) in a cell or an organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, 10000, different cellular component targets.

Figure 4:
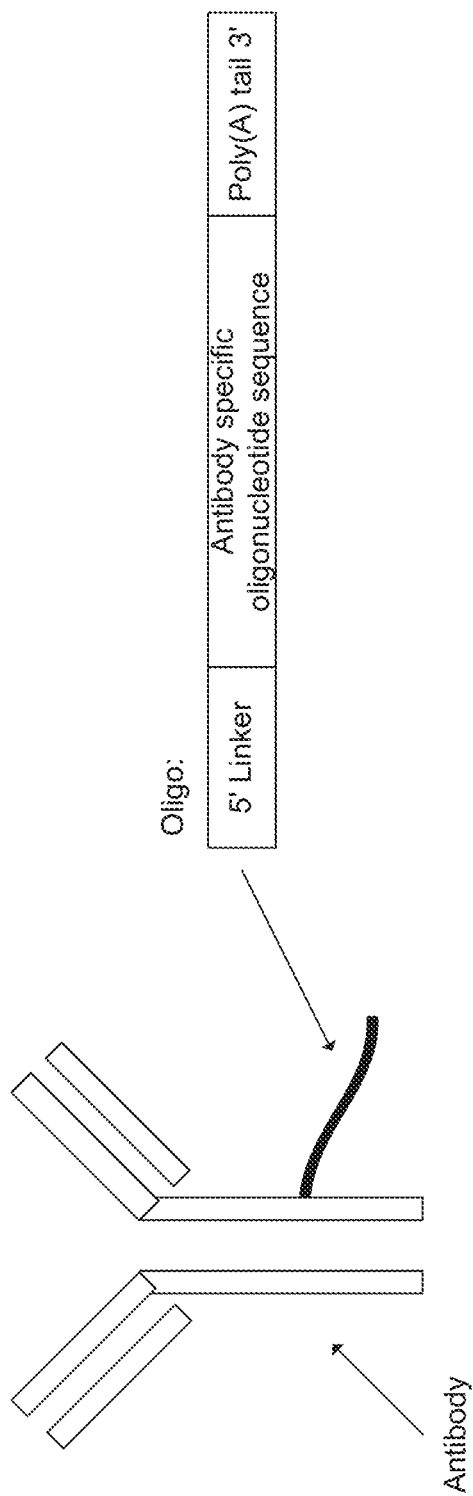
FIG. 4 shows a schematic illustration of an exemplary protein binding reagent (antibody illustrated here) conjugated with an oligonucleotide comprising a unique identifier for the protein binding reagent.

FIG. 4 shows a schematic illustration of an exemplary cellular component binding reagent, e.g., an antibody, that is conjugated with an oligonucleotide comprising a unique identifier sequence for the antibody. An oligonucleotide-conjugated with a cellular component binding reagent, an oligonucleotide for conjugation with a cellular component binding reagent, or an oligonucleotide previously conjugated with a cellular component binding reagent can be referred to herein as an antibody oligonucleotide (abbreviated as a binding reagent oligonucleotide). An oligonucleotide-conjugated with an antibody, an oligonucleotide for conjugation with an antibody, or an oligonucleotide previously conjugated with an antibody can be referred to herein as an antibody oligonucleotide (abbreviated as an "AbOligo" or "AbO"). The oligonucleotide can also comprise additional components, including but not limited to, one or more linker, one or more unique identifier for the antibody, optionally one or more barcode sequences (e.g., molecular labels), and a poly(A) tail. In some embodiments, the oligonucleotide can comprise, from 5' to 3', a linker, a unique identifier, a barcode sequence (e.g., a molecular label), and a poly(A) tail. An antibody oligonucleotide can be an mRNA mimic.

Figure 5:
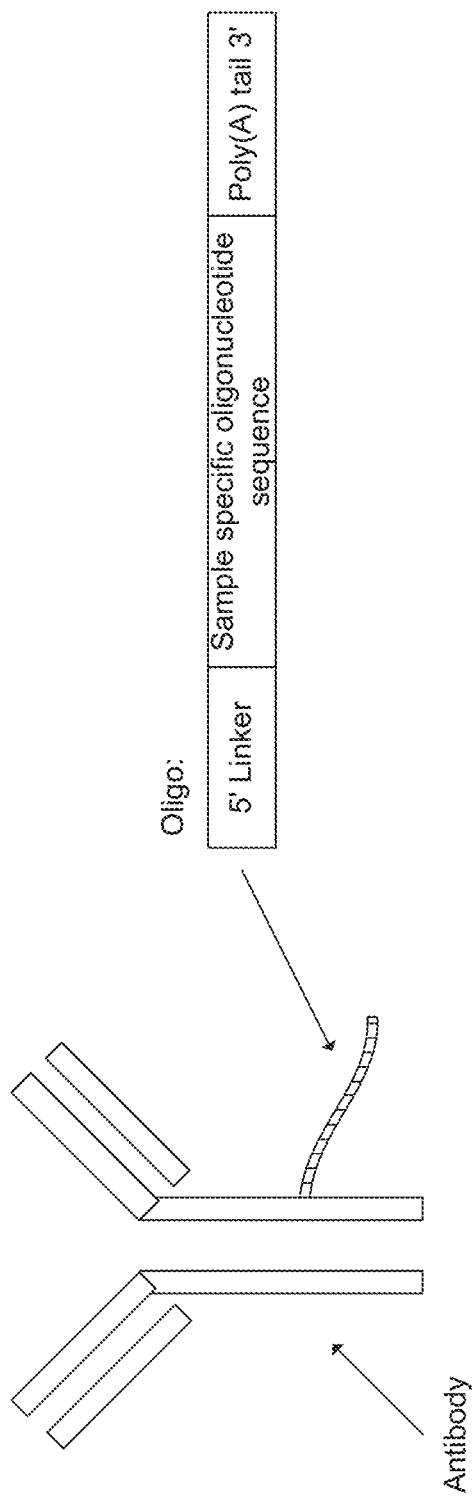
FIG. 5 shows a schematic illustration of an exemplary binding reagent (antibody illustrated here) conjugated with an oligonucleotide comprising a unique identifier for sample indexing to determine cells from the same or different samples.

FIG. 5 shows a schematic illustration of an exemplary cellular component binding reagent, e.g., an antibody, that is conjugated with an oligonucleotide comprising a unique identifier sequence for the antibody. The cellular component binding reagent can be capable of specifically binding to at least one cellular component target, such as an antigen target or a protein target. A binding reagent oligonucleotide (e.g., a sample indexing oligonucleotide, or an antibody oligonucleotide) can comprise a sequence (e.g., a sample indexing sequence) for performing the methods of the disclosure. For example, a sample indexing oligonucleotide can comprise a sample indexing sequence for identifying sample origin of one or more cells of a sample. Indexing sequences (e.g., sample indexing sequences) of at least two compositions comprising two cellular component binding reagents (e.g., sample indexing compositions) of the plurality of compositions comprising cellular component binding reagents can comprise different sequences. In some embodiments, the binding reagent oligonucleotide is not homologous to genomic sequences of a species. The binding reagent oligonucleotide can be configured to be detachable or non-detachable from the cellular component binding reagent.

The oligonucleotide conjugated to a cellular component binding reagent can, for example, comprise a barcode sequence (e.g., a molecular label sequence), a poly(A) tail, or a combination thereof. An oligonucleotide conjugated to a cellular component binding reagent can be an mRNA mimic. In some embodiments, the sample indexing oligonucleotide comprises a sequence complementary to a capture sequence of at least one barcode of the plurality of barcodes. A target binding region of the barcode can comprise the capture sequence. The target binding region can, for example, comprise a poly(dT) region. In some embodiments, the sequence of the sample indexing oligonucleotide complementary to the capture sequence of the barcode can comprise a poly(A) tail. The sample indexing oligonucleotide can comprise a molecular label.

In some embodiments, the binding reagent oligonucleotide (e.g., the sample oligonucleotide) comprises a nucleotide sequence of, or a nucleotide sequence of about, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, the binding reagent oligonucleotide comprises a nucleotide sequence of at least, or of at most, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

In some embodiments, the cellular component binding reagent comprises an antibody, a tetramer, an aptamers, a protein scaffold, or a combination thereof. The binding reagent oligonucleotide can be conjugated to the cellular component binding reagent, for example, through a linker. The binding reagent oligonucleotide can comprise the linker. The linker can comprise a chemical group. The chemical group can be reversibly, or irreversibly, attached to the molecule of the cellular component binding reagent. The chemical group can be selected from the group consisting of a UV photocleavable group, a disulfide bond, a streptavidin, a biotin, an amine, and any combination thereof.

In some embodiments, the cellular component binding reagent can bind to ADAM10, CD156c, ANO6, ATP1B2, ATP1B3, BSG, CD147, CD109, CD230, CD29, CD298, ATP1B3, CD44, CD45, CD47, CD51, CD59, CD63, CD97, CD98, SLC3A2, CLDND1, HLA-ABC, ICAM1, ITFG3, MPZL1, NA K ATPase alpha1, ATP1A1, NPTN, PMCA ATPase, ATP2B1, SLC1A5, SLC29A1, SLC2A1, SLC44A2, or any combination thereof.

In some embodiments, the protein target is, or comprises, an extracellular protein, an intracellular protein, or any combination thereof. In some embodiments, the antigen or protein target is, or comprises, a cell-surface protein, a cell marker, a B-cell receptor, a T-cell receptor, a major histocompatibility complex, a tumor antigen, a receptor, an integrin, or any combination thereof. The antigen or protein target can be, or comprise, a lipid, a carbohydrate, or any combination thereof. The protein target can be selected from a group comprising a number of protein targets. The number of antigen target or protein targets can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. The number of protein targets can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

The cellular component binding reagent (e.g., a protein binding reagent) can be associated with two or more binding reagent oligonucleotide (e.g., sample indexing oligonucleotides) with an identical sequence. The cellular component binding reagent can be associated with two or more binding reagent oligonucleotides with different sequences. The number of binding reagent oligonucleotides associated with the cellular component binding reagent can be different in different implementations. In some embodiments, the number of binding reagent oligonucleotides, whether having an identical sequence, or different sequences, can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of binding reagent oligonucleotides can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000.

The plurality of compositions comprising cellular component binding reagents (e.g., the plurality of sample indexing compositions) can comprise one or more additional cellular component binding reagents not conjugated with the binding reagent oligonucleotide (such as sample indexing oligonucleotide), which is also referred to herein as the binding reagent oligonucleotide-free cellular component binding reagent (such as sample indexing oligonucleotide-free cellular component binding reagent). The number of additional cellular component binding reagents in the plurality of compositions can be different in different implementations. In some embodiments, the number of additional cellular component binding reagents can be, or be about, 1, 2, 3, 4, 5, 6, 7, 8, 9, 10, 20, 30, 40, 50, 60, 70, 80, 90, 100, or a number or a range between any two of these values. In some embodiments, the number of additional cellular component binding reagents can be at least, or be at most, 1, 2, 3, 4, 5, 6, 7, 8, 9, 10, 20, 30, 40, 50, 60, 70, 80, 90, or 100. The cellular component binding reagent and any of the additional cellular component binding reagents can be identical, in some embodiments.

In some embodiments, a mixture comprising cellular component binding reagent(s) that is conjugated with one or more binding reagent oligonucleotides (e.g., sample indexing oligonucleotides) and cellular component binding reagent(s) that is not conjugated with binding reagent oligonucleotides is provided. The mixture can be used in some embodiments of the methods disclosed herein, for example, to contact the sample(s) and/or cell(s). The ratio of (1) the number of a cellular component binding reagent conjugated with a binding reagent oligonucleotide and (2) the number of another cellular component binding reagent (e.g., the same cellular component binding reagent) not conjugated with the binding reagent oligonucleotide (e.g., sample indexing oligonucleotide) or other binding reagent oligonucleotide(s) in the mixture can be different in different implementations. In some embodiments, the ratio can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

In some embodiments, the ratio can be, or be about, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, or a number or a range between any two of the values. In some embodiments, the ratio can be at least, or be at most, 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, or 10000:1.

A cellular component binding reagent can be conjugated with a binding reagent oligonucleotide (e.g., a sample indexing oligonucleotide), or not. In some embodiments, the percentage of the cellular component binding reagent conjugated with a binding reagent oligonucleotide (e.g., a sample indexing oligonucleotide) in a mixture comprising the cellular component binding reagent that is conjugated with the binding reagent oligonucleotide and the cellular component binding reagent(s) that is not conjugated with the binding reagent oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the cellular component binding reagent conjugated with a sample indexing oligonucleotide in a mixture can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, the percentage of the cellular component binding reagent not conjugated with a binding reagent oligonucleotide (e.g., a sample indexing oligonucleotide) in a mixture comprising a cellular component binding reagent conjugated with a binding reagent oligonucleotide (e.g., a sample indexing oligonucleotide) and the cellular component binding reagent that is not conjugated with the sample indexing oligonucleotide can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values. In some embodiments, the percentage of the cellular component binding reagent not conjugated with a binding reagent oligonucleotide in a mixture can be at least, or be at most, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

Cellular Component Cocktails

In some embodiments, a cocktail of cellular component binding reagents (e.g., an antibody cocktail) can be used to increase labeling sensitivity in the methods disclosed herein. Without being bound by any particular theory, it is believed that this may be because cellular component expression or protein expression can vary between cell types and cell states, making finding a universal cellular component binding reagent or antibody that labels all cell types challenging. For example, cocktail of cellular component binding reagents can be used to allow for more sensitive and efficient labeling of more sample types. The cocktail of cellular component binding reagents can include two or more different types of cellular component binding reagents, for example a wider range of cellular component binding reagents or antibodies. Cellular component binding reagents that label different cellular component targets can be pooled together to create a cocktail that sufficiently labels all cell types, or one or more cell types of interest.

In some embodiments, each of the plurality of compositions (e.g., sample indexing compositions) comprises a cellular component binding reagent. In some embodiments, a composition of the plurality of compositions comprises two or more cellular component binding reagents, wherein each of the two or more cellular component binding reagents is associated with a binding reagent oligonucleotide (e.g., a sample indexing oligonucleotide), wherein at least one of the two or more cellular component binding reagents is capable of specifically binding to at least one of the one or more cellular component targets. The sequences of the binding reagent oligonucleotides associated with the two or more cellular component binding reagents can be identical. The sequences of the binding reagent oligonucleotides associated with the two or more cellular component binding reagents can comprise different sequences. Each of the plurality of compositions can comprise the two or more cellular component binding reagents.

The number of different types of cellular component binding reagents (e.g., a CD147 antibody and a CD47 antibody) in a composition can be different in different implementations. A composition with two or more different types of cellular component binding reagents can be referred to herein as a cellular component binding reagent cocktail (e.g., a sample indexing composition cocktail). The number of different types of cellular component binding reagents in a cocktail can vary. In some embodiments, the number of different types of cellular component binding reagents in cocktail can be, or be about 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or a number or a range between any two of these values. In some embodiments, the number of different types of cellular component binding reagents in cocktail can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, or 100000. The different types of cellular component binding reagents can be conjugated to binding reagent oligonucleotides with the same or different sequences (e.g., sample indexing sequences).

Methods of Quantitative Analysis of Cellular Component Targets

In some embodiments, the methods disclosed herein can also be used for quantitative analysis of a plurality of cellular component targets (for example, protein targets) in a sample using the compositions disclosed herein and oligonucleotide probes that can associate a barcode sequence (e.g., a molecular label sequence) to the oligonucleotides of the cellular component binding reagents (e.g., protein binding reagents). The oligonucleotides of the cellular component binding reagents can be, or comprise, an antibody oligonucleotide, a sample indexing oligonucleotide, a cell identification oligonucleotide, a control particle oligonucleotide, a control oligonucleotide, an interaction determination oligonucleotide, etc. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, etc., or a mixture of cells from different subjects.

In some embodiments, the sample can comprise a plurality of single cells separated into individual compartments, such as microwells in a microwell array.

In some embodiments, the binding target of the plurality of cellular component target (i.e., the cellular component target) can be, or comprise, a carbohydrate, a lipid, a protein, an extracellular protein, a cell-surface protein, a cell marker, a B-cell receptor, a T-cell receptor, a major histocompatibility complex, a tumor antigen, a receptor, an integrin, an intracellular protein, or any combination thereof. In some embodiments, the cellular component target is a protein target. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular components can be at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 70%, at least 80%, at least 90%, at least 95%, at least 98%, at least 99%, or more, of all the encoded cellular components in an organism. In some embodiments, the plurality of cellular component targets can comprise at least 2, at least 3, at least 4, at least 5, at least 10, at least 20, at least 30, at least 40, at least 50, at least 100, at least 1000, at least 10000, or more different cellular component targets.

In some embodiments, the plurality of cellular component binding reagents is contacted with the sample for specific binding with the plurality of cellular component targets. Unbound cellular component binding reagents can be removed, for example, by washing. In embodiments where the sample comprises cells, any cellular component binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1%, 5%, 10%, 15%, 20%, 25%, 30%, 35%, 40%, 45%, 50%, 55%, 60%, 65%, 70%, 75%, 80%, 85%, 90%, 95% or 100%, of wells of the substrate receive a single cell. The population of cells can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100%, of wells of the substrate receive a single cell. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100%, of the number of wells on the substrate. In some instances, the population of cells is diluted such that the number of cell is about 10% of the number of wells in the substrate.

Distribution of single cells into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one cell. There can be at least a 0.1%, 0.5%, 1%, 2%, 3%, 4%, 5%, 6%, 7%, 8%, 9%, or 10%, or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the cellular component binding reagents can be additionally conjugated with fluorescent molecules to enable flow sorting of cells into individual compartments.

In some embodiments, the methods disclosed herein provide contacting a plurality of compositions with the sample for specific binding with the plurality of cellular component targets. It would be appreciated that the conditions used may allow specific binding of the cellular component binding reagents, e.g., antibodies, to the cellular component targets. Following the contacting step, unbound compositions can be removed. For example, in embodiments where the sample comprises cells, and the compositions specifically bind to cellular component targets are cell-surface cellular components, such as cell-surface proteins, unbound compositions can be removed by washing the cells with buffer such that only compositions that specifically bind to the cellular component targets remain with the cells.

In some embodiments, the methods disclosed herein can comprise associating an oligonucleotide (e.g., a barcode, or a stochastic barcode), including a barcode sequence (such as a molecular label), a cell label, a sample label, etc., or any combination thereof, to the plurality of oligonucleotides associated with the cellular component binding reagents. For example, a plurality of oligonucleotide probes comprising a barcode can be used to hybridize to the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality associated with oligonucleotides of the cellular component binding reagents, the plurality of oligonucleotides of the cellular component binding reagents can hybridize to the oligonucleotide probes. The oligonucleotide probes can be contacted at a non-depletable ratio such that each distinct oligonucleotide of the cellular component binding reagents can associate with oligonucleotide probes having different barcode sequences (e.g., molecular labels) of the disclosure.

In some embodiments, the methods disclosed herein provide detaching the oligonucleotides from the cellular component binding reagents that are specifically bound to the cellular component targets. Detachment can be performed in a variety of ways to separate the chemical group from the cellular component binding reagent, such as UV photocleaving, chemical treatment (e.g., dithiothreitol treatment), heating, enzyme treatment, or any combination thereof. Detaching the oligonucleotide from the cellular component binding reagent can be performed either before, after, or during the step of hybridizing the plurality of oligonucleotide probes to the plurality of oligonucleotides of the compositions.

Methods of Simultaneous Quantitative Analysis of Cellular Component and Nucleic Acid Targets In some embodiments, the methods disclosed herein can also be used for simultaneous quantitative analysis of a plurality of cellular component targets (e.g., protein targets) and a plurality of nucleic acid target molecules in a sample using the compositions disclosed herein and oligonucleotide probes that can associate a barcode sequence (e.g., a molecular label sequence) to both the oligonucleotides of the cellular component binding reagents and nucleic acid target molecules. Other methods of simultaneous quantitative analysis of a plurality of cellular component targets and a plurality of nucleic acid target molecules are described in U.S. patent application Ser. No. 15/715,028, filed on Sep. 25, 2017; the content of which is incorporated herein by reference in its entirety. In some embodiments, the sample can be a single cell, a plurality of cells, a tissue sample, a tumor sample, a blood sample, or the like. In some embodiments, the sample can comprise a mixture of cell types, such as normal cells, tumor cells, blood cells, B cells, T cells, maternal cells, fetal cells, or a mixture of cells from different subjects.

In some embodiments, the sample can comprise a plurality of single cells separated into individual compartments, such as microwells in a microwell array.

In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular cellular components. In some embodiments, the plurality of cellular components can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values, of all the cellular components, such as expressed proteins, in an organism, or one or more cell of the organism. In some embodiments, the plurality of cellular components can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all the cellular components, such as proteins could be expressed, in an organism, or one or more cells of the organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, or 10000, different cellular component targets.

In some embodiments, the plurality of cellular component binding reagents is contacted with the sample for specific binding with the plurality of cellular component targets. Unbound cellular component binding reagents can be removed, for example, by washing. In embodiments where the sample comprises cells, any cellular component binding reagents not specifically bound to the cells can be removed.

In some instances, cells from a population of cells can be separated (e.g., isolated) into wells of a substrate of the disclosure. The population of cells can be diluted prior to separating. The population of cells can be diluted such that at least 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that at most 1%, 5%, 10%, 15%, 20%, 25%, 30%, 35%, 40%, 45%, 50%, 55%, 60%, 65%, 70%, 75%, 80%, 85%, 90%, 95%, or 100% of wells of the substrate receive a single cell. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. The population of cells can be diluted such that the number of cells in the diluted population is, or is at least, 1%, 5%, 10%, 15%, 20%, 25%, 30%, 35%, 40%, 45%, 50%, 55%, 60%, 65%, 70%, 75%, 80%, 85%, 90%, 95%, or 100% of the number of wells on the substrate. In some instances, the population of cells is diluted such that the number of cell is about 10% of the number of wells in the substrate.

Distribution of single cells into wells of the substrate can follow a Poisson distribution. For example, there can be at least a 0.1%, 0.5%, 1%, 2%, 3%, 4%, 5%, 6%, 7%, 8%, 9%, or 10%, or more probability that a well of the substrate has more than one cell. There can be at least a 0.1%, 0.5%, 1%, 2%, 3%, 4%, 5%, 6%, 7%, 8%, 9%, or 10%, or more probability that a well of the substrate has more than one cell. Distribution of single cells into wells of the substrate can be random. Distribution of single cells into wells of the substrate can be non-random. The cells can be separated such that a well of the substrate receives only one cell.

In some embodiments, the cellular component binding reagents can be additionally conjugated with fluorescent molecules to enable flow sorting of cells into individual compartments.

In some embodiments, the methods disclosed herein provide contacting a plurality of compositions with the sample for specific binding with the plurality of cellular component targets. It would be appreciated that the conditions used may allow specific binding of the cellular component binding reagents, e.g., antibodies, to the cellular component targets. Following the contacting step, unbound compositions can be removed. For example, in embodiments where the sample comprises cells, and the compositions specifically bind to cellular component targets are on the cell surface, such as cell-surface proteins, unbound compositions can be removed by washing the cells with buffer such that only compositions that specifically bind to the cellular component targets remain with the cells.

In some embodiments, the methods disclosed herein can provide releasing the plurality of nucleic acid target molecules from the sample, e.g., cells. For example, the cells can be lysed to release the plurality of nucleic acid target molecules. Cell lysis may be accomplished by any of a variety of means, for example, by chemical treatment, osmotic shock, thermal treatment, mechanical treatment, optical treatment, or any combination thereof. Cells may be lysed by addition of a cell lysis buffer comprising a detergent (e.g., SDS, Li dodecyl sulfate, Triton X-100, Tween-20, or NP-40), an organic solvent (e.g., methanol or acetone), or digestive enzymes (e.g., proteinase K, pepsin, or trypsin), or any combination thereof.

It would be appreciated by one of ordinary skill in the art that the plurality of nucleic acid molecules can comprise a variety of nucleic acid molecules. In some embodiments, the plurality of nucleic acid molecules can comprise, DNA molecules, RNA molecules, genomic DNA molecules, mRNA molecules, rRNA molecules, siRNA molecules, or a combination thereof, and can be double-stranded or single-stranded. In some embodiments, the plurality of nucleic acid molecules comprise, or comprise about, 100, 1000, 10000, 20000, 30000, 40000, 50000, 100000, 1000000, or a number or a range between any two of these values, species. In some embodiments, the plurality of nucleic acid molecules comprise at least, or comprise at most, 100, 1000, 10000, 20000, 30000, 40000, 50000, 100000, or 1000000, species. In some embodiments, the plurality of nucleic acid molecules can be from a sample, such as a single cell, or a plurality of cells. In some embodiments, the plurality of nucleic acid molecules can be pooled from a plurality of samples, such as a plurality of single cells.

In some embodiments, the methods disclosed herein can comprise associating a barcode (e.g., a stochastic barcode), which can include a barcode sequence (such as a molecular label), a cell label, a sample label, etc., or any combination thereof, to the plurality of nucleic acid target molecules and the plurality of oligonucleotides of the cellular component binding reagents. For example, a plurality of oligonucleotide probes comprising a stochastic barcode can be used to hybridize to the plurality of nucleic acid target molecules and the plurality of oligonucleotides of the compositions.

In some embodiments, the plurality of oligonucleotide probes can be immobilized on solid supports. The solid supports can be free floating, e.g., beads in a solution. The solid supports can be embedded in a semi-solid or solid array. In some embodiments, the plurality of oligonucleotide probes may not be immobilized on solid supports. When the plurality of oligonucleotide probes are in close proximity to the plurality of nucleic acid target molecules and the plurality of oligonucleotides of the cellular component binding reagents, the plurality of nucleic acid target molecules and the plurality of oligonucleotides of the cellular component binding reagents can hybridize to the oligonucleotide probes. The oligonucleotide probes can be contacted at a non-depletable ratio such that each distinct nucleic acid target molecules and oligonucleotides of the cellular component binding reagents can associate with oligonucleotide probes having different barcode sequences (e.g., molecular labels) of the disclosure.

In some embodiments, the methods disclosed herein provide detaching the oligonucleotides from the cellular component binding reagents that are specifically bound to the cellular component targets. Detachment can be performed in a variety of ways to separate the chemical group from the cellular component binding reagent, such as UV photocleaving, chemical treatment (e.g., dithiothreitol treatment), heating, enzyme treatment, or any combination thereof. Detaching the oligonucleotide from the cellular component binding reagent can be performed either before, after, or during the step of hybridizing the plurality of oligonucleotide probes to the plurality of nucleic acid target molecules and the plurality of oligonucleotides of the compositions.

Simultaneous Quantitative Analysis of Protein and Nucleic Acid Targets

Figure 6:
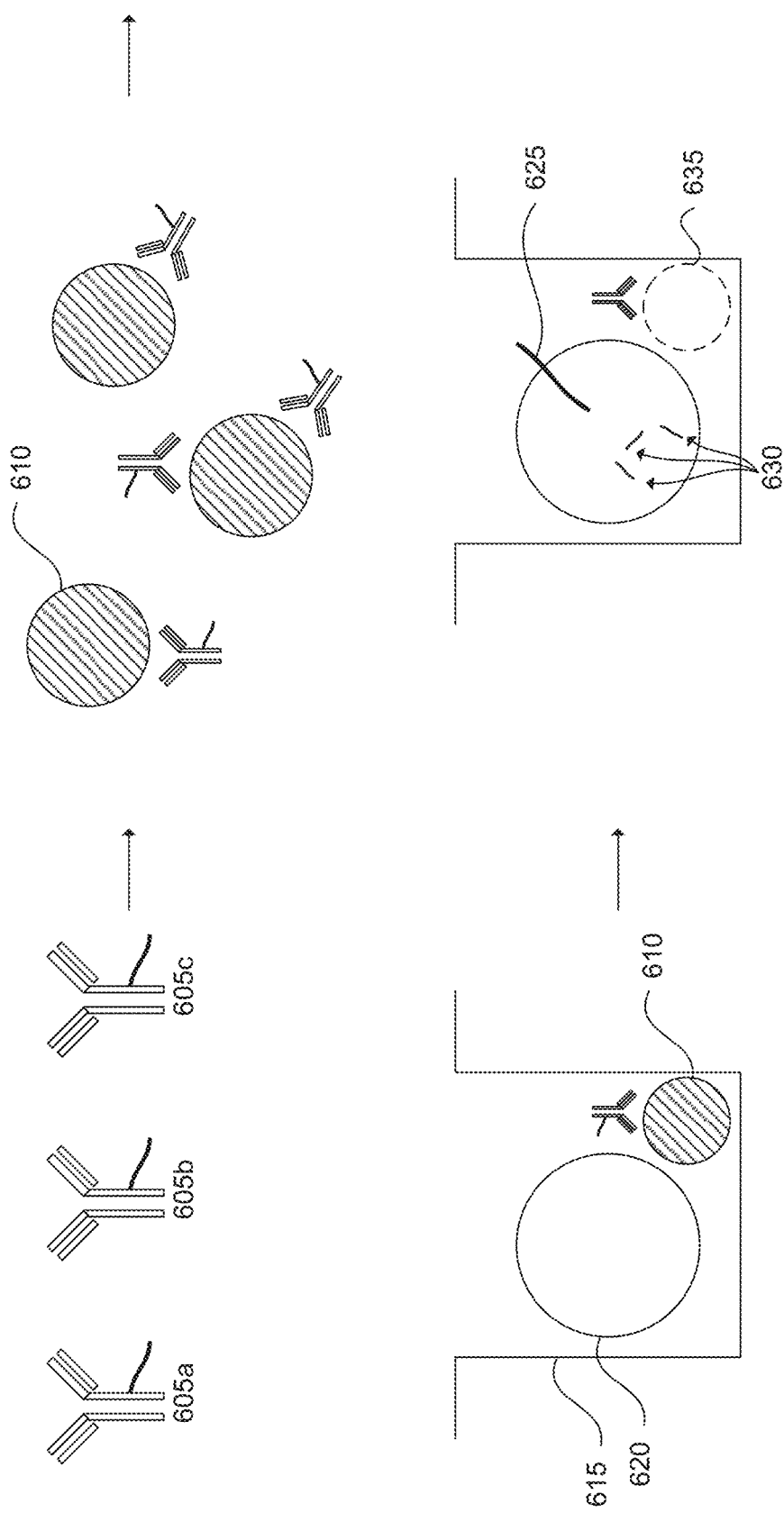
FIG. 6 shows a schematic illustration of an exemplary workflow using oligonucleotide-conjugated antibodies to determine protein expression and gene expression simultaneously in a high throughput manner.

In some embodiments, the methods disclosed herein also can be used for simultaneous quantitative analysis of multiple types of target molecules, for example protein and nucleic acid targets. For example, the target molecules can be, or comprise, cellular components. FIG. 6 shows a schematic illustration of an exemplary method of simultaneous quantitative analysis of both nucleic acid targets and other cellular component targets (e.g., proteins) in single cells. In some embodiments, a plurality of compositions 605, 605b, 605c, etc., each comprising a cellular component binding reagent, such as an antibody, is provided. Different cellular component binding reagents, such as antibodies, which bind to different cellular component targets are conjugated with different unique identifiers. Next, the cellular component binding reagents can be incubates with a sample containing a plurality of cells 610. The different cellular component binding reagents can specifically bind to cellular components on the cell surface, such as a cell marker, a B-cell receptor, a T-cell receptor, an antibody, a major histocompatibility complex, a tumor antigen, a receptor, or any combination thereof. Unbound cellular component binding reagents can be removed, e.g., by washing the cells with a buffer. The cells with the cellular component binding reagents can be then separated into a plurality of compartments, such as a microwell array, wherein a single compartment 615 is sized to fit a single cell and a single bead 620. Each bead can comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The oligonucleotides 625 conjugated to the cellular component binding reagent can be detached from the cellular component binding reagent using chemical, optical or other means. The cell can be lysed 635 to release nucleic acids within the cell, such as genomic DNA or cellular mRNA 630. Cellular mRNA 630, oligonucleotides 625 or both can be captured by the oligonucleotide probes on bead 620, for example, by hybridizing to the poly(dT) sequence. A reverse transcriptase can be used to extend the oligonucleotide probes hybridized to the cellular mRNA 630 and the oligonucleotides 625 using the cellular mRNA 630 and the oligonucleotides 625 as templates. The extension products produced by the reverse transcriptase can be subject to amplification and sequencing. Sequencing reads can be subject to demultiplexing of sequences or identifies of cell labels, barcodes (e.g., molecular labels), genes, cellular component binding reagent specific oligonucleotides (e.g., antibody specific oligonucleotides), etc., which can give rise to a digital representation of cellular components and gene expression of each single cell in the sample.

Association of Barcodes

The oligonucleotides associated with the cellular component binding reagents (e.g., antigen binding reagents or protein binding reagents) and/or the nucleic acid molecules may randomly associate with the oligonucleotide probes. The oligonucleotides associated with the cellular component binding reagents, referred to herein as binding reagent oligonucleotides, can be, or comprise oligonucleotides of the disclosure, such as an antibody oligonucleotide, a sample indexing oligonucleotide, a cell identification oligonucleotide, a control particle oligonucleotide, a control oligonucleotide, an interaction determination oligonucleotide, etc. Association can, for example, comprise hybridization of an oligonucleotide probe's target binding region to a complementary portion of the target nucleic acid molecule and/or the oligonucleotides of the protein binding reagents. For example, a oligo(dT) region of a barcode (e.g., a stochastic barcode) can interact with a poly(A) tail of a target nucleic acid molecule and/or a poly(A) tail of an oligonucleotide of a protein binding reagent. The assay conditions used for hybridization (e.g., buffer pH, ionic strength, temperature, etc.) can be chosen to promote formation of specific, stable hybrids.

The disclosure provides for methods of associating a molecular label with a target nucleic acid and/or an oligonucleotide associated with a cellular component binding reagent using reverse transcription. As a reverse transcriptase can use both RNA and DNA as template. For example, the oligonucleotide originally conjugated on the cellular component binding reagent can be either RNA or DNA bases, or both. A binding reagent oligonucleotide can be copied and linked (e.g., covalently linked) to a cell label and a barcode sequence (e.g., a molecular label) in addition to the sequence, or a portion thereof, of the binding reagent sequence. As another example, an mRNA molecule can be copied and linked (e.g., covalently linked) to a cell label and a barcode sequence (e.g., a molecular label) in addition to the sequence of the mRNA molecule, or a portion thereof.

In some embodiments, molecular labels can be added by ligation of an oligonucleotide probe target binding region and a portion of the target nucleic acid molecule and/or the oligonucleotides associated with (e.g., currently, or previously, associated with) with cellular component binding reagents. For example, the target binding region may comprise a nucleic acid sequence that can be capable of specific hybridization to a restriction site overhang (e.g., an EcoRI sticky-end overhang). The methods can further comprise treating the target nucleic acids and/or the oligonucleotides associated with cellular component binding reagents with a restriction enzyme (e.g., EcoRI) to create a restriction site overhang. A ligase (e.g., T4 DNA ligase) may be used to join the two fragments.

Determining the Number or Presence of Unique Molecular Label Sequences

In some embodiments, the methods disclosed herein comprise determining the number or presence of unique molecular label sequences for each unique identifier, each nucleic acid target molecule, and/or each binding reagent oligonucleotides (e.g., antibody oligonucleotides). For example, the sequencing reads can be used to determine the number of unique molecular label sequences for each unique identifier, each nucleic acid target molecule, and/or each binding reagent oligonucleotide. As another example, the sequencing reads can be used to determine the presence or absence of a molecular label sequence (such as a molecular label sequence associated with a target, a binding reagent oligonucleotide, an antibody oligonucleotide, a sample indexing oligonucleotide, a cell identification oligonucleotide, a control particle oligonucleotide, a control oligonucleotide, an interaction determination oligonucleotide, etc. in the sequencing reads).

In some embodiments, the number of unique molecular label sequences for each unique identifier, each nucleic acid target molecule, and/or each binding reagent oligonucleotide indicates the quantity of each cellular component target (e.g., an antigen target or a protein target) and/or each nucleic acid target molecule in the sample. In some embodiments, the quantity of a cellular component target and the quantity of its corresponding nucleic acid target molecules, e.g., mRNA molecules, can be compared to each other. In some embodiments, the ratio of the quantity of a cellular component target and the quantity of its corresponding nucleic acid target molecules, e.g., mRNA molecules, can be calculated. The cellular component targets can be, for example, cell surface protein markers. In some embodiments, the ratio between the protein level of a cell surface protein marker and the level of the mRNA of the cell surface protein marker is low.

The methods disclosed herein can be used for a variety of applications. For example, the methods disclosed herein can be used for proteome and/or transcriptome analysis of a sample. In some embodiments, the methods disclosed herein can be used to identify a cellular component target and/or a nucleic acid target, i.e., a biomarker, in a sample. In some embodiments, the cellular component target and the nucleic acid target correspond to each other, i.e., the nucleic acid target encodes the cellular component target. In some embodiments, the methods disclosed herein can be used to identify cellular component targets that have a desired ratio between the quantity of the cellular component target and the quantity of its corresponding nucleic acid target molecule in a sample, e.g., mRNA molecule. In some embodiments, the ratio is, or is about, 0.001, 0.01, 0.1, 1, 10, 100, 1000, or a number or a range between any two of the above values. In some embodiments, the ratio is at least, or is at most, 0.001, 0.01, 0.1, 1, 10, 100, or 1000. In some embodiments, the methods disclosed herein can be used to identify cellular component targets in a sample that the quantity of its corresponding nucleic acid target molecule in the sample is, or is about, 1000, 100, 10, 5, 2 1, 0, or a number or a range between any two of these values. In some embodiments, the methods disclosed herein can be used to identify cellular component targets in a sample that the quantity of its corresponding nucleic acid target molecule in the sample is more than, or less than, 1000, 100, 10, 5, 21, or 0.

Compositions and Kits

Some embodiments disclosed herein provide kits and compositions for simultaneous quantitative analysis of a plurality of cellular components (e.g., proteins) and/or a plurality of nucleic acid target molecules in a sample. The kits and compositions can, in some embodiments, comprise a plurality of cellular component binding reagents (e.g., a plurality of protein binding reagents) each conjugated with an oligonucleotide, wherein the oligonucleotide comprises a unique identifier for the cellular component binding reagent, and a plurality of oligonucleotide probes, wherein each of the plurality of oligonucleotide probes comprises a target binding region, a barcode sequence (e.g., a molecular label sequence), wherein the barcode sequence is from a diverse set of unique barcode sequences. In some embodiments, each of the oligonucleotides can comprise a molecular label, a cell label, a sample label, or any combination thereof. In some embodiments, each of the oligonucleotides can comprise a linker. In some embodiments, each of the oligonucleotides can comprise a binding site for an oligonucleotide probe, such as a poly(A) tail. For example, the poly(A) tail can be, e.g., oligodA$_{18}$ (unanchored to a solid support) or oligoA$_{18}$V (anchored to a solid support). The oligonucleotides can comprise DNA residues, RNA residues, or both.

Disclosed herein includes a plurality of sample indexing compositions. Each of the plurality of sample indexing compositions can comprise two or more cellular component binding reagents. Each of the two or more cellular component binding reagents can be associated with a sample indexing oligonucleotide. At least one of the two or more cellular component binding reagents can be capable of specifically binding to at least one cellular component target. The sample indexing oligonucleotide can comprise a sample indexing sequence for identifying sample origin of one or more cells of a sample. Sample indexing sequences of at least two sample indexing compositions of the plurality of sample indexing compositions can comprise different sequences.

Disclosed herein include kits comprising control particle compositions. In some embodiments, the control particle composition comprises a plurality of control particle oligonucleotides associated with a control particle, wherein each of the plurality of control particle oligonucleotides comprises a control barcode sequence and a poly(dA) region. At least two of the plurality of control particle oligonucleotides can comprise different control barcode sequences. The control particle oligonucleotide can comprise a molecular label sequence. The control particle oligonucleotide can comprise a binding site for a universal primer. Also disclosed herein include kits for sequencing control. In some embodiments, the kit comprises: a control particle composition comprising a plurality of control particle oligonucleotides associated with a control particle, wherein each of the plurality of control particle oligonucleotides comprises a control barcode sequence and a poly(dA) region.

Disclosed herein include kits comprising a plurality of control compositions for sequencing control. In some embodiments, each of the plurality of control compositions comprises a cellular component binding reagent associated with a control oligonucleotide, wherein the cellular component binding reagent is capable of specifically binding to at least one of a plurality of binding targets, and wherein the control oligonucleotide comprises a control barcode sequence and a pseudo-target region comprising a sequence substantially complementary to the target-binding region of at least one of the plurality of barcodes. In some embodiments, the pseudo-target region comprises a poly(dA) region.

Disclosed herein include kits comprising sample indexing compositions for cell identification. In some embodiments. Each of two sample indexing compositions comprises a cellular component binding reagent (e.g., a protein binding reagent) associated with a sample indexing oligonucleotide, wherein the cellular component binding reagent is capable of specifically binding to at least one of one or more cellular component targets (e.g., one or more protein targets), wherein the sample indexing oligonucleotide comprises a sample indexing sequence, and wherein sample indexing sequences of the two sample indexing compositions comprise different sequences. In some embodiments, the sample indexing oligonucleotide comprises a molecular label sequence, a binding site for a universal primer, or a combination thereof.

Disclosed herein includes kits for cell identification. In some embodiments, the kit comprises: two or more sample indexing compositions. Each of the two or more sample indexing compositions can comprise a cellular component binding reagent (e.g., an antigen binding reagent) associated with a sample indexing oligonucleotide, wherein the cellular component binding reagent is capable of specifically binding to at least one of one or more cellular component targets, wherein the sample indexing oligonucleotide comprises a sample indexing sequence, and wherein sample indexing sequences of the two sample indexing compositions comprise different sequences. In some embodiments, the sample indexing oligonucleotide comprises a molecular label sequence, a binding site for a universal primer, or a combination thereof. Disclosed herein includes kits for multiplet identification. In some embodiments, the kit comprises two sample indexing compositions. Each of two sample indexing compositions can comprise a cellular component binding reagent (e.g., an antigen binding reagent) associated with a sample indexing oligonucleotide, wherein the antigen binding reagent is capable of specifically binding to at least one of one or more cellular component targets (e.g., antigen targets), wherein the sample indexing oligonucleotide comprises a sample indexing sequence, and wherein sample indexing sequences of the two sample indexing compositions comprise different sequences.

Disclosed herein include kits for identifying interactions between cellular components, for example protein-protein interactions. In some embodiments, the kit comprises: a first pair of interaction determination compositions, wherein each of the first pair of interaction determination compositions comprises a protein binding reagent associated with an interaction determination oligonucleotide, wherein the protein binding reagent of one of the first pair of interaction determination compositions is capable of specifically binding to a first protein target and a protein binding reagent of the other of the first pair of interaction determination compositions is capable of specifically binding to the second protein target, wherein the interaction determination oligonucleotide comprises an interaction determination sequence and a bridge oligonucleotide hybridization region, and wherein the interaction determination sequences of the first pair of interaction determination compositions comprise different sequences; and a plurality of bridge oligonucleotides each comprising two hybridization regions capable of specifically binding to the bridge oligonucleotide hybridization regions of the first pair of interaction determination compositions.

The unique identifiers (or oligonucleotides associated with cellular component binding reagents, such as binding reagent oligonucleotides, antibody oligonucleotides, sample indexing oligonucleotides, cell identification oligonucleotides, control particle oligonucleotides, control oligonucleotides, or interaction determination oligonucleotides) can have any suitable length, for example, from about 25 nucleotides to about 45 nucleotides long. In some embodiments, the unique identifier can have a length that is, is about, is less than, is greater than, 4 nucleotides, 5 nucleotides, 6 nucleotides, 7 nucleotides, 8 nucleotides, 9 nucleotides, 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 70 nucleotides, 80 nucleotides, 90 nucleotides, 100 nucleotides, 200 nucleotides, or a range that is between any two of the above values.

In some embodiments, the unique identifiers are selected from a diverse set of unique identifiers. The diverse set of unique identifiers can comprise, or comprise about, 20, 30, 40, 50, 60, 70, 80, 90, 100, 200, 300, 400, 500, 600, 700, 800, 900, 1000, 2000, 5000, or a number or a range between any two of these values, different unique identifiers. The diverse set of unique identifiers can comprise at least, or comprise at most, 20, 30, 40, 50, 60, 70, 80, 90, 100, 200, 300, 400, 500, 600, 700, 800, 900, 1000, 2000, or 5000, different unique identifiers. In some embodiments, the set of unique identifiers is designed to have minimal sequence homology to the DNA or RNA sequences of the sample to be analyzed. In some embodiments, the sequences of the set of unique identifiers are different from each other, or the complement thereof, by, or by about, 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a number or a range between any two of these values. In some embodiments, the sequences of the set of unique identifiers are different from each other, or the complement thereof, by at least, or by at most, 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides.

In some embodiments, the unique identifiers can comprise a binding site for a primer, such as universal primer. In some embodiments, the unique identifiers can comprise at least two binding sites for a primer, such as a universal primer. In some embodiments, the unique identifiers can comprise at least three binding sites for a primer, such as a universal primer. The primers can be used for amplification of the unique identifiers, for example, by PCR amplification. In some embodiments, the primers can be used for nested PCR reactions.

Any suitable cellular component binding reagents are contemplated in this disclosure, such as any protein binding reagents (e.g., antibodies or fragments thereof, aptamers, small molecules, ligands, peptides, oligonucleotides, etc., or any combination thereof). In some embodiments, the cellular component binding reagents can be polyclonal antibodies, monoclonal antibodies, recombinant antibodies, single-chain antibody (scAb), or fragments thereof, such as Fab, Fv, etc. In some embodiments, the plurality of protein binding reagents can comprise, or comprise about, 20, 30, 40, 50, 60, 70, 80, 90, 100, 200, 300, 400, 500, 600, 700, 800, 900, 1000, 2000, 5000, or a number or a range between any two of these values, different protein binding reagents. In some embodiments, the plurality of protein binding reagents can comprise at least, or comprise at most, 20, 30, 40, 50, 60, 70, 80, 90, 100, 200, 300, 400, 500, 600, 700, 800, 900, 1000, 2000, or 5000, different protein binding reagents.

In some embodiments, the oligonucleotide is conjugated with the cellular component binding reagent through a linker. In some embodiments, the oligonucleotide can be conjugated with the protein binding reagent covalently. In some embodiment, the oligonucleotide can be conjugated with the protein binding reagent non-covalently. In some embodiments, the linker can comprise a chemical group that reversibly or irreversibly attached the oligonucleotide to the protein binding reagents. The chemical group can be conjugated to the linker, for example, through an amine group. In some embodiments, the linker can comprise a chemical group that forms a stable bond with another chemical group conjugated to the protein binding reagent. For example, the chemical group can be a UV photocleavable group, a disulfide bond, a streptavidin, a biotin, an amine, etc. In some embodiments, the chemical group can be conjugated to the protein binding reagent through a primary amine on an amino acid, such as lysine, or the N-terminus. The oligonucleotide can be conjugated to any suitable site of the protein binding reagent, as long as it does not interfere with the specific binding between the protein binding reagent and its protein target. In embodiments where the protein binding reagent is an antibody, the oligonucleotide can be conjugated to the antibody anywhere other than the antigen-binding site, for example, the Fc region, the $C_H1$ domain, the $C_H2$ domain, the $C_H3$ domain, the $C_L$ domain, etc. In some embodiments, each protein binding reagent can be conjugated with a single oligonucleotide molecule. In some embodiments, each protein binding reagent can be conjugated with, or with about, 2, 3, 4, 5, 10, 20, 30, 40, 50, 100, 1000, or a number or a range between any two of these values, oligonucleotide molecules, wherein each of the oligonucleotide molecule comprises the same unique identifier. In some embodiments, each protein binding reagent can be conjugated with more than one oligonucleotide molecule, for example, at least, or at most, 2, 3, 4, 5, 10, 20, 30, 40, 50, 100, or 1000, oligonucleotide molecules, wherein each of the oligonucleotide molecule comprises the same unique identifier.

In some embodiments, the plurality of cellular component binding reagents (e.g., protein binding reagents) are capable of specifically binding to a plurality of cellular component targets (e.g., protein targets) in a sample. The sample can be, or comprise, a single cell, a plurality of cells, a tissue sample, a tumor sample, a blood sample, or the like. In some embodiments, the plurality of cellular component targets comprises a cell-surface protein, a cell marker, a B-cell receptor, a T-cell receptor, an antibody, a major histocompatibility complex, a tumor antigen, a receptor, or any combination thereof. In some embodiments, the plurality of cellular component targets can comprise intracellular proteins. In some embodiments, the plurality of cellular component targets can comprise intracellular proteins. In some embodiments, the plurality of cellular component targets can be, or be about, 1%, 2%, 3%, 4%, 5%, 6%, 7%, 8%, 9%, 10%, 20%, 30%, 40%, 50%, 60%, 70%, 80%, 90%, 95%, 98%, 99%, or a number or a range between any two of these values of all cellular component targets (e.g., proteins expressed or could be expressed) in an organism. In some embodiments, the plurality of cellular component targets can be at least, or be at most, 1%, 2%, 3%, 4%, 5%, 6%, 7%, 8%, 9%, 10%, 20%, 30%, 40%, 50%, 60%, 70%, 80%, 90%, 95%, 98%, or 99%, of all cellular component targets (e.g., proteins expressed or could be expressed) in an organism. In some embodiments, the plurality of cellular component targets can comprise, or comprise about, 2, 3, 4, 5, 10, 20, 30, 40, 50, 100, 1000, 10000, or a number or a range between any two of these values, different cellular component targets. In some embodiments, the plurality of cellular component targets can comprise at least, or comprise at most, 2, 3, 4, 5, 10, 20, 30, 40, 50, 100, 1000, or 10000, different cellular component targets.

Sample Indexing Using Oligonucleotide-Conjugated Cellular Component Binding Reagent Disclosed herein include methods for sample identification. In some embodiments, the method comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; barcoding (e.g., stochastically barcoding) the sample indexing oligonucleotides using a plurality of barcodes (e.g., stochastic barcodes) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

An oligonucleotide-conjugated with an antibody, an oligonucleotide for conjugation with an antibody, or an oligonucleotide previously conjugated with an antibody is referred to herein as an antibody oligonucleotide ("AbOligo"). Antibody oligonucleotides in the context of sample indexing are referred to herein as sample indexing oligonucleotides. An antibody conjugated with an antibody oligonucleotide is referred to herein as a hot antibody or an oligonucleotide antibody. An antibody not conjugated with an antibody oligonucleotide is referred to herein as a cold antibody or an oligonucleotide free antibody. An oligonucleotide-conjugated with a binding reagent (e.g., a protein binding reagent), an oligonucleotide for conjugation with a binding reagent, or an oligonucleotide previously conjugated with a binding reagent is referred to herein as a reagent oligonucleotide. Reagent oligonucleotides in the context of sample indexing are referred to herein as sample indexing oligonucleotides. A binding reagent conjugated with an antibody oligonucleotide is referred to herein as a hot binding reagent or an oligonucleotide binding reagent. A binding reagent not conjugated with an antibody oligonucleotide is referred to herein as a cold binding reagent or an oligonucleotide free binding reagent.

Figure 7:
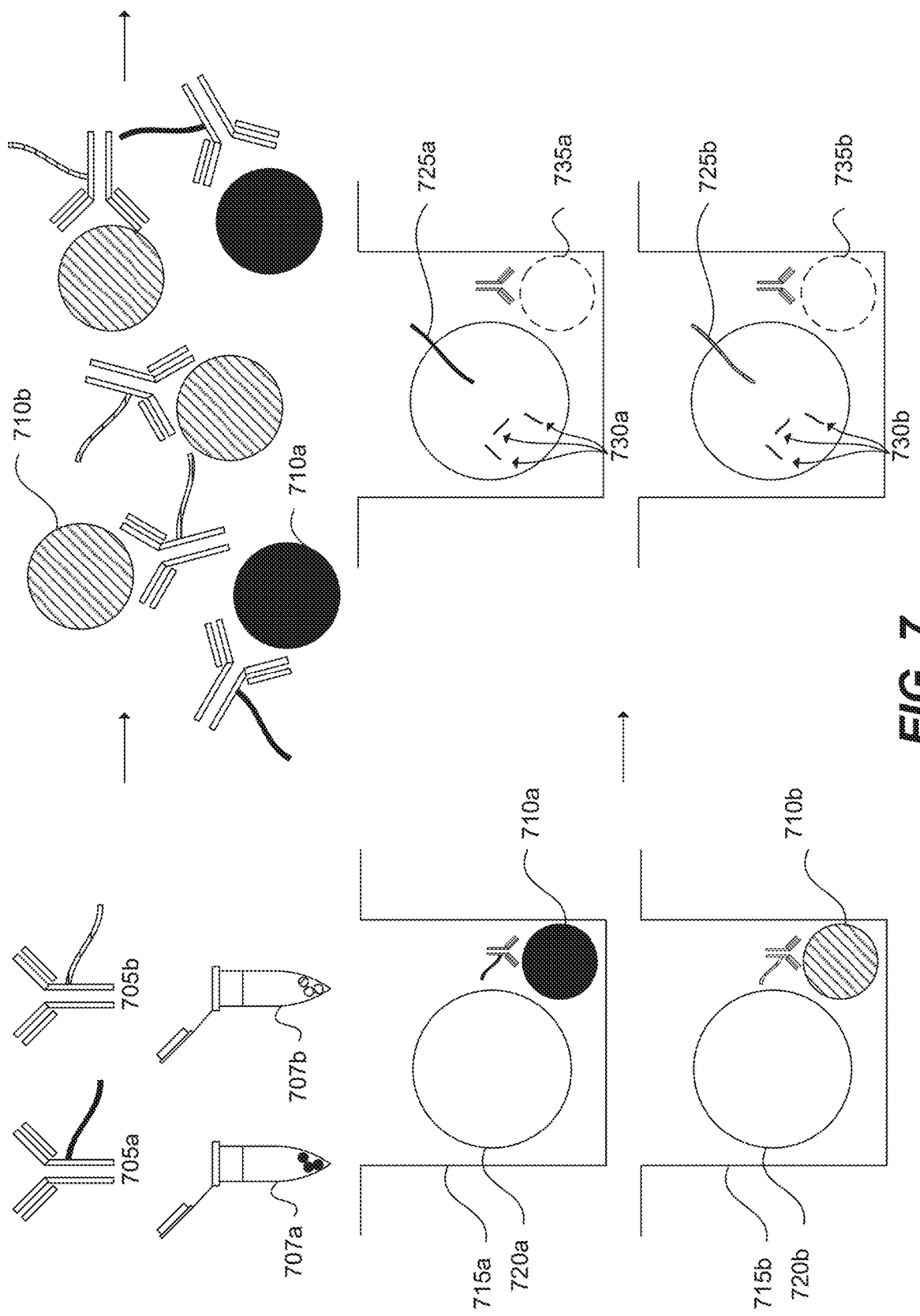
FIG. 7 shows a schematic illustration of an exemplary workflow of using oligonucleotide-conjugated antibodies for sample indexing.

FIG. 7 shows a schematic illustration of an exemplary workflow using oligonucleotide-conjugated cellular component binding reagents for sample indexing. In some embodiments, a plurality of compositions 705a, 705b, etc., each comprising a binding reagent is provided. The binding reagent can be a protein binding reagent, such as an antibody. The cellular component binding reagent can comprise an antibody, a tetramer, an aptamers, a protein scaffold, or a combination thereof. The binding reagents of the plurality of compositions 705a, 705b can bind to an identical cellular component target. For example, the binding reagents of the plurality of compositions 705, 705b can be identical (except for the sample indexing oligonucleotides associated with the binding reagents).

Different compositions can include binding reagents conjugated with sample indexing oligonucleotides with different sample indexing sequences. The number of different compositions can be different in different implementations. In some embodiments, the number of different compositions can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of different compositions can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

In some embodiments, the sample indexing oligonucleotides of binding reagents in one composition can include an identical sample indexing sequence. The sample indexing oligonucleotides of binding reagents in one composition may not be identical. In some embodiments, the percentage of sample indexing oligonucleotides of binding reagents in one composition with an identical sample indexing sequence can be, or be about, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values. In some embodiments, the percentage of sample indexing oligonucleotides of binding reagents in one composition with an identical sample indexing sequence can be at least, or be at most, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.9%.

The compositions 705a and 705b can be used to label samples of different samples. For example, the sample indexing oligonucleotides of the cellular component binding reagent in the composition 705a can have one sample indexing sequence and can be used to label cells 710a, shown as black circles, in a sample 707a, such as a sample of a patient. The sample indexing oligonucleotides of the cellular component binding reagents in the composition 705b can have another sample indexing sequence and can be used to label cells 710b, shown as hatched circles, in a sample 707b, such as a sample of another patient or another sample of the same patient. The cellular component binding reagents can specifically bind to cellular component targets or proteins on the cell surface, such as a cell marker, a B-cell receptor, a T-cell receptor, an antibody, a major histocompatibility complex, a tumor antigen, a receptor, or any combination thereof. Unbound cellular component binding reagents can be removed, e.g., by washing the cells with a buffer.

The cells with the cellular component binding reagents can be then separated into a plurality of compartments, such as a microwell array, wherein a single compartment 715a, 715b is sized to fit a single cell 710a and a single bead 720a or a single cell 710b and a single bead 720b. Each bead 720a, 720b can comprise a plurality of oligonucleotide probes, which can comprise a cell label that is common to all oligonucleotide probes on a bead, and molecular label sequences. In some embodiments, each oligonucleotide probe can comprise a target binding region, for example, a poly(dT) sequence. The sample indexing oligonucleotides 725a conjugated to the cellular component binding reagent of the composition 705a can be configured to be detachable or non-detachable from the cellular component binding reagent. The sample indexing oligonucleotides 725a conjugated to the cellular component binding reagent of the composition 705a can be detached from the cellular component binding reagent using chemical, optical or other means. The sample indexing oligonucleotides 725b conjugated to the cellular component binding reagent of the composition 705b can be configured to be detachable or non-detachable from the cellular component binding reagent. The sample indexing oligonucleotides 725b conjugated to the cellular component binding reagent of the composition 705b can be detached from the cellular component binding reagent using chemical, optical or other means.

The cell 710a can be lysed to release nucleic acids within the cell 710a, such as genomic DNA or cellular mRNA 730a. The lysed cell 735a is shown as a dotted circle. Cellular mRNA 730a, sample indexing oligonucleotides 725a, or both can be captured by the oligonucleotide probes on bead 720a, for example, by hybridizing to the poly(dT) sequence. A reverse transcriptase can be used to extend the oligonucleotide probes hybridized to the cellular mRNA 730a and the oligonucleotides 725a using the cellular mRNA 730a and the oligonucleotides 725a as templates. The extension products produced by the reverse transcriptase can be subject to amplification and sequencing.

Similarly, the cell 710b can be lysed to release nucleic acids within the cell 710b, such as genomic DNA or cellular mRNA 730b. The lysed cell 735b is shown as a dotted circle. Cellular mRNA 730b, sample indexing oligonucleotides 725b, or both can be captured by the oligonucleotide probes on bead 720b, for example, by hybridizing to the poly(dT) sequence. A reverse transcriptase can be used to extend the oligonucleotide probes hybridized to the cellular mRNA 730b and the oligonucleotides 725b using the cellular mRNA 730b and the oligonucleotides 725b as templates. The extension products produced by the reverse transcriptase can be subject to amplification and sequencing.

Sequencing reads can be subject to demultiplexing of cell labels, molecular labels, gene identities, and sample identities (e.g., in terms of sample indexing sequences of sample indexing oligonucleotides 725a and 725b). Demultiplexing of cell labels, molecular labels, and gene identities can give rise to a digital representation of gene expression of each single cell in the sample. Demultiplexing of cell labels, molecular labels, and sample identities, using sample indexing sequences of sample indexing oligonucleotides, can be used to determine a sample origin.

In some embodiments, cellular component binding reagents against cellular component binding reagents on the cell surface can be conjugated to a library of unique sample indexing oligonucleotides to allow cells to retain sample identity. For example, antibodies against cell surface markers can be conjugated to a library of unique sample indexing oligonucleotides to allow cells to retain sample identity. This will enable multiple samples to be loaded onto the same Rhapsody™ cartridge as information pertaining sample source is retained throughout library preparation and sequencing. Sample indexing can allow multiple samples to be run together in a single experiment, simplifying and shortening experiment time, and eliminating batch effect.

Disclosed herein include methods for sample identification. In some embodiments, the method comprise: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions. The method can include barcoding (e.g., stochastically barcoding) the sample indexing oligonucleotides using a plurality of barcodes (e.g., stochastic barcodes) to create a plurality of barcoded sample indexing oligonucleotides; obtaining sequencing data of the plurality of barcoded sample indexing oligonucleotides; and identifying sample origin of at least one cell of the one or more cells based on the sample indexing sequence of at least one barcoded sample indexing oligonucleotide of the plurality of barcoded sample indexing oligonucleotides.

In some embodiments, the method for sample identification comprises: contacting one or more cells from each of a plurality of samples with a sample indexing composition of a plurality of sample indexing compositions, wherein each of the one or more cells comprises one or more cellular component targets, wherein each of the plurality of sample indexing compositions comprises a cellular component binding reagent associated with a sample indexing oligonucleotide, wherein the cellular component binding reagent is capable of specifically binding to at least one of the one or more cellular component targets, wherein the sample indexing oligonucleotide comprises a sample indexing sequence, and wherein sample indexing sequences of at least two sample indexing compositions of the plurality of sample indexing compositions comprise different sequences; removing unbound sample indexing compositions of the plurality of sample indexing compositions; and identifying sample origin of at least one cell of the one or more cells based on the sample indexing sequence of at least one sample indexing oligonucleotide of the plurality of sample indexing compositions.

In some embodiments, identifying the sample origin of the at least one cell comprises: barcoding (e.g., stochastically barcoding) sample indexing oligonucleotides of the plurality of sample indexing compositions using a plurality of barcodes (e.g., stochastic barcodes) to create a plurality of barcoded sample indexing oligonucleotides; obtaining sequencing data of the plurality of barcoded sample indexing oligonucleotides; and identifying the sample origin of the cell based on the sample indexing sequence of at least one barcoded sample indexing oligonucleotide of the plurality of barcoded sample indexing oligonucleotides. In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, identifying the sample origin of the at least one cell can comprise identifying the presence or absence of the sample indexing sequence of at least one sample indexing oligonucleotide of the plurality of sample indexing compositions. Identifying the presence or absence of the sample indexing sequence can comprise: replicating the at least one sample indexing oligonucleotide to generate a plurality of replicated sample indexing oligonucleotides; obtaining sequencing data of the plurality of replicated sample indexing oligonucleotides; and identifying the sample origin of the cell based on the sample indexing sequence of a replicated sample indexing oligonucleotide of the plurality of sample indexing oligonucleotides that correspond to the least one barcoded sample indexing oligonucleotide in the sequencing data.

In some embodiments, replicating the at least one sample indexing oligonucleotide to generate the plurality of replicated sample indexing oligonucleotides comprises: prior to replicating the at least one barcoded sample indexing oligonucleotide, ligating a replicating adaptor to the at least one barcoded sample indexing oligonucleotide. Replicating the at least one barcoded sample indexing oligonucleotide can comprise replicating the at least one barcoded sample indexing oligonucleotide using the replicating adaptor ligated to the at least one barcoded sample indexing oligonucleotide to generate the plurality of replicated sample indexing oligonucleotides.

In some embodiments, replicating the at least one sample indexing oligonucleotide to generate the plurality of replicated sample indexing oligonucleotides comprises: prior to replicating the at least one barcoded sample indexing oligonucleotide, contacting a capture probe with the at least one sample indexing oligonucleotide to generate a capture probe hybridized to the sample indexing oligonucleotide; and extending the capture probe hybridized to the sample indexing oligonucleotide to generate a sample indexing oligonucleotide associated with the capture probe. Replicating the at least one sample indexing oligonucleotide can comprise replicating the sample indexing oligonucleotide associated with the capture probe to generate the plurality of replicated sample indexing oligonucleotides.

Daisy-Chaining Oligonucleotides

Disclosed herein include systems, methods, kits, and compositions for extending barcoded oligonucleotides (such as a sample indexing oligonucleotide, a control particle oligonucleotide, a control oligonucleotide, or an oligonucleotide conjugated to an antibody for determining protein expression), by PCR amplification of barcoded oligonucleotides using primers with long overhangs (e.g., 160 or more nucleotides in length). Such primers can be, for example, 200 or more nucleotides in length, such as Ultramer® DNA Oligonucleotides, Megamer® Single-Stranded DNA Fragments, or single-stranded DNA fragments of gBlocks® Gene Fragments (Integrated DNA Technologies, Inc. (Coralville, Iowa)). The barcoded oligonucleotides can contain a common sequence (e.g., a common sequence that is 40 nucleotides in length) for the long primer to bind and extend during PCR. In some embodiments, the long overhang can include a secondary barcode sequence (e.g., a molecular label sequence) to add complexity to the sample. Thus, the length of barcoded oligonucleotides can be increased from, for example, 200-300 nucleotides, to more than 400 nucleotides. Such longer barcoded oligonucleotides can survive ever increasing size selection during DNA purification using, for example, Solid Phase Reversible Immobilization (SPRI) magnetic beads (Applied Biological Materials Inc. (Richmond, British Columbia, Canada)).

In some embodiments, oligonucleotides associated with (e.g., attached to) cellular component binding reagents (e.g., antibody molecules) can be barcoded (e.g., stochastically barcoded), after dissociation from the cellular component binding reagents, to generate the barcoded oligonucleotides. The barcoded oligonucleotides can be further lengthened using a primer with a long overhang. Thus, the lengths of the oligonucleotides associated with cellular component binding reagents and the lengths of barcoded oligonucleotides, which may be limited by DNA synthesis technologies or experimental design considerations, do not limit the subsequent workflow (e.g., size selection during DNA purification). One non-limiting exemplary experimental design consideration is the effects of long oligonucleotides attached to cellular component binding reagents on the reagents' binding specificity and/or efficacy. PCR daisy-chaining of barcoded oligonucleotides can overcome or address limitations of DNA synthesis technologies while maintaining antibody specificity and/or efficacy. The methods of the disclosure for lengthening barcoded oligonucleotides with a common sequence using a primer with a long overhang is referred to herein as daisy-chaining the barcoded oligonucleotides using daisy-chaining amplification primers to generate daisy-chaining elongated amplicons.

Disclosed herein include methods for extending sample indexing oligonucleotides (or other barcoded oligonucleotides, such as control particle oligonucleotides). In some embodiments, after contacting one or more cells from each of a plurality of samples with a sample indexing composition of a plurality of sample indexing compositions, the sample indexing oligonucleotides can be barcoded using a plurality of barcodes to create a plurality of barcoded sample indexing oligonucleotides (See FIG. 7). The plurality of barcoded sample indexing oligonucleotides can be amplified using a plurality of primers with long overhangs (referred to herein as daisy-chaining amplification primers) to create a plurality of longer amplicons (referred to herein as daisy-chaining elongated amplicons). Such longer amplicons can be, for example, substantially longer (e.g., 160 nucleotides longer) than the barcoded sample indexing oligonucleotides.

FIGS. 8A8 and 8A2 show a schematic illustration of an exemplary workflow of daisy-chaining a barcoded oligonucleotide. In some embodiments, a sample indexing composition 805 can include a cellular component binding reagent, such as an antibody, that is associated with a sample indexing oligonucleotide 825. The sample indexing oligonucleotide 825 can include a sample indexing sequence 825s, a common region 825d for binding to a daisy-chaining amplification primer (referred to herein as a daisy-chaining amplification primer-binding region or sequence 825d), and a poly(A) tail 825a. In some embodiments, the common region 825d for binding to a daisy-chaining amplification primer can be the same for all or some of sample indexing oligonucleotides 825. In some embodiments, the daisy-chaining amplification primer-binding region 825d of different sample indexing oligonucleotides 825 are different. A sample indexing oligonucleotide 825 can be an mRNA mimic. The sample indexing sequences 825s of at least two sample indexing compositions 805 of the plurality of sample indexing compositions can comprise different sequences.

The daisy-chaining amplification primer-binding region 825d can be different in different implementations, ranging from 10 to 200 nucleotides in length. In some embodiments, daisy-chaining amplification primer-binding region 825d can be, or be about, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, or a number or a range between any two of these values, nucleotides in length. In some embodiments, the daisy-chaining amplification primer-binding region 825d can be at least, or be at most, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 nucleotides in length.

The sample indexing oligonucleotides 825 can be barcoded using a plurality of barcodes 815 (e.g., barcodes 815 associated with a particle, such as a bead 81) to create a plurality of barcoded sample indexing oligonucleotides 840.

In some embodiments, a barcode 815 can include a poly(dT) region 815*t* for binding to a sample indexing oligonucleotide 825, optionally a molecular label 815*m* (e.g., for determining the number of occurrences of the sample indexing oligonucleotides), a cell label 815*c*, and a universal label 815*u*. A barcoded sample indexing oligonucleotide 840 can include a reverse complement 825*d_rt* of the daisy-chaining amplification primer-binding region 825*d*.

Barcoded sample indexing oligonucleotides 840 can be amplified using forward and reverse primers 845, 850, including a plurality of daisy-chaining amplification primers 845, to create a plurality of daisy-chaining elongated amplicons 860. A daisy-chaining amplification primer 845 can comprise the sequence 845*d*, a complement, a reverse complement, or a combination thereof, of the daisy-chaining amplification primer-binding region 825*d* (referred to herein as barcoded sample indexing oligonucleotide-binding region 845*d*). A daisy-chaining amplification primer-binding region 825*d* and a barcoded sample indexing oligonucleotide-binding region 845*d* can be the same lengths, or different lengths. The barcoded sample indexing oligonucleotide-binding region 845*d* of a daisy-chaining amplification primer 845 can bind to its reverse complementary sequence 825*d_rt* on a barcoded sample indexing oligonucleotide 840. A daisy-chaining amplification primer 845 can include an overhang region 845*o* (the overhang region 845*o* is an overhang of the daisy-chaining amplification primer 845 when the daisy-chaining amplification primer 845 binds to a barcoded sample indexing oligonucleotide 850). The plurality of daisy-chaining elongated amplicons 860, or a portion thereof, can be sequenced for sample identification (or protein expression profiling, sequencing control, etc.). As illustrated in FIG. 8A1-8A2, a sample indexing oligonucleotide 825 can be 200 nucleotides in length, a barcoded sample indexing oligonucleotides 840 can be 240 nucleotides in length, and a daisy-chaining elongated amplicon 860 can be 400 nucleotides in length.

The barcoded sample indexing oligonucleotide-binding region 845*d* can have different lengths in different implementations, for example, ranging from 10 to 200 nucleotides in length. In some embodiments, the barcoded sample indexing oligonucleotide-binding region 845*d* can be, or be about, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, or a number or a range between any two of these values, nucleotides in length. In some embodiments, the barcoded sample indexing oligonucleotide-binding region 845*d* can be at least, or be at most, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, or 200 nucleotides in length.

In some embodiments, at least two daisy-chaining amplification primers 845 can comprise barcoded sample indexing oligonucleotide-binding regions 845*d* with an identical sequence. Two or more daisy-chaining amplification primers 845 can comprise barcoded sample indexing oligonucleotide-binding regions 845*d* with different sequences. Some or all of daisy-chaining amplification primers 845 can comprise barcoded sample indexing oligonucleotide-binding regions 845*d* with an identical sequence. The barcoded sample indexing oligonucleotide-binding regions 845*d* can comprise the daisy-chaining amplification primer binding sequence 825*d*, a complement thereof, a reverse complement thereof, or a combination thereof. Daisy-chaining amplification primer binding sequences 825*d* of at least two sample indexing compositions 805 can comprise an identical sequence. Daisy-chaining amplification primer binding sequences 825*d* of at least two sample indexing compositions 805 can comprise different sequences.

In some embodiments, the overhang region 845*o* can comprise a barcode sequence (referred to herein as a daisy-chaining amplification primer barcode sequence), such as a molecular label. For example, two daisy-chaining amplification primers 845*o* can comprise overhang regions 845*o* with an identical daisy-chaining amplification primer barcode sequence. As another example, two daisy-chaining amplification primers 845 can comprise overhang regions 845*o* with two different daisy-chaining amplification primer barcode sequences. Overhang regions 845*o* of daisy-chaining amplification primers 845 can comprise different daisy-chaining amplification primer barcode sequences.

The overhang region 845 can have different lengths in different implementations, for example, ranging from 50 to 1000 nucleotides in length. In some embodiments, the overhang region 845 can be, or be about, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 or a number or a range between any two of these values, nucleotides in length. In some embodiments, the overhang region 845 can be at least, or be at most, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000.

The daisy-chaining elongated amplicon 860 can have different lengths in different implementations, for example, ranging from 50 to 1000 nucleotides in length. In some embodiments, the daisy-chaining elongated amplicon 860 can be, or be about, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 or a number or a range between any two of these values, nucleotides in length. In some embodiments, the daisy-chaining elongated amplicon 860 can be at least, or be at most, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000.

FIGS. 8B1 and 8B2 show a schematic illustration of another exemplary workflow of daisy-chaining a barcoded oligonucleotide. In this workflow, the reverse complementary sequence of a switch oligonucleotide 860 can be optionally added to a barcoded sample indexing oligonucleotide 840. During reverse transcription, upon reaching the 5' end of the sample indexing oligonucleotide 824, the terminal transferase activity of an enzyme (e.g., a reverse transcriptase, such as a Moloney murine leukemia virus (MMLV)) adds a few additional nucleotides (mostly deoxycytidine) to the 3' end of the newly synthesized strand 840. These bases can function as an anchoring site of the template switch (TS) oligonucleotide 860. Upon base pairing between the template switch oligonucleotide 860 and the appended deoxycytidine stretch, the enzyme "switches" template strands, from sample indexing oligonucleotide 825 to the template switch oligonucleotide 860, and continues replication to the 5' end of the TS oligonucleotide 860. Thus, the resulting barcoded sample indexing oligonucleotide 840 contains a reverse complement of the sample indexing oligonucleotide 825 and the template switch oligonucleotide 860.

Barcoded sample indexing oligonucleotides 840 with a reverse complement sequence of the template switch oligonucleotide 860 can be amplified using forward and reverse primers 845, 850 to create daisy-chaining elongated amplicons 860 with the reverse complement of the template switch oligonucleotide 860. One of the two primers can bind to the Read 1 sequence 845r1, a universal sequence for amplification, which can be equivalent to the universal label 845u in FIGS. 8A1-8A2. The second primer, a daisy-chaining amplification primers 845, can bind to the reverse complement sequence 825d_rt of the daisy-chaining amplification primer-binding region 825d. Accordingly, a long tail can be added to the barcoded sample indexing oligonucleotide 860. After enzymatic fragmentation, end repair, A-tailing, and optionally sample index PCR, the resulting amplicons can include the P5 sequence 865p5, P7 sequence 865p7, Read 1 sequence 815r1, and Read 2 sequence 865r2 for next generation sequencing (e.g., using bridge amplification). As illustrated in FIGS. 8A1-8A2, a sample indexing oligonucleotide 825 can be 200 nucleotides in length, a barcoded sample indexing oligonucleotides 840 can be approximately 260 nucleotides in length, and a daisy-chaining elongated amplicon 860 can be more than 406 nucleotides in length.

Single Cell Sequencing Control Particles

Figure 9A:
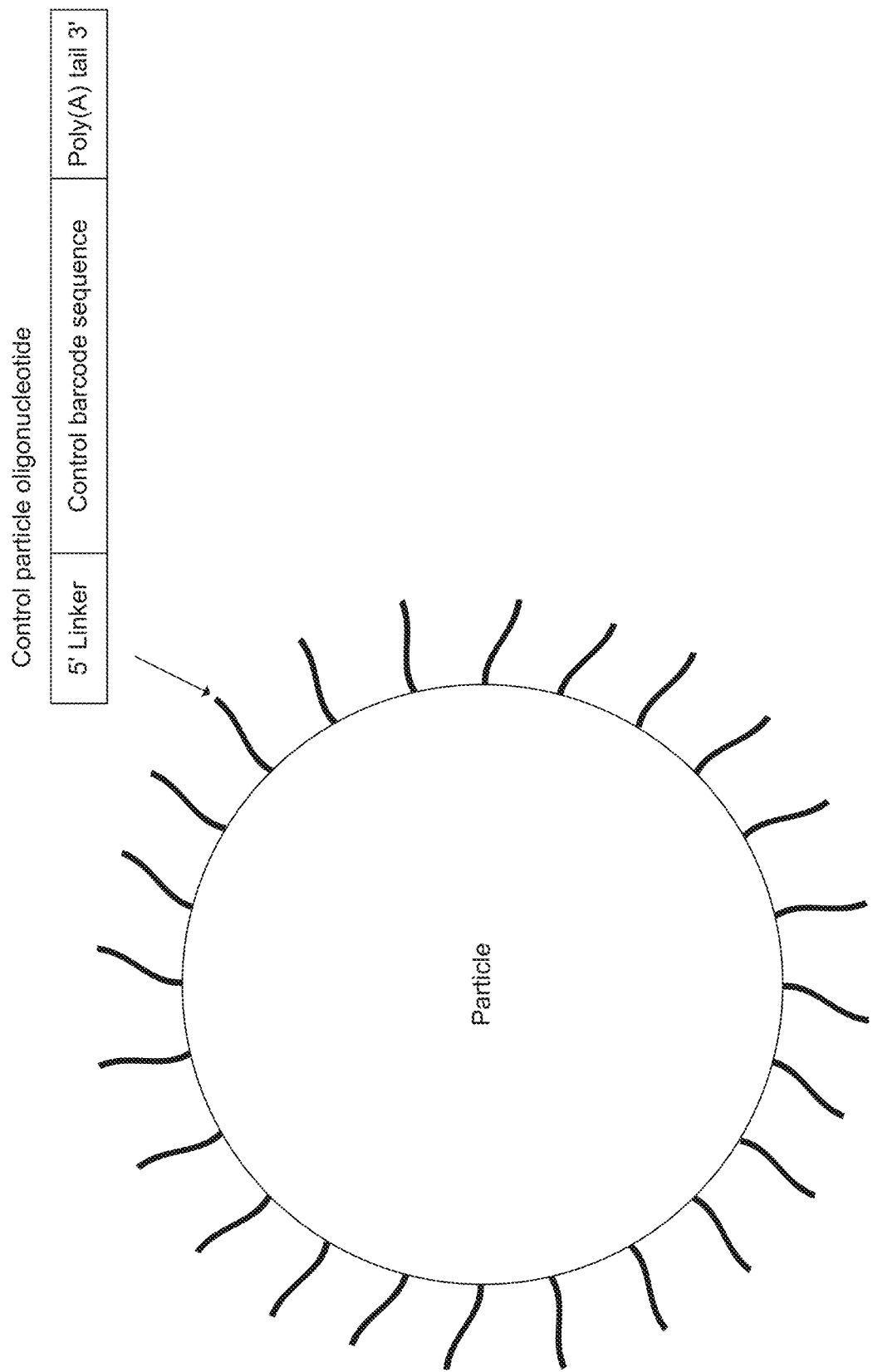
FIGS. 9A-9E show non-limiting exemplary schematic illustrations of particles functionalized with oligonucleotides.

Disclosed herein includes control particle compositions that can be used for, for example, single cell sequencing control. In some embodiments, the control particle composition comprises a plurality of control particle oligonucleotides associated with a control particle. The control particle associated with the plurality of control particle oligonucleotides is referred to herein also as a functionalized control particle. FIG. 9A is a non-limiting exemplary schematic illustration of a particle functionalized with a plurality of oligonucleotides. FIG. 9A shows that the control particle oligonucleotide associated with the control particle can comprise a control barcode sequence and a poly(dA) region, mimicking a mRNA poly(A) tail. The control particle oligonucleotide can comprise a molecular label sequence, a binding site for a universal primer, or a combination thereof. The control particle oligonucleotides associated with the control particles can be the same or different from one another. In some embodiments, at least two of the control particle oligonucleotides associated with the control particle have different control barcode sequence. In some embodiments, a plurality of a first control particle oligonucleotides and a plurality of a second control oligonucleotides are associated with the control particle, wherein the first and the second particle oligonucleotides have different control barcode sequence.

A bead, such as the CompBead™ Plus (BD (Franklin Lake, New Jersey)) can be functionalized with antibodies conjugated with oligonucleotides. CompBeads Plus are about 7.5 microns in size, which is similar to the size of an immune cell. When functionalized with antibodies conjugated with oligonucleotides, CompBead Plus can be used as control cells or control particles for single cell workflows. The AbO functionalized bead can be used with any single cell workflow as a single cell sequencing control.

Control Particle Oligonucleotide

The length of the control barcode sequence can be different in different implementations. In some embodiments, the control barcode sequence is, or is about, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, the control barcode sequence is at least, or is at most, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length.

The length of the control particle oligonucleotide can be different in different implementations. In some embodiments, the control particle oligonucleotide is, or is about, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, the control particle oligonucleotide is at least, or is at most, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length.

In some embodiments, the number of the plurality of control particle oligonucleotides can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 1000000, 10000000, 100000000, 1000000000, or a number or a range between any two of these values. In some embodiments, the number of the plurality of control particle oligonucleotides can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 1000000, 10000000, 100000000, or 1000000000.

The plurality of control particle oligonucleotides can comprise the same or different control barcode sequences. For example, at least two of the plurality of control particle oligonucleotides can comprise different control barcode sequences. In some embodiments, the control barcode sequences of at least or at most 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 1000000, 10000000, 100000000, or 1000000000 of the plurality of control particle oligonucleotides can be identical. In some embodiments, the control barcode sequences of, or of about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 1000000, 10000000, 100000000, 1000000000, or a number or a range between any two of these values, of the plurality of control particle oligonucleotides can be identical.

The control barcode sequences of at least or at most 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values of the plurality of control particle oligonucleotides can be identical. The control barcode sequences of, or of about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values, of the plurality of control particle oligonucleotides can be identical.

In some embodiments, the control barcode sequence is not homologous to genomic sequences of a species. The control barcode sequence can be homologous to genomic sequences of a species. The species can be a non-mammalian species. The non-mammalian species can be a phage species. The phage species can be T7 phage, a PhiX phage, or a combination thereof.

Control Particle

In some embodiments, at least one of the plurality of control particle oligonucleotides is associated with the control particle through a linker. The at least one of the plurality of control particle oligonucleotides can comprise the linker. The linker can comprise a chemical group. The chemical group can be reversibly or irreversibly attached to the at least one of the plurality of control particle oligonucleotides. The chemical group can comprise a UV photocleavable group, a disulfide bond, a streptavidin, a biotin, an amine, a disulfide linkage, or any combination thereof.

The diameter of the control particle can be, or be about, 1-1000 micrometers, such as 10-100 micrometer or 7.5 micrometer. In some embodiments, the diameter of the control particle can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 micrometers, or a number or a range between any two of these values. In some embodiments, the diameter of the control particle can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000 micrometers.

In some embodiments, the plurality of control particle oligonucleotides is immobilized on the control particle. The plurality of control particle oligonucleotides can be partially immobilized on the control particle. The plurality of control particle oligonucleotides can be enclosed in the control particle. The plurality of control particle oligonucleotides can be partially enclosed in the control particle. The control particle can be disruptable.

In some embodiments, the control particle can be a bead. The bead can be, or comprise, a Sepharose bead, a streptavidin bead, an agarose bead, a magnetic bead, a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof. The control particle can comprise a material of polydimethylsiloxane (PDMS), polystyrene, glass, polypropylene, agarose, gelatin, hydrogel, paramagnetic, ceramic, plastic, glass, methylstyrene, acrylic polymer, titanium, latex, Sepharose, cellulose, nylon, silicone, or any combination thereof. The control particle can comprise a disruptable hydrogel particle.

Protein Binding Reagent

Figure 9B:
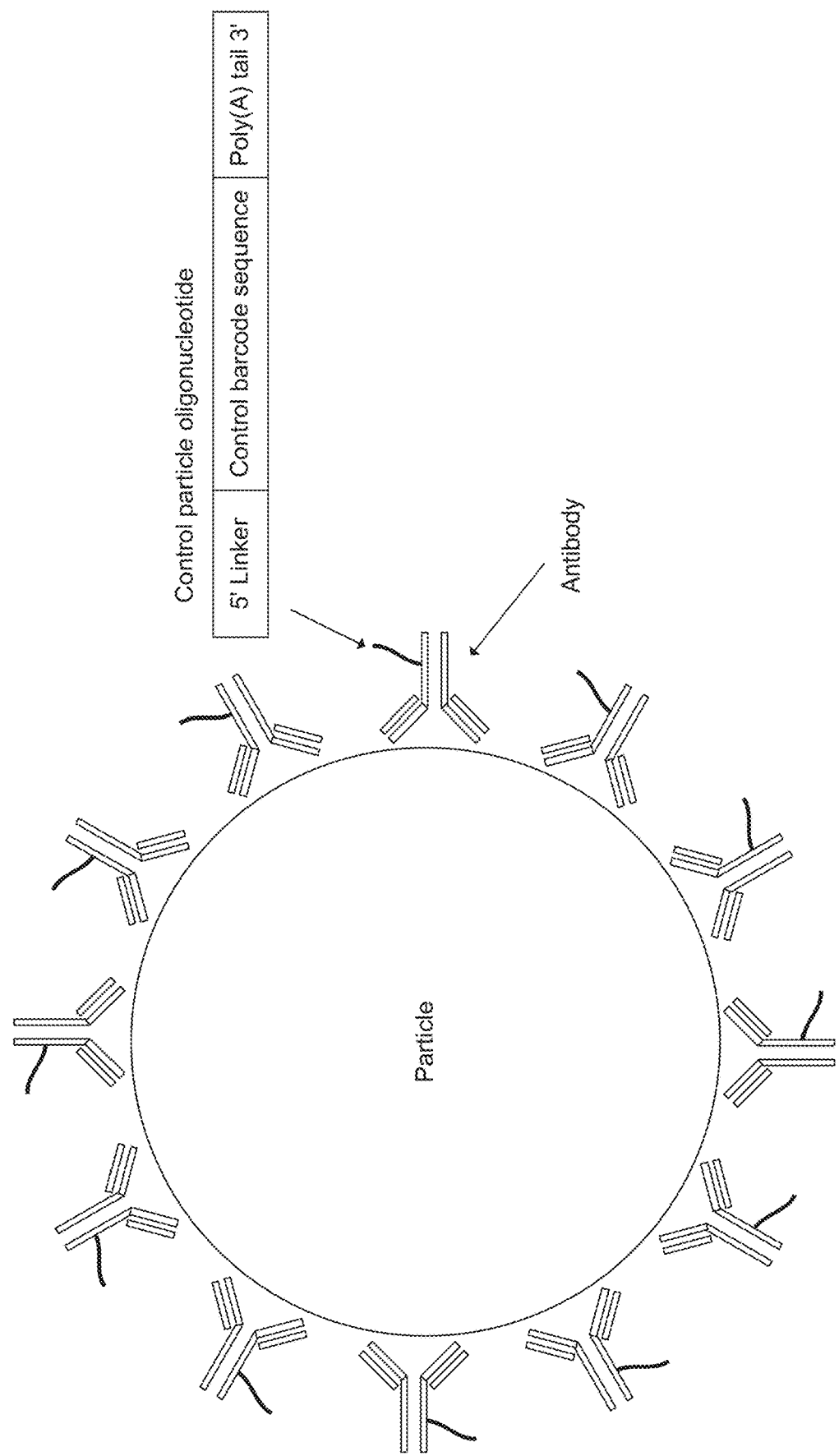

In some embodiments, the control particle is associated with a plurality of first protein binding reagents, and at least one of the plurality of first protein binding reagents is associated with one of the plurality of control particle oligonucleotides. FIG. 9B shows a non-limiting exemplary particle coated with a number of antibodies functionalized with oligonucleotides. The first protein binding reagent can comprise a first antibody (e.g., a primary antibody, or a secondary antibody). The control particle oligonucleotide can be conjugated to the first protein binding reagent through a linker. The first control particle oligonucleotide can comprise the linker. The linker can comprise a chemical group. The chemical group can be reversibly or irreversibly attached to the first protein binding reagent. The chemical group can comprise a UV photocleavable group, a disulfide bond, a streptavidin, a biotin, an amine, a disulfide linkage, or any combination thereof.

Figure 9C:
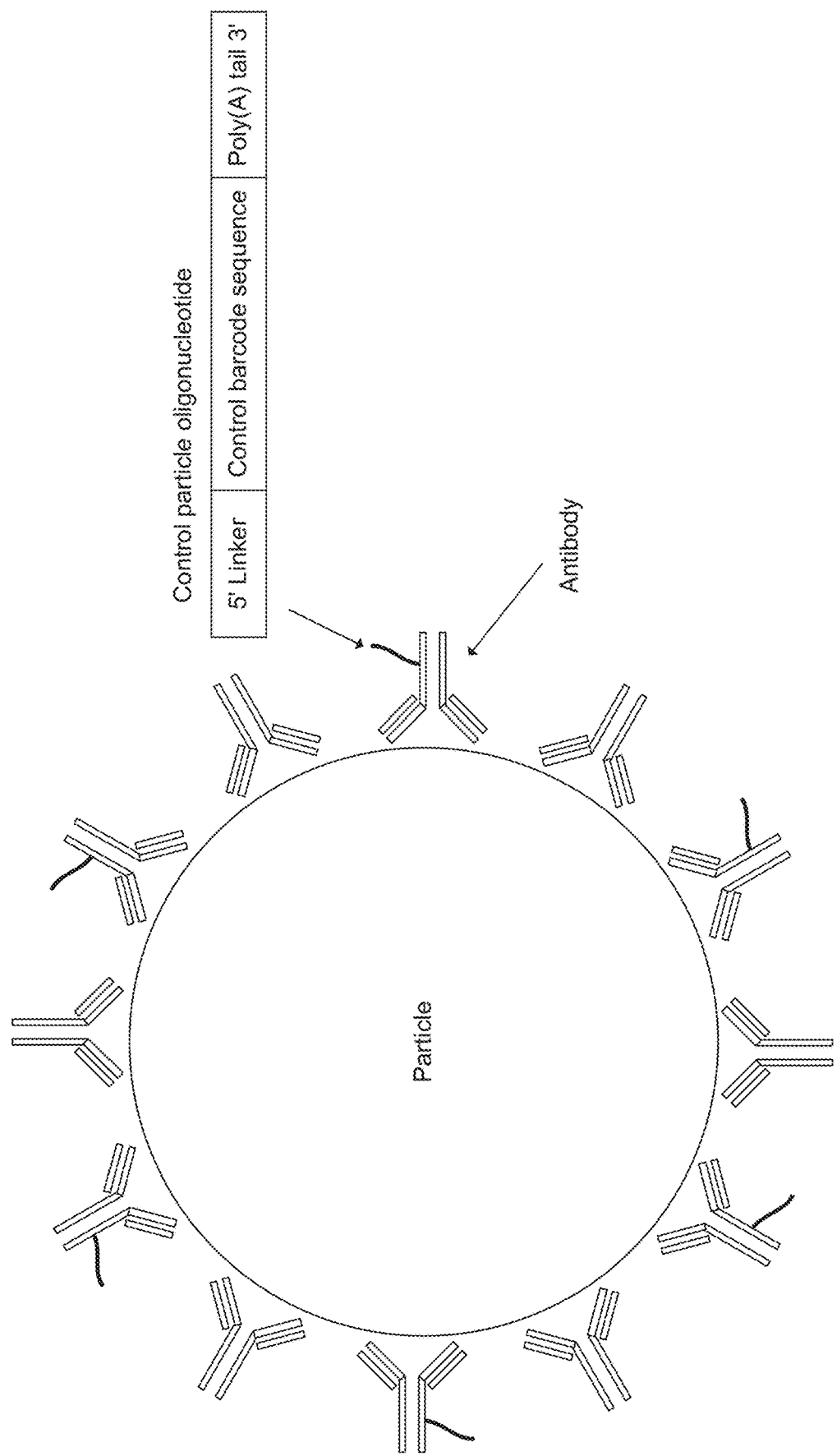

In some embodiments, the control particle is associated with a plurality of second protein binding reagents. At least one of the plurality of second protein binding reagents can be associated with one of the plurality of control particle oligonucleotides. FIG. 9C shows a non-limiting exemplary particle coated with a plurality of first antibodies functionalized with oligonucleotides and a plurality of second antibodies not functionalized with oligonucleotides. The antibodies on the control particle can be titrated with ratios of hot antibodies (e.g., associated with control particle oligonucleotide) and cold antibodies (e.g., not associated with control particle oligonucleotides) to alter the amount of sequencing reads obtained from a control particle. The first antibodies and the second antibodies can be the same or different.

Figure 9D:
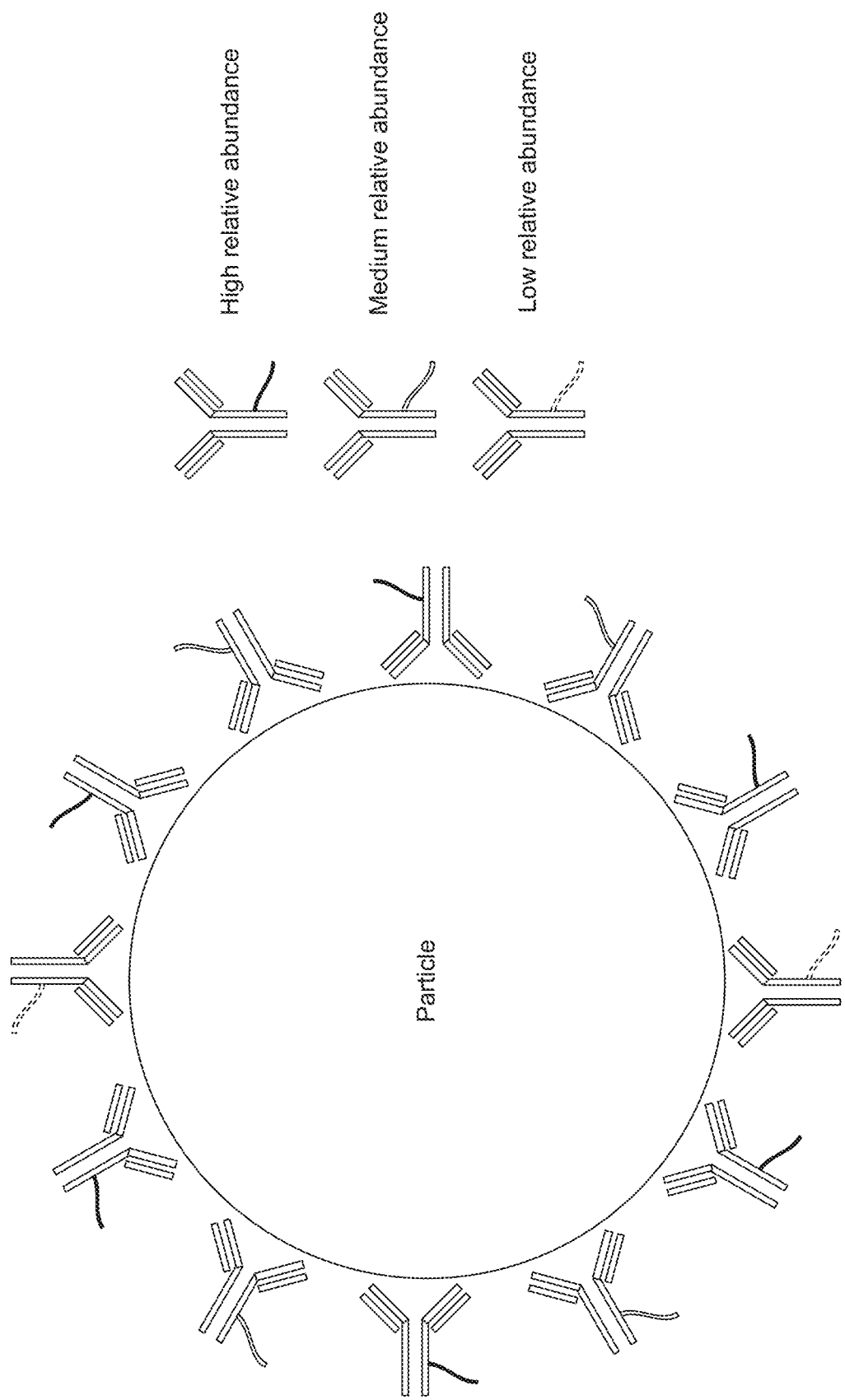

FIG. 9D is a non-limiting exemplary schematic illustration of a particle functionalized with a plurality of first control particle oligonucleotides, a plurality of second control particle oligonucleotides conjugated to a plurality of second antibodies and a plurality of third control particle oligonucleotides with relative high, medium, and low abundance. The plurality of first control particle oligonucleotides can be conjugated to a plurality of first protein binding reagents. The plurality of second control particle oligonucleotides can be conjugated to a plurality of second protein binding reagents. The plurality of third control particle oligonucleotides can be conjugated to a plurality of third protein binding reagents.

The relative abundance of the first, second, and third control particle oligonucleotides can mimic mRNAs with different expression levels. The control particle oligonucleotide associated with the first protein binding reagent and the control particle oligonucleotide associated with the second protein binding reagent can comprise different control barcode sequences. Different protein binding reagents, such as antibodies, and the different control particle oligonucleotides on the control particle can be titrated to generate a standard curve. The first protein binding reagents, the second protein binding reagents, or the third protein binding reagents can be identical or different protein binding reagents.

In some embodiments, the ratio of the number of the plurality of first control particle oligonucleotides and the number of the plurality of second (or third) control particle oligonucleotides can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, or a number or a range between any two of these numbers. In some embodiments, the ratio of the number of the plurality of first control particle oligonucleotides and the number of the plurality of second (or third) control particle oligonucleotides can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, or 1:100.

In some embodiments, the first protein binding reagent can be associated with a partner binding reagent (e.g., a secondary antibody), and the first protein binding reagent is associated with the control particle using the partner binding reagent. The partner binding reagent can comprise a partner antibody. The partner antibody can comprise an anti-cat antibody, an anti-chicken antibody, an anti-cow antibody, an anti-dog antibody, an anti-donkey antibody, an anti-goat antibody, an anti-guinea pig antibody, an anti-hamster antibody, an anti-horse antibody, an anti-human antibody, an anti-llama antibody, an anti-monkey antibody, an anti-mouse antibody, an anti-pig antibody, an anti-rabbit antibody, an anti-rat antibody, an anti-sheep antibody, or a combination thereof. The partner antibody can comprise an immunoglobulin G (IgG), a F(ab') fragment, a F(ab')2 fragment, a combination thereof, or a fragment thereof.

In some embodiments, the first protein binding reagent is associated with two or more of the plurality of control particle oligonucleotides with an identical control barcode sequence. The first protein binding reagent can be associated with two or more of the plurality of control particle oligonucleotides with different control barcode sequences. In some embodiments, at least one of the plurality of first protein binding reagents is not associated with any of the plurality of control particle oligonucleotides. The first protein binding reagent associated with the control particle oligonucleotide and the first protein binding reagent not associated with any control particle oligonucleotide can be identical protein binding reagents.

Control Barcode Diversity

The plurality of control particle oligonucleotides associated with one control particle can comprise a number of control particle oligonucleotides with different control barcode sequences. The number of control barcode sequences that control particle oligonucleotides have can be different in different implementation. In some embodiments, the number of control barcode sequences that the control particle oligonucleotides have can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of control barcode sequences that the control particle oligonucleotides have can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the number of control particle oligonucleotides with the same control particle oligonucleotide sequence can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of control particle oligonucleotides with the same control particle oligonucleotide sequence can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the plurality of control particle oligonucleotides comprises a plurality of first control particle oligonucleotides each comprising a first control barcode sequence, and a plurality of second control particle oligonucleotides each comprising a second control barcode sequence, and the first control barcode sequence and the second control barcode sequence have different sequences. The number of the plurality of first control particle oligonucleotides and the number of the plurality of second control particle oligonucleotides can be about the same. The number of the plurality of first control particle oligonucleotides and the number of the plurality of second control particle oligonucleotides can be different. The number of the plurality of first control particle oligonucleotides can be at least 2 times, 10 times, 100 times, or more greater than the number of the plurality of second control particle oligonucleotides. In some embodiments, the ratio of the number of the plurality of first control particle oligonucleotides and the number of the plurality of second control particle oligonucleotides can be, or be about, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, 1:10000, or a number or a range between any two of the values. In some embodiments, the ratio of the number of the plurality of first control particle oligonucleotides and the number of the plurality of second control particle oligonucleotides can be at least, or be at most, 1:1, 1:1.1, 1:1.2, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:200, 1:300, 1:400, 1:500, 1:600, 1:700, 1:800, 1:900, 1:1000, 1:2000, 1:3000, 1:4000, 1:5000, 1:6000, 1:7000, 1:8000, 1:9000, or 1:10000.

Detectable Moiety

Figure 9E:
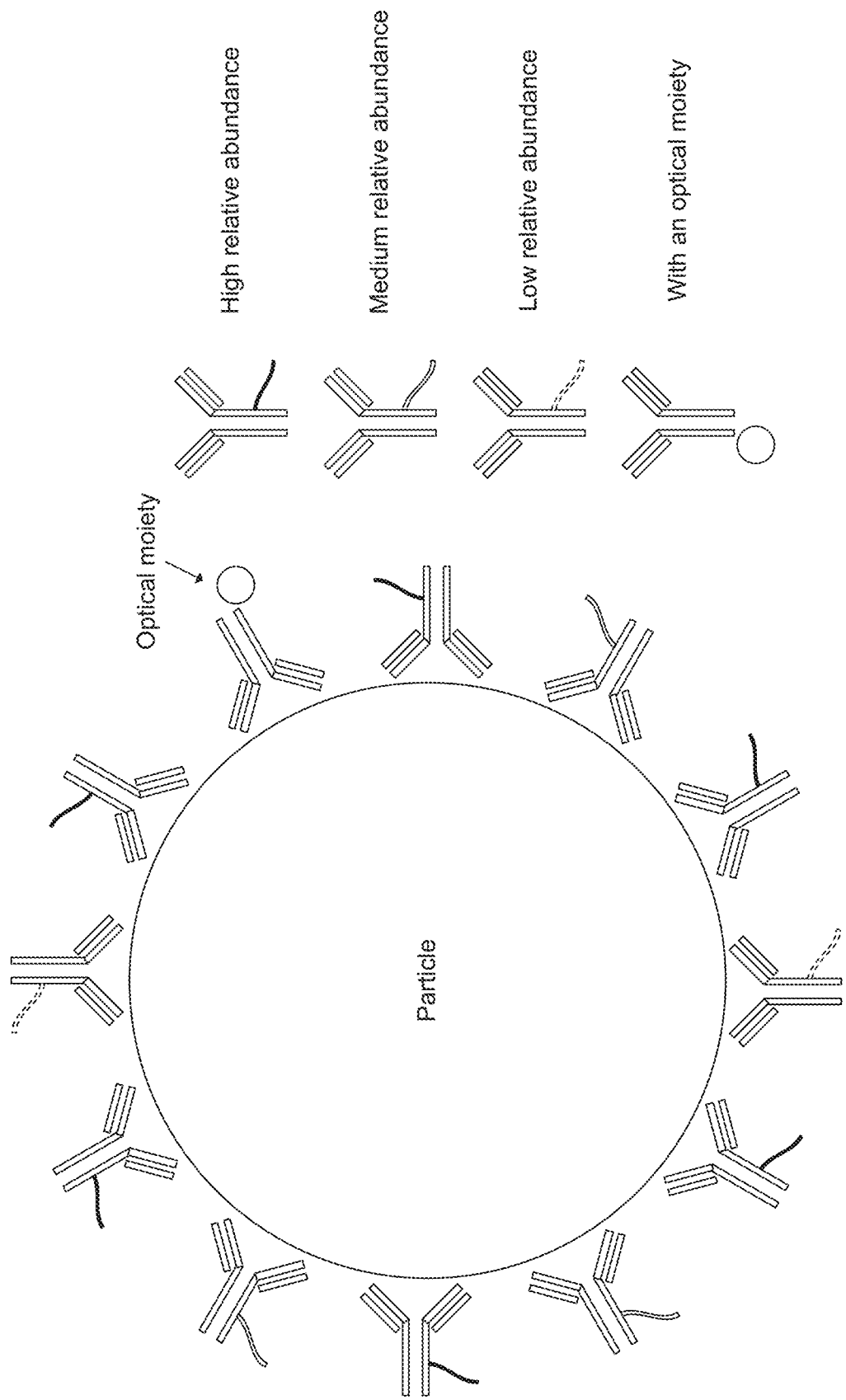

In some embodiments, the control particle is associated with a detectable moiety, for example an optical moiety, such as a fluorophore or a chromophore. The control particle oligonucleotide can be associated with a detectable moiety, for example an optical moiety. In some embodiments, the first protein binding reagent can be associated with an optical moiety (FIG. 9E). The second protein binding reagent can be associated with an optical moiety. A control particle associated with an optical moiety (e.g., a bead fluorescently tagged) can also be used for imaging and flow cytometry.

The detectable moiety can be selected from a group of spectrally-distinct detectable moieties. Spectrally-distinct detectable moieties include detectable moieties with distinguishable emission spectra even if their emission spectral may overlap. Non-limiting examples of detectable moieties include Xanthene derivatives: fluorescein, rhodamine, Oregon green, eosin, and Texas red; Cyanine derivatives: cyanine, indocarbocyanine, oxacarbocyanine, thiacarbocyanine, and merocyanine; Squaraine derivatives and ring-substituted squaraines, including Seta, SeTau, and Square dyes; Naphthalene derivatives (dansyl and prodan derivatives); Coumarin derivatives; oxadiazole derivatives: pyridyloxazole, nitrobenzoxadiazole and benzoxadiazole; Anthracene derivatives: anthraquinones, including DRAQ5, DRAQ7 and CyTRAK Orange; Pyrene derivatives: cascade blue; Oxazine derivatives: Nile red, Nile blue, cresyl violet, oxazine 170; Acridine derivatives: proflavin, acridine orange, acridine yellow; Arylmethine derivatives: auramine, crystal violet, malachite green; and Tetrapyrrole derivatives: porphin, phthalocyanine, bilirubin. Other non-limiting examples of detectable moieties include Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Hoechst 33342, DAPI, Hoechst 33258, SYTOX Blue, Chromomycin A3, Mithramycin, YOYO-1, Ethidium Bromide, Acridine Orange, SYTOX Green, TOTO-1, TO-PRO-1, TO-PRO: Cyanine Monomer, Thiazole Orange, CyTRAK Orange, Propidium Iodide (PI), LDS 751, 7-AAD, SYTOX Orange, TOTO-3, TO-PRO-3, DRAQ5, DRAQ7, Indo-1, Fluo-3, Fluo-4, DCFH, DHR, and SNARF.

The excitation wavelength of the detectable moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values. The emission wavelength of the detectable moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or a number or a range between any two of these values.

The molecular weights of the detectable moieties can vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 Daltons (Da), or a number or a range between any two of these values. The molecular weights of the detectable moieties can also vary, for example be, or be about, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 kilo Daltons (kDa), or a number or a range between any two of these values.

The group of spectrally distinct detectable moieties can, for example, include five different fluorophores, five different chromophores, a combination of five fluorophores and chromophores, a combination of four different fluorophores and a non-fluorophore, a combination of four chromophores and a non-chromophore, or a combination of four fluorophores and chromophores and a non-fluorophore non-chromophore. In some embodiments, the detectable moieties can be one of 1, 2, 3, 4, 5, 6, 7, 8, 9, 10, 20, 30, 40, 50, 60, 70, 80, 90, 100, 1000, 2000, 3000, 4000, 5000, 6000, 7000, 8000, 9000, 10000, or a number or a range between any two of these values, of spectrally-distinct moieties.

Control Particle Workflow

The AbO functionalized bead can be used with any single cell workflow as a single cell sequencing control. Single cell workflows can utilize microwell arrays or microwell cartridges (e.g., BD Rhapsody™) or microfluidics devices (e.g., 10× Genomics (San Francisco, CA), Drop-seq (McCarroll Lab, Harvard Medical School (Cambridge, Massachusetts); Macosko et al., Cell, 2015 May 21 16; 5:1202, the content of which is incorporated herein by reference in its entirety), or Abseq (Mission Bio (San Francisco, CA); Shahi et al., Sci Rep. 2017 Mar. 14; 7:44447, the content of which is hereby incorporated by reference in its entirety) in combination with solid or semisolid particles associated with stochastic barcodes (e.g., BD Rhapsody, or Drop-seq) or disruptable hydrogel particles enclosing releasable stochastic barcodes (e.g., 10× Genomics, or Abseq). The functionalized bead can be a control for determining efficiency of single cell workflows, analogous to external RNA control consortiums (ERCCs) being used for bulk RNAseq or microarray studies.

Disclosed herein include methods for determining the numbers of targets using a plurality of control particle oligonucleotides. The methods for determining the number of targets (e.g., gene expression) can be used with other methods disclosed herein. For example, a workflow can be used for determining protein expression and gene expression using a plurality of control particle oligonucleotides. In some embodiments, the method comprises: barcoding (e.g., stochastically barcoding) a plurality of targets of a cell of a plurality of cells and a plurality of control particle oligonucleotides using a plurality of barcodes (e.g., stochastic barcodes) to create a plurality of barcoded targets (e.g., stochastically barcoded targets) and a plurality of barcoded control particle oligonucleotides (e.g., stochastically barcoded control particle oligonucleotides), wherein each of the plurality of barcodes comprises a cell label sequence, a barcode sequence (e.g., a molecular label), and a target-binding region, wherein at least two barcodes of the plurality of barcodes comprise different barcode sequences (e.g., molecular labels), and wherein at least two barcodes of the plurality of barcodes comprise an identical cell label sequence, wherein a control particle composition comprises a control particle associated with the plurality of control particle oligonucleotides, wherein each of the plurality of control particle oligonucleotides comprises a control barcode sequence and a pseudo-target region comprising a sequence substantially complementary to the target-binding region of at least one of the plurality of barcodes. The method can comprise: obtaining sequencing data of the plurality of barcoded targets and the plurality of barcoded control particle oligonucleotides; counting the number of barcode sequences (e.g., molecular labels) with distinct sequences associated with the plurality of control particle oligonucleotides with the control barcode sequence in the sequencing data. The method can comprise: for at least one target of the plurality of targets: counting the number of barcode sequences with distinct sequences associated with the target in the sequencing data; and estimating the number of the target, wherein the number of the target estimated correlates with the number of barcodes sequences (e.g., molecular labels) with distinct sequences associated with the target counted and the number of barcode sequences (e.g., molecular labels) with distinct sequences associated with the control barcode sequence. In some embodiments, the pseudo-target region comprises a poly(dA) region. The pseudo-target region can comprise a subsequence of the target.

In some embodiments, the number of the target estimated can correlate with the number of barcode sequences (e.g., molecular labels) with distinct sequences associated with the target counted, the number of barcode sequences (e.g., molecular labels) with distinct sequences associated with the control barcode sequence, and the number of the plurality of control particle oligonucleotides comprising the control barcode sequence. The number of the target estimated can correlate with the number of barcode sequences (e.g., molecular labels) with distinct sequences associated with the target counted, and a ratio of the number of the plurality of control particle oligonucleotides comprising the control barcode sequence and the number of barcode sequences (e.g., molecular labels) with distinct sequences associated with the control barcode sequence.

For example, if the control particle has 100 control particle oligonucleotides with a particular control barcode sequence and the number of barcode sequences (e.g., molecular labels) with distinct sequences associated with the control barcode sequence (e.g., the number of control particle oligonucleotides with the control barcode sequence that survive the library preparation process) is 80, then the efficiency of the library preparation (e.g., reverse transcription, amplification, etc.) is 80%. Thus, data from different library preparations can be compared by normalizing using the library preparation efficiency.

As another example, the control particle can comprise five control particle oligonucleotides with a particular control barcode sequencing mimicking a low expression gene. If the number of barcode sequences (e.g., molecular labels) with distinct sequences associated with the control barcode sequence is five, and a low expression gene is not detected, then a conclusion that the low expression gene is not expressed (or the cell has fewer than five mRNAs of the gene) can be made. However, if the number of barcode sequences (e.g., molecular labels) with distinct sequences associated with the control barcode sequence is zero, and a low expression gene is not detected, then a conclusion that the low expression gene is not expressed cannot be made.

Capture efficiency can be determined for control particle oligonucleotides with different abundance. Normalization can be performed based on the capture efficiency of control particle oligonucleotides with two or more control barcode sequences. In some embodiments, counting the number of barcode sequences (e.g., molecular labels) with distinct sequences associated with the plurality of control particle oligonucleotides with the control barcode sequence in the sequencing data comprises: counting the number of barcode sequences (e.g., molecular labels) with distinct sequences associated with the first control barcode sequence in the sequencing data; and counting the number of barcode sequences (e.g., molecular labels) with distinct sequences associated with the second control barcode sequence in the sequencing data. The number of the target estimated can correlate with the number of barcode sequences (e.g., molecular labels) with distinct sequences associated with the target counted, the number of barcode sequences (e.g., molecular labels) with distinct sequences associated with the first control barcode sequence, and the number of barcode sequences (e.g., molecular labels) with distinct sequences associated with the second control barcode sequence.

In some embodiments, the method comprises releasing the at least one of the plurality of control particle oligonucleotides from the control particle prior to stochastically barcoding the plurality of targets and the control particle and the plurality of control particle oligonucleotides.

In some embodiments, barcoding (e.g., stochastically barcoding) the plurality of targets and the plurality of control particle oligonucleotides using the plurality of barcodes (e.g., stochastic barcodes) comprises: contacting the plurality of barcodes with targets of the plurality of targets and control particle oligonucleotides of the plurality of control particle oligonucleotides to generate barcodes hybridized to the targets and the control particle oligonucleotides; and extending the barcodes hybridized to the targets and the control particle oligonucleotides to generate the plurality of barcoded targets and the plurality of barcoded control particle oligonucleotides (e.g., the plurality of stochastically barcoded targets and the plurality of stochastically barcoded control particle oligonucleotides). Extending the barcodes can comprise extending the barcodes using a DNA polymerase, a reverse transcriptase, or a combination thereof.

In some embodiments, the method comprises amplifying the plurality of stochastically barcoded targets and the plurality of stochastically barcoded control particle oligonucleotides to produce a plurality of amplicons. Amplifying the plurality of stochastically barcoded targets and the plurality of stochastically barcoded control particle oligonucleotides can comprise amplifying, using polymerase chain reaction (PCR), at least a portion of the barcode sequence (e.g., molecular label) and at least a portion of the control particle oligonucleotide or at least a portion of the barcode sequence (e.g., molecular label) and at least a portion of the control particle oligonucleotide. Obtaining the sequencing data can comprise obtaining sequencing data of the plurality of amplicons. Obtaining the sequencing data can comprise sequencing the at least a portion of the barcode sequence (e.g., molecular label) and the at least a portion of the control particle oligonucleotide, or the at least a portion of the barcode sequence (e.g., molecular label) and the at least a portion of the control particle oligonucleotide.

Microwell Cartridge or Array Workflow

Figure 10A:
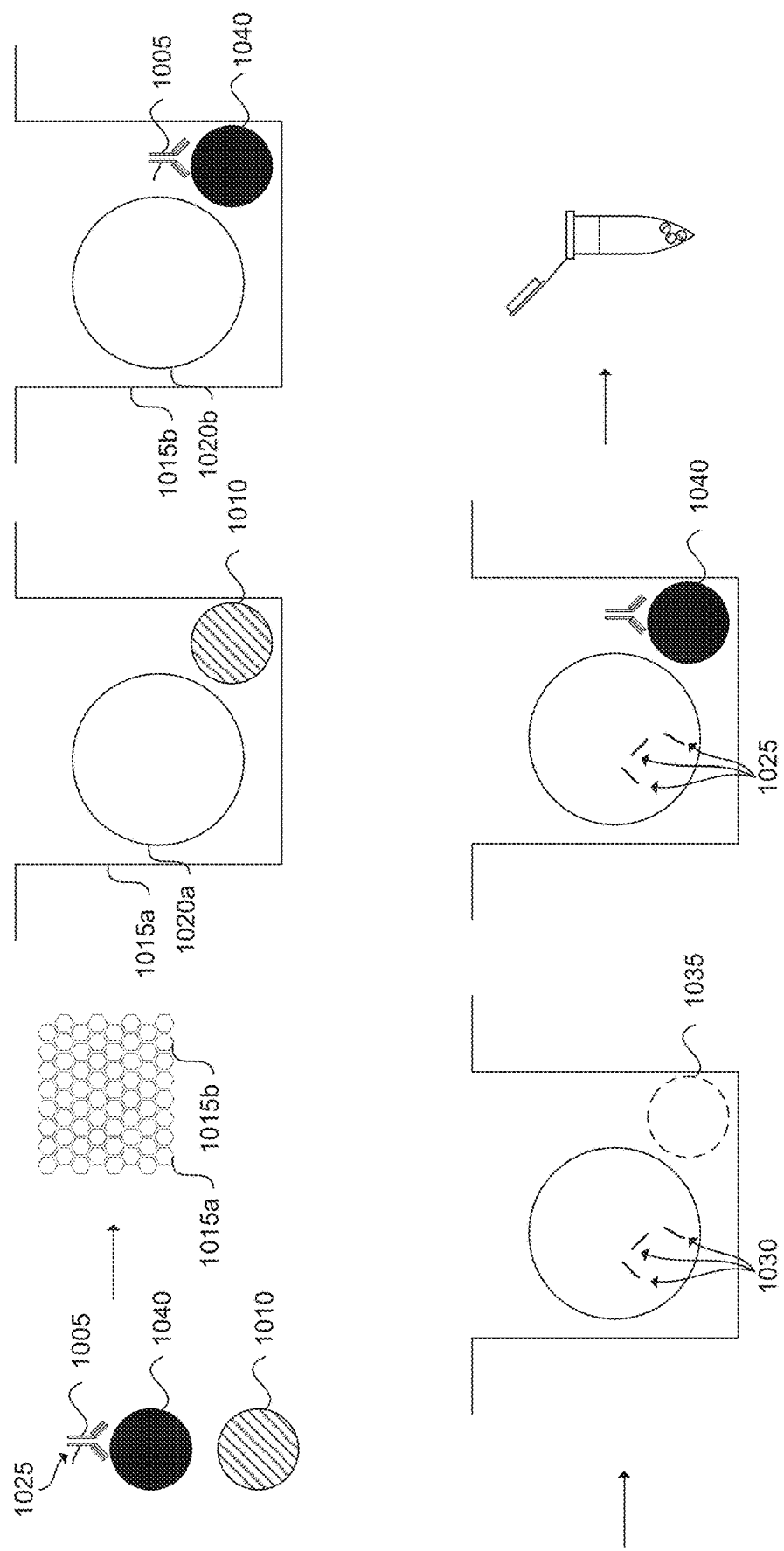
FIG. 10A is a schematic illustration of an exemplary workflow of using particles functionalized with oligonucleotides for single cell sequencing control.
Figure 10B:
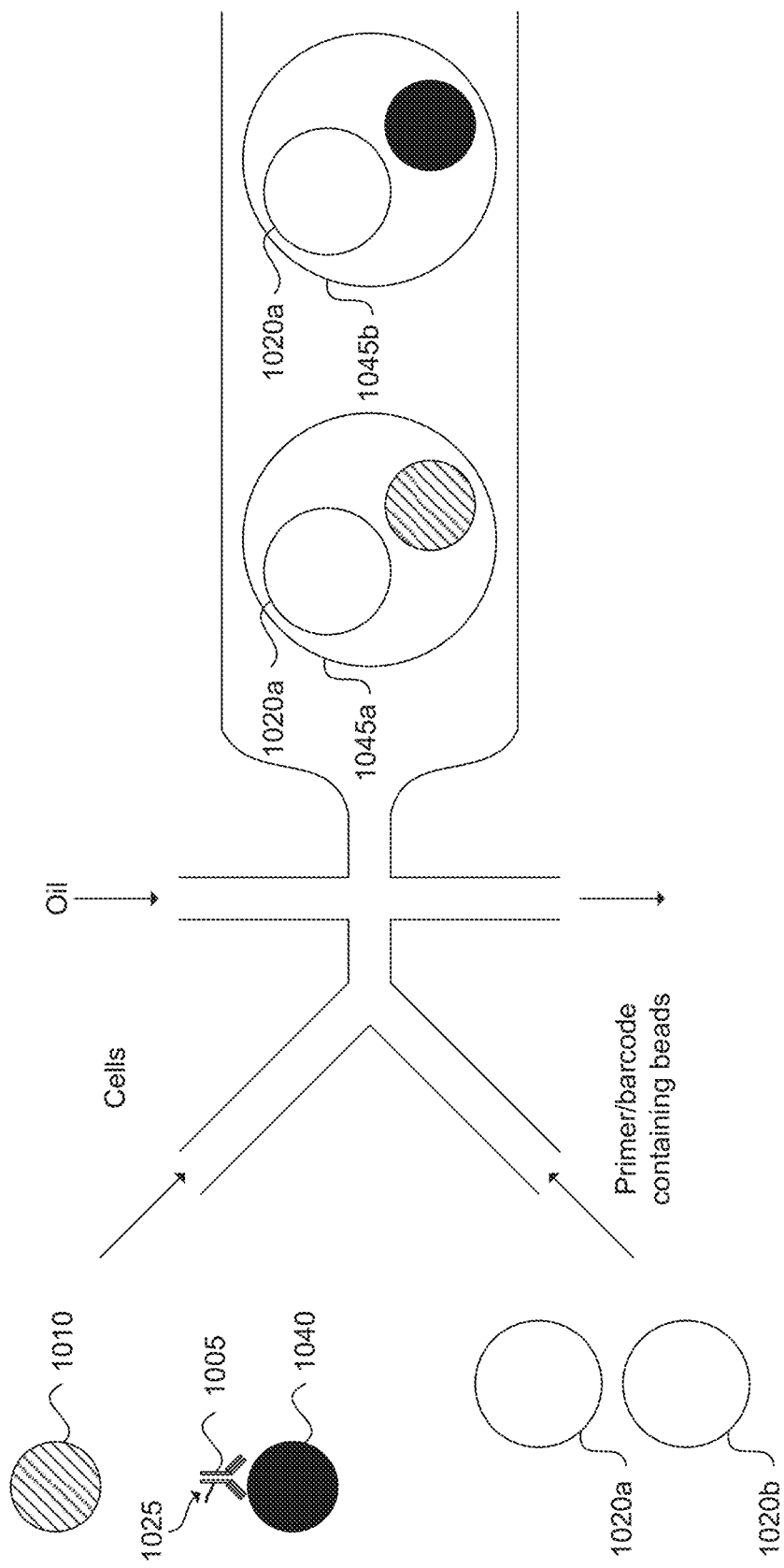
FIG. 10B is a schematic illustration of another exemplary workflow of using particles functionalized with oligonucleotides for single cell sequencing control.

FIG. 10 is a schematic illustration of an exemplary workflow of using particles functionalized with oligonucleotides for single cell sequencing control. In some embodiments, a control particle composition comprises a plurality of control particle oligonucleotides associated with a control particle 1004. For example, a control particle 1040 can be associated with a control particle oligonucleotide 1025 conjugated to an antibody 1005 bound to the control particle 1040. A plurality of control particles 1040 functionalized with control particle oligonucleotides 1025 can be spiked into a plurality of cells at, for example, 5%. Control particles 1040 can be treated as "cells" in the subsequent workflow. The control particles 1040 can also be referred to as control cells or control cell particles. Cells 1010 and the control particles 1040 can be then separated into a plurality of compartments, such as wells of a microwell array, wherein a single compartment 1015a, 1015b is sized to fit a single cell or control particle and a single bead 1020a, 1020b. Beads 1020a, 1020b can be loaded into the compartments 1015a, 1015b

Each bead can comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The oligonucleotides 1025 conjugated to the antibody 1005 can be detached from the antibody 1005 using chemical, optical or other means. The cell 1010 can be lysed 1035 to release nucleic acids within the cell, such as genomic DNA or cellular mRNA 1030. Cellular mRNAs 1030 and control particle oligonucleotides 1025 can be captured by the oligonucleotide probes on beads 1020a, 1020b respectively, for example, by hybridizing to the poly(dT) sequence. Beads can be retrieved and the captured cellular mRNAs 1030 and control particle oligonucleotides 1025 (e.g., corresponding to around 5000 cells in total) can be pooled.

A reverse transcriptase can be used to extend the oligonucleotide probes hybridized to the cellular mRNA 1030 and the control particle oligonucleotides 1025 using the cellular mRNA 1030 and the oligonucleotides 1025 as templates. The extension products produced by the reverse transcriptase can be subject to amplification and sequencing. Sequencing reads can be subject to demultiplexing of a cell label, a barcode sequence (e.g., a molecular label), gene identity, control particle oligonucleotide sequence, etc., which can be used to determine single cell gene expression profiles and quantity efficiency of the entire or part of the workflow (e.g., cell capture efficiency). For example, the number of control particles captured can be determined based on the number of cell labels associated with the control barcode sequence in the data. The efficiency of the workflow can be a ratio of the number of control particles captured and the number of control particles spiked in.

Microfluidics Workflow

FIG. 10 is a schematic illustration of another exemplary workflow of using particles functionalized with oligonucleotides for single cell sequencing control. A plurality of control particles 1040 functionalized with control particle oligonucleotides 1025 can be spiked into a plurality of cells at, for example, 5%. Control particles 1040 can be treated as "cells" in the subsequent workflow. The control particles 1040 can also be referred to as control cells or control cell particles. Cells 1010 and the control particles 1040 can be then separated using a microfluidics device into a plurality of compartments, such as droplets 1045a, 1045. Each droplet 1045a, 1045b can include one cell 1010 or one control particle 1040 and a hydrogel bead 1020a, 1020b.

Each bead 1020a, 1020b can comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The bead 1020a, 1020b can include reagents for the subsequent workflow (e.g., reverse transcription). The oligonucleotides 1025 conjugated to the antibody 1005 can be detached from the antibody 1005 using chemical, optical or other means. The cell 1010 can be lysed 1035 to release nucleic acids within the cell, such as genomic DNA or cellular mRNA 1030. Cellular mRNAs 630 and control particle oligonucleotides 1025 can be captured by the oligonucleotide probes released from beads 1020a, 1020b respectively, for example, by hybridizing to the poly(dT)

sequence. A reverse transcriptase can be used to extend the oligonucleotide probes hybridized to the cellular mRNA 1030 and the oligonucleotides 1025 using the cellular mRNA 1030 and the oligonucleotides 1025 as templates.

After breaking up the droplets 1045a, 1045b, the extension products produced by the reverse transcriptase can be pooled and subject to amplification and sequencing. Sequencing reads can be subject to demultiplexing of cell label, molecular label, gene identity, control particle oligonucleotide sequence, etc. to determine single cell gene expression profiles and quantity efficiency of the entire or part of the workflow.

Control Oligonucleotides for Determining Single Cell Sequencing Efficiency

Also disclosed herein include methods, kits and systems for determining single cell sequencing efficiency. Such methods, kits and systems can be used in, or in combination with, any suitable methods, kits and systems disclosed herein, such as the methods, kits and systems for measuring cellular component expression level (for example protein expression level) using cellular component binding reagents associated with oligonucleotides.

In some embodiments, by labeling single cells with antibodies conjugated with oligonucleotides (e.g., with a universal antibody or biomarker antibody) and generating next generation sequencing libraries with them, the signals from the oligonucleotides in NGS reads can be used to determine single cell NGS efficiency. This can then be used as a QC step or an evaluation tool for efficacy for different single cell sequencing platforms. For example, the control oligonucleotides can be used in any suitable methods, kits and systems disclosed herein, for example the methods, kits and systems for measuring cellular component expression level (for example protein expression level) using cellular component binding reagents associated with oligonucleotides.

Antibodies conjugated with oligonucleotides (referred to herein as "AbOs" can be used with any single cell workflow as a single cell sequencing control. Single cell workflows can utilize microwell arrays or microwell cartridges (e.g., BD Rhapsody™) or microfluidics devices (e.g., 10× Genomics (San Francisco, CA), Drop-seq (McCarroll Lab, Harvard Medical School (Cambridge, Massachusetts); Macosko et al., Cell, 2015 May 21 16; 5:1202, the content of which is incorporated herein by reference in its entirety), or Abseq (Mission Bio (San Francisco, CA); Shahi et al., Sci Rep. 2017 Mar. 14; 7:44447, the content of which is hereby incorporated by reference in its entirety) in combination with solid or semisolid particles associated with barcodes, such as stochastic barcodes (e.g., BD Rhapsody, or Drop-seq), or disruptable hydrogel particles enclosing releasable barcodes, such as stochastic barcodes (e.g., 10X Genomics, or Abseq). AbOs can be a control for determining efficiency of single cell workflows. For example, the single cell sequencing platform from 10× Genomics performs single cell capture using emulsions to encapsulate single cells in droplets. Because these droplets cannot be easily visualized, capture efficiency of single cells cannot be easily determined. The use of AbOs upstream of such single cell sequencing workflow allows users to evaluate the single cell capture efficiency after sequencing and rate of doublet formation.

Figure 11:
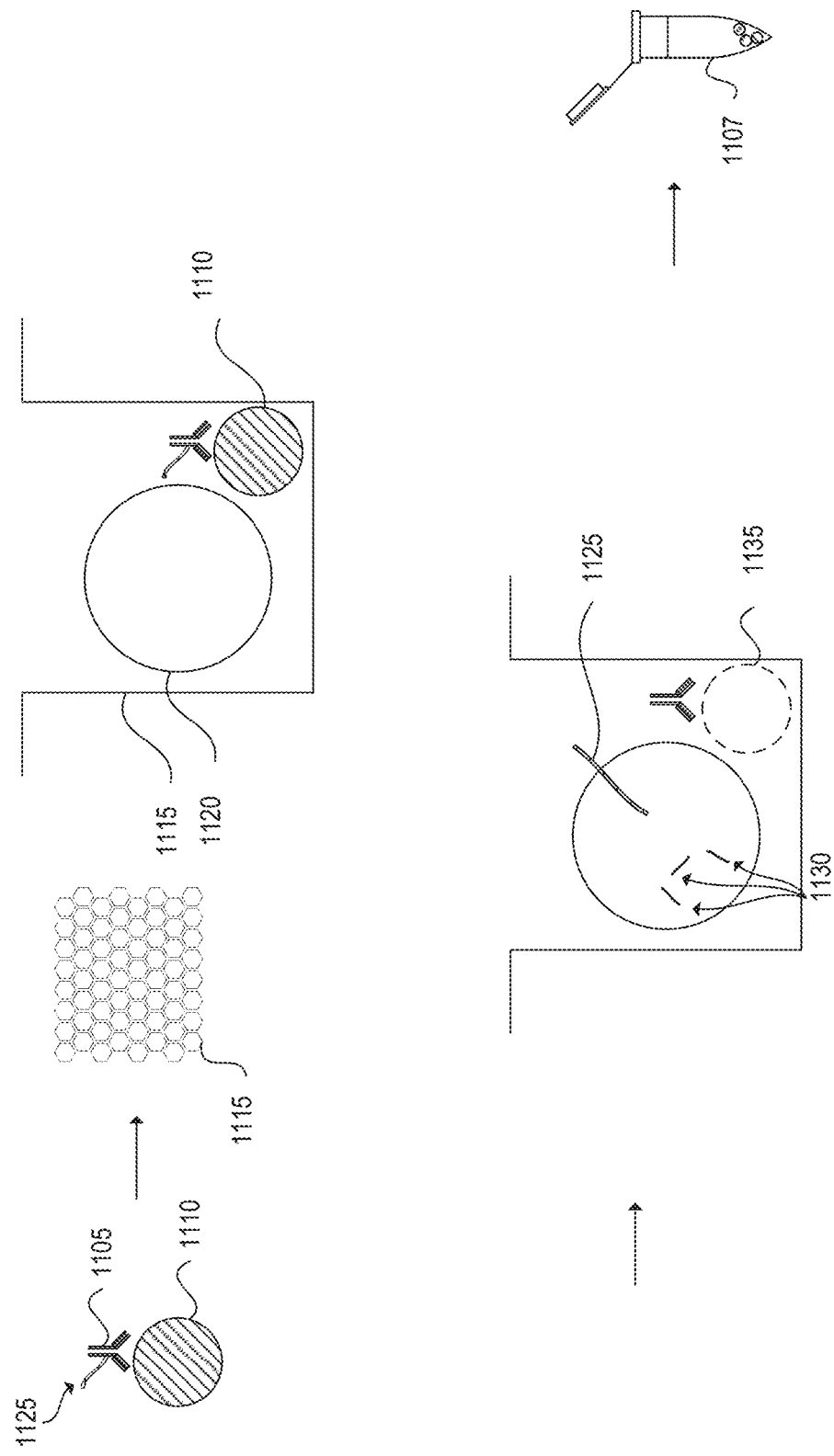
FIG. 11 shows a schematic illustration of an exemplary workflow of using control oligonucleotide-conjugated antibodies for determining single cell sequencing efficiency.

FIG. 11 shows a schematic illustration of an exemplary workflow of using control oligonucleotide-conjugated antibodies for determining single cell sequencing efficiency. In some embodiments, one or more cells (e.g., 5000) 1100 can be stained with an antibody 1105 conjugated with a control oligonucleotide 1125 prior to being loading onto a microwell 1115 of a microwell cartridge or array. Cells 1110 can be then separated into a plurality of compartments, such as wells of a microwell array, wherein a single compartment 1115 is sized to fit a single cell and a single bead 1120.

The bead can, for example, comprise a plurality of oligonucleotide probes, which can comprise a cell label that is common to all oligonucleotide probes on a bead, and barcode sequences (e.g., molecular label sequences). In some embodiments, each oligonucleotide probe can comprise a target binding region, for example, a poly(dT) sequence. The oligonucleotides 1125 conjugated to the antibody 1105 can be detached from the antibody 1105 using chemical, optical or other means. The cell 1110 can be lysed 1135 to release nucleic acids within the cell, such as genomic DNA or cellular mRNA 1130. Cellular mRNAs 1130 and control oligonucleotides 1125 can be captured by the oligonucleotide probes on a bead 1120, for example, by hybridizing to the poly(dT) sequence. Beads can be retrieved and the captured cellular mRNAs 1130 (e.g., corresponding to around 5000 cells in total) can be pooled.

A reverse transcriptase can be used to extend the oligonucleotide probes hybridized to the cellular mRNA 1130 and the oligonucleotides 1125 using the cellular mRNA 1130 and the oligonucleotides 1125 as templates. The extension products produced by the reverse transcriptase can be subject to amplification and sequencing. Sequencing reads can be subject to demultiplexing of a cell label, a barcode sequence (e.g., a molecular label), gene identity, control oligonucleotide sequence, etc. to determine single cell gene expression profiles and quantity efficiency of the entire or part of the workflow (e.g., cell capture efficiency). The number of cells that are captured and go through the library preparation successfully (e.g., fewer than 5000 cells) can be determined.

Figure 12:
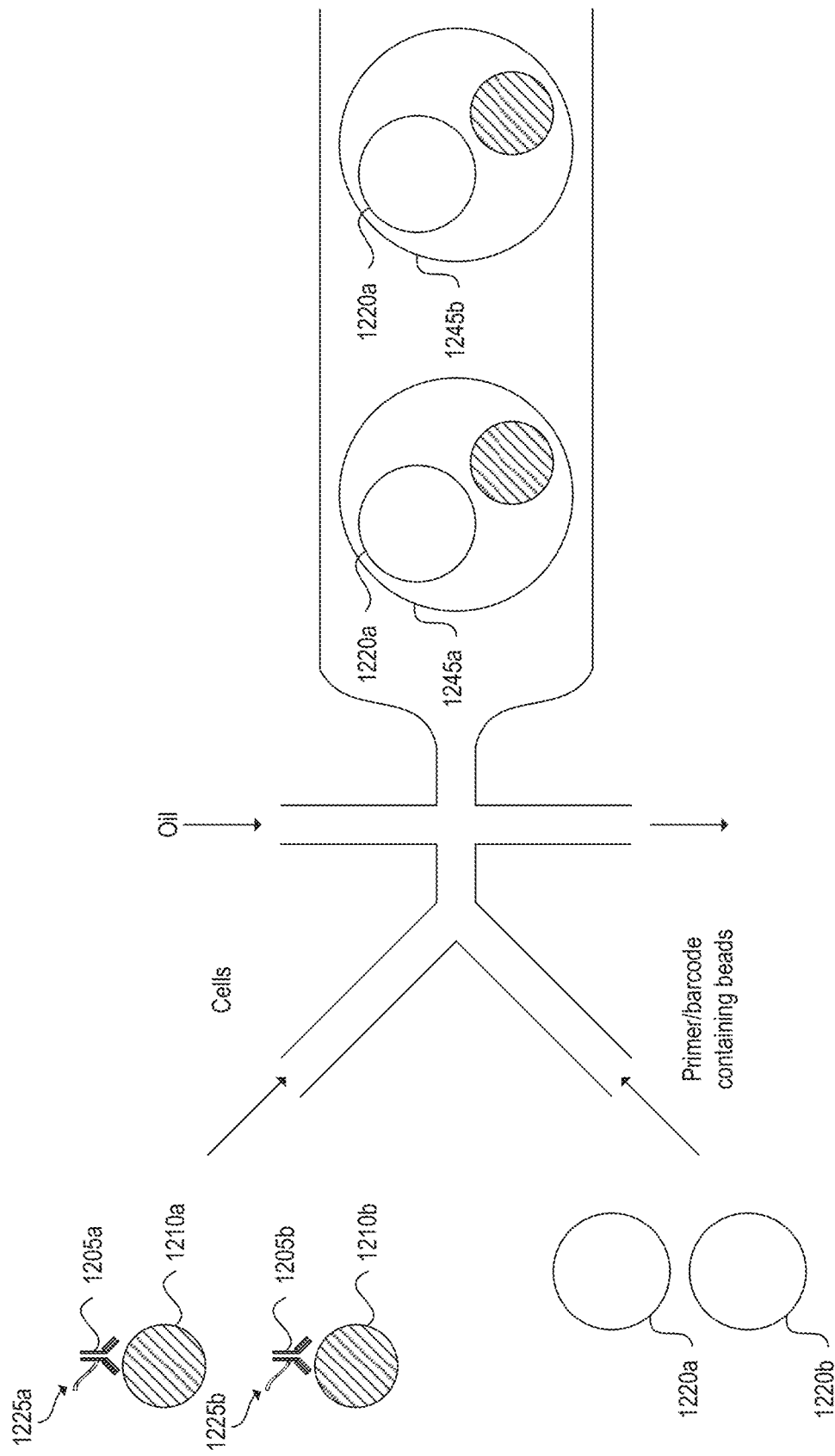
FIG. 12 shows another schematic illustration of an exemplary workflow of using control oligonucleotide-conjugated antibodies for determining single cell sequencing efficiency.

FIG. 12 shows another schematic illustration of an exemplary workflow of using control oligonucleotide-conjugated antibodies for determining single cell sequencing efficiency. In FIG. 12, droplets 1245a, 1245b containing a single cell 1210a, 1210b and a single particle 1220a, 1220b can be formed using a microfluidic device. The single cells 1210a, 1210b can be bound to antibodies 1205a, 1205b conjugated with control oligonucleotides 1225a, 1225b. After cell lysis and reverse transcription in droplets 1245a, 1245b, droplets can be broken up and the content pooled for library preparation. The number of cells that are captured and go through the library preparation successfully can be determined.

Figures 13A, 13B:
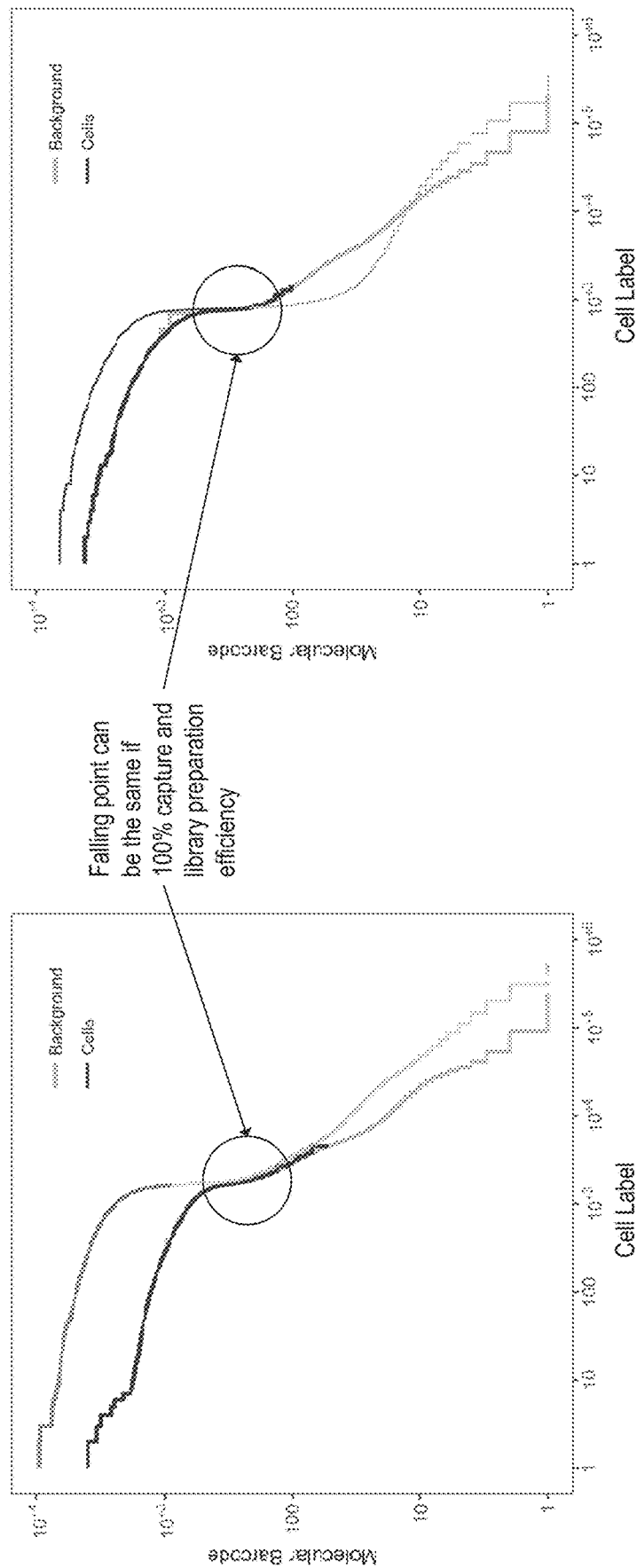
FIGS. 13A-13C are plots showing that control oligonucleotides can be used for cell counting.
Figure 13C:
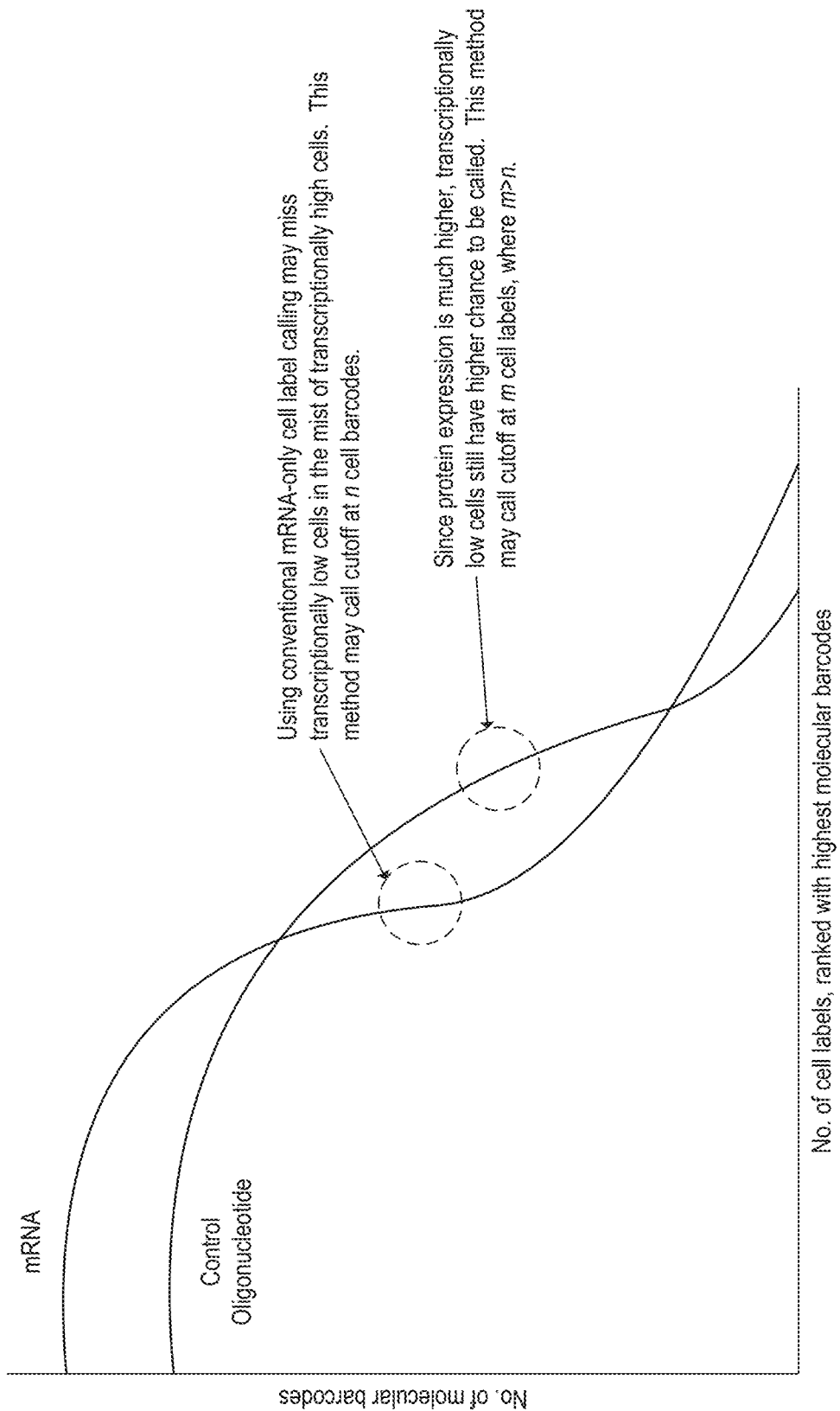

FIGS. 13A-13C are plots showing that control oligonucleotides can be used for cell counting. FIGS. 13A-13B show that control oligonucleotides of AbOs can be used as a control for cell counting. The falling points of the mRNA counts plot and the control oligonucleotide counts plot can coincide if 100% capture and library preparation efficiency is achieved. FIG. 13C shows that using conventional mRNA-only cell label calling may miss transcriptionally low cells in the mist of transcriptionally high cells. This method may call cutoff at n cell labels. This may occur when quiescent T cells within a large population of activated T cells, where activated T cells can have several fold higher in RNA transcription. This may also occur when in a targeted panel (e.g., cancer panel), non-targeted cells (non-cancer cells) with low expression of targeted genes are going to be dropped off. However, since protein expression is much higher, transcriptionally low cells still have higher chance to be called. This method may call cutoff at m cell labels, where m>n.

Disclosed herein include methods for sequencing control. For example, the methods can be used for determining single cell sequencing efficiency. The methods for determining single cell sequencing efficiency can be used with other methods disclosed herein. For example, the method for used for single cell sequencing efficiency can be used with the method for determining protein expression. As another example, a workflow can be used for determining single cell sequencing efficiency, protein expression, and/or gene expression.

In some embodiments, the method comprises: contacting one or more cells of a plurality of cells with a control composition of a plurality of control compositions, wherein a cell of the plurality of cells comprises a plurality of targets and a plurality of protein targets, wherein each of the plurality of control compositions comprises a protein binding reagent associated with a control oligonucleotide, wherein the protein binding reagent is capable of specifically binding to at least one of the plurality of protein targets, and wherein the control oligonucleotide comprises a control barcode sequence and a pseudo-target region comprising a sequence substantially complementary to the target-binding region of at least one of the plurality of barcodes; barcoding the control oligonucleotides using a plurality of barcodes to create a plurality of barcoded control oligonucleotides, wherein each of the plurality of barcodes comprises a cell label sequence, a barcode sequence (e.g., a molecular label sequence), and a target-binding region, wherein the barcode sequences (e.g., the molecular label sequences) of at least two barcodes of the plurality of barcodes comprise different sequences, and wherein at least two barcodes of the plurality of barcodes comprise an identical cell label sequence; obtaining sequencing data of the plurality of barcoded control oligonucleotides; determining at least one characteristic (e.g., the number of cells that are captured and go through the library preparation successfully) of the one or more cells using at least one characteristic of the plurality of barcoded control oligonucleotides in the sequencing data. In some embodiments, the pseudo-target region comprises a poly(dA) region.

In some embodiments, determining the at least one characteristic of the one or more cells comprises: determining the number of cell label sequences with distinct sequences associated with the plurality of barcoded control oligonucleotides in the sequencing data; and determining the number of the one or more cells using the number of cell label sequences with distinct sequences associated with the plurality of barcoded control oligonucleotides. The method can comprise: determining single cell capture efficiency based the number of the one or more cells determined. The method can comprise: comprising determining single cell capture efficiency based on the ratio of the number of the one or more cells determined and the number of the plurality of cells.

In some embodiments, determining the at least one characteristic of the one or more cells using the characteristics of the plurality of barcoded control oligonucleotides in the sequencing data comprises: for each cell label in the sequencing data, determining the number of barcode sequences (e.g., molecular label sequences) with distinct sequences associated with the cell label and the control barcode sequence; and determining the number of the one or more cells using the number of barcode sequences with distinct sequences associated with the cell label and the control barcode sequence. Determining the number of barcode sequences with distinct sequences associated with the cell label and the control barcode sequence can comprise: for each cell label in the sequencing data, determining the number of barcode sequences with the highest number of distinct sequences associated with the cell label and the control barcode sequence. Determining the number of the one or more cells using the number of barcode sequences with distinct sequences associated with the cell label and the control barcode sequence can comprise: generating a plot of the number of barcode sequences with the highest number of distinct sequences with the number of cell labels in the sequencing data associated with the number of barcode sequences with the highest number of distinct sequences; and determining a cutoff in the plot as the number of the one or more cells.

In some embodiments, the method comprises releasing the control oligonucleotide from the cellular component binding reagent (e.g., the protein binding reagent) prior to barcoding the control oligonucleotides. In some embodiments, the method comprises removing unbound control compositions of the plurality of control compositions. Removing the unbound control compositions can comprise washing the one or more cells of the plurality of cells with a washing buffer. Removing the unbound control compositions can comprise selecting cells bound to at least one cellular component binding reagent of the control composition using flow cytometry.

In some embodiments, barcoding the control oligonucleotides comprises: barcoding the control oligonucleotides using a plurality of stochastic barcodes to create a plurality of stochastically barcoded control oligonucleotides. In some embodiments, barcoding the plurality of control oligonucleotides using the plurality of barcodes comprises: contacting the plurality of barcodes with control oligonucleotides of the plurality of control compositions to generate barcodes hybridized to the control oligonucleotides; and extending the stochastic barcodes hybridized to the control oligonucleotides to generate the plurality of barcoded control oligonucleotides. Extending the barcodes can comprise extending the barcodes using a DNA polymerase, a reverse transcriptase, or a combination thereof. In some embodiments, the method comprises amplifying the plurality of barcoded control oligonucleotides to produce a plurality of amplicons. Amplifying the plurality of barcoded control oligonucleotides can comprise amplifying, using polymerase chain reaction (PCR), at least a portion of the stochastic barcode sequence (e.g., a molecular label sequence) and at least a portion of the control oligonucleotide. In some embodiments, obtaining the sequencing data comprises obtaining sequencing data of the plurality of amplicons. Obtaining the sequencing data can comprise sequencing the at least a portion of the molecular label sequence and the at least a portion of the control oligonucleotide.

Cell Overloading and Multiplet Identification

Also disclosed herein include methods, kits and systems for identifying cell overloading and multiplet. Such methods, kits and systems can be used in, or in combination with, any suitable methods, kits and systems disclosed herein, for example the methods, kits and systems for measuring cellular component expression level (such as protein expression level) using cellular component binding reagents associated with oligonucleotides.

Using current cell-loading technology, when about 20000 cells are loaded into a microwell cartridge or array with ~60000 microwells, the number of microwells or droplets with two or more cells (referred to as doublets or multiplets) can be minimal. However, when the number of cells loaded increases, the number of microwells or droplets with multiple cells can increase significantly. For example, when about 50000 cells are loaded into about 60000 microwells of a microwell cartridge or array, the percentage of microwells with multiple cells can be quite high, such as 11-14%. Such loading of high number of cells into microwells can be referred to as cell overloading. However, if the cells are divided into a number of groups (e.g., 5), and cells in each group are labeled with sample indexing oligonucleotides with distinct sample indexing sequences, a cell label (e.g., a cell label of a barcode, such as a stochastic barcode) associated with two or more sample indexing sequences can be identified in sequencing data and removed from subsequent processing. In some embodiments, the cells are divided into a large number of groups (e.g., 10000), and cells in each group are labeled with sample indexing oligonucleotides with distinct sample indexing sequences, a sample label associated with two or more sample indexing sequences can be identified in sequencing data and removed from subsequent processing. In some embodiments, different cells are labeled with cell identification oligonucleotides with distinct cell identification sequences, a cell identification sequence associated with two or more cell identification oligonucleotides can be identified in sequencing data and removed from subsequent processing. Such higher number of cells can be loaded into microwells relative to the number of microwells in a microwell cartridge or array.

Disclosed herein includes methods for sample identification. In some embodiments, the method comprises: contacting a first plurality of cells and a second plurality of cells with two sample indexing compositions respectively, wherein each of the first plurality of cells and each of the second plurality of cells comprise one or more cellular components, wherein each of the two sample indexing compositions comprises a cellular component binding reagent associated with a sample indexing oligonucleotide, wherein the cellular component binding reagent is capable of specifically binding to at least one of the one or more cellular components, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying one or more cell label sequences that is each associated with two or more sample indexing sequences in the sequencing data obtained; and removing the sequencing data associated with the one or more cell label sequences that is each associated with two or more sample indexing sequences from the sequencing data obtained and/or excluding the sequencing data associated with the one or more cell label sequences that is each associated with two or more sample indexing sequences from subsequent analysis (e.g., single cell mRNA profiling, or whole transcriptome analysis). In some embodiments, the sample indexing oligonucleotide comprises a barcode sequence (e.g., a molecular label sequence), a binding site for a universal primer, or a combination thereof.

For example, the method can be used to load 50000 or more cells (compared to 10000-20000 cells) using sample indexing. Sample indexing can use oligonucleotide-conjugated cellular component binding reagents (e.g., antibodies) or cellular component binding reagents against a cellular component (e.g., a universal protein marker) to label cells from different samples with a unique sample index. When two or more cells from different samples, two or more cells from different populations of cells of a sample, or two or more cells of a sample, are captured in the same microwell or droplet, the combined "cell" (or contents of the two or more cells) can be associated with sample indexing oligonucleotides with different sample indexing sequences (or cell identification oligonucleotides with different cell identification sequences). The number of different populations of cells can be different in different implementations. In some embodiments, the number of different populations can be, or be about, 2, 3, 4, 5, 6, 7, 8, 9, 10, 20, 30, 40, 50, 60, 70, 80, 90, 100, or a number or a range between any two of these values. In some embodiments, the number of different populations can be at least, or be at most, 2, 3, 4, 5, 6, 7, 8, 9, 10, 20, 30, 40, 50, 60, 70, 80, 90, or 100. The number, or the average number, of cells in each population can be different in different implementations. In some embodiments, the number, or the average number, of cells in each population can be, or be about, 1, 2, 3, 4, 5, 6, 7, 8, 9, 10, 20, 30, 40, 50, 60, 70, 80, 90, 100, or a number or a range between any two of these values. In some embodiments, the number, or the average number, of cells in each population can be at least, or be at most, 1, 2, 3, 4, 5, 6, 7, 8, 9, 10, 20, 30, 40, 50, 60, 70, 80, 90, or 100. When the number, or the average number, of cells in each population is sufficiently small (e.g., equal to, or fewer than, 50, 25, 10, 5, 4, 3, 2, or 1 cells per population), the sample indexing composition for cell overloading and multiplet identification can be referred to as cell identification compositions.

Cells of a sample can be divided into multiple populations by aliquoting the cells of the sample into the multiple populations. A "cell" associated with more than one sample indexing sequence in the sequencing data can be identified as a "multiplet" based on two or more sample indexing sequences associated with one cell label sequence (e.g., a cell label sequence of a barcode, such as a stochastic barcode) in the sequencing data. The sequencing data of a combined "cell" is also referred to herein as a multiplet. A multiplet can be a doublet, a triplet, a quartet, a quintet, a sextet, a septet, an octet, a nonet, or any combination thereof. A multiplet can be any n-plet. In some embodiments, n is, or is about, 2, 3, 4, 5, 6, 7, 8, 9, 10, 11, 12, 13, 14, 15, 16, 17, 18, 19, 20, or a range between any two of these values. In some embodiments, n is at least, or is at most, 2, 3, 4, 5, 6, 7, 8, 9, 10, 11, 12, 13, 14, 15, 16, 17, 18, 19, or 20.

When determining expression profiles of single cells, two cells may be identified as one cell and the expression profiles of the two cells may be identified as the expression profile for one cell (referred to as a doublet expression profile). For example, when determining expression profiles of two cells using barcoding (e.g., stochastic barcoding), the mRNA molecules of the two cells may be associated with barcodes having the same cell label. As another example, two cells may be associated with one particle (e.g., a bead). The particle can include barcodes with the same cell label. After lysing the cells, the mRNA molecules in the two cells can be associated with the barcodes of the particle, thus the same cell label. Doublet expression profiles can skew the interpretation of the expression profiles.

A doublet can refer to a combined "cell" associated with two sample indexing oligonucleotides with different sample indexing sequences. A doublet can also refer to a combined "cell" associated with sample indexing oligonucleotides with two sample indexing sequences. A doublet can occur when two cells associated with two sample indexing oligonucleotides of different sequences (or two or more cells associated with sample indexing oligonucleotides with two different sample indexing sequences) are captured in the same microwell or droplet, the combined "cell" can be associated with two sample indexing oligonucleotides with different sample indexing sequences. A triplet can refer to a combined "cell" associated with three sample indexing oligonucleotides all with different sample indexing sequences, or a combined "cell" associated with sample indexing oligonucleotides with three different sample indexing sequences. A quartet can refer to a combined "cell" associated with four sample indexing oligonucleotides all with different sample indexing sequences, or a combined "cell" associated with sample indexing oligonucleotides with four different sample indexing sequences. A quintet can refer to a combined "cell" associated with five sample indexing oligonucleotides all with different sample indexing sequences, or a combined "cell" associated with sample indexing oligonucleotides with five different sample indexing sequences. A sextet can refer to a combined "cell" associated with six sample indexing oligonucleotides all with different sample indexing sequences, or a combined "cell" associated with sample indexing oligonucleotides with six different sample indexing sequences. A septet can refer to a combined "cell" associated with seven sample indexing oligonucleotides all with different sample indexing sequences, or a combined "cell" associated with sample indexing oligonucleotides with seven different sample indexing sequences. A octet can refer to a combined "cell" associated with eight sample indexing oligonucleotides all with different sample indexing sequences, or a combined "cell" associated with sample indexing oligonucleotides with eight different sample indexing sequences. A nonet can refer to a combined "cell" associated with nine sample indexing oligonucleotides all with different sample indexing sequences, or a combined "cell" associated with sample indexing oligonucleotides with nine different sample indexing sequences. A multiplet can occur when two or more cells associated with two or more sample indexing oligonucleotides of different sequences (or two or more cells associated with sample indexing oligonucleotides with two or more different sample indexing sequences) are captured in the same microwell or droplet, the combined "cell" can be associated with sample indexing oligonucleotides with two or more different sample indexing sequences.

As another example, the method can be used for multiplet identification, whether in the context of sample overloading or in the context of loading cells onto microwells of a microwell array or generating droplets containing cells. When two or more cells are loaded into one microwell, the resulting data from the combined "cell" (or contents of the two or more cells) is a multiplet with aberrant gene expression profile. By using sample indexing, one can recognize some of these multiplets by looking for cell labels that are each associated with or assigned to two or more sample indexing oligonucleotides with different sample indexing sequences (or sample indexing oligonucleotides with two or more sample indexing sequences). With sample indexing sequence, the methods disclosed herein can be used for multiplet identification (whether in the context of sample overloading or not, or in the context of loading cells onto microwells of a microwell array or generating droplets containing cells). In some embodiments, the method comprises: contacting a first plurality of cells and a second plurality of cells with two sample indexing compositions respectively, wherein each of the first plurality of cells and each of the second plurality of cells comprise one or more cellular components, wherein each of the two sample indexing compositions comprises a cellular component binding reagent associated with a sample indexing oligonucleotide, wherein the cellular component binding reagent is capable of specifically binding to at least one of the one or more cellular components, wherein the sample indexing oligonucleotide comprises a sample indexing sequence, and wherein sample indexing sequences of the two sample indexing compositions comprise different sequences; barcoding the sample indexing oligonucleotides using a plurality of barcodes to create a plurality of barcoded sample indexing oligonucleotides, wherein each of the plurality of barcodes comprises a cell label sequence, a barcode sequence (e.g., a molecular label sequence), and a target-binding region, wherein barcode sequences of at least two barcodes of the plurality of barcodes comprise different sequences, and wherein at least two barcodes of the plurality of barcodes comprise an identical cell label sequence; obtaining sequencing data of the plurality of barcoded sample indexing oligonucleotides; and identifying one or more multiplet cell label sequences that is each associated with two or more sample indexing sequences in the sequencing data obtained.

The number of cells that can be loaded onto microwells of a microwell cartridge or into droplets generated using a microfluidics device can be limited by the multiplet rate. Loading more cells can result in more multiplets, which can be hard to identify and create noise in the single cell data. With sample indexing, the method can be used to more accurately label or identify multiplets and remove the multiplets from the sequencing data or subsequent analysis. Being able to identify multiplets with higher confidence can increase user tolerance for the multiplet rate and load more cells onto each microwell cartridge or generating droplets with at least one cell each.

In some embodiments, contacting the first plurality of cells and the second plurality of cells with the two sample indexing compositions respectively comprises: contacting the first plurality of cells with a first sample indexing compositions of the two sample indexing compositions; and contacting the first plurality of cells with a second sample indexing compositions of the two sample indexing compositions. The number of pluralities of cells and the number of pluralities of sample indexing compositions can be different in different implementations. In some embodiments, the number of pluralities of cells and/or sample indexing compositions can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of pluralities of cells and/or sample indexing compositions can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000. The number of cells can be different in different implementations. In some embodiments, the number, or the average number, of cells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number, or the average number, or cells can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the method comprises: removing unbound sample indexing compositions of the two sample indexing compositions. Removing the unbound sample indexing compositions can comprise washing cells of the first plurality of cells and the second plurality of cells with a washing buffer. Removing the unbound sample indexing compositions can comprise selecting cells bound to at least one cellular component binding reagent of the two sample indexing compositions using flow cytometry. In some embodiments, the method comprises: lysing the one or more cells from each of the plurality of samples.

In some embodiments, the sample indexing oligonucleotide is configured to be detachable or non-detachable from the cellular component binding reagent. The method can comprise detaching the sample indexing oligonucleotide from the cellular component binding reagent. Detaching the sample indexing oligonucleotide can comprise detaching the sample indexing oligonucleotide from the cellular component binding reagent by UV photocleaving, chemical treatment (e.g., using reducing reagent, such as dithiothreitol), heating, enzyme treatment, or any combination thereof.

In some embodiments, barcoding the sample indexing oligonucleotides using the plurality of barcodes comprises: contacting the plurality of barcodes with the sample indexing oligonucleotides to generate barcodes hybridized to the sample indexing oligonucleotides; and extending the barcodes hybridized to the sample indexing oligonucleotides to generate the plurality of barcoded sample indexing oligonucleotides. Extending the barcodes can comprise extending the barcodes using a DNA polymerase to generate the plurality of barcoded sample indexing oligonucleotides. Extending the barcodes can comprise extending the barcodes using a reverse transcriptase to generate the plurality of barcoded sample indexing oligonucleotides.

In some embodiments, the method comprises: amplifying the plurality of barcoded sample indexing oligonucleotides to produce a plurality of amplicons. Amplifying the plurality of barcoded sample indexing oligonucleotides can comprise amplifying, using polymerase chain reaction (PCR), at least a portion of barcode sequence (e.g., the molecular label sequence) and at least a portion of the sample indexing oligonucleotide. In some embodiments, obtaining the sequencing data of the plurality of barcoded sample indexing oligonucleotides can comprise obtaining sequencing data of the plurality of amplicons. Obtaining the sequencing data comprises sequencing at least a portion of the barcode sequence and at least a portion of the sample indexing oligonucleotide. In some embodiments, identifying the sample origin of the at least one cell comprises identifying sample origin of the plurality of barcoded targets based on the sample indexing sequence of the at least one barcoded sample indexing oligonucleotide.

In some embodiments, barcoding the sample indexing oligonucleotides using the plurality of barcodes to create the plurality of barcoded sample indexing oligonucleotides comprises stochastically barcoding the sample indexing oligonucleotides using a plurality of stochastic barcodes to create a plurality of stochastically barcoded sample indexing oligonucleotides.

In some embodiments, the method includes: barcoding a plurality of targets of the cell using the plurality of barcodes to create a plurality of barcoded targets, wherein each of the plurality of barcodes comprises a cell label sequence, and wherein at least two barcodes of the plurality of barcodes comprise an identical cell label sequence; and obtaining sequencing data of the barcoded targets. Barcoding the plurality of targets using the plurality of barcodes to create the plurality of barcoded targets can include: contacting copies of the targets with target-binding regions of the barcodes; and reverse transcribing the plurality targets using the plurality of barcodes to create a plurality of reverse transcribed targets.

In some embodiments, the method comprises: prior to obtaining the sequencing data of the plurality of barcoded targets, amplifying the barcoded targets to create a plurality of amplified barcoded targets. Amplifying the barcoded targets to generate the plurality of amplified barcoded targets can comprise: amplifying the barcoded targets by polymerase chain reaction (PCR). Barcoding the plurality of targets of the cell using the plurality of barcodes to create the plurality of barcoded targets can comprise stochastically barcoding the plurality of targets of the cell using a plurality of stochastic barcodes to create a plurality of stochastically barcoded targets.

In some embodiments, the method for cell identification comprise: contacting a first plurality of one or more cells and a second plurality of one or more cells with two cell identification compositions respectively, wherein each of the first plurality of one or more cells and each of the second plurality of one or more cells comprise one or more cellular components, wherein each of the two cell identification compositions comprises a cellular component binding reagent associated with a cell identification oligonucleotide, wherein the cellular component binding reagent is capable of specifically binding to at least one of the one or more cellular components, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein the barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more cell label sequences that is each associated with two or more cell identification sequences in the sequencing data obtained; and removing the sequencing data associated with the one or more cell label sequences that is each associated with two or more cell identification sequences from the sequencing data obtained and/or excluding the sequencing data associated with the one or more cell label sequences that is each associated with two or more cell identification sequences from subsequent analysis (e.g., single cell mRNA profiling, or whole transcriptome analysis). In some embodiments, the cell identification oligonucleotide comprises a barcode sequence (e.g., a molecular label sequence), a binding site for a universal primer, or a combination thereof.

A multiplet (e.g., a doublet, triplet, etc.) can occur when two or more cells associated with two or more cell identification oligonucleotides of different sequences (or two or more cells associated with cell identification oligonucleotides with two or more different cell identification sequences) are captured in the same microwell or droplet, the combined "cell" can be associated with cell identification oligonucleotides with two or more different cell identification sequences.

Cell identification compositions can be used for multiplet identification, whether in the context of cell overloading or in the context of loading cells onto microwells of a microwell array or generating droplets containing cells. When two or more cells are loaded into one microwell, the resulting data from the combined "cell" (or contents of the two or more cells) is a multiplet with aberrant gene expression profile. By using cell identification, one can recognize some of these multiplets by looking for cell labels (e.g., cell labels of barcodes, such as stochastic barcodes) that are each associated with or assigned to two or more cell identification oligonucleotides with different cell identification sequences (or cell identification oligonucleotides with two or more cell identification sequences). With cell identification sequence, the methods disclosed herein can be used for multiplet identification (whether in the context of sample overloading or not, or in the context of loading cells onto microwells of a microwell array or generating droplets containing cells). In some embodiments, the method comprises: contacting a first plurality of one or more cells and a second plurality of one or more cells with two cell identification compositions respectively, wherein each of the first plurality of one or more cells and each of the second plurality of one or more cells comprise one or more cellular components, wherein each of the two cell identification compositions comprises a cellular component binding reagent associated with a cell identification oligonucleotide, wherein the cellular component binding reagent is capable of specifically binding to at least one of the one or more cellular components, wherein the cell identification oligonucleotide comprises a cell identification sequence, and wherein cell identification sequences of the two cell identification compositions comprise different sequences; barcoding the cell identification oligonucleotides using a plurality of barcodes to create a plurality of barcoded cell identification oligonucleotides, wherein each of the plurality of barcodes comprises a cell label sequence, a barcode sequence (e.g., a molecular label sequence), and a target-binding region, wherein barcode sequences of at least two barcodes of the plurality of barcodes comprise different sequences, and wherein at least two barcodes of the plurality of barcodes comprise an identical cell label sequence; obtaining sequencing data of the plurality of barcoded cell identification oligonucleotides; and identifying one or more multiplet cell label sequences that is each associated with two or more cell identification sequences in the sequencing data obtained.

The number of cells that can be loaded onto microwells of a microwell cartridge or into droplets generated using a microfluidics device can be limited by the multiplet rate. Loading more cells can result in more multiplets, which can be hard to identify and create noise in the single cell data. With cell identification, the method can be used to more accurately label or identify multiplets and remove the multiplets from the sequencing data or subsequent analysis. Being able to identify multiplets with higher confidence can increase user tolerance for the multiplet rate and load more cells onto each microwell cartridge or generating droplets with at least one cell each.

In some embodiments, contacting the first plurality of one or more cells and the second plurality of one or more cells with the two cell identification compositions respectively comprises: contacting the first plurality of one or more cells with a first cell identification compositions of the two cell identification compositions; and contacting the first plurality of one or more cells with a second cell identification compositions of the two cell identification compositions. The number of pluralities of cell identification compositions can be different in different implementations. In some embodiments, the number of cell identification compositions can be, or be about, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number of cell identification compositions can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000. The number, or average number, of cells in each plurality of one or more cells can be different in different implementations. In some embodiments, the number, or average number, of cells in each plurality of one or more cells can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, 1000000, or a number or a range between any two of these values. In some embodiments, the number, or average number, of cells in each plurality of one or more cells can be at least, or be at most, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000, or 1000000.

In some embodiments, the method comprises: removing unbound cell identification compositions of the two cell identification compositions. Removing the unbound cell identification compositions can comprise washing cells of the first plurality of one or more cells and the second plurality of one or more cells with a washing buffer. Removing the unbound cell identification compositions can comprise selecting cells bound to at least one cellular component binding reagent of the two cell identification compositions using flow cytometry. In some embodiments, the method comprises: lysing the one or more cells from each of the plurality of samples.

In some embodiments, the cell identification oligonucleotide is configured to be detachable or non-detachable from the cellular component binding reagent. The method can comprise detaching the cell identification oligonucleotide from the cellular component binding reagent. Detaching the cell identification oligonucleotide can comprise detaching the cell identification oligonucleotide from the cellular component binding reagent by UV photocleaving, chemical treatment (e.g., using reducing reagent, such as dithiothreitol), heating, enzyme treatment, or any combination thereof.

In some embodiments, barcoding the cell identification oligonucleotides using the plurality of barcodes comprises: contacting the plurality of barcodes with the cell identification oligonucleotides to generate barcodes hybridized to the cell identification oligonucleotides; and extending the barcodes hybridized to the cell identification oligonucleotides to generate the plurality of barcoded cell identification oligonucleotides. Extending the barcodes can comprise extending the barcodes using a DNA polymerase to generate the plurality of barcoded cell identification oligonucleotides. Extending the barcodes can comprise extending the barcodes using a reverse transcriptase to generate the plurality of barcoded cell identification oligonucleotides.

In some embodiments, the method comprises: amplifying the plurality of barcoded cell identification oligonucleotides to produce a plurality of amplicons. Amplifying the plurality of barcoded cell identification oligonucleotides can comprise amplifying, using polymerase chain reaction (PCR), at least a portion of barcode sequence (e.g., the molecular label sequence) and at least a portion of the cell identification oligonucleotide. In some embodiments, obtaining the sequencing data of the plurality of barcoded cell identification oligonucleotides can comprise obtaining sequencing data of the plurality of amplicons. Obtaining the sequencing data comprises sequencing at least a portion of the barcode sequence and at least a portion of the cell identification oligonucleotide. In some embodiments, identifying the sample origin of the at least one cell comprises identifying sample origin of the plurality of barcoded targets based on the cell identification sequence of the at least one barcoded cell identification oligonucleotide.

In some embodiments, barcoding the cell identification oligonucleotides using the plurality of barcodes to create the plurality of barcoded cell identification oligonucleotides comprises stochastically barcoding the cell identification oligonucleotides using a plurality of stochastic barcodes to create a plurality of stochastically barcoded cell identification oligonucleotides.

Determining Cellular Component-Cellular Component Interactions

Disclosed herein include methods, for example multiplexed proximity ligation methods, for determining interactions between cellular components. Such methods, kits and systems can be used in combination with any suitable methods, kits and systems disclosed herein, for example the methods, kits and systems for measuring cellular component expression level (such as protein expression level) using cellular component binding reagents associated with oligonucleotides.

The methods disclosed herein can be used to detect, identify, determine, and/or measure interactions between one or multiple cellular components (for example, proteins). For example, the methods can be used to detect, identify, determine, and/or measure interactions between two, three, four, five, six, seven, eight, nine, ten, twenty, thirty, forty, fifty, one hundred, two hundred, three hundred, or more pairs of cellular components. The cellular component targets in one pair of cellular components targets can overlap with the cellular component targets in another pair of cellular component targets. For example, the first pair of cellular component targets can include protein A and protein B, and the second pair of cellular component targets can include protein A and protein C.

In some embodiments, the method uses cellular component binding reagents associated with interaction determination oligonucleotides to determine interactions between targets of the cellular component binding reagents (referred to herein as cellular component targets). For example, the method can use antibody-oligonucleotide conjugates to detect protein-protein interactions in single cells. The antibodies can be homodimers or heterodimers. Each cellular component binding reagent can be associated with (e.g., attached to or bind to) an interaction determination oligonucleotide containing a unique interaction determination sequence. For example, each antibody can be conjugated to an oligonucleotide containing a unique barcode sequence. Determining the pairs of interaction determination oligonucleotides that are ligated together can reveal the cellular component targets that interact with each other. For example, determining the barcode pairs that are ligated together can reveal the proteins interact with each other. This method can also be used in conjunction with single cell mRNA sequencing methods, such as well-based and droplet-based single cell mRNA sequencing methods.

In some embodiments, the method can utilize linear amplification to generate amplicons for sequencing. The method may not generate a circular template and use rolling circle amplification to generate sufficient template for downstream detection by fluorescent probes, or other methods. The method can be used to determine interactions between cellular component targets in single cells. For example, the method can be used to detect hundreds of cellular component-cellular component interactions (e.g., protein-protein interactions) across thousands to tens of thousands of single cells and uses sequencing as readouts. Interactions between the same proteins or cellular component targets can also be determined. The method does not rely on fluorescence and quantitative PCR (qPCR) as the readouts, which require bulk RNA as input, can only process few cells (e.g., less than 100 cells) at a time, and can detect a limited amount of cellular component-cellular component interactions at a time. The multiplexed method can utilize barcoded oligonucleotides associated with or conjugated to antibodies or cellular component binding reagents can be used to determine cellular component-cellular component interactions in a large number of single cells in a high throughput manner.

Furthermore, the method can also be used with other single cell RNA sequencing methods. For example, one single workflow can be used to determine mRNA expression levels, protein expression levels (or levels of cellular component targets), and/or protein-protein interactions (or interactions between cellular components). As a result, in a single experiment, data about mRNA expression, protein expression, and protein-protein interactions from in a single cell (or multiple single cells) can be obtained.

In some embodiments, the method can be used to detect cellular component-cellular component interactions between two cells and intracellular cellular component-cellular component interactions. For example, the method can be used to detect protein-protein interactions between two cells, as well as intracellular protein-protein interactions. The method may require additional cell preparation before antibody staining or incubation (e.g., cell fixation to allow binding of antibodies to intracellular proteins or targets).

FIGS. 14A-14F show a schematic illustration of an exemplary workflow of determining interactions between cellular components (e.g., proteins) using a pair of interaction determination compositions. The method can utilize two types of antibody-oligonucleotide compositions 1404a, 1404b (e.g., antibody-oligonucleotide conjugates) illustrated in FIG. 14A. The two types of antibody-oligonucleotide compositions 1404a, 1404b can include two identical or different antibodies 1408a, 1408b associated with two types of oligonucleotides 1412a, 1412b. The association (e.g., conjugation) can be reversible or non-reversible (e.g., cleavable or non-cleavable). One type of oligonucleotides 1412a (referred to herein as the type 1 oligonucleotide 1412a) can have a universal sequencing region 1416. In some embodiments, the universal sequencing region 1416 can be common to all antibody-oligonucleotide compositions for amplification with a universal primer. The other type of oligonucleotides 1412b (referred to herein as the type 2 oligonucleotide 1412b) can have a poly(dA) sequence 1420 for hybridization to barcodes, such as stochastic barcodes. For example, the poly(dA) sequence 1420 of the type two oligonucleotide 1412b can hybridize to stochastic barcodes associated with a bead (e.g., immobilized on the bead, partially immobilized on the bead, releasably enclosed in the bead, partially enclosed in the bead, or any combination thereof). Both oligonucleotide types 1412a, 1412b also include a barcode sequence 1424a, 1424b unique to each antibody 1404a, 1404b. The two oligonucleotide types 1412a, 1412b can include different sequences 1428a, 1428b for hybridization to a bridge oligo 1432 illustrated in FIG. 14B. Although the type one oligonucleotide 1412a and the type two oligonucleotide 1412b are shown to be associated with the antibodies 1408a, 1408b in the 5' to 3' direction and the 3' to 5' direction, they are illustrative only and are not intended to be limiting. In some embodiments, the type one oligonucleotide 1412a and the type two oligonucleotide 1412b can be associated with the antibodies 1408a, 1408b in the 3' to 5' direction and the 5' to 3' direction.

Figure 14A:
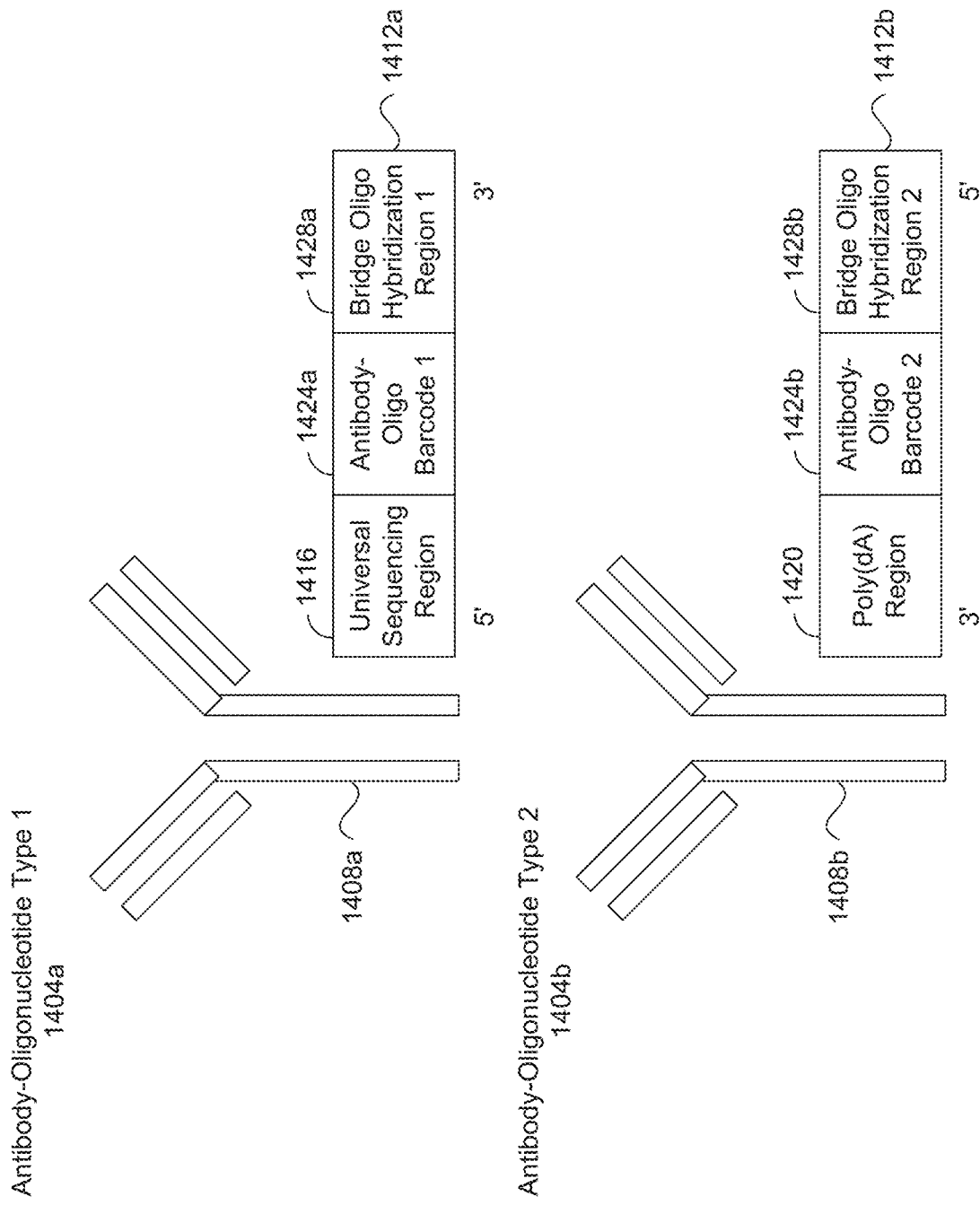
FIGS. 14A-14F show a schematic illustration of an exemplary workflow of determining interactions between cellular components (e.g., proteins) using a pair of interaction determination compositions.
Figure 14B:
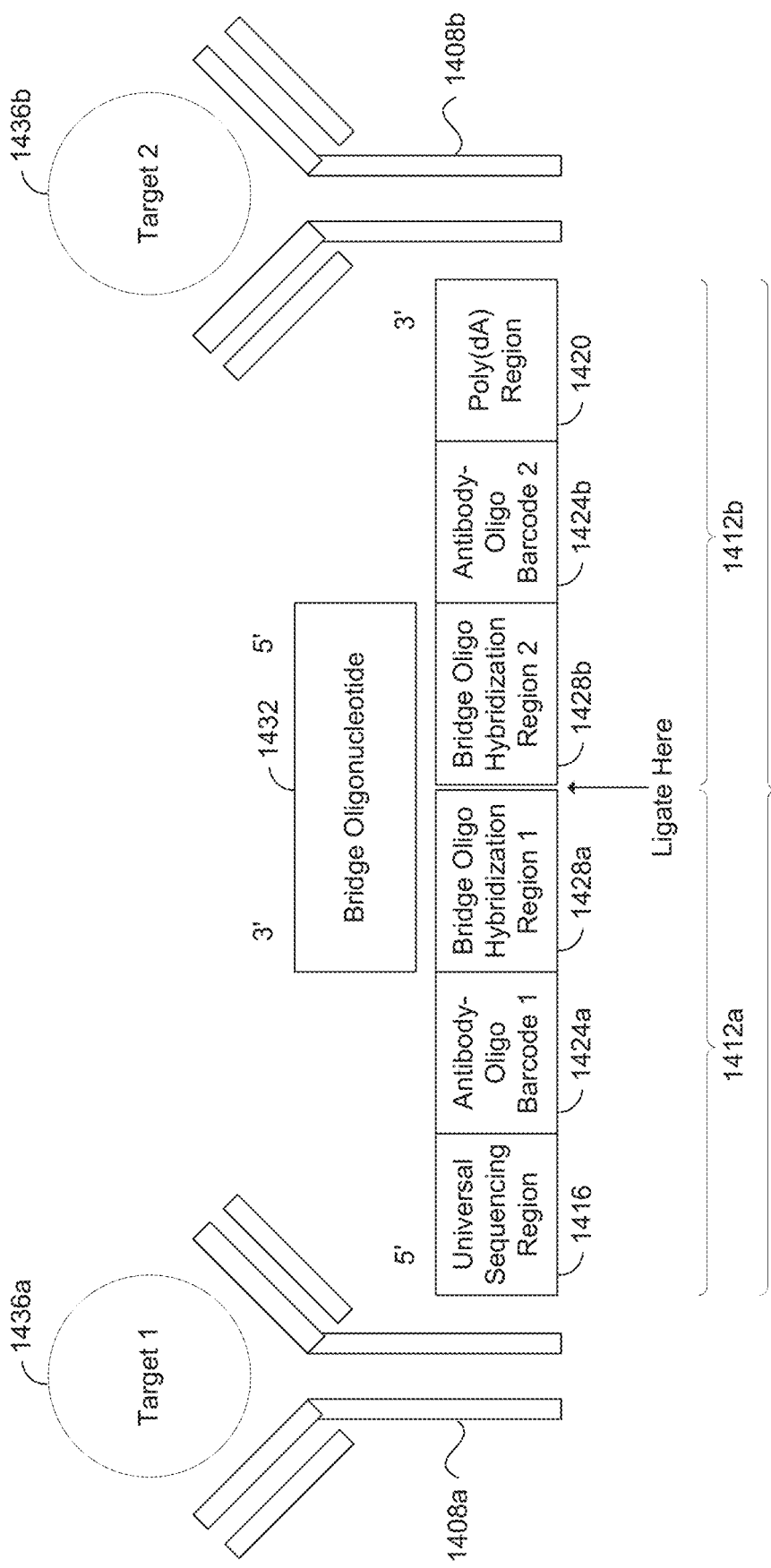

Referring to FIG. 14B, the bridge oligonucleotide 1432 can bind to the bridge oligonucleotide hybridization regions 1428a, 1428b to bring the antibody-oligonucleotide compositions 1404a, 1404b together for ligation. The sequences of the bridge oligonucleotide hybridization regions 1428a, 1428b can be different for each composition 1404a, 1404b. In some embodiments, a different bridge oligonucleotide 1432 can be used for each antibody pair.

The methods can be based on bringing together pairs of antibody-oligonucleotide compositions 1404a, 1404b so that the associated oligonucleotides 1412a, 1412b can be joined together or ligated to each other, and later captured by barcodes (e.g., stochastic barcodes) associated with beads for sequencing. The oligonucleotides 1412a, 1412b can be ligated to each other if the targets 1436a, 1436b of the antibodies 1408a, 1408b are within a certain threshold distance or range of each other, such as 30-40 nm.

The multiplexed method can utilize barcoded oligonucleotides associated with or conjugated to antibodies or cellular component binding reagents to determine protein-protein interactions, or interactions between cellular components, in a large number of single cells in a high throughput manner. In some embodiments, the interactions between cellular components in, or in about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, $10^5$, $10^6$, $10^7$, $10^8$, $10^9$, or a number or a range between any two of these values, cells can be determined in a cell workflow. In some embodiments, the interactions between cellular components in at least, or in at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, $10^5$, $10^6$, $10^7$, $10^8$, $10^9$, or a number or a range between any two of these values, cells can be determined in a cell workflow.

Staining

To perform the assay, cells can be first stained with antibody-oligonucleotide compositions 1404a, 1404b or pairs of antibody-oligonucleotide compositions 1404a, 1404b (or cellular component binding reagent-oligonucleotide compositions). The number of antibody-oligonucleotide compositions 1404a, 1404b (or cellular component binding reagents) can be different in different implementations. In some embodiments, the number of antibody-oligonucleotide compositions 1404a, 1404b can be, or be about, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of antibody-oligonucleotide compositions 1404a, 1404b can be at least, or be at most, 2, 3, 4, 5, 6, 7, 8, 9, 10, 20, 30, 40, 50, 60, 70, 80, 90, 100, 200, 300, 400, 500, 600, 700, 800, 900, or 1000.

The antibodies 1408a, 1408b (or cellular component binding reagents) of different compositions 1404a, 1404b can be associated with or bind to interaction determination oligonucleotides 1412a, 1412b with different or identical barcode sequences 1424a, 1424b. In some embodiments, the number of antibodies 1408a, 1408b of different compositions 1404a, 1404b associated with or bind to interaction determination oligonucleotides 1412a, 1412b with different barcode sequences or identical barcode sequences 1424a, 1424b can be, or be about, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of antibodies 1408a, 1408b of different compositions 1404a, 1404b associated with or bind to interaction determination oligonucleotides 1412a, 1412b with different barcode sequences or identical barcode sequences 1424a, 1424b can be at least, or be at most, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the percentage of antibodies 1408a, 1408b of different compositions 1404a, 1404b associated with or bind to interaction determination oligonucleotides 1412a, 1412b with different barcode sequences or identical barcode sequences 1424a, 1424b can be, or be about, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, 100%, or a number or a range between any two of these values. In some embodiments, the percentage of antibodies 1408a, 1408b of different compositions 1404a, 1404b associated with or bind to interaction determination oligonucleotides 1412a, 1412b with different barcode sequences or identical barcode sequences 1424a, 1424b can be at least, or be at most, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, or 100%.

Some, all, or none of the antibodies 1408a, 1408b (or cellular component binding reagents) can be associated with or bind to interaction determination oligonucleotides 1412a, 1412b having bridge oligonucleotide hybridization regions 1428a, 1428b with identical sequence. In some embodiments, the number of antibodies 1408a, 1408b associated with or bind to interaction determination oligonucleotides 1412a, 1412b having bridge oligonucleotide hybridization regions 1428a, 1428b with identical sequence or different sequences can be, or be about, 0, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of antibodies 1408a, 1408b associated with or bind to interaction determination oligonucleotides 1412a, 1412b having bridge oligonucleotide hybridization regions 1428a, 1428b with identical sequence or different sequences can be at least, or be at most, 0, 1, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the percentage of antibodies 1408a, 1408b associated with or bind to interaction determination oligonucleotides 1412a, 1412b having bridge oligonucleotide hybridization regions 1428a, 1428b with identical sequence or different sequences can be, or be about, 0%, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, 100%, or a number or a range between any two of these values. In some embodiments, the percentage of antibodies 1408a, 1408b associated with or bind to interaction determination oligonucleotides 1412a, 1412b having bridge oligonucleotide hybridization regions 1428a, 1428b with identical sequence or different sequences can be at least, or be at most, 0%, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, or 100%.

Some, all, or none of the antibodies 1408a (or cellular component binding reagents) can be associated with or bind to interaction determination oligonucleotides 1412a having universal sequencing regions with identical sequence or different sequences. In some embodiments, the number of antibodies 1408a associated with or bind to interaction determination oligonucleotides 1412a having universal sequencing regions 1416a with identical sequence or different sequences can be, or be about, 0, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of antibodies 1408a associated with or bind to interaction determination oligonucleotides 1412a having universal sequencing regions 1416a with identical sequence or different sequences can be at least, or be at most, 0, 1, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the percentage of antibodies 1408a associated with or bind to interaction determination oligonucleotides 1412a having universal sequencing regions 1416a with identical sequence or different sequences can be, or be about, 0%, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, 100%, or a number or a range between any two of these values. In some embodiments, the number of antibodies 1408a associated with or bind to interaction determination oligonucleotides 1412a having universal sequencing regions 1416a with identical sequence or different sequences can be at least, or be at most, 0%, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, or 100%.

The number of pairs of antibody-oligonucleotide compositions 1404a, 1404b (cellular component binding reagent-oligonucleotide compositions) can be different in different implementations. In some embodiments, the number of pairs of antibody-oligonucleotide compositions 1404a, 1404b can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of pairs of antibody-oligonucleotide compositions 1404a, 1404b can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000.

The antibodies 1408a, 1408b (or cellular component binding reagents) of different pairs of compositions 1404a, 1404b can be associated with or bind to interaction determination oligonucleotides 1412a, 1412b with different or the identical barcode sequences 1424a, 1424b. In some embodiments, the number of antibodies 1408a, 1408b of different pairs of compositions 1404a, 1404b associated with or bind to interaction determination oligonucleotides 1412a, 1412b with different barcode sequences or identical barcode sequences 1424a, 1424b can be, or be about, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of antibodies 1408a, 1408b of different pairs of compositions 1404a, 1404b associated with or bind to interaction determination oligonucleotides 1412a, 1412b with different barcode sequences or identical barcode sequences 1424a, 1424b can be at least, or be at most, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the percentage of antibodies 1408a, 1408b of different pairs of compositions 1404a, 1404b associated with or bind to interaction determination oligonucleotides 1412a, 1412b with different barcode sequences or identical barcode sequences 1424a, 1424b can be, or be about, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, 100%, or a number or a range between any two of these values. In some embodiments, the percentage of antibodies 1408a, 1408b of different pairs of compositions 1404a, 1404b associated with or bind to interaction determination oligonucleotides 1412a, 1412b with different barcode sequences or identical barcode sequences 1424a, 1424b can be at least, or be at most, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, or 100%.

Some, all, or none of the antibodies 1408a, 1408b (or cellular component binding reagents) of different pairs of compositions 1404a, 1404b can be associated with or bind to interaction determination oligonucleotides 1412a, 1412b with identical bridge oligonucleotide hybridization regions. In some embodiments, the number of antibodies 1408a, 1408b of different pairs of compositions 1404a, 1404b associated with or bind to interaction determination oligonucleotides 1412a, 1412b having bridge oligonucleotide hybridization regions 1428a, 1428b with identical sequence or different sequences can be, or be about, 0, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of antibodies 1408a, 1408b of different pairs of compositions 1404a, 1404b associated with or bind to interaction determination oligonucleotides 1412a, 1412b having bridge oligonucleotide hybridization regions 1428a, 1428b with identical sequence or different sequences can be at least, or be at most, 0, 1, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the % of antibodies 1408a, 1408b of different pairs of compositions 1404a, 1404b associated with or bind to interaction determination oligonucleotides 1412a, 1412b having bridge oligonucleotide hybridization regions 1428a, 1428b with identical sequence or different sequences can be, or be about, 0%, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, 100%, or a number or a range between any two of these values. In some embodiments, the percentage of antibodies 1408a, 1408b of different pairs of compositions 1404a, 1404b associated with or bind to interaction determination oligonucleotides 1412a, 1412b having bridge oligonucleotide hybridization regions 1428a, 1428b with identical sequence or different sequences can be at least, or be at most, 0%, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, or 100%.

Some, all, or none of the antibodies 1408a (or cellular component binding reagents) of different compositions 1404a can be associated with or bind to interaction determination oligonucleotides 1412a having universal sequencing regions with identical sequence or different sequences. In some embodiments, the number of antibodies 1408a of different compositions 1404a associated with or bind to interaction determination oligonucleotides 1412a having universal sequencing regions 1416a with identical sequence or different sequences can be, or be about, 0, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of antibodies 1408a of different compositions 1404a associated with or bind to interaction determination oligonucleotides 1412a having universal sequencing regions 1416a with identical sequence or different sequences can be at least, or be at most, 0, 1, 2, 3, 4, 5, 6, 7, 8, 9, 10, 20, 30, 40, 50, 60, 70, 80, 90, 100, 200, 300, 400, 500, 600, 700, 800, 900, or 1000. In some embodiments, the percentage of antibodies 1408a of different compositions 1404a associated with or bind to interaction determination oligonucleotides 1412a having universal sequencing regions 1416a with identical sequence or different sequences can be, or be about, 0%, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, 100%, or a number or a range between any two of these values. In some embodiments, the percentage of antibodies 1408a of different compositions 1404a associated with or bind to interaction determination oligonucleotides 1412a having universal sequencing regions 1416a with identical sequence or different sequences can be at least, or be at most, 0%, 0.1%, 1%, 2%, 3%, 4%, 5%, 6%, 7%, 8%, 9%, 10%, 20%, 33%, 40%, 50%, 60%, 70%, 80%, 90%, 99.9%, 99.99%, or 100%.

The number of targets 1436a, 1436b can be different in different implementations, such as 2 to at least 50-100 protein targets. In some embodiments, the number of targets 1436a, 1436b can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, or a number or a range between any two of these values. In some embodiments, the number of targets 1436a, 1436b can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000.

Ligation

After washing away unbound compositions 1404a, 1404b, a bridge oligonucleotide 1432 can be added. Pairs made of type 1 and type 2 compositions 1404a, 1404b can be linked together via the bridge oligonucleotide 1432 which can hybridize to bridge oligonucleotide hybridization regions. For example, pairs made of type 1 and type 2 compositions 1404a, 1404b can be linked together via the bridge oligonucleotide 1432 which can hybridize to bridge oligonucleotide hybridization regions if the corresponding protein targets 1436a, 1436b are within a threshold distance, such as 30-40 nm. DNA ligase can then be added to ligate the two oligonucleotides 1412a, 1412b to form a ligated oligonucleotide 1412, resulting in the compositions 1436a, 1436b being ligated together. For example, the bridge oligonucleotide 1432 can make the ligation region double-stranded to facilitate ligation. The bridge oligonucleotide 1432 can bind to the hybridization regions 1428a, 1428b on each oligonucleotide 1412a, 1412b, which allows a DNA ligase to ligate the two oligonucleotides 1412a, 1412b together.

The threshold distance can be different in different implementations. In some embodiments, the threshold distance can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000 nm, or a number or a range between any two of these values. For example, the distance can be in the range 30-40 nm. In some embodiments, the threshold distance can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, or 1000 nm. The threshold distance can be affected by the lengths of the oligonucleotides 1412a, 1412b, locations of the associations or attachments of the oligonucleotides 1412a, 1412b to the antibodies 1408a, 1408b, the size of the targets 1436a, 1436b, or any combination thereof.

Cell Lysis and Ligated Oligonucleotide Hybridization to Barcode

Figure 14C:
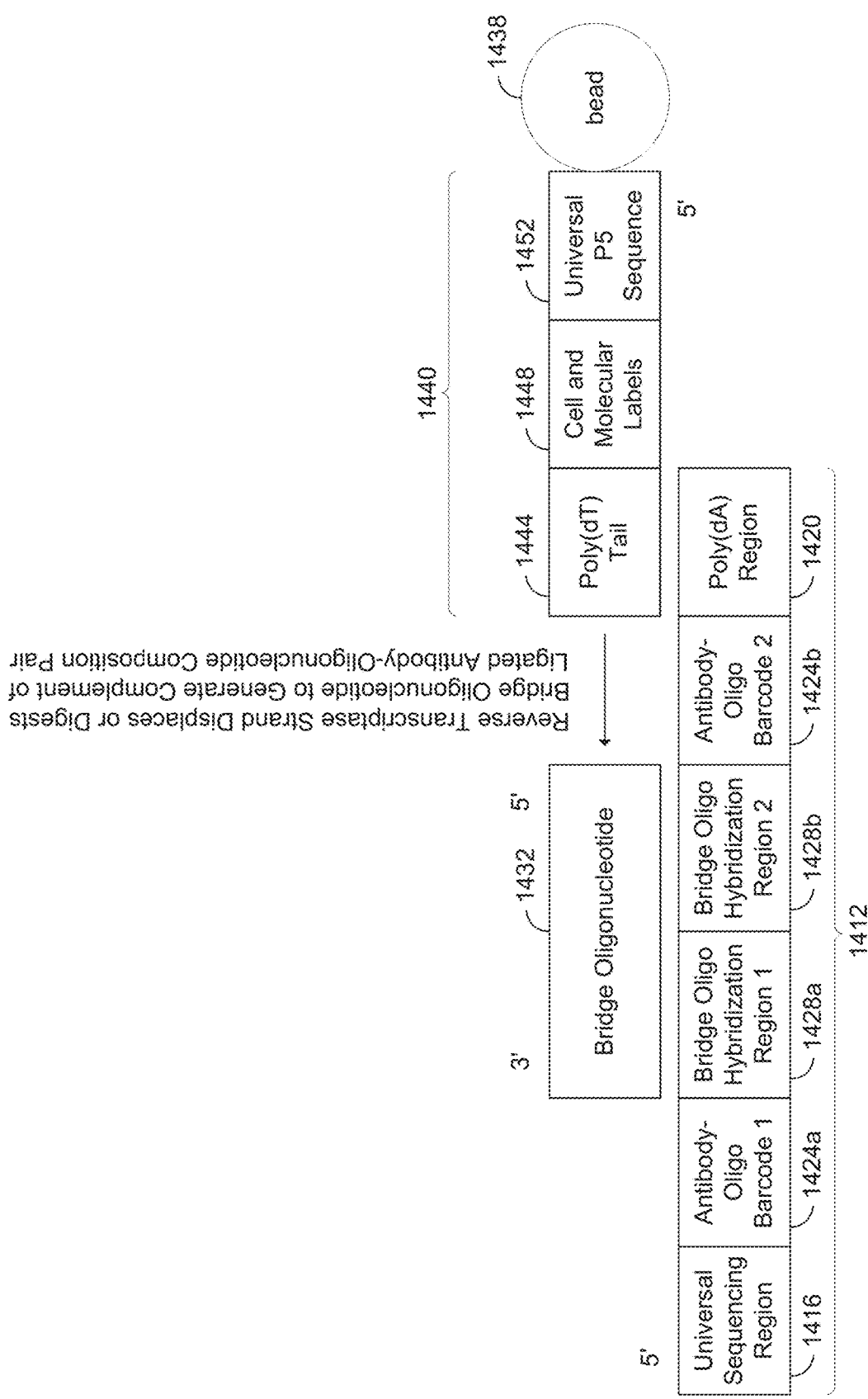

Then, cells can be lysed to allow capture of the ligated oligonucleotide 1412 as illustrated in FIG. 14C. For example, a bead 1438 with a barcode 1440 (e.g., a stochastic barcode) having a poly(dT) region 1444 can capture the ligated oligonucleotide 1412 via the poly(dA) region. The bead 1438 can additional include labels, such as cell and/or molecular labels 1448 and a universal sequence 1452 for subsequence amplification.

Reverse Transcription

Figure 14D:
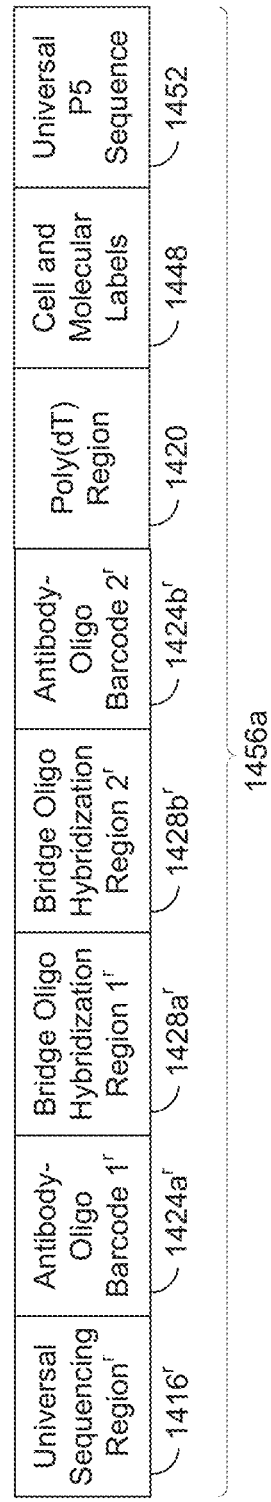

Reverse transcription can then performed to generate the complementary sequence 1456 of the ligated oligonucleotide 1412 shown in FIG. 14D. For example, a Moloney Murine Leukemia Virus (MMLV)-based or Taq-based reverse transcriptase can be used to generate the complementary sequence of the ligated oligonucleotide 1412. The MMLV-based reverse transcriptase has a strand-displacing mechanism to displace the bridge oligonucleotide 1432 during generation of the complementary strand. The Taq-based reverse transcriptase has 5' to 3' exonuclease activity to remove the bridge oligonucleotide 1432.

Library Preparation

Figure 14E:
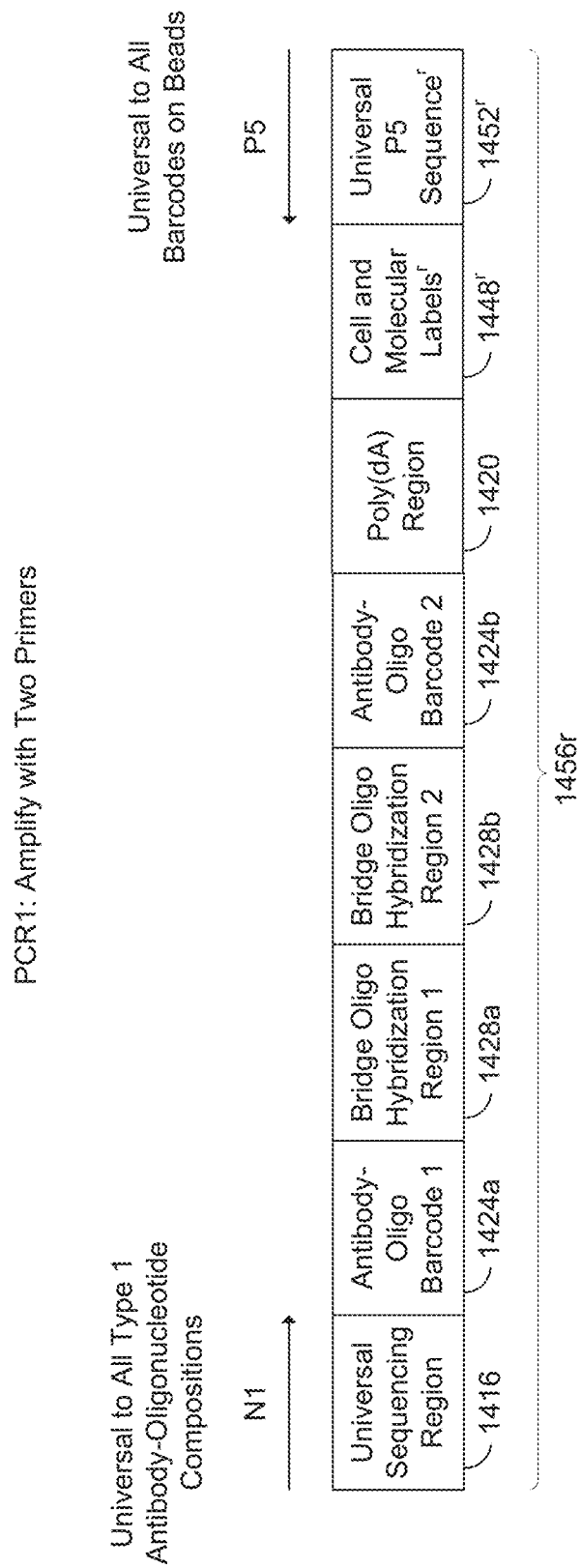

After reverse transcription, a sequencing library can be prepared, for example, following standard protocols for single cell mRNA sequencing. Referring to FIG. 14E, the complementary sequence 1456 (or a reverse complement thereof 1456r) can be amplified via the universal sequence 1452 (e.g., the universal P5 sequence or a partial universal P5 sequence) on the barcode 1440 and the universal sequencing region 1416 (e.g., the universal N1 sequence) of the type one antibody-oligonucleotide composition 1404a. The superscript r denotes a reverse complement. The first round of PCR (referred to herein as PCR1) can use universal primers (e.g., primers with P5 and N1 sequences, or reverse complements thereof) to generate full length (or close to full length) amplicons that correspond to ligated oligonucleotide 1456r with one or more labels and the universal sequence.

Figure 14F:
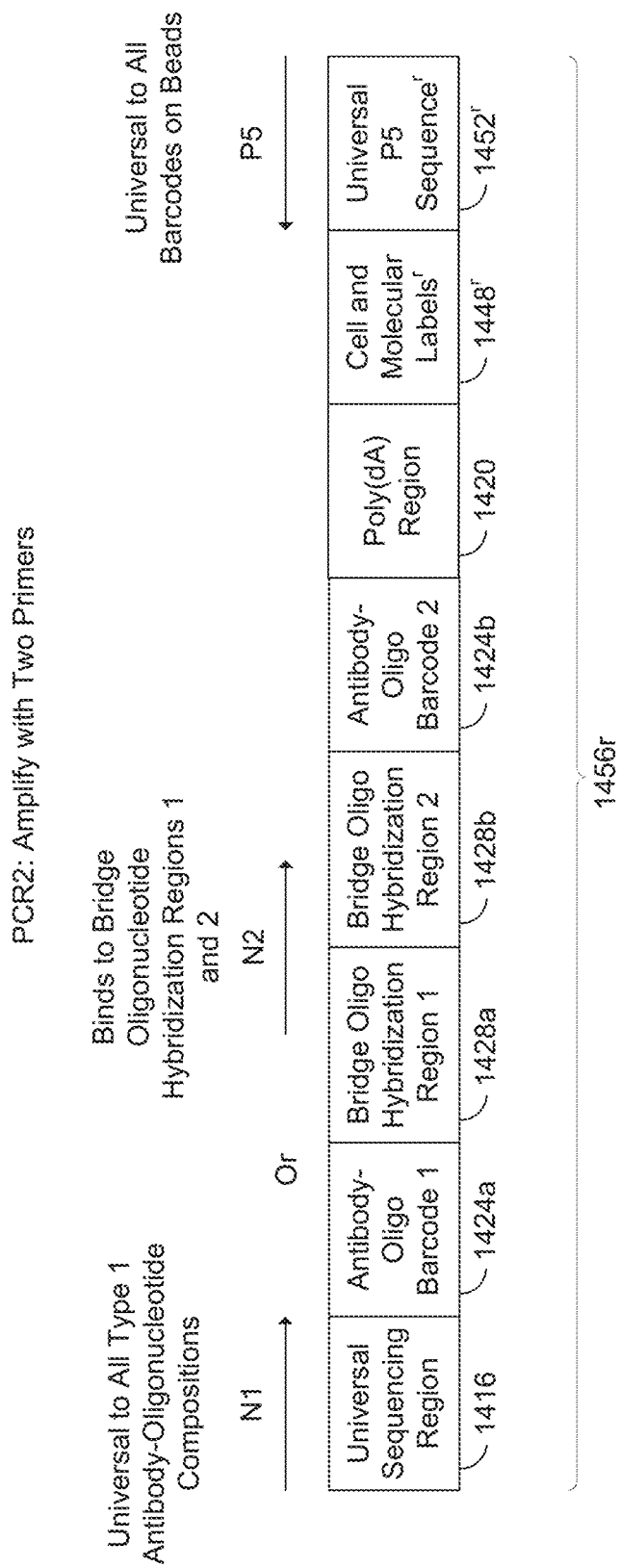

The same primers can be used for the second around of PCR amplification referred to herein as PCR2), or the N1 primer can be replaced by an N2 primer that binds to both bridge oligonucleotide hybridization regions 1428a, 1428b for further specificity as illustrated in FIG. 14F. When this N2 primer is used, a majority of ligated oligonucleotide 1456r with both the universal sequencing region 1416 and the universal sequence 1452 can be amplified. In some embodiments, when this N2 primer is used for the second round of PCR, a majority of ligated oligonucleotide 1456r with both the universal sequencing region 1416 and the universal sequence 1452 can be amplified.

Using Pairs of Interaction Determination Compositions to Determine Interactions between Cellular Components Disclosed herein include systems, methods, and kits for determining protein-protein interactions. In some embodiments, the method comprises: contacting a cell with a first pair of interaction determination compositions 1404a, 1404b illustrated in FIG. 14A. The cell can comprise a first protein target 1436a and a second protein target 1436b. Each of the first pair of interaction determination compositions 1404a, 1404b comprises a protein binding reagent 1408a, 1408b associated with an interaction determination oligonucleotide 1412a, 1412b. The protein binding reagent 1408a, 1408b of one of the first pair of interaction determination compositions is capable of specifically binding to the first protein target 1436a, and the protein binding reagent 1408b of the other of the first pair of interaction determination compositions is capable of specifically binding to the second protein target 1436b. The interaction determination oligonucleotide 1412a, 1412b comprises an interaction determination sequence 1424a, 1434b and a bridge oligonucleotide hybridization region 1428a, 1428b. The interaction determination sequences 1424a, 1424b of the first pair of interaction determination compositions 1404a, 1404b can comprise different sequences.

Referring to FIG. 14B, the method can include ligating the interaction determination oligonucleotides 1412a, 1412b of the first pair of interaction determination compositions 1404a, 1404b using a bridge oligonucleotide 1432 to generate a ligated interaction determination oligonucleotide 1412. The bridge oligonucleotide 1432 can comprise two hybridization regions capable of specifically binding to the bridge oligonucleotide hybridization regions 1428a, 1428b of the first pair of interaction determination compositions 1404a, 1404b Referring to FIG. 14C, the method can include barcoding the ligated interaction determination oligonucleotide 1412 using a plurality of barcodes 1440 to create a plurality of barcoded interaction determination oligonucleotides 1456. Each of the plurality of barcodes 1440 can comprise a barcode sequence 1448 and a capture sequence 1444. The method can include obtaining sequencing data of the plurality of barcoded interaction determination oligonucleotides 1456. The method can include determining an interaction between the first and second protein targets 1436a, 1436b based on the association of the interaction determination sequences 1424a, 1424b of the first pair of interaction determination compositions 1404a, 1404b in the obtained sequencing data.

Disclosed herein include systems, methods, and kits for determining interactions between cellular component targets. In some embodiments, the method comprises: contacting a cell with a first pair of interaction determination compositions 1404a, 1404b illustrated in FIG. 14A. The cell can comprise a first cellular component target and a second cellular component target (e.g., a first protein target 1436a and a second protein target 1436b). Each of the first pair of interaction determination compositions can comprise a cellular component binding reagent (e.g., the antibody 1408a, 1408b) associated with an interaction determination oligonucleotide 1412a, 1412b. The cellular component binding reagent of one of the first pair of interaction determination compositions 1404a, 1404b is capable of specifically binding to the first cellular component target (e.g., the protein target 1436a), and the cellular component binding reagent of the other 1404b of the first pair of interaction determination compositions is capable of specifically binding to the second cellular component target (e.g., the protein target 1436b). The interaction determination oligonucleotide 1412a, 1412b can comprise an interaction determination sequence 1424a, 1424b and a bridge oligonucleotide hybridization region 1428a, 1428b. The interaction determination sequences 1424a, 1424b of the first pair of interaction determination compositions 1404a, 1404b can comprise different sequences.

Referring to FIG. 14B, the method can include ligating the interaction determination oligonucleotides 1412a, 1412b of the first pair of interaction determination compositions 1404a, 1404b using a bridge oligonucleotide 1432 to generate a ligated interaction determination oligonucleotide 1412. The bridge oligonucleotide 1432 can comprise two hybridization regions capable of specifically binding to the bridge oligonucleotide hybridization regions 1428a, 1428b of the first pair of interaction determination compositions 1404a, 1404b.

Referring to FIG. 14C, the method can include barcoding the ligated interaction determination oligonucleotide 1412 using a plurality of barcodes 1440 to create a plurality of barcoded interaction determination oligonucleotides 1456. Each of the plurality of barcodes 1440 can comprise a barcode sequence 1448 and a capture sequence 1444. The method can include obtaining sequencing data of the plurality of barcoded interaction determination oligonucleotides 1456. The method can include determining an interaction between the first and second cellular component targets 1436a, 1436b based on the association of the interaction determination sequences 1424a, 1424b of the first pair of interaction determination compositions 1404a, 1404b in the obtained sequencing data. In some embodiments, at least one of the two cellular component binding reagent can comprise a protein binding reagent. The protein binding reagent can be associated with one of the two interaction determination oligonucleotides. The one or more cellular component targets can comprise at least one protein target.

In some embodiments, contacting the cell with the first pair of interaction determination compositions 1404a, 1404b comprises: contacting the cell with each of the first pair of interaction determination compositions 1404a, 1404b sequentially or simultaneously. The first protein target 1436a can be the same as the second protein target 1436b. The first protein target 1436a can be different from the second protein target 1436b. The first and the second cellular component targets can be the same or different.

The interaction determination oligonucleotides 1412a, 1412 be can have different lengths in different implementations. In some embodiments, an interaction determination oligonucleotide 1412a, 1412b is, or is about, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or a number or a range between any two of these values, nucleotides in length. In some embodiments, an interaction determination oligonucleotide 1412a, 1412b is at least, or is at most, 6, 7, 8, 9, 10, 11, 12, 13, 14, 15, 16, 17, 18, 19, 20, 25, 30, 35, 40, 45, 50, 60, 70, 80, 90, 100, 110, 120, 128, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000, nucleotides in length.

In some embodiments, the method comprises: contacting the cell with a second pair of interaction determination compositions. The cell can comprise a third cellular component target and a fourth cellular component target (e.g., a third protein target and a fourth protein target). Each of the second pair of interaction determination compositions can comprise a cellular component binding reagent associated with an interaction determination oligonucleotide. The cellular component binding reagent of one of the second pair of interaction determination compositions can be capable of specifically binding to the third cellular component target and the cellular component binding reagent of the other of the second pair of interaction determination compositions can be capable of specifically binding to the fourth cellular component target. In some embodiments, at least one of the third and fourth cellular component targets can be different from one of the first and second cellular component targets. In some embodiments, at least one of the third and fourth cellular component targets and at least one of the first and second cellular component targets can be identical.

In some embodiments, the method comprises: contacting the cell with three or more pairs of interaction determination compositions. The interaction determination sequences of a number of interaction determination compositions of the plurality of pairs of interaction determination compositions can comprise the same or different sequences. In some embodiments, the number of interaction determination compositions having interaction determination sequences with the same or different sequences can be, or be about, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, or a number or a range between any two of these values. In some embodiments, the number of interaction determination compositions having interaction determination sequences with the same or different sequences can be at least, or be at most, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10000.

In some embodiments, the bridge oligonucleotide hybridization regions 1428a, 1428b of the first pair of interaction determination compositions 1404a, 1404b comprise different sequences. At least one of the bridge oligonucleotide hybridization regions 1428a, 1428b can be complementary to at least one of the two hybridization regions of the bridge oligonucleotide 1432.

In some embodiments, ligating the interaction determination oligonucleotides 1412a, 1412b of the first pair of interaction determination compositions 1404a, 1404b using the bridge oligonucleotide 1432 comprises: hybridizing a first hybridization regions of the bridge oligonucleotide 1432 with a first bridge oligonucleotide hybridization region 1428a of the bridge oligonucleotide hybridization regions of the interaction determination oligonucleotides; hybridizing a second hybridization region of the bridge oligonucleotide with a second bridge oligonucleotide hybridization region 1428b of the bridge oligonucleotide hybridization regions of the interaction determination oligonucleotides; and ligating the interaction determination oligonucleotides 1428a, 1428b that are hybridized to the bridge oligonucleotide 1432 to generate a ligated interaction determination oligonucleotide.

In some embodiments, the at least one of the one or more cellular component targets (e.g., protein targets 1436a, 1436b) is on a cell surface. In some embodiments, the method can comprise: fixating the cell prior to contacting the cell with the first pair of interaction determination compositions 1404a, 1404b. In some embodiments, the method can comprise: removing unbound interaction determination compositions of the first pair of interaction determination compositions 1404a, 1404b. Removing the unbound interaction determination compositions can comprise washing the cell with a washing buffer. Removing the unbound interaction determination compositions can comprise selecting the cell using flow cytometry. In some embodiments, the method can comprise: lysing the cell.

In some embodiments, the interaction determination oligonucleotide is configured to be detachable or non-detachable from the protein binding reagent. The method can comprise: detaching the interaction determination oligonucleotide 1412a, 1412b or the ligated interaction determination oligonucleotide 1412 from the cellular component binding reagent. Detaching the interaction determination oligonucleotide 1412a, 1412b can comprise detaching the interaction determination oligonucleotide 1412a, 1412b from the cellular component binding reagent by UV photocleaving, chemical treatment, heating, enzyme treatment, or any combination thereof. The interaction determination oligonucleotide 1412a, 1412b may be not homologous to genomic sequences of the cell. The interaction determination oligonucleotide 1412a, 1412b can be homologous to genomic sequences of a species.

In some embodiments, the interaction determination oligonucleotide 1412b of the one of the first pair of interaction determination compositions 1404a, 1404b comprises a sequence 1420 complementary to the capture sequence 1444. The capture sequence 1444 can comprise a poly(dT) region. The sequence 1420 of the interaction determination oligonucleotide complementary to the capture sequence 1444 can comprise a poly(dA) region. In some embodiments, the interaction determination oligonucleotide 1412a, 1412b comprises a second barcode sequence. The interaction determination oligonucleotide 1412a of the other of the first pair of interaction identification compositions 1404a, 1404b can comprise a binding site for a universal primer 1416. The interaction determination oligonucleotide 1404a, 1404b can be associated with a detectable moiety.

In some embodiments, the cellular component binding reagent can be associated with two or more interaction determination oligonucleotides 1412a, 1412b with the same or different interaction determination sequences 1428a, 1428b. In some embodiments, one of the plurality of interaction determination compositions 1404a, 1404b comprises a second protein binding reagent not associated with the interaction determination oligonucleotide. The cellular component binding reagent and the second cellular component binding reagent can be identical. The cellular component binding reagent can be associated with a detectable moiety. The cellular component binding reagent 1404a, 1404b can be associated with two or more interaction determination oligonucleotides 1412a, 1412b with an identical sequence.

In some embodiments, the method comprises: contacting two or more cells with the first pair of interaction determination compositions 1404a, 1404b. Each of the two or more cells can comprise the first and the second cellular component targets (e.g., the first and the second protein targets 1436a, 1436b). At least one of the two or more cells can comprise a single cell.

Referring to FIG. 14B, the barcode 1440 comprises a cell label sequence 1448, a binding site for a universal primer, or any combination thereof. At least two barcodes of the plurality of barcodes can comprise an identical cell label sequence 1448.

In some embodiments, the cellular component target is, or comprises, an extracellular protein, an intracellular protein, or any combination thereof. The cellular component target can be, or comprise, a lipid, a carbohydrate, or any combination thereof. The cellular component target can be selected from a group comprising 10-100 different cellular component targets.

In some embodiments, the plurality of barcodes is associated with a particle (e.g., a bead 1438). At least one barcode the plurality of barcodes can be immobilized on the particle. At least one barcode of the plurality of barcodes can be partially immobilized on the particle. At least one barcode of the plurality of barcodes can be enclosed in the particle. At least one barcode of the plurality of barcodes can be partially enclosed in the particle. The particle can be disruptable. In some embodiments, the barcodes of the particle comprise barcode sequences selected from at least 1000, 10000, or more different barcode sequences Referring to FIG. 14C, barcoding the interaction determination oligonucleotides 1412 using the plurality of barcodes 1440 comprises: contacting the plurality of barcodes 1440 with the interaction determination oligonucleotides 1412 to generate barcodes hybridized to the interaction determination oligonucleotides; and extending the barcodes hybridized to the interaction determination oligonucleotides to generate the plurality of barcoded interaction determination oligonucleotides 1456. Extending the barcodes 1440 can comprise extending the barcodes 1440 using a DNA polymerase to generate the plurality of barcoded interaction determination oligonucleotides 1456. Extending the barcodes 1440 can comprise extending the barcodes 1440 using a reverse transcriptase to generate the plurality of barcoded interaction determination oligonucleotides 14. Extending the barcodes 14 can comprise extending the barcodes 14 using a Moloney Murine Leukemia Virus (M-MLV) reverse transcriptase or a Taq DNA polymerase to generate the plurality of barcoded interaction determination oligonucleotides 1456. Extending the barcodes 14 can comprise displacing the bridge oligonucleotide 1432 from the ligated interaction determination oligonucleotide 1412.

Referring to FIGS. 14D and 14E, the method can comprise: amplifying the plurality of barcoded interaction determination oligonucleotides 1456 to produce a plurality of amplicons. Amplifying the plurality of barcoded interaction determination oligonucleotides 1456 can comprise amplifying, using polymerase chain reaction (PCR), at least a portion of the barcode sequence 1448 and at least a portion of the interaction determination oligonucleotide 1428a, 1428b. Obtaining the sequencing data of the plurality of barcoded interaction determination oligonucleotides 1456 can comprise obtaining sequencing data of the plurality of amplicons. Obtaining the sequencing data can comprise sequencing at least a portion of the barcode sequence 1448 and at least a portion of the interaction determination oligonucleotide 1428a, 1428b. In some embodiments, obtaining sequencing data of the plurality of barcoded interaction determination oligonucleotides 1456 comprises obtaining partial and/or complete sequences of the plurality of barcoded interaction determination oligonucleotides 1456 (or a reverse, a complement, a reverse complement 1456r, or any combination thereof).

Referring to FIG. 14C, the plurality of barcodes 1440 can comprise a plurality of stochastic barcodes. The barcode sequence of each of the plurality of stochastic barcodes can comprise a molecular label sequence 1448. The molecular label sequences 1448 of at least two stochastic barcodes of the plurality of stochastic barcodes can comprise different sequences. Barcoding the interaction determination oligonucleotides 1412 using the plurality of barcodes 1440 to create the plurality of barcoded interaction determination oligonucleotides 1456 can comprise stochastically barcoding the interaction determination oligonucleotides 1412 using the plurality of stochastic barcodes to create a plurality of stochastically barcoded interaction determination oligonucleotides.

The method can also be used with other single cell RNA sequencing methods. For example, one single workflow can be used to determine mRNA expression levels, protein expression levels (or expression levels of cellular component targets), and/or protein-protein interactions (or interactions between cellular components). As a result, in a single experiment, data about mRNA expression, protein expression, and protein-protein interactions from in a single cell (or multiple single cells) can be obtained. In some embodiments, the method comprises: barcoding a plurality of targets (e.g., mRNA species of interest) of the cell using the plurality of barcodes 1440 to create a plurality of barcoded targets; and obtaining sequencing data of the barcoded targets. Barcoding the plurality of targets using the plurality of barcodes 1440 to create the plurality of barcoded targets can comprise: contacting copies of the targets with target-binding regions (e.g., the poly(dT) region 1444) of the barcodes 1440; and reverse transcribing the plurality targets using the plurality of barcodes 1440 to create a plurality of reverse transcribed targets. The method can comprise: prior to obtaining the sequencing data of the plurality of barcoded targets, amplifying the barcoded targets to create a plurality of amplified barcoded targets (similar to amplifying the barcoded interaction determination oligonucleotides 1456 illustrated in FIGS. 14E and 14F). Amplifying the barcoded targets to generate the plurality of amplified barcoded targets can comprise: amplifying the barcoded targets by polymerase chain reaction (PCR). Barcoding the plurality of targets of the cell using the plurality of barcodes 1440 to create the plurality of barcoded targets can comprise stochastically barcoding the plurality of targets of the cell using the plurality of stochastic barcodes to create a plurality of stochastically barcoded targets.

Embodiments disclosed herein also include kits for identifying cellular component-cellular component interactions (e.g., protein-protein interactions). In some embodiments, the kit comprises: a first pair of interaction determination compositions, wherein each of the first pair of interaction determination compositions comprises a cellular component binding reagent associated with an interaction determination oligonucleotide, wherein the cellular component binding reagent of one of the first pair of interaction determination compositions is capable of specifically binding to a first cellular component target and a cellular component binding reagent of the other of the first pair of interaction determination compositions is capable of specifically binding to the second cellular component target, wherein the interaction determination oligonucleotide comprises an interaction determination sequence and a bridge oligonucleotide hybridization region, and wherein the interaction determination sequences of the first pair of interaction determination compositions comprise different sequences; and a plurality of bridge oligonucleotides each comprising two hybridization regions capable of specifically binding to the bridge oligonucleotide hybridization regions of the first pair of interaction determination compositions.

In some embodiments, the kit comprises: a second pair of interaction determination compositions, wherein each of the second pair of interaction determination compositions comprises a cellular component binding reagent associated with an interaction determination oligonucleotide, wherein the cellular component binding reagent of one of the second pair of interaction determination compositions is capable of specifically binding to a third cellular component target and the cellular component binding reagent of the other of the second pair of interaction determination compositions is capable of specifically binding to a fourth cellular component target. In some embodiments, the kit comprises: three or more pairs of interaction determination compositions.

In some embodiments, the kit comprises: a plurality of barcodes, wherein each of the plurality of barcodes comprises a barcode sequence and a capture sequence. The plurality of barcodes can comprise a plurality of stochastic barcodes, wherein the barcode sequence of each of the plurality of stochastic barcodes comprises a barcode sequence (e.g., a molecular label sequence), wherein the barcode sequences of at least two stochastic barcodes of the plurality of stochastic barcodes comprise different sequences. In some embodiments, the plurality of barcodes is associated with a particle. At least one barcode of the plurality of barcodes can be immobilized on the particle, partially immobilized on the particle, enclosed in the particle, partially enclosed in the particle, or any combination thereof. The particle can be disruptable. The particle can comprise a bead.

In some embodiments, the kit comprises: a DNA polymerase. The kit can comprise a reverse transcriptase. The kit can comprise: a Moloney Murine Leukemia Virus (M-MLV) reverse transcriptase or a Taq DNA polymerase. In some embodiments, the method comprises a fixation agent (e.g., formalin, paraformaldehyde, glutaraldehyde/osmium tetroxide, Alcoholic fixatives, Hepes-glutamic acid buffer-mediated organic solvent protection effect (HOPE), Bouin solution, or any combination thereof).

EXAMPLES

Some aspects of the embodiments discussed above are disclosed in further detail in the following examples, which are not in any way intended to limit the scope of the present disclosure.

Example 1

Oligonucleotides for Conjugation with Protein Binding Reagents

This example demonstrates designing of oligonucleotides that can be conjugated with protein binding reagents. The oligonucleotides can be used to determine protein expression and gene expression simultaneously. The oligonucleotides can also be used for sample indexing to determine cells of the same or different samples.

95mer Oligonucleotide Design

The following method was used to generate candidate oligonucleotide sequences and corresponding primer sequences for simultaneous determination of protein expression and gene expression or sample indexing.

1. Sequence Generation and Elimination

The following process was used to generate candidate oligonucleotide sequences for simultaneous determination of protein expression and gene expression or sample indexing.

Step 1a. Randomly generate a number of candidate sequences (50000 sequences) with the desired length (45 bps).

Step 1b. Append the transcriptional regulator LSRR sequence to the 5' end of the sequences generated and a poly(A) sequence (25 bps) to the 3' end of the sequences generated.

Step 1c. Remove sequences generated and appended that do not have GC contents in the range of 40% to 50%.

Step 1d. Remove remaining sequences with one or more hairpin structures each.

The number of remaining candidate oligonucleotide sequences was 423.

2. Primer Design

The following method was used to design primers for the remaining 423 candidate oligonucleotide sequences.

2.1 N1 Primer: Use the universal N1 sequence: 5'-GTTGTCAAGATGCTACCGTTCAGAG-3' (LSRR sequence; SEQ ID NO. 5) as the N1 primer.

2.2 N2 Primer (for amplifying specific sample index oligonucleotides; e.g., N2 primer in FIGS. 15B-15D):

2.2a. Remove candidate N2 primers that do not start downstream of the N1 sequence.

2.2b. Remove candidate N2 primers that overlap in the last 35 bps of the candidate oligonucleotide sequence.

2.2c. Remove the primer candidates that are aligned to the transcriptome of the species of cells being studied using the oligonucleotides (e.g., the human transcriptome or the mouse transcriptome).

2.2d. Use the ILR2 sequence as the default control (ACACGACGCTCTTCCGATCT; SEQ ID NO. 8) to minimize or avoid primer-primer interactions.

Of the 423 candidate oligonucleotide sequences, N2 primers for 390 candidates were designed.

3. Filtering

The following process was used to filter the remaining 390 candidate primer sequences.

3a. Eliminate any candidate oligonucleotide sequence with a random sequence ending in As (i.e., the effective length of the poly(A) sequence is greater than 25 bps) to keep poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 15A shows a non-limiting exemplary candidate oligonucleotide sequence generated using the method above.

200mer Oligonucleotide Design

The following method was used to generate candidate oligonucleotide sequences and corresponding primer sequences for simultaneous determination of protein expression and gene expression and sample indexing.

1. Sequence generation and elimination

The following was used to generate candidate oligonucleotide sequences for simultaneous determination of protein expression and gene expression and sample indexing.

1a. Randomly generate a number of candidate sequences (100000 sequences) with the desired length (128 bps).

1b. Append the transcriptional regulator LSRR sequence and an additional anchor sequence that is non-human, non-mouse to the 5' end of the sequences generated and a poly(A) sequence (25 bps) to the 3' end of the sequences generated.

1c. Remove sequences generated and appended that do not have GC contents in the range of 40% to 50%.

1d. Sort remaining candidate oligonucleotide sequences based on hairpin structure scores.

1e. Select 1000 remaining candidate oligonucleotide sequences with the lowest hairpin scores.

2. Primer Design

The following method was used to design primers for 400 candidate oligonucleotide sequences with the lowest hairpin scores.

2.1 N1 Primer: Use the universal N1 sequence: 5'-GTTGTCAAGATGCTACCGTTCAGAG-3' (LSRR sequence; SEQ ID NO. 5) as the N1 primer.

2.2 N2 Primer (for amplifying specific sample index oligonucleotides; e.g., N2 primer in FIGS. 15B and 15C):

2.2a. Remove candidate N2 primers that do not start 23 nts downstream of the N1 sequence (The anchor sequence was universal across all candidate oligonucleotide sequences).

2.2b. Remove candidate N2 primers that overlap in the last 100 bps of the target sequence. The resulting primer candidates can be between the 48th nucleotide and 100th nucleotide of the target sequence.

2.2c. Remove the primer candidates that are aligned to the transcriptome of the species of cells being studied using the oligonucleotides (e.g., the human transcriptome or the mouse transcriptome).

2.2d. Use the ILR2 sequence, 5'-ACACGACGCTCTTCCGATCT-3' (SEQ ID NO. 8) as the default control to minimize or avoid primer-primer interactions.

2.2e. Remove N2 primer candidates that overlap in the last 100 bps of the target sequence.

Of the 400 candidate oligonucleotide sequences, N2 primers for 392 candidates were designed.

3. Filtering

The following was used to filter the remaining 392 candidate primer sequences.

3a. Eliminate any candidate oligonucleotide sequence with a random sequence ending in As (i.e., the effective length of the poly(A) sequence is greater than 25 bps) to keep poly(A) tail the same length for all barcodes.

3b. Eliminate any candidate oligonucleotide sequences with 4 or more consecutive Gs (>3Gs) because of extra cost and potentially lower yield in oligo synthesis of runs of Gs.

FIG. 15B shows a non-limiting exemplary candidate oligonucleotide sequence generated using the method above. The nested N2 primer shown in FIG. 15B can bind to the antibody or sample specific sequence for targeted amplification. FIG. 15C shows the same non-limiting exemplary candidate oligonucleotide sequence with a nested universal N2 primer that corresponds to the anchor sequence for targeted amplification. FIG. 15D shows the same non-limiting exemplary candidate oligonucleotide sequence with a N2 primer for one step targeted amplification.

Altogether, these data indicate that oligonucleotide sequences of different lengths can be designed for simultaneous determination of protein expression and gene expression or sample indexing. The oligonucleotide sequences can include a universal primer sequence, an antibody specific oligonucleotide sequence or a sample indexing sequence, and a poly(A) sequence.

Example 2

Comparison of Detection Sensitivity with Different Antibody:Oligonucleotide Ratios This example demonstrates detection sensitivity of CD4 protein using an anti-CD4 antibody conjugated with 1, 2, or 3 oligonucleotides.

Figure 16:
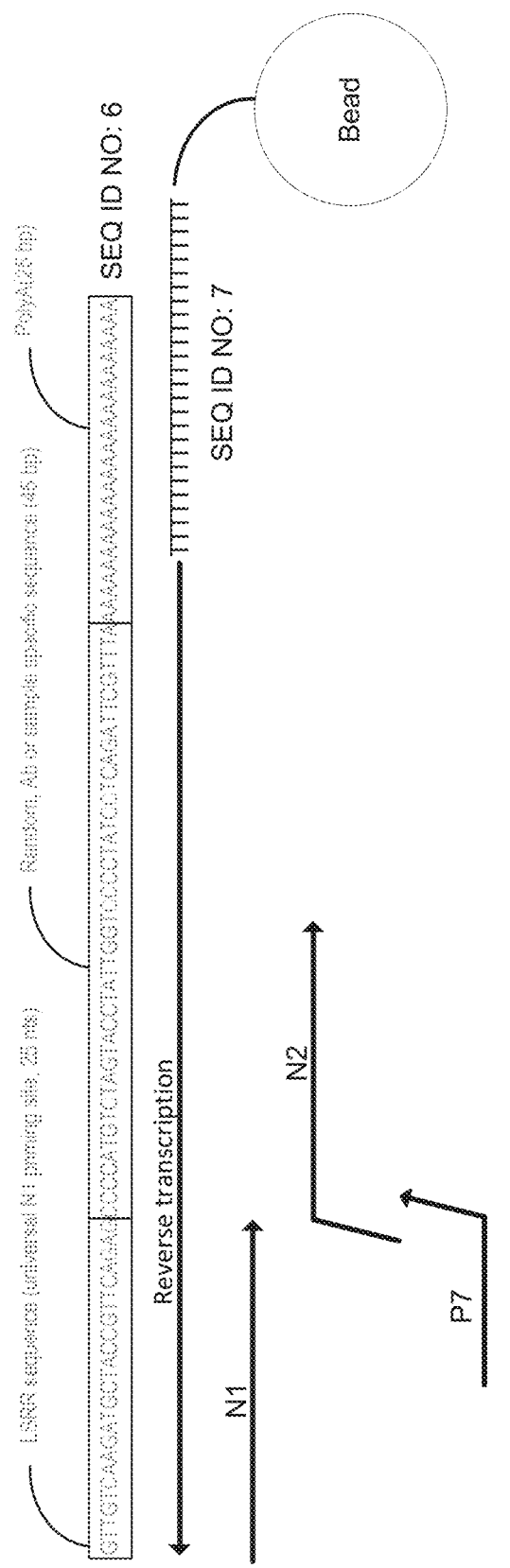
FIG. 16 shows a schematic illustration of a non-limiting exemplary oligonucleotide sequence for determining protein expression and gene expression simultaneously and for sample indexing.

Frozen peripheral blood mononuclear cells (PBMCs) of a subject were thawed. The thawed PBMCs were stained with three types of anti-CD4 antibody at 0.06 μg/100 μl (1:333 dilution of oligonucleotide-conjugated antibody stocks) at room temperature for 20 minutes. Each type of the types of anti-CD4 antibody was conjugated with 1, 2, or 3 oligonucleotides ("antibody oligonucleotides"). The sequence of the antibody oligonucleotide is shown in FIG. 16. The cells were washed to remove unbound anti-CD4 antibodies. The cells were stained with Calcein AM (BD (Franklin Lake, New Jersey)) and Drag7™ (Abcam (Cambridge, United Kingdom)) for sorting with flow cytometry to obtain live cells. The cells were washed to remove excess Calcein AM and Drag7™. Single cells stained with Calcein AM (live cells) and not Drag7™ (cells that were not dead or permeabilized) were sorted, using flow cytometry, into a BD Rhapsody™ cartridge.

Of the wells containing a single cell and a bead, 3500 of the single cells in the wells were lysed in a lysis buffer with 5 mM DTT. The CD4 mRNA expression profile was determined using BD Rhapsody™ beads. The CD4 protein expression profile was determined using BD Rhapsody™ beads and the antibody oligonucleotides. Briefly, the mRNA molecules were released after cell lysis. The Rhapsody™ beads were associated with stochastic barcodes each containing a molecular label, a cell label, and a polyT region. The poly(A) regions of the mRNA molecules released from the lysed cells hybridized to the polyT regions of the stochastic barcodes. The poly(A) regions of the oligonucleotides hybridized to the polyT regions of the stochastic barcodes. The mRNA molecules were reverse transcribed using the stochastic barcodes. The antibody oligonucleotides were replicated using the stochastic barcodes. The reverse transcription and replication occurred in one sample aliquot at the same time.

The reverse transcribed products and replicated products were PCR amplified for 15 cycles at 60 degrees annealing temperature using primers for determining the mRNA expression profiles of 488 blood panel genes, using blood panel N1 primers, and the expression profile of CD4 protein, using the antibody oligonucleotide N1 primers ("PCR 1"). Excess stochastic barcodes were removed with Ampure cleanup. The products from PCR1 were divided into two aliquots, one aliquot for determining the mRNA expression profiles of the 488 blood panel genes, using the blood panel N2 primers, and one aliquot for determining the expression profile of CD4 protein, using the antibody oligonucleotide N2 primers ("PCR 2"). Both aliquots were PCR amplified for 15 cycles at 60 degrees annealing temperature. The expression of CD4 protein in the lysed cells was determined based on the antibody oligonucleotides as illustrated in FIG. 16 ("PCR 2"). Sequencing data was obtained and analyzed after sequencing adaptor ligation ("PCR 3"). Cell types were determined based on the expression profiles of the 488 blood panel genes.

Figure 17A:
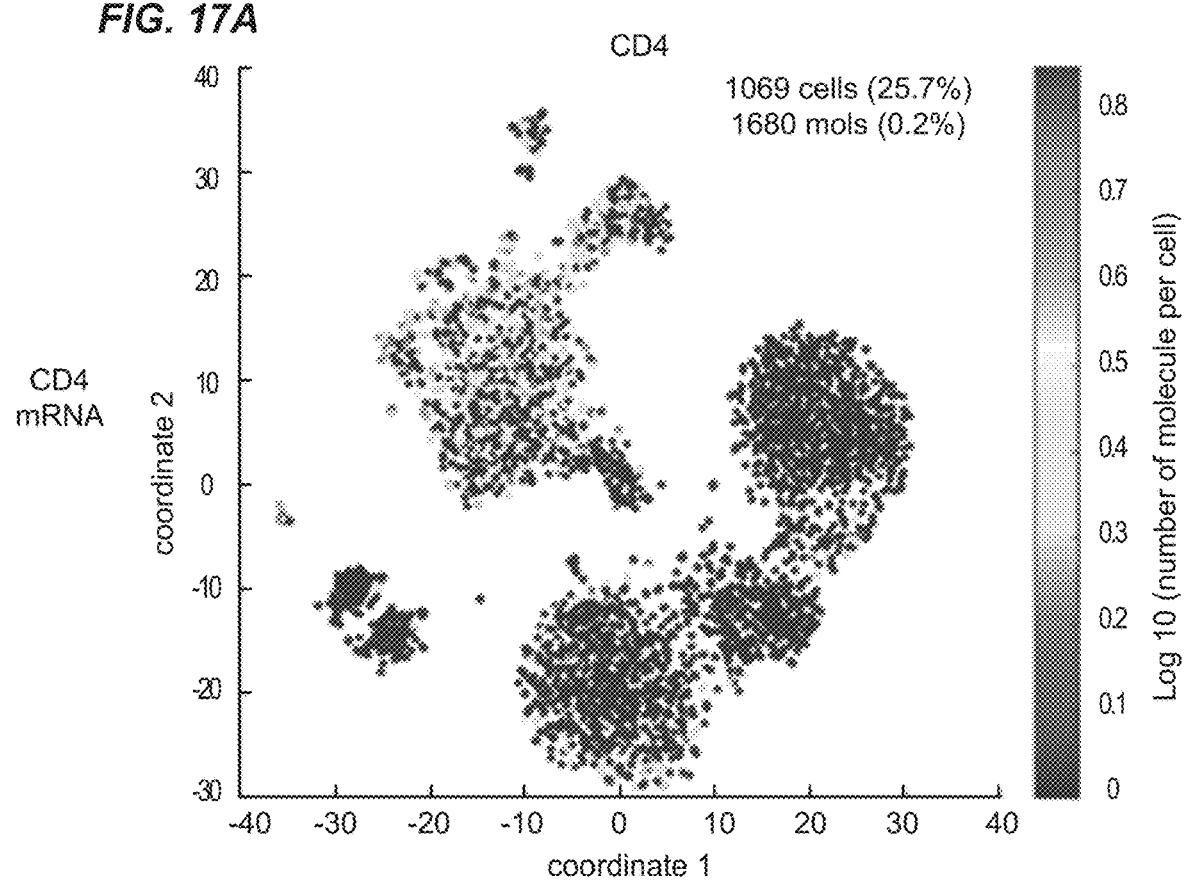
FIGS. 17A-17F are non-limiting exemplary tSNE projection plots showing results of using oligonucleotide-conjugated antibodies to measure CD4 protein expression and gene expression simultaneously in a high throughput manner.
Figure 17B:
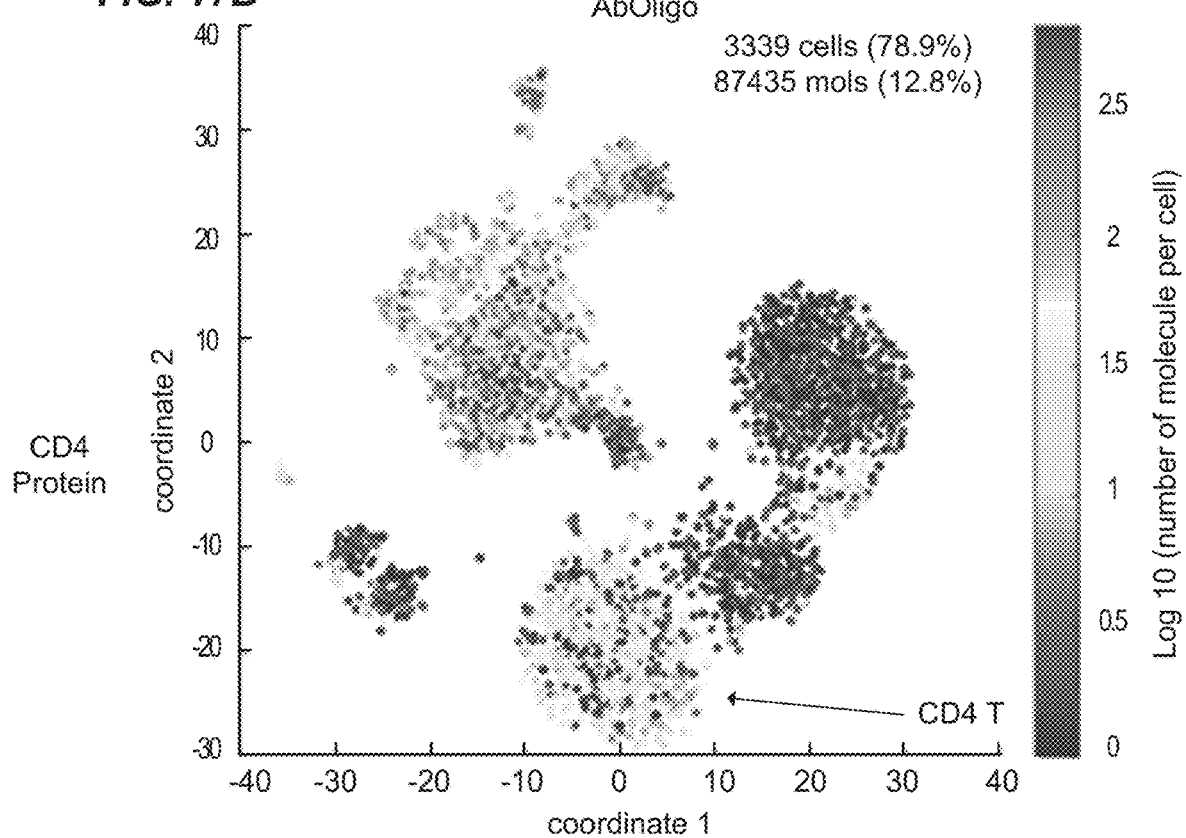
Figure 17C:
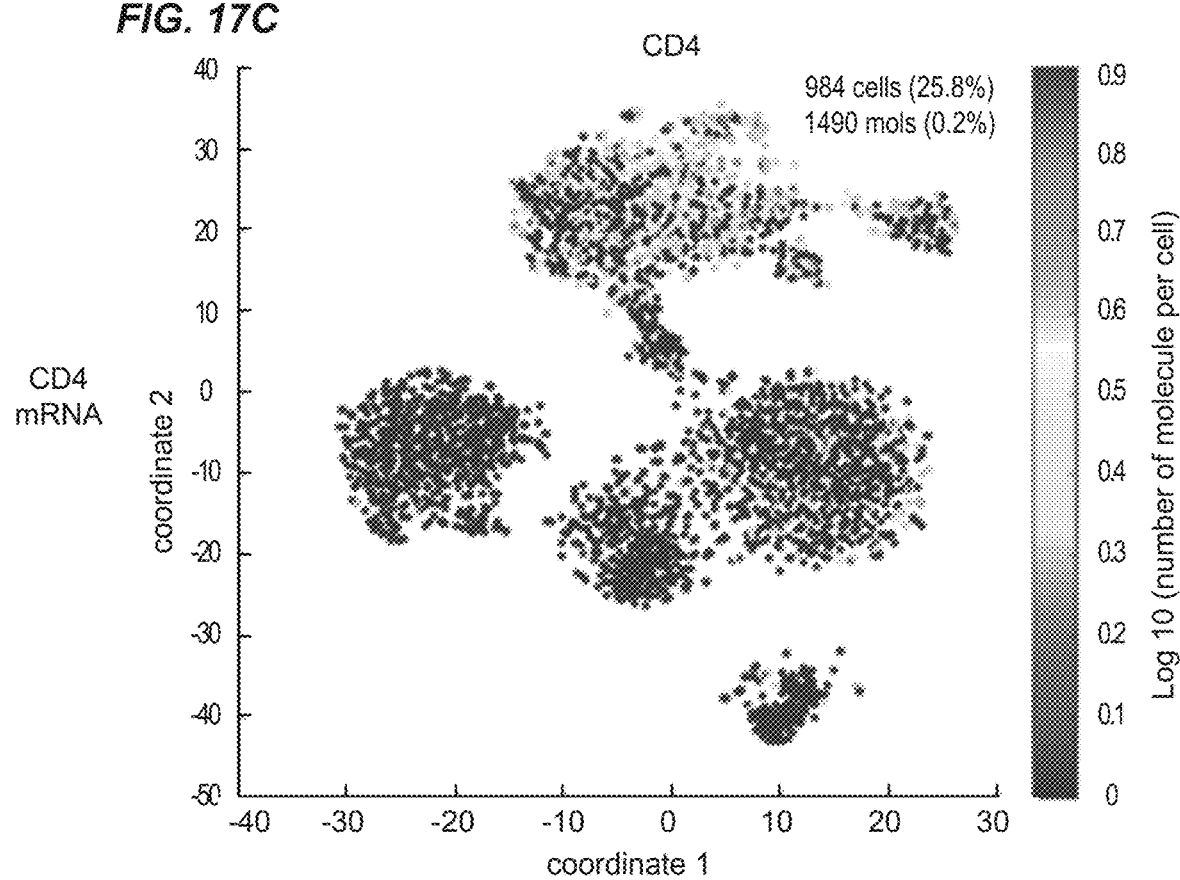
Figure 17D:
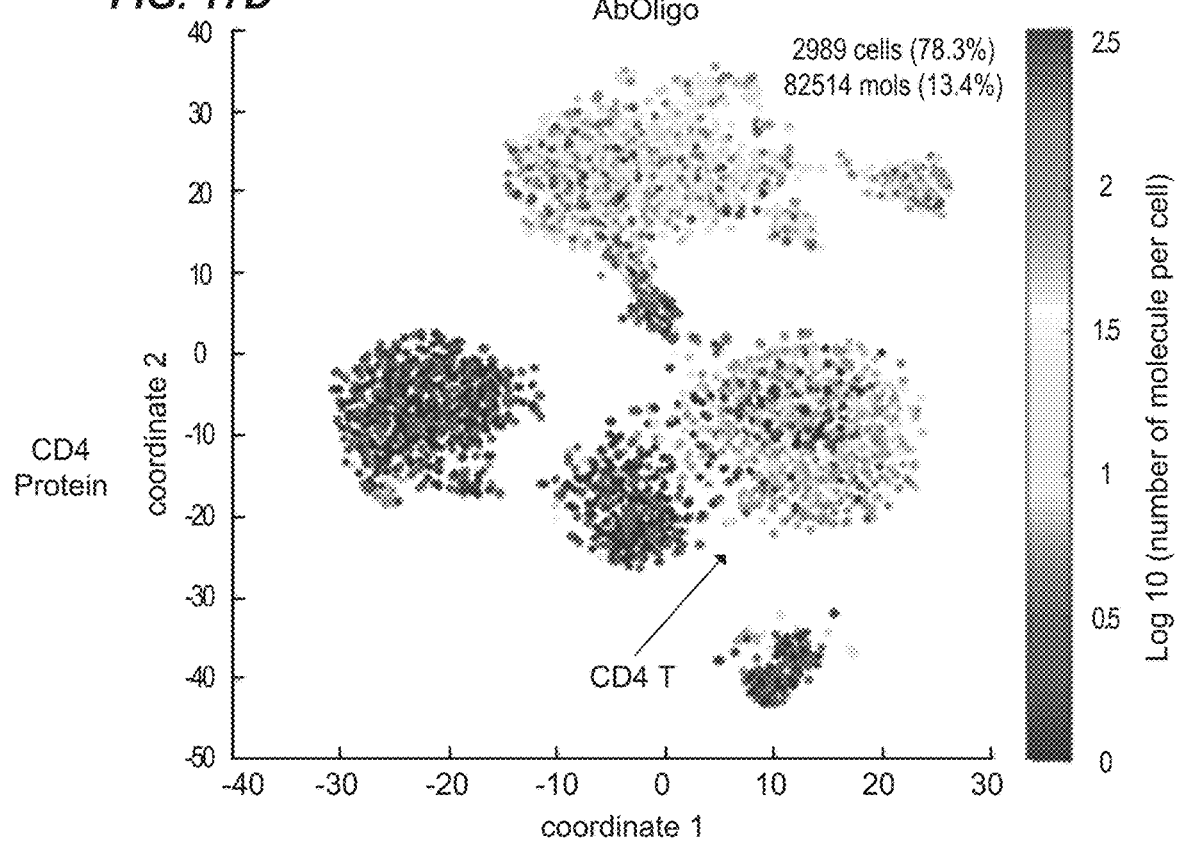
Figure 17E:
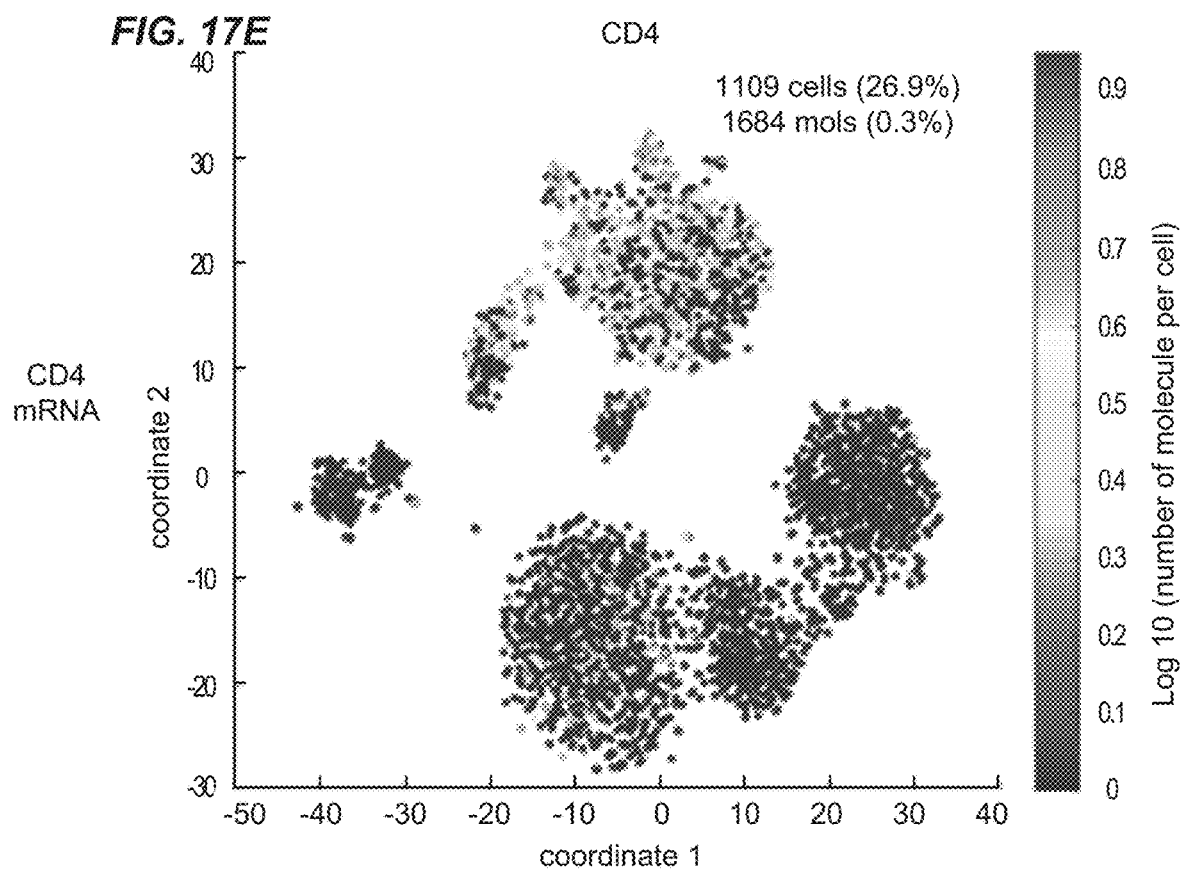
Figure 17F:
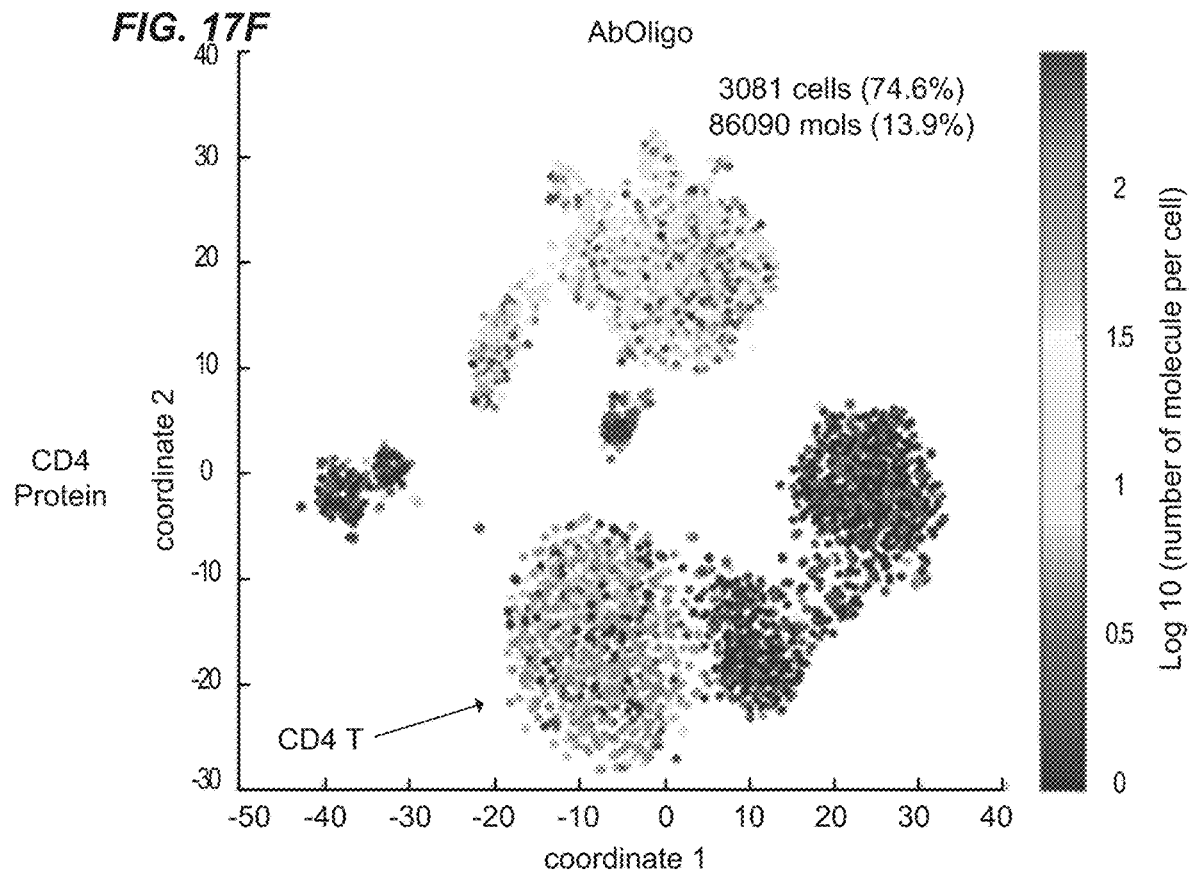
Figure 19:
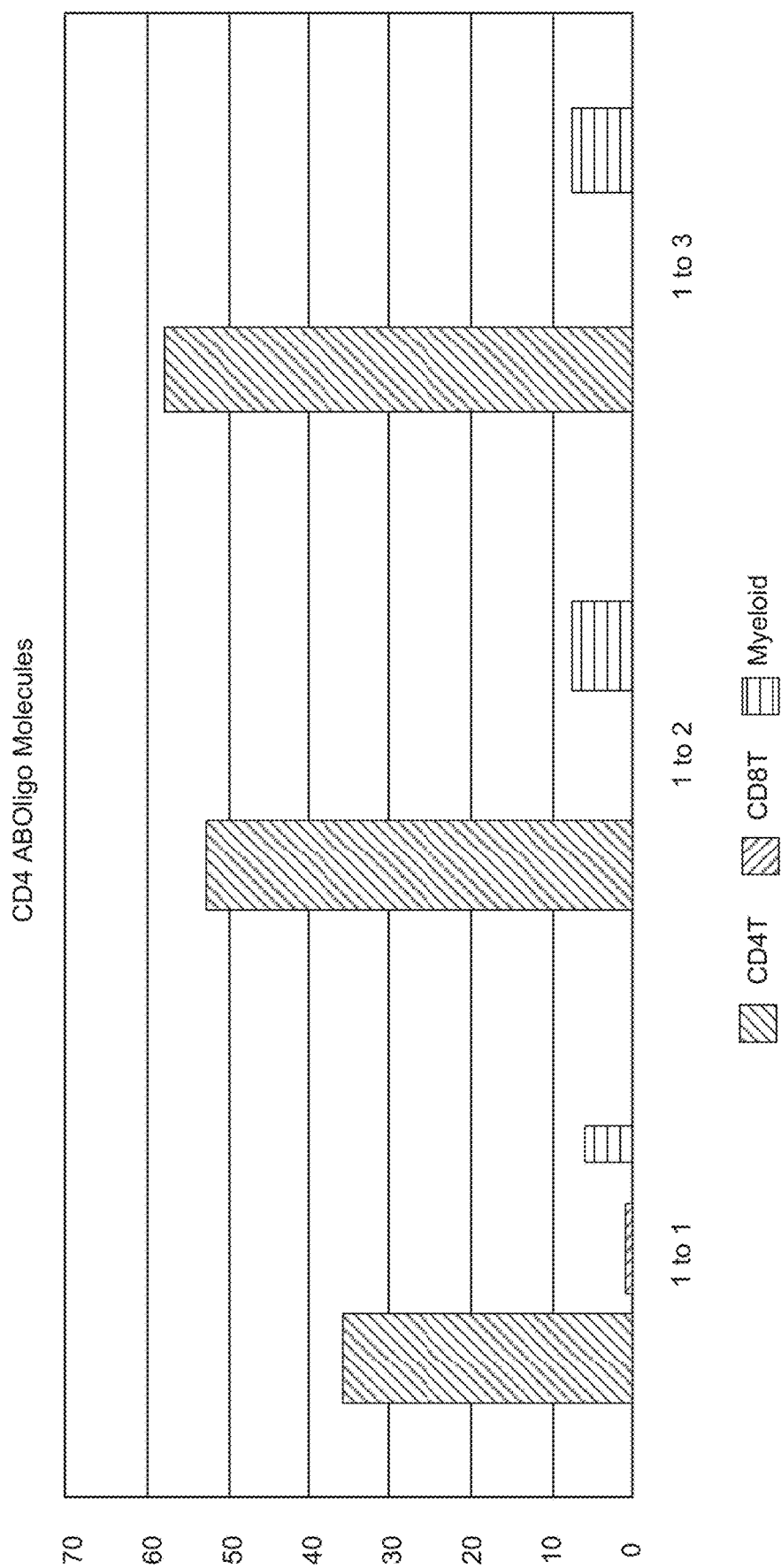
FIG. 19 is a non-limiting exemplary bar chart showing that, with similar sequencing depth, detection sensitivity for CD4 protein level increased with higher ratios of antibody: oligonucleotide, with the 1:3 ratio performing better than the 1:1 and 1:2 ratios.
Figure 21A:
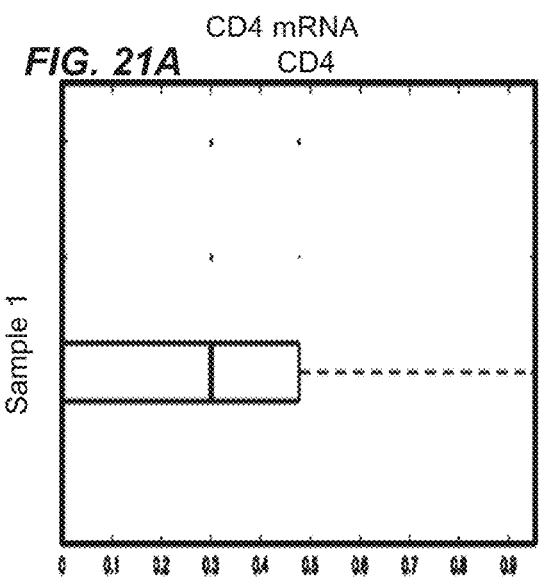
FIGS. 21A-21F are non-limiting exemplary bar charts showing the expressions of CD4 mRNA and protein in CD4 T cells, CD8 T cells, and Myeloid cells of two samples.
Figure 21B:
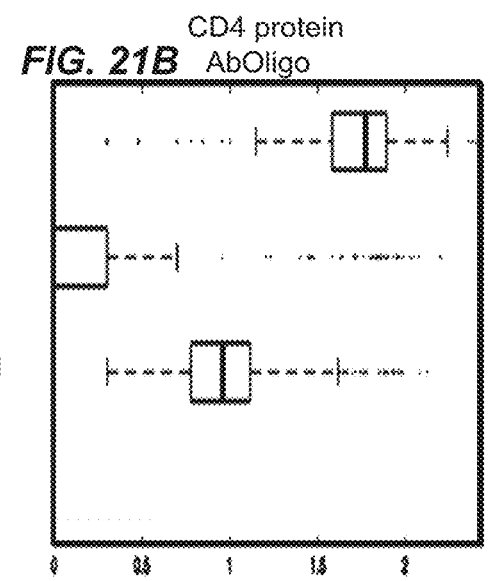
Figure 21C:
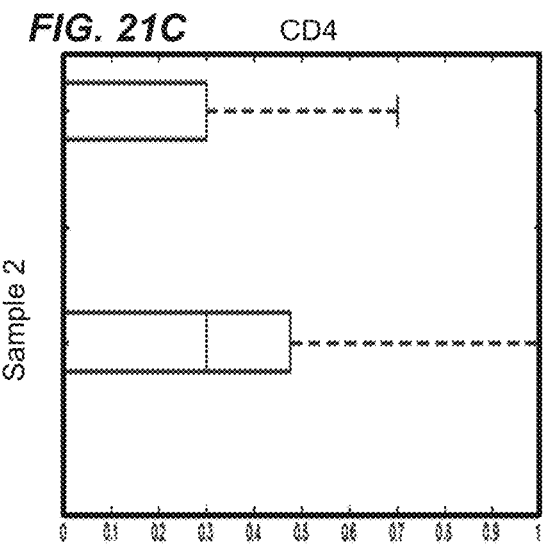
Figure 21D:
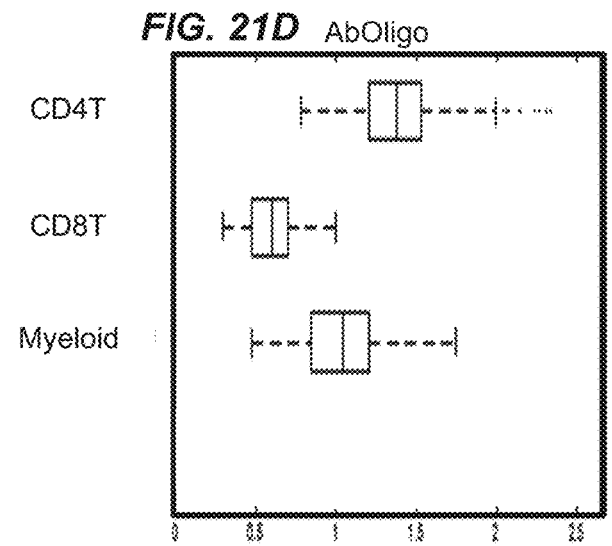
Figure 21E:
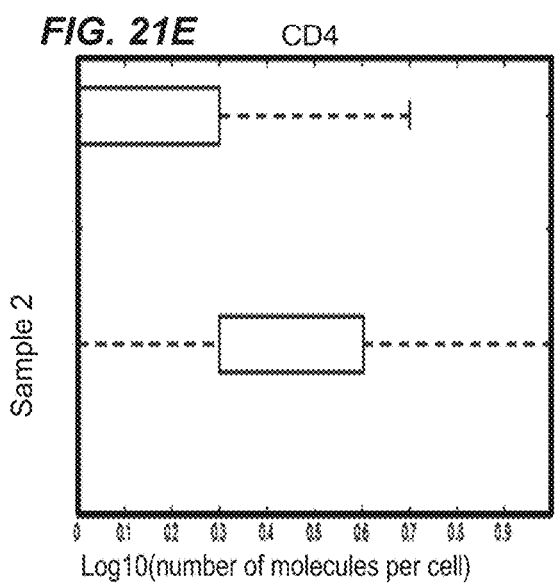
Figure 21F:
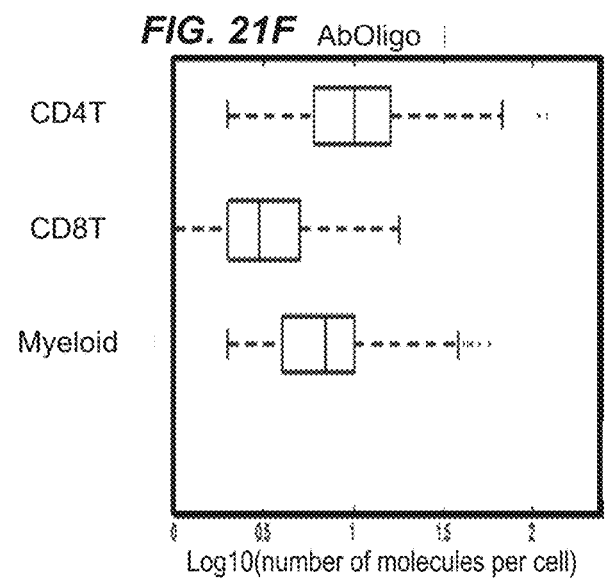
Figure 22:
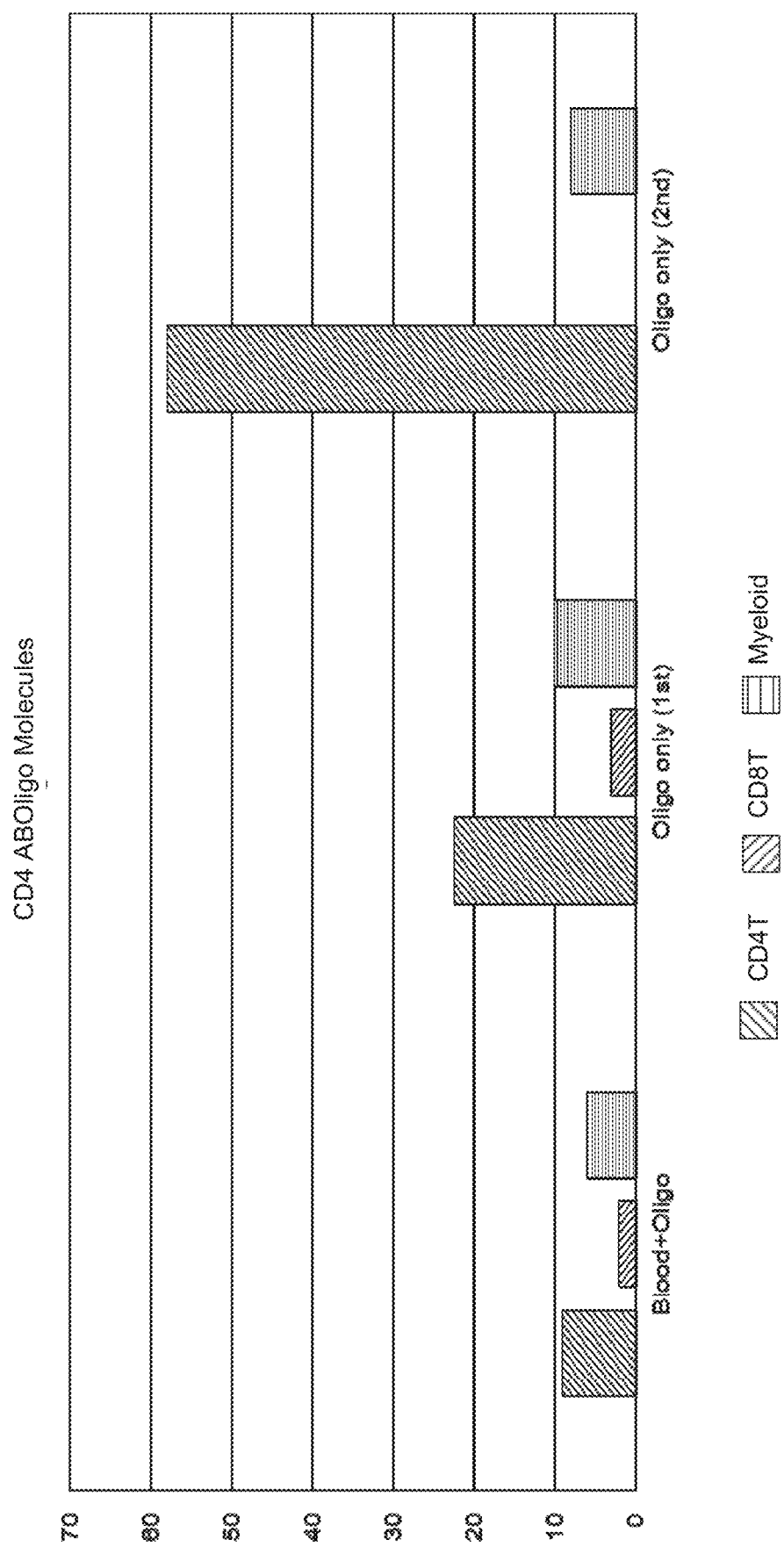
FIG. 22 is a non-limiting exemplary bar chart showing detection sensitivity for CD4 protein level determined using different sample preparation protocols with an antibody: oligonucleotide ratio of 1:3.

FIGS. 17A-17F are non-limiting exemplary t-Distributed Stochastic Neighbor Embedding (tSNE) projection plots showing results of using oligonucleotide-conjugated antibodies to measure CD4 protein expression and gene expression simultaneously in a high throughput manner. CD4 protein expression was distinctly and robustly detected in CD4 expressing cell types (e.g., CD4 T cells) with anti-CD4 antibodies conjugated to 1, 2, or 3 antibody oligonucleotides (FIGS. 17B, 17D, and 17F respectively). FIGS. 18A-18F are non-limiting exemplary bar charts showing the expressions of CD4 mRNA and protein in CD4 T cells (high CD4 expression), CD8 T cells (minimal CD4 expression), and Myeloid cells (some CD4 expression). With similar sequencing depth, detection sensitivity for CD4 protein level increased with higher ratios of antibody:oligonucleotide, with the 1:3 ratio performing better than the 1:1 and 1:2 ratios (FIG. 19). The expression of CD4 protein on cell surface of cells sorted using flow cytometry was confirmed using FlowJo (FlowJo (Ashland, OR)) as shown in FIGS. 20A-20D. FIGS. 21A-21F are non-limiting exemplary bar charts showing the expressions of CD4 mRNA and CD4 protein in CD4 T cells, CD8 T cells, and Myeloid cells of two samples. The second sample was prepared using two different sample preparation protocols. FIG. 22 is a non-limiting exemplary bar chart showing detection sensitivity for CD4 protein level determined using different sample preparation protocols with an antibody:oligonucleotide ratio of 1:3.

Altogether, these data indicate that CD4 protein expression can be distinctly and robustly detected based on oligonucleotide-conjugated with anti-CD4 antibodies. Detection sensitivity for CD4 protein level can increase with higher antibody:oligonucleotide ratios.

Example 3

Sample Indexing

This example demonstrates identifying cells of different samples using sample indexing with high labeling efficiency and low non-specific labeling or spill over. This example also demonstrates the effects of the lengths of the sample indexing oligonucleotides and the cleavability of sample indexing oligonucleotides on sample indexing.

Figure 23:
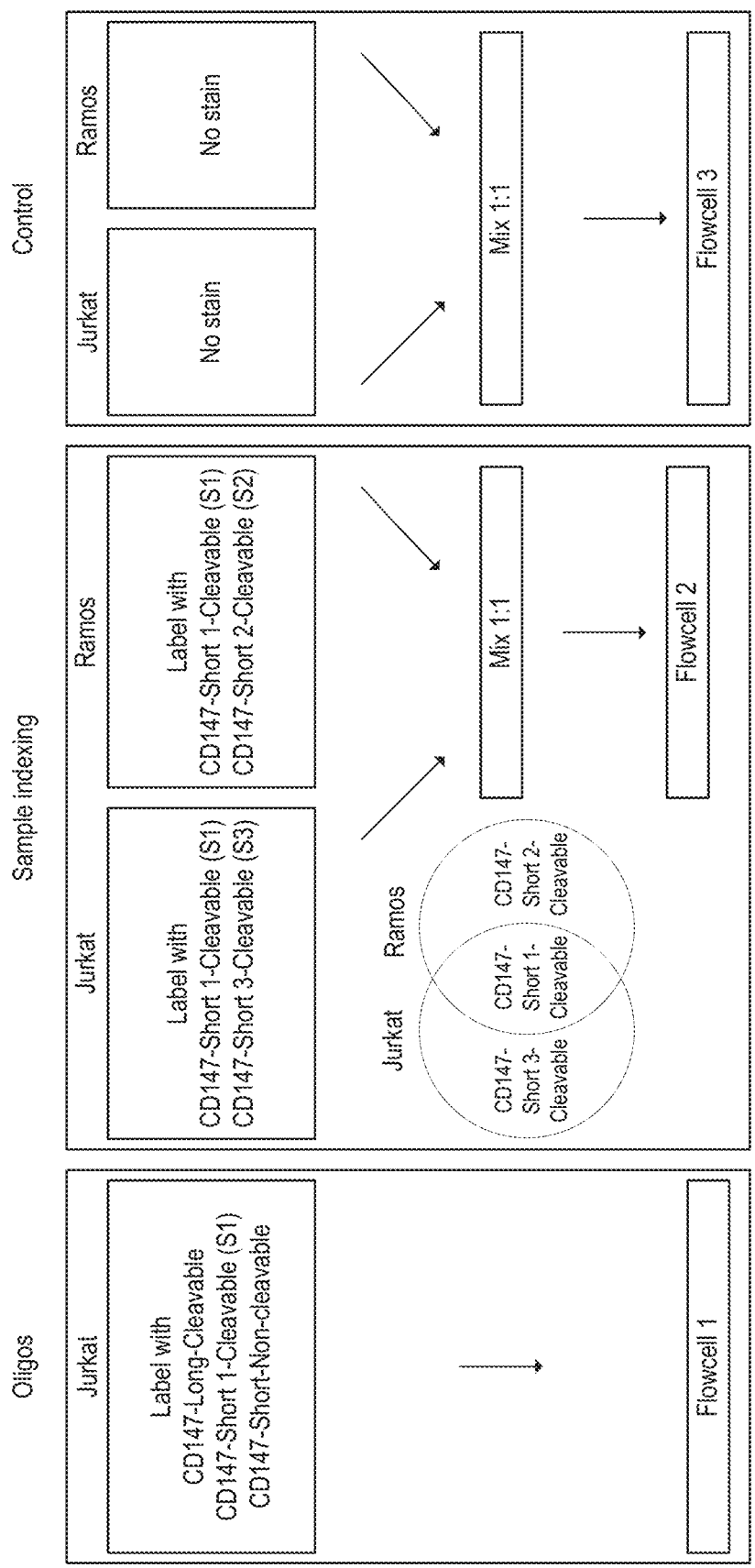
FIG. 23 shows a non-limiting exemplary experimental design for performing sample indexing and determining the effects of the lengths of the sample indexing oligonucleotides and the cleavability of sample indexing oligonucleotides on sample indexing.

FIG. 23 shows a non-limiting exemplary experimental design for performing sample indexing and determining the effects of the lengths of the sample indexing oligonucleotides and the cleavability of sample indexing oligonucleotides on sample indexing. The left column in FIG. 23 shows that Jurkat cells were labeled with anti-CD147 antibodies with different sample indexing oligonucleotides to determine the effects of the lengths of the sample indexing oligonucleotides and the cleavability of sample indexing oligonucleotides on sample indexing. The oligonucleotide-conjugated with the anti-CD147 antibodies were 200 nucleotides in length that were cleavable from the antibody (T-linker), 95 nucleotides in length that were cleavable (T-linker), and 95 nucleotides in length that were not cleavable. After further sample preparation, the effects of the lengths of the sample indexing oligonucleotides and the cleavability of sample indexing oligonucleotides on sample indexing were determined using a Rhapsody™ flowcell (labeled "Flowcell F" in FIG. 23, abbreviated as "FC1"). Sample preparation included Calcein AM and Drag7™ staining, cell sorting using flow cytometry, and stochastic barcoding.

The middle column in FIG. 23 shows that cells were labeled with anti-CD147 antibodies conjugated with three different sample indexing oligonucleotides that were cleavable (the sample indexing oligonucleotides, labeled "Short 1," "Short 2," and "Short 3" in FIG. 23, can be abbreviated as S1, S2, and S3). Ramos cells were labeled with two types of anti-CD147 antibodies conjugated with different sample indexing oligonucleotides that are cleavable (the sample indexing oligonucleotides are labeled "Short F" and "Short 2" in FIG. 23). Jurkat cells were labeled with two types of anti-CD147 antibodies conjugated with different sample indexing oligonucleotides that are cleavable (the sample indexing oligonucleotides are labeled "Short F" and "Short 3" in FIG. 23). The labeled cells were mixed in a 1:1 ratio, followed by further sample preparation and determination of the efficiency and specificity of sample indexing using a Rhapsody™ flowcell (labeled "Flowcell 2" in FIG. 23, abbreviated as "FC2"). The right column in FIG. 23 shows the control experiment where Jurkat cells and Ramos cells that were not labeled were mixed in a 1:1 ratio prior to further sample preparation and analysis using a Rhapsody™ flowcell (labeled as "Flowcell 3" in FIG. 23, abbreviated as "FC3").

The cells were stained with antibodies conjugated with sample indexing oligonucleotides a 1:3 antibody:oligonucleotide ratio at room temperature for 20 minutes. The antibodies were diluted from oligonucleotide-conjugated antibody stocks at 1:20 dilution in 100 µl using a pH 7.5 diluent. The cells were washed to remove unbound anti-CD147 antibodies. The cells were stained with Calcein AM (staining for live cells) and Drag7™ (staining for cells that were dead or permeabilized)) for sorting with flow cytometry to obtain live cells. The cells were washed to remove excess Calcein AM and Drag7™. Single cells stained with Calcein AM and not Drag7™ were sorted, using flow cytometry, into a BD Rhapsody™ cartridge containing a flowcell.

Of the wells containing a single cell and a bead, 1000 of the single cells in the wells were lysed in a lysis buffer. The CD147 mRNA expression profile was determined using BD Rhapsody™ beads. Briefly, the mRNA molecules were released after cell lysis. The Rhapsody™ beads were associated with stochastic barcodes each containing a molecular label, a cell label, and a polyT region. The poly(A) regions of the mRNA molecules released from the lysed cells hybridized to the polyT regions of the stochastic barcodes. The poly(A) regions of the sample indexing oligonucleotides, cleaved from the antibodies if cleavable, hybridized to the polyT regions of the stochastic barcodes. The mRNA molecules were reverse transcribed using the stochastic barcodes. The antibody oligonucleotides were replicated using the stochastic barcodes. The reverse transcription and replication occurred in one sample aliquot at the same time for 15 cycles at 60 degrees annealing temperature.

The reverse transcribed products and replicated products were PCR amplified for 15 cycles at 60 degrees annealing temperature using primers for determining the mRNA expression profiles of 488 blood panel genes, using blood panel N1 primers, and the expression of CD147 protein, using the sample indexing oligonucleotide N1 primers ("PCR 1"). Excess primers were removed with Ampure cleanup. The products from PCR1 were further PCR amplified ("PCR 2") for 15 cycles at 60 degrees annealing temperature using blood panel N2 primers and sample indexing oligonucleotide N1 primers with a flanking sequence for adaptor ligation. Sequencing data was obtained and analyzed after sequencing adaptor ligation ("PCR 3"). Cell types were determined based on the expression profiles of the 488 blood panel genes.

Table 1 shows metrics of the sequencing data obtained using the experimental design illustrated in FIG. 23. Three types of anti-CD147 antibody, conjugated with any one of the three types of sample indexing oligonucleotides (cleavable 95mer, non-cleavable 95mer, and cleavable 200mer shown at the left column in FIG. 23), were successfully used for sample indexing. More than 11% of total numbers of reads in the sequencing data were attributed to the sample indexing oligonucleotides.

TABLE 1

Sequencing metrics of sample indexing oligonucleotides.

| | FC1 (Oligos) | | | FC2 (sample indexing) | | |
|---|---|---|---|---|---|---|
| | Sample | | | | | |
| | Jurkat (J) | | | J & R | Ramos (R) | J |
| | Oligo type | | | | | |
| | 95mer, cleavable | 95mer, non-cleavable | 200mer, cleavable | 95mer, cleavable | | |
| % of total reads | 11.4 | 22.4 | 11.8 | 16.7 | 12.9 | 11 |
| % of total molecules | 29 | 41.4 | 7.5 | 28.1 | 20.3 | 16.3 |
| Average # of mols per cell | 1043 | 1679 | 303 | NA | NA | NA |

TABLE 1-continued

Sequencing metrics of sample indexing oligonucleotides.

| | FC1 (Oligos) | | | FC2 (sample indexing) | | |
|---|---|---|---|---|---|---|
| Sample | Jurkat (J) | | | J & R | Ramos (R) | J |
| Oligo type | 95mer, cleavable | 95mer, non-cleavable | 200mer, cleavable | 95mer, cleavable | | |
| Median # of mols per cell | 895 | 1536 | 256 | NA | NA | NA |
| Oligo RSEC seq depth | 3.9 | 4.6 | 11.54 | 1.74 | 1.87 | 2 |
| Blood panel RSEC seq depth | 10.72 | 10.72 | 10.72 | 4.1 | 4.1 | 4.1 |

Three types of anti-CD147 antibody, conjugated with any one of the three cleavable 95mers (labeled "Short 1," "Short 2," and "Short 3" at the middle column in FIG. 23), were successfully used for sample indexing to distinguish Ramos and Jurkat cells of different samples. More than 11% of the total number of reads in the sequencing data were attributed to the sample indexing oligonucleotides. The percentage was the highest (16.7%) for a sample containing both Jurkat and Ramos cells.

Figure 24A:
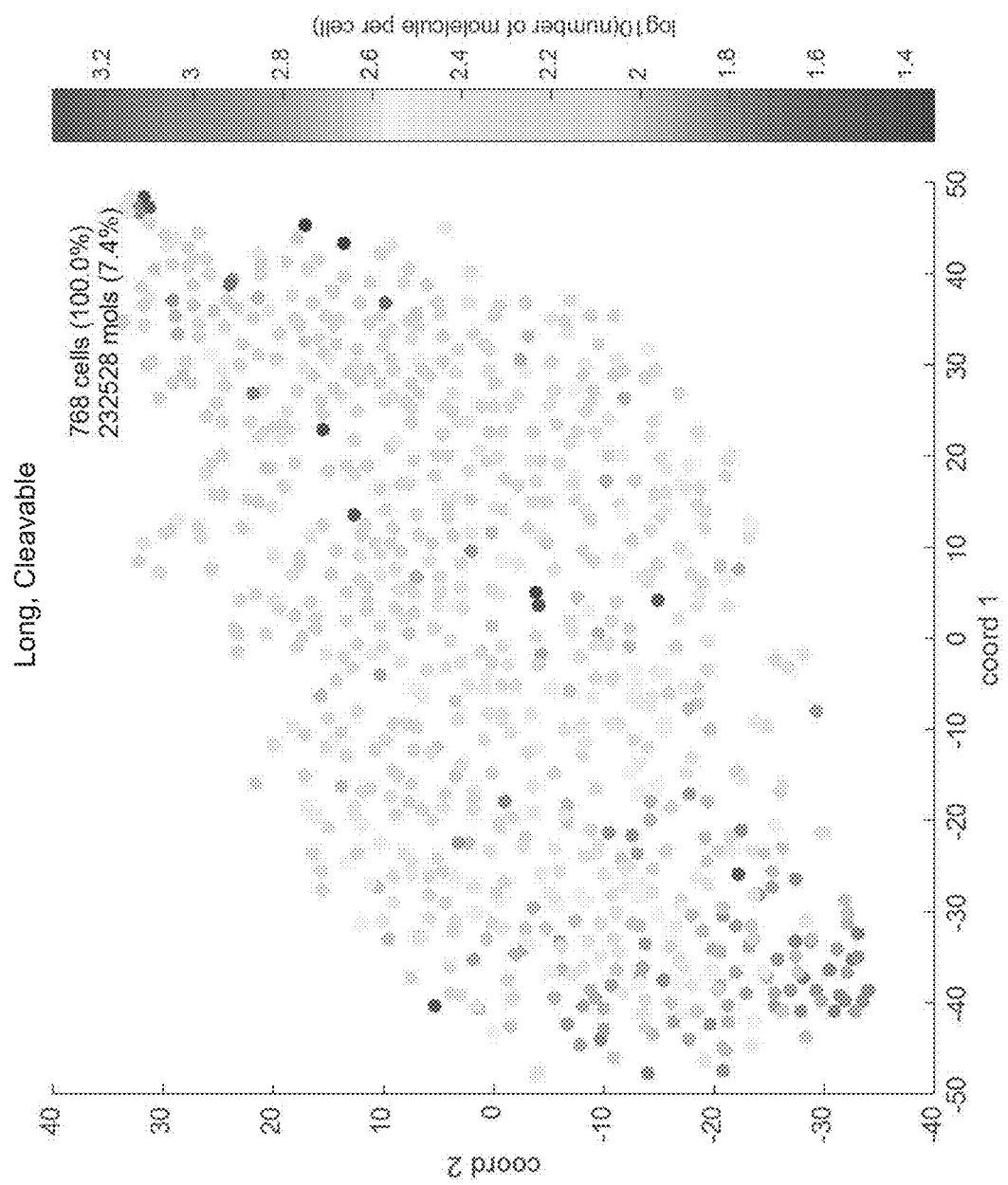
FIGS. 24A-24C are non-limiting exemplary tSNE plots showing that the three types of anti-CD147 antibody conjugated with different sample indexing oligonucleotides (cleavable 95mer, non-cleavable 95mer, and cleavable 200mer) can be used for determining the protein expression level of CD147.
Figure 24B:
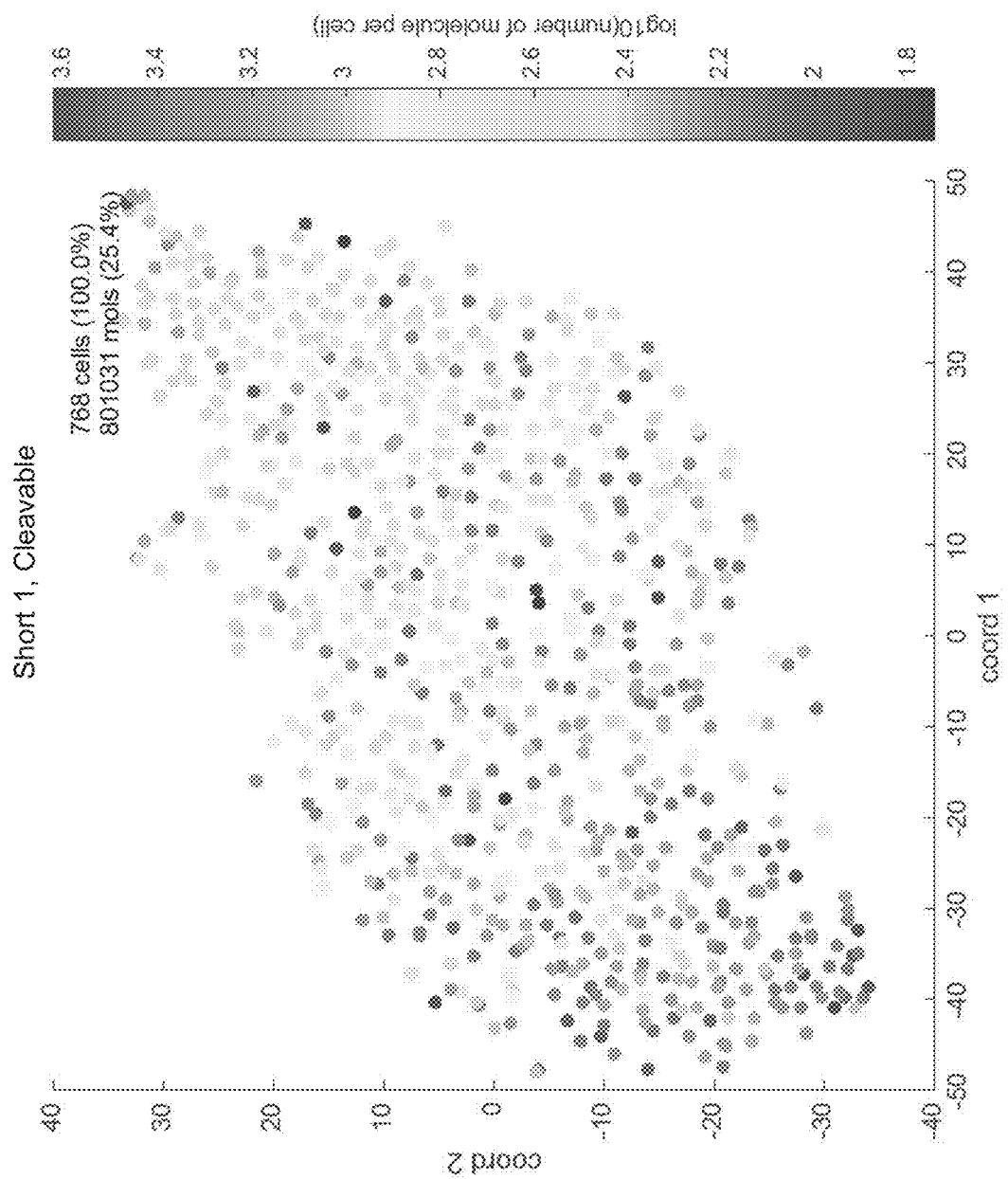
Figure 24C:
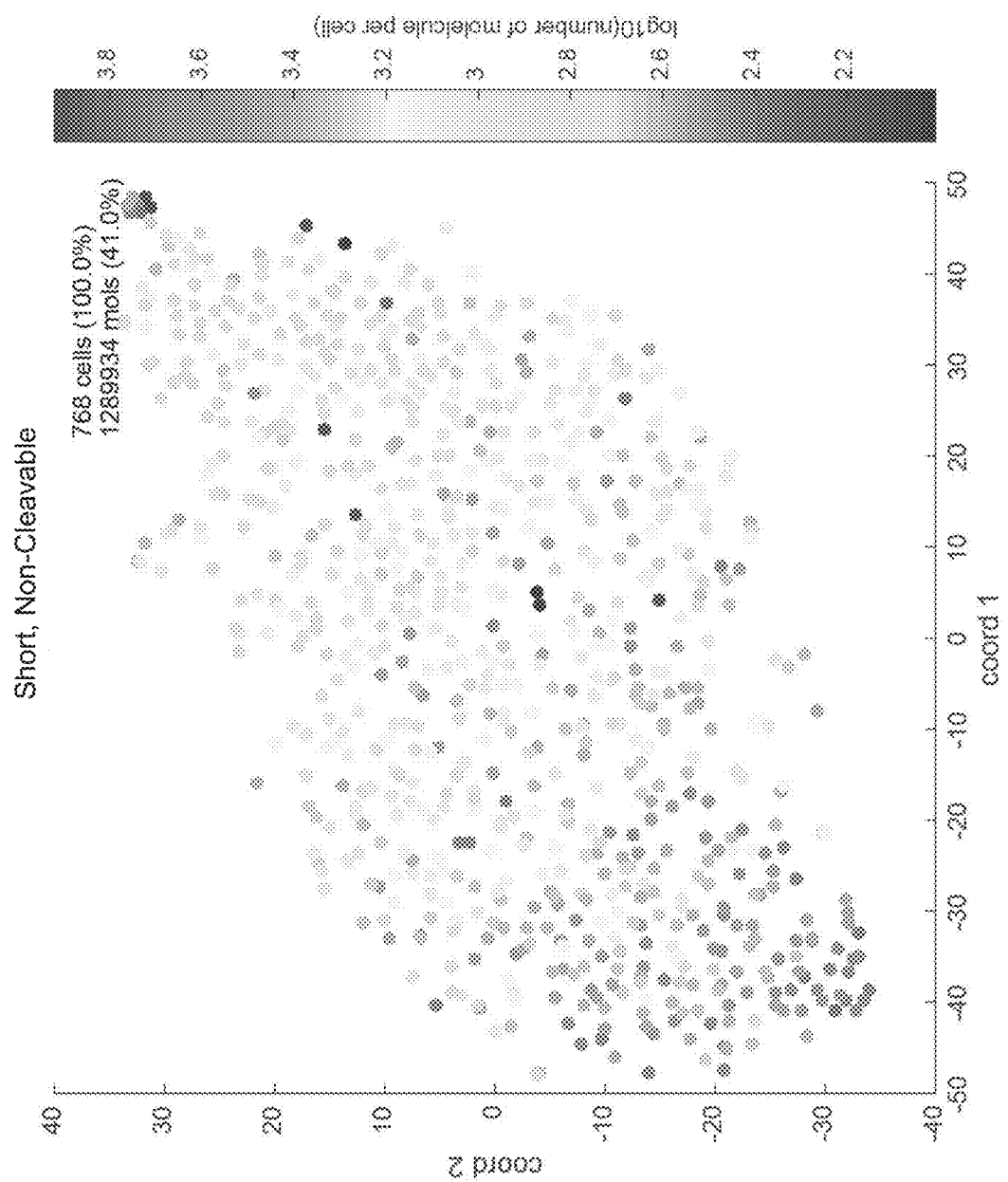
Figure 25:
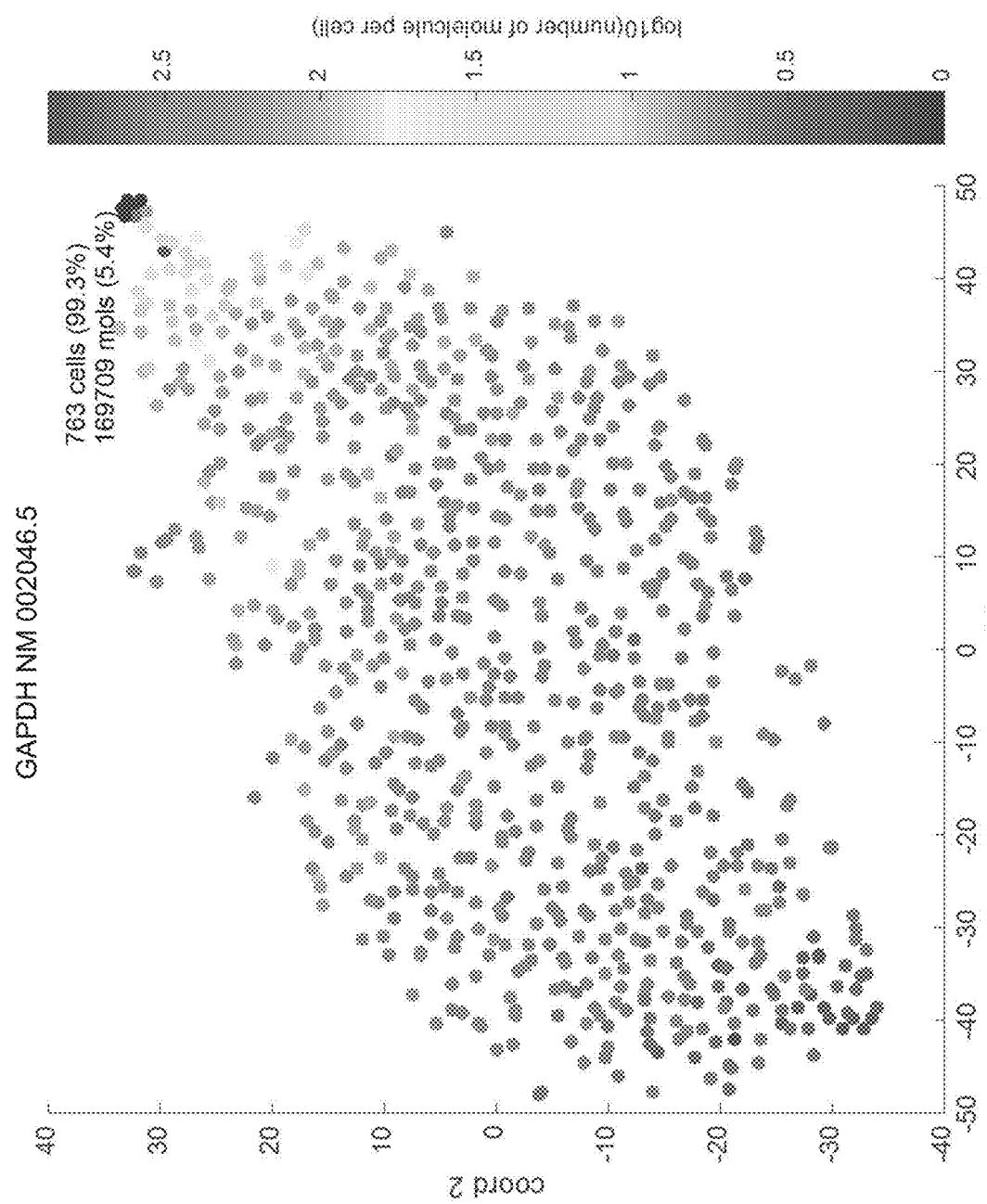
FIG. 25 is a non-limiting exemplary tSNE plot with an overlay of GAPDH expression per cell.

FIGS. 24A-24C are non-limiting exemplary tSNE plots of expression profiles of cells showing that the three types of anti-CD147 antibody conjugated with different sample indexing oligonucleotides (cleavable 95mer, non-cleavable 95mer, and cleavable 200mer) can be used for determining the protein expression level of CD147. The overlays of the CD147 expression, determined using sample indexing oligonucleotides, on tSNE projection plots of the expression profiles of the cells show that the CD147 expression patterns determined using different sample indexing oligonucleotides were similar. Detection of the three sample indexing oligonucleotides was 100%. FIG. 25 is a non-limiting exemplary tSNE plot with an overlay of GAPDH expression per cell. "Cells" at the top right corner of the plot were low in GAPDH, suggesting that they were not real cells. These "cells" were high in sample indexing oligonucleotides.

Figure 26A:
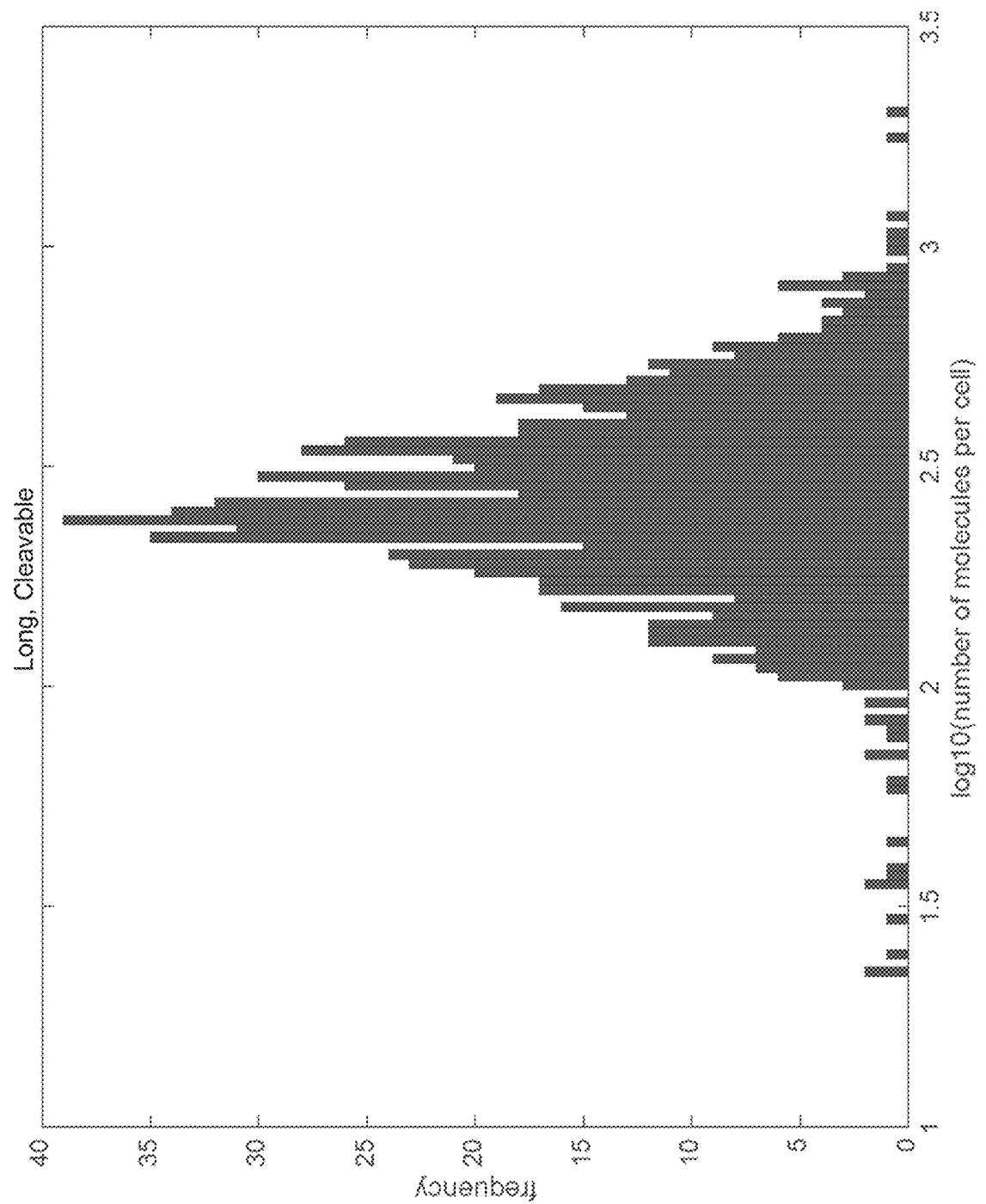
FIGS. 26A-26C are non-limiting exemplary histograms showing the numbers of molecules of sample indexing oligonucleotides detected using the three types of sample indexing oligonucleotides.
Figure 26B:
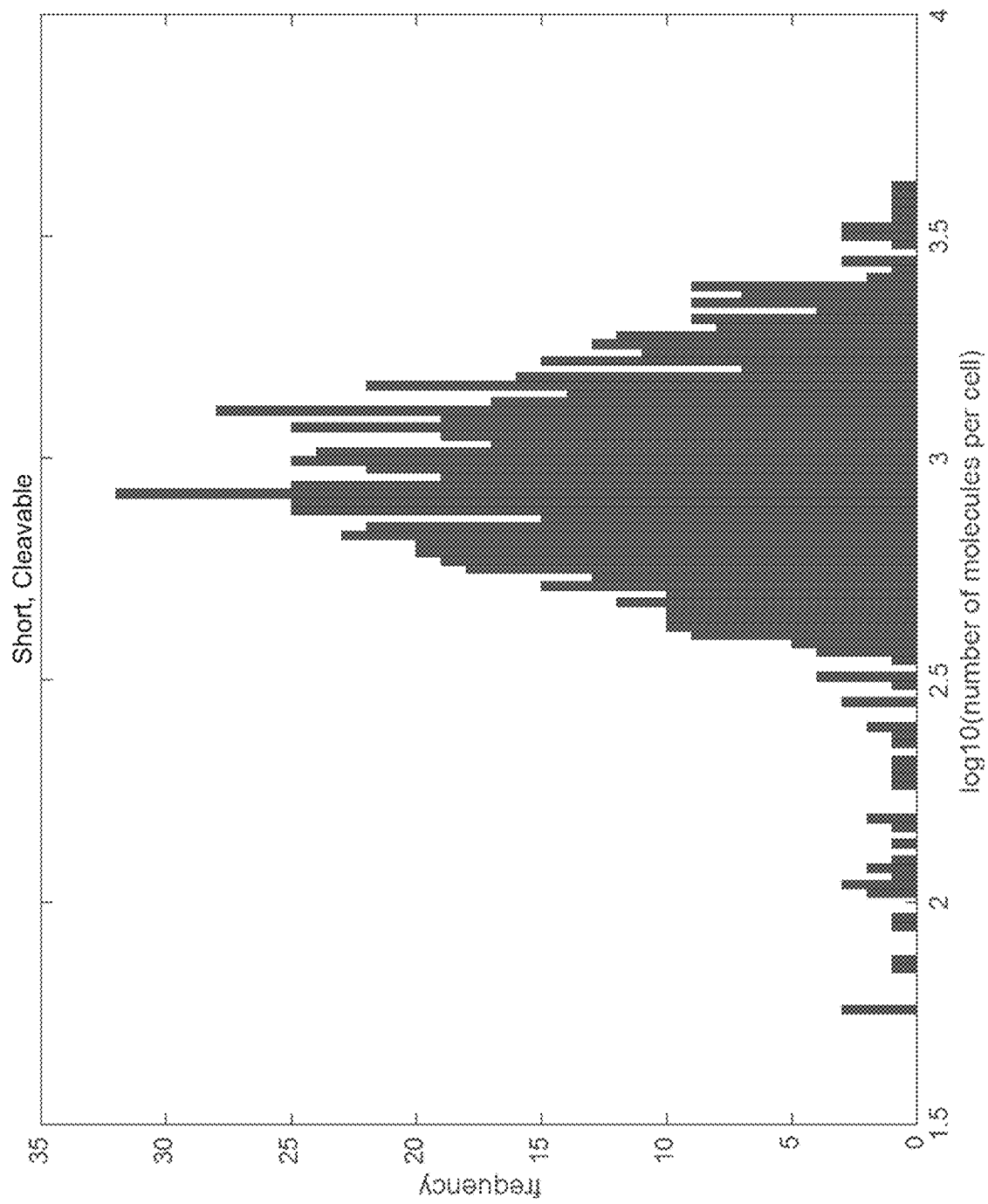
Figure 26C:
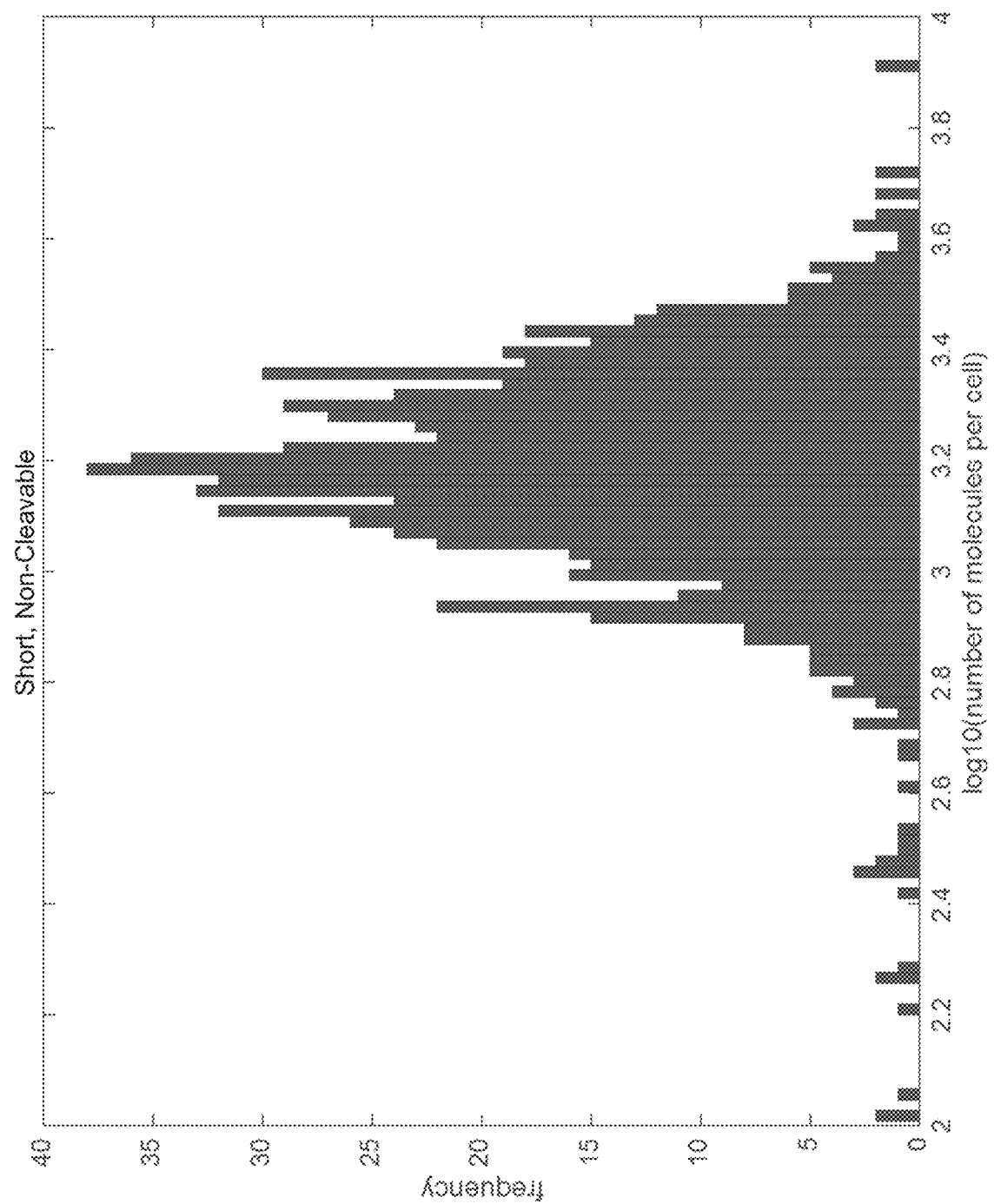

FIGS. 26A-26C are non-limiting exemplary histograms showing the number of molecules of sample indexing oligonucleotides detected using the three types of sample indexing oligonucleotides. The non-cleavable sample indexing oligonucleotide was the most sensitive in terms of the number of molecules detected.

Figure 27A:
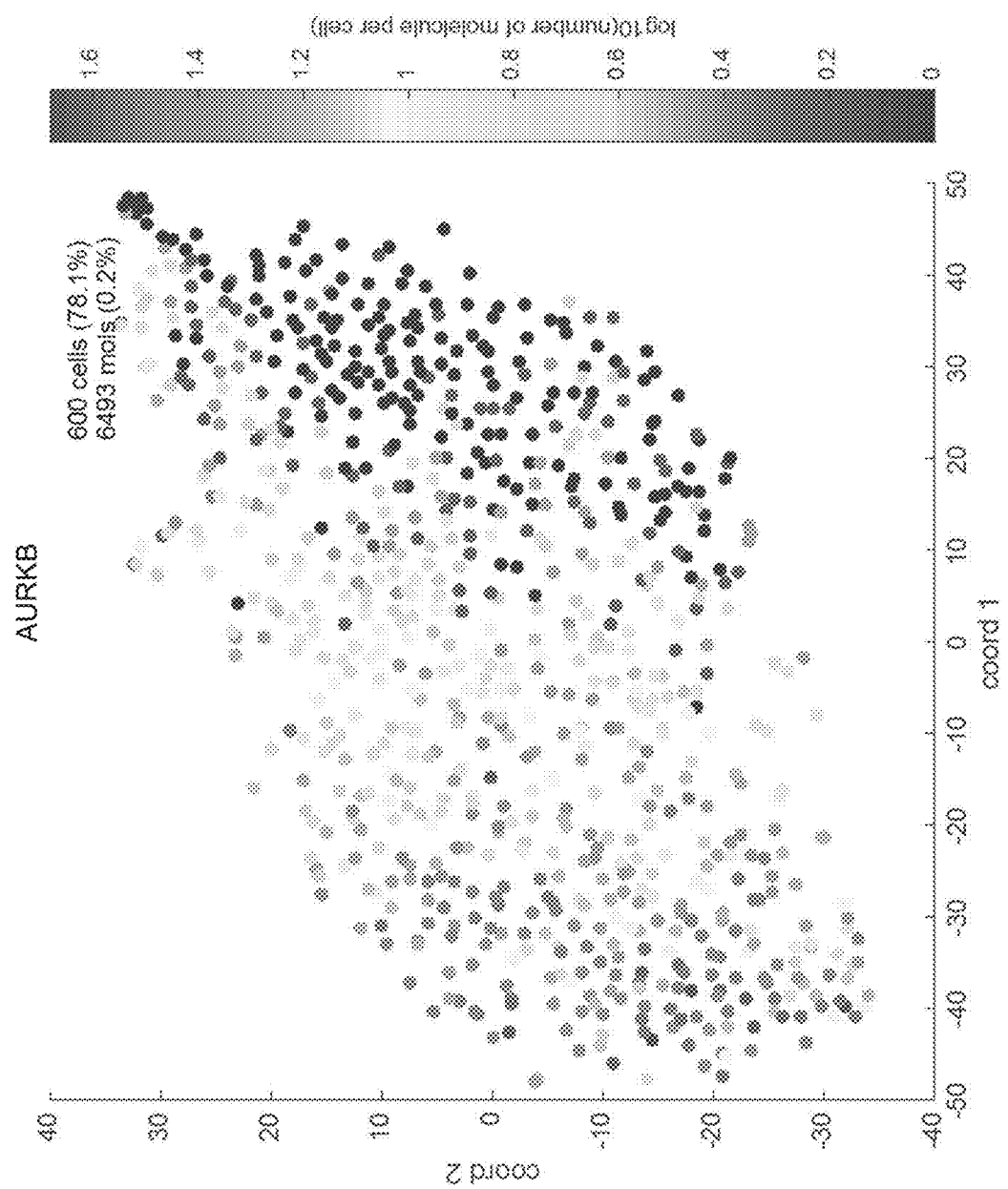
FIGS. 27A-27C are non-limiting exemplary plots and bar charts showing that CD147 expression was higher in dividing cells.
Figure 27B:
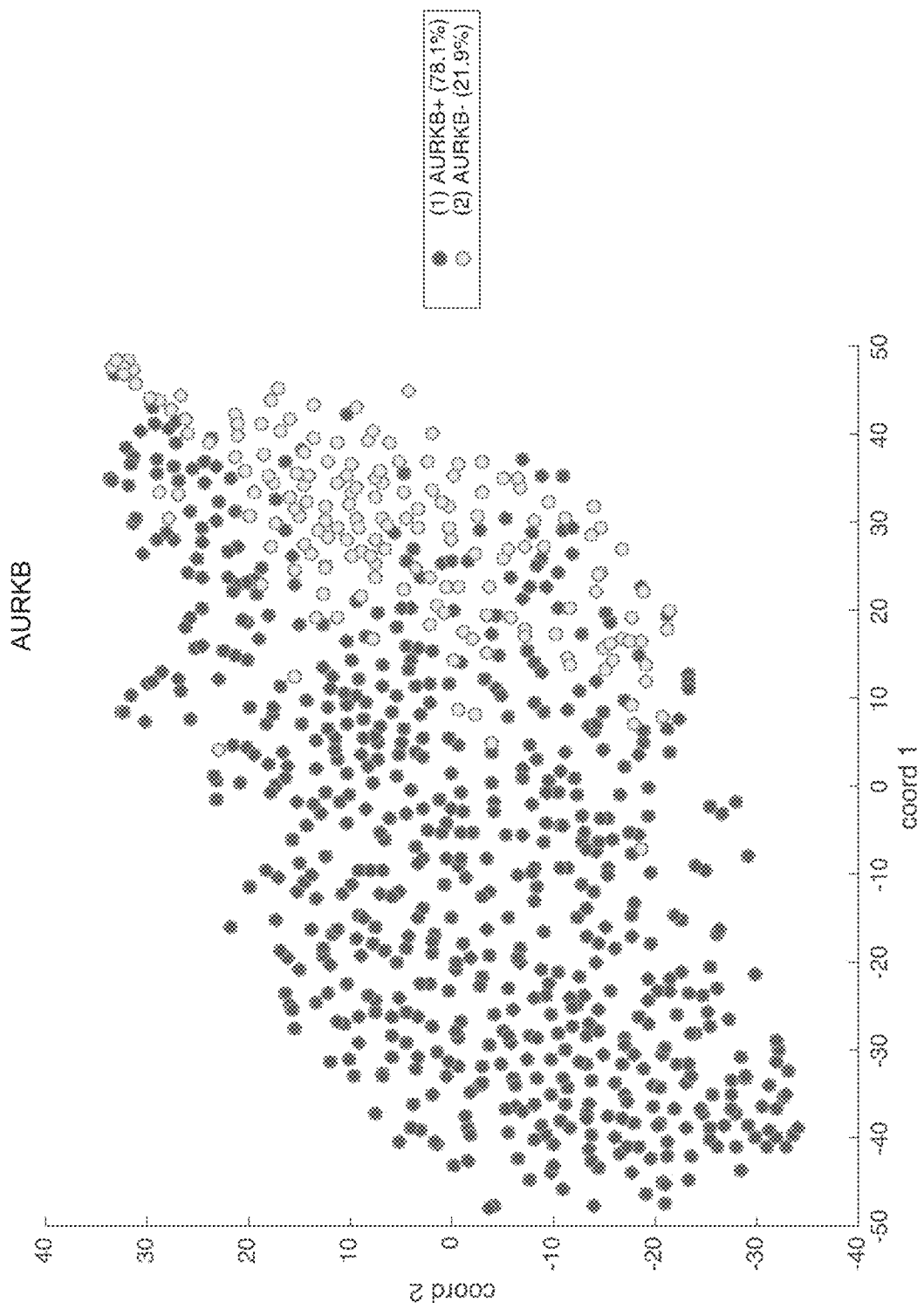
Figure 27C:
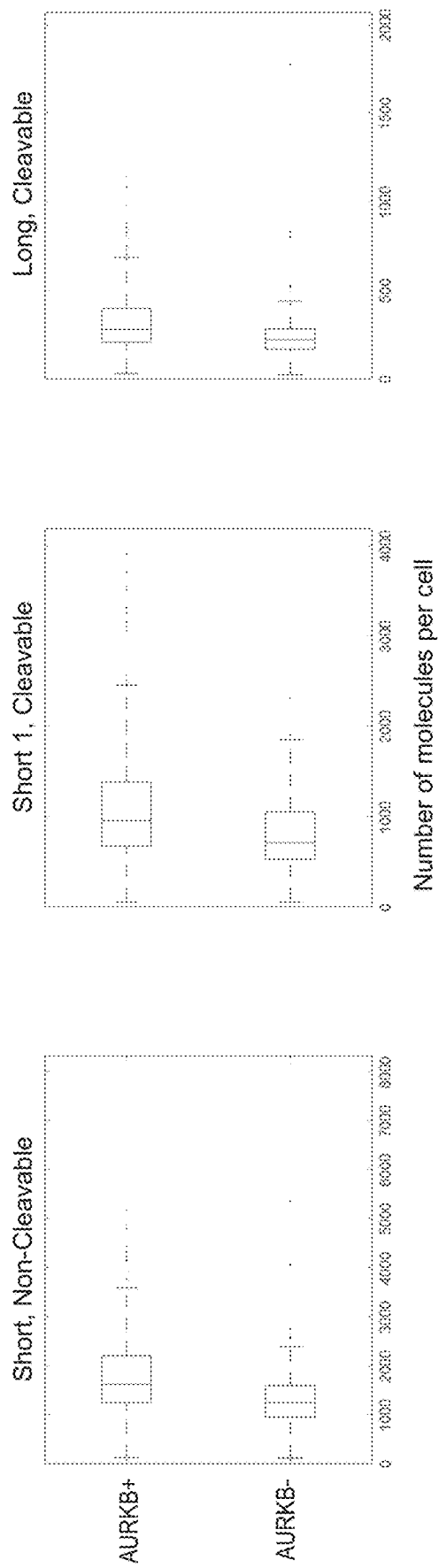

FIGS. 27A-27C are plots and bar charts showing that CD147 expression was higher in dividing cells (determined using "Flowcell F" in FIG. 23). CD147 expression was not uniform across cells in the sample of Jurkat cells. Cells can be classified based on the cell cycle gene AURKB. The mRNA expression of the AURKB gene correlated with the CD147 protein expression determined using sample indexing. FIG. 27C shows a comparison of CD147 expression, determined using the three sample indexing oligonucleotides, in AURKB+ and AURKB− cells.

Figure 28A:
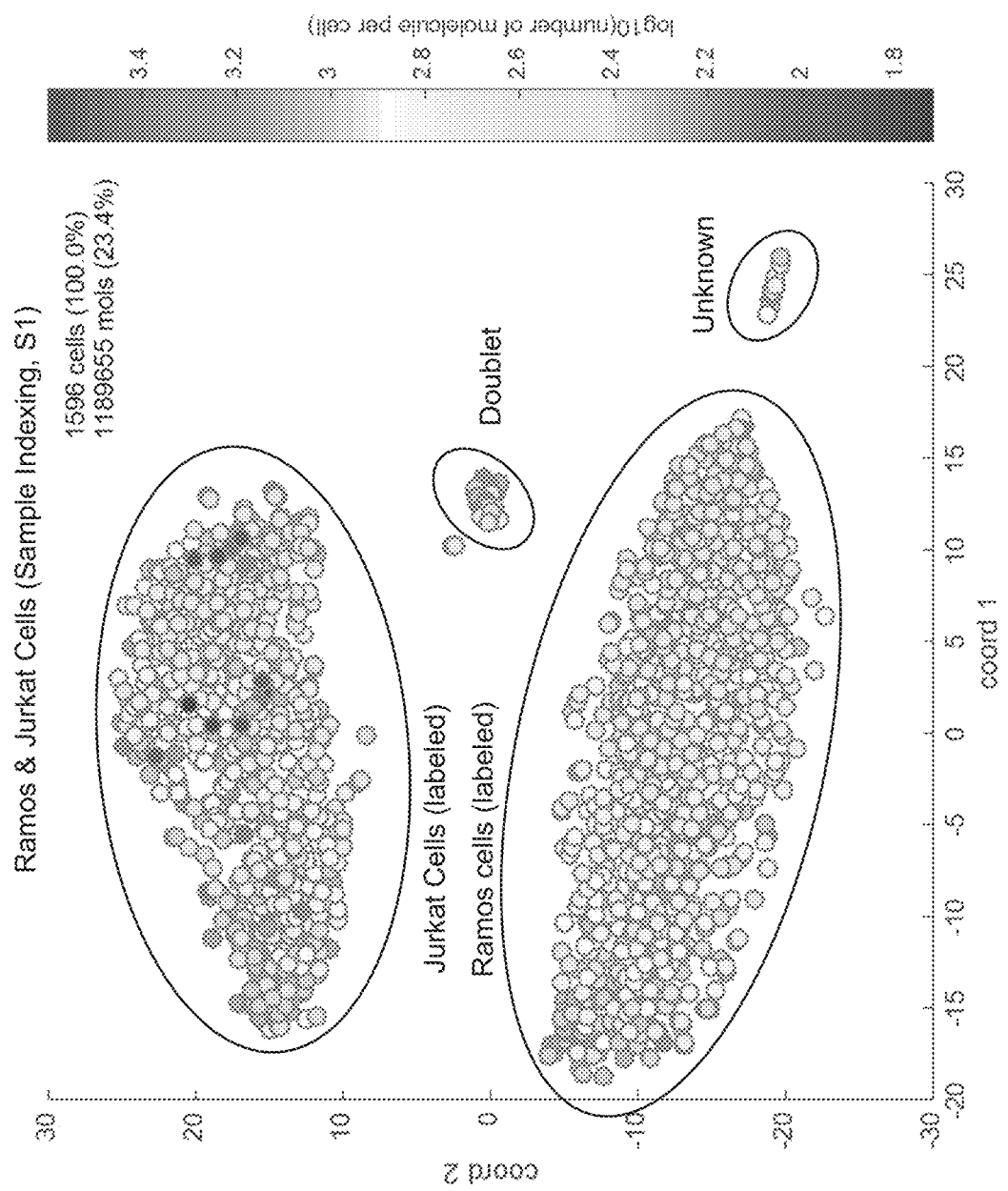
FIGS. 28A-28C are non-limiting exemplary tSNE projection plots showing that sample indexing can be used to identify cells of different samples.
Figure 28B:
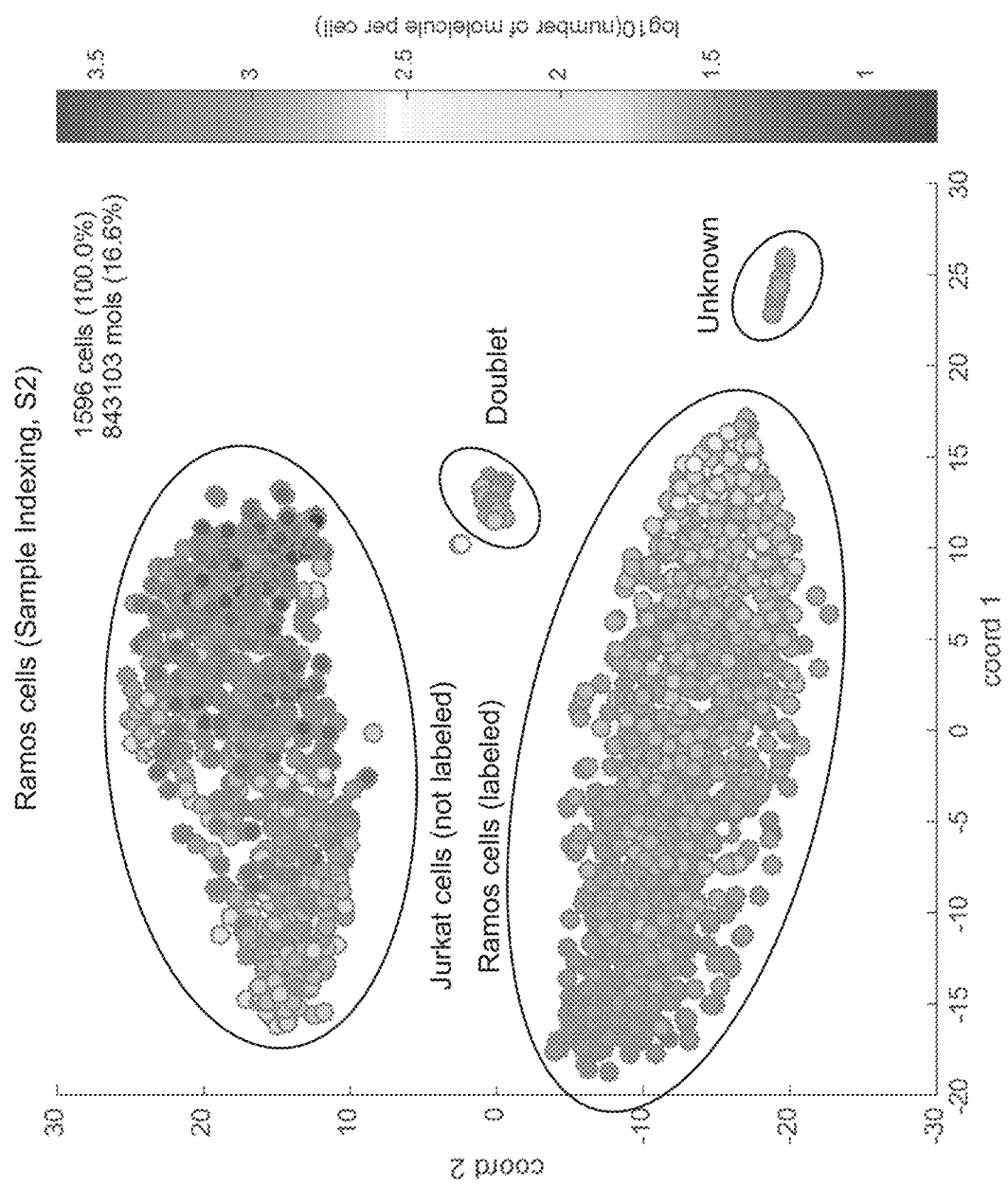
Figure 28C:
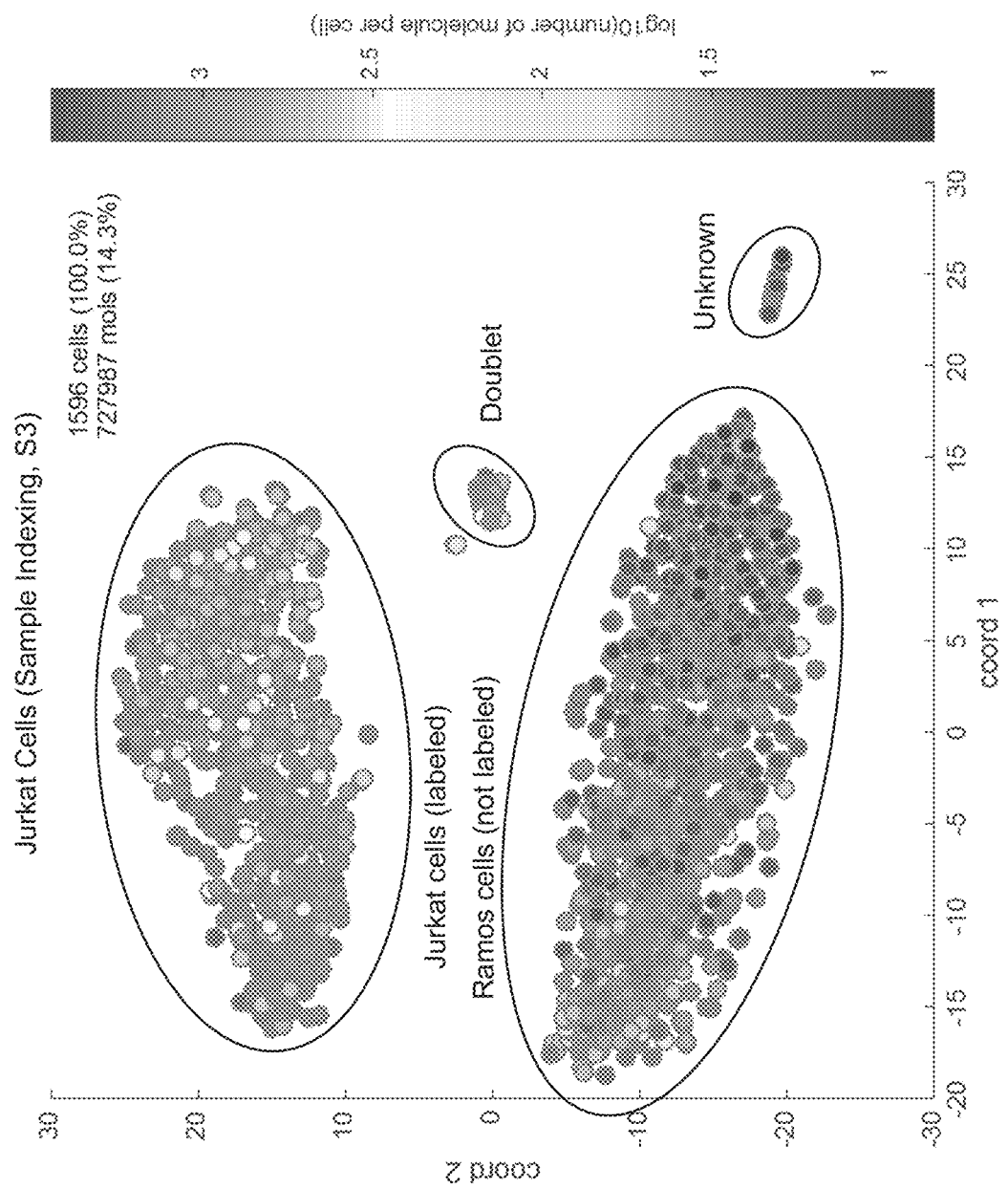

FIGS. 28A-28C are non-limiting exemplary tSNE projection plots of expression profiles of cells, showing that sample indexing can be used to identify cells of different samples. Reads of sample indexing oligonucleotides in the sequencing data, containing expression profiles of the 488 blood panel genes, were filtered. The tSNE projection plots in FIGS. 28A-28C were generated using the filtered sequencing data. The cluster corresponding to Jurkat cells and the cluster corresponding to Ramos cells (determined based on the abundance of the sample indexing oligonucleotides labeled "Short F" in FIG. 23) are clearly separated in the tSNE projection plot of FIG. 28A (similarly for FIGS. 28B-28C).

Sample indexing correctly matched the cell type. For example, FIG. 28B shows that Ramos cells, which were labeled with the sample indexing oligonucleotides labeled "Short 2" in FIG. 23, had high expression of CD147, while Jurkat cells which were not labeled had minimal expression of CD147. FIG. 28C shows that Jurkat cells, which were labeled with the sample indexing oligonucleotides labeled "Short 3" in FIG. 23, had high expression of CD147, while Ramos cells which were not labeled had low expression of CD147. The small doublet cluster at 3.6% frequency closely matched the expected doublet rate of 3.92% from image analysis of occupancy of wells.

Figure 29A:
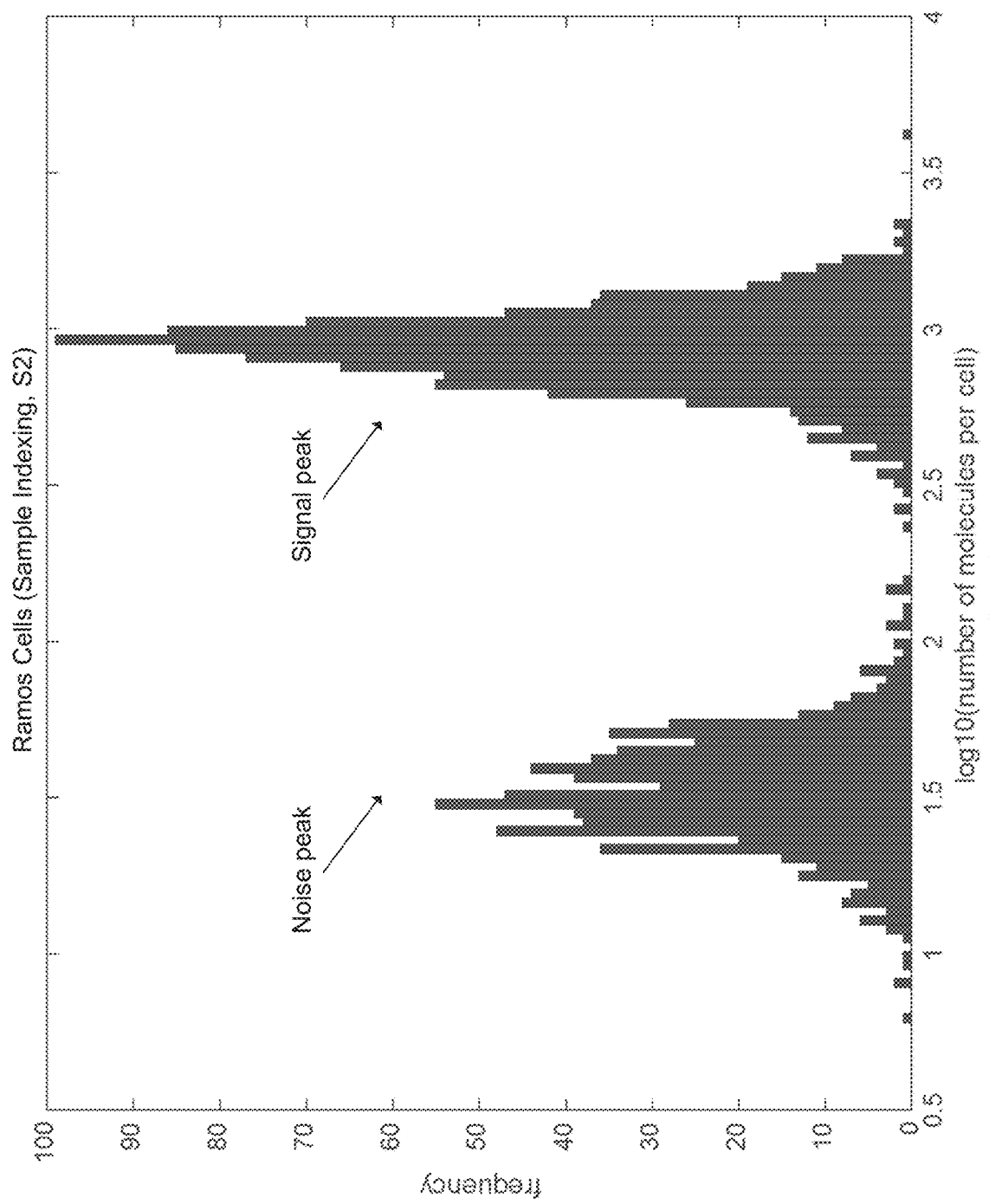
FIGS. 29A-29C are non-limiting exemplary histograms of the sample indexing sequences per cell based on the numbers of molecules of the sample indexing oligonucleotides determined.
Figure 29B:
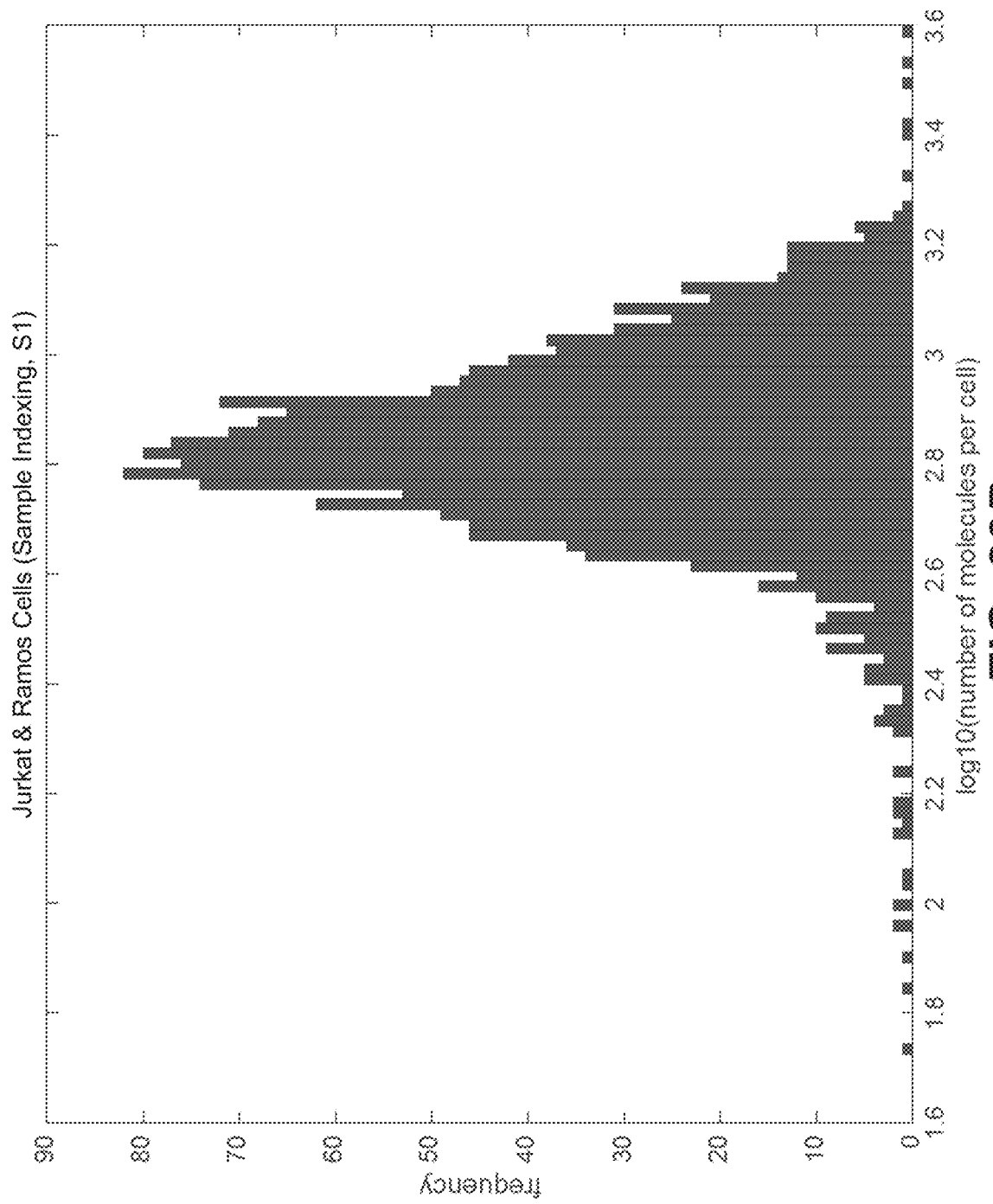
Figure 29C:
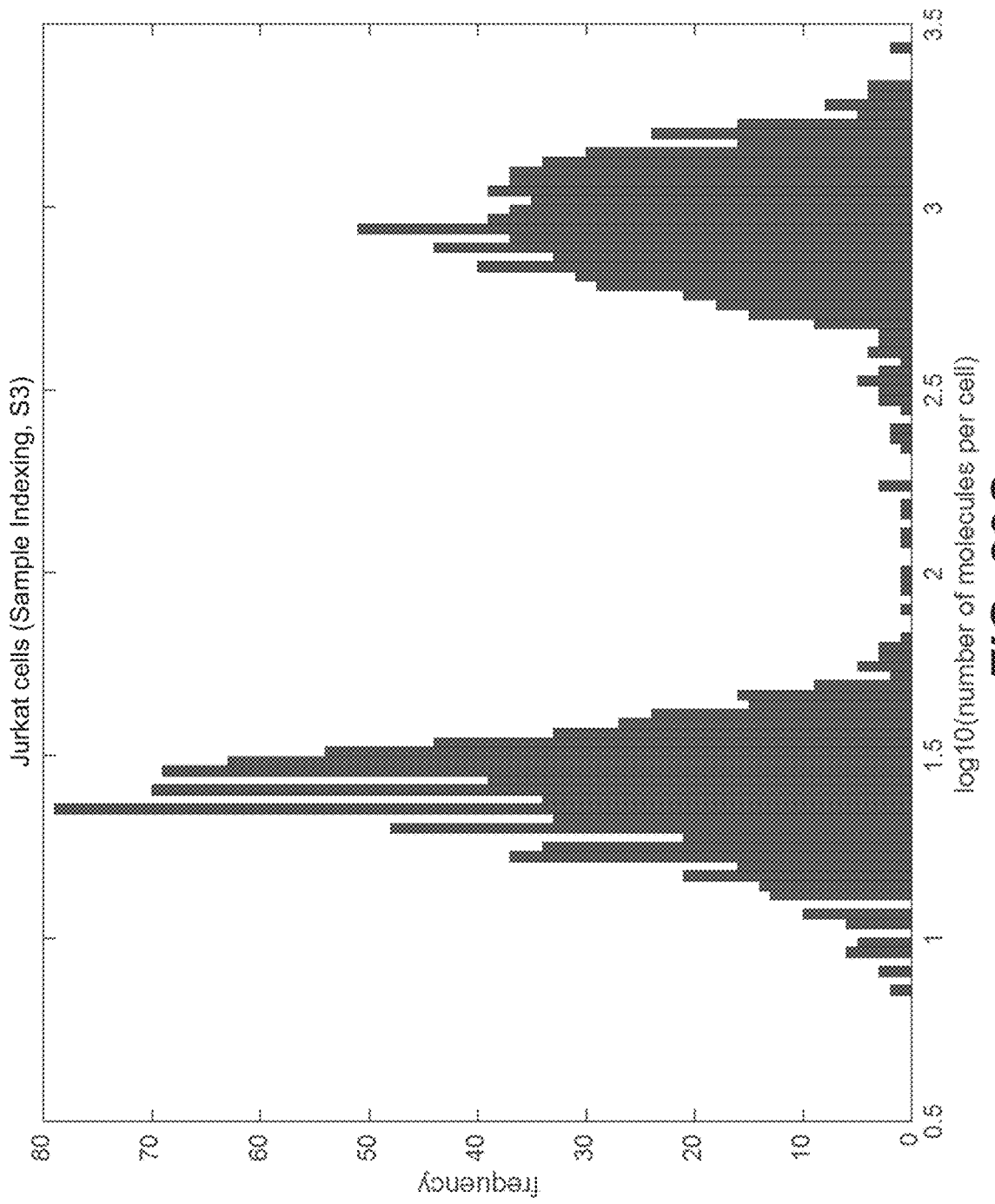

FIGS. 29A-29C are non-limiting exemplary histograms of the sample indexing sequences per cell based on the numbers of molecules of the sample indexing oligonucleotides determined. The sequencing data was corrected with distribution based error correction (DBEC) with a cutoff of 250. DBEC has been described in U.S. patent application Ser. No. 15/605,874, filed on May 25, 2017, the content of which is incorporated herein by reference in its entirety. After DBEC, there seemed to be a clear "noise" peak in the 100s that was distinguishable from the "signal" peak in the 1000s (FIGS. 29B-29C). FIGS. 29B-29C also show that the detection of sample indexing oligonucleotides to be in the high 100s after a noise subtraction of 250.

Figure 30A:
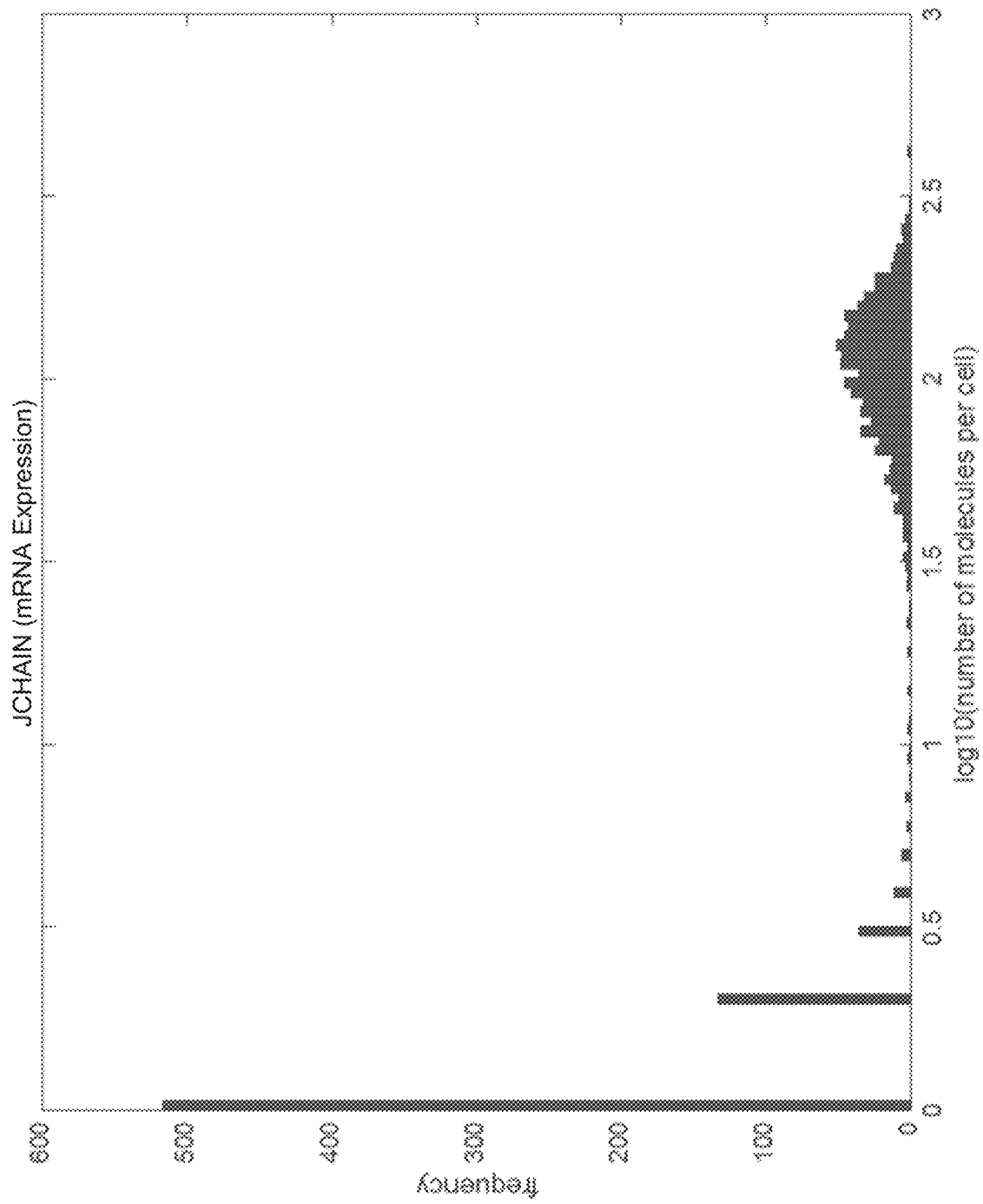
Figure 30B:
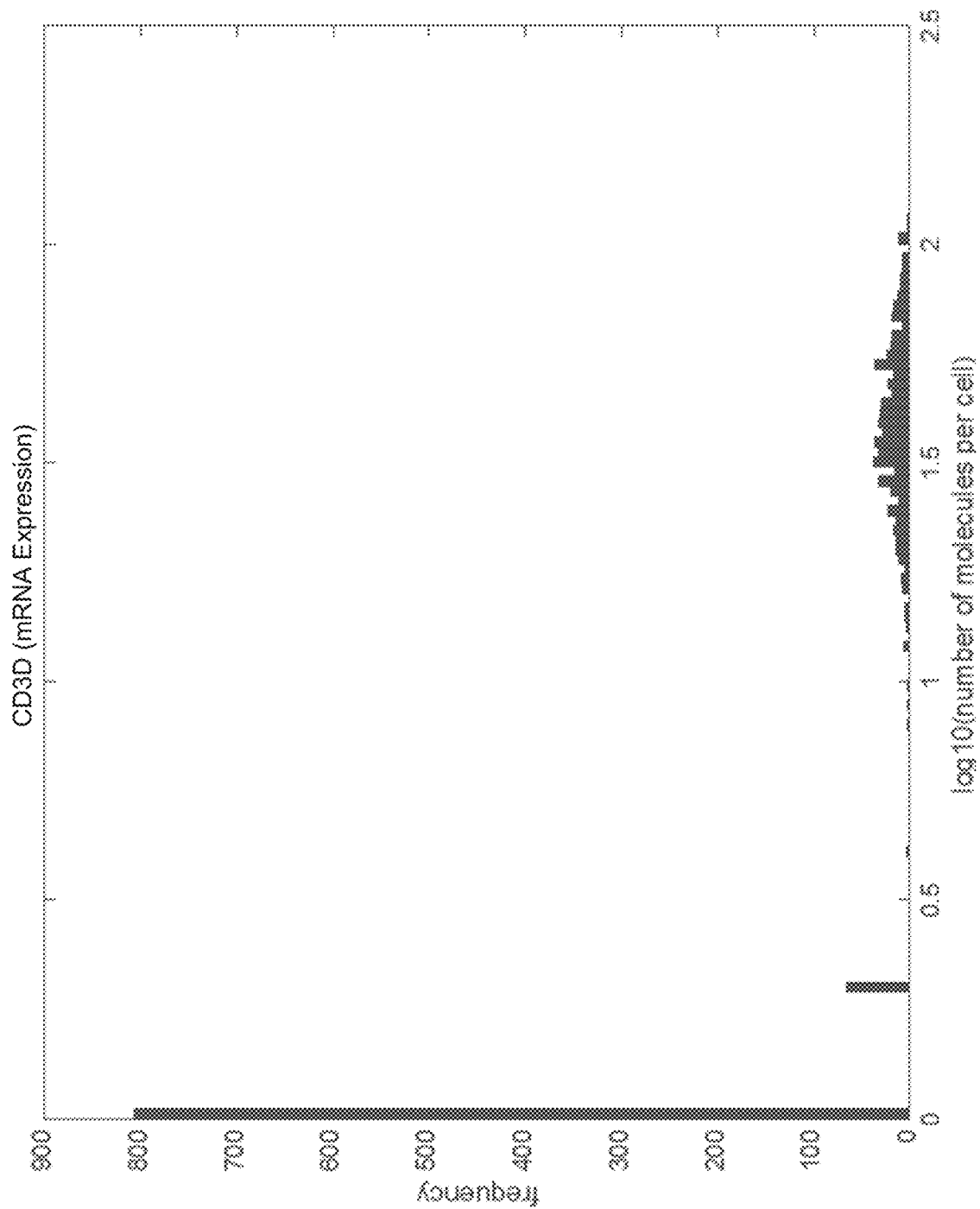
Figure 30C:
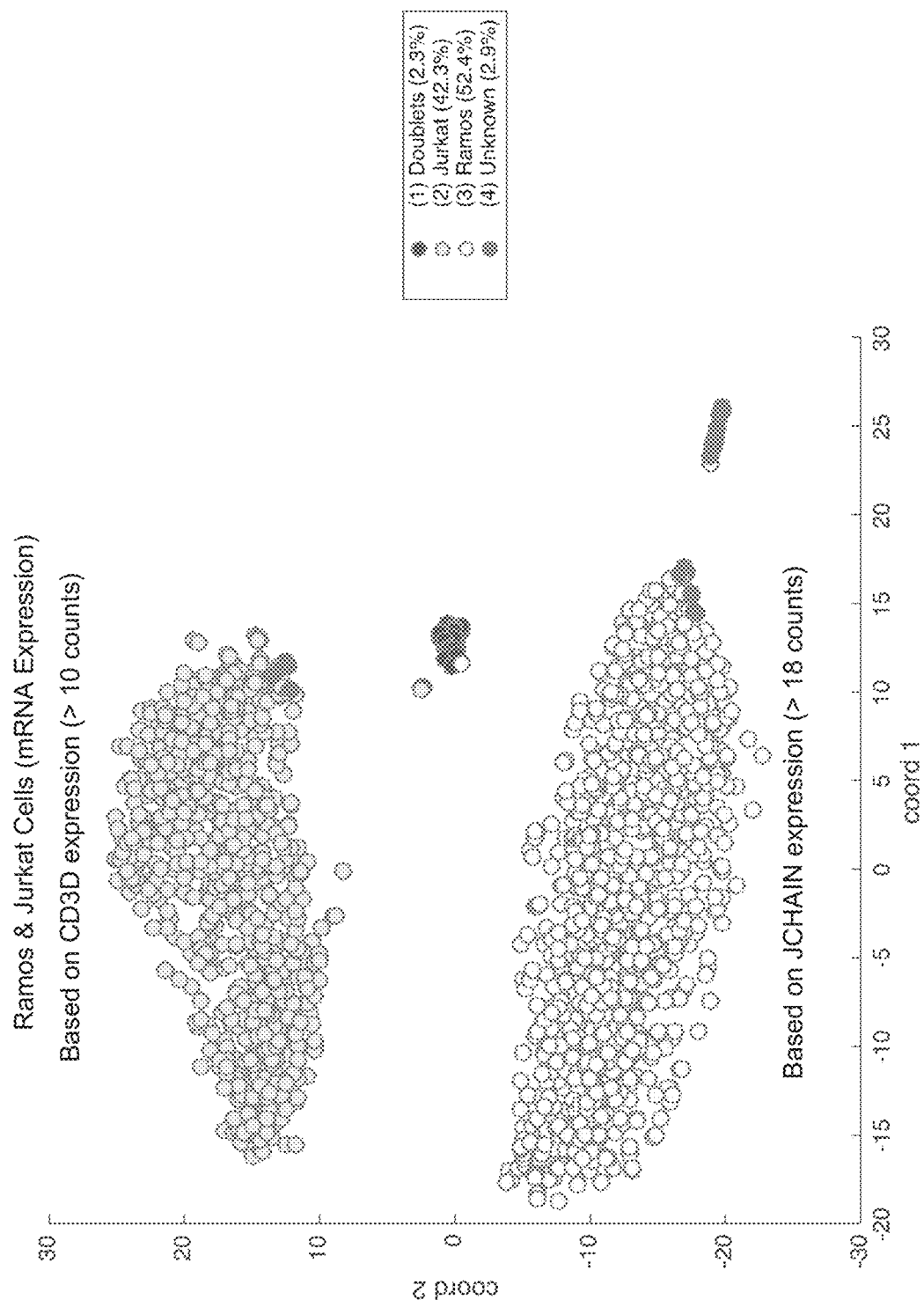

FIGS. 30A-30D are non-limiting exemplary plots comparing annotations of cell types determined based on mRNA expression of CD3D (for Jurkat cells) and JCHAIN (for Ramos cells) and sample indexing of Jurkat and Ramos cells. FIG. 30A is a non-limiting exemplary histogram showing clear separation of a signal peak of JCHAIN expression and noise signals with low numbers of molecules of sample indexing oligonucleotides per cell. FIG. 30B is a non-limiting exemplary histogram showing clear separation of a signal peak of Ramos expression and noise signals with low numbers of molecules of sample indexing oligonucleotides per cell. Doublets were identified as cells with more than one sample indexing sequence with more than 250 counts. In FIG. 30C, Ramos cells were identified using the mRNA expression of JCHAIN, and Jurkat cells were identified using the mRNA expression of CD3D.

Ramos cells were labeled with two types of anti-CD147 antibodies conjugated with different sample indexing oligonucleotides that are cleavable (the sample indexing oligonucleotides are labeled "Short 1" and "Short 2" in FIG. 23). Jurkat cells were labeled with two types of anti-CD147 antibodies conjugated with different sample indexing oligonucleotides that are cleavable (the sample indexing oligonucleotides are labeled "Short 1" and "Short 3" in FIG. 23). In FIG. 30D, the identity of the Ramos cells were identified based on the numbers of counts of the "Short 2" sample indexing oligonucleotide (greater than 250) in the sequencing data, and the identity of the Jurkat cells were identified based on the numbers of counts of the "Short 3" sample indexing oligonucleotide (greater than 250) in the sequencing data.

Figure 31A:
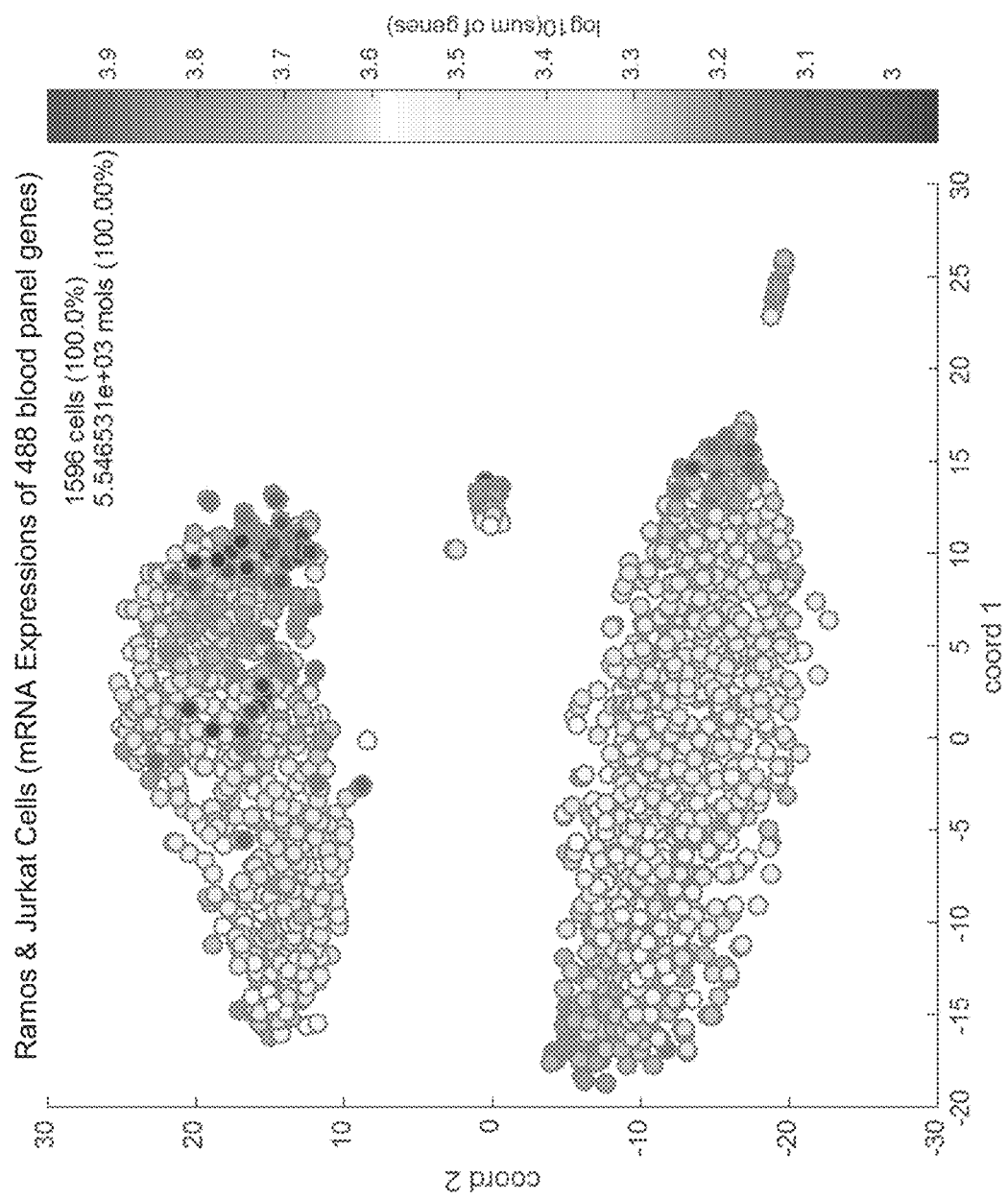
FIGS. 31A-31C are non-limiting tSNE projection plots of the mRNA expression profiles of Jurkat and Ramos cells with overlays of the mRNA expressions of CD3D and JCHAIN (FIG. 31A), JCHAIN (FIG. 31B), and CD3D (FIG. 31C).
Figure 31B:
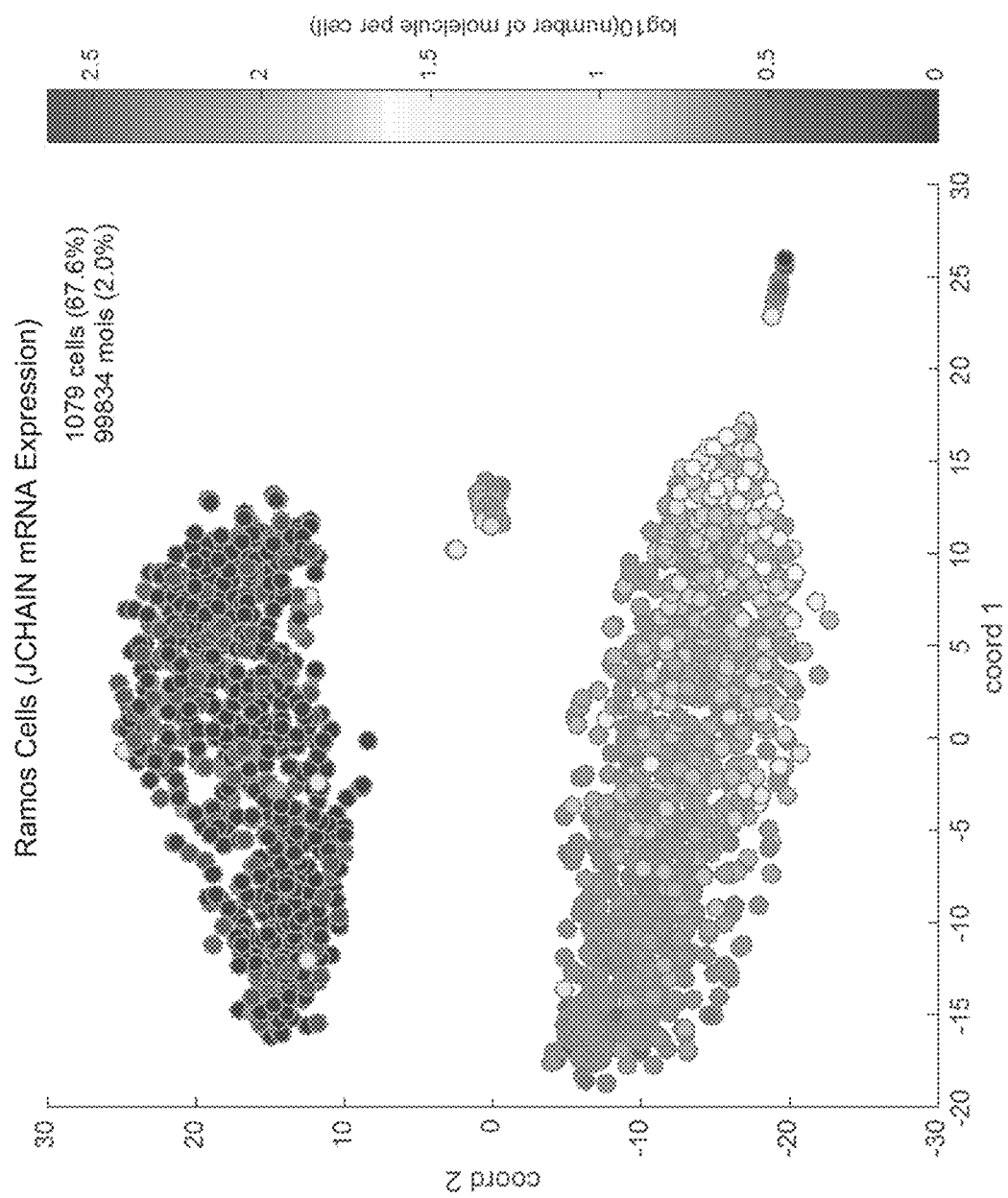
Figure 31C:
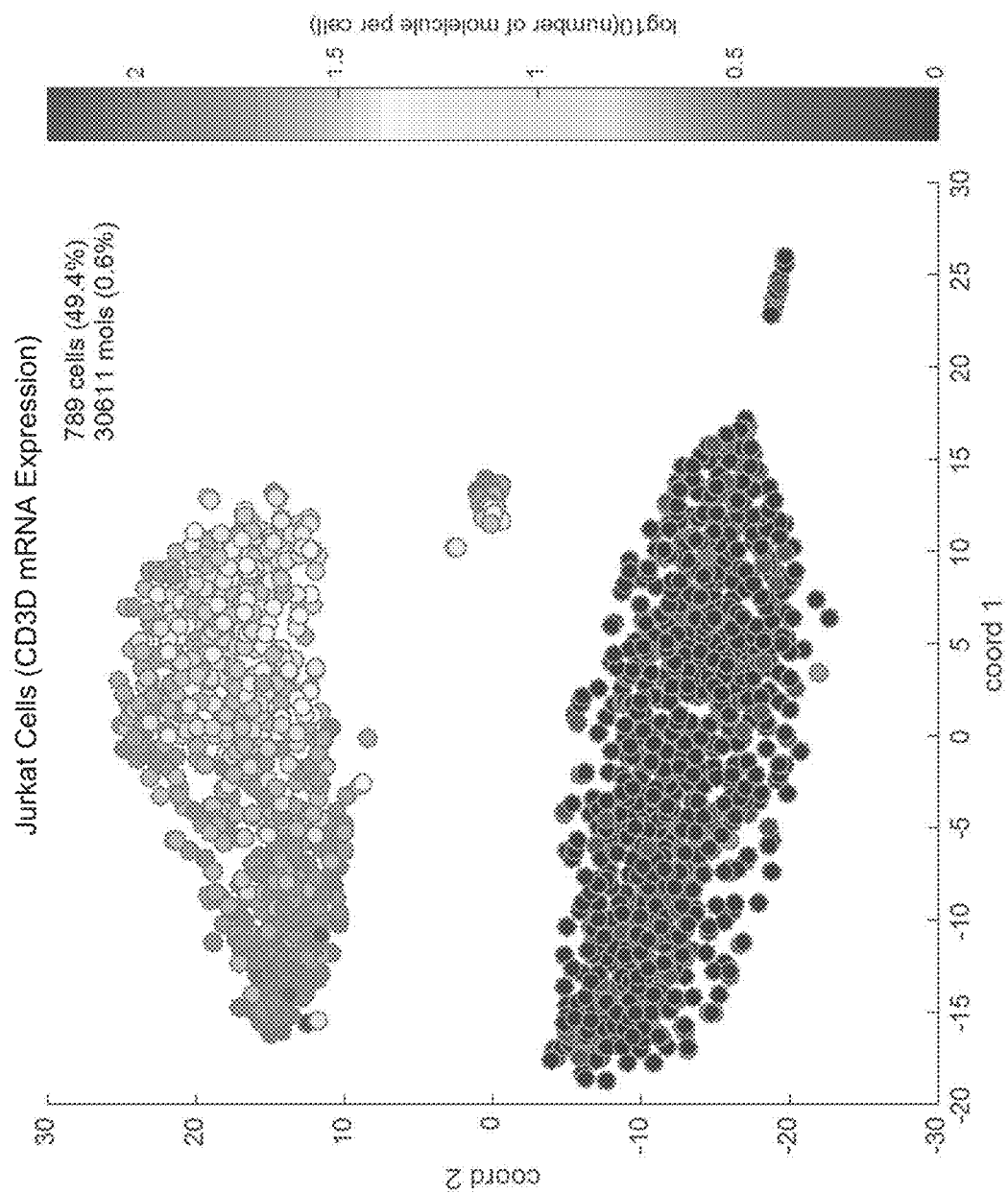

FIGS. 31A-31C are non-limiting tSNE projection plots of the mRNA expression profiles of Jurkat and Ramos cells with overlays of the mRNA expressions of CD3D and JCHAIN (FIG. 31A), JCHAIN (FIG. 31B), and CD3D (FIG. 31C). The mRNA expression of JCHAIN was higher in Ramos cells (FIG. 31B) and minimal in Jurkat cells (FIG. 31C) as expected. The mRNA expression of CD3D was higher in Jurkat cells (FIG. 31C) and minimal in Ramos cells (FIG. 31B).

The comparisons of FIGS. 28B-28C with FIGS. 31B-31C revealed the high performance of sample indexing in distinguishing cells of different samples. The performance of sample indexing in determining sample origin is shown in FIG. 32. FIG. 32 is a non-limiting exemplary tSNE projection plot of expression profiles of Jurkat and Ramos cells with an overlay of the cell types determined using sample indexing with a DBEC cutoff of 250. Table 2 is a summary of the cell types determined using sample indexing shown in FIG. 32. Table 3 shows the sensitivity and specificity of sample indexing, with doublets and undefined cells in Table 2 excluded, in determining sample origin.

TABLE 2

Summary of sample origin determination using sample indexing.

|  | S2 | S2 + S3 | S3 | not labeled |
|---|---|---|---|---|
| Doublets | 0 | 36 | 1 | 0 |
| Jurkat | 0 | 5 | 658 | 12 |
| Ramos | 833 | 4 | 0 | 0 |
| Unknown | 30 | 0 | 17 | 0 |

TABLE 3

Specificity and sensitivity of sample indexing in determining sample origin.

|  | Specificity | Sensitivity |
|---|---|---|
| S2 (Ramos) | 99.5% (833/(833 + 4)) | 100% (833/(833 + 0)) |
| S3 (Jurkat) | 99.25% (658/(658 + 4)) | 98.2% (658/(658 + 12)) |

Figure 33A:
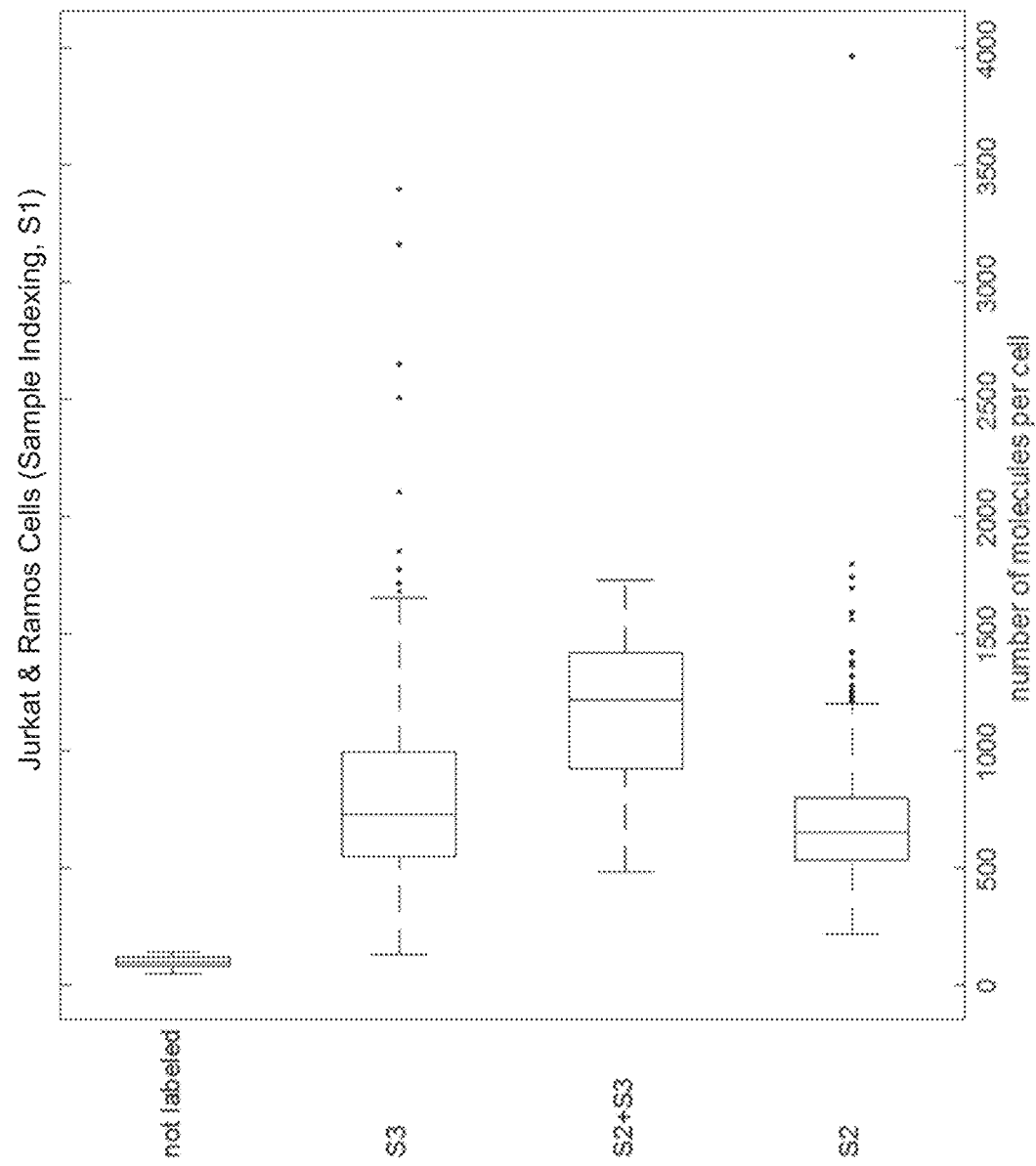
FIGS. 33A-33C are non-limiting exemplary bar charts of the numbers of molecules of sample indexing oligonucleotides per cell for Ramos & Jurkat cells (FIG. 33A), Ramos cells (FIG. 33B), and Jurkat cells (FIG. 33C) that were not labeled or labeled with "Short 3" sample indexing oligonucleotides, "Short 2" & "Short 3" sample indexing oligonucleotides, and "Short 2" sample indexing oligonucleotides.
Figure 33B:
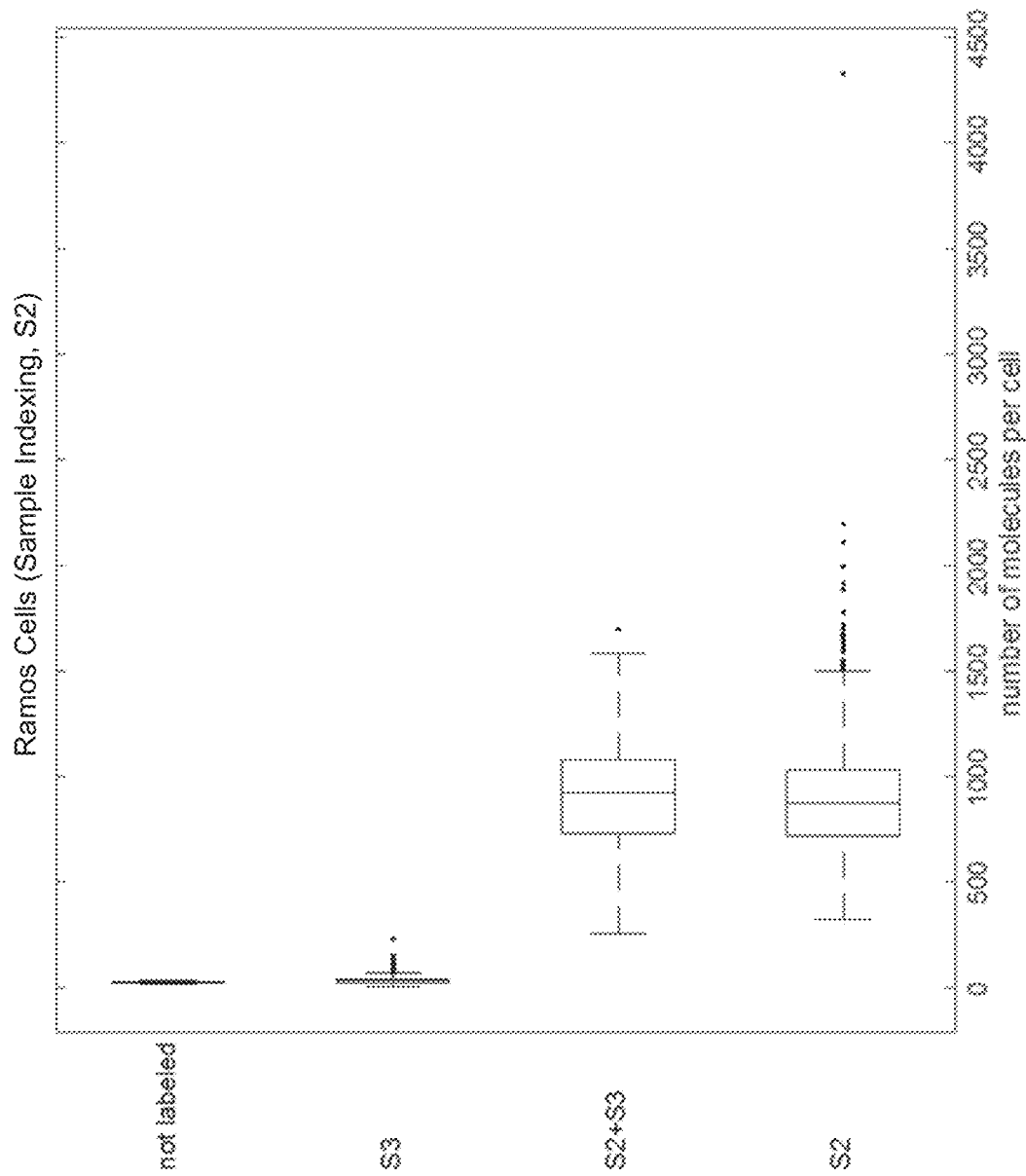
Figure 33C:
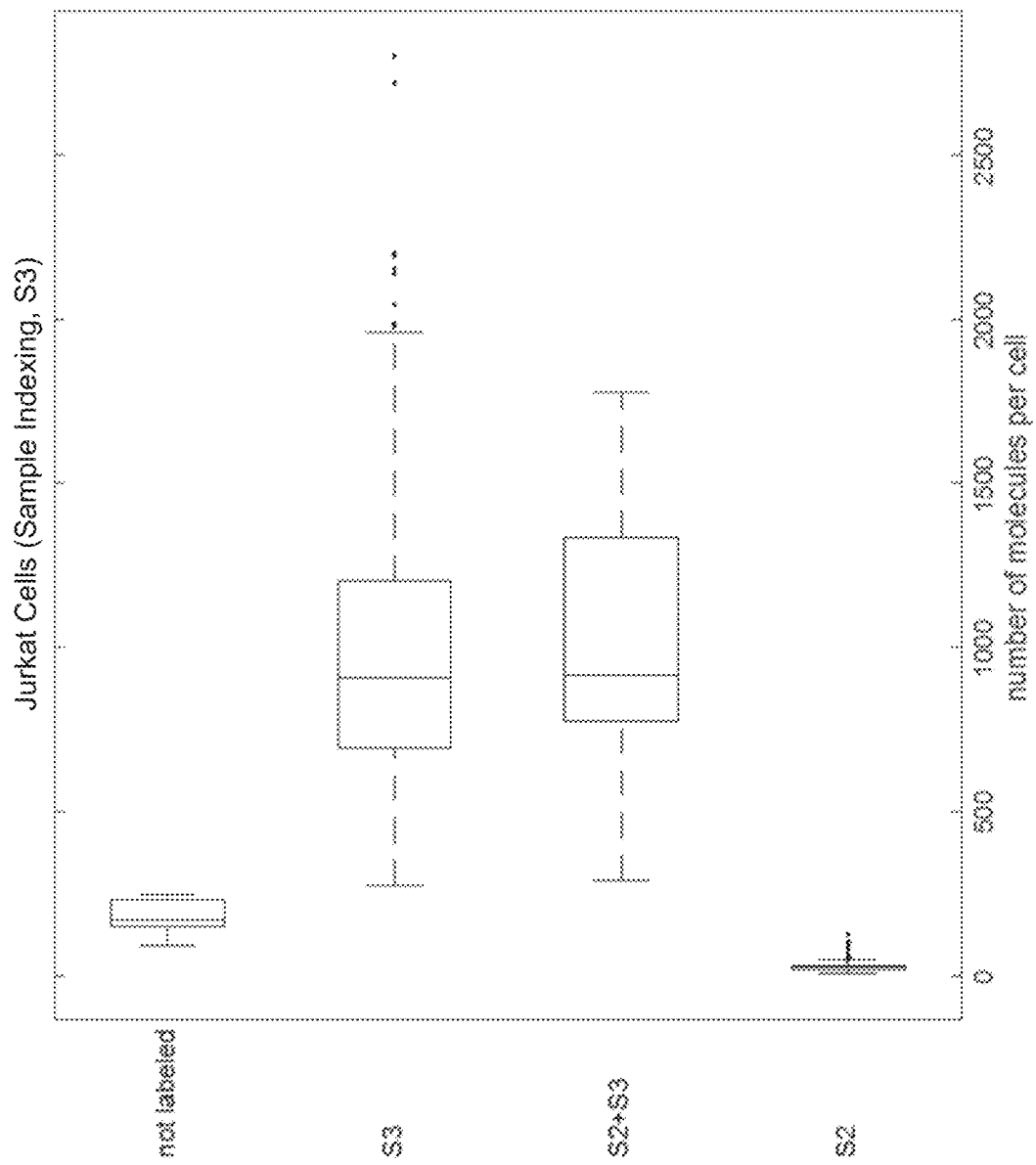
Figure 34B:
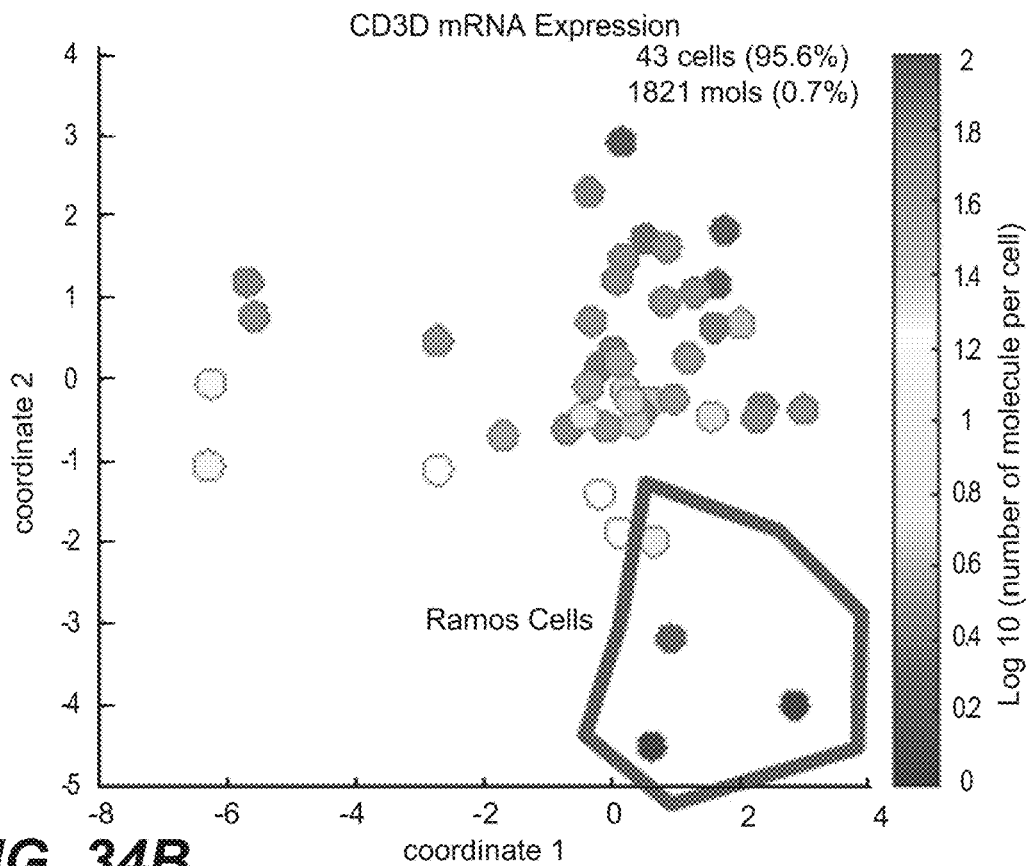
Figure 34C:
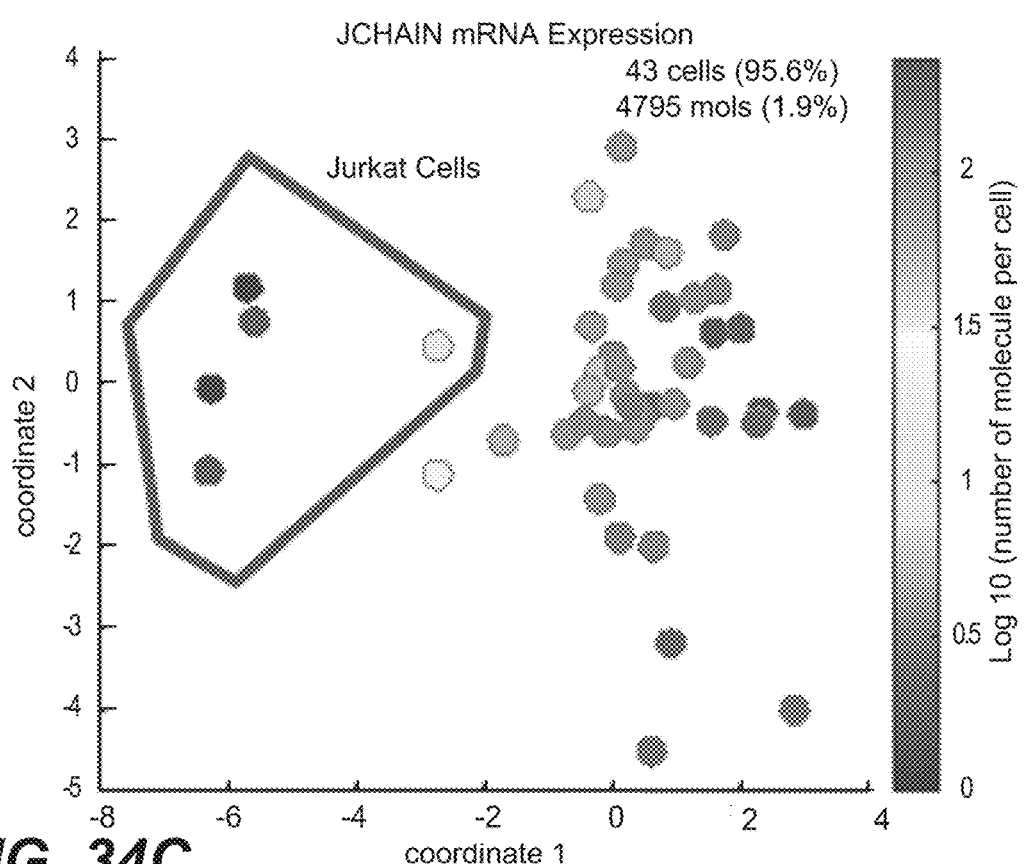

FIGS. 33A-33C are non-limiting exemplary bar charts of the numbers of molecules of sample indexing oligonucleotides per cell for Ramos & Jurkat cells (FIG. 33A), Ramos cells (FIG. 33B), and Jurkat cells (FIG. 33C) that were not labeled or labeled with "Short 3" sample indexing oligonucleotides, "Short 2" & "Short 3" sample indexing oligonucleotides, and "Short 2" sample indexing oligonucleotides. Less than 1% of single cells were labeled with both the "Short 2" and "Short 3" sample indexing oligonucleotides FIGS. 34A-34C).

Figure 35A:
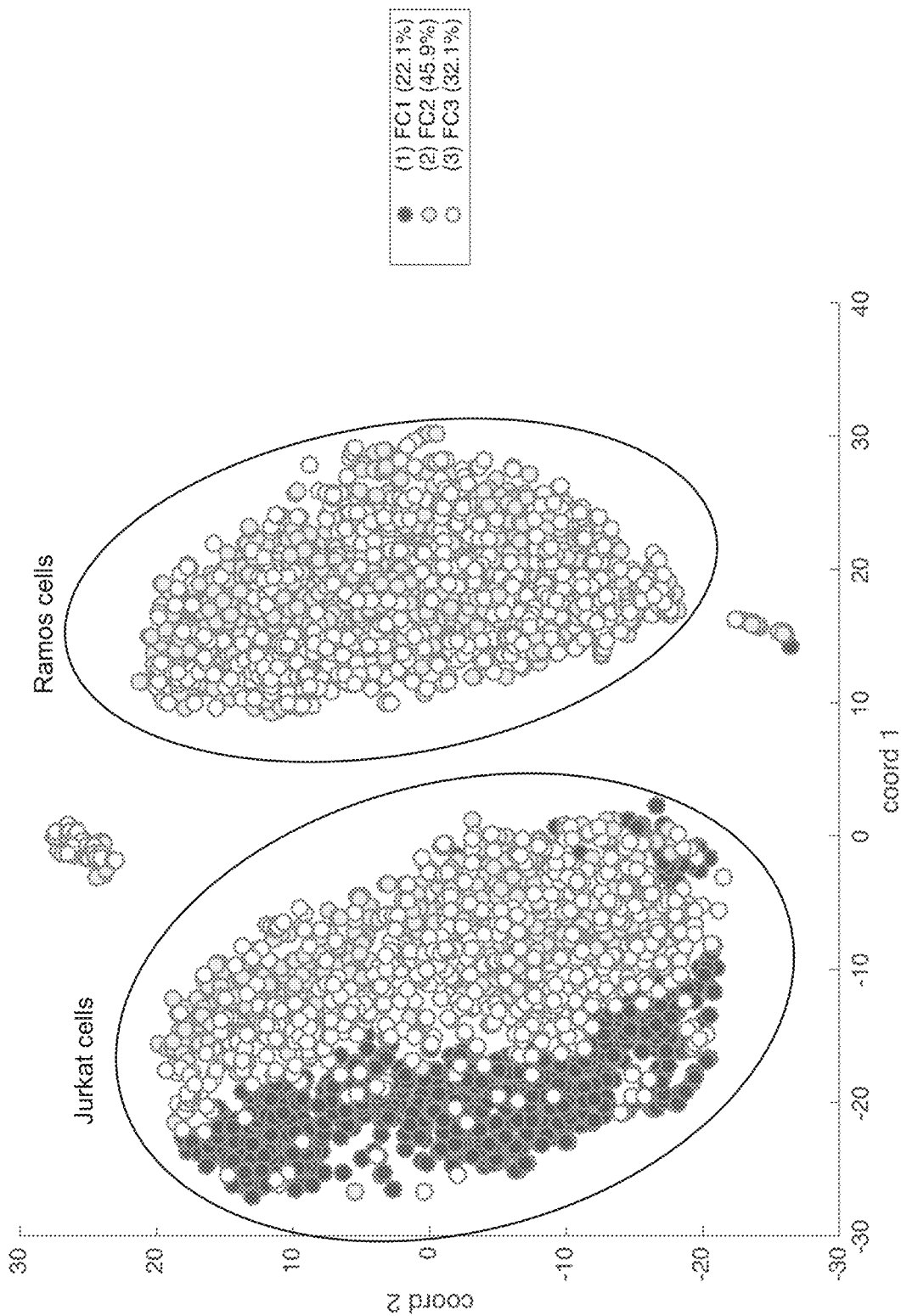
FIGS. 35A-35C are non-limiting exemplary tSNE plots showing batch effects on expression profiles of Jurkat and Ramos cells among samples prepared using different flow-cells as outlined in FIG. 23.
Figure 35B:
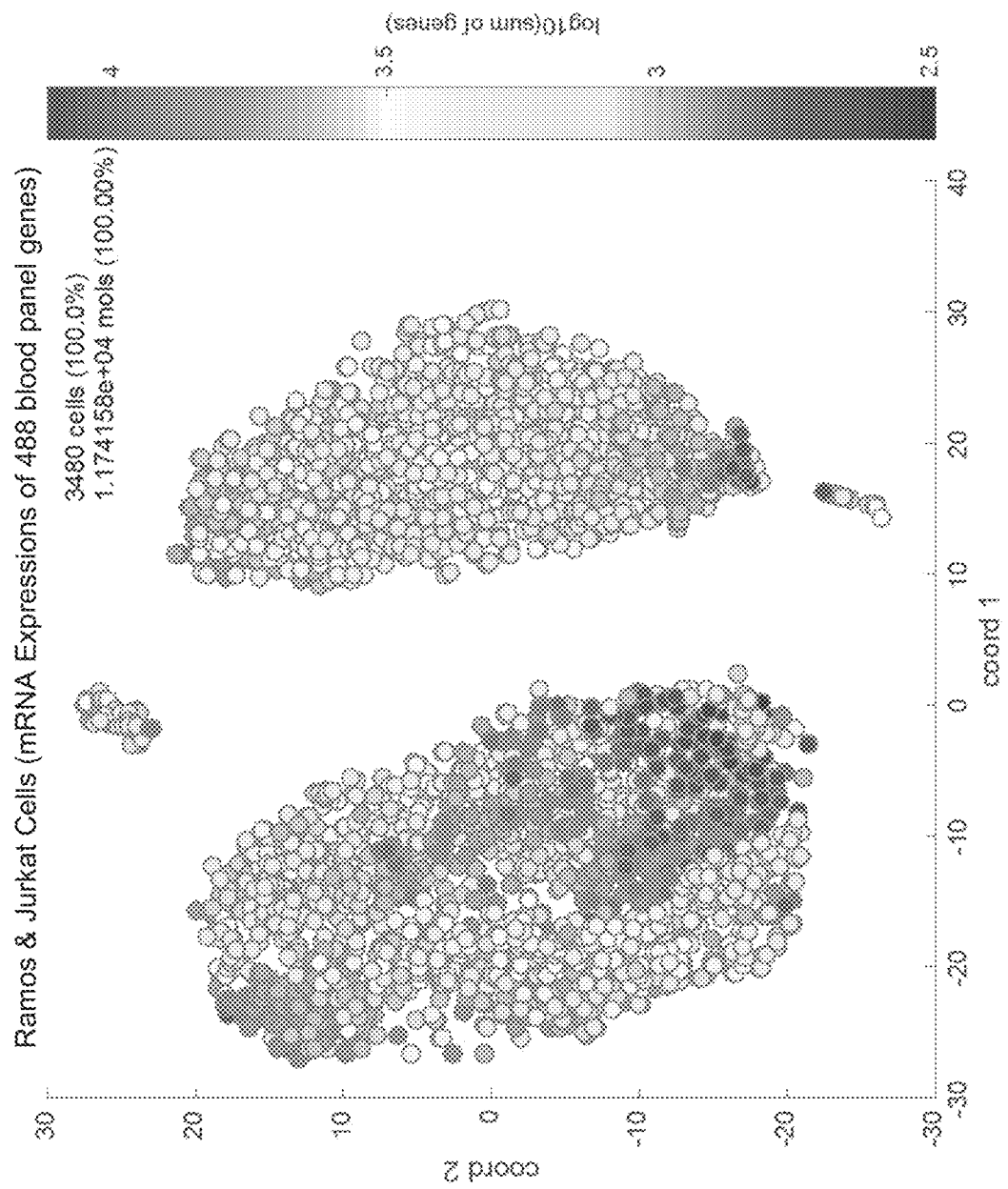
Figure 35C:
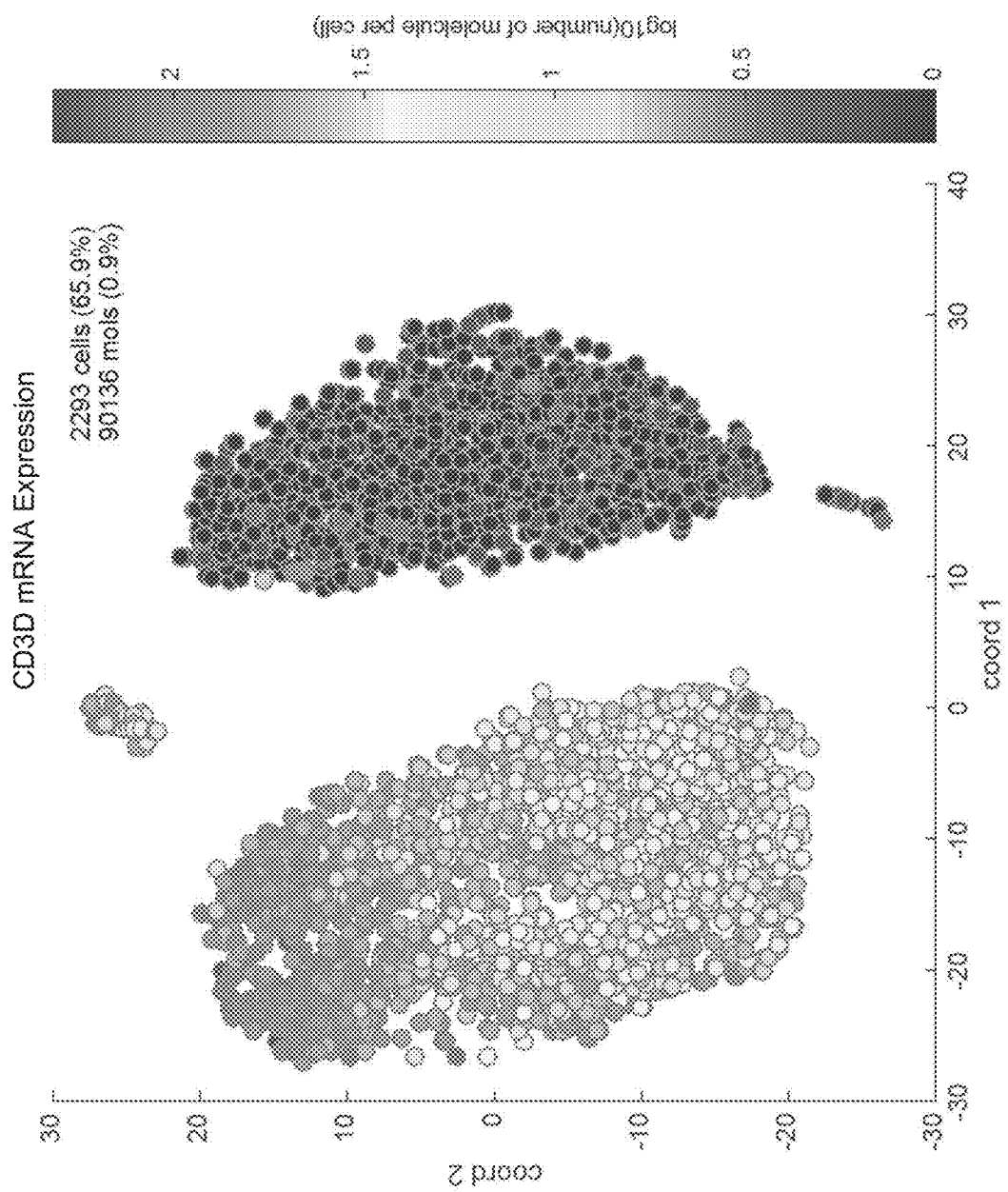
Figure 36B:
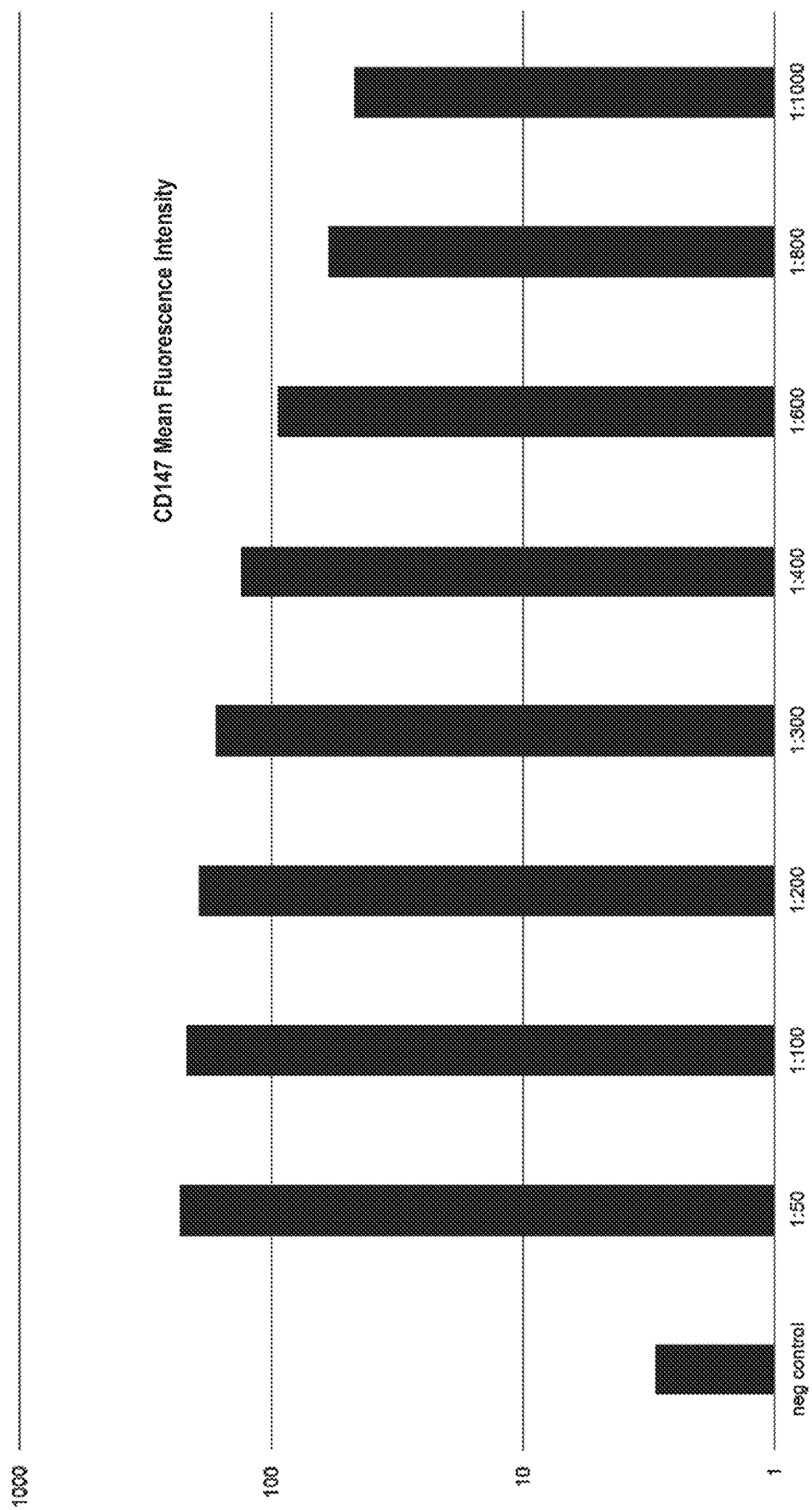
Figure 36C:
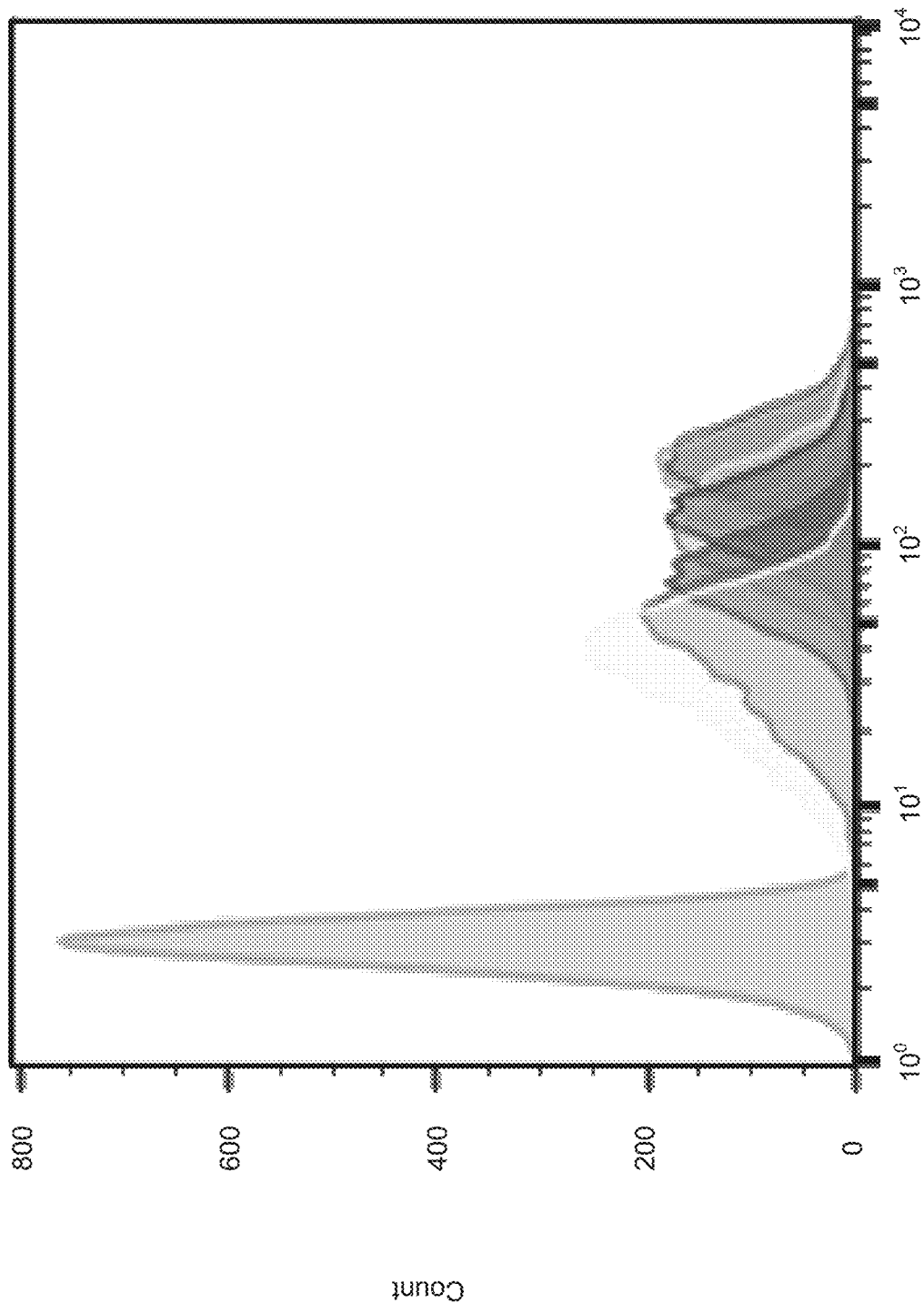

FIGS. 35A-35C are non-limiting exemplary tSNE plots showing batch effects on expression profiles of Jurkat and Ramos cells between samples prepared using different flowcells as outlined in FIG. 23. FIG. 35A shows a non-limiting exemplary tSNE projection plot of expression profiles of Jurkat and Ramos cells with an overlay of different sample preparations of the cells. The variations in mRNA expression profiles in the 488 blood panel genes (FIG. 35B) and the CD3D gene (FIG. 35C) between different sample preparations may be a result of batch effect due to different sequencing depths of the samples prepared using the different flowcells.

Altogether, these data indicate that all three versions of sample indexing oligonucleotides (95mer cleavable, 95mer non-cleavable, and 200mer cleavable) can be used for sample indexing, with the 95mer non-cleavable having the highest efficiency. Sample indexing for determining sample origin can have high specificity and sensitivity.

Example 4

Hot:Cold Antibody Titration

This example demonstrates determining a ratio of oligonucleotide-conjugated antibodies ("hot antibodies") and antibodies not conjugated with oligonucleotides ("cold antibody") such that the antibody oligonucleotides account for a desired percentage (e.g., 2%) of total reads in sequencing data.

An anti-CD147 antibody stock was diluted at 1:20, 1:100, 1:200, 1:300, 1:400, 1:600, 1:800, and 1:1000 dilutions with PE buffer. Around 150000 Jurkat cells in 100 μl of staining buffer (FBS) (BD (Franklin Lake, New Jersey)) were stained at various antibody dilutions for 20 minutes at room temperature. After staining, the cells were washed once with 500 μl of staining buffer and resuspended in 200 μl for measurement of fluorescence intensity. Muse™ Autophagy LC3-antibody (EMD Millipore (Billerica, MA)) was used to detect the anti-CD147 antibody bound to the Jurkat cells. The fluorescence intensities from cells stained at various anti-CD147 antibody dilutions or cells not stained were determined and compared to determine an optimal dilution for the antibody (FIGS. 36A1-36A9, 36B and 36C). Fluorescence intensity decreased with higher dilution. More than 99% of the cells were stained with a dilution ratio of 1:800. Fluorescence signals began to drop out at 1:800. Cells were stained to saturation up to a dilution ratio of 1:200. Cells were stained close to saturation up to a dilution ratio of 1:400.

Figure 37:
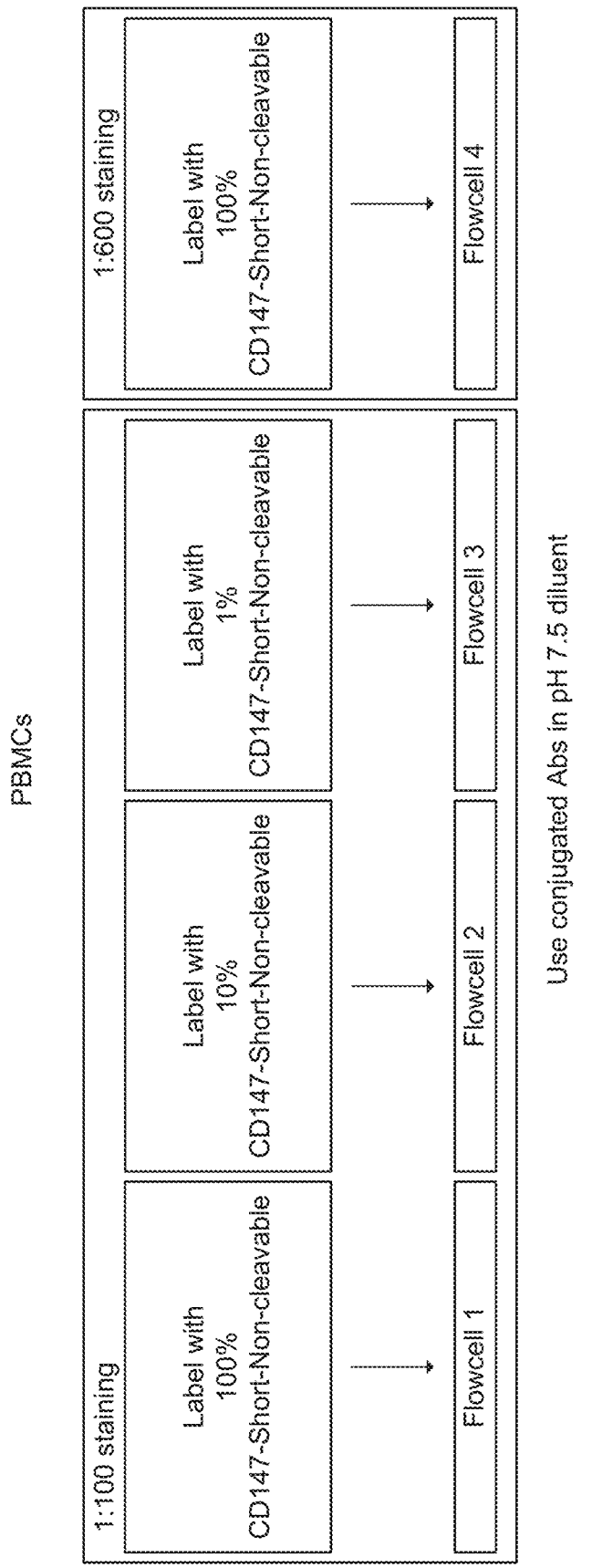
FIG. 37 shows a non-limiting exemplary experimental design for determining a staining concentration of oligonucleotide-conjugated antibodies such that the antibody oligonucleotides account for a desired percentage of total reads in sequencing data.

FIG. 37 shows a non-limiting exemplary experimental design for determining a staining concentration of oligonucleotide-conjugated antibodies such that the antibody oligonucleotides account for a desired percentage of total reads in sequencing data. An anti-CD147 antibody was conjugated with a cleavable 95mer antibody oligonucleotide at an antibody:oligonucleotide ratio of 1:3 ("hot antibody"). The hot antibody was diluted using a pH 7.5 diluent at a 1:100 ratio or a 1:800 ratio. A mixture of 10% hot antibody: 90% cold antibody was prepared using 9 μl of cold anti-CD147 antibody and 1 μl of the hot antibody. A mixture of 1% hot antibody:90% cold antibody was prepared using 9 μl of the cold anti-CD147 antibody and 1 μl of the mixture of 10% hot antibody:90% cold antibody.

Thawed peripheral blood mononuclear cells (PBMCs) with around 0.5 million cells were stained in 100 μl of staining buffer (FBS) with the 1:100 diluted stock with 100% hot antibody (1% of the stock hot antibody), the mixture of 10% hot antibody:90% cold antibody (0.1% of the stock hot antibody), the mixture of 1% hot antibody:99% cold antibody (0.01% of the stock hot antibody), and the 1:800 diluted stock with 100% hot antibody (0.0125% of the stock hot antibody). After staining, the cells were washed to remove unbound antibody molecules. The cells were stained with Calcein AM and Drag7™ for sorting with flow cytometry to obtain live cells. The cells were washed to remove excess Calcein AM and Drag7™. Single cells stained with Calcein AM (live cells) and not Drag7™ (cells that were not dead or permeabilized) were sorted, using flow cytometry, into a BD Rhapsody™ cartridge.

Of the wells containing a single cell and a bead, 1000 of the single cells in the wells were lysed in a lysis buffer. For each single cell, the mRNA molecules were reverse transcribed and the antibody oligonucleotides were replicated using stochastic barcodes conjugated with a bead for the cell. The samples after reverse transcription and replication were PCR amplified for 15 cycles at 60 degrees annealing temperature using primers for determining the mRNA expression profiles of 488 blood panel genes, using blood panel N1 primers, and the expression of CD147 protein, using the sample indexing oligonucleotide N1 primers ("PCR 1"). Excess primers were removed with Ampure cleanup. The products from PCR1 were further PCR amplified ("PCR 2") for 15 cycles at 60 degrees annealing temperature using blood panel N2 primers and sample indexing oligonucleotide N1 primers with a flanking sequence for adaptor ligation. Sequencing data was obtained and analyzed after sequencing adaptor ligation ("PCR 3").

FIGS. 38A-38D are non-limiting exemplary bioanalyzer traces showing peaks (indicated by asterisks) consistent with the expected size of the antibody oligonucleotide. The antibody oligonucleotide peaks decreased as the hot antibody was titrated with the cold antibody.

Table 4 is a summary of sequencing data metrics. By staining the cells with the mixture of 1% hot antibody:99% cold antibody prepared using the 1:100 diluted stock, the antibody oligonucleotides accounted for 2.4% of the total raw reads in the sequencing data. However, as shown in FIGS. 39A1-39A3 and 39B1-39B3 and FIGS. 40B, 41B, and 42B, a distribution histogram of the numbers of molecules of antibody oligonucleotides detected after recursive substitution error correction (RSEC) or distribution-based error correction (DBEC) did not include a clear signal peak if the cells were stained with the mixture of 1% hot antibody: 99% cold antibody prepared using the 1:100 diluted stock. RSEC has been described in U.S. patent application Ser. No. 15/605,874, filed on May 25, 2017, the content of which is incorporated herein by reference in its entirety.

Figure 40A:
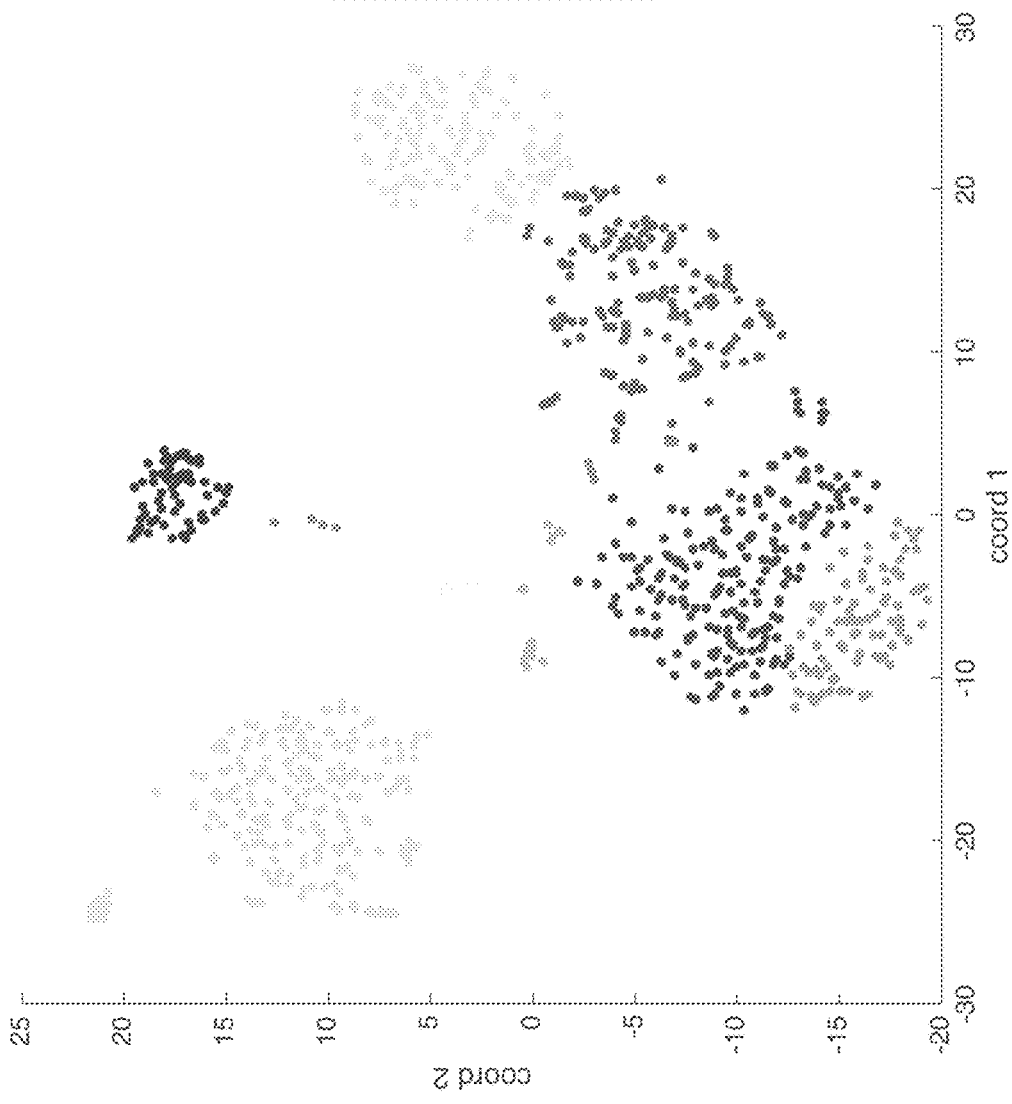
FIGS. 40A-40C are non-limiting exemplary plots showing that oligonucleotide-conjugated anti-CD147 antibody molecules can be used to label various cell types. The cell types were determined using the expression profiles of 488 genes in a blood panel (FIG. 40A). The cells were stained with a mixture of 10% hot antibody:90% cold antibody prepared using a 1:100 diluted stock, resulting in a clear signal in a histogram showing the numbers of molecules of antibody oligonucleotides detected (FIG. 40B). The labeling of the various cell types by the antibody oligonucleotide is shown in FIG. 40C.
Figure 40B:
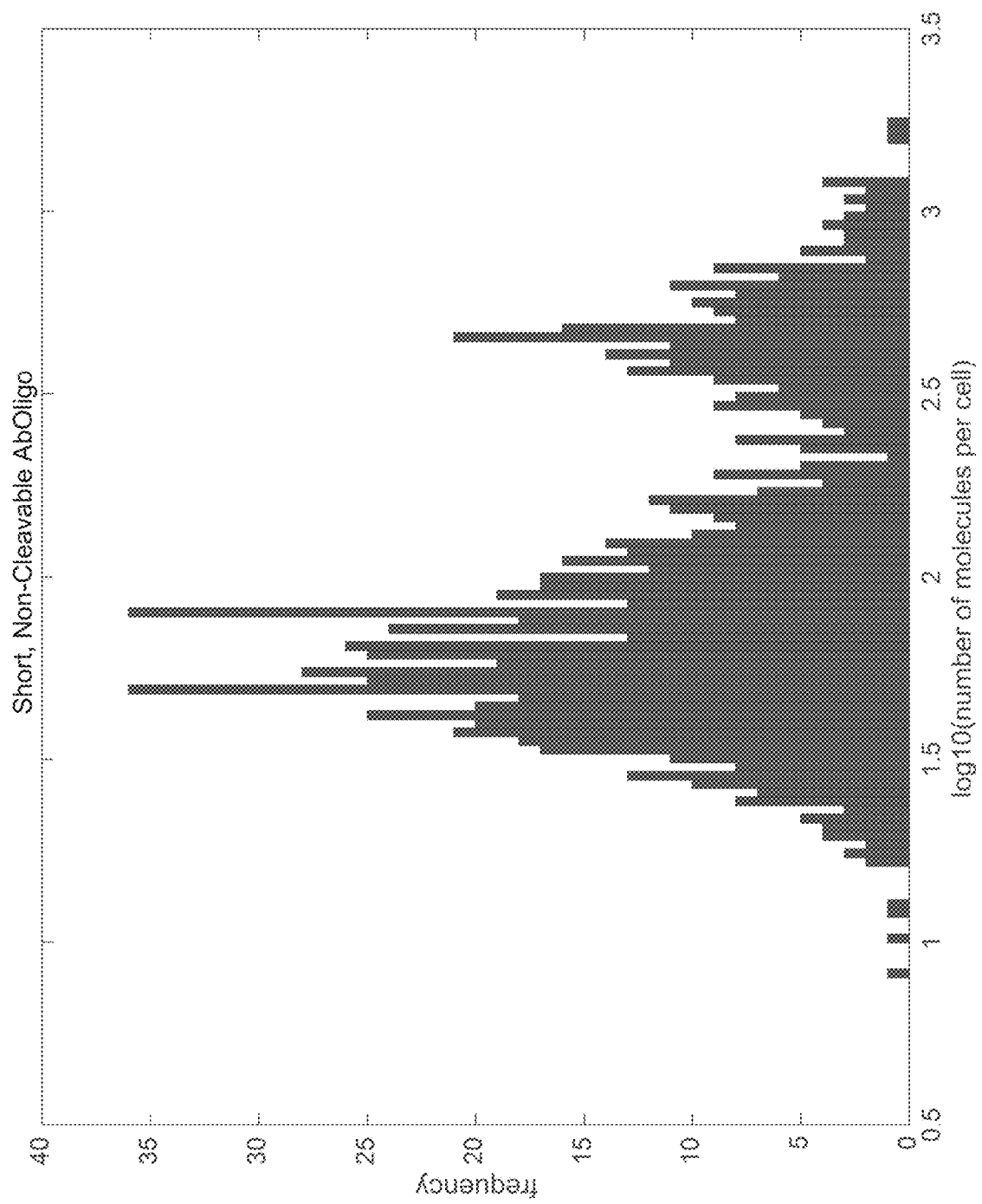
Figure 40C:
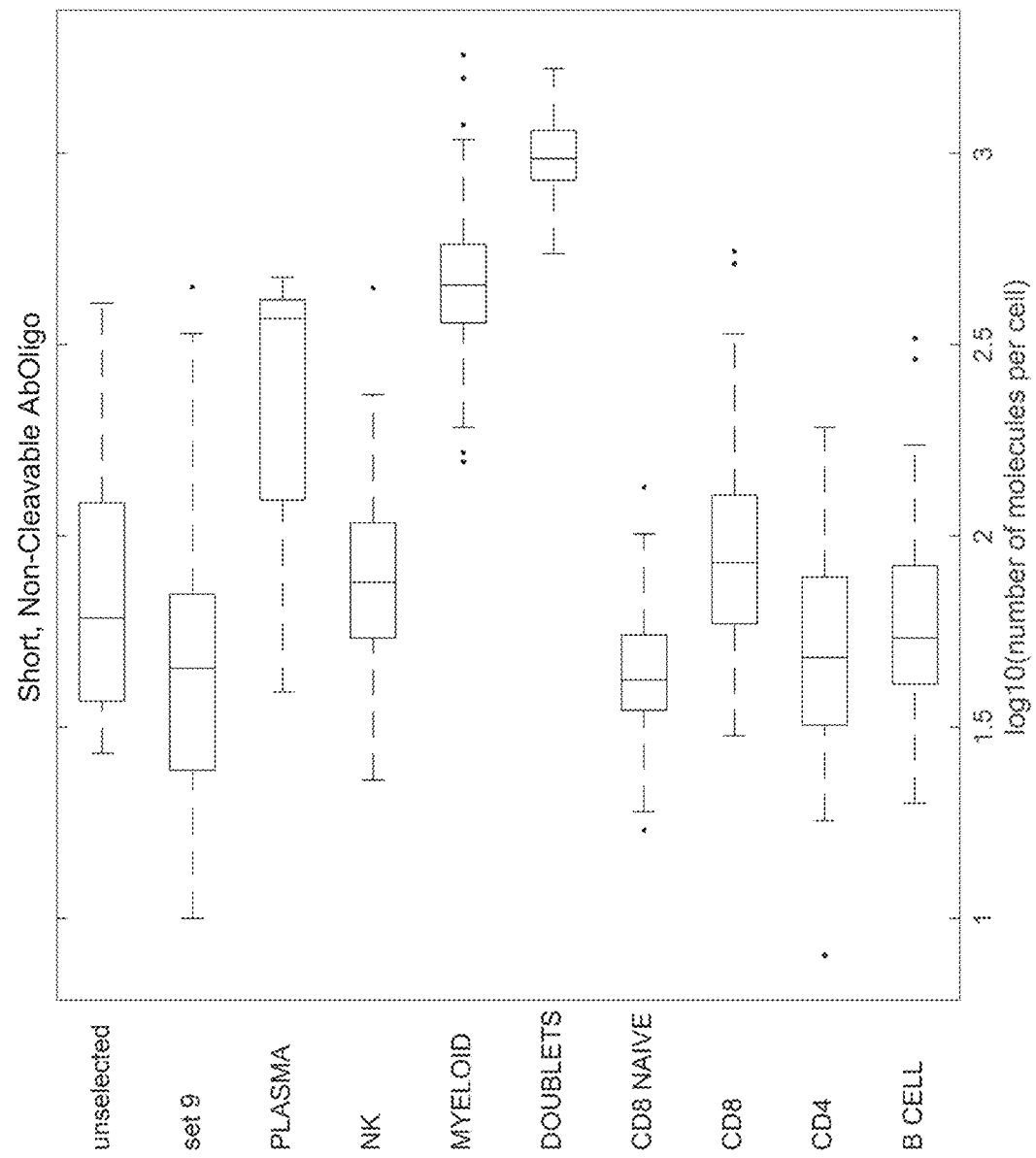

FIGS. 40A-40C are non-limiting exemplary plots showing that oligonucleotide-conjugated anti-CD147 antibody molecules can be used to label various cell types. The cell types were determined using the expression profiles of 488 genes in a blood panel (FIG. 40A). The cells were stained with a mixture of 10% hot antibody:90% cold antibody prepared using a 1:100 diluted stock, resulting in a clear signal in a histogram showing the numbers of molecules of antibody oligonucleotides detected (FIG. 40B). The labeling of the various cell types by the antibody oligonucleotide is shown in FIG. 40C.

Figure 41A:
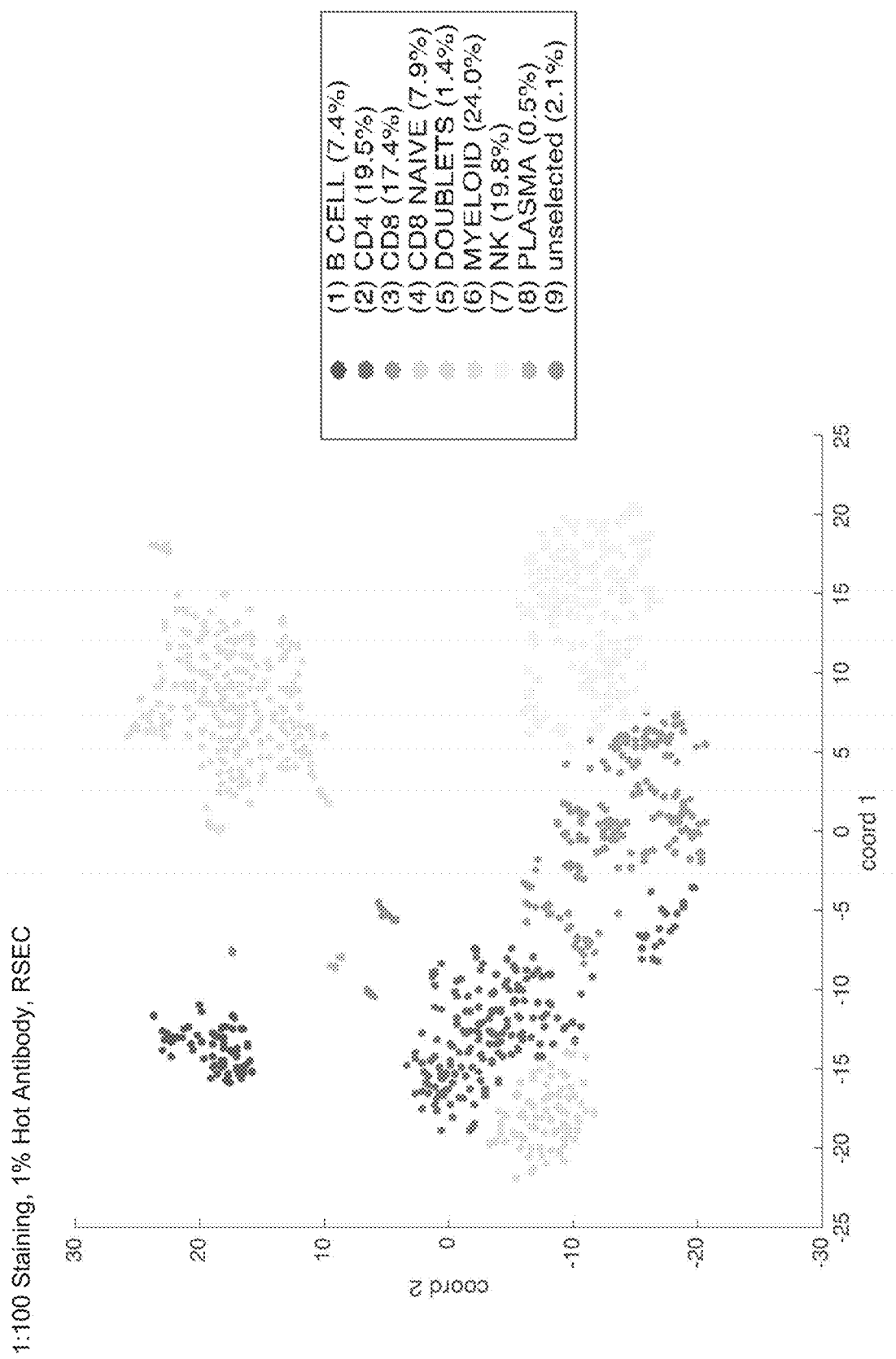
Figure 41C:
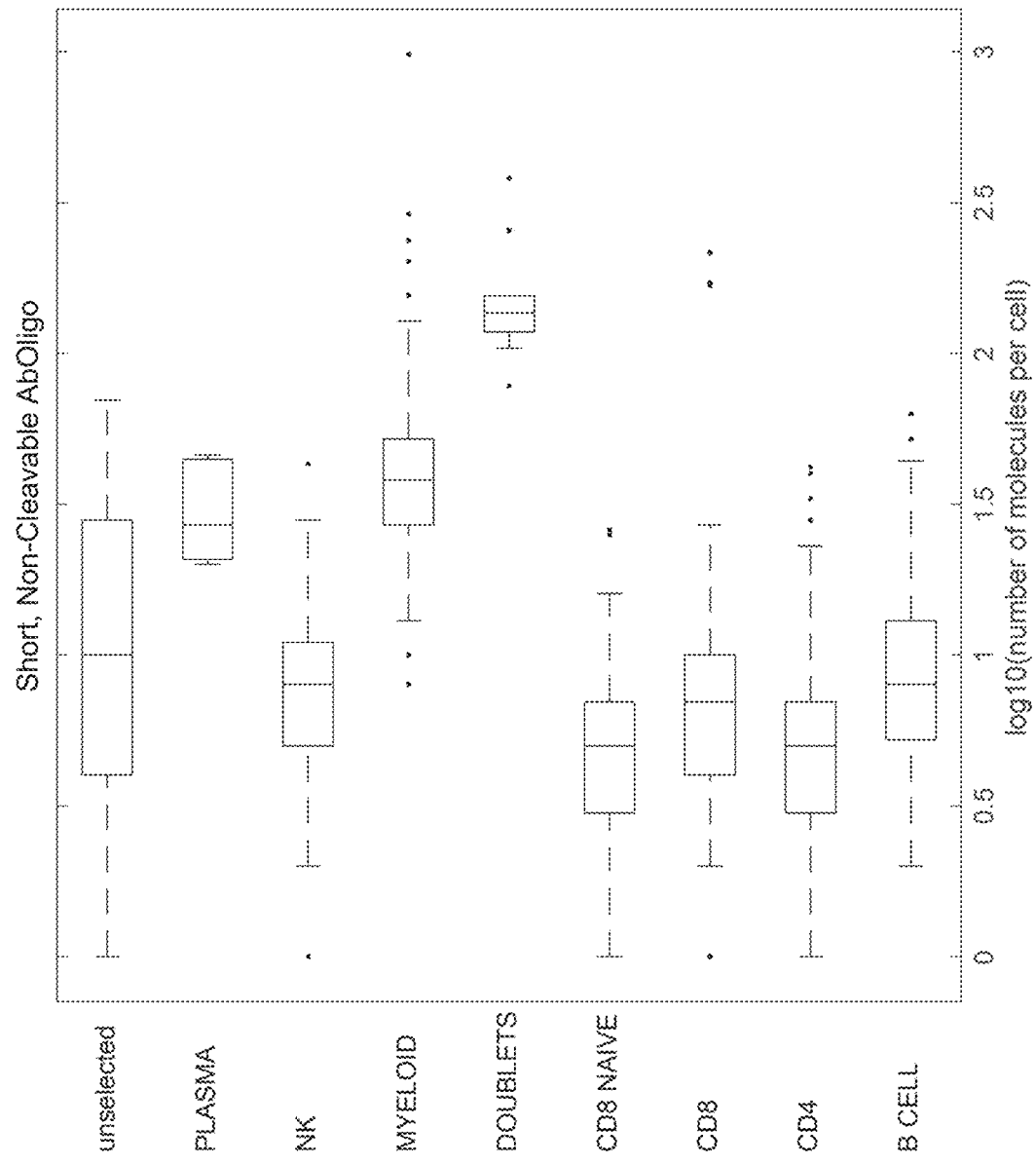

FIGS. 41A-41C are non-limiting exemplary plots showing that oligonucleotide-conjugated anti-CD147 antibodies can be used to label various cell types. The cell types were determined using the expression profiles of 488 genes in a blood panel (FIG. 41A). The cells were stained with a mixture of 1% hot antibody:99% cold antibody prepared using a 1:100 diluted stock, resulting in no clear signal in a histogram showing the numbers of molecules of antibody oligonucleotides detected (FIG. 41B). The labeling of the various cell types by the antibody oligonucleotide is shown in FIG. 41C.

Figure 42A:
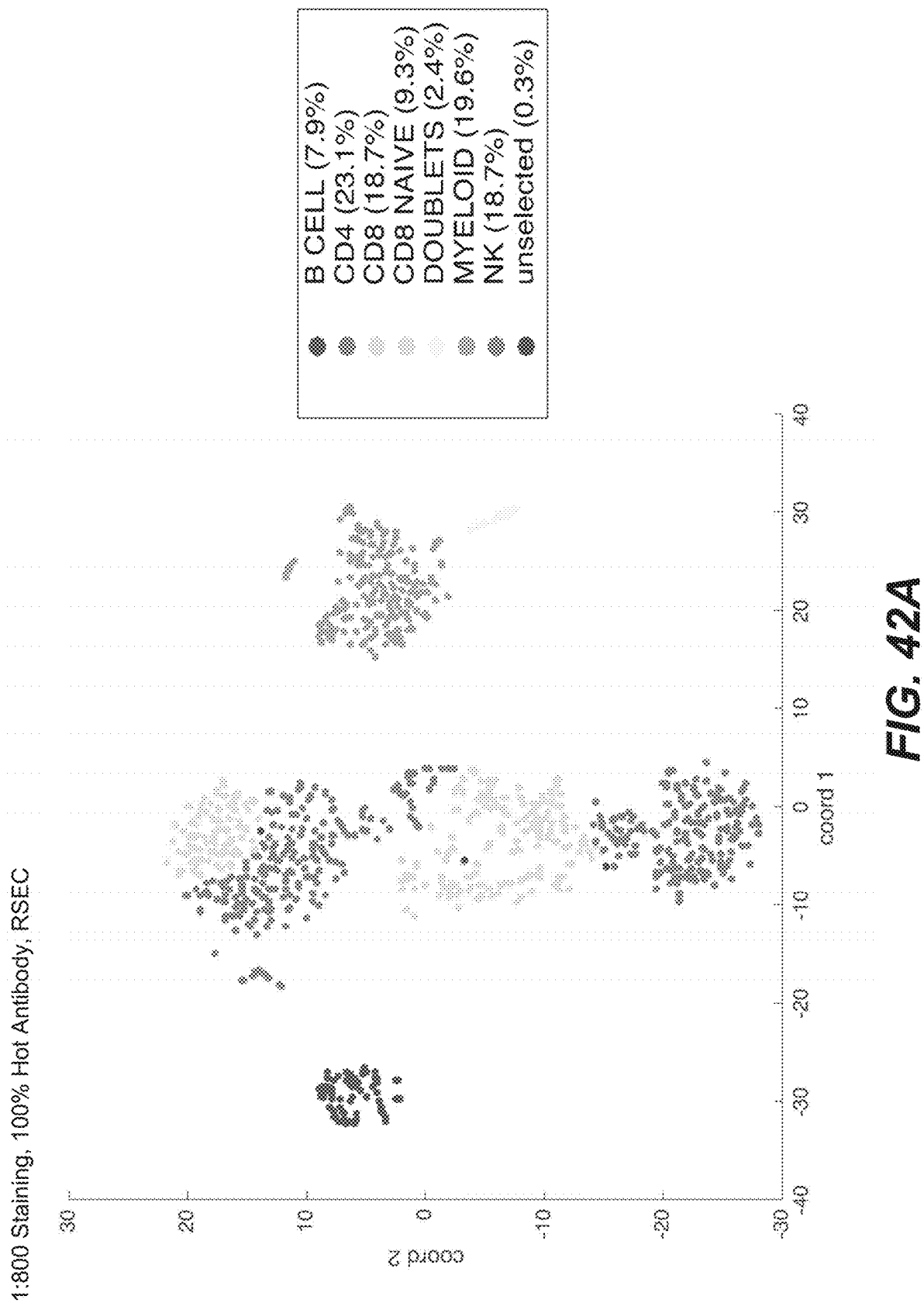
FIGS. 42A-42C are non-limiting exemplary plots showing that oligonucleotide-conjugated anti-CD147 antibody molecules can be used to label various cell types. The cell types were determined using the expression profiles of 488 genes in a blood panel (FIG. 42A). The cells were stained with a 1:800 diluted stock, resulting in a clear signal in a histogram showing the numbers of molecules of antibody oligonucleotides detected (FIG. 42B). The labeling of the various cell types by the antibody oligonucleotide is shown in FIG. 42C.
Figure 42B:
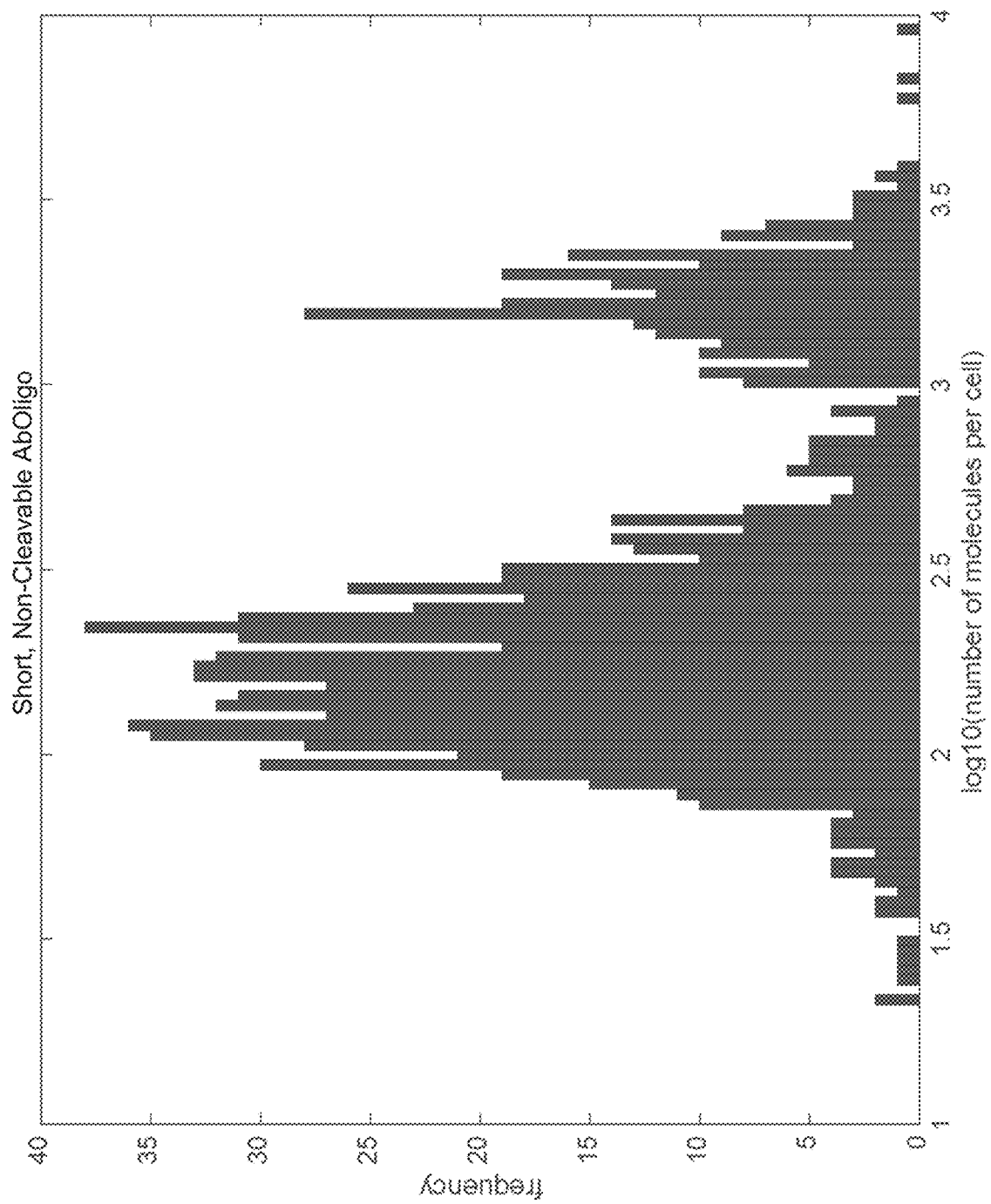
Figure 42C:
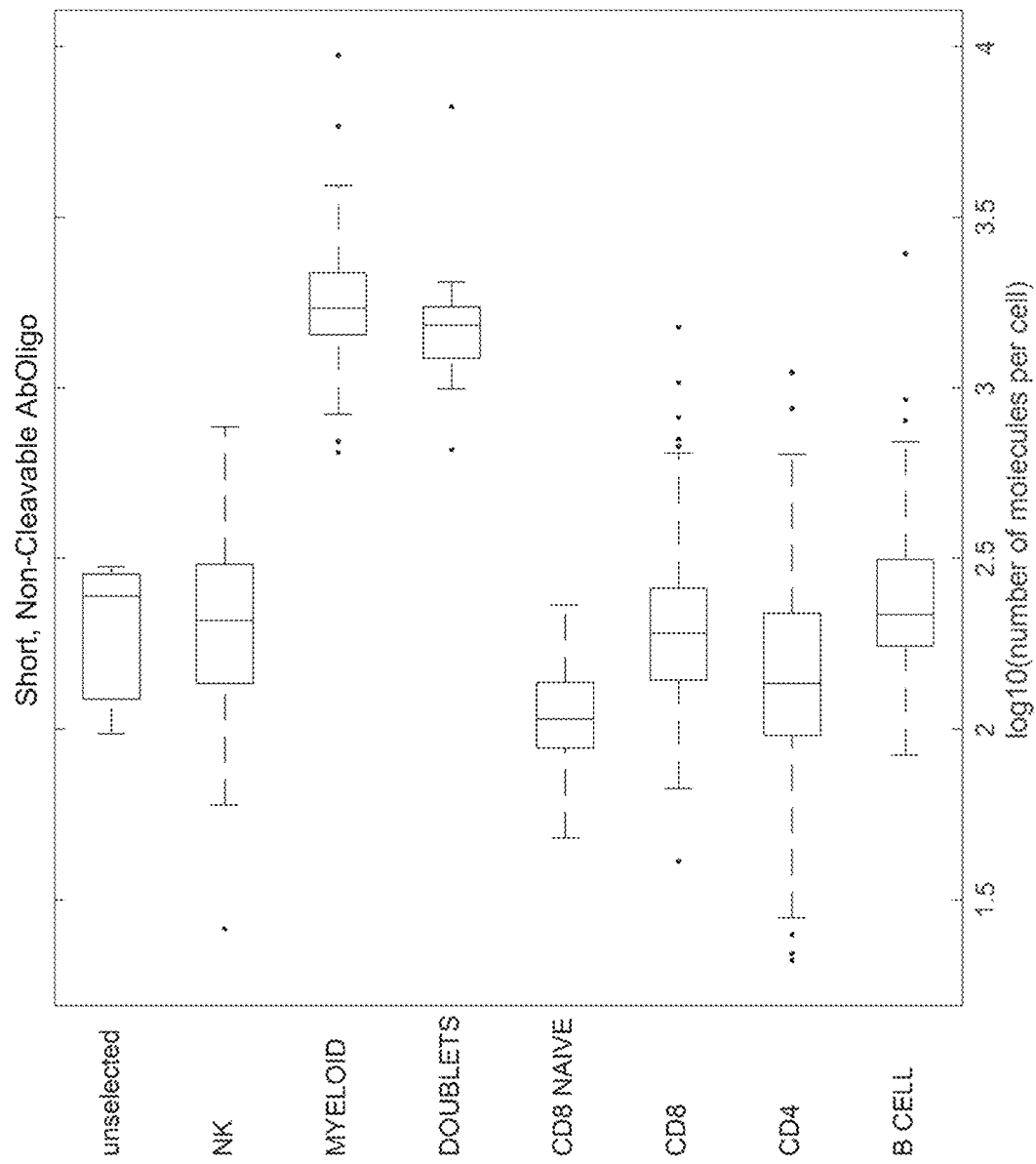

FIGS. 42A-42C are non-limiting exemplary plots showing that oligonucleotide-conjugated anti-CD147 antibody molecules can be used to label various cell types. The cell types were determined using the expression profiles of 488 genes in a blood panel (FIG. 42A). The cells were stained with a 1:800 diluted stock, resulting in a clear signal in a histogram showing the numbers of molecules of antibody oligonucleotides detected (FIG. 42B). The labeling of the various cell types by the antibody oligonucleotide is shown in FIG. 42C.

TABLE 4

Summary of sequencing data metrics.

| Sample | FC4 - 1:800 Dilution, No Cold Antibody | FC3 - 1:100 Dilution, 1:100 Cold Antibody | FC2 - 1:100 Dilution, 1:10 Cold Antibody |
|---|---|---|---|
| Total Raw Reads | 31.3M | 27.3M | 29.2M |
| Total Raw Reads Assigned to Oligos | 9161642 (29.2%) | 660044 (2.4%) | 4013438 (13.7%) |
| Cell Detected | 1010 | 983 | 907 |
| RSEC Oligo MI | 577110 | 20054 | 170742 |
| DBEC Oligo MI | 477216 | 9319 | 110629 |
| % Q30 | 76.45 | 71.89 | 73.45 |
| % assigned to cell labels | 84.63 | 79.47 | 82.58 |
| % aligned uniquely to amplicons | 73.19 | 65.4 | 69.58 |
| Mean raw seq depth | 5.58 | 6.52 | 6.4 |
| Mean RSEC seq depth | 8.69 | 10.41 | 10.25 |
| Mean DBEC seq depth | 15.96 | 23.29 | 22.48 |
| AbOligo RSEC seq depth | 8.08 | 12.9 | 11.2 |
| AbOligo DBEC Seq depth | 12.4 | 30.9 | 21.2 |
| Mean reads per cell | 11257 | 14414 | 15150 |
| mean molecules per cell | 553.8 | 608.3 | 647.1 |
| Median mols per cell | 246.5 | 279 | 278 |
| No. of genes in panel | 489 | 489 | 489 |
| Total genes detected | 438 | 439 | 441 |
| Mean genes per cell | 68.39 | 73.6 | 73.12 |

Altogether, these data indicate that the ratio of oligonucleotide-conjugated antibodies ("hot antibodies") and antibodies not conjugated with oligonucleotides ("cold antibody") can be adjusted such that the antibody oligonucleotides account for a desired percentage of total reads in sequencing data and data representing signal antibody oligonucleotides is clearly separated from data representing noise antibody oligonucleotides.

Example 5

Normalization

This example demonstrates how normalization, using a mixture of oligonucleotide-conjugated antibodies ("hot antibodies") and antibodies not conjugated with oligonucleotides ("cold antibody"), can result in the antibody oligonucleotides accounting for a desired percentage of total reads in sequencing data with a desired coverage, irrespective of the abundance of the protein targets of the antibodies.

Table 5 shows a comparison of quantification of three cell surface markers of varying abundance in 10000 B cells using hot antibodies. Total number of reads required to resolve relative expression levels of the three cell surface markers was 47.52 million reads.

TABLE 5

Example protein quantification using hot antibodies.

| Antigen | Molecules per Cell | Relative abundance | Ratio of Hot:Cold Antibodies | Number of Molecules per Cell Detected by Sequencing | Number of reads given sequencing depth of 4 |
|---|---|---|---|---|---|
| CD21 | 210000 | 105 | 1:0 | 840 | 33.6M |
| HLA-DR | 85000 | 42.5 | 1:0 | 340 | 13.6M |
| CD40 | 2000 | 1 | 1:0 | 8 | 0.32M |

TABLE 6

Example protein quantification using hot and cold antibodies.

| Antigen | Molecules per Cell | Relative abundance | Ratio of Hot:Cold Antibodies | Number of Molecules per Cell detected by sequencing | Number of reads given sequencing depth of 4 | Expected number of molecules based on Antibody ratio | Relative abundance by sequencing |
|---|---|---|---|---|---|---|---|
| CD21 | 210000 | 105 | 1:100 | 8.3 | 0.33M | 8.3 × 100 = 830 | 103.75 |
| HLA-DR | 85000 | 42.5 | 1:40 | 8.5 | 0.34M | 8.5 × 40 = 340 | 42.5 |
| CD40 | 2000 | 1 | 1:0 | 8 | 0.32M | 8 × 1 = 8 | 1 |

Table 6 shows that the total number of reads required to resolve relative expression levels of the three cell surface markers was 1 million reads using mixtures of hot antibodies:cold antibodies. Also, only 2% of the number of reads, compared to the quantification result shown in Table 5 (1 million reads vs. 47.52 million reads), is needed to achieve optimal coverage (e.g., sequencing depth of 4) of all three protein markers when mixtures of hot antibodies:cold antibodies were used to quantify expression levels of the three cell surface markers. Normalizing high expressing protein molecules, using a mixture with higher percentage of cold antibodies, decreased tradeoffs between detection of low abundance proteins, number of parameters, and sequencing cost, making the assay more attractive as a tool.

Altogether, these data indicate that a desired number of total reads in sequencing data with a desired coverage can be achieved for protein targets (e.g., antigens) of different abundance using mixtures of hot antibodies:cold antibodies.

Example 6

Control Particles

This example demonstrates generating control particles comprising control particle oligonucleotides with different sequences and use of the functionalized control particles to determine capture efficiency.

Materials

BD CompBead Plus Anti-Mouse Ig (7.5 um) Particles Set (51-9006274)

BD staining buffer (FBS)

Procedure

1. Vortex BD CompBead Plus thoroughly before use (1 minute at least).

2. Add 800 uL of staining buffer to tube (Table 7 shows the composition of the staining buffer with CD147 conjugated to oligonucleotides with five sequences at different abundance. FIG. 43A is a plot showing the composition of the staining buffer).

3. Add 5 full drops (approximately 300 uL) of CompBead Plus Anti-Mouse.

4. Add 20 uL of the staining cocktail below to the tube. Vortex.

5. Incubate 30 minutes at room temperature away from light.

6. Spin beads at 200 g for 10 minutes.

7. Remove supernatant carefully and resuspend with 1 mL staining buffer.

8. Spin beads at 200 g for 10 minutes.

9. Remove supernatant carefully and resuspend with 1 mL staining buffer to generate the functionalized CompBead stock solution.

10. Count beads.

TABLE 7

Staining Cocktail Composition

| Antibodies | Final % in Staining Buffer | Prior Dilution | Staining Solution (μl) |
|---|---|---|---|
| CD147-LZ15 | 1 | 1:1 | 1 |
| CD147-LZ16 | 0.2 | 1:5 | 1 |
| CD147-LZ17 | 0.1 | 1:10 | 1 |
| CD147-LZ18 | 0.02 | 1:50 | 1 |
| CD147-LZ19 | 0.01 | 1:100 | 1 |
| Staining Buffer | | | 95 |

Results

Figure 44B:
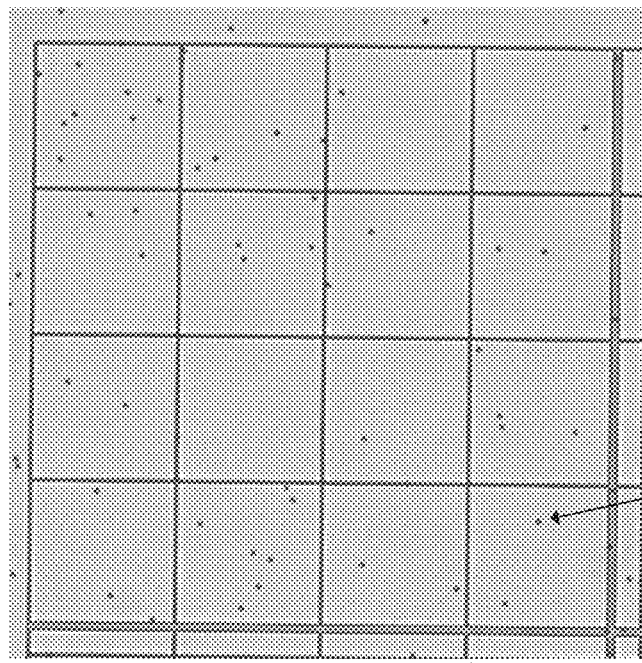
FIGS. 44A-44B are brightfield images of cells (FIG. 44A, white circles) and control particles (FIG. 44B, black circles) in a hemocytometer.
Figure 44A:
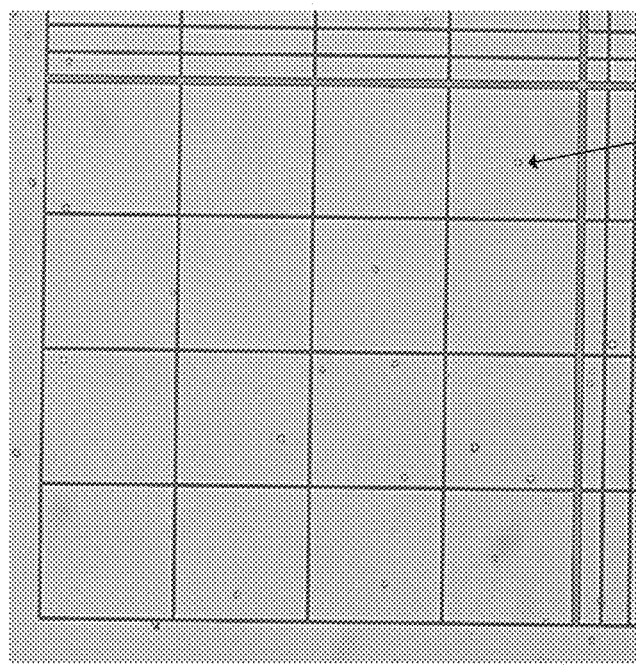
Figure 45B:
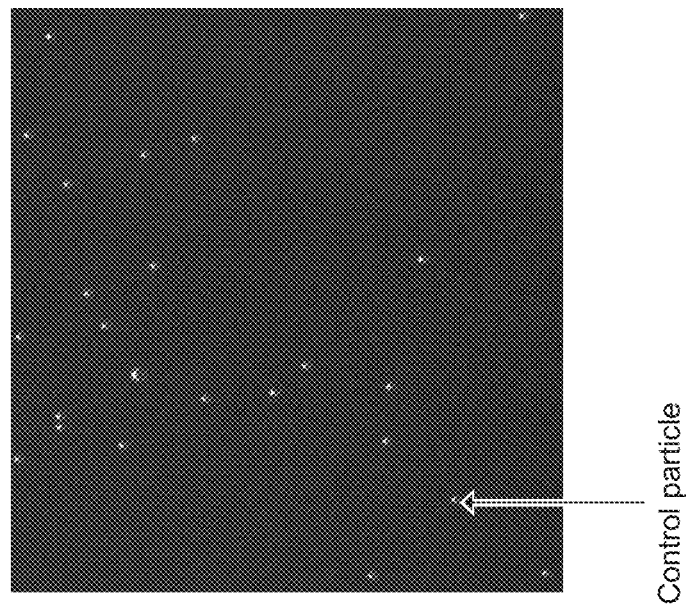
FIGS. 45A-45B are phase contrast (FIG. 45A, 10×) and fluorescent (FIG. 45B, 10×) images of control particles bound to oligonucleotide-conjugated antibodies associated with fluorophores.
Figure 45A:
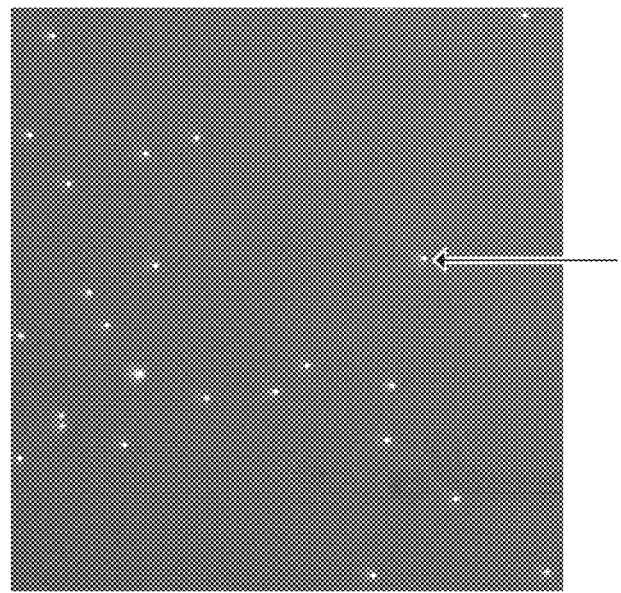

FIGS. 44A-44B are brightfield images of cells (FIG. 44A, white circles) and control particles (FIG. 44B, black circles) in a hemocytometer. FIGS. 45A-45B are phase contrast (FIG. 45A, 10×) and fluorescent (FIG. 45B, 10×) images of control particles bound to oligonucleotide-conjugated antibodies associated with fluorophores. Fluorescent microscope was used to determine that 5 ul of the functionalized CompBead stock solution contained ~2000 cells (4% of total input) with ~400000 functionalized CompBeads made.

Figure 46:
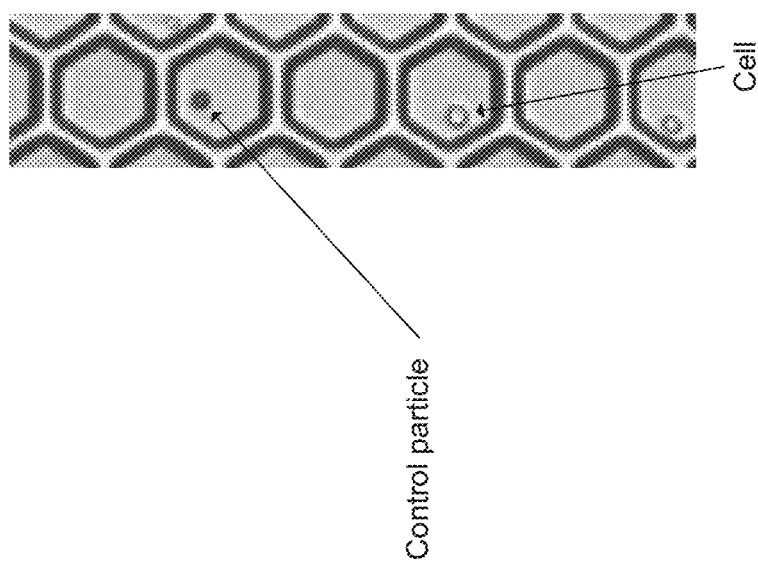
FIG. 46 is an image showing cells and a control particle being loaded into microwells of a cartridge.

FIG. 46 is an image of a control particle showing cells and a particle being loaded into microwells of a cartridge. CompBeads can be used with regular Rhapsody™ experiments. 522 functionalized CompBeads were added into a plurality of cells. Of the 20000 cells (including control particles) sequences, 156 had a sum of all control particle oligonucleotides greater than 20. Thus, 156 control particles were sequences. FIG. 43B is a plot showing the number of control particle oligonucleotides with the five different control barcode sequences (LZ15-LZ19) correlated with their abundance in the staining buffer.

Altogether, these data show that particles (e.g., CompBead Plus) can be functionalized with oligonucleotides (e.g., control particle oligonucleotides). Functionalized particles can be used with single cell sequencing workflow to determine the number of particles captured and sequenced.

Example 7

Antibody Cocktail for Sample Indexing

This example demonstrates using an antibody cocktail for sample indexing can increase labeling sensitivity.

Figure 47A:
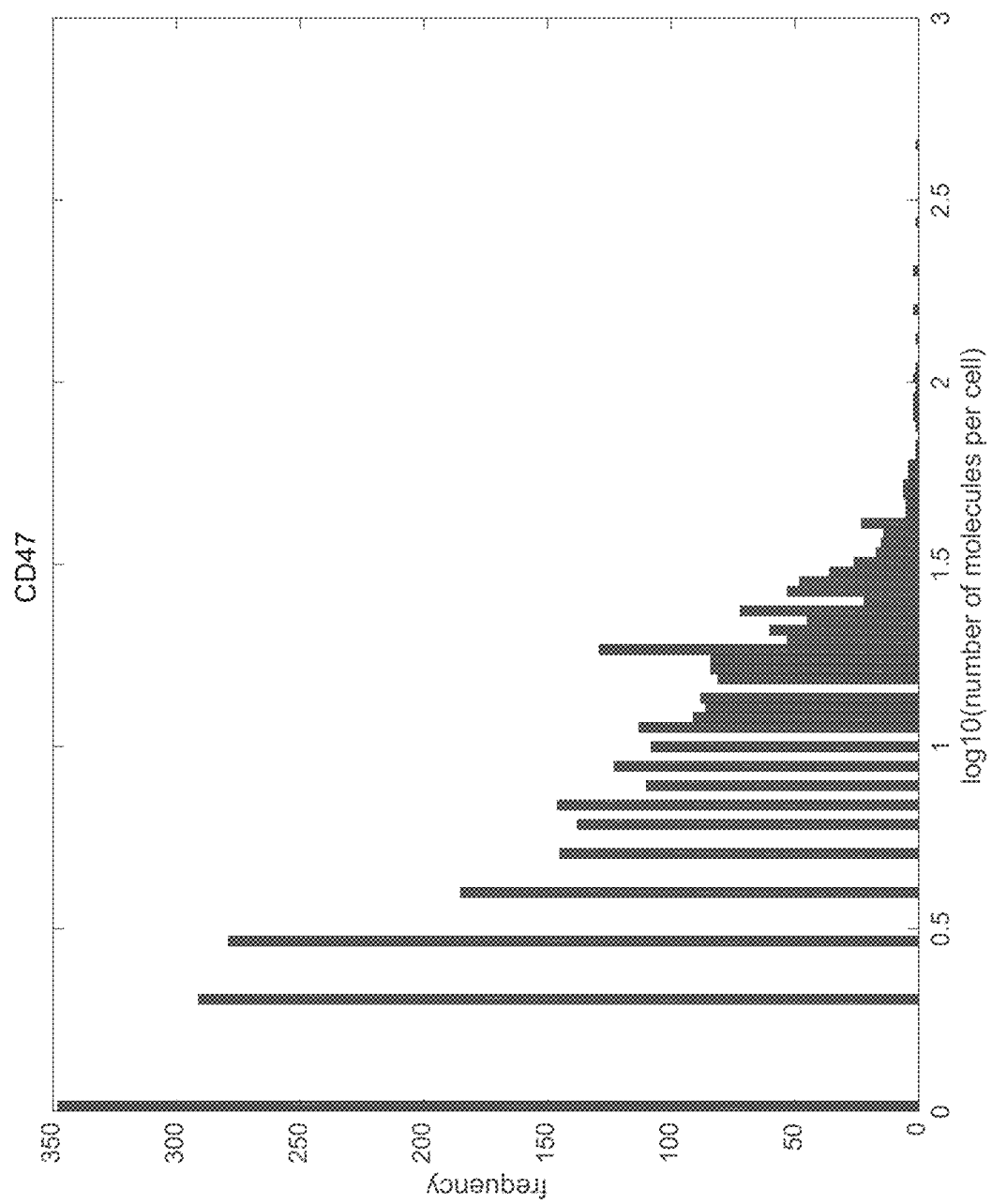
Figure 47B:
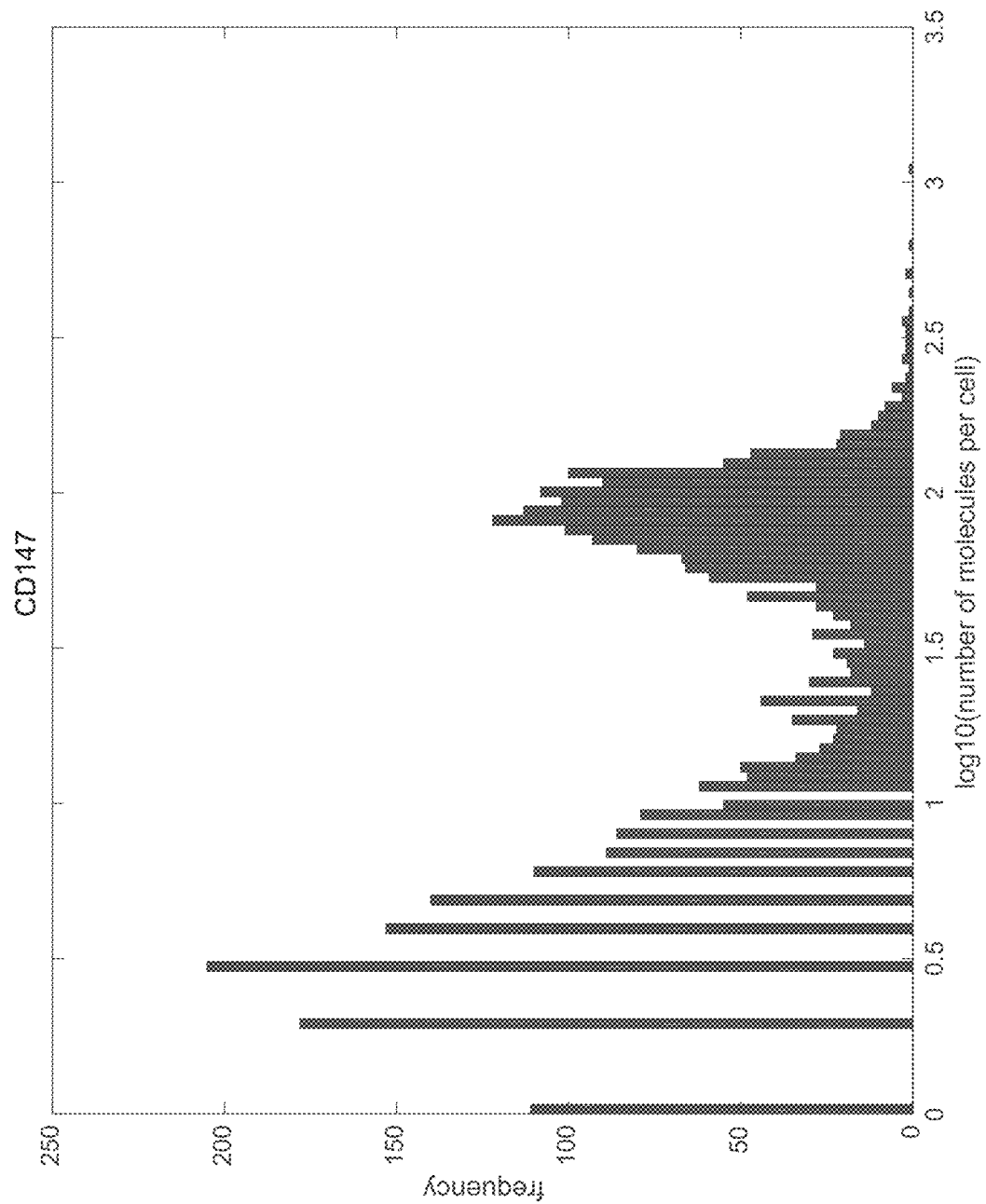

Sample indexing can utilize oligonucleotide-conjugated antibodies against multiple protein targets to label samples. In this example, instead of using a single antibody, a cocktail of two antibodies were used instead. The cocktail of antibodies were labeled with the same sample indexing oligonucleotides. FIGS. 47A-47C are plots showing using an antibody cocktail for sample indexing can increase labeling sensitivity. FIGS. 47A-47C show the labeling sensitivity of PBMCs with a CD147 antibody, a CD47 antibody, and both CD147 and CD47 antibodies. FIG. 47C shows that more cells were labeled when both CD147 and CD47 antibodies were used and better signal to noise separation was achieved. Table 8 shows increased labeling sensitivity when both CD147 and CD47 antibodies were used. The use of both CD147 and CD47 antibodies resulted in higher sensitivity for labeling heterogeneous sample types.

TABLE 8

Labeling sensitivity with CD147, CD47, or both CD147 and CD47 antibodies.

| Antibody | Sensitivity |
|---|---|
| CD147 | 86.2% |
| CD47 | 82.5% |
| CD147 + CD47 | 92.6% |

Altogether, the data show that using an antibody cocktail can increase labeling sensitivity. This may be because protein expression can vary between cell types and cell states, making finding a universal antibody that labels all cell types challenging. Using an antibody cocktail can allow for more sensitive and efficient labeling of more sample types. An antibody cocktail can also include a wider range of antibodies. Antibodies that label different sample types well can be pooled together to create a cocktail that sufficiently labels all cell types or cell types of interest.

Example 8

Presence of Multiplets in Datasets

This example describes that multiplets in sequencing data can be identified and removed by tagging cells with different sample indexing oligonucleotides.

Figure 48:
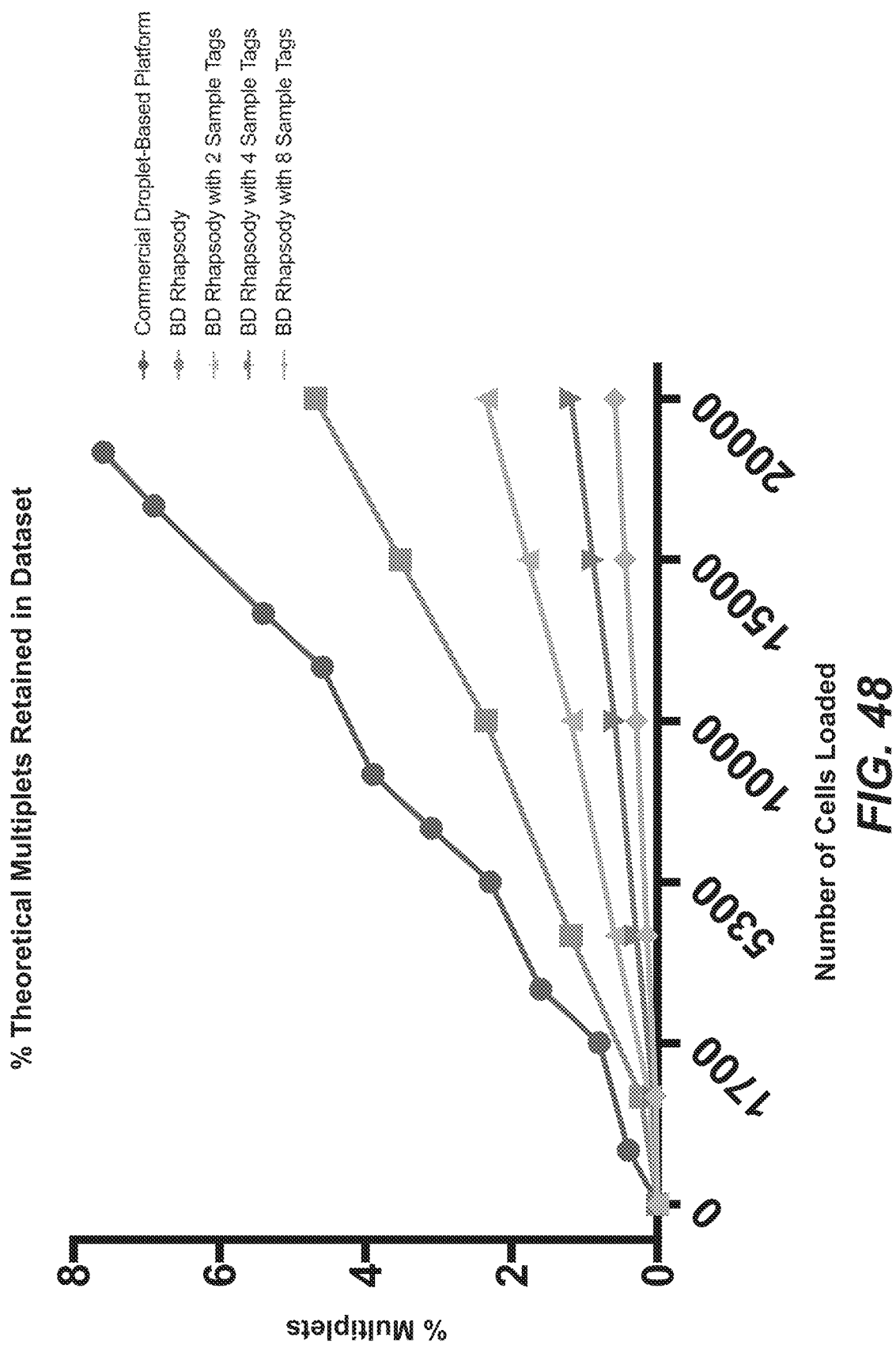
FIG. 48 is a non-limiting exemplary plot showing that multiplets can be identified and removed from sequencing data using sample indexing.

FIG. 48 is a non-limiting exemplary plot showing that multiplets can be identified and removed from sequencing data using sample indexing. As shown in FIG. 48, the rate of multiplets in droplets and single cell expression data can be close to eight percent when a sample with single 20000 cells are partitioned into droplets using a droplet-based platform. The rate of multiplets in a microwell array and single cell expression data can be much lower (e.g., close to only four percent) when a sample with single 20000 cells are partitioned into wells of a Rhapsody™ (Becton, Dickinson and Company (Franklin Lakes, NJ)). Multiplets in sequencing data can be identified and removed using sample indexing oligonucleotides with different sample indexing sequences. For example, when a sample with 20000 single cells is divided into two subpopulations, cells in each subpopulation are labeled with sample indexing oligonucleotides with an identical sample indexing sequence, and cells in different subpopulations are labeled with sample indexing oligonucleotides with two different sample indexing sequences, sequence data associated with multiplets can be identified and removed, with the resulting sequencing data containing around two % multiplets. With sample indexing oligonucleotides with eight different sample indexing sequences, sequencing data of 20000 single cells can include only around 0.5% multiplets. With a higher number of sample indexing sequences, the rate of multiplet in sequencing data can be even lower.

Thus, the rate of multiplets remaining in single cell sequencing data can be substantially lowered, or eliminated, by labeling cells with sample indexing oligonucleotides with different sample indexing sequences.

Example 9

Sample Indexing for Identifying Multiplets

This example demonstrates using sample tags to identify and remove multiplets in sequencing data.

Six tissues (bone marrow, fat (gonadal white adipose tissue (gWAT)), colon, liver, lung, and spleen) from two mice were obtained. CD45+ single cells from the isolated tissues were isolated and sorted using fluorescence-activated cell sorting (FACS) to create 12 samples. CD45+ single cells of the 12 samples were tagged with 12 different sample tags (referred to herein as sample indexing compositions) using BD™ Single-Cell Multiplexing Kit for RNA-Sequencing and loaded onto a Rhapsody™ cartridge. A sample tag was an antibody conjugated to an oligonucleotide (referred to herein as sample indexing oligonucleotides) that can be captured and amplified in a 3' RNA-seq assay (such as the BD Rhapsody™ assay). Such a sample tag had high specificity and sensitivity (>99%). The mRNA molecules from the cells and the sample indexing oligonucleotides were captured using Rhapsody™ magnetic beads, and barcoded and amplified using Rhapsody™ Immune Response Panel-Mouse (Mouse). Expression profiles of the cells were determined and identified as singlet expression profiles and multiplet expression profiles using synthetic multiplet expression profiles.

Figure 49A:
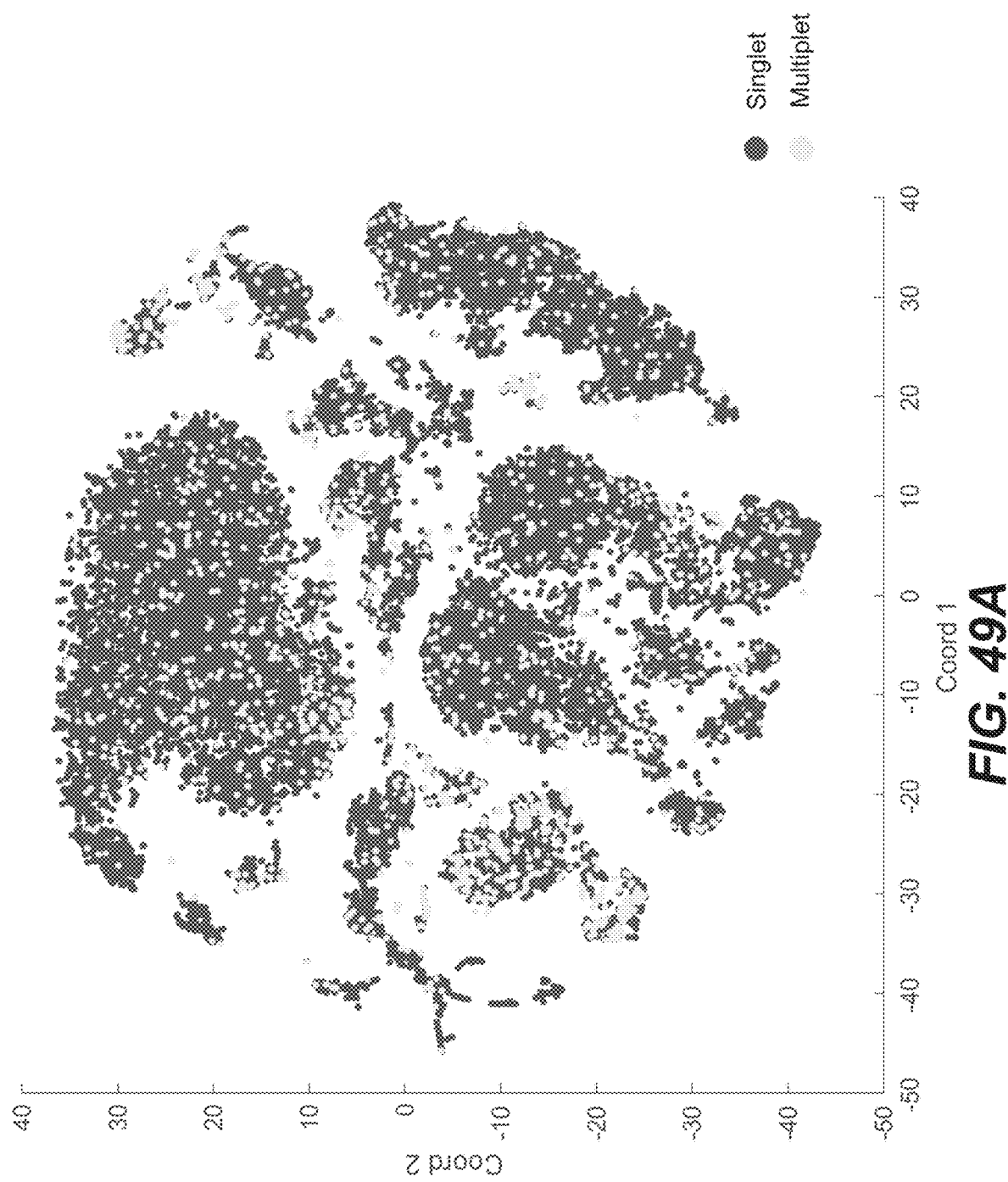
FIG. 49A is a non-limiting exemplary tSNE projection plot of expression profiles of CD45+ single cells from 12 samples of six tissues from two mice identified as singlets or multiplets using sample indexing oligonucleotides.
Figure 49B:
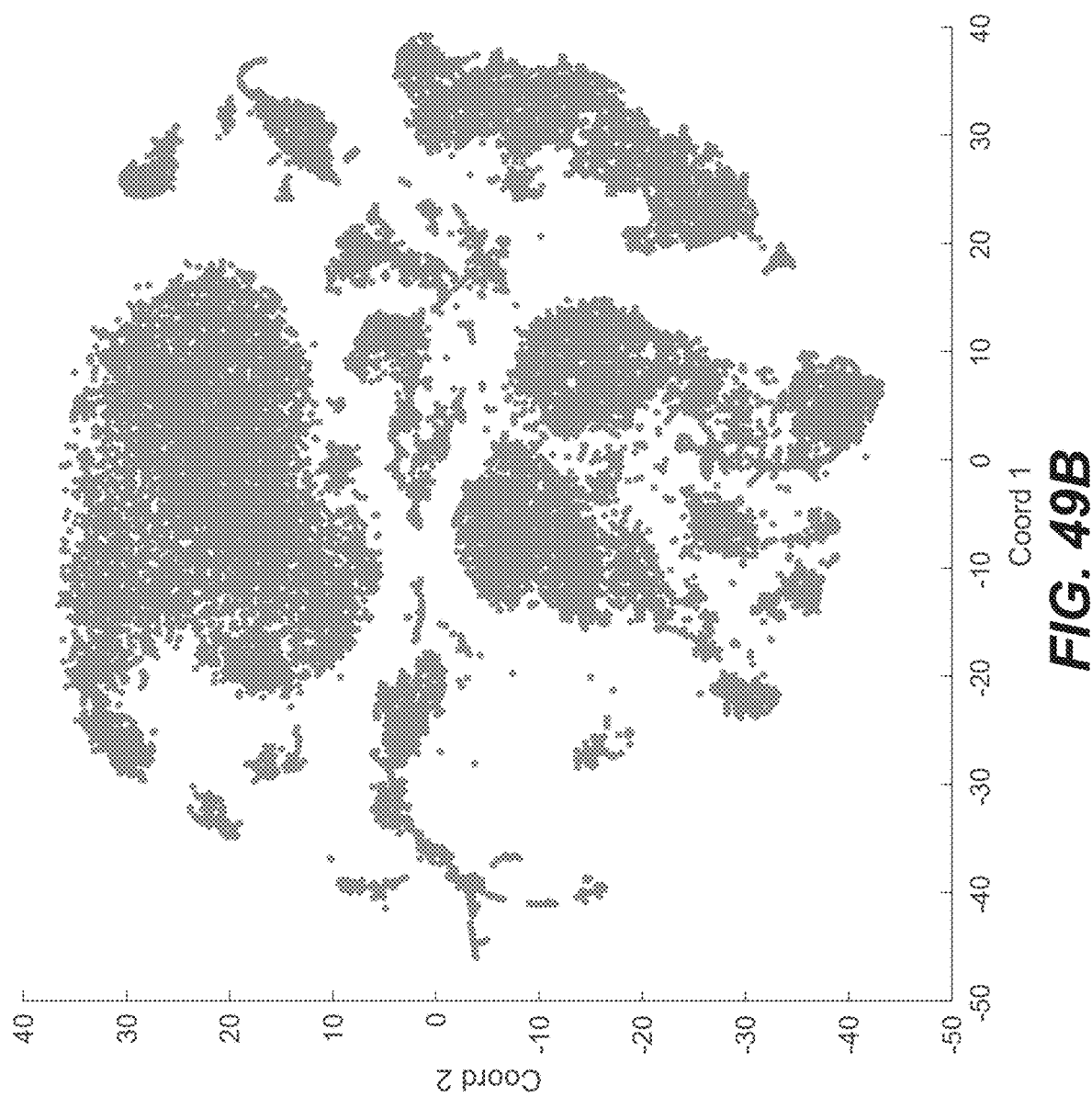
FIG. 49B is a non-limiting exemplary tSNE projection plot of expression profiles of CD45+ single cells of 12 samples of six tissues from two mice with multiplets identified using sample indexing oligonucleotides and shown in FIG. 49A removed.

FIG. 49 is a non-limiting exemplary tSNE projection plot of expression profiles of CD45+ single cells from 12 samples of six tissues from two mice identified as singlets or multiplets using sample tags. FIG. 49 shows the multiplet expression profiles as multiple clusters. Sample tag sequences (also referred to herein as sample indexing indices of sample indexing oligonucleotides) for tagging the different tissues were used to identify multiplet expression profiles each including the expression profiles of cells of two or more cell types or subtypes. Multiplets of CD45+ cells from two different tissues were identified based on the presence of the sample tag sequences in the sequence data obtained from the cells. The performance of using nucleic acid sample tags to index samples and identify multiplets was comparable to the performance of using synthetic multiplet expression profiles to identify multiplets. FIG. 49B is a non-limiting exemplary tSNE projection plot of expression profiles of CD45+ single cells of 12 samples of six tissues from two mice with multiplets identified using sample indexing oligonucleotides removed.

Figure 50A:
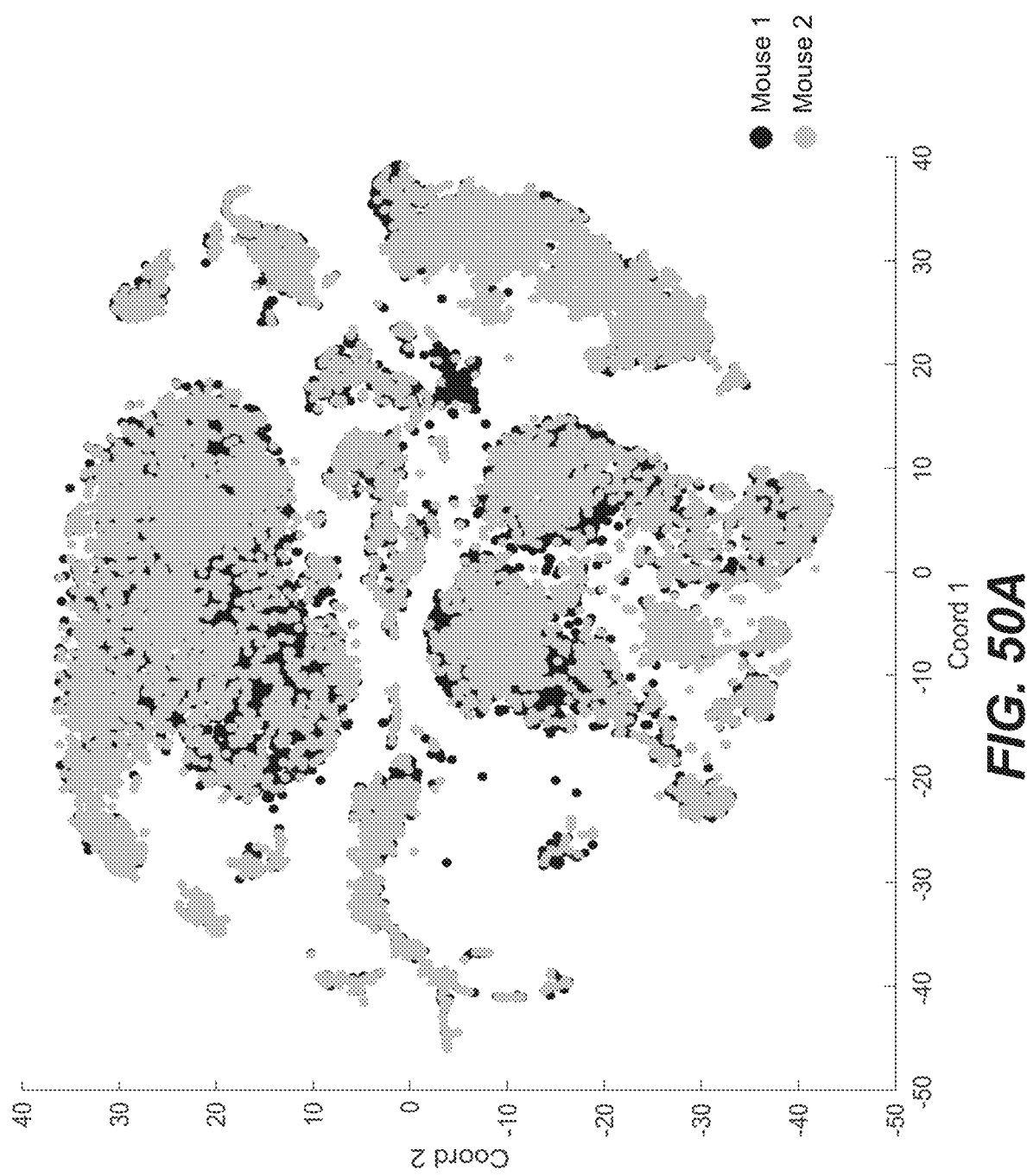
FIG. 50A is a non-limiting exemplary tSNE projection plot of expression profiles of CD45+ single cells from two mice with multiplets identified using sample indexing oligonucleotides removed.
Figure 51A:
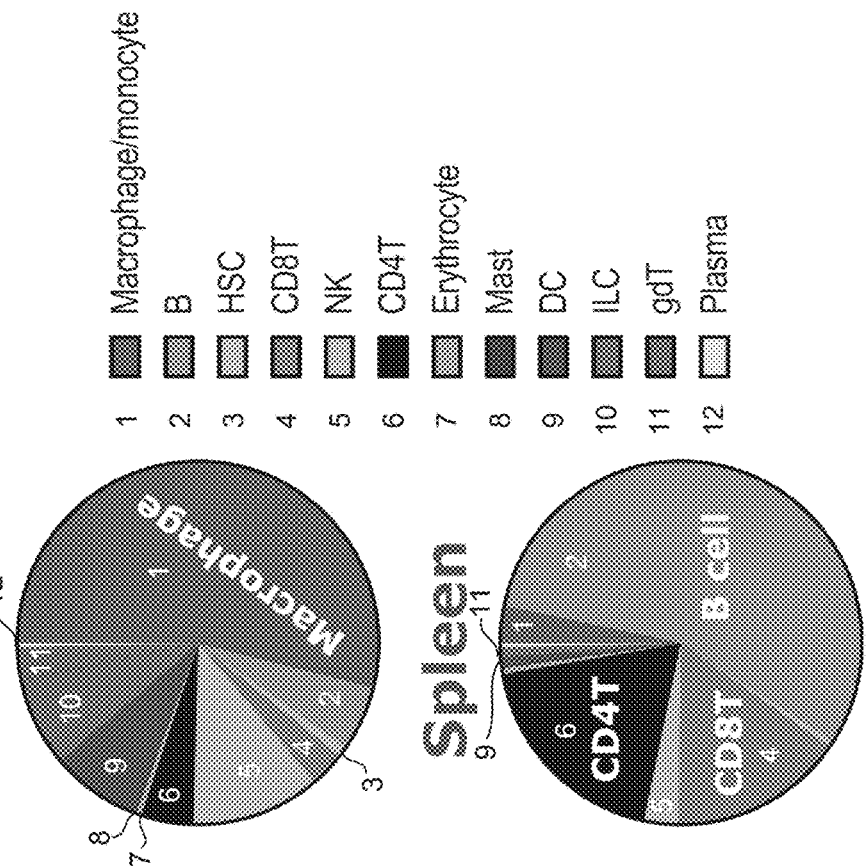
FIGS. 51A-51F are non-limiting exemplary pie charts showing immune cell profiles of six different tissues with multiplet expression profiles in sequencing data identified and removed using sample indexing oligonucleotides.
Figure 51B:
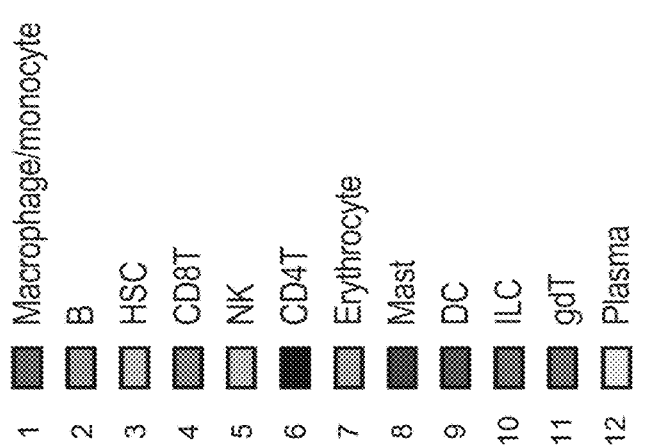
Figure 51C:
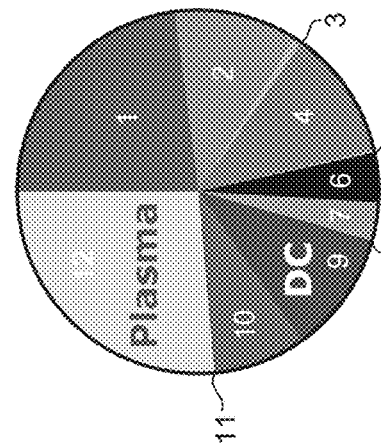
Figure 51D:
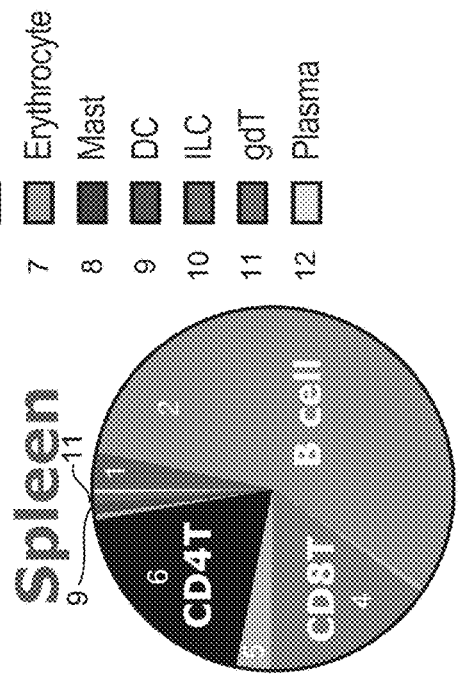
Figure 51E:
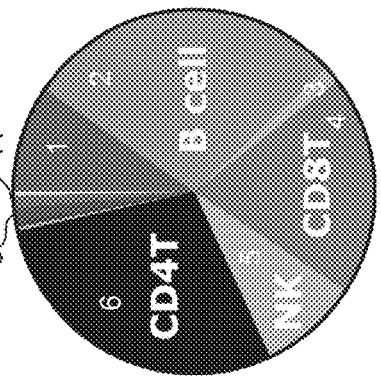
Figure 51F:
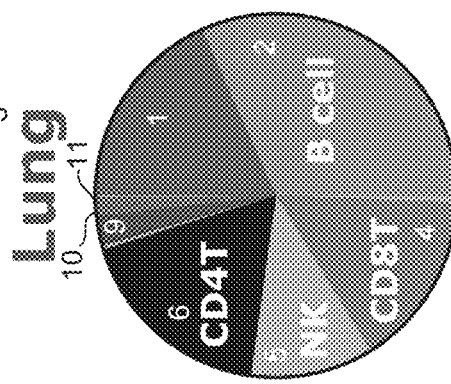

FIG. 50A is a non-limiting exemplary tSNE projection plot of expression profiles of CD45+ single cells from two mice with multiplets identified using sample indexing oligonucleotides removed. With multiplet expression profiles removed, the two mice, which were biological replicates, exhibited similar expression profiles as shown in FIGS. 50A-50C. The results of immune profiling of the six different tissues after removing multiplet expression profiles are shown in FIGS. 51A-51F. The different cell types (e.g., B cells, macrophages, etc.) in the six sample shown in FIGS. 51A-51F were identified based on the expression profiles of the cells.

Figure 52A:
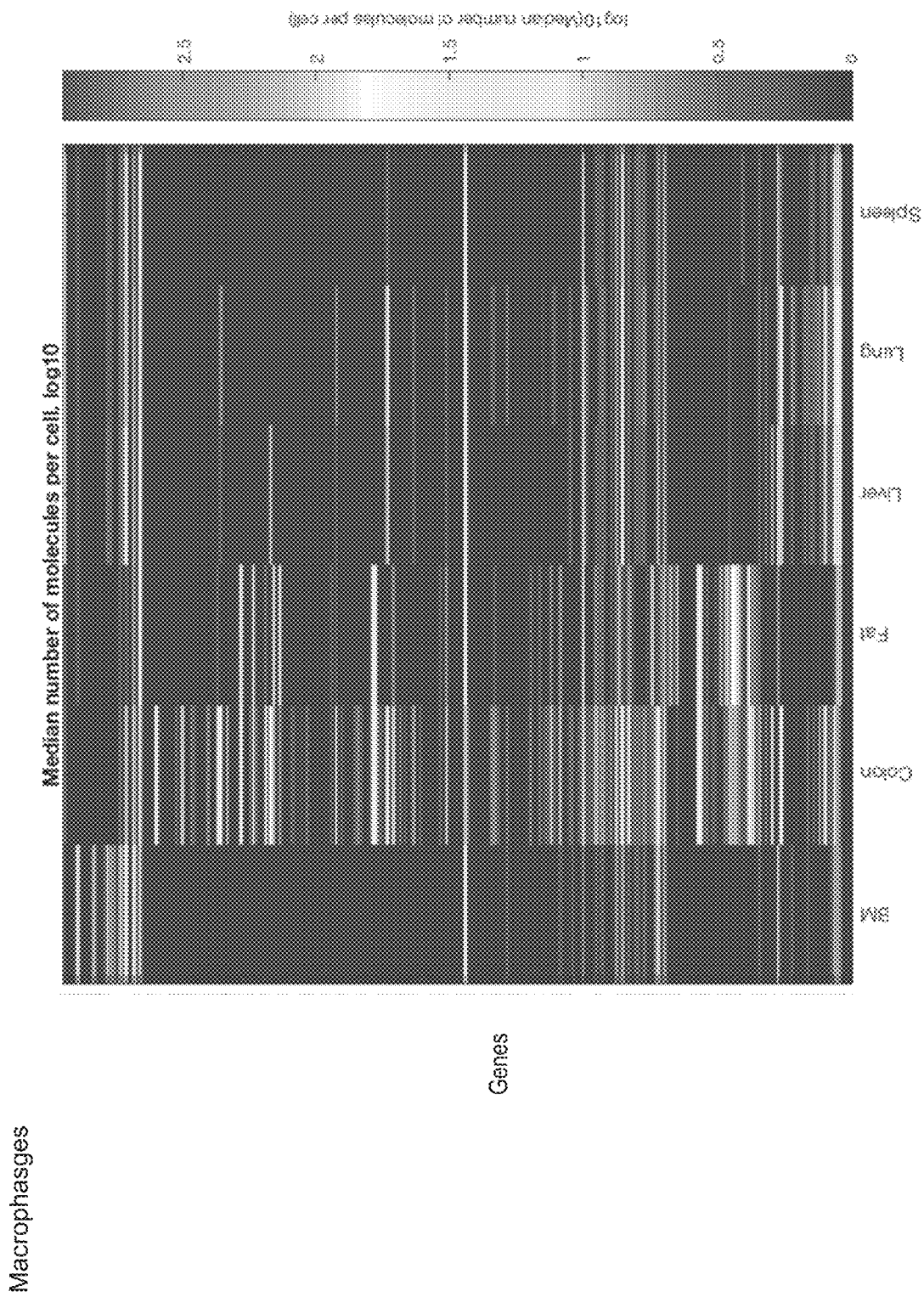
FIGS. 52A-52C are non-limiting exemplary graphs showing expression profiles of macrophages, T cells, and B cells from six different tissues after multiplet expression profiles in sequencing data identified and removed using sample indexing oligonucleotides.
Figure 52B:
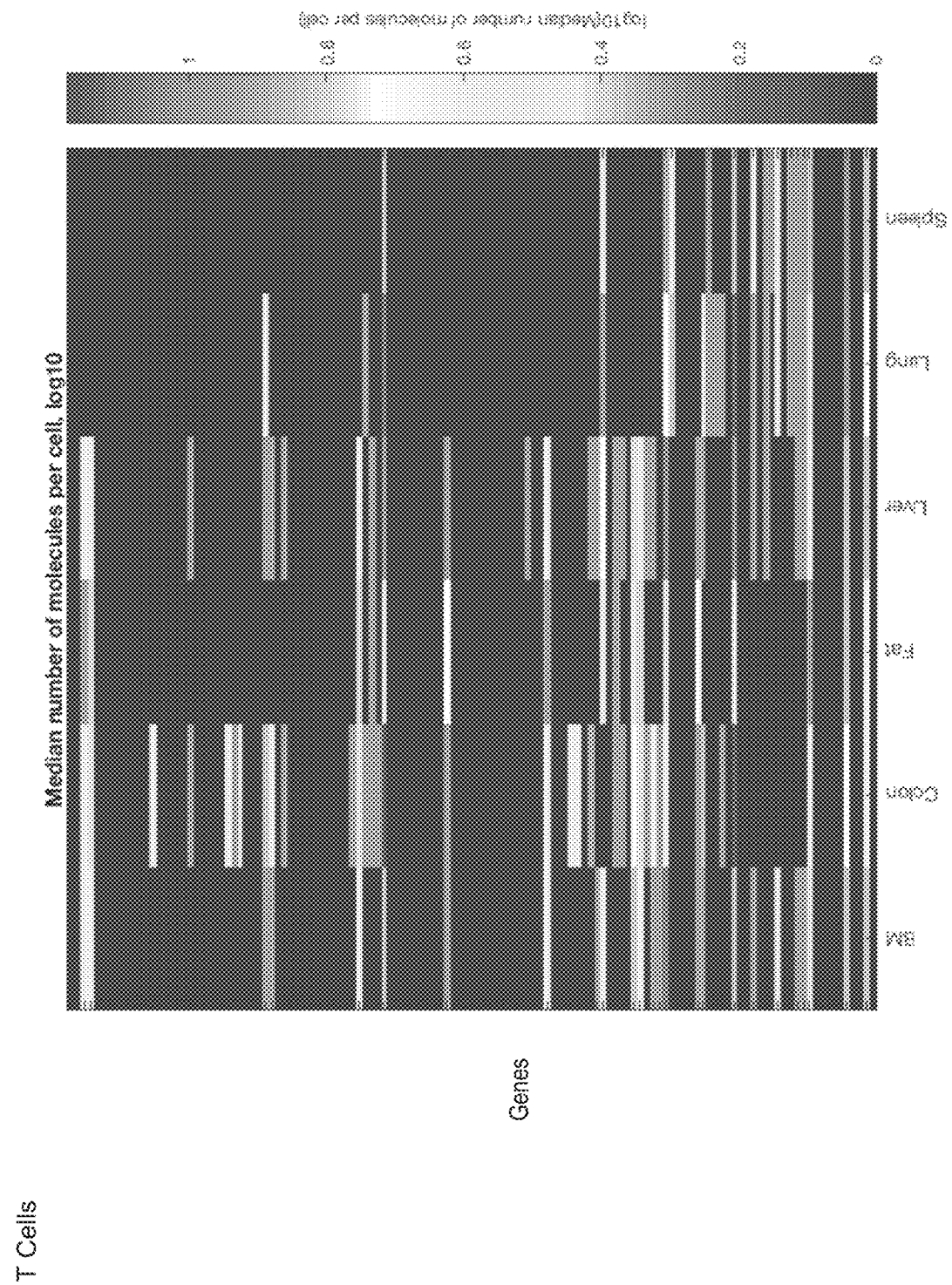
Figure 52C:
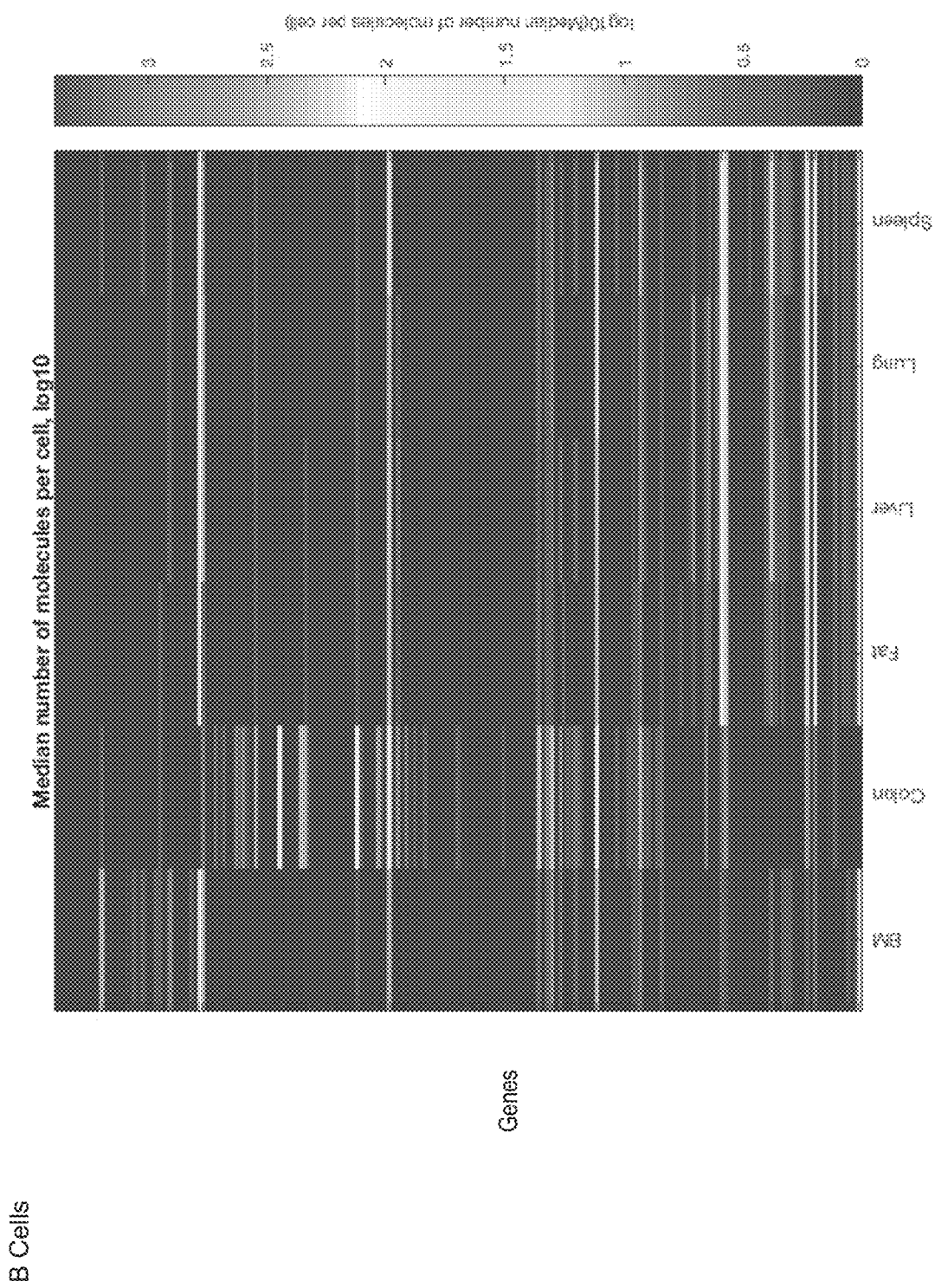
Figure 53A:
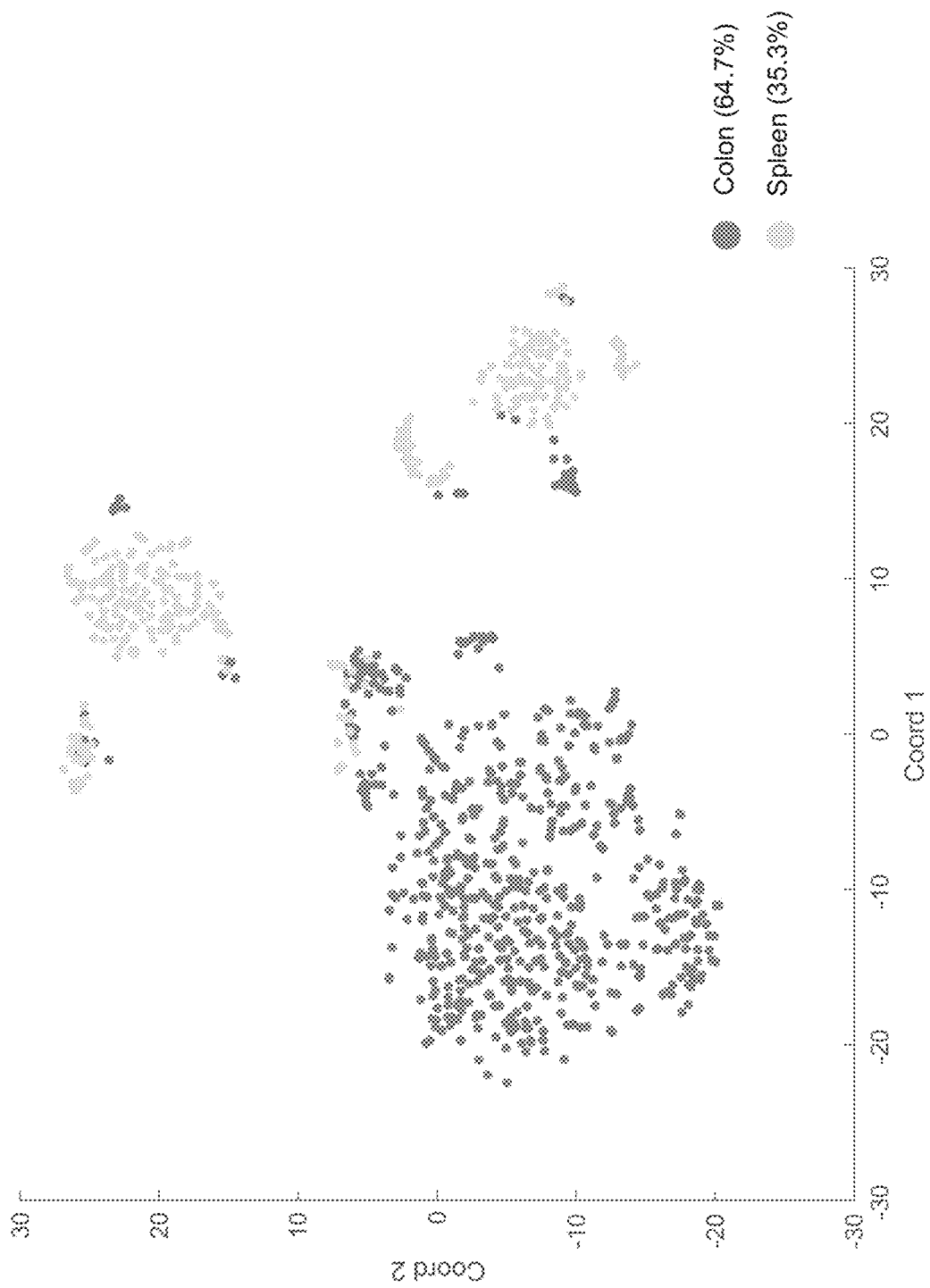
FIGS. 53A-53D are non-limiting exemplary plots comparing macrophages in the colon and spleen.
Figure 53B:
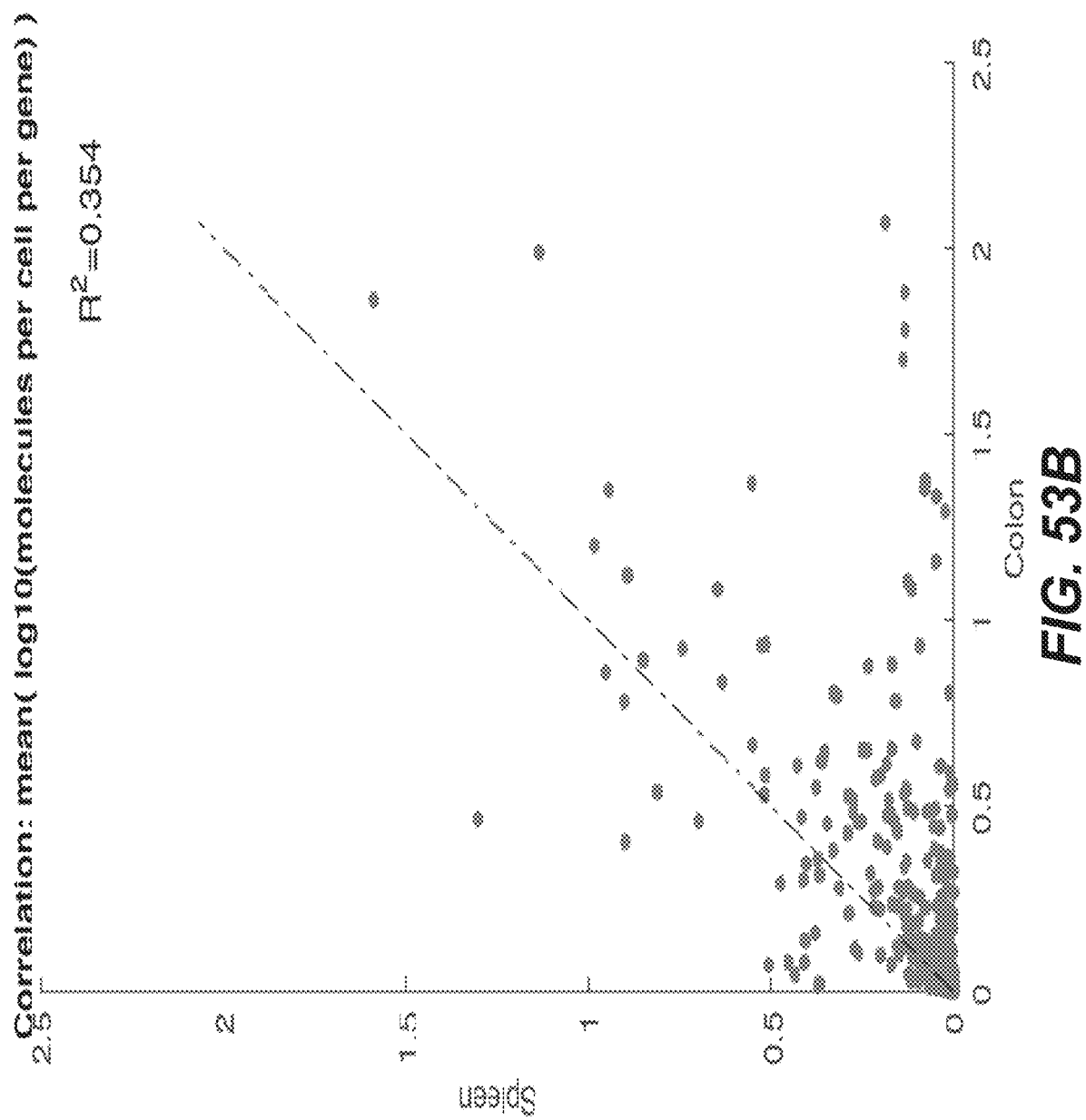
Figure 53C:
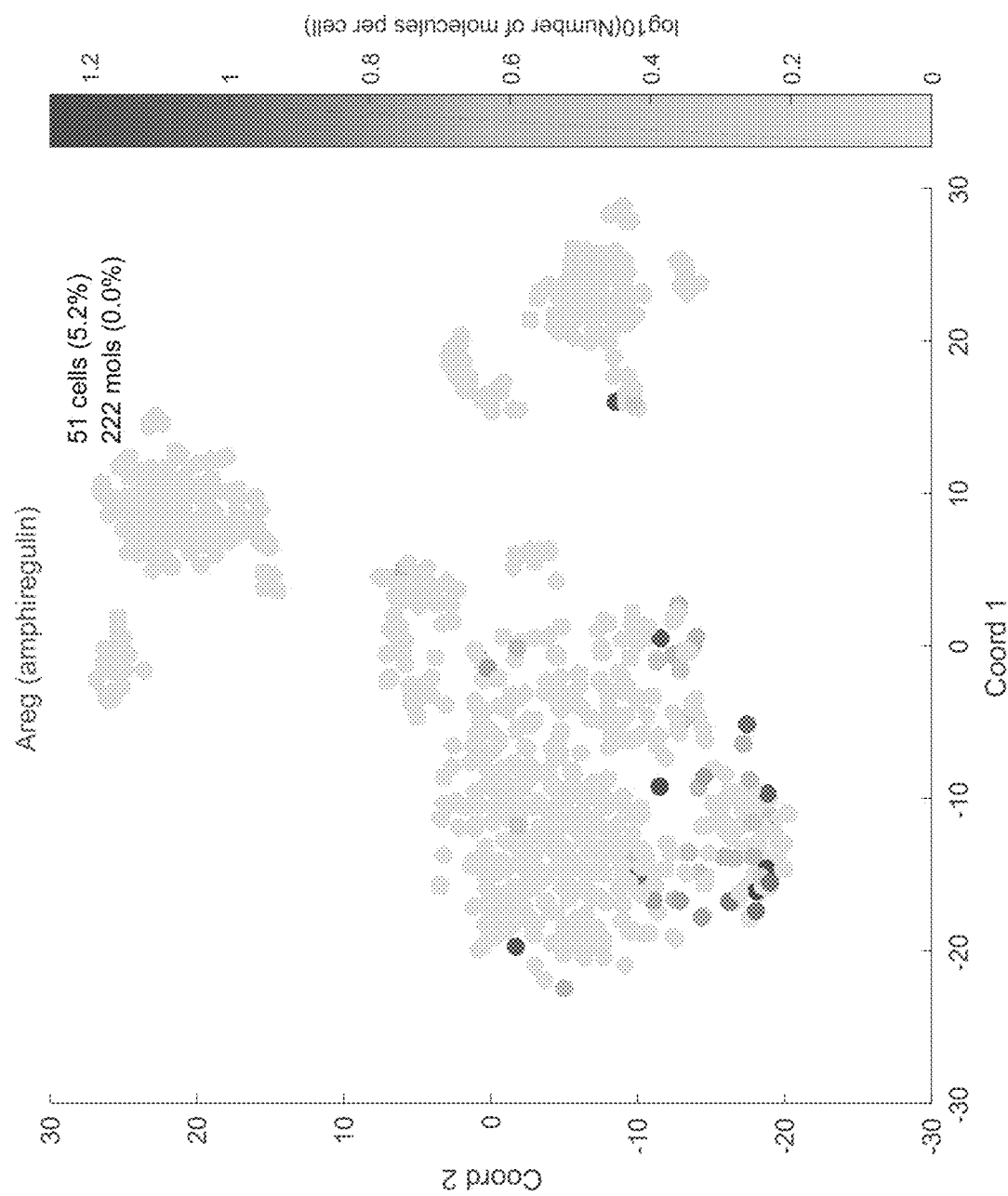
Figure 53D:
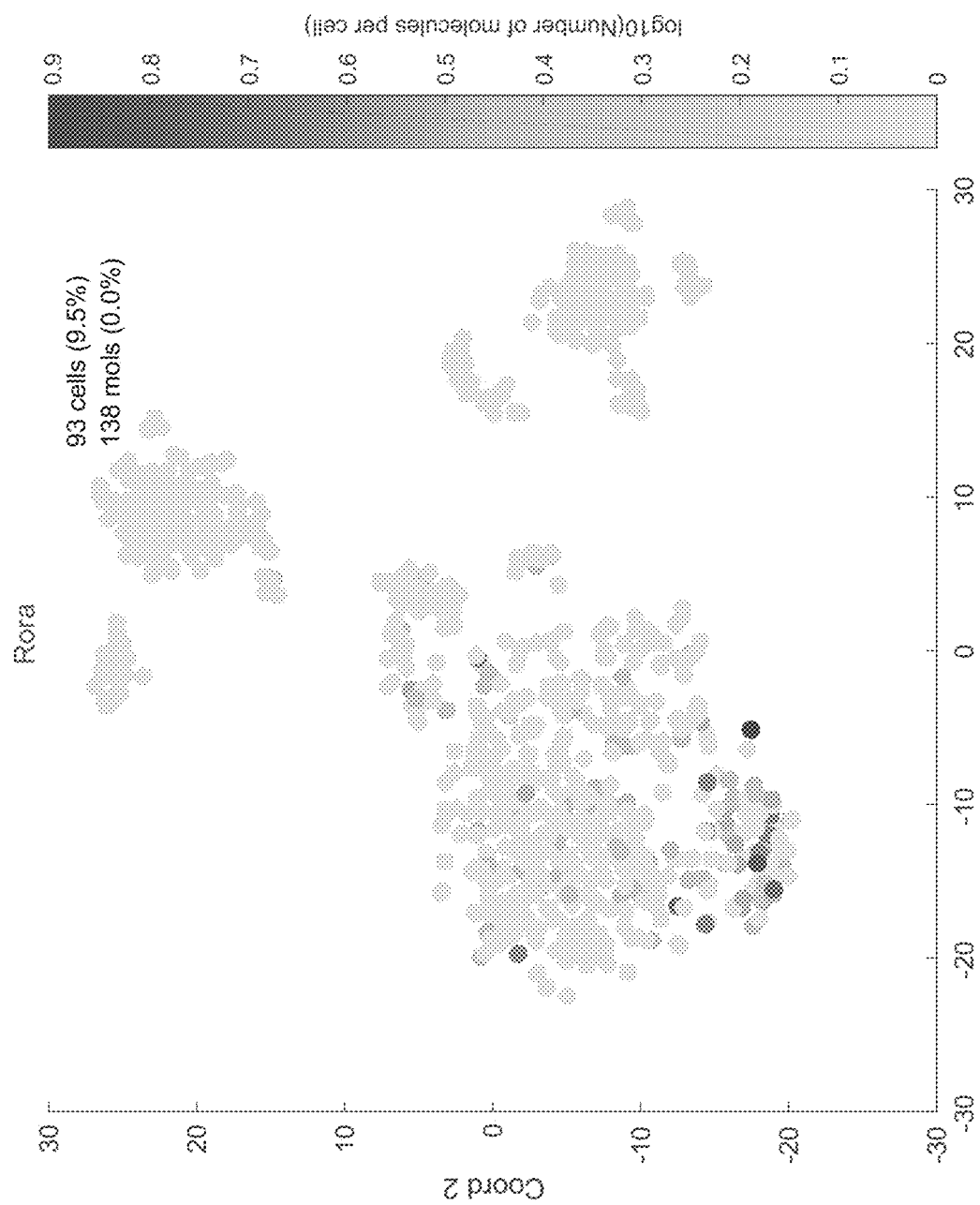

Exemplary expression profiles of macrophages, T cells, and B cells from the six different tissues are shown in FIGS. 52A-52C. FIGS. 52A-52C show that the same cell types in different tissues exhibited unique expression profiles and colon immune populations were the most distinct out of the six tissues. FIGS. 53A-53D are non-limiting exemplary plots comparing macrophages in the colon and spleen. FIG. 53A is a non-limiting exemplary tSNE projection plot comparing the expression profiles of macrophages in the colon and spleen, showing that macrophages in the two tissues had distinct expression profiles. FIG. 53B is a non-limiting exemplary plot showing the expression profiles of macrophages in the colon and spleen had low correlation. The low correlation further supported that macrophages in the two tissues had distinct expression profiles shown in FIG. 53A. FIGS. 53C and 53D are non-limiting exemplary tSNE projection plots of expression profiles of the Areg gene and Rora gene in macrophages in the colon and spleen. These two genes were expressed in 5.2% and 9.5% of the macrophages in the colon and spleen. FIGS. 53A, 53C, and 53D show that these two genes were expressed only in macrophages in the colon. Single-cell profiling of more than 28000 mouse immune cells from six different tissues as shown in FIGS. 52A-52C and 53A-53D revealed tissue specific gene expression signatures for major immune cell types.

Altogether, these data show that sample tagging can allow pooling of multiple samples onto the same single-cell experiment. Sample Tagging can increase sample throughput, eliminate batch effect between samples due to technical errors and enable detection of multiplets.

Example 10

Sample Indexing and Expression Profiles

This example demonstrates using sample tagging of cells does not alter mRNA expression profiles of cells.

Figure 54:
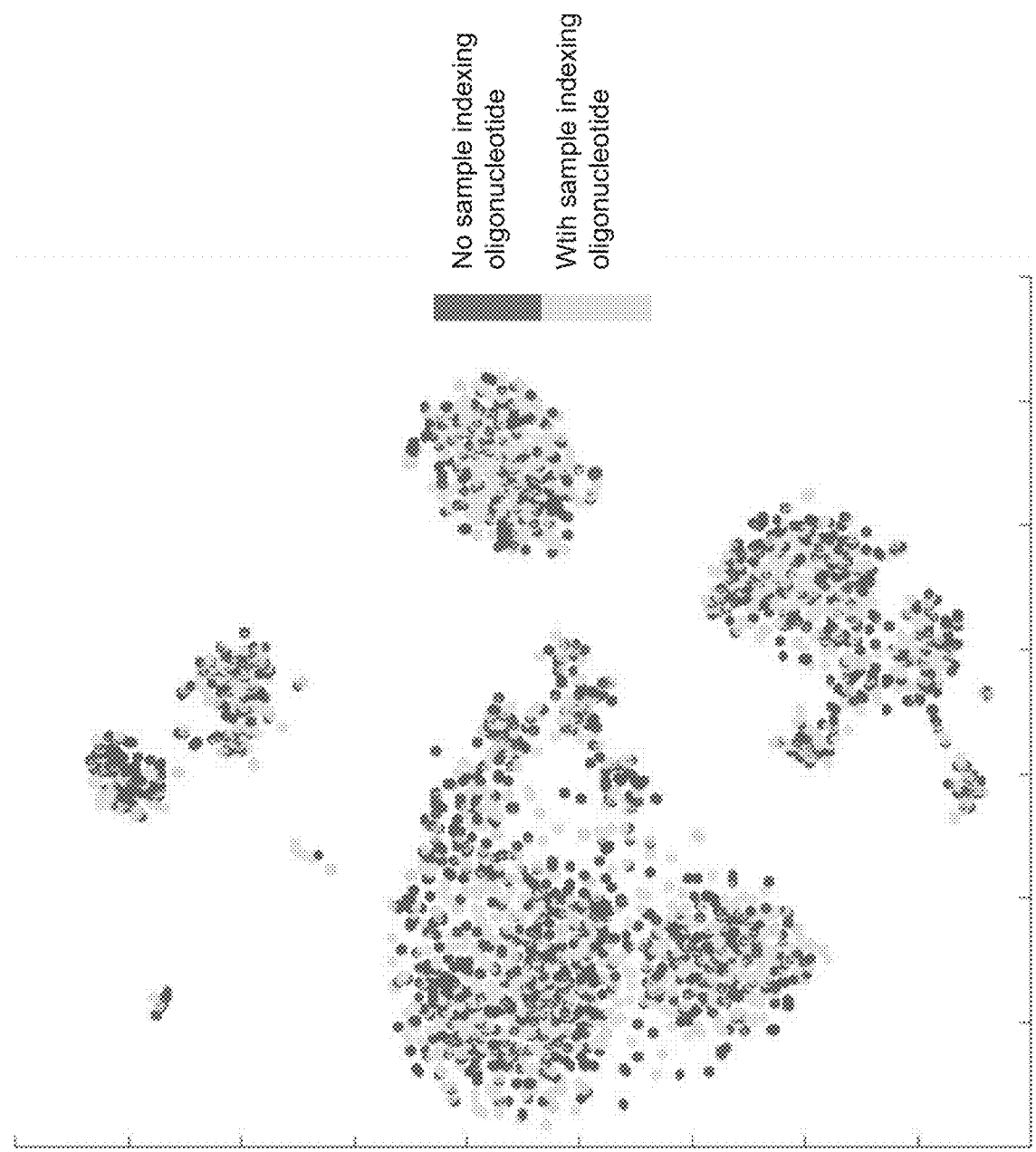
FIG. 54 is a non-limiting exemplary plot showing that tagging cells with sample indexing compositions did not alter mRNA expression profiles in PBMCs.

FIG. 54 is a non-limiting exemplary plot showing that tagging or staining cells with sample indexing compositions did not alter mRNA expression profiles in peripheral blood mononuclear cell (PBMCs). FIG. 54 shows an overlay of tSNE projection plots of expression profiles of PBMCs with or without sample tagging. The overlap shows that sample tagging did not alter mRNA expression profiles in PBMCs.

Altogether, the data show that sample tagging or staining with antibodies conjugated with oligonucleotides do not alter expression profiles of cells. Thus, sample tagging can allow pooling of multiple samples, increase sample throughput, eliminate batch effect between samples, and/or enable detection of multiplets without altering the expression profiles of the tagged cells.

Terminology

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for cell identification, comprising:
   (a) contacting a first plurality of cells and a second plurality of cells with two sample indexing compositions, respectively,
      wherein each of the first plurality of cells and each of the second plurality of cells comprises one or more cellular component targets,
      wherein each of the two sample indexing compositions comprises a cellular component binding reagent associated with a sample indexing oligonucleotide,
      wherein the cellular component binding reagent is capable of specifically binding to at least one of the one or more cellular component targets, and
      wherein the sample indexing oligonucleotide comprises a sample indexing sequence, and wherein sample indexing sequences of the two sample indexing compositions comprise different sequences;
   (b) barcoding the sample indexing oligonucleotides using a plurality of barcodes to create a plurality of barcoded sample indexing oligonucleotides,
      wherein the plurality of barcodes each comprises a cell label sequence, and wherein at least two of the plurality of barcodes comprise an identical cell label sequence;
   (c) obtaining sequencing data of the plurality of barcoded sample indexing oligonucleotides;
   (d) identifying a cell label sequence associated with two or more sample indexing sequences in the sequencing data obtained; and
   (e) removing sequencing data associated with the cell label sequence identified in step (d) from the sequencing data obtained.

2. The method of claim 1, wherein sample indexing sequences of at least 10 of the plurality of sample indexing compositions comprise different sequences.

3. The method of claim 1, wherein the cellular component binding reagent comprises an antibody, a tetramer, an aptamers, a protein scaffold, or a combination thereof.

4. The method of claim 1, wherein the at least one of the one or more cellular component targets is a cell surface component.

5. The method of claim 1, wherein the at least one of the one or more cellular component targets comprises a carbohydrate, a lipid, a protein, an extracellular protein, a cell-surface protein, a cell marker, a B-cell receptor, a T-cell receptor, a major histocompatibility complex, a tumor antigen, a receptor, an intracellular protein or any combination thereof.

6. The method of claim 1, further comprising removing unbound sample indexing compositions of the two sample indexing compositions after step (a).

7. The method of claim 1, wherein the sample indexing oligonucleotide is detachably associated with the cellular component binding reagent.

8. The method of claim 7, comprising disassociating the sample indexing oligonucleotide from the cellular component binding reagent.

9. The method of claim 1, wherein the sample indexing oligonucleotide is not homologous to genomic sequences of any of the first plurality of cells and/or the second plurality of cells.

10. The method of claim 1, wherein the sample indexing composition of the plurality of sample indexing compositions comprises a second cellular component binding reagent not conjugated with the sample indexing oligonucleotide.

11. The method of claim 10, where the cellular component binding reagent and the second cellular component binding reagent are identical.

12. The method of claim 1,
   wherein each of the plurality of barcodes comprises one or more of a target-binding region, a molecular label sequence and a binding site for a universal primer, and
   wherein molecular label sequences of at least two of the plurality of barcodes comprise different molecule label sequences.

13. The method of claim 12, wherein the molecular label sequences of the barcodes comprise random sequences.

14. The method of claim 12, wherein the sample indexing oligonucleotide comprises a sequence complementary to the target-binding region, or a portion thereof, of at least one barcode of the plurality of barcodes.

15. The method of claim 12, wherein the target-binding region or a portion thereof comprises a poly(dT) sequence.

16. The method of claim 12, wherein the plurality of barcodes is associated with a particle.

17. The method of claim 16, wherein the plurality of barcodes is immobilized on the particle, partially immobilized on the particle, enclosed in the particle, partially enclosed in the particle, or a combination thereof.

18. The method of claim 16, wherein the particle is disruptable.

19. The method of claim 16, wherein the particle is a sepharose bead, a streptavidin bead, an agarose bead, a magnetic bead, a hydrogel bead a conjugated bead, a protein A conjugated bead, a protein G conjugated bead, a protein A/G conjugated bead, a protein L conjugated bead, an oligo(dT) conjugated bead, a silica bead, a silica-like bead, an anti-biotin microbead, an anti-fluorochrome microbead, or any combination thereof.

20. The method of claim 16, wherein one or more of the cellular component binding reagent, the particle and the sample indexing oligonucleotide is associated with a detectable moiety.

21. The method of claim 1, wherein barcoding the sample indexing oligonucleotides using the plurality of barcodes comprises:
   contacting the plurality of barcodes with the sample indexing oligonucleotides to generate barcodes hybridized to the sample indexing oligonucleotides; and
   extending the barcodes hybridized to the sample indexing oligonucleotides to generate the plurality of barcoded sample indexing oligonucleotides.

22. The method of claim 21, wherein extending the barcodes comprises extending the barcodes using a DNA polymerase to generate the plurality of barcoded sample indexing oligonucleotides, or extending the barcodes using a reverse transcriptase to generate the plurality of barcoded sample indexing oligonucleotides.

23. The method of claim 21, comprising amplifying the plurality of barcoded sample indexing oligonucleotides to produce a plurality of amplicons.

24. The method of claim 23, wherein amplifying the plurality of barcoded sample indexing oligonucleotides comprises amplifying, using polymerase chain reaction (PCR), at least a portion of the molecular label sequence and at least a portion of the sample indexing oligonucleotide.

25. The method of claim 23, wherein obtaining the sequencing data of the plurality of barcoded sample indexing oligonucleotides comprises obtaining sequencing data of the plurality of amplicons.

26. The method of claim 1, further comprising identifying the sample origin of the at least one cell comprises identifying sample origin of the plurality of barcoded targets based on the sample indexing sequence of the at least one barcoded sample indexing oligonucleotide.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 1
aaaaaaaaaa aaaaaaaaaa                                                  20

<210> SEQ ID NO 2
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 2
tttttttttt tttttttttt                                                  20

<210> SEQ ID NO 3
```

```
<211> LENGTH: 95
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: 5AmMC6
<222> LOCATION: (1)..(1)
<223> OTHER INFORMATION: 5' Amino Modifier C6

<400> SEQUENCE: 3
gttgtcaaga tgctaccgtt cagagtacgt ggagttggtg gcccgacccc gagcgctacg     60
agccccccgg aaaaaaaaaa aaaaaaaaaa aaaaa                                95

<210> SEQ ID NO 4
<211> LENGTH: 200
<212> TYPE: DNA
<213> ORGANISM: Artificial Sequence
<220> FEATURE:
<223> OTHER INFORMATION: note="Description of Artificial Sequence:
      Synthetic Oligonucleotide"
<220> FEATURE:
<221> NAME/KEY: 5AmMC6
<222> LOCATION: (1)..(1)
<223> OTHER INFORMATION: 5' Amino Modifier C6

<400> SEQUENCE: 4
gttgtcaaga tgctaccgtt cagagctact gtccgaagtt accgtgtatc taccacgggt     60 ggttttcga atccggaaaa gatagtaata agtgttttag ttggaataag tcgcaacttt    120
tggagacggt tacctctcaa ttttttctgat ccgtaggccc cccgatctcg gcctcaaaaa   180
aaaaaaaaaa aaaaaaaaa                                                 200

<210> SEQ ID NO 5
<211> LENGTH: 25
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 5
gttgtcaaga tgctaccgtt cagag                                          25

<210> SEQ ID NO 6
<211> LENGTH: 95
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 6
gttgtcaaga tgctaccgtt cagagcccca tgtctagtac ctattggtcc cctatcctca    60
gattcgttta aaaaaaaaaa aaaaaaaaaa aaaaa                                95

<210> SEQ ID NO 7
<211> LENGTH: 26
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 7
```

```
tttttttttt tttttttttt ttttt                                     26

<210> SEQ ID NO 8
<211> LENGTH: 20
<212> TYPE: DNA
<213> ORGANISM: Artificial Sequence
<220> FEATURE:
<223> OTHER INFORMATION: note="Description of Artificial Sequence:
      Synthetic Oligonucleotide"

<400> SEQUENCE: 8
acacgacgct cttccgatct                                           20
```